United States Patent
Boren et al.

(10) Patent No.: US 7,998,995 B2
(45) Date of Patent: Aug. 16, 2011

(54) LXR AND FXR MODULATORS

(75) Inventors: Brant Clayton Boren, San Diego, CA (US); Brett B. Busch, San Diego, CA (US); Xiao-Hui Gu, Potomac, MD (US); Vasu Jammalamadaka, Pleasanton, CA (US); Shao Po Lu, San Diego, CA (US); Richard Martin, San Diego, CA (US); Raju Mohan, Encinitas, CA (US); Edwin Schweiger, San Diego, CA (US); William C. Stevens, La Jolla, CA (US); Tie-Lin Wang, San Diego, CA (US); Yinong Xie, Mission Viejo, CA (US); Wei Xu, Danville, CA (US)

(73) Assignee: Exelixis Patent Company LLC, South San Francisco, CA (US)

( * ) Notice: Subject to any disclaimer, the term of this patent is extended or adjusted under 35 U.S.C. 154(b) by 0 days.

(21) Appl. No.: 12/517,800

(22) PCT Filed: Dec. 7, 2007

(86) PCT No.: PCT/US2007/086787
§ 371 (c)(1),
(2), (4) Date: Oct. 21, 2009

(87) PCT Pub. No.: WO2008/073825
PCT Pub. Date: Jun. 19, 2008

(65) Prior Publication Data
US 2010/0069367 A1  Mar. 18, 2010

Related U.S. Application Data

(60) Provisional application No. 60/869,198, filed on Dec. 8, 2006.

(51) Int. Cl.
*A61K 31/4178* (2006.01)
*A61K 31/4164* (2006.01)
*C07D 233/56* (2006.01)
*C07D 233/58* (2006.01)
*C07D 233/66* (2006.01)
*C07D 233/64* (2006.01)

(52) U.S. Cl. ........... 514/397; 514/398; 548/343.5; 548/311.1; 548/316.4; 548/321.5

(58) Field of Classification Search ............ 514/397, 514/399; 548/311.1, 333.5
See application file for complete search history.

(56) References Cited

U.S. PATENT DOCUMENTS
5,466,823 A  11/1995  Talley et al.
(Continued)

FOREIGN PATENT DOCUMENTS
DE  103 15 569 A1  10/2004
(Continued)

OTHER PUBLICATIONS

U.S. Appl. No. 2009-993529, concurrently owned, filed Dec. 4, 2009.*
Finn et al., "Discovery of a potent and selective series of pyrazole bacterial methionyl-trna sythetase inhibitors" Bioorganic & Medicinal Chemistry Letters, 13(13), 2003, 2231-2234.
Bennett et al., "Liver X receptor agonist as a treatment for atherosclerosis", Expert Opinion on Therapeutic Patents, 2004, 14(7), 967-982.
(Continued)

*Primary Examiner* — Yong Chu
*Assistant Examiner* — Michael Barker
(74) *Attorney, Agent, or Firm* — Mary VanAtten; Gerard P. Norton; Fox Rothschild LLP

(57) ABSTRACT

Compounds of the invention are disclosed, such as compounds of formulae LX-LXIV, and pharmaceutically acceptable salts, isomers, or prodrugs thereof, which are useful as modulators of the activity of liver X receptors (LXR) and Farnesoid X receptors (FXR), where $R^{00}$, $R^{200}$, $R^{400}$, $R^{500}$, $J^{11}$, $J^{21}$, $G^1$, $G^{21}$, and Q are defined herein. Pharmaceutical compositions containing the compounds and methods of using the compounds are also disclosed.

LX

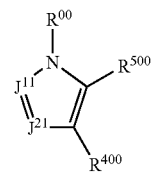

LXI

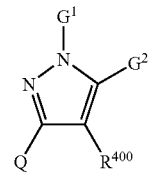

LXII

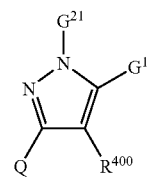

LXII

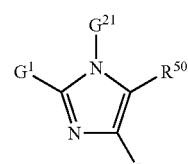

LXIV

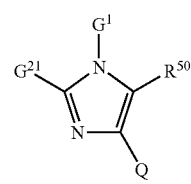

45 Claims, No Drawings

U.S. PATENT DOCUMENTS

| | | | |
|---|---|---|---|
| 5,504,215 | A | 4/1996 | Talley et al. |
| 5,760,068 | A | 6/1998 | Talley et al. |
| 6,071,955 | A | 6/2000 | Elias et al. |
| 6,184,215 | B1 | 2/2001 | Elias et al. |
| 6,294,558 | B1 | 9/2001 | Ando et al. |
| 6,358,634 | B1 | 3/2002 | Igarashi et al. |
| RE37,936 | E | 12/2002 | Huang et al. |
| 6,492,411 | B1 | 12/2002 | Talley et al. |
| 6,635,655 | B1 | 10/2003 | Jayyosi et al. |
| 7,566,709 | B2 | 7/2009 | Schiemann et al. |
| 2002/0035156 | A1 | 3/2002 | Roniker et al. |
| 2004/0152739 | A1 | 8/2004 | Hanau et al. |
| 2004/0157883 | A1 | 8/2004 | Chen et al. |
| 2004/0248956 | A1 | 12/2004 | Hagmann et al. |
| 2005/0004115 | A1 | 1/2005 | Sharma et al. |
| 2006/0241157 | A1 | 10/2006 | Conner et al. |
| 2006/0276650 | A1 | 12/2006 | Schadt et al. |
| 2007/0010531 | A1 | 1/2007 | Schadt et al. |
| 2008/0090834 | A1* | 4/2008 | Hoover et al. ........... 514/253.06 |

FOREIGN PATENT DOCUMENTS

| | | |
|---|---|---|
| DE | 103 15 571 A1 | 10/2004 |
| DE | 103 15 573 A1 | 10/2004 |
| EP | 0 839 810 A1 | 5/1998 |
| EP | 1 285 908 A1 | 2/2003 |
| EP | 1 398 029 A | 3/2004 |
| EP | 1 884 513 A | 2/2008 |
| JP | 2004-146368 A | 5/2004 |
| WO | 03/086287 A2 | 10/2003 |
| WO | 2004/011446 A1 | 2/2004 |
| WO | 2004/033432 A1 | 4/2004 |
| WO | 2004/056740 A1 | 7/2004 |
| WO | 2004/069158 A | 8/2004 |
| WO | 2004/071447 A2 | 8/2004 |
| WO | 2004/080972 A1 | 9/2004 |
| WO | 2004/089303 A2 | 10/2004 |
| WO | 2004/089888 A1 | 10/2004 |
| WO | 2004/089932 A1 | 10/2004 |
| WO | 2004/106307 A | 12/2004 |
| WO | 2005/009435 A1 | 2/2005 |
| WO | 2005/012263 A | 2/2005 |
| WO | 2005/037199 A | 4/2005 |
| WO | 2005/037763 A1 | 4/2005 |
| WO | 2005037271 A1 | 4/2005 |
| WO | 2005/044130 A | 5/2005 |
| WO | 2005/047266 A | 5/2005 |
| WO | 2005/049578 A1 | 6/2005 |
| WO | 2005/054176 A1 | 6/2005 |
| WO | 2005/066137 A1 | 7/2005 |
| WO | 2006/044528 A1 | 4/2006 |
| WO | 2006/076202 A1 | 7/2006 |
| WO | 2007/002559 A | 1/2007 |
| WO | 2007/002559 A1 | 1/2007 |
| WO | 2007/002563 A1 | 1/2007 |

OTHER PUBLICATIONS

Tischenko et al., "Some derivatives of 1,2,5-triphenylimidazole", Deposited Doc. (1980) SPSTL 358Khp-D80, Caplus Accession No. 1982:423694, 8pp.

Tischenko et al., "Synthesis and luminescence of 1,2,5-triphenylimidazoles", Sisintill Org Lyuminofory, 1972, 93-9.

Lettau et al., "Imidazol-N-oxide 1); Eline einfache Synthese substituierter Imidazole", Zeischrift fuer Chemie, 1971, 11(1), 10-11.

Weissenfels et al., "Diimidazoles. II. Synthesis of aliphatically and aromatically bridged N,N'-diimidazoles", Journal fuer Praktische Chemie (Leipzig), 1963, 22(3-4), 130-9.

Yanborisov et al., "Synthesis and pharmaceutical activity of heteroylpyruvic acids and their derivatives", Khimiko-Farmatsevticheskii Zhurnal [Pharmaceutical Chemistry Journal], 1998, 32(9), 480-2.

Kalaany et al., "LXRs regulate the balance between fat storage and oxidation", Cell Metabolism, 2005, vol. 1, 231-244 and Supplemental Data (4 sheets).

Giorelli et al., "Immunomodulatory properties of increased levels of liver X receptor β in peripheral blood mononuclear cells from multiple sclerosis patients", Experimental Neurology, 2007, vol. 204, 759-766.

Zanlungo et al., "The Molecular and Metabolic Basis of Biliary Cholesterol Secretion and Gallstone Disease", Frontiers in Bioscience, 2003, vol. 8, 1166-1174.

Zelcer et al., "Liver X receptors as integrators of metabolic and inflammatory signaling", The Journal of Clinical Investigation, 2006, 116(3), 607-614.

Joseph et al., "Synthetic LXR ligand inhibits the development of atherosclerosis in mice", PNAS, 2002, 99(11), 7604-7609.

Tontonoz et al., "Liver X Receptor Signaling Pathways in Cardiovascular Disease", Molecular Endocrinology, 2003, 17(6), 985-993.

Goralski et al., "Chipping away at gallstones", Nature Medicine, 2004, 10(12), 1301-1302.

* cited by examiner

LXR AND FXR MODULATORS

CROSS-REFERENCE TO RELATED APPLICATIONS

This application is a US national phase of International Application No. PCT/US2007/086787, filed Dec. 7, 2007, which claims the benefit of priority of U.S. provisional application 60/869,198, filed Dec. 8, 2006.

BACKGROUND OF THE INVENTION

Field of the Invention

This invention relates to compounds that modulate the activity of liver X receptors (LXRs), and/or farnesoid (X) receptors (FXRs). The invention also provides pharmaceutical compositions comprising the compounds of the invention and methods of utilizing those compositions for modulating the activity of liver X receptor and farnesoid X receptor. In particular, pyrazole and imidazole isomers and derivatives are provided for modulating the activity of LXRs and/or FXRs.

Nuclear Receptors

Nuclear receptors are a superfamily of regulatory proteins that are structurally and functionally related and are receptors for, e.g., steroids, retinoids, vitamin D and thyroid hormones (see, e.g., Evans (1988) *Science* 240:889-895). These proteins bind to cis-acting elements in the promoters of their target genes and modulate gene expression in response to ligands for the receptors.

Nuclear receptors can be classified based on their DNA binding properties (see, e.g., Evans, supra and Glass (1994) *Endocr. Rev.* 15:391-407). For example, one class of nuclear receptors includes the glucocorticoid, estrogen, androgen, progestin and mineralocorticoid receptors which bind as homodimers to hormone response elements (HREs) organized as inverted repeats (see, e.g., Glass, supra). A second class of receptors, including those activated by retinoic acid, thyroid hormone, vitamin $D_3$, fatty acids/peroxisome proliferators (i.e., peroxisome proliferator activated receptors or PPARs) and ecdysone, bind to HREs as heterodimers with a common partner, the retinoid X receptors (i.e., RXRs, also known as the 9-cis retinoic acid receptors; see, e.g., Levin et al. (1992) *Nature* 355:359-361 and Heyman et al. (1992) *Cell* 68:397-406).

RXRs are unique among the nuclear receptors in that they bind DNA as a homodimer and are required as a heterodimeric partner for a number of additional nuclear receptors to bind DNA (see, e.g., Mangelsdorf et al. (1995) *Cell* 83:841-850). The latter receptors, termed the class II nuclear receptor subfamily, include many which are established or implicated as important regulators of gene expression.

There are three RXR genes (see, e.g., Mangelsdorf et al. (1992) *Genes Dev.* 6:329-344), coding for RXRα, β, and γ, all of which are able to heterodimerize with any of the class II receptors, although there appear to be preferences for distinct RXR subtypes by partner receptors in vivo (see, e.g., Chiba et al. (1997) *Mol. Cell. Biol.* 17:3013-3020). In the adult liver, RXRα is the most abundant of the three RXRs (see, e.g., Mangelsdorf et al. (1992) *Genes Dev.* 6:329-344), suggesting that it might have a prominent role in hepatic functions that involve regulation by class II nuclear receptors. See also, Wan et al. (2000) *Mol. Cell. Biol.* 20:4436-4444.

Orphan Nuclear Receptors

Included in the nuclear receptor superfamily of regulatory proteins are nuclear receptors for which the ligand is known and those which lack known ligands. Nuclear receptors falling in the latter category are referred to as orphan nuclear receptors. The search for activators for orphan receptors has led to the discovery of previously unknown signaling pathways (see, e.g., Levin et al., (1992), supra and Heyman et al., (1992), supra). For example, it has been reported that bile acids, which are involved in physiological processes such as cholesterol catabolism, are ligands for the farnesoid X receptor (FXR).

Because it is known that products of intermediary metabolism act as transcriptional regulators in bacteria and yeast, such molecules may serve similar functions in higher organisms (see, e.g., Tomkins (1975) *Science* 189:760-763 and O'Malley (1989) *Endocrinology* 125:1119-1120). For example, one biosynthetic pathway in higher eukaryotes is the mevalonate pathway, which leads to the synthesis of cholesterol, bile acids, porphyrin, dolichol, ubiquinone, carotenoids, retinoids, vitamin D, steroid hormones and farnesylated proteins.

LXRα and LXRβ

LXRα is found predominantly in the liver, with lower levels found in kidney, intestine, spleen and adrenal tissue (see, e.g., Willy, et al. (1995) *Gene Dev.* 9(9):1033-1045) LXRβ is ubiquitous in mammals and was found in nearly all tissues examined. LXRs are activated by certain naturally occurring, oxidized derivatives of cholesterol (see, e.g., Lehmann, et al. (1997) *J. Biol. Chem.* 272(6):3137-3140): LXRα is activated by oxycholesterol and promotes cholesterol metabolism (Peet et al. (1998) *Cell* 93:693-704). Thus, LXRs appear to play a role in, e.g., cholesterol metabolism (see, e.g., Janowski, et al. (1996) *Nature* 383:728-731).

FXR

FXR (originally isolated as RIP14 (retinoid X receptor-interacting protein-14), see, e.g., Seol et al. (1995) *Mol. Endocrinol.* 9:72-85) is a member of the nuclear hormone receptor superfamily and is primarily expressed in the liver, kidney and intestine (see, e.g., Seol et al, supra and Forman et al. (1995) *Cell* 81:687-693). It functions as a heterodimer with the retinoid X receptor (RXR) and binds to response elements in the promoters of target genes to regulate gene transcription. The FXR-RXR heterodimer binds with highest affinity to an inverted repeat-1 (IR-1) response element, in which consensus receptor-binding hexamers are separated by one nucleotide. FXR is part of an interrelated process, in that FXR is activated by bile acids (the end product of cholesterol metabolism) (see, e.g., Makishima et al (1999) *Science* 284: 1362-1365, Parks et al. (1999) *Science* 284:1365-1368, Wang et al. (1999) *Mol. Cell.* 3:543-553), which serve to inhibit cholesterol catabolism. See also, Urizar et al. (2000) *J. Biol. Chem.* 275:39313-39317.

Nuclear Receptors and Disease

Nuclear receptor activity has been implicated in a variety of diseases and disorders, including, but not limited to, hypercholesterolemia (see, e.g., International Patent Application Publication No. WO 00/57915), osteoporosis and vitamin deficiency (see, e.g., U.S. Pat. No. 6,316,5103), hyperlipoproteinemia (see, e.g., International Patent Application Publication No. WO 01/60818), hypertriglyceridemia, lipodystrophy, hyperglycemia and diabetes mellitus (see, e.g., International Patent Application Publication No. WO 01/82917), atherosclerosis and gallstones (see, e.g., International Patent Application Publication No. WO 00/37077), disorders of the skin and mucous membranes (see, e.g, U.S. Pat. Nos. 6,184,215 and 6,187,814, and International Patent Application Publication No. WO 98/32444), acne (see, e.g., International Patent Application Publication No. WO 00/49992), and cancer, Parkinson's disease and Alzheimer's disease (see e.g., International Patent Application Publication No. WO 00/17334). Activity of nuclear receptors, including LXRs, FXRs and PPARs, and orphan nuclear receptors, has been implicated in physiological processes including, but not limited to, bile acid biosynthesis, cholesterol metabolism or catabolism, and modulation of cholesterol 7α-hydroxylase gene (CYP7A1) transcription (see, e.g., Chiang et al. (2000) *J. Biol. Chem.* 275:10918-10924), HDL metabolism (see, e.g., Urizar et al. (2000) *J. Biol. Chem.* 275:39313-39317 and International Patent Application Publication No. WO 01/03705), and increased cholesterol efflux and increased expression of ATP binding cassette transporter protein (ABC1) (see, e.g., International Patent Application Publication No. WO 00/78972).

The nuclear receptors FXR and LXR are structurally and closely related receptors. Furthermore, FXR and LXR play critical and functionally distinct roles in coordinate control of bile acid, cholesterol, and triglyceride metabolism to maintain lipid homeostasis. Nuclear receptors and bile acid/oxysterol-regulated genes are potential targets for developing drug therapies for lowering serum cholesterol and triglycerides and treating cardiovascular and liver diseases. Compounds with dual activity for both LXR and FXR, then, can have profound effects on lipid homeostasis, and can more effectively control disease conditions implicating both FXR and LXR.

In addition to the anti-atherogenic effect of LXR agonists, studies in cell culture and animal model systems have demonstrated that LXR agonists increase the plasma triglyceride levels and promote the increased production of VLDL lipoprotein particles. Schultz et al., Genes & Development 14:2831-2838 (2000); Repa et al. Genes & Development 14:28119-2830 (2000). In contrast, activation of FXR via FXR agonists decreases plasma triglyceride levels; Maloney et al., J. Med. Chem. 43:2971-2974, (2000) and inhibits the production of VLDL lipoprotein particle. Hiorkane et al., J. Biol. Chem., 279: 45685-45692 (2004); Sirvent et al., FEBS Lett. 566: 173-177 (2004); Watanabe et al., J. C. Invest. 113: 1408-1418 (2004); unpublished Exelixis data. A LXR/FXR dual agonist combining the agonist activity of both LXR and FXR in a single molecule should display anti-atherogenic activity while attenuating the unwanted side effects of hypertriglyceridemia and enhanced VLDL secretion.

Thus, there is a need for compounds, compositions and methods of modulating the activity of nuclear receptors, including LXRs, FXRs, PPARs and orphan nuclear receptors. Such compounds are useful in the treatment, prevention, inhibition or amelioration of one or more symptoms of diseases or disorders in which nuclear receptor activity is implicated.

SUMMARY OF THE INVENTION

In one aspect, the present invention comprises a compound according to the following formulae Ia-d, IIa-d, and III

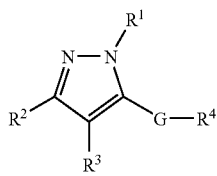
Ia

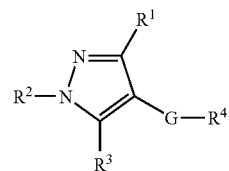
Ib

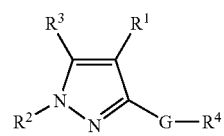
Ic

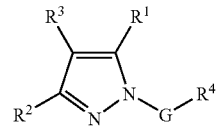
Id

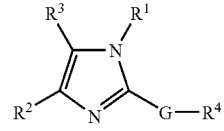
IIa

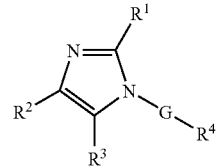
IIb

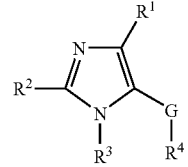
IIc

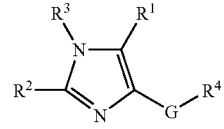
IId

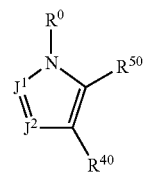
(III)

or a pharmaceutically acceptable salt, isomer, or prodrug thereof, which are useful as modulators of the activity of liver X receptors (LXR), where $R^0$, $R^{11}$, $R^2$, $R^{21}$, $R^3$, $R^4$, $R^{40}$, $R^{50}$, $J^1$, $J^2$, and G are defined herein.

In another aspect, the present invention comprises a compound according to the following formulae LX and LXa-b,

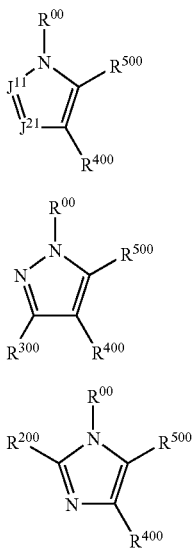

(LX)

(LXa)

(LXb)

or a pharmaceutically acceptable salt, isomer, or prodrug thereof, which are useful as modulators of the activity of liver X receptors (LXR), where $R^{00}$, $R^{200}$, $R^{300}$, $R^{400}$, $R^{5000}$, $J^{11}$ and $J^{21}$ are defined herein.

Compounds for use in compositions and methods for modulating the activity of nuclear receptors are provided. In particular, compounds of the invention which are useful for modulating liver X receptors, $LXR_\alpha$ and $LXR_\beta$, FXR, PPAR and/or orphan nuclear receptors are provided.

In one aspect, the compounds provided herein are agonists of LXR. In another aspect, the compounds provided herein are antagonists of LXR. Agonists that exhibit low efficacy are, in certain aspect, antagonists. In certain aspects the compounds provided herein are agonists of FXR. In other aspects, the compounds provided herein are LXR/FXR dual agonists.

Another aspect of this invention is directed to methods of treating, preventing, inhibiting, or ameliorating the symptoms of a disease or disorder that is modulated or otherwise affected by nuclear receptor activity or in which nuclear receptor activity is implicated, comprising administering to a subject in need thereof a therapeutically effective amount of a compound of formulae I through CIII or a pharmaceutically acceptable derivative thereof.

Another aspect of this invention is directed to methods of reducing cholesterol levels in a subject in need thereof, comprising administering an effective cholesterol level-reducing amount of a compound of formulae I through CIII or a pharmaceutically acceptable derivative thereof.

Another aspect of this invention is directed to methods of treating, preventing, inhibiting, or ameliorating one or more symptoms of a disease or disorder which is affected by cholesterol, triglyceride, or bile acid levels, comprising administering to a subject in need thereof a therapeutically effective amount of a compound of formulae I through CIII or a pharmaceutically acceptable derivative thereof.

Another aspect of this invention is directed to methods of modulating nuclear receptor activity, comprising contacting the nuclear receptor with a compound of formulae I through CIII or a pharmaceutically acceptable derivative thereof.

Another aspect of this invention is directed to methods of modulating cholesterol metabolism, comprising administering an effective cholesterol metabolism-modulating amount of a compound of formulae I through CIII or a pharmaceutically acceptable derivative thereof.

Another aspect of this invention is directed to methods of treating, preventing, inhibiting or ameliorating one or more symptoms of hypocholesterolemia in a subject in need thereof, comprising administering a therapeutically effective amount of a compound of formulae I through CIII or a pharmaceutically acceptable derivative thereof.

Another aspect of this invention is directed to methods of increasing cholesterol efflux from cells of a subject, comprising administering an effective cholesterol efflux-increasing amount of a compound of formulae I through CIII or a pharmaceutically acceptable derivative thereof.

Another aspect of this invention is directed to methods of increasing the expression of ATP-Binding Cassette (ABC1) in the cells of a subject, comprising administering an effective ABC1 expression-increasing mount of a compound of formulae I through CIII or a pharmaceutically acceptable derivative thereof.

Another aspect of this invention is directed to in vitro methods for altering nuclear receptor activity, comprising contacting the nuclear receptor with a compound of formulae I through CIII or a pharmaceutically acceptable derivative thereof.

Another aspect of this invention is directed to methods of reducing cholesterol levels in a subject in need thereof, comprising administering an effective cholesterol level-reducing amount of a compound of formulae I through CIII or a pharmaceutically acceptable derivative thereof.

Another aspect of this invention is directed to pharmaceutical compositions comprising a pharmaceutically acceptable carrier, excipient and/or diluent and a compound of formulae I through CIII.

Another aspect of this invention is directed to regulation of cholesterol transport and inflammatory signaling pathways that are implicated in human disease pathology including atherosclerosis and associated diseases such as myocardial infarction and ischemic stroke in a subject in need thereof, comprising administering an effective cholesterol transport and inflammatory signaling pathways regulating amount of a compound of formulae I through CIII or a pharmaceutically acceptable derivative thereof.

Another aspect of this invention is directed to treatment of the metabolic syndrome which comprises a constellation of disorders of the body's metabolism including obesity, hypertension and insulin resistance and diabetes including treatment of diseases resulting from compromised metabolism and immunity including atherosclerosis and diabetes as well as autoimmune disorders and diseases in a subject in need thereof, comprising administering a therapeutically effective amount of a compound of formulae I through CIII or a pharmaceutically acceptable derivative thereof.

DETAILED DESCRIPTION OF THE INVENTION

The first aspect of the invention is directed to compounds represented by Formulae Ia, Ib, Ic, Id, IIa, IIb, IIc or IId:

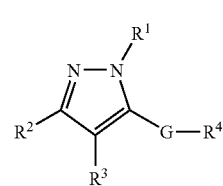

Ia

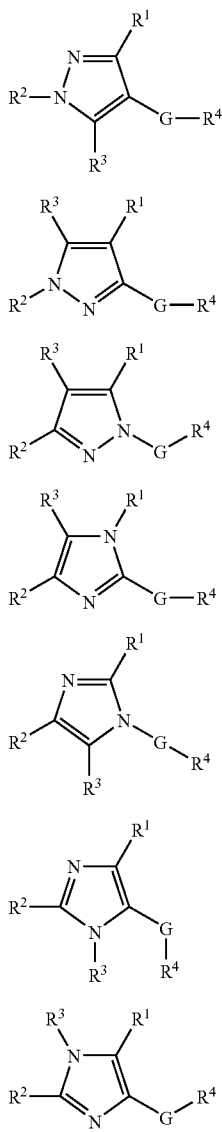

or as an isomer, a mixture of stereoisomers, a racemic mixture of stereoisomers, or as a tautomer; or as a pharmaceutically acceptable salt, prodrug, solvate or polymorph thereof,
wherein:
  each $R^1$ substituent is independently selected from the group consisting of $R^5$ and -$L^1$-$R^5$;
  each $R^5$ is independently selected from the group consisting of hydrogen, $C_{1-6}$ aliphatic, $C_{0-6}$ alkyl$OR^{11}$, $C_{1-6}$ alkoxy, $C_{0-6}$ alkyl$SO_2R^{11}$, $C_{0-6}$ alkyl$SR^{11}$, $C_{0-6}$ alkyl$SO_2N(R^{11})_2$, $C_{0-6}$alkyl$SO_2NR^{11}COR^{11}$, cyclo$C_{3-6}$ alkyl, arylalkyl, $C_{1-6}$ haloalkyl, halogen, $C_{0-6}$ alkylC≡N, $OC_{0-6}$ alkylC(O)$OR^{11}$, $C_{0-6}$ alkylCON$(R^{11})_2$, $C_{0-6}$ alkylN$(R^{11})_2$; and 5-12 membered aromatic or non-aromatic ring, and 5-12 membered heterocyclyl or heteroaryl having one or more heteroatoms N, O or S;
  each $R^5$ is optionally substituted at a substitutable position with one or more radicals of $R^{5a}$;
  each $R^{5a}$ is independently selected from halogen, $C_{1-6}$ haloalkyl, $C_{1-6}$ haloalkyl$OR^{11}$, nitro, $C_{1-6}$ aliphatic, $C_{1-6}$ alkoxy, $C_{0-6}$ alkyl$OR^{11}$, $OC_{1-6}$ alkyl$OR^{11}$, $C_{0-6}$ alkyl$COR^{11}$, $OCON(R^{11})_2$, $C_{0-6}$ alkyl$NR^{11}COR^{11}$, $C_{0-6}$ alkyl$NR^{11}CON(R^{11})_2$, $C_{0-6}$ alkyl$SO_2R^{11}$, $C_{0-6}$ alkyl$SR^{11}$, $C_{0-6}$ alkyl$SO_2N(R^{11})_2$, $C_{0-6}$ alkyl$NR^{11}COOR^{11}$, $C_{0-6}$ alkyl$N_3$, 5-12 membered heteroaryl or heterocyclyl having one or more heteroatoms N, S, O; 5-12 membered aromatic or non-aromatic ring, arylalkyl, aryloxyaryl, aryl$C_{1-6}$ alkoxy, $OC_{1-6}$ alkyl$N(R^{11})_2$, $C_{0-6}$ alkyl$N(R^{11})_2$, $C_{0-6}$ alkyl$COOR^{11}$, $C_{0-6}$ alkyl$OCON(R^{11})_2$, $C_{0-6}$ alkyl$CON(R^{11})OR^{11}$, $C_{0-6}$ alkylC≡N, $OC_{0-6}$ alkyl$COOR^{11}$, $C_{0-6}$ alkyl$OCON(R^{11})_2$, $C_{0-6}$ alkylCON $(R^{11})_2$, $OC_{1-6}$ alkyl$CON(R^{11})_2$ or $C_{1-6}$ alkyl$OC_{1-6}$ alkyl;
  each $R^{5a}$ is optionally substituted at substitutable position with $C_{1-6}$ aliphatic, $C_{1-6}$ alkoxy, $C_{0-6}$ alkyl$SO_2R^{11}$, $C_{0-6}$ alkyl$COOR^{11}$, $C_{1-6}$ alkoxyaryl, 5-12 membered aromatic or non-aromatic ring, or 5-12 membered heterocyclyl or heteroaryl having one or more heteroatoms N, O or S;
  each $L^1$ is independently a direct bond, —CS—, —$C_{1-6}$ alkoxy-, -carbonyl-, —$SO_2$—, —$CON(R^{11})$, —$CONR^{11}N(R^{11})$, —C(=$NR^{11}$), —C(=$NOR^{11}$), —C(=N—$N(R^{11})_2$)—, 5-12 membered aromatic or non-aromatic ring, 5-12 membered heteroaryl or heterocyclyl having one or more heteroatoms N, O, or S which is optionally substituted at a substitutable position with one or more radicals of $R^{14}$; —$(CH_2)_m$—V—$(CH_2)_n$— or —V—$(CH_2)_n$—V—; m is 0-6; n is 0-6;
  V is independently —$C(R^{11})_2$—, —$C(R^{11})_2C(R^{11})_2$—, —$C(R^{11})$=$C(R^{11})$—, —$C(R^{11})_2O$—, —$C(R^{11})_2NR^{11}$—, —C≡C—, —O—, —S—, —$NR^{11}$, —$N(R^{10})$CO—, —$N(R^{10})CO_2$—, —$CON(R^{10})$—, —CO—, —$CO_2$—, —OC(=O)—, —OC(=O)$N(R^{10})$—, —$CONR^{11}NR^{11}$—, —$CONR^{11}$—, —$OCONR^{11}$—, —$SO_2$—, —$N(R^{10})SO_2$—, —$SO_2N(R^{10})$—, —$NR^{10}OCONR^{10}$—, —$NR^{10}CSNR^{10}$cyclo$C_{3-6}$ alkyl, cyclo$C_{3-6}$haloalkyl; 5-12 membered aromatic or non-aromatic ring, 5-12 membered heteroaryl or heterocyclyl having one or more heteroatoms N, O or S, which is optionally substituted at a substitutable position with one or more radicals of $R^{14}$; or $C_{2-6}$ alkylidene chain wherein the alkylidene chain is optionally interrupted by —$C(R^{11})_2$, —$C(R^{11})_2C(R^{11})_2$—, —$C(R^{11})$=C$(R^{11})$—, —$C(R^{11})_2O$—, —C_C—, —O—, —S—, —$N(R^{10})CO$—, —$N(R^{10})CO_2$—, —$CON(R^{11})$—, —CO—, —$CO_2$—, —OC(=O)—, —OC(=O)N$(R^{10})$—, —$SO_2$—, —$N(R^{10})SO_2$—, or —$SO_2N(R^{10})$—;
  each $R^2$ is independently selected from the group consisting of $R^7$ and $L^3$-$R^7$;
  each $R^7$ is independently selected from hydrogen, $C_{1-6}$ alkyl, halogen, $C_{0-6}$ alkyl$OR^{11}$, $C_{0-6}$ alkyl$COR^{11}$, $C_{1-6}$ haloalkyl, $C_{1-6}$ alkoxy, $C_{1-6}$ haloalkyl$(OR^{11})$, $C_{0-6}$ alkyl$COOR^{11}$, $C_{0-6}$ alkyl$CON(R^{11})_2$, $C_{0-6}$ alkyl$N(R^{11})_2$, $C_{0-6}$ alkylC≡N, cyclo$C_{3-6}$ alkylC-N, $C_{0-6}$ alkyl$SO_2N(R^{11})_2$, $C_{0-6}$ alkyl$CONR^{11}N(R^{11})_2$, $C_{0-6}$ alkyl$CONR^{11}OR^{11}$, $C_{0-6}$ alkyl$OCOR^{11}$, cyclo$C_{3-6}$ alkyl, cyclo$C_{3-6}$ alkyl$OR^{11}$, 5-12 membered aromatic or non-aromatic ring; or 5-12 membered heteroaryl and heterocyclyl having one or more heteroatoms N, O or S;
  $R^7$ is optionally substituted at a substitutable position with one or more radicals of $R^{7a}$;
  each $R^{7a}$ is independently a halogen, $C_{1-6}$ alkyl, $CR^{11}$=$CR^{11}COOH$, $C_{1-6}$ alkoxy, $C_{0-6}$ alkyl$OR^{11}$, $C_{0-6}$ alkyl$COR^{11}$, $C_{0-6}$ alkyl$OVCOOR^{11}$, $C_{0-6}$ alkyl$NR^{11}COR^{11}$, $C_{0-6}$ alkyl $SO_2NR^{11}COR^{11}$, $C_{0-6}$ alkyl $SO_2N(R^{11})_2$; $C_{0-6}$ alkyl$SR^{11}$, $(C_{0-6}$ alkyl)C=O$(OR^{11})$, $OVOR^{11}$, $C_{1-6}$ haloalkyl, $C_{1-6}$ haloalkyl$OR^{11}$, $OC_{1-6}$ haloalkyl, haloaryl, aryloxy, aralkyloxy, aryloxyalkyl, $C_{1-6}$alkoxyaryl, aryl$C_{0-6}$ alkylcarboxy, $NR^{11}SO_2R^{11}$, $OC_{1-6}$ alkyl, $OC_{0-6}$ alkylCOOR$^{11}$, $C_{1-6}$ alkoxyheteroaryl, $C_{1-6}$alkoxyheterocyclyl, cycloC$_{3-6}$ alkylCOOR$^{11}$, cycloC$_{3-6}$alkylamine; 5-12 membered aromatic or non-aromatic ring, or 5-12 membered heteroaryl or heterocyclyl having one or more heteroatoms N, O or S; each R$^{7a}$ may be substituted at a substitutable position with one or more radicals of R$^8$;

each R$^8$ is independently halogen, $C_{1-6}$ alkyl, $C_{1-6}$ alkoxy, $C_{1-6}$ haloalkyl, $C_{1-6}$ haloalkyl(OR$^{11}$), $C_{0-6}$ alkylOR$^{11}$, $C_{0-6}$ alkylCON(R$^{11}$)$_2$, $C_{0-6}$ alkylCOR$^{11}$, $C_{0-6}$ alkyl-COOR$^{11}$, or $C_{0-6}$ alkylSO$_2$R$^{11}$;

each L$^3$ is independently selected from a direct bond, —CS—, —CO—, —CONR$^{11}$—, —C(=N)(R$^{11}$)—, —C(=NOR$^{11}$)—, —C[=N—N(R$^{11}$)$_2$]—; —(CH$_2$)$_m$—V$^1$—(CH$_2$)$_n$—, or —V$^1$—(CH$_2$)$_n$—V$^1$—; m is 0-6; n is 0-6; V$^1$ is independently —C(R$^{11}$)$_2$—, —C(R$^{11}$)$_2$C(R$^{11}$)$_2$—, —C(R$^{11}$)=C(R$^{11}$)—, —C(R$^{11}$)$_2$O—, —C(R$^{11}$)$_2$NR$^{11}$—, —C≡C—, —O—, —S—, —NR$^{11}$—, —N(R$^{10}$)CO—, —N(R$^{10}$)CO$_2$—, —CON(R$^{10}$)—, —OCO—, —CO—, —CO$_2$—, —OC(=O)—, —OC(=O)N(R$^{10}$)—, —SO$_2$—, —N(R$^{10}$)SO$_2$—, —SO$_2$N(R$^{10}$)—, —NR$^{10}$CONR$^{10}$—, —NR$^{10}$CSNR$^{10}$—, cycloC$_{3-6}$ alkyl, cycloC$_{3-6}$ haloalkyl; $C_{0-6}$ alkylidene chain wherein the alkylidene chain is optionally interrupted by —C(R$^{11}$)$_2$—, —C(R$^{11}$)$_2$C(R$^{11}$)$_2$—, —C(R$^{11}$)=C(R$^{11}$)—, —C(R$^{11}$)$_2$O—, —C_C—, —O—, —S—, —N(R$^{10}$)CO—, —N(R$^{10}$)CO$_2$—, —NR$^{11}$—, —CON(R$^{10}$)—, —CO—, —CO$_2$—, —OC(=O)—, —OC(=O)N(R$^{10}$)—, —SO$_2$—, —N(R$^{10}$)SO$_2$—, or —SO$_2$N(R$^{10}$)—;

each R$^3$ is independently selected from the group consisting of R$^6$ and L-R$^6$;

each R$^6$ is independently hydrogen, halogen, $C_{1-6}$ alkyl, $C_{1-6}$haloalkyl, $C_{0-6}$ alkylOR$^{11}$, nitro, $C_{1-6}$ alkoxy, OCOR$^{11}$, NR$^{11}$COR$^{11}$, OCON(R$^{11}$)$_2$, OC$_{1-6}$ alkylN(R$^{11}$)$_2$, OC$_{1-6}$alkylCOR$^{11}$, $C_{0-6}$ alkylN(R$^{11}$)$_2$, $C_{0-6}$ alkylCOOR$^{11}$, $C_{0-6}$ alkylCON(R$^{11}$)$_2$, OC$_{0-6}$ alkylCOOR$^{11}$, and OCON(R$^{11}$)$_2$, $C_{1-6}$ haloalkylOR$^{11}$, $C_{0-6}$ alkyl-COR$^{11}$, CONR$^{11}$OR$^{11}$, 5-12 membered aromatic or non-aromatic ring; or 5-12 membered heteroaryl or heterocyclyl having one or more heteroatoms N, O or S; each R$^6$ is optionally substituted at a substitutable position with one or more radicals of R$^{6a}$;

each R$^{6a}$ is independently halogen, $C_{1-6}$ alkyl, $C_{1-6}$ alkoxy, $C_{1-6}$ haloalkyl, $C_{1-6}$ haloalkylOR$^{11}$, CON(R$^{11}$)$_2$, CONR$^{11}$OR$^{11}$, $C_{0-6}$ alkylCOOR$^{11}$; CR$^{11}$=CR$^{11}$COOH, $C_{0-6}$ alkylOR$^{11}$, $C_{0-6}$ alkylCOR$^{11}$, $C_{0-6}$ alkylSO$_2$R$^{11}$, $C_{0-6}$ alkylOCOOR$^{11}$, $C_{0-6}$ alkylNR$^{11}$COR$^{11}$, $C_{0-6}$ alkylSO$_2$NR$^{11}$COR$^{11}$, $C_{0-6}$ alkyl SO$_2$N(R$^{11}$)$_2$, $C_{0-6}$ alkylSR$^{11}$, (C$_{0-6}$ alkyl)C=O (OR$^{11}$), OVOR$^{15}$, OC$_{1-6}$ haloalkyl, aryloxy, aralkyloxy, aryloxyalkyl, $C_{1-6}$ alkoxyaryl, arylC$_{0-6}$ alkylcarboxy, NR$^{11}$SO$_2$R', OC$_{1-6}$ alkyl, OC$_{0-6}$ alkylCOOR$^{11}$, $C_{1-6}$alkoxyheteroaryl, $C_{1-6}$alkoxyheterocyclyl, or cycloalkylCOOR$^{11}$;

each L is independently selected from direct bond, —CS—, —CO—, —CONR$^{11}$—, —C(=NR$^{11}$)—, —C(=NOR$^{11}$)—, —C(=N—N(R$^{11}$)$_2$)—; —(CH$_2$)$_m$—V$^0$—(CH$_2$)$_n$— or —V$^0$—(CH$_2$)$_n$—V$^0$—; m is 0-6; n is 0-6; V$^0$ is independently —C(R$^{11}$)$_2$—, —C(R$^{11}$)$_2$C(R$^{11}$)$_2$—, —C(R$^{11}$)=C(R$^{11}$)—, —C(R$^{11}$)$_2$O—, —C(R$^{11}$)$_2$NR$^{11}$—, —C≡C—, —O—, —S—, —NR$^{11}$—, —CR$^{11}$NR$^{11}$—, —N(R$^{10}$)CO—, —N(R$^{10}$)CO$_2$—, —CON(R$^{10}$)—, —OCO—, —CO—, —CO$_2$—, —OC(=O)—, —OC(=O)N(R$^{10}$)—, —SO$_2$—, —N(R$^{10}$)SO$_2$—, —SO$_2$N(R$^{11}$)—, —NR$^{11}$CONR$^{10}$—, —NR$^{11}$CSNR$^{10}$—, cycloC$_{3-6}$ alkyl, cycloC$_{3-6}$haloalkyl; $C_{2-6}$ alkylidene chain wherein the alkylidene chain is optionally interrupted by —C(R$^{11}$)$_2$—, —C(R$^{11}$)$_2$C(R$^{11}$)$_2$—, —C(R$^{11}$)=C(R$^{11}$)—, —C(R$^{11}$)$_2$O—, —C_C—, —O—, —S—, —N(R$^{10}$)CO—, —N(R$^{10}$)CO$_2$—, —NR$^{11}$—, —CON(R$^{10}$)—, —CO—, —CO$_2$—, —OC(=O)—, —OC(=O)N(R$^{10}$)—, —SO$_2$—, —N(R$^{10}$)SO$_2$—, or —SO$_2$N(R$^{10}$)—;

each R$^4$ is independently selected from hydrogen, $C_{1-6}$ alkyl, CR$^{11}$=CR$^{11}$COOR$^{11}$, $C_{1-6}$ alkoxy, $C_{0-6}$ alkylOR$^{11}$, $C_{1-6}$ haloalkylOR$^{11}$, $C_{0-6}$ alkylCOR$^{11}$, $C_{0-6}$ alkylC=N, $C_{0-6}$ alkylSO$_2$R$^{11}$, $C_{0-6}$ alkylOCOOR$^{11}$, $C_{0-6}$ alkylNR$^{11}$COR$^{11}$, $C_{0-6}$ alkylSO$_2$NR$^{11}$COR$^{11}$, $C_{0-6}$ alkylSO$_2$N(R$^{11}$)$_2$, $C_{0-6}$ alkylSR$^{11}$, (C$_{0-6}$ alkyl)C=O (OR$^{11}$), OVOR$^{11}$, halogen, $C_{1-6}$haloalkyl, OC$_{1-6}$ haloalkyl, aryloxy, aralkyloxy, aryloxyalkyl, $C_{1-6}$ alkoxyaryl, arylC$_{0-6}$ alkylcarboxy, $C_{0-6}$ alkylNR$^{11}$SO$_2$R$^{11}$, OC$_{1-6}$ alkyl, OC$_{0-6}$ alkylCOOR$^{11}$, $C_{1-6}$alkoxyheteroaryl, $C_{1-6}$alkoxyheterocyclyl, cycloalkylCOOR$^{11}$, cycloC$_{3-6}$ alkylC=N, nitro, $C_{0-6}$ alkylN(R$^{11}$)$_2$, $C_{0-6}$ alkylN$_3$, cycloC$_{3-6}$ alkylOR$^{11}$, $C_{0-6}$ alkylNR$^{11}$COR$^{11}$, $C_{0-6}$ alkylOCON(R$^{11}$)$_2$, $C_{0-6}$ alkylCON(R$^{11}$)$_2$, a 5-12 membered aromatic ring or non-aromatic ring, or 5-12 membered heteroaryl or heterocyclyl having one or more heteroatoms N, O or S; each R$^4$ is optionally substituted at a substitutable position with one or more radicals of R$^{4a}$;

each R$^{4a}$ is independently selected from hydrogen, $C_{1-6}$ alkyl, ($C_{1-6}$ alkyl)C=O(OR$^{11}$); $C_{1-6}$ alkoxy, $C_{0-6}$alkylOR$^{11}$, $C_{0-6}$ alkylCOR$^{11}$, $C_{0-6}$ alkylSO$_2$R$^{11}$, $C_{0-6}$ alkylSO$_2$N(R$^{11}$)$_2$, $C_{0-6}$ alkylSR$^{11}$, (C$_{0-6}$ alkyl)C=O (OR$^{11}$), halogen, $C_{1-6}$ haloalkyl, $C_{1-6}$ haloalkylOR$^{11}$, $C_{0-6}$ alkylC=N, aryloxy, aralkyloxy, aryloxyalkyl, $C_{1-6}$ alkoxyaryl, arylC$_{0-6}$ alkylcarboxy, NR$^{11}$SO$_2$R$^{11}$, OC$_{1-6}$ alkyl, or OC$_{0-6}$ alkylCOOR$^{11}$;

each R$^{10}$ is independently selected from R$^{11}$, C(=O)R$^{11}$, CO$_2$R$^{11}$, or SO$_2$R$^{11}$;

each R$^{11}$ is independently selected from hydrogen, substituted or unsubstituted $C_{1-8}$ aliphatic group; $C_{1-6}$ haloalkyl, N(R$^{12}$)$_2$; 5-12 membered aromatic or non-aromatic ring, or 5-12 membered heteroaryl or heterocyclyl having one or more heteroatoms, N, S or O; which is optionally substituted at a substitutable position with one or more radicals of R$^{12}$;

each R$^{12}$ is independently halogen, $C_{1-6}$haloalkyl, $C_{1-6}$ alkyl, $C_{1-6}$ alkoxy, (C$_{0-6}$ alkyl)C=O(OR$^{13}$); $C_{0-6}$ alkylOR$^{13}$, $C_{0-6}$ alkylCOR$^{13}$, $C_{0-6}$ alkylSO$_2$R$^{13}$, $C_{0-6}$ alkylCON(R$^{13}$)$_2$, $C_{0-6}$ alkylCONR$^{13}$OR$^{13}$, $C_{0-6}$ alkylSO$_2$N(R$^{13}$)$_2$, $C_{0-6}$ alkylSR$^{13}$, $C_{0-6}$ haloalkylOR$^{13}$, aryloxy, aralkyloxy, aryloxyalkyl, $C_{1-6}$ alkoxyaryl, arylC$_{0-6}$ alkylcarboxy, $C_{0-6}$ alkylNR$^{13}$SO$_2$R$^{13}$ or OC$_{0-6}$ alkylCOOR$^{13}$;

each R$^{13}$ is independently hydrogen or substituted or unsubstituted $C_{1-8}$ aliphatic group;

each R$^{14}$ is independently $C_{1-6}$ alkyl, $C_{1-6}$ alkoxy, halogen, $C_{1-6}$haloalkyl, $C_{0-6}$ alkylCON(R$^{11}$)$_2$, $C_{0-6}$ alkylCONR$^{11}$OR$^{11}$, $C_{0-6}$ alkylOR$^{11}$, or $C_{0-6}$ alkylCOOR$^{11}$;

G is -L$^2$-K—;

K is selected from a 5-12 membered aromatic or non-aromatic ring, or 5-12 membered heterocyclyl or heteroaryl having one or more hetero atoms, N, S or O, where K is optionally substituted at a substitutable position with one or more radicals of R$^4$;

each L$^2$ is —CS—, —C$_{1-6}$ alkyl-, —C$_{1-6}$ alkoxy-, —C$_{0-6}$ alkylCOO—, —CH=CHCOO—, —C$_{0-6}$ alkylCON(R$^{11}$)—, —C(=N)(R$^{11}$)—, —C(=N)(OR$^{11}$)—, —C(=N)(N(R$^{11}$)—, —OC$_{0-6}$alkylCOO—, —$C_{0-6}$alkylSO$_2$—, —$C_{0-6}$alkyN(R$^{11}$)—, —$C_{0-6}$alkylO—, —$C_{0-6}$ alkylCO—, -cycloalkylamine-, —(CH$_2$)$_m$—V$^2$ (CH$_2$)$_n$—, or —V$^2$—(CH$_2$)$_m$—V$^2$—;
m is 0-6;
n is 0-6;
V$^2$ is independently —C(R$^{11}$)$_2$—, —C(R$^{11}$)$_2$C(R$^{11}$)$_2$—, —C(R$^{11}$)=C(R$^{11}$)—, —C(R$^{11}$)$_2$O—, —C(R$^{11}$)$_2$NR$^{11}$—, —C≡C—, —O—, —S—, —N(R$^{10}$)CO—, —N(R$^{10}$)CO$_2$—, —CON(R$^{10}$)—, —CON(R$^{11}$)—, —CON(R$^{11}$)O—, —CO—, —CO$_2$—, —OR$^{11}$N—, —OR$^{11}$COO—, —OC(=O)—, —OC(=O)N(R$^{10}$)—, —SO$_2$—, —N(R$^{10}$)SO$_2$—, —SO$_2$N(R$^{10}$)—, —NR$^{11}$CONR$^{10}$—, —NR$^{11}$CSNR$^{10}$—, cycloC$_{3-6}$ alkyl, cycloC$_{3-6}$ haloalkyl; $C_{0-6}$ alkylidene chain wherein alkylidene chain is optionally interrupted by —C(R$^{11}$)$_2$—, —C(R$^{11}$)$_2$C(R$^{11}$)$_2$—, —C(R$^{11}$)=C(R$^{11}$)—, —C(R$^{11}$)$_2$O—, —C≡C—, —O—, —S—, —N(R$^{10}$)CO—, —N(R$^{11}$)CO$_2$—, —CON(R$^{10}$)—, —CON(R$^{11}$)—, —CON(R$^{11}$)O—, —CO—, —CO$_2$—, —OC(=O)—, —OC(=O)N(R$^{10}$)—, —SO$_2$—, —N(R$^{10}$)SO$_2$— or —SO$_2$N(R$^{11}$)—; 5-12 membered aromatic or non-aromatic ring, or 5-12 membered heteroaryl or heterocyclyl having one or more heteroatoms, N, S or O which is optionally substituted at a substitutable position with one or more radicals of R$^9$;
each R$^9$ is independently halogen, $C_{1-6}$ haloalkyl, $C_{1-6}$ alkyl, $C_{1-6}$ alkoxy, $C_{0-6}$ alkylOR$^{11}$ or $C_{1-6}$ alkylCOOR$^{11}$.

A preferred L$^2$ in the first aspect of the invention is selected from the group consisting of —CONH—, —CONHCH$_2$—, —CH$_2$O—, —OCH$_2$COOCH$_2$—, —CONHCH$_2$—, and —C_C—.

Examples of Ring K in the first aspect of the invention include phenyl, pyridinyl, thienyl, furanyl, morpholinyl, thiazolyl, indolyl, oxazolyl, biphenyl, naphthyl, piperidinyl, piperazinyl, isoxazolyl, pyrimidinyl, or imidazolyl. Preferred Ring K moieties are phenyl, pyridinyl, and biphenyl. When Ring K is a phenyl or pyridinyl, it is preferably substituted by methylsulfonyl. Ring K is optionally substituted at a substitutable position with one or more radicals of R$^4$, wherein R$^4$ is methylsulfonyl, or $C_{1-6}$ aliphatic or substituents selected from the group consisting of CR$^{11}$=CR$^{11}$COOR$^{11}$, $C_{1-6}$ alkyl, $C_{1-6}$ alkoxy, $C_{0-6}$ alkylOR$^{11}$, $C_{1-6}$ alkylCOR$^{11}$, $C_{0-6}$ alkylSO$_2$R$^{11}$, $C_{0-6}$ alkylOCOOR$^{11}$, $C_{0-6}$ alkylNR$^{11}$COR$^{11}$, $C_{0-6}$ alkyl SO$_2$NR$^{11}$COR$^{11}$, $C_{0-6}$ alkyl SO$_2$N(R$^{11}$)$_2$, $C_{0-6}$ alkylSR$^{11}$, (C$_{0-6}$ alkyl)C=O(OR$^{11}$), OVOR$^{11}$, $C_{0-6}$ alkylC≡N, halogen, $C_{1-6}$haloalkyl, OC$_{1-6}$ haloalkyl, aryloxy, aralkyloxy, aryloxyalkyl, $C_{1-6}$ alkoxyaryl, arylC$_{0-6}$ alkylcarboxy, NR$^{11}$SO$_2$R$^{11}$, OC$_{1-6}$ alkyl, OC$_{0-6}$ alkylCOOR$^{11}$, $C_{1-6}$alkoxyheteroaryl, $C_{1-6}$alkoxyheterocyclyl, cycloalkyl COOR$^{11}$, 5-12 membered aromatic ring or non-aromatic ring, and 5-12 membered heteroaryl or heterocyclyl having one or more heteroatoms N, O or S.

Examples of preferred R$^4$ groups include OH, CN, C(CH$_3$)$_2$ OH, SO$_2$CH$_3$, SO$_2$NH$_2$, SO$_2$CH$_2$CH$_3$, SO$_2$C(CH$_3$)$_3$, SCH$_2$CH$_3$, SCH$_3$, OCH$_3$, $C_{1-6}$ alkyl, CH$_2$COOH, C(CH$_3$)$_2$COOH, NHSO$_2$CH$_3$, F, Cl, Br, C(CH$_2$CH$_3$)$_2$COOH, CH$_2$COOCH$_3$, C(CH$_3$)$_2$COOCH$_3$, CH$_2$CH$_2$COOH, CH=CHCOOH, OCH$_2$COOCH$_3$, COCH$_3$, OCH$_3$, COOC(CH$_3$)$_3$, cyclobutane-COOH, OC(CH$_3$)$_2$COOH, CH$_2$CH$_3$, CH$_3$, CH(CH$_3$)$_2$, CH$_2$COOCH$_3$, OCON(CH$_2$CH$_3$)$_2$, NHCOCH$_3$, or CF$_3$.

Additional preferred R$^4$ moieties include methylsulfonyl, or $C_{1-6}$ aliphatic or substituents selected from the group consisting of CR$^{11}$=CR$^{11}$COOH, $C_{1-6}$ alkyl, $C_{1-6}$ alkoxy, $C_{0-6}$ alkylOR$^{11}$, $C_{1-6}$ alkylCOR$^{11}$, $C_{0-6}$ alkylSO$_2$R$^{11}$, $C_{0-6}$ alkylO-COOR$^{11}$, $C_{0-6}$ alkylNR$^{11}$COR$^{11}$, $C_{0-6}$ alkyl SO$_2$NR$^{11}$COR$^{11}$, $C_{0-6}$ alkyl SO$_2$N(R$^{11}$)$_2$, $C_{0-6}$ alkylSR$^{11}$, (C$_{0-6}$ alkyl)C=O(OR$^{11}$), OVOR$^{11}$, halogen, $C_{1-6}$haloalkyl, OC$_{1-6}$ haloalkyl, aryloxy, aralkyloxy, aryloxyalkyl, $C_{1-6}$ alkoxyaryl, arylC$_{0-6}$ alkylcarboxy, NR$^{11}$SO$_2$R$^{11}$, OC$_{1-6}$ alkyl, OC$_{0-6}$ alkylCOOR$^{11}$, $C_{1-6}$alkoxyheteroaryl, $C_{1-6}$alkoxyheterocyclyl, cycloalkyl COOR$^{11}$, a 5-12 membered aromatic ring or non-aromatic ring, and 5-12 membered heteroaryl or heterocyclyl having one or more heteroatoms N, O or S.

In a preferred embodiment of the first aspect of the invention, R$^1$ is R$^5$ and/or R$^2$ is R$^7$, and one or more of the following is true:

a) R$^5$ selected from the group consisting of thienyl, furanyl, morpholinyl, thiazolyl, indolyl, oxazolyl, pyridinyl, isoxazolyl, pyrimidinyl, imidazolyl and phenyl; R$^5$ is optionally substituted at a substitutable position with one or more radicals of R$^{5a}$;

b) R$^7$ selected from the group consisting of phenyl, pyridinyl, thienyl, furanyl, morpholinyl, thiazolyl, oxazolyl, pyridinyl, isoxazolyl, pyrimidinyl, imidazolyl, CF$_3$, and COOCH$_3$; R$^7$ is optionally substituted at a substitutable position with one or more radicals of R$^{7a}$;

c) R$^3$ is hydrogen or optionally substituted phenyl;

d) L$^2$ is selected from the group consisting of —CONH—, —CONHCH$_2$—, —CH$_2$O—, —OCH$_2$COOCH$_2$—, —O—, C≡C—, —OCH$_2$CH$_2$—, —CONHOCH$_2$CH(OH)CH$_2$O—, and —CS—;

e) Ring K is substituted phenyl, biphenyl, pyridinyl, piperidinyl, piperazinyl, morpholinyl, thienyl, or naphthyl; and f) R$^4$ is selected from the group consisting of SO$_2$CH$_3$, SO$_2$CH$_2$CH$_3$, SO$_2$CH$_2$ CH$_2$CH$_3$, SCH$_2$CH$_3$, SCH$_3$, OCH$_3$, $C_{1-6}$ alkyl, CH$_2$COOH, C(CH$_3$)$_2$COOH, NHSO$_2$CH$_3$, F, Cl, Br, C(CH$_3$)$_2$COOH, CH$_2$COOCH$_3$, C(CH$_3$)$_2$COOCH$_3$, CH$_2$CH$_2$COOH, OCH$_2$CON(R$^{11}$)$_2$, OCH$_2$CH$_2$N(CH$_3$)$_2$, OCH$_2$COOH, OCH$_2$COOCH$_3$, CH$_2$OH, COCH$_3$, COOC(CH$_3$)$_3$, cyclobutane-COOH, OC(CH$_3$)$_2$COOH and CF$_3$.

In another preferred embodiment of the first aspect of the invention aspect, R$^1$ is L$^1$-R$^5$ and/or R$^2$ is R$^7$, and one or more of the following is true:

a) R$^5$ is substituted phenyl or pyridinyl;

b) R$^{5a}$ is halogen, trifluoromethyl, $C_{1-6}$ alkyl, $C_{1-6}$ haloalkyl, nitro, $C_{1-6}$ alkoxy, or OCON(C$_{1-6}$ alkyl)$_2$;

c) L$^1$ is —CS—, —CH$_2$—, —CH$_2$O—, —CH$_2$CH$_2$—, —C═O—, —SO$_2$—, —CONH—, —CONHC(CH$_3$)$_2$—, —CONH(CH$_2$)$_3$OCH$_2$—, —CONHCH$_2$CH$_2$N(CH$_3$)$_2$—, or —OCH$_2$CH$_2$—;

d) R$^2$ is R$^7$ is selected from the group consisting of phenyl, pyridinyl, thienyl, furanyl, morpholinyl, thiazolyl, oxazolyl, pyridinyl, CF$_3$, or COOCH$_3$;

e) R$^3$ is hydrogen or phenyl optionally substituted with R$^{6a}$;

f) Ring K is substituted phenyl, thienyl, furanyl, piperazinyl, piperidinyl or pyridinyl;

g) L$^2$ is —CONH—, —CONHCH$_2$—, —CH$_2$O—, —OCH$_2$COOCH$_2$—, —O—, —C≡C—, —OCH$_2$CH$_2$—, or —CONHOCH$_2$CH(OH)CH$_2$O—; and h) R$^4$ is selected from the group consisting of halogen, $C_{1-6}$ haloalkyl, $C_{1-6}$ alkylCOOR$^{11}$, and methyl sulfonyl.

In another preferred embodiment of the first aspect of the invention R$^1$ is R$^5$ and/or R$^2$ is L$^3$-R$^7$, and one or more of the following is true:

a) R$^5$ is selected from the group consisting of thienyl, furanyl, morpholinyl, thiazolyl, indolyl, oxazolyl, pyridinyl, imidazolyl, isoxazolyl, pyrimidinyl and phenyl; R$^5$ is optionally substituted at a substitutable position with one or more radicals of R$^{5a}$;

b) $R^{5a}$ is halogen or trifluoromethyl;

c) $R^2$ is $L^3$-$R^7$; $R^7$ is selected from the group consisting of phenyl, pyridinyl, thienyl, furanyl, morpholinyl, thiazolyl, oxazolyl, pyridinyl, phenyl, imidazolyl, isoxazolyl, pyrimidinyl, $CF_3$, cycloC$_{3-6}$ alkylC≡N, C$_{0-6}$ alkylC≡N, and COOCH$_3$; $R^7$ is optionally substituted at a substitutable position with one or more radicals of $R^{7a}$;

d) $L^3$ is —CS—, CH$_2$, CH$_2$OCH$_2$, NCH$_2$ (CH$_2$)$_2$, CH$_2$N(CH$_2$)$_2$, CH$_2$CN, CONH, CO, or CONHCH$_2$;

e) $R^3$ is hydrogen or optionally substituted phenyl;

f) Ring K is substituted phenyl, pyridinyl, furanyl, biphenyl or naphthyl;

g) $L^2$ is —CS—, CONH, CONHCH$_2$, CH$_2$O, OCH$_2$COOCH$_2$, OCH$_2$CH$_2$, or OCH$_2$; and h) $R^4$ is SO$_2$CH$_3$, SO$_2$CH$_2$CH$_3$, SCH$_2$CH$_3$, CH$_2$COOH, C(CH$_3$)$_2$COOH, NHSO$_2$CH$_3$, F, Cl, Br, SCH$_3$, OCH$_3$, C$_{1-6}$ alkyl, COOCH$_2$CO, OCH$_3$, CH$_2$COOH, CH$_2$COOCH$_3$, CH(CH$_3$)$_2$COOH, OC(CH$_3$)$_2$COOH, COOC(CH$_3$)$_3$, cyclobutane-COOH, C(CH$_3$)$_2$COOH, OCH$_2$COOCH$_3$, and CF$_3$.

In another preferred embodiment of the first aspect of the invention, the compound is selected from those with one of the following structures:

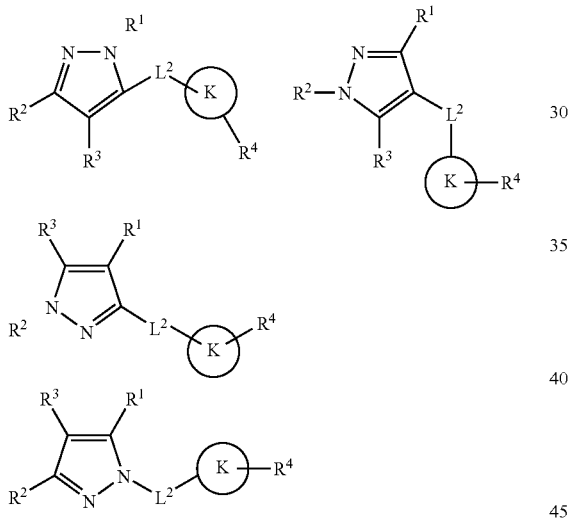

In this embodiment, $R^1$ is $R^5$ selected from the group consisting of thienyl, furanyl, morpholinyl, thiazolyl, indolyl, oxazolyl, pyridinyl, isoxazolyl, pyrimidinyl, imidazolyl, and phenyl; $R^5$ is optionally substituted at a substitutable position with one or more radicals of $R^{5a}$ Preferably, $R^5$ is phenyl or pyridinyl optionally substituted with $R^{5a}$.

$R^2$ is $R^7$ selected from the group consisting of trifluoromethyl, COOCH$_3$, CH$_2$OH, CONHCH$_2$CH$_3$, CONHOCH$_2$CH(OH)CH$_2$OH, CONHCH$_2$CH$_2$N(CH$_3$)$_2$, CONHCH$_2$CH$_2$OCH$_3$, CONHCH$_2$CH$_2$OCH$_3$, CH$_2$COOCH$_3$, CON(CH$_3$)$_2$, COOCH(CH$_3$)$_2$, CONHCH$_2$CH$_2$CH$_2$OCH$_3$, OCOCH(CH$_3$)$_2$, OCH$_2$CON(CH$_3$)$_2$, CH$_2$CONHCH$_2$(CH$_3$), C(CH$_3$)$_2$OH, COOH, nitro or COOCH(CH$_3$)$_2$, CH$_2$C≡N, C(CH$_3$)$_2$C≡N, cycloC$_{3-6}$ alkylC≡N, thienyl, furanyl, morpholinyl, thiazolyl, indolyl, oxazolyl, pyridinyl, imidazolyl, isoxazolyl, pyrimidinyl and phenyl; $R^7$ is optionally substituted at a substitutable position with one or more radicals of $R^{7a}$.

$L^1$ is independently selected from direct bond, —CO—, —CONH—, —CONR$^{11}$—, —C(=NR$^{11}$)—, —C(=NOR$^{11}$)—, —C(=N—N(R$^{11}$)$_2$)—; C$_{2-6}$ alkylidene chain wherein the alkylidene chain is optionally interrupted by —C(R$^{11}$)$_2$—, —C(R$^{11}$)$_2$C(R$^{11}$)$_2$—, —C(R$^{11}$)=C(R$^{11}$)—, —C≡C—, —O—, —S—, —N(R$^{10}$)CO—, —N(R$^{10}$)CO$_2$, —NR$^{11}$—, —OR$^{11}$—, —CON(R$^{10}$)—, —CO—, —CO$_2$—, —OC(=O)—, —OC(=O)N(R$^{10}$)—, —SO$_2$—, —N(R$^{10}$)SO$_2$—, or —SO$_2$N(R$^{11}$)—; —(CH$_2$)$_m$—V$^0$—(CH$_2$)$_n$— or —V$^0$—(CH$_2$)$_n$—V$^0$—;

m is 0-6;

n is 0-6;

V$^0$ is independently —C(R$^{11}$)$_2$—, —C(R$^{11}$)$_2$C(R$^{11}$)$_2$—, —C(R$^{11}$)=C(R$^{11}$)—, —C(R$^{11}$)$_2$O—, —C(R$^{11}$)$_2$NR$^{11}$—, —C≡C—, —O—, —S—, —NR$^{11}$—, —CR$^{11}$NR$^{11}$—, —N(R$^{10}$)CO—, —N(R$^{10}$)CO$_2$—, —CON(R$^{10}$)—, —OCO—, —COR$^{11}$—, —COOR$^{11}$—, —CO—, —CO$_2$, —OC(=O), —OC(=O)N(R$^{10}$)—, —SO$_2$—, —N(R$^{10}$)SO$_2$—, —NR$^{10}$COR$^{10}$—, —NR$^{10}$CSNR$^{10}$—, CycloC$_{3-6}$haloalkyl or —SO$_2$N(R$^{10}$)—.

More specifically, $L^1$ is selected from the group consisting of —CONH—, —C$_{1-6}$ alkyl-, —C$_{1-6}$ alkoxy-, —CO—, —SO$_2$—, —CH$_2$—, —CH$_2$O—, —CH$_2$CH$_2$—, —C=O—, —CONH—, —CONHC(CH$_3$)$_2$—, —CONH(CH$_2$)$_3$OCH$_2$—, —OCH$_2$CH$_2$—, —OCH$_2$CH$_2$N(CH$_3$)$_2$—, and —CONHCH$_2$CH$_2$N(CH$_3$)$_2$—.

$L^3$ is independently selected from direct bond, —CO—, —CONH—, —CONR$^{11}$—, —C(=NR$^{11}$)—, —C(=NOR$^{11}$)—, —C(=N—N(R$^{11}$)$_2$)—; C$_{2-6}$ alkylidene chain wherein the alkylidene chain is optionally interrupted by —C(R$^{11}$)$_2$—, —C(R$^{11}$)$_2$C(R$^{11}$)$_2$—, —C(R$^{11}$)=C(R$^{11}$)—, —C≡C—, —O—, —S—, —N(R$^{10}$)CO—, —N(R$^{10}$)CO$_2$, —NR$^{11}$—, —OR$^{11}$—, —CON(R$^{10}$)—, —CO—, —CO$_2$—, —OC(=O)—, —OC(=O)N(R$^{10}$)—, —SO$_2$—, —N(R$^{10}$)SO$_2$—, or —SO$_2$N(R$^{11}$)—; —(CH$_2$)$_m$—V$^0$—(CH$_2$)$_n$— or —V$^0$—(CH$_2$)$_n$—V$^0$—;

m is 0-6;

n is 0-6;

V$^0$ is independently —C(R$^{11}$)$_2$—, —C(R$^{11}$)$_2$C(R$^{11}$)$_2$—, —C(R$^{11}$)=C(R$^{11}$)—, —C(R$^{11}$)$_2$O—, —C(R$^{11}$)$_2$NR$^{11}$—, —C≡C—, —O—, —S—, —NR$^{11}$—, —CR$^{11}$NR$^{11}$—, —N(R$^{10}$)CO—, —N(R$^{10}$)CO$_2$—, —CON(R$^{10}$)—, —OCO—, —COR$^{11}$—, —COOR$^{11}$—, —CO—, —CO$_2$, —OC(=O), —OC(=O)N(R$^{10}$)—, —SO$_2$—, —N(R$^{10}$)SO$_2$—, —NR$^{11}$COR$^{10}$—, —NR$^{10}$CSNR$^{10}$—, CycloC$_{3-6}$haloalkyl or —SO$_2$N(R$^{10}$)—.

More specifically, $L_3$ is —CO—, —C$_{1-6}$ alkylidene-, —CONH—, —CONR$^{11}$—, —CONR$^{11}$NR$^{11}$—, —CH$_2$OCH$_2$—, —CH$_2$OCH$_2$CH$_2$—, —OCH$_2$—, —CH$_2$N(CH$_3$)$_2$—, —CH$_2$NHCH$_2$—, —CONR$^{11}$O—, —CH$_2$OCOCH$_2$—, —CH$_3$N(CH$_3$)(CH$_2$)—, —CH$_2$N(cyclopropane)CH$_2$—, —CH$_2$NC(CH$_3$)$_2$CH$_2$—, —CH$_2$N(cyclohexane)CH$_2$—, —CH$_2$NCH(CH$_3$)$_2$CH$_2$—, —CH$_2$N(CF$_3$)(CH$_2$)$_2$—, —CH$_2$N(CH$_3$)(CH$_2$)CH$_2$OCOCH$_2$CH$_2$—, —CONHCH$_2$CH$_2$N(CH$_3$)$_2$—, or —CH$_2$N(CH$_2$C≡N)CH$_2$—.

$R^{7a}$ is selected from the group consisting of halogen, trifluoromethyl, C$_{1-6}$alkyl, C$_{1-6}$alkoxy, CH=CHCOOH, CH$_2$COOH, OCH$_2$COOH, OCONHCH(CH$_3$)$_2$, NHCOCH$_3$, OH, OCH$_3$, COOH, COOCH$_3$, OCH$_2$C(CH$_3$)$_3$, OCH$_2$CH(CH$_3$)$_2$, OCH(CH$_3$)$_2$OCOCH(CH$_3$)$_2$, OCONHCH$_3$, OCH$_2$CH$_3$, or OCH(CH$_3$)$_2$.

$L^2$ is independently selected from direct bond, —CO—, —CONH—, —CONR$^{11}$—, —C(=NR$^{11}$)—, —C(=NOR$^{11}$)—, —C(=N—N(R$^{11}$)$_2$)—; C$_{2-6}$ alkylidene chain wherein the alkylidene chain is optionally interrupted by —C(R$^{11}$)$_2$—, —C(R$^{11}$)$_2$C(R$^{11}$)$_2$—, —C(R$^{11}$)=C(R$^{11}$)—, —C≡C—, —O—, —S—, —N(R$^{10}$)CO—, —N(R$^{10}$)CO$_2$—, —NR$^{11}$—, —OR$^{11}$—, —CON(R$^{10}$)—, —CO—, —CO$_2$—, —OC(=O)—, OC(=O)N(R$^{10}$)—, —SO$_2$—, —N(R$^{10}$)SO$_2$—, or —SO$_2$N(R$^{10}$)—; —(CH$_2$)$_m$—V$^0$—(CH$_2$)$_n$— or —V$^0$—(CH$_2$)$_n$—V$^0$—;

m is 0-6;
n is 0-6;
V$^0$ is independently —C(R$^{11}$)$_2$—, —C(R$^{11}$)$_2$C(R$^{11}$)$_2$—, —C(R$^{11}$)=C(R$^{11}$)—, —C(R$^{11}$)$_2$O—, —C(R$^{11}$)$_2$NR$^{11}$—, —C≡C—, —O—, —S—, —NR$^{11}$—, —CR$^{11}$NR$^{11}$—, —N(R$^{10}$)CO—, —N(R$^{10}$)CO$_2$—, —CON(R$^{10}$)—, —OCO—, —COR$^{11}$—, —COOR$^{11}$—, —CO—, —CO$_2$, —OC(=O), —OC(=O)N(R$^{10}$)—, —SO$_2$—, —N(R$^{10}$)SO$_2$—, —NR$^{11}$COR$^{10}$—, —NR$^{10}$CSNR$^{10}$—, CycloC$_{3-6}$haloalkyl or —SO$_2$N(R$^{10}$)—.

More specifically, L$_2$ is selected from the group consisting of —CONH—, —CONHCH$_2$—, —CH$_2$O—, —OCH$_2$COOCH$_2$—, —O—, C≡C—, —OCH$_2$CH$_2$— and —CONHOCH$_2$CH(OH)CH$_2$O—.

R$^{5a}$ is independently selected from the group consisting of OCH$_2$C(CH$_3$)$_3$, Cl, F, Br, OCH$_2$CH(CH$_3$)$_2$, OCH$_2$CH$_3$, CF$_3$, COOH, OCH$_3$, OH, NO$_2$, OCOCH(CH$_3$)$_2$, OCOC(CH$_3$)$_3$, NHCOCH$_3$, OCON(CH$_3$)$_2$, OCONHCH$_3$, OCON(CH$_2$)$_2$CH$_3$, OCONHCH(CH$_3$)$_2$, O(CH$_2$)$_2$CONH$_2$, O(CH)(CH$_3$)$_2$, C$_{1-6}$ alkyl, OCH$_2$COOH, OCH$_2$COOC(CH$_3$)$_3$, O(CH$_2$)$_2$N(CH$_2$CH$_3$)$_2$, OC(CH$_3$)$_2$ COOC(CH$_3$)$_3$, and OCH$_2$CH$_2$OH. Preferred R$^{5a}$ is halogen or trifluoromethyl.

R$^4$ is selected from the group consisting of OH, CN, C(CH$_3$)$_2$OH, SO$_2$CH$_3$, SO$_2$C(CH$_3$)$_3$, SO$_2$NH$_2$, SO$_2$CH$_2$CH$_3$, SCH$_2$CH$_3$, SCH$_3$, OCH$_3$, C$_{1-6}$ alkyl, CH$_2$COOH, C(CH$_3$)$_2$COOH, NHSO$_2$CH$_3$, F, Cl, Br, C(CH$_3$)$_2$COOH, CH$_2$COOCH$_3$, C(CH$_3$)$_2$COOCH$_3$, CH$_2$CH$_2$COOH, OCH$_2$COOCH$_3$, COCH$_3$, COOC(CH$_3$)$_3$, cyclobutane-COOH, OC(CH$_3$)$_2$COOH, COOCH$_2$CH$_3$, OCF$_3$, and CF$_3$.

In another preferred embodiment of the first aspect of the invention, the compound is selected from those with one of the following structures:

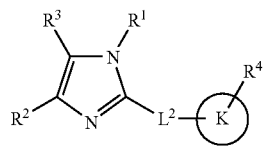
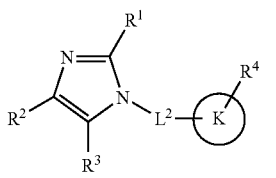
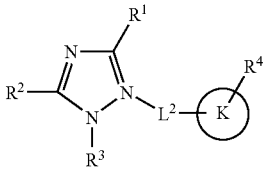

Preferably in this embodiment, R$^1$ is R$^5$ selected from the group consisting of thienyl, furanyl, morpholinyl, thiazolyl, indolyl, oxazolyl, pyridinyl, isoxazolyl, pyrimidinyl, imidazolyl, and phenyl; R$^5$ is optionally substituted at a substitutable position with one or more radicals of R$^{5a}$. Preferred R$^5$ is phenyl or pyridinyl optionally substituted with R$^{5a}$.

R$^2$ is R$^7$ selected from the group consisting of trifluoromethyl, COOCH$_3$, CH$_2$OH, CONHCH$_2$CH$_3$, CONHOCH$_2$CH(OH)CH$_2$OH, CONHCH$_2$CH$_2$N(CH$_3$)$_2$, CONHCH$_2$CH$_2$OCH$_3$, CONHCH$_2$CH$_2$OCH$_3$, CH$_2$COOCH$_3$, CON(CH$_3$)$_2$, COOCH(CH$_3$)$_2$, CONHCH$_2$CH$_2$CH$_2$OCH$_3$, OCOCH(CH$_3$)$_2$, OCH$_2$CON(CH$_3$)$_2$, CH$_2$CONHCH$_2$(CH$_3$), C(CH$_3$)$_2$OH, COOH, nitro or COOCH(CH$_3$)$_2$, CH$_2$C≡N, C(CH$_3$)$_2$C≡N, cycloC$_{3-6}$ alkylC≡N, thienyl, furanyl, morpholinyl, thiazolyl, indolyl, oxazolyl, pyridinyl, imidazolyl, isoxazolyl, pyrimidinyl and phenyl; R$^7$ is optionally substituted at a substitutable position with one or more radicals of R$^{7a}$.

L$^1$ is independently selected from direct bond, —CO—, —CONH—, —CONR$^{11}$—, —C(=NR$^{11}$)—C(=NOR$^{11}$)—, —C(=N—N(R$^{11}$)$_2$)—; C$_{2-6}$ alkylidene chain wherein the alkylidene chain is optionally interrupted by —C(R$^{11}$)$_2$—, —C(R$^{11}$)$_2$C(R$^{11}$)$_2$—, —C(R$^{11}$)=C(R$^{11}$)—, —C≡C—, —O—, —S—, —N(R$^{10}$)CO—, —N(R$^{10}$)CO$_2$—, —NR$^{11}$—, —OR$^{11}$—, —CON(R$^{10}$)—, —CO—, —CO$_2$—, —OC(=O)—, —OC(=O)N(R$^{10}$)—, —SO$_2$—, —N(R$^{10}$)SO$_2$—, or —SO$_2$N(R$^{11}$)—; —(CH$_2$)$_m$—V$^0$—(CH$_2$)$_n$— or —V$^0$—(CH$_2$)$_n$—V$^0$—;

m is 0-6;
n is 0-6;
V$^0$ is independently —C(R$^{11}$)$_2$—, —C(R$^{11}$)$_2$C(R$^{11}$)$_2$—, —C(R$^{11}$)=C(R$^{11}$)—, —C(R$^{11}$)$_2$O—, —C(R$^{11}$)$_2$NR$^{11}$—, —C≡C—, —O—, —S—, —NR$^{11}$—, —CR$^{11}$NR$^{11}$—, —N(R$^{10}$)CO—, —N(R$^{10}$)CO$_2$—, —CON(R$^{10}$)—, —OCO—, —COR$^{11}$—, —COOR$^{11}$—, —CO—, —CO$_2$, —OC(=O), —OC(=O)N(R$^{10}$)—, —SO$_2$—, —N(R$^{10}$)SO$_2$—, —NR$^{11}$COR$^{10}$—, —NR$^{11}$CSNR$^{10}$—, CycloC$_{3-6}$haloalkyl or —SO$_2$N(R$^{10}$)—.

More specifically, L$^1$ is selected from the group consisting of —CONH—, —C$_{1-6}$ alkyl-, —C$_{1-6}$ alkoxy-, —CO—, —SO$_2$—, —CH$_2$—, —CH$_2$O—, —CH$_2$CH$_2$—, —C=O—, —CONH—, —CONHC(CH$_3$)$_2$—, —CONH(CH$_2$)$_3$OCH$_2$—, —OCH$_2$CH$_2$—, —OCH$_2$CH$_2$N(CH$_3$)$_2$—, and —CONHCH$_2$CH$_2$N(CH$_3$)$_2$—.

L$^3$ is independently selected from direct bond, —CO—, —CONH—, —CONR$^{11}$—, —C(=NR$^{11}$)—, —C(=NOR$^{11}$)—, —C(=N—N(R$^{11}$)$_2$)—; C$_{2-6}$ alkylidene chain wherein the alkylidene chain is optionally interrupted by —C(R$^{11}$)$_2$—, —C(R$^{11}$)$_2$C(R$^{11}$)$_2$—, —C(R$^{11}$)=C(R$^{11}$)—, —C≡C—, —O—, —S—, —N(R$^{10}$)CO—, —N(R$^{10}$)CO$_2$—, —NR$^{11}$—, —OR$^{11}$—, —CON(R$^{10}$)—, —CO—, —CO$_2$—, —OC(=O)—, —OC(=O)N(R$^{10}$)—, —SO$_2$—, —N(R$^{10}$)SO$_2$—, or —SO$_2$N(R$^{11}$)—; —(CH$_2$)$_m$—V$^0$—(CH$_2$)$_n$— or —V$^0$—(CH$_2$)$_m$—V$^0$;

m is 0-6;
n is 0-6;
V$^0$ is independently —C(R$^{11}$)$_2$—, —C(R$^{11}$)$_2$C(R$^{11}$)$_2$—, —C(R$^{11}$)=C(R$^{11}$)—, —C(R$^{11}$)$_2$O—, —C(R$^{11}$)$_2$NR$^{11}$—, —C≡C—, —O—, —S—, —NR$^{11}$—, —CR$^{11}$NR$^{11}$—, —N(R$^{10}$)CO—, —N(R$^{10}$)CO$_2$—, CON(R$^{10}$)—, —OCO—, —COR$^{11}$—, —COOR$^{11}$—, —CO—, —CO$_2$, —OC(=O), —OC(=O)N(R$^{10}$)—, —SO$_2$—, —N(R$^{10}$)SO$_2$—, —NR$^{11}$COR$^{10}$—, —NR$^{10}$CSNR$^{10}$—, CycloC$_{3-6}$haloalkyl or —SO$_2$N(R$^{10}$)—.

More specifically, $L^3$ is —CO—, —$C_{1-6}$ alkylidene-, —CONH—, —CONR$^{11}$—, —CONR$^{11}$NR$^{11}$—, —CH$_2$OCH$_2$—, —CH$_2$OCH$_2$CH$_2$—, —OCH$_2$—, —CH$_2$N(CH$_3$)$_2$—, —CH$_2$NHCH$_2$—, —CONR$^{11}$O—, —CH$_2$OCOCH$_2$—, —CH$_3$N(CH$_3$)(CH$_2$)—, —CH$_2$N(cyclopropane)CH$_2$—, —CH$_2$NC(CH$_3$)$_2$CH$_2$—, —CH$_2$N(cyclohexane)CH$_2$—, —CH$_2$NCH(CH$_3$)$_2$CH$_2$—, —CH$_2$N(CF$_3$)(CH$_2$)$_2$—, —CH$_2$N(CH$_3$)(CH$_2$)CH$_2$OCOCH$_2$CH$_2$—, —CONHCH$_2$CH$_2$N(CH$_3$)$_2$—, or —CH$_2$N(CH$_2$C≡N)CH$_2$—.

$R^{7a}$ is selected from the group consisting of halogen, trifluoromethyl, $C_{1-6}$alkyl, $C_{1-6}$alkoxy, CH=CHCOOH, CH$_2$COOH, OCH$_2$COOH, OCONHCH(CH$_3$)$_2$, NHCOCH$_3$, OH, OCH$_3$, COOH, COOCH$_3$, OCH$_2$C(CH$_3$)$_3$, OCH$_2$CH(CH$_3$)$_2$, OCH(CH$_3$)$_2$OCOCH(CH$_3$)$_2$, OCONHCH$_3$, OCH$_2$CH$_3$, or OCH(CH$_3$)$_2$.

$L^2$ is independently selected from direct bond, —CO—, —CONH—, —CONR$^{11}$—, —C(=NR$^{11}$)—, —C(=NOR$^{11}$)—, —C(=N—N(R$^{11}$)$_2$)—; $C_{2-6}$ alkylidene chain wherein the alkylidene chain is optionally interrupted by —C(R$^{11}$)$_2$—, —C(R$^{11}$)$_2$C(R$^{11}$)$_2$—, —C(R$^{11}$)=C(R$^{11}$)—, —C≡C—, —O—, —S—, —N(R$^{10}$)CO—, —N(R$^{10}$)CO$_2$—, —NR$^{11}$—, —OR$^{11}$—, —CON(R$^{10}$)—, —CO—, —CO$_2$—, —OC(=O)—, —OC(=O)N(R$^{10}$)—, —SO$_2$—, —N(R$^{10}$)SO$_2$—, or —SO$_2$N(R$^{11}$)—; —(CH$_2$)$_m$—V$^0$—(CH$_2$)$_n$— or —V$^0$—(CH$_2$)$_n$—V$^0$—;

m is 0-6;
n is 0-6;

$V^0$ is independently —C(R$^{11}$)$_2$—, —C(R$^{11}$)$_2$C(R$^{11}$)$_2$—, —C(R$^{11}$)=C(R$^{11}$)—, —C(R$^{11}$)$_2$O—, —C(R$^{11}$)$_2$NR$^{11}$—, —C≡C—, —O—, —S—, —NR$^{11}$—, —CR$^{11}$NR$^{11}$—, —N(R$^{10}$)CO—, —N(R$^{10}$)CO$_2$—, —CON(R$^{10}$)—, —OCO—, —COR$^{11}$—, —COOR$^{11}$—, —CO—, —CO$_2$, —OC(=O), —OC(=O)N(R$^{10}$)—, —SO$_2$—, —N(R$^{10}$)SO$_2$—, —NR$^{11}$COR$^{10}$—, —NR$^{11}$CSNR$^{10}$—, CycloC$_{3-6}$haloalkyl or —SO$_2$N(R$^{11}$)—. More specifically, $L^2$ is selected from the group consisting of —CONH—, —CONHCH$_2$—, —CH$_2$O—, —OCH$_2$COOCH$_2$—, —O—, C≡C—, —OCH$_2$CH$_2$, and —CONHOCH$_2$CH(OH)CH$_2$O—.

$R^{5a}$ is independently selected from the group consisting of OCH$_2$C(CH$_3$)$_3$, Cl, F, Br, OCH$_2$CH(CH$_3$)$_2$, OCH$_2$CH$_3$, CF$_3$, COOH, OCH$_3$, OH, NO$_2$, OCOCH(CH$_3$)$_2$, OCOC(CH$_3$)$_3$, NHCOCH$_3$, OCON(CH$_3$)$_2$, OCONHCH$_3$, OCON(CH$_2$)$_2$CH$_3$, OCONHCH(CH$_3$)$_2$, O(CH$_2$)$_2$, CONH$_2$, O(CH)(CH$_3$)$_2$, $C_{1-6}$ alkyl, OCH$_2$COOH, OCH$_2$COOC(CH$_3$)$_3$, O(CH$_2$)$_2$N(CH$_2$CH$_3$)$_2$, OC(CH$_3$)$_2$ COOC(CH$_3$)$_3$, and OCH$_2$CH$_2$OH. $R^4$ is selected from the group consisting of SO$_2$CH$_3$, SO$_2$C(CH$_3$)$_3$, SO$_2$NH$_2$, SO$_2$CH$_2$CH$_3$, SCH$_2$CH$_3$, SCH$_3$, OCH$_3$, $C_{1-6}$ alkyl, CH$_2$COOH, C(CH$_3$)$_2$COOH, NHSO$_2$CH$_3$, F, Cl, Br, C(CH$_3$)$_2$COOH, CH$_2$COOCH$_3$, C(CH$_3$)$_2$COOCH$_3$, CH$_2$CH$_2$COOH, OCH$_2$COOCH$_3$, COCH$_3$, COOC(CH$_3$)$_3$, cyclobutane-COOH, OC(CH$_3$)$_2$ COOH, COOCH$_2$CH$_3$, OCF$_3$, and CF$_3$.

In a preferred embodiment of the first aspect of the invention, -G-$R^4$ is

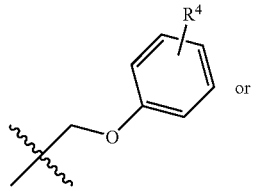

or

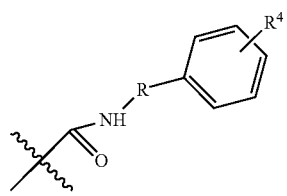

In this embodiment,

R is selected from the group consisting of $C_{0-6}$ alkylidene chain wherein the alkylidene chain is optionally interrupted by —C(R$^{11}$)$_2$—, —C(R$^{11}$)$_2$C(R$^{11}$)$_2$—, —C(R$^{11}$)=C(R$^{11}$)—, —C(R$^{11}$)$_2$O—, —C(R$^{11}$)$_2$NR$^{11}$—, —C≡C—, —O—, —S—, —N(R$^{10}$)CO—, —N(R$^{10}$)CO$_2$—, —CON(R$^{10}$)—, —CO—, —CO$_2$—, —OC(=O)—, —OC(=O)N(R$^{10}$)—, —SO$_2$—, —N(R$^{10}$)SO$_2$—, or —SO$_2$N(R$^{10}$)—;

$R^4$ is independently selected from hydrogen, $C_{1-6}$ alkyl, CR$^{11}$=CR$^{11}$COOR$^{11}$, $C_{1-6}$ alkoxy, $C_{0-6}$ alkylOR$^{11}$, $C_{0-6}$ alkylCOR$^{11}$, $C_{0-6}$ alkylSO$_2$R$^{11}$, $C_{0-6}$ alkylOCOOR$^{11}$, $C_{0-6}$ alkylNR$^{11}$COR$^{11}$, $C_{0-6}$ alkylSO$_2$NR$^{11}$COR$^{11}$, $C_{0-6}$ alkyl SO$_2$N(R$^{11}$)$_2$, $C_{0-6}$ alkylSR$^{11}$, ($C_{0-6}$ alkyl)C=O(OR$^{11}$), OVOR$^{11}$, halogen, $C_{1-6}$haloalkyl, $C_{1-6}$haloalkylOR$^{11}$, OC$_{1-6}$ haloalkyl, aryloxy, aralkyloxy, aryloxyalkyl, $C_{1-6}$ alkoxyaryl, arylC$_{0-6}$ alkylcarboxy, NR$^{11}$SO$_2$R$^{11}$, OC$_{1-6}$ alkyl, OC$_{0-6}$ alkylCOOR$^{11}$, $C_{0-6}$ alkylC=N, $C_{1-6}$alkoxyheteroaryl, $C_{1-6}$alkoxyheterocyclyl, cycloalkylCOOR$^{11}$, a 5-12 membered aromatic ring or non-aromatic ring, or 5-12 membered heteroaryl or heterocyclyl having one or more heteroatoms N, O or S;

$R^4$ is optionally substituted at a substitutable position with one or more radicals of R$^{4a}$; each R$^{4a}$ is independently selected from hydrogen, $C_{1-6}$ alkyl, ($C_{1-6}$ alkyl)C=O(OR$^{11}$); $C_{1-6}$ alkoxy, $C_{0-6}$ alkylOR$^{11}$, $C_{0-6}$ alkylCOR$^{11}$, $C_{0-6}$ alkylSO$_2$R$^{11}$, $C_{0-6}$ alkylSO$_2$N(R$^{11}$)$_2$; $C_{0-6}$ alkylSR$^{11}$, ($C_{0-6}$ alkyl)OC=O(OR$^{11}$), halogen, $C_{1-6}$ haloalkyl, aryloxy, aralkyloxy, aryloxyalkyl, $C_{1-6}$ alkoxyaryl, arylC$_{0-6}$ alkylcarboxy, NR$^{11}$SO$_2$R$^{11}$, OC$_{1-6}$ alkyl, $C_{0-6}$ alkylC=N, or OC$_{0-6}$ alkylCOOR$^{11}$.

Preferred $R^4$ is selected from the group consisting of SO$_2$CH$_3$, SO$_2$C(CH$_3$)$_3$, SO$_2$CH$_2$CH$_3$, SCH$_2$CH$_3$, SCH$_3$, OCH$_3$, $C_{1-6}$ alkyl, CH$_2$COOH, C(CH$_3$)$_2$COOH, NHSO$_2$CH$_3$, F, Cl, Br, cyclobutane-COOH, OC(CH$_3$)$_2$COOH, CF$_3$, C(CH$_3$)$_2$COOH, CH$_2$COOCH$_3$, CH$_2$CH$_2$COOH, OCH$_2$COOCH$_3$, and COCH$_3$. More preferably, $R^4$ is SO$_2$CH$_3$, SO$_2$CH$_2$CH$_3$, SCH$_2$CH$_3$, or SCH$_3$.

In another embodiment, the invention comprises the compound according to one of formulae Ia-d or IIa-d which is listed in Table I.

TABLE I

| # | IUPAC Name | Structure |
|---|---|---|
| 1 | 5-[(biphenyl-3-yloxy)methyl]-1-(2-chlorophenyl)-3-(trifluoromethyl)-1H-pyrazole | 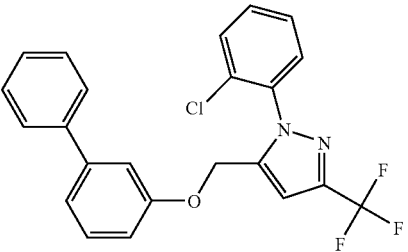 |
| 4 | 1-(2-chlorophenyl)-5-[({4-[(phenylmethyl)oxy]phenyl}oxy)methyl]-3-(trifluoromethyl)-1H-pyrazole | 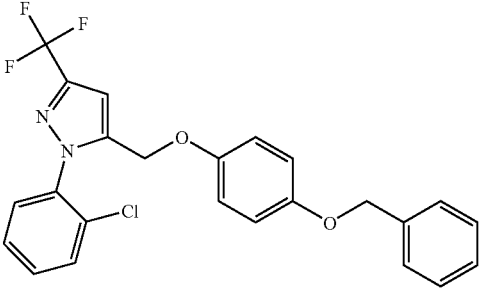 |
| 5 | 1-(2-chlorophenyl)-5-[({3-[(phenylmethyl)oxy]phenyl}oxy)methyl]-3-(trifluoromethyl)-1H-pyrazole | 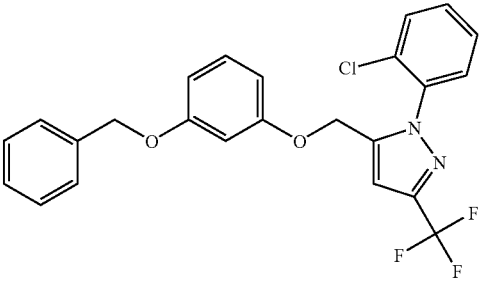 |
| 6 | [4-({[1-(2-chlorophenyl)-3-(trifluoromethyl)-1H-pyrazol-5-yl]methyl}oxy)phenyl](phenyl)methanone | 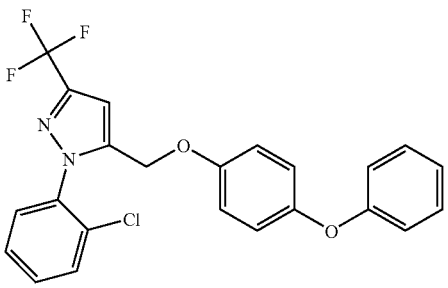 |
| 7 | phenylmethyl 4-({[1-(2-chlorophenyl)-3-(trifluoromethyl)-1H-pyrazol-5-yl]methyl}oxy)benzoate | 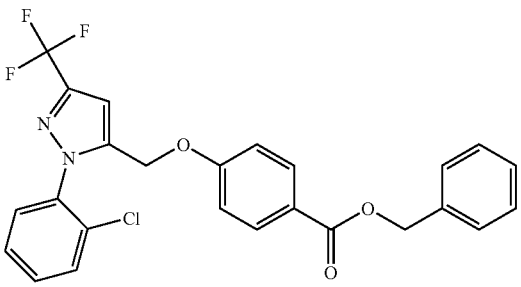 |

TABLE I-continued

| # | IUPAC Name | Structure |
|---|---|---|
| 8 | 1-(2-chlorophenyl)-5-({[4-(1H-pyrrol-1-yl)phenyl]oxy}methyl)-3-(trifluoromethyl)-1H-pyrazole | 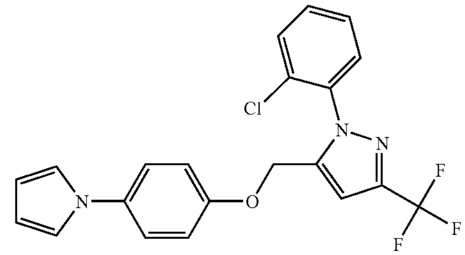 |
| 9 | 5-({[1-(2-chlorophenyl)-3-(trifluoromethyl)-1H-pyrazol-5-yl]methyl}oxy)-1H-indole-2-carboxylic acid | 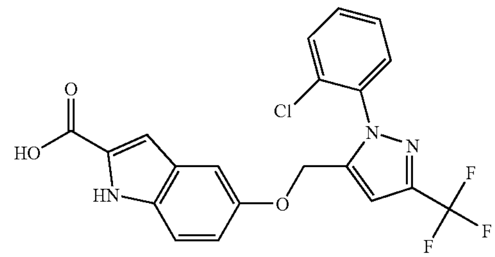 |
| 10 | 7-({[1-(2-chlorophenyl)-3-(trifluoromethyl)-1H-pyrazol-5-yl]methyl}oxy)-6-(methyloxy)-3,4-dihydroisoquinoline | 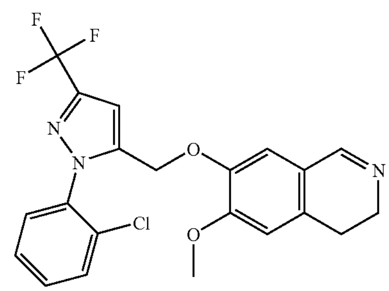 |
| 11 | [2-({[1-(2-chlorophenyl)-3-(trifluoromethyl)-1H-pyrazol-5-yl]methyl}oxy)phenyl](phenyl)methanone | 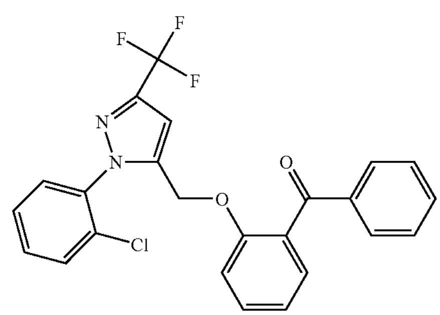 |
| 12 | 4'-({[1-(2-chlorophenyl)-3-(trifluoromethyl)-1H-pyrazol-yl]methyl}oxy)biphenyl-4-carboxylic acid | 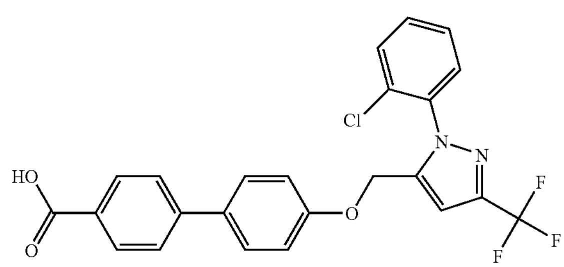 |

TABLE I-continued

| # | IUPAC Name | Structure |
|---|---|---|
| 13 | (2R)-2-{[4-({[1-(2-chlorophenyl)-3-(trifluoromethyl)-1H-pyrazol-5-yl]methyl}oxy)phenyl]oxy}propanoic acid | 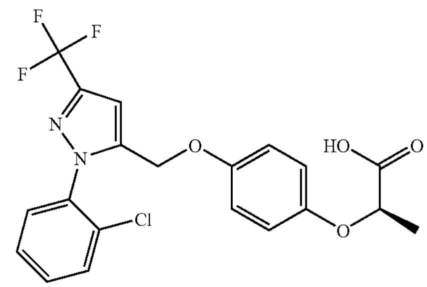 |
| 14 | 4-{[4-({[1-(2-chlorophenyl)-3-(trifluoromethyl)-1H-pyrazol-5-yl]methyl}oxy)-3-methylphenyl]sulfonyl}-2-methylphenol | 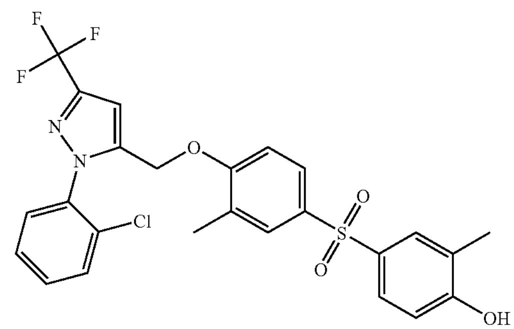 |
| 15 | [3-({[1-(2-chlorophenyl)-3-(trifluoromethyl)-1H-pyrazol-5-yl]methyl}oxy)phenyl](phenyl)methanone | 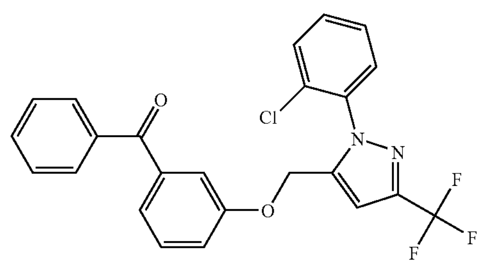 |
| 16 | 7-({[1-(2-chlorophenyl)-3-(trifluoromethyl)-1H-pyrazol-5-yl]methyl}oxy)quinoline | 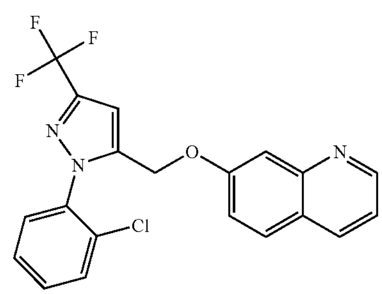 |
| 17 | 5-({[3,4-bis(methyloxy)phenyl]oxy}methyl)-1-(2-chlorophenyl)-3-(trifluoromethyl)-1H-pyrazole | 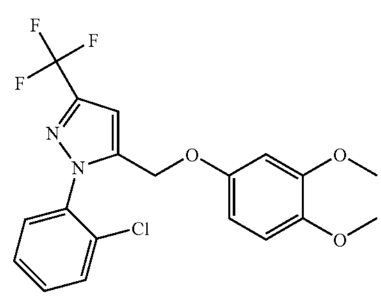 |

TABLE I-continued

| # | IUPAC Name | Structure |
|---|---|---|
| 18 | 4-{[4-({[1-(2-chlorophenyl)-3-(trifluoromethyl)-1H-pyrazol-5-yl]methyl}oxy)phenyl]oxy}phenol | 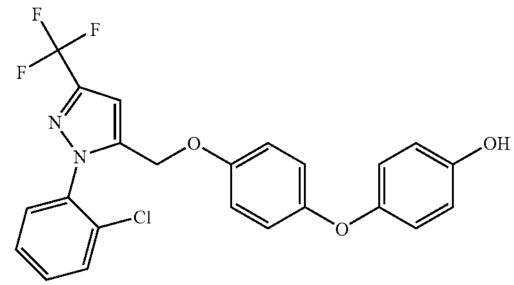 |
| 19 | 7-({[1-(2-chlorophenyl)-3-(trifluoromethyl)-1H-pyrazol-5-yl]methyl}oxy)isoquinoline | 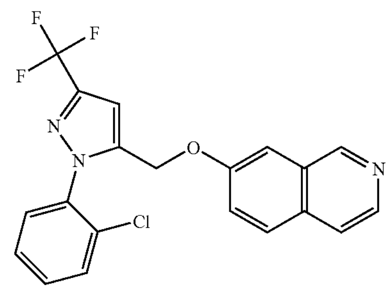 |
| 20 | 5-({[1-(2-chlorophenyl)-3-(trifluoromethyl)-1H-pyrazol-5-yl]methyl}oxy)quinoline | 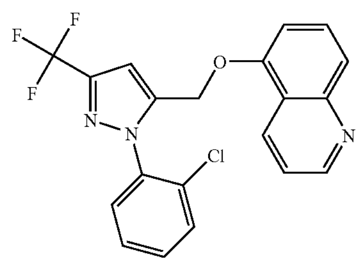 |
| 21 | 7-({[1-(2-chlorophenyl)-3-(trifluoromethyl)-1H-pyrazol-5-yl]methyl}oxy)-2H-chromen-2-one | 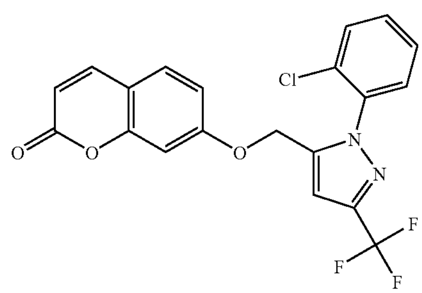 |
| 22 | 1-[4-({[1-(2-chlorophenyl)-3-(trifluoromethyl)-1H-pyrazol-5-yl]methyl}oxy)phenyl]-1H-1,2,4-triazole | 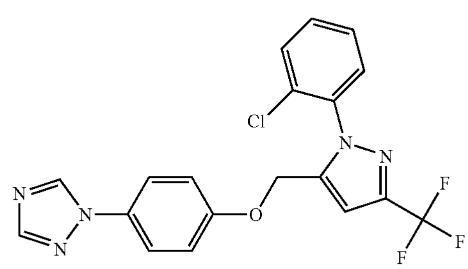 |

TABLE I-continued

| # | IUPAC Name | Structure |
|---|---|---|
| 23 | 4-({[1-(2-chlorophenyl)-3-(trifluoromethyl)-1H-pyrazol-5-yl]methyl}oxy)-6-fluoro-2-methylquinoline | 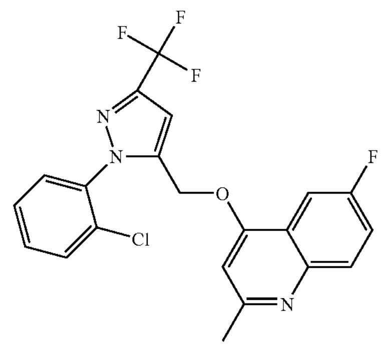 |
| 24 | 4-({[1-(2-chlorophenyl)-3-(trifluoromethyl)-1H-pyrazol-5-yl]methyl}oxy)-8-fluoroquinoline | 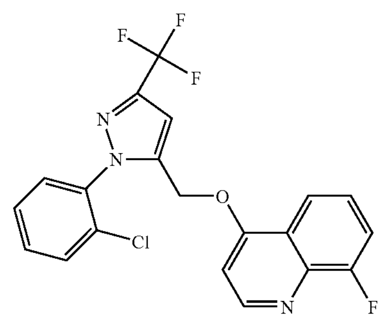 |
| 25 | 5-[2-({[1-(2-chlorophenyl)-3-(trifluoromethyl)-1H-pyrazol-5-yl]methyl}oxy)phenyl]isoxazole | 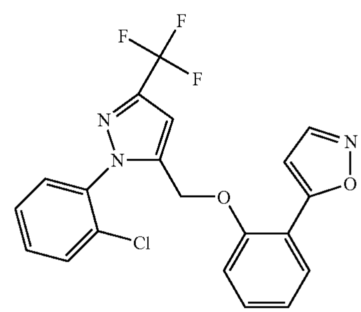 |
| 26 | (2E)-3-[3-({[1-(2-chlorophenyl)-3-(trifluoromethyl)-1H-pyrazol-5-yl]methyl}oxy)phenyl]prop-2-enoic acid | 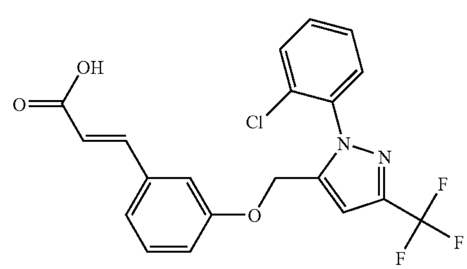 |
| 27 | 1-(2-chlorophenyl)-5-({[4-(1H-imidazol-1-yl)phenyl]oxy}methyl)-3-(trifluoromethyl)-1H-pyrazole | 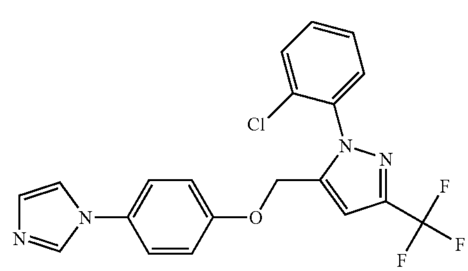 |

TABLE I-continued

| # | IUPAC Name |
|---|---|
| 28 | 1-[3-({[1-(2-chlorophenyl)-3-(trifluoromethyl)-1H-pyrazol-5-yl]methyl}oxy)phenyl]ethanone |
| 29 | 2-{[4-({[1-(2-chlorophenyl)-3-(trifluoromethyl)-1H-pyrazol-5-yl]methyl}oxy)phenyl]amino}-1,3-thiazol-4(5H)-one |
| 30 | 4-({[1-(2-chlorophenyl)-3-(trifluoromethyl)-1H-pyrazol-5-yl]methyl}oxy)-2-methylquinoline |
| 31 | 6-({[1-(2-chlorophenyl)-3-(trifluoromethyl)-1H-pyrazol-5-yl]methyl}oxy)quinoline |
| 32 | 7-({[1-(2-chlorophenyl)-3-(trifluoromethyl)-1H-pyrazol-5-yl]methyl}oxy)-4-[(methyloxy)methyl]-2H-chromen-2-one |

TABLE I-continued

| # | IUPAC Name |
|---|---|
| 33 | 7-({[1-(2-chlorophenyl)-3-(trifluoromethyl)-1H-pyrazol-5-yl]methyl}oxy)-4-methyl-2H-chromen-2-one |
| 34 | 2-({[1-(2-chlorophenyl)-3-(trifluoromethyl)-1H-pyrazol-5-yl]methyl}oxy)-9H-fluoren-9-one |
| 35 | ethyl 4-({[1-(2-chlorophenyl)-3-(trifluoromethyl)-1H-pyrazol-5-yl]methyl}oxy)benzoate |
| 36 | 5-({[1-(2-chlorophenyl)-3-(trifluoromethyl)-1H-pyrazol-5-yl]methyl}oxy)-2-methyl-1,3-benzothiazole |
| 37 | ethyl 5-({[1-(2-chlorophenyl)-3-(trifluoromethyl)-1H-pyrazol-5-yl]methyl}oxy)-2-methyl-1H-indole-3-carboxylate |

US 7,998,995 B2

TABLE I-continued

| # | IUPAC Name | Structure |
|---|---|---|
| 38 | ethyl 5-({[1-(2-chlorophenyl)-3-(trifluoromethyl)-1H-pyrazol-5-yl]methyl}oxy)-1H-indole-2-carboxylate | 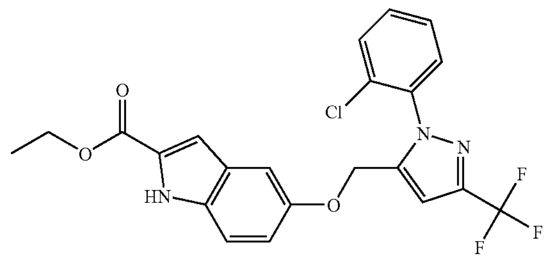 |
| 39 | 8-({[1-(2-chlorophenyl)-3-(trifluoromethyl)-1H-pyrazol-5-yl]methyl}oxy)-2-methylquinoline | 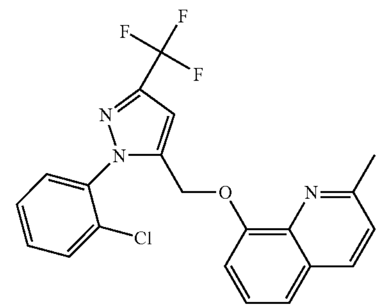 |
| 40 | 4-{[4-({[1-(2-chlorophenyl)-3-(trifluoromethyl)-1H-pyrazol-5-yl]methyl}oxy)phenyl]thio}phenol | 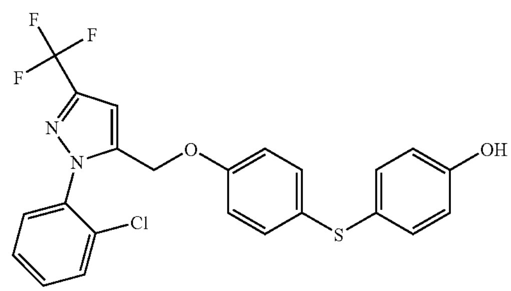 |
| 41 | 2-({[1-(2-chlorophenyl)-3-(trifluoromethyl)-1H-pyrazol-5-yl]methyl}oxy)-1,3-benzothiazole | 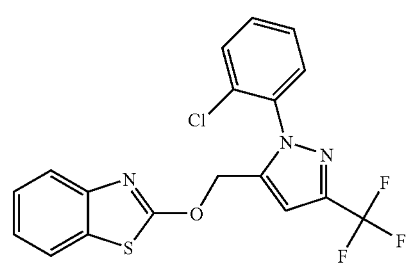 |
| 42 | 5-({[1-(2-chlorophenyl)-3-(trifluoromethyl)-1H-pyrazol-5-yl]methyl}oxy)isoquinoline | 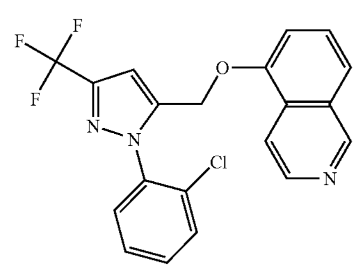 |

TABLE I-continued

| # | IUPAC Name | Structure |
|---|---|---|
| 43 | 1-(2-chlorophenyl)-5-({[4-methylsulfonyl)phenyl]oxy}methyl)-3-(trifluoromethyl)-1H-pyrazole | 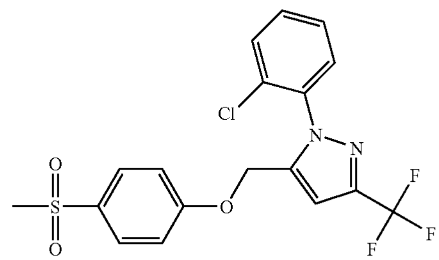 |
| 44 | 1-(2-chlorophenyl)-5-({[4'-(methylsulfonyl)biphenyl-4-yl]oxy}methyl)-3-(trifluoromethyl)-1H-pyrazole | 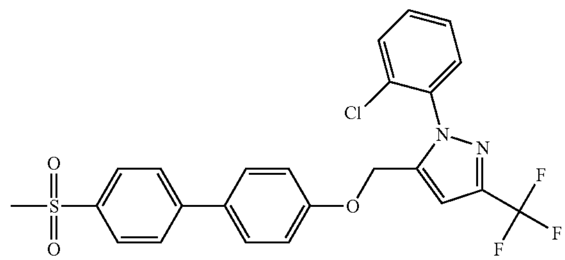 |
| 45 | 1-(2-chlorophenyl)-5-({[3'-(methylsulfonyl)biphenyl-4-yl]oxy}methyl)-3-(trifluoromethyl)-1H-pyrazole | 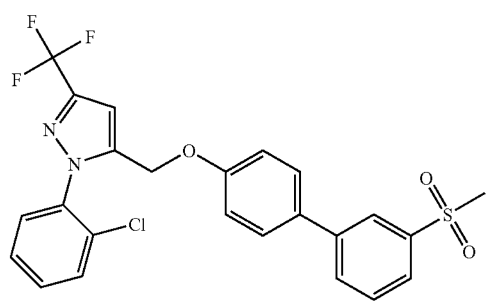 |
| 46 | 1-(2-chlorophenyl)-5-({[5'-fluoro-2'-(methyloxy)biphenyl-4-yl]oxy}methyl)-3-(trifluoromethyl)-1H-pyrazole | 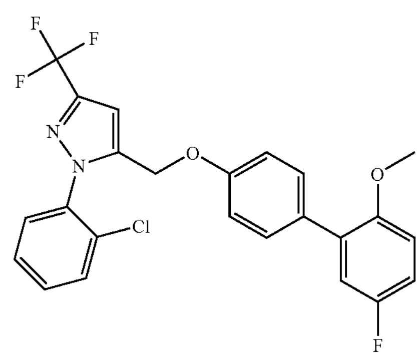 |
| 47 | [4'-({[1-(2-chlorophenyl)-3-(trifluoromethyl)-1H-pyrazol-5-yl]methyl}oxy)biphenyl-3-yl]methanol | 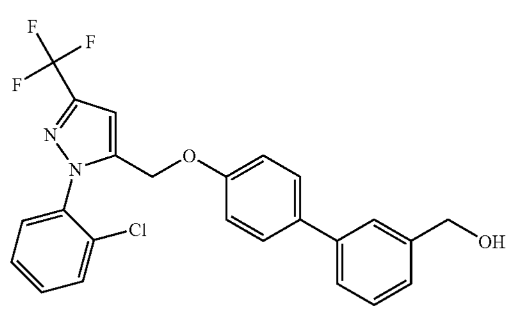 |

TABLE I-continued

| # | IUPAC Name | Structure |
|---|---|---|
| 48 | 4'-({[1-(2-chlorophenyl)-3-(trifluoromethyl)-1H-pyrazol-5-yl]methyl}oxy)-N,N-dimethylbiphenyl-4-amine | 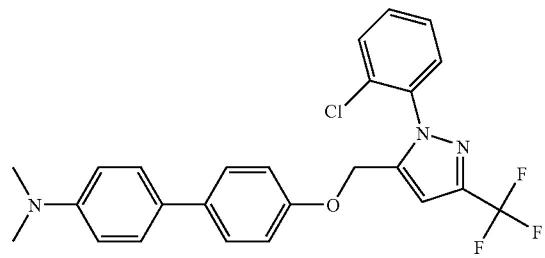 |
| 49 | 1-(2-chlorophenyl)-5-({[3'-(methyloxy)biphenyl-4-yl]oxy}methyl)-3-(trifluoromethyl)-1H-pyrazole | 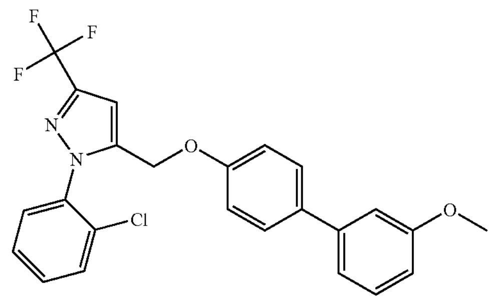 |
| 50 | 1-(2-chlorophenyl)-5-({[2'-(methyloxy)biphenyl-4-yl]oxy}methyl)-3-(trifluoromethyl)-1H-pyrazole | 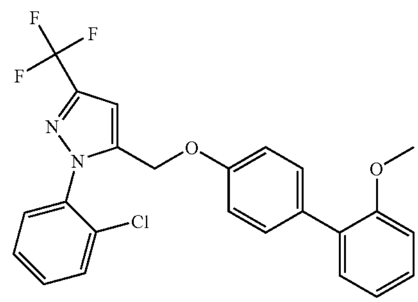 |
| 51 | 5-({[3',4'-bis(methyloxy)biphenyl-4-yl]oxy}methyl)-1-(2-chlorophenyl)-3-(trifluoromethyl)-1H-pyrazole | 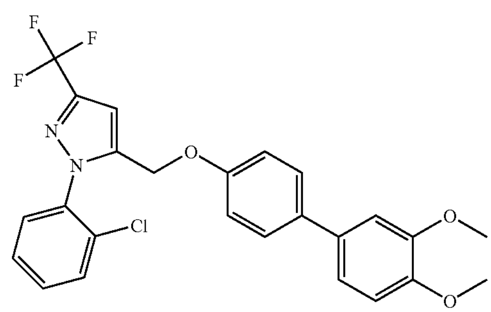 |
| 52 | 4'-({[1-(2-chlorophenyl)-3-(trifluoromethyl)-1H-pyrazol-5-yl]methyl}oxy)-N,N-dimethylbiphenyl-3-sulfonamide | 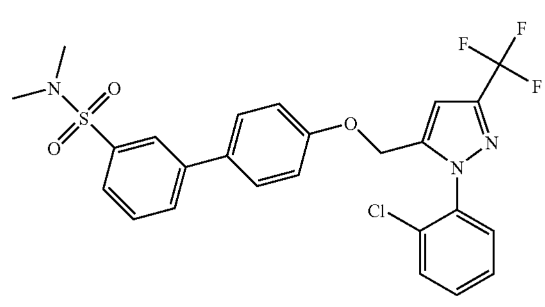 |

TABLE I-continued

| # | IUPAC Name |
|---|---|
| 53 | 5-[4-({[1-(2-chlorophenyl)-3-(trifluoromethyl)-1H-pyrazol-5-yl]methyl}oxy)phenyl]pyrimidine |
| 54 | 1-(2-chlorophenyl)-5-({[2'-fluoro-5'-(trifluoromethyl)biphenyl-4-yl]oxy}methyl)-3-(trifluoromethyl)-1H-pyrazole |
| 55 | [4'-({[1-(2-chlorophenyl)-3-(trifluoromethyl)-1H-pyrazol-5-yl]methyl}oxy)biphenyl-4-yl]methanol |
| 56 | 4'-({[1-(2-chlorophenyl)-3-(trifluoromethyl)-1H-pyrazol-5-yl]methyl}oxy)biphenyl-4-carbonitrile |
| 57 | 5-({[2',5'-bis(methyloxy)biphenyl-4-yl]oxy}methyl)-1-(2-chlorophenyl)-3-(trifluoromethyl)-1H-pyrazole |

TABLE I-continued

| # | IUPAC Name |
|---|---|
| 58 | 5-({[2',4'-bis(methyloxy)biphenyl-4-yl]oxy}methyl)-1-(2-chlorophenyl)-3-(trifluoromethyl)-1H-pyrazole |
| 59 | 5-({[4-(1,3-benzodioxol-5-yl)phenyl]oxy}methyl)-1-(2-chlorophenyl)-3-(trifluoromethyl)-1H-pyrazole |
| 60 | 1-(2-chlorophenyl)-5-({[2'-fluoro-6'-(methyloxy)biphenyl-4-yl]oxy}methyl)-3-(trifluoromethyl)-1H-pyrazole |
| 61 | 1-(2-chlorophenyl)-5-({[4-(2,3-dihydro-1,4-benzodioxin-6-yl)phenyl]oxy}methyl)-3-(trifluoromethyl)-1H-pyrazole |
| 62 | 4'-({[1-(2-chlorophenyl)-3-(trifluoromethyl)-1H-pyrazol-5-yl]methyl}oxy)biphenyl-3-carbonitrile |

TABLE I-continued

| # | IUPAC Name | Structure |
|---|---|---|
| 63 | 2-chloro-5-[4-({[1-(2-chlorophenyl)-3-(trifluoromethyl)-1H-pyrazol-5-yl]methyl}oxy)phenyl]pyridine | 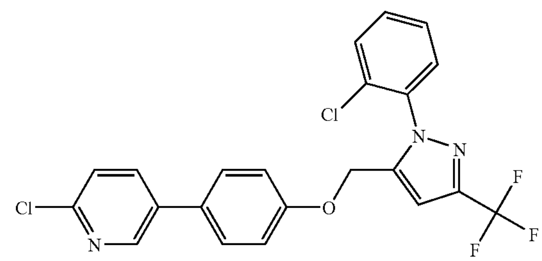 |
| 64 | 5-[4-({[1-(2-chlorophenyl)-3-(trifluoromethyl)-1H-pyrazol-5-yl]methyl}oxy)phenyl]-1H-indole | 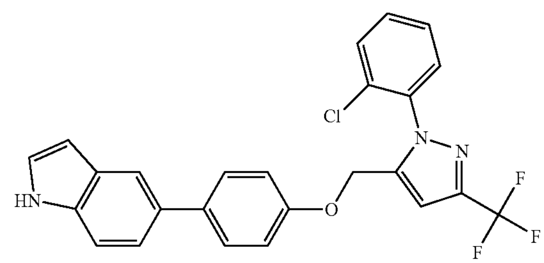 |
| 65 | 1-[4'-({[1-(2-chlorophenyl)-3-(trifluoromethyl)-1H-pyrazol-5-yl]methyl}oxy)biphenyl-4-yl]ethanone | 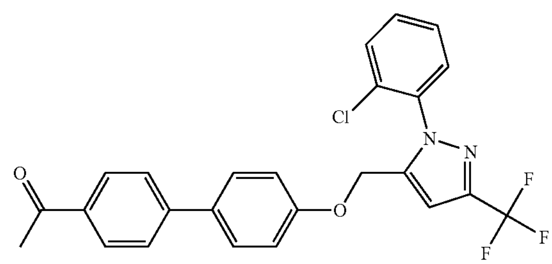 |
| 66 | 1-[4'-({[1-(2-chlorophenyl)-3-(trifluoromethyl)-1H-pyrazol-5-yl]methyl}oxy)biphenyl-2-yl]ethanone | 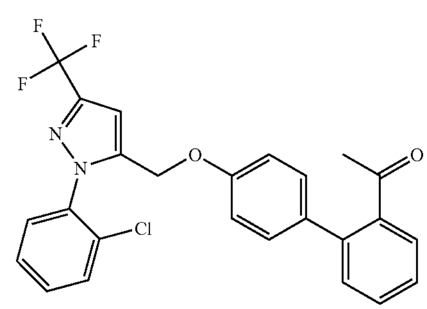 |
| 67 | 5-[4-({[1-(2-chlorophenyl)-3-(trifluoromethyl)-1H-pyrazol-5-yl]methyl}oxy)phenyl]-2-(methyloxy)pyridine | 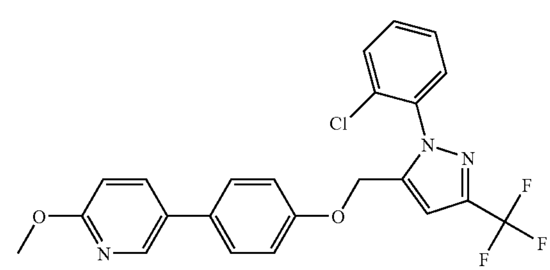 |

TABLE I-continued

| # | IUPAC Name |
|---|---|
| 68 | 1-(2-chlorophenyl)-5-({[5'-methyl-2'-(methyloxy)biphenyl-4-yl]oxy}methyl)-3-(trifluoromethyl)-1H-pyrazole |
| 69 | 4'-({[1-(2-chlorophenyl)-3-(trifluoromethyl)-1H-pyrazol-5-yl]methyl}oxy)biphenyl-4-amine |
| 70 | 1-[4'-({[1-(2-chlorophenyl)-3-(trifluoromethyl)-1H-pyrazol-5-yl]methyl}oxy)biphenyl-3-yl]ethanone |
| 71 | methyl 4'-({[1-(2-chlorophenyl)-3-(trifluoromethyl)-1H-pyrazol-5-yl]methyl}oxy)biphenyl-3-carboxylate |
| 72 | 1-(2-chlorophenyl)-5-{[(2',5'-difluorobiphenyl-4-yl)oxy]methyl}-3-(trifluoromethyl)-1H-pyrazole |

TABLE I-continued

| # | IUPAC Name | Structure |
|---|---|---|
| 73 | N-[4'-({[1-(2-chlorophenyl)-3-(trifluoromethyl)-1H-pyrazol-5-yl]methyl}oxy)biphenyl-4-yl]acetamide | 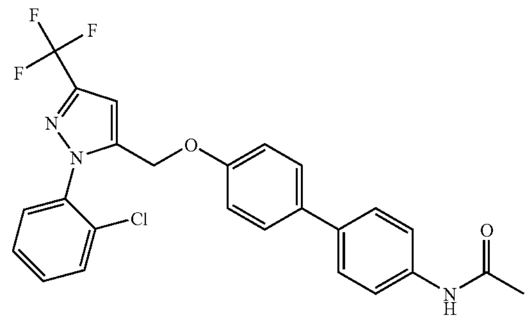 |
| 74 | 5-({[2',3'-bis(methyloxy)biphenyl-4-yl]oxy}methyl)-1-(2-chlorophenyl)-3-(trifluoromethyl)-1H-pyrazole | 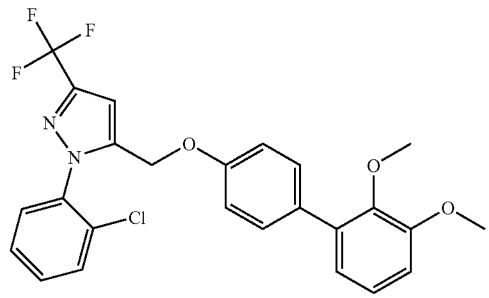 |
| 75 | 1-(2-chlorophenyl)-5-{[(3'-nitrobiphenyl-4-yl)oxy]methyl}-3-(trifluoromethyl)-1H-pyrazole | 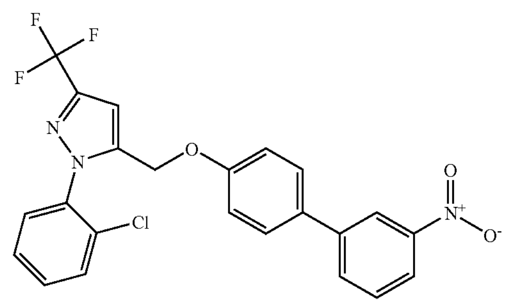 |
| 76 | methyl N-{[4'-({[1-(2-chlorophenyl)-3-(trifluoromethyl)-1H-pyrazol-5-yl]methyl}oxy)biphenyl-4-yl]carbonyl}glycinate | 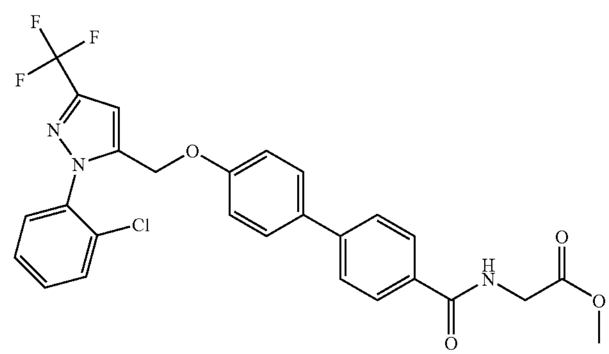 |
| 77 | 4'-({[1-(2-chlorophenyl)-3-(trifluoromethyl)-1H-pyrazol-5-yl]methyl}oxy)-N,N-diethylbiphenyl-3-carboxamide | 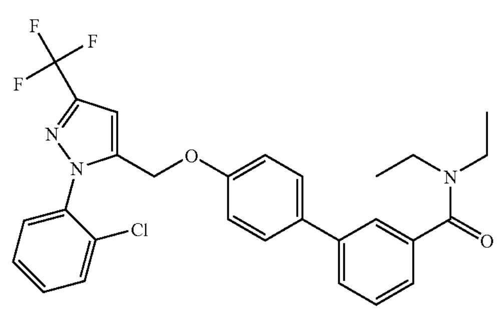 |

TABLE I-continued

| # | IUPAC Name | Structure |
|---|---|---|
| 78 | 4-{[4'-({[1-(2-chlorophenyl)-3-(trifluoromethyl)-1H-pyrazol-5-yl]methyl}oxy)biphenyl-3-yl]carbonyl}thiomorpholine | 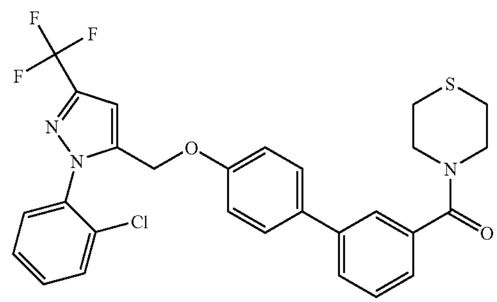 |
| 79 | 4'-({[1-(2-chlorophenyl)-3-(trifluoromethyl)-1H-pyrazol-5-yl]methyl}oxy)-N-ethylbiphenyl-3-carboxamide | 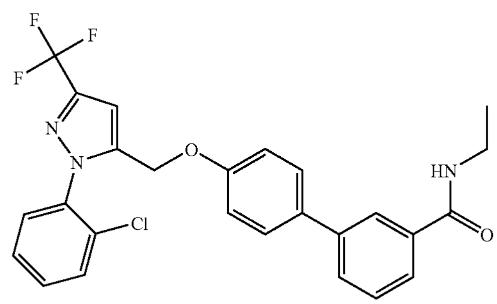 |
| 80 | 4'-({[1-(2-chlorophenyl)-3-(trifluoromethyl)-1H-pyrazol-5-yl]methyl}oxy)-5-fluorobiphenyl-3-carboxylic acid | 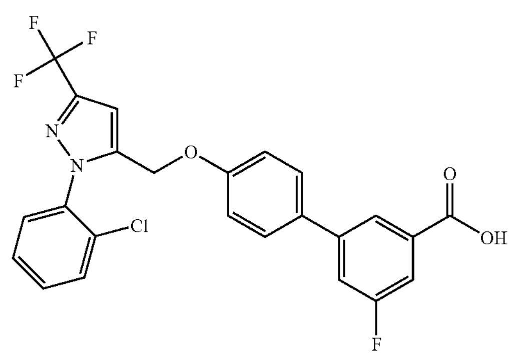 |
| 81 | 3-chloro-4'-({[1-(2-chlorophenyl)-3-(trifluoromethyl)-1H-pyrazol-5-yl]methyl}oxy)-N-(phenylmethyl)biphenyl-4-carboxamide | 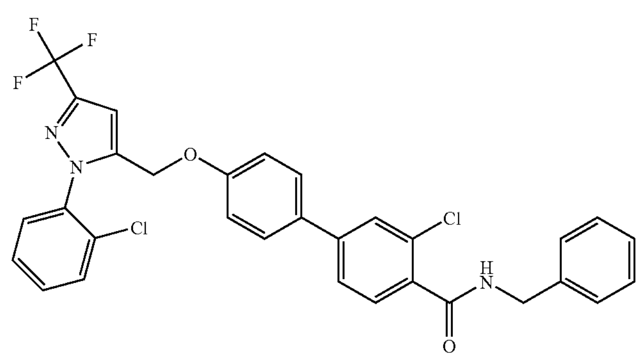 |

TABLE I-continued

| # | IUPAC Name | Structure |
|---|---|---|
| 82 | 4'-({[1-(2-chlorophenyl)-3-(trifluoromethyl)-1H-pyrazol-5-yl]methyl}oxy)-N,N-diethylbiphenyl-4-carboxamide | 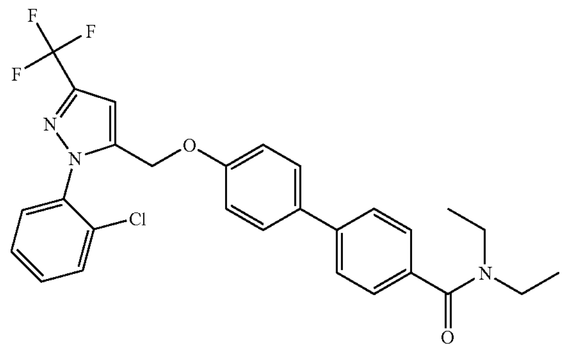 |
| 83 | 4'-({[1-(2-chlorophenyl)-3-(trifluoromethyl)-1H-pyrazol-5-yl]methyl}oxy)-N-methylbiphenyl-4-carboxamide | 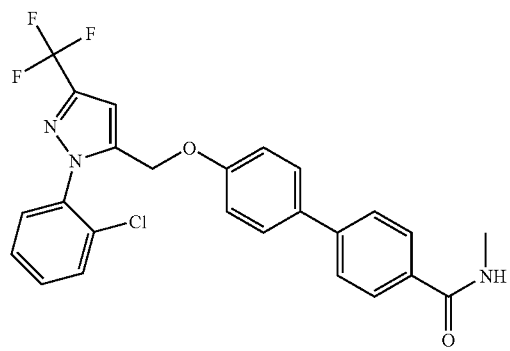 |
| 84 | 1-(2-chlorophenyl)-5-({[4'-fluoro-2'-(methyloxy)biphenyl-4-yl]oxy}methyl)-3-(trifluoromethyl)-1H-pyrazole | 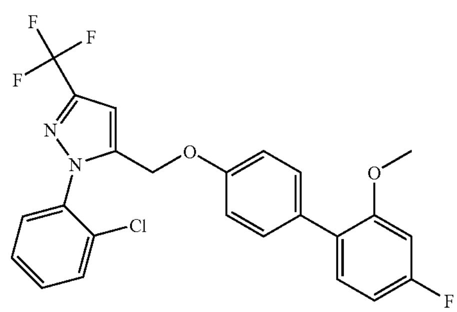 |
| 85 | 1-(2-chlorophenyl)-5-({[2'-fluoro-3'-(methyloxy)biphenyl-4-yl]oxy}methyl)-3-(trifluoromethyl)-1H-pyrazole | 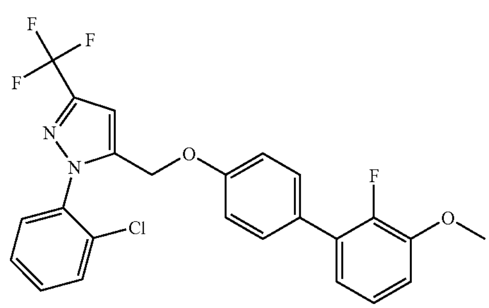 |
| 86 | 1-(2-chlorophenyl)-5-({[3'-(pyrrolidin-1-ylcarbonyl)biphenyl-4-yl]oxy}methyl)-3-(trifluoromethyl)-1H-pyrazole | 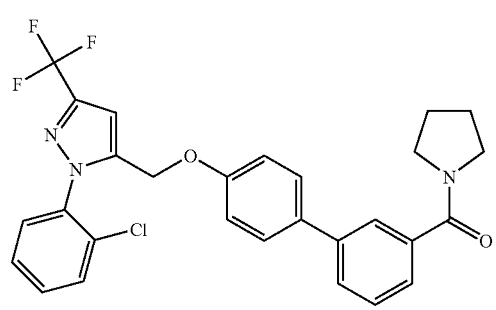 |

TABLE I-continued

| # | IUPAC Name | Structure |
|---|---|---|
| 87 | methyl [4'-({[1-(2-chlorophenyl)-3-(trifluoromethyl)-1H-pyrazol-5-yl]methyl}oxy)biphenyl-4-yl]carbamate | 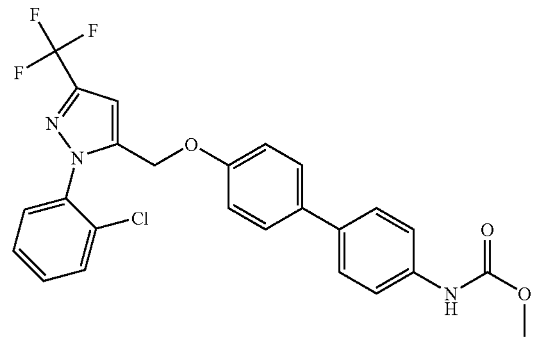 |
| 88 | 1-(2-chlorophenyl)-5-({[4'-(ethylsulfonyl)biphenyl-4-yl]oxy}methyl)-3-(trifluoromethyl)-1H-pyrazole | 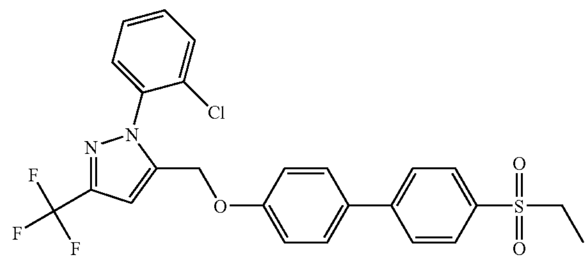 |
| 89 | 4-{[3-chloro-4'-({[1-(2-chlorophenyl)-3-(trifluoromethyl)-1H-pyrazol-5-yl]methyl}oxy)biphenyl-4-yl]carbonyl}morpholine | 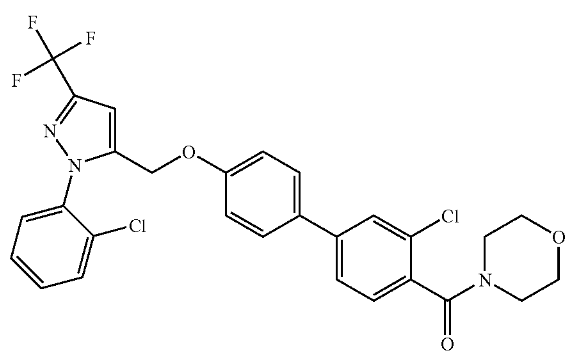 |
| 90 | 1-{[3-chloro-4'-({[1-(2-chlorophenyl)-3-(trifluoromethyl)-1H-pyrazol-5-yl]methyl}oxy)biphenyl-4-yl]carbonyl}piperidine | 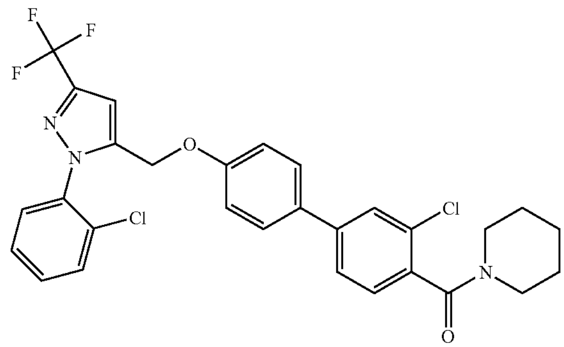 |

TABLE I-continued

| # | IUPAC Name |
|---|---|
| 91 | 1-(2-chlorophenyl)-5-[({2'-[(1-methylethyl)oxy]-5'-(trifluoromethyl)biphenyl-4-yl}oxy)methyl]-3-(trifluoromethyl)-1H-pyrazole |
| 92 | 2-[4'-({[1-(2-chlorophenyl)-3-(trifluoromethyl)-1H-pyrazol-5-yl]methyl}oxy)biphenyl-3-yl]-2-methylpropanoic acid |
| 93 | [4'-({[1-(2-chlorophenyl)-3-(trifluoromethyl)-1H-pyrazol-5-yl]methyl}oxy)biphenyl-3-yl]acetic acid |
| 94 | (2E)-3-[4-({[1-(2-chlorophenyl)-3-(trifluoromethyl)-1H-pyrazol-5-yl]methyl}oxy)phenyl]prop-2-enoic acid |
| 95 | 3-({[1-(2-chlorophenyl)-3-(trifluoromethyl)-1H-pyrazol-5-yl]methyl}oxy)phenyl benzoate |

TABLE I-continued

| # | IUPAC Name | Structure |
|---|---|---|
| 96 | 1-(2-chlorophenyl)-5-({[4'-(methyloxy)biphenyl-4-yl]oxy}methyl)-3-(trifluoromethyl)-1H-pyrazole | 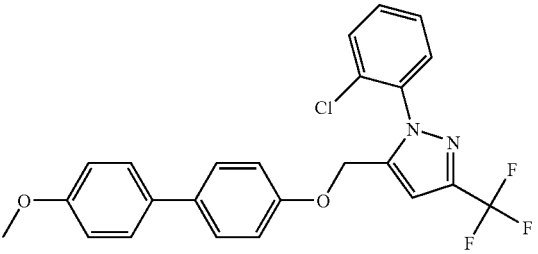 |
| 97 | 1-(2-chlorophenyl)-5-{[(3'-nitrobiphenyl-4-yl)oxy]methyl}-3-(trifluoromethyl)-1H-pyrazole | 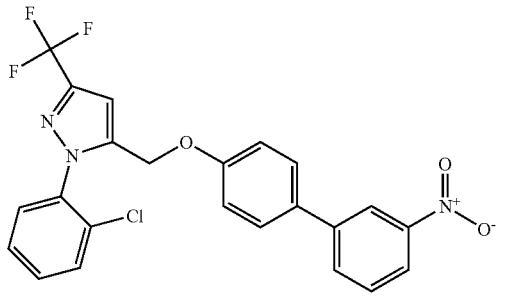 |
| 98 | [4'-({[1-(2-chlorophenyl)-3-(trifluoromethyl)-1H-pyrazol-5-yl]methyl}oxy)biphenyl-4-yl]acetic acid | 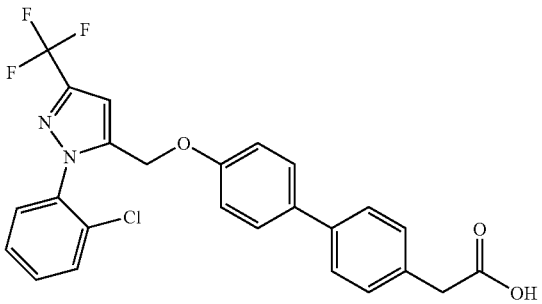 |
| 99 | 1-(2,5-dichlorophenyl)-N-[3-(methylsulfonyl)phenyl]-3-(trifluoromethyl)-1H-pyrazole-5-carboxamide | 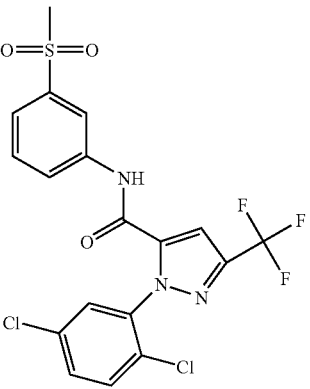 |
| 100 | 1-(2,5-dichlorophenyl)-3-(trifluoromethyl)-N-{[3-(trifluoromethyl)phenyl]methyl}-1H-pyrazole-5-carboxamide | 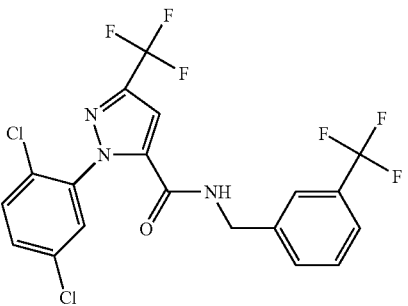 |

TABLE I-continued

| # | IUPAC Name | Structure |
|---|---|---|
| 101 | 1-(2,5-dichlorophenyl)-N-{[4-(methylsulfonyl)phenyl]methyl}-3-(trifluoromethyl)-1H-pyrazole-5-carboxamide | 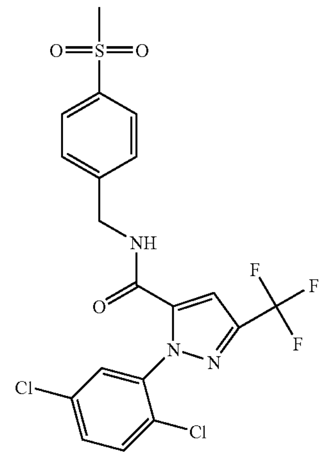 |
| 102 | N-[(3-chlorophenyl)methyl]-1-(2,5-dichlorophenyl)-3-(trifluoromethyl)-1H-pyrazole-5-carboxamide | 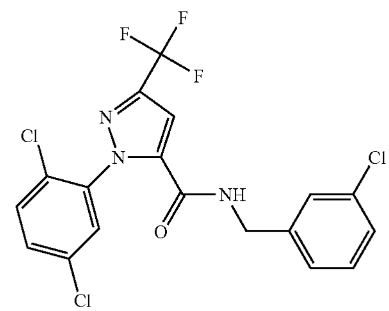 |
| 103 | 1-(2-chlorophenyl)-N-{[3-(methylsulfonyl)phenyl]methyl}-3-(trifluoromethyl)-1H-pyrazole-5-carboxamide | 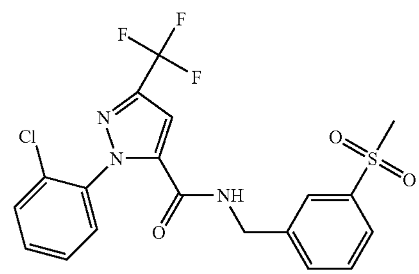 |
| 104 | 1-{2-[(1-methylethyl)oxy]phenyl}-3-(trifluoromethyl)-N-{[3-(trifluoromethyl)phenyl]methyl}-1H-pyrazole-5-carboxamide | 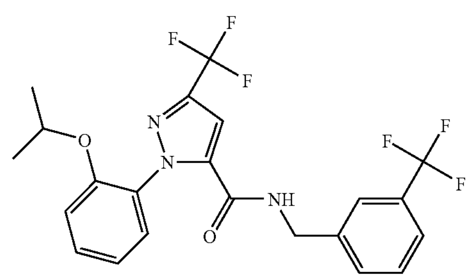 |
| 105 | N-(3-acetylphenyl)-N'-{3-(trifluoromethyl)-1-[2-(trifluoromethyl)phenyl]-1H-pyrazol-5-yl}urea | 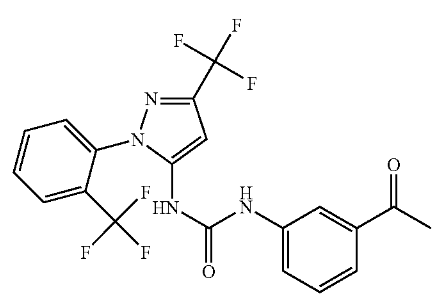 |

TABLE I-continued

| # | IUPAC Name | Structure |
|---|---|---|
| 106 | 1-(2-chlorophenyl)-3-(trifluoromethyl)-N-{[3-(trifluoromethyl)phenyl]methyl}-1H-pyrazole-5-carboxamide | 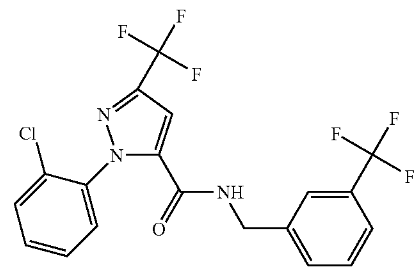 |
| 107 | 3-{[1-(2-chlorophenyl)-3-(trifluoromethyl)-1H-pyrazol-5-yl]ethynyl}benzenesulfonamide | 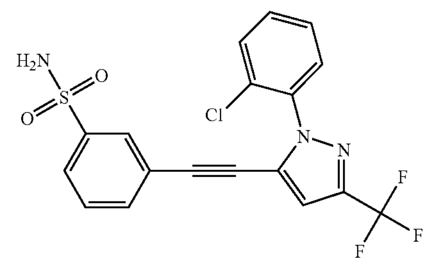 |
| 108 | 1-(2-chlorophenyl)-5-{[3-(methylsulfonyl)phenyl]ethynyl}-3-(trifluoromethyl)-1H-pyrazole | 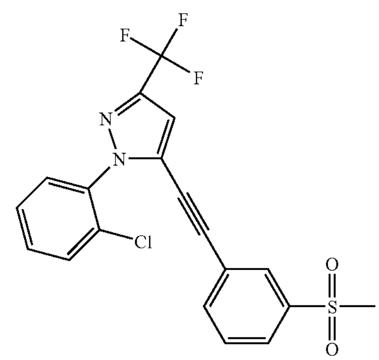 |
| 109 | 1-(2-chlorophenyl)-5-{[4-(methylsulfonyl)phenyl]ethynyl}-3-(trifluoromethyl)-1H-pyrazole | 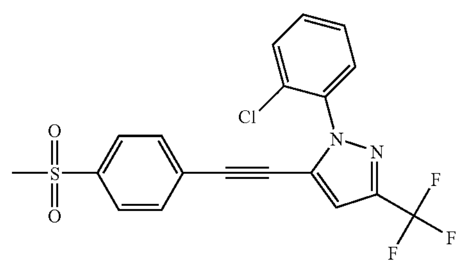 |
| 110 | 1-(2-chlorophenyl)-5-({4-[(methylsulfonyl)methyl]phenyl}ethynyl)-3-(trifluoromethyl)-1H-pyrazole | 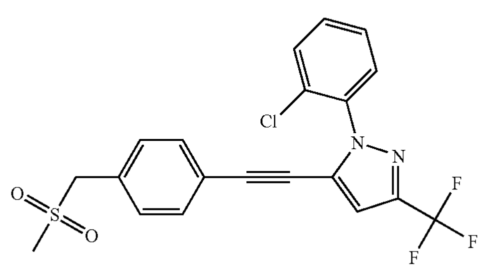 |

TABLE I-continued

| # | IUPAC Name | Structure |
|---|---|---|
| 975 | 1-(2-chlorophenyl)-N-(3-(methylsulfonyl)phenyl)-3-(trifluoromethyl)-1H-pyrazole-5-carboxamide | 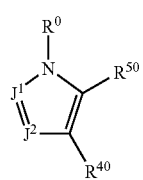 |

The compounds of the invention in all of the following aspects and embodiments of Formulas (III)-(LXXII), including all formulas of the form, for example, IIIa, IIIb, IVa, XXVa, specifically exclude compounds #1-1889 of PCT Application Publication No. WO 2007-02559-A1, published Jan. 4, 2007; and compounds #1-487 of PCT Application Publication No. WO 2007-005263-A1, published Jan. 4, 2007.

In a second aspect, the present invention comprises a compound according to Formula (III), (III)

or a pharmaceutically acceptable salt thereof, wherein
$J^1$ is —N— or —$CR^{20}$—, provided that
(i) when $J^1$ is N, then $J^2$ is —$CR^{30}$—; and (ii) when $J^1$ is —$CR^{20}$—, then $J^2$ is N;
$R^0$ is $G^1$, $G^2$, or $R^N$;
$R^{20}$, $R^{30}$, $R^{40}$, and $R^{50}$ are independently $G^1$, $G^2$, or $R^C$;
  provided that one and only one of $R^0$, $R^{20}$, $R^{30}$, $R^{40}$, and $R^{50}$ is $G^1$; and one and only one of $R^0$, $R^{20}$, $R^{30}$, $R^{40}$, and $R^{50}$ is $G^2$;
$G^1$ is -$L^{10}$-R, wherein
$L^{10}$ is a bond, $L^{50}$, $L^{60}$, -$L^{50}$-$L^{60}$-$L^{50}$-, or -$L^{60}$-$L^{50}$-$L^{60}$-, wherein
each $L^{50}$ is independently —$[C(R^{150})_2]_m$—;
each $L^{60}$ is independently —CS—, —CO—, —$SO_2$—, —O—, —$CON(R^{110})$—, —$CONR^{110}N(R^{110})$—, —$C(=NR^{110})$—, —$C(=NOR^{110})$—, —C(=N—N($R^{110})_2$)—, $C_3$-$C_8$cycloalkyl-, or -heterocyclyl-,
wherein the cycloalkyl or heterocyclyl is optionally substituted with one to 4 $R^{140}$ groups;
or each $L^{60}$ is independently $C_2$-$C_6$ alidiyl,
wherein the alidiyl chain is optionally interrupted by —$C(R^{110})$—, —$C(R^{110})_2C(R^{110})_2$—, —$C(R^{110})$=$C(R^{110})$—, —$C(R^{110})_2O$—, —$C(R^{110})_2NR^{110}$—, —C≡C—, —O—, —S—, —$N(R^{100})CO$—, —$N(R^{100})CO_2$—, —$CON(R^{100})$—, —CO—, —$CO_2$—, —OC(=O)—, —$OC(=O)N(R^{100})$—, —$SO_2$—, —$N(R^{100})SO_2$—, or —$SO_2N(R^{100})$; and
R is aryl, heterocyclyl, heteroaryl, or —($C_3$-$C_6$)cycloalkyl, wherein R is optionally substituted with 1 to 4 R', wherein
each R' is independently halogen, nitro, heterocyclyl, $C_2$-$C_6$ alkenyl, $C_2$-$C_6$ alkynyl, $C_3$-$C_8$ cycloalkyl, ($C_3$-$C_8$ cycloalkyl)-$C_1$-$C_6$ alkyl-, ($C_3$-$C_8$ cycloalkenyl)-$C_1$-$C_6$ alkyl-, ($C_3$-$C_8$ cycloalkyl)-$C_2$-$C_6$ alkenyl-, arylalkyl, aryloxy, aryl$C_{1-6}$alkoxy, $C_1$-$C_6$ alkyl, $C_1$-$C_6$ haloalkyl, $SO_2R^{110}$, $OR^{110}$, $SR^{110}$, $N_3$, $SOR^{110}$, $COR^{110}$, $SO_2N(R^{110})_2$ $SO_2NR^{110}COR^{110}$, C≡N, $C(O)OR^{110}$, $CON(R^{110})$, $CON(R^{110})OR^{110}$, $OCON(R^{110})_2$, $NR^{110}OCOR^{110}$, $NR^{110}CON(R^{110})_2$, $NR^{110}COOR^{110}$, —C(=N—OH)$R^{110}$, —C(=S)N($R^{110})_2$, —S(=O)N($R^{110})_2$, —S(=O)$OR^{110}$, —N($R^{110}$)S(=O)$_2R^{110}$, —C(=O)N($R^{110}$)N($R^{110})_2$, —OC(=O)—$R^{110}$, —OC(=O)—$OR^{110}$ or N($R^{110})_2$, wherein each R' is optionally substituted with 1 to 4 groups which independently are -halogen, —$C_1$-$C_6$ alkyl, aryloxy $C_{0-6}$ alkyl$SO_2R^{110}$, $C_{0-6}$ alkyl$COOR^{110}$, $C_{1-6}$ alkoxyaryl, $C_1$-$C_6$ haloalkyl, —$SO_2R^{110}$, —$OR^{110}$, —$SR^{110}$, —$N_3$, —$SO_2R^{110}$, —$COR^{110}$, —$SO_2N(R^{110})_2$, —$SO_2NR^{110}COR^{110}$, —C≡N, —$C(O)OR^{110}$, —$CON(R^{110})_2$, —$CON(R^{110})OR^{110}$, —$OCON(R^{110})_2$, —$NR^{110}COR^{110}$, —$NR^{110}CON(R^{110})_2$, —$NR^{110}COOR^{110}$, or —$N(R^{110})_2$;
$G^2$ is -$L^{20}$-K', wherein
K' is aryl, heteroaryl, or heterocyclyl, each optionally substituted with one to four $R^K$ groups, wherein
each $R^K$ is independently hydrogen, halogen, oxo, nitro, $CR^{110}$=$CR^{110}COOR^{110}$, aryloxy, aralkyloxy, aryloxyalkyl, aryl$C_0$-$C_6$ alkylcarboxy, aryl, —($C_1$-$C_6$)alkyl-aryl, heteroaryl, —($C_1$-$C_6$)alkyl-heteroaryl, heterocyclyl, —($C_1$-$C_6$)alkyl-heterocyclyl, heteroaryloxy, heterocyclyloxy, —Z, —Y—Z, or —X—Y—Z, wherein each $R^K$ is optionally substituted with 1 to 4 $R^{K'}$, wherein
each $R^{K'}$ is independently oxo, aryloxy, aralkyloxy, aryloxyalkyl, $C_1$-$C_6$ alkoxyaryl, aryl$C_0$-$C_6$ alkylcarboxy, —Z, —Y—Z, or —X—Y—Z,
or two $R^K$ bonded to the same carbon atom taken together with the carbon atom to which they are bonded form a $C_3$-$C_8$ cycloalkyl or heterocyclyl, each optionally substituted with 1 to 4 $R^{K'}$; and
$L^{20}$ is —$[C(R^{150})_2]_m$—$V^{20}$—$[C(R^{150})_2]_n$—, —$V^{20}$—[C($R^{150})_2]_m$—$V^{20}$, —$V^{20}$—[C($R^{150})_2]_m$—$V^{20}$—[C($R^{150})_2]_n$; or —$V^{20}$—[C($R^{150})_2]_m$—$V^{20}$—[C($R^{150})_2]_n$—$V^{20}$; wherein
each $V^{20}$ is independently —$CH_2$—, —CH(Z)-, —C($R^{110}$)(Z)-, —C($R^{110})_2$—, —C($R^{110})_2C(R^{110})_2$—, —C(O)C($R^{110}$)=C($R^{110}$)—, —C($R^{110}$)=C($R^{110}$)—, —C($R^{10})_2O$—, —C($R^{110})_2NR^{110}$—, —OC($R^{110})_2$—, —$NR^{110}C(R^{110})_2$—, —$OCH_2C(O)$—, —$OCH_2C(O)N(R^{110})$—, —C≡C—, —O—, —N($R^{110}$)—, —S—, —$SO_2$—, —$N(R^{100})CO$—, —$N(R^{100})CO_2$—, —$CON(R^{100})$—, —$CON(R^{110})O$—, —CO—, —CS—, —$CO_2$—, —OC(=O)—, —$OC(=O)N(R^{100})$—, —$N(R^{100})C(=O)O$—, —$N(R^{100})SO_2$—, —$SO_2N(R^{100})$—, —$NR^{100}CONR^{100}$—, or —$NR^{100}CSNR^{100}$—,
or $V^{20}$ is $C_{2-6}$ alidiyl, wherein alidiyl chain is optionally interrupted by —C($R^{110})_2$—, —C($R^{110})_2C(R^{110})_2$—, —C($R^{110}$)—C($R^{110}$)—, —C($R^{110}$)—, —C($R^{110}$)$_2$NR$^{110}$—, —C($R^{110}$)NR$^{110}$—, —C≡C—, —O—, —S—, —N(O)CO—, —N($R^{100}$)CO$_2$—, —CON($R^{100}$)—, —CON($R^{110}$)—, —CON($R^{110}$)O—, —CO—, —CO$_2$—, —OC(═O)—, —OC(═O)N($R^{100}$)—, —SO$_2$—, —N($R^{100}$)SO$_2$— or —SO$_2$N($R^{100}$)—;

or V$^{20}$ is $C_3$-$C_6$cycloalkyl-, $C_3$-$C_6$cyclohaloalkyl, or heterocyclyl, each of which is optionally substituted with 1 to 4 $R^{90}$, wherein each $R^{90}$ is independently halogen, oxo, $C_1$-$C_6$ haloalkyl, $C_1$-$C_6$ alkyl, $C_1$-$C_6$ alkyloxy, $C_0$-$C_6$ alkyl or $C_1$-$C_6$ alkyl-COOR$^{110}$;

each $R^C$ is independently -$L^{30}$-$R^{70}$, wherein each $L^{30}$ is independently a bond or —(CH$_2$)$_m$—V$^{10}$—(CH$_2$)$_n$—, wherein V$^{10}$ is —C($R^{110}$)$_2$—, —C($R^{110}$)$_2$C($R^{110}$)$_2$—, —C($R^{110}$)═C($R^{110}$)—, —C($R^{110}$)$_2$O—, —C($R^{110}$)$_2$NR$^{110}$—, —C≡C—, —O—, —S—, —NR$^{110}$—, —N($R^{100}$)CO—, —N($R^{110}$)CO$_2$—, —OCO—, —CO—, —CS—, —CONR$^{100}$—, —C(═N—R$^{110}$)—, —C(═N—OR$^{110}$)—, —C[═N—N($R^{110}$)$_2$], —CO$_2$—, —OC(═O)—, —OC(═O)N($R^{100}$)—, —SO$_2$—, —N($R^{100}$)SO$_2$—, —SO$_2$N($R^{110}$)—, —NR$^{100}$CONR$^{100}$—, —NR$^{100}$CSNR$^{100}$—, $C_3$-$C_6$cycloalkyl, or $C_3$-$C_6$ cyclohaloalkyl;

or each $L^{30}$ is independently $C_2$-$C_6$ alidiyl, wherein the alidiyl chain is optionally interrupted by —C($R^{110}$)$_2$—, —C($R^{110}$)$_2$C($R^{110}$)$_2$—, —C($R^{110}$)═C($R^{110}$)—, —C($R^{110}$)$_2$O—, —C($R^{110}$)$_2$NR$^{110}$—, —C≡C—, —O—, —S—, —N($R^{110}$)CO—, —N($R^{110}$)CO$_2$—, —NR$^{110}$—, —CON($R^{100}$)—, —CO—, —CO$_2$—, —OC(═O)—, —OC(═O)N($R^{100}$)—, —SO$_2$—, —N($R^{100}$)SO$_2$—, or —SO$_2$N($R^{100}$)—; and each $R^{70}$ is independently hydrogen, halogen, nitro, aryl, heteroaryl, heterocyclyl, —Z, —Y—Z, or —X—Y—Z, wherein the aryl, heteroaryl, and heterocyclyl, are each optionally substituted with 1 to 4 $R^{70a}$, wherein each $R^{70a}$ is independently aryloxy, aralkyloxy, aryloxyalkyl, aryl$C_0$-$C_6$ alkylcarboxy, C($R^{110}$)═C($R^{110}$)—COOH, 'heteroaryloxy, oxo, —Z, —Y'—Z, or —X—Y—Z, wherein each $R^{70a}$ is optionally substituted with 1 to 4 $R^{80}$, wherein each $R^{80}$ is independently halogen, $C_1$-$C_6$ alkyl, $C_1$-$C_6$ alkoxy, $C_1$-$C_6$ haloalkyl, $C_1$-$C_6$ haloalkyl(OR$^{110}$), $C_0$-$C_6$ alkylOR$^{110}$, $C_0$-$C_6$ alkylCON($R^{110}$)$_2$, $C_0$-$C_6$ alkyl-COR$^{110}$, $C_0$-$C_6$ alkylCOOR$^{110}$, or $C_0$-$C_6$ alkylSO$_2$R$^{110}$;

$R^N$ is -$L^{31}$-$R^{60}$, wherein $L^{31}$ is a bond, —X$^3$—(CH$_2$)$_n$—X$^3$—, —(CH$_2$)$_m$—X$^3$—(CH$_2$)$_n$— or —(CH$_2$)$_{1+w}$—Y$^3$—(CH$_2$)$_w$— wherein each w is independently 0-5; and each X$^3$ is independently a bond, —C($R^{110}$)$_2$—, —C($R^{110}$)$_2$C($R^{110}$)$_2$—, —C($R^{110}$)═C($R^{110}$)—, —C≡C—, —CO—, —CS—, —CONR$^{100}$—, —C(═N)($R^{110}$)—, —C(═N—OR$^{110}$)—, —C[═N—N($R^{110}$)$_2$], —CO$_2$—, —SO$_2$—, or —SO$_2$N($R^{100}$)—; and Y$^3$ is —O—, —S—, —NR$^{70}$—, —N($R^{100}$)CO—, —N($R^{100}$)CO$_2$—, —OCO—, —OC(═O)N($R^{100}$)—, —NR$^{100}$CONR$^{100}$—, —N($R^{110}$)SO$_2$—, or —NR$^{100}$CSNR$^{100}$;

or $L^{31}$ is $C_{2-6}$ alidiyl chain wherein the alidiyl chain is optionally interrupted by —C($R^{110}$)$_2$—, —C($R^{110}$)$_2$C($R^{110}$)$_2$—, —C($R^{110}$)═C($R^{110}$)—, —C($R^{110}$)$_2$O—, —C($R^{110}$)$_2$NR$^{110}$—, —C≡C—, —O—, —S—, —N($R^{110}$)CO—, —N($R^{110}$)CO$_2$—, —CON($R^{110}$)—, —CO—, —CO$_2$—, —OC(═O)—, —OC(═O)N($R^{100}$)—, —SO$_2$—, —N($R^{100}$)SO$_2$—, or —SO$_2$N($R^{110}$); and $R^{60}$ is $C_1$-$C_6$ alkyl, $C_1$-$C_6$ haloalkyl, aryl, $C_3$-$C_8$ cycloalkyl, heteroaryl, heterocyclyl, —CN, —C(═O)R$^{110}$, —C(═O)OR$^{110}$, —C(═O)N($R^{110}$)$_2$, —N($R^{110}$)$_2$, —SO$_2$R$^{110}$, —S(═O)$_2$N($R^{110}$)$_2$, —C(═O)N($R^{110}$)N($R^{110}$)$_2$, —C(═O)N($R^{110}$)(OR$^{110}$), wherein the aryl, heteroaryl, cycloalkyl, or heterocyclyl is optionally substituted with 1 to 4 $R^{60a}$, wherein each $R^{60a}$ is independently —Z, —Y—Z, or —X—Y—Z;

each $R^{100}$ is independently —R$^{110}$, —C(═O)R$^{110}$, —CO$_2$R$^{110}$, or —SO$_2$R$^{110}$;

each $R^{110}$ is independently -hydrogen, —$C_1$-$C_6$ alkyl, $C_2$-$C_6$ alkenyl, $C_2$-$C_6$ alkynyl, $C_3$-$C_8$ cycloalkyl, ($C_3$-$C_8$ cycloalkyl)-$C_1$-$C_6$ alkyl-, ($C_3$-$C_8$ cycloalkenyl)-$C_1$-$C_6$ alkyl-, ($C_3$-$C_8$ cycloalkyl)-$C_2$-$C_6$ alkenyl-, —$C_1$-$C_6$ haloalkyl, —N($R^{120}$), aryl, —($C_1$-$C_6$)alkyl-aryl, heteroaryl, —($C_1$-$C_6$)alkyl-heteroaryl, heterocyclyl, or —($C_1$-$C_6$)alkyl-heterocyclyl, wherein any of $R^{110}$ is optionally substituted with 1 to 4 radicals of $R^{120}$;

each $R^{120}$ is independently halogen, cyano, nitro, oxo, —B(OR$^{130}$)$_2$, $C_0$-$C_6$ alkylN($R^{130}$)$_2$, $C_1$-$C_6$haloalkyl, $C_1$-$C_6$ alkyl, $C_1$-$C_6$ alkoxy, ($C_0$-$C_6$ alkyl)C═O(R$^{130}$), $C_0$-$C_6$ alkylOR$^{130}$, $C_0$-$C_6$ alkylCOR$^{130}$, $C_0$-$C_6$ alkylSO$_2$R$^{130}$, $C_0$-$C_6$ alkylCON($R^{130}$)$_2$, $C_0$-$C_6$ alkylCONR$^{130}$OR$^{130}$, $C_0$-$C_6$ alkylSO$_2$N($R^{30}$)$_2$, $C_0$-$C_6$ alkylSR$^{130}$, $C_0$-$C_6$ haloalkylOR$^{130}$, $C_0$-$C_6$ alkylCN, aryloxy, aralkyloxy, aryloxyalkyl, $C_{1-6}$ alkoxyaryl, aryl$C_{0-6}$ alkylcarboxy, —$C_0$-$C_6$alkylN($R^{130}$), —NR$^{130}$SO$_2$R$^{130}$, or —OC$_{0-6}$ alkylCOOR$^{130}$;

each $R^{130}$ is independently hydrogen, $C_1$-$C_6$ alkyl, $C_2$-$C_6$ alkenyl, $C_2$-$C_6$ alkynyl, $C_3$-$C_8$ cycloalkyl, ($C_3$-$C_8$ cycloalkyl)-$C_1$-$C_6$ alkyl-, ($C_3$-$C_8$ cycloalkenyl)-$C_1$-$C_6$ alkyl-, or ($C_3$-$C_8$ cycloalkyl)-$C_2$-$C_6$ alkenyl-;

each $R^{140}$ is independently $C_1$-$C_6$ alkyl, $C_1$-$C_6$ alkoxy, halogen, $C_1$-$C_6$ haloalkyl, $C_0$-$C_6$ alkylCON($R^{110}$)$_2$, $C_0$-$C_6$ alkylCONR$^{110}$OR$^{110}$, $C_0$-$C_6$ alkylOR$^{110}$, or $C_0$-$C_6$ alkyl-COOR$^{110}$; and each $R^{150}$ is independently hydrogen, halogen, OR$^{130}$, ($C_1$-$C_6$)alkyl, ($C_3$-$C_6$)cycloalkyl, or ($C_1$-$C_6$)haloalkyl, wherein each alkyl or cycloalkyl is optionally substituted with at least one group which are each independently halogen, cyano, nitro, azido, OR$^{130}$, C(O)R$^{130}$, C(O)OR$^{130}$, C(O)N($R^{130}$)$_2$, N($R^{130}$)$_2$, N($R^{130}$)C(O)R$^{130}$, N($R^{130}$)S(O)$_2$R$^{130}$, OC(O)OR$^{130}$, OC(O)N($R^{130}$)$_2$, N($R^{130}$)C(O)OR$^{130}$, N($R^{130}$)C(O)N($R^{130}$), SR$^{130}$, S(O)R$^{130}$, S(O)$_2$R$^{130}$, or S(O)$_2$N($R^{130}$)$_2$;

or two $R^{150}$ (bonded to same or different atoms) taken together with the carbon(s) to which they are bonded form a $C_3$-$C_6$ cycloalkyl;

X is —O—, —S—, or —N($R^{100}$)—;

each Y is independently —[C($R^{150}$)$_2$]$_p$—, —$C_2$-$C_6$ alkenyl, $C_3$-$C_8$ cycloalkyl, heterocyclyl, aryl, or heteroaryl, wherein p is 1, 2, 3, 4, 5, or 6; and the aryl, heteroaryl, cycloalkyl, or heterocyclyl is optionally substituted with 1 to 3 Z groups;

each Y' is independently —[C($R^{150}$)$_2$]$_p$—, —$C_2$-$C_6$ alkenyl, $C_3$-$C_8$ cycloalkyl, or heterocyclyl, wherein the cycloalkyl or heterocyclyl is optionally substituted with 1 to 3 Z groups; and each Z is independently —H, halogen, —OR$^{110}$, —SR$^{110}$, —C(═O)R$^{110}$, —C(═O)OR$^{110}$, —C(═O)N($R^{110}$)$_2$, —N($R^{100}$)$_2$, —N$_3$, —NO$_2$, —C(═N—OH)R$^{110}$, —C(═S)N($R^{110}$)$_2$, —CN, —S(═O)R$^{110}$, —S(═O)N($R^{110}$)$_2$, —S(═O)OR$^{110}$, —S(═O)$_2$R$^{110}$, S(═O)$_2$N($R^{110}$)$_2$, —N($R^{110}$)C(═O)N($R^{110}$)$_2$, —NR$^{110}$COR$^{110}$, —N($R^{110}$)COOR$^{110}$, —N($R^{110}$)S(═O)$_2$R$^{110}$, —C(═O)

$N(R^{110})N(R^{110})_2$, $-C(=O)N(R^{110})(OR^{110})$, $-OC(=O)-R^{110}-$, $-OC(=O)-OR^{110}$, or $-OC(=O)-N(R^{110})_2$; and each m and n is independently 0, 1, 2, 3, 4, 5, or 6,
provided that the compound is not
(i) within the scope of the first aspect of the invention;
(ii) (1-benzyl-1H-imidazol-2-yl)methyl 4-(1-(2-chlorophenyl)-3-(trifluoromethyl)-1H-pyrazol-5-yl)benzoate;
(iii) 4-[1-(2-chlorophenyl)-3-(trifluoromethyl)-1H-pyrazol-5-yl]-N-[3-methyl-1-(4-methylphenyl)-1H-pyrazol-5-yl]benzamide;
(iv) 4-(1-(2-chlorophenyl)-3-(trifluoromethyl)-1H-pyrazol-5-yl)-N-(3-methyl-1-phenyl-1H-pyrazol-5-yl)benzamide;
(v) N-(3-cyclopropyl-1H-pyrazol-5-yl)-5-[1-methyl-5-(trifluoromethyl)-1H-pyrazol-3-yl]thiophene-2-sulfonamide;
(vi) 1-{[1-(2-chlorophenyl)-5-{5-[3-(methylsulfonyl)phenyl]-2-thienyl}-1H-pyrazol-3-yl]carbonyl}-4-[5-(2-thienyl)-1H-pyrazol-3-yl]piperidine;
(vii) 4-[1-(2-chlorophenyl)-3-(trifluoromethyl)-1H-pyrazol-5-yl]-N-(3-cyclopropyl-1H-pyrazol-5-yl)benzamide;
(viii) 4-[1-(2-chlorophenyl)-3-(trifluoromethyl)-1H-pyrazol-5-yl]-N-[1-methyl-3-(2-thienyl)-1H-pyrazol-5-yl]benzamide;
(ix) (5-methyl-1-phenyl-1H-pyrazol-4-yl)methyl 4-[1-(2-chlorophenyl)-3-(trifluoromethyl)-1H-pyrazol-5-yl]benzoate;
(x) 4-[1-(2-chlorophenyl)-3-(trifluoromethyl)-1H-pyrazol-5-yl]-N-(5-hydroxy-1H-pyrazol-3-yl)benzamide; and
(xi) 4-[1-(2-chlorophenyl)-3-(trifluoromethyl)-1H-pyrazol-5-yl]-N-(5-furan-2-yl-1H-pyrazol-3-yl)benzamide.

The invention also provides the compound according to Formula (III), wherein
$G^2$ is -$L^{20}$-K', wherein
K' is aryl, heteroaryl, or heterocyclyl, each optionally substituted with 1 to 4 $R^K$ groups; and
$L^{20}$ is $-[C(R^{150})_2]_{m'}-V^{20}-[C(R^{150})_2]_{n'}-$, $-V^{20}-[C(R^{150})_2]_{m'}-V^{20}$, or $-V^{20}-[C(R^{150})_2]_{m'}-V^{20}-[C(R^{150})_2]_{n'}$, wherein
m' and n' are independently 0, 1, 2, 3, or 4; and
$V^{20}$ is $-CH_2-$, $-CH(Z)-$, $-C(R^{110})(Z)-$, $-C(R^{110})_2-$, $-C(R^{110})_2C(R^{110})_2-$, $-C(R^{110})=C(R^{110})-$, $-C\equiv C-$, $-O-$, $-N(R^{100})-$, $-S-$, $-SO_2-$, $-N(R^{100})CO-$, $-CON(R^{110})-$, $-OCH_2C(O)-$, $-OCH_2C(O)N(R^{100})-$, $-CO-$, $-CO_2-$, $-OC(=O)-$, $-NR^{100}CONR^{100}-$, $-N(R^{100})SO_2-$, or $-SO_2N(R^{100})-$;
such compounds are referred to hereafter as Formula (IIIa).

The invention also provides the compound according to Formula (III), wherein
$G^1$ is -$L^{10}$-R, wherein
$L^{10}$ is a bond, $L^{50}$, or $L^{60}$, wherein
$L^{50}$ is $-[CH_2]_q-$, wherein q is 1, 2, or 3;
$L^{60}$ is $-CS-$, $-CO-$, $-SO_2-$, or $-CON(R^{110})-$; and
R is aryl, heterocyclyl, or heteroaryl, wherein R is optionally substituted with 1 to 4 R';
such compounds are referred to hereafter as Formula (IIIb).

The invention also provides the compound according to Formula (III), wherein
$G^2$ is -$L^{20}$-K', wherein
K' is aryl or heteroaryl, optionally substituted with 1 to 4 $R^K$ groups; and
$L^{20}$ is $-CH_2-$, $-C(R^{110})_2-$, $-C(R^{110})_2C(R^{110})_2-$, $-C(R^{110})=C(R^{110})-$, or $-C\equiv C-$;
such compounds are referred to hereafter as Formula (IIIc) respectively.

The invention also provides the compound according to Formula (III), wherein
$G^2$ is -$L^{20}$-K', wherein
K' is aryl or heteroaryl, optionally substituted with 1 to 4 $R^K$ groups; and
$L^{20}$ is $-[C(R^{150})_2]_{m'}-V^{20}-$, or $-V^{20}-[C(R^{150})_2]_{m'}-$, wherein m' is 0, 1, 2, 3, or 4; and
$V^{20}$ is $-O-$, $-N(R^{100})-$, $-S-$, $-SO_2-$, $-N(R^{100})CO-$, $-CON(R^{100})-$, $-NR^{100}CONR^{100}-$, $-CO-$, $-CO_2-$, $-OC(=O)-$, $-N(R^{100})SO_2-$, or $-SO_2N(R^{100})-$;
such compounds are referred to hereafter as Formula (IIId).

The invention also provides the compound according to Formula (III), wherein
$G^2$ is -$L^{20}$-K', wherein
K' is aryl or heteroaryl, optionally substituted with 1 to 4 $R^K$ groups; and
$L^{20}$ is $-V^{21}-[C(R^{150})_2]_{m'}-V^{22}-[C(R^{150})_2]_{n'}-$ or $-V^{22}-[C(R^{150})_2]_{m'}-V^{21}-[C(R^{150})_2]_{n'}-$, wherein
$V^{21}$ is $-O-$, $-N(R^{100})-$, $-S-$; and
$V^{22}$ is $-SO_2-$, $-N(R^{100})CO-$, $-CON(R^{100})-$, $-CO-$, $-CO_2-$, $-OC(=O)-$, $-N(R^{100})SO_2-$, or $-SO_2N(R^{100})-$;
such compounds are referred to hereafter as Formula (IIIe).

In a preferred embodiment, the invention comprises the compound according to Formula (III), wherein $G^2$ is selected from the group consisting of

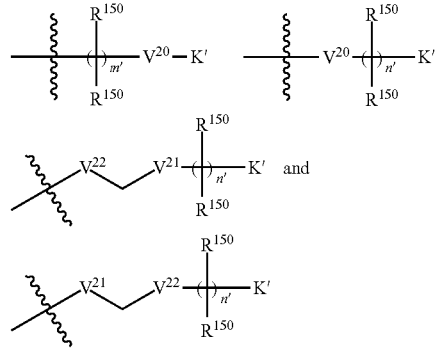

wherein m' and n' are each independently 0, 1, 2, 3, or 4; $V^{20}$ is as defined for formula (IIa); $V^{21}$ and $V^{22}$ are as defined for formula (IIe); and K', R, $L^{10}$, $R^{30}$, $R^{40}$, $R^{50}$, $R^{100}$, and $R^{150}$ are as defined for formula (ITT); such compounds are referred to hereafter as Formula (IIIf).

In a more preferred embodiment, the invention comprises the compound according to Formula (III), wherein $G^2$ is selected from the group consisting of

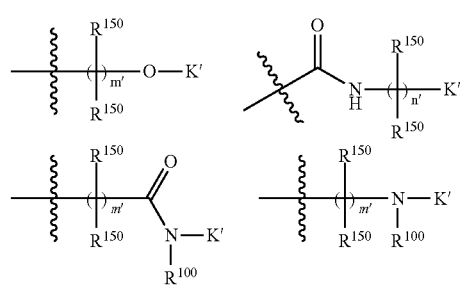

-continued

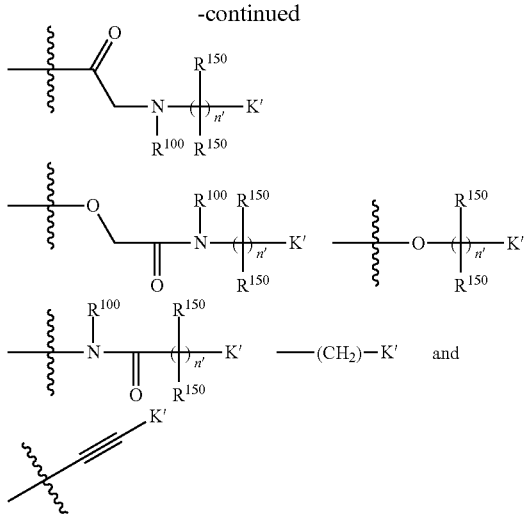

wherein m' and n' are each independently 0, 1, 2, 3, or 4; and K', $R^{100}$, and $R^{150}$ are as defined for formula (III), such compounds are referred to hereafter as Formula (IIIg).

In a more preferred embodiment, the invention comprises the compound according to Formula (III), wherein $G^2$ is

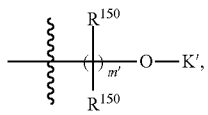

wherein m' is 0, 1, 2, 3, or 4; and K' and $R^{150}$ are as defined for formula (III), such compounds are referred to hereafter as Formula (IIIh).

In a more preferred embodiment, the invention comprises the compound according to Formula (III), wherein $G^2$ is

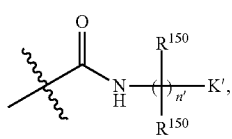

wherein n' is 0, 1, 2, 3, or 4; and K' and $R^{150}$ are as defined for formula (III), such compounds are referred to hereafter as Formula (IIIi).

In a more preferred embodiment, the invention comprises the compound according to Formula (III), wherein $G^2$ is

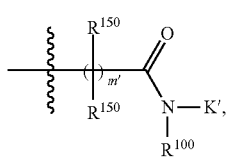

wherein m' is 0, 1, 2, 3, or 4; and K', $R^{100}$, and $R^{150}$ are as defined for formula (III), such compounds are referred to hereafter as Formula (IIIj).

In a more preferred embodiment, the invention comprises the compound according to Formula (III), wherein $G^2$ is

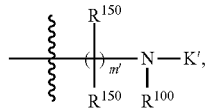

wherein m' is 0, 1, 2, 3, or 4; and K', $R^{100}$, and $R^{150}$ are as defined for formula (III), such compounds are referred to hereafter as Formula (IIIk).

In a more preferred embodiment, the invention comprises the compound according to Formula (III), wherein $G^2$ is

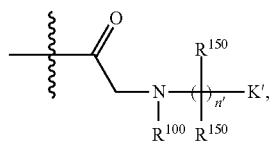

wherein n' is 0, 1, 2, 3, or 4; and K', $R^{100}$, and $R^{150}$ are as defined for formula (III), such compounds are referred to hereafter as Formula (IIIl).

In a more preferred embodiment, the invention comprises the compound according to Formula (III), wherein $G^2$ is

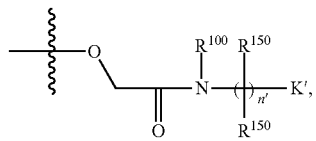

wherein n' is 0, 1, 2, 3, or 4; and K', $R^{100}$, and $R^{150}$ are as defined for formula (III), such compounds are referred to hereafter as Formula (IIIm).

In a more preferred embodiment, the invention comprises the compound according to Formula (III), wherein $G^2$ is

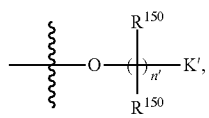

wherein n' is 0, 1, 2, 3, or 4; and K' and $R^{150}$ are as defined for formula (III), such compounds are referred to hereafter as Formula (IIIn).

In a more preferred embodiment, the invention comprises the compound according to Formula (III), wherein $G^2$ is

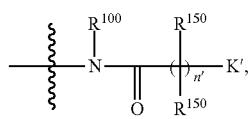

wherein n' is 0, 1, 2, 3, or 4; and K', $R^{100}$, and $R^{150}$ are as defined for formula (III), such compounds are referred to hereafter as Formula (IIIo).

In a more preferred embodiment, the invention comprises the compound according to Formula (III), wherein $G^2$ is

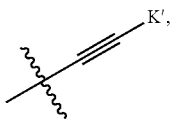

and K' is as defined for formula (III), such compounds are referred to hereafter as Formula (IIIp).

In a more preferred embodiment, the invention comprises the compound according to Formula (III), wherein $G^2$ is —$CH_2$—K'; and K' is as defined for formula (III), such compounds are referred to hereafter as Formula (IIIq).

Preferred compounds of formulas (IIIa)-(IIIq) include those wherein, $G^1$ is -$L^{10}$-R, wherein
  $L^{10}$ is —$[C(R^{150})_2]_m$—, —CO—, —$SO_2$—, or —$C_3$-$C_8$cycloalkyl, wherein m is 1, 2, 3, 4, 5, or 6; and R is aryl, heterocyclyl, or heteroaryl, wherein R is optionally substituted with 1 to 4 R';
such compounds are referred to hereafter as Formula (IIIr).

More preferred compounds of formulas (IIIa)-(IIIq) include those wherein,
  $G^1$ is -$L^{10}$-R, wherein
  $L^{10}$ a bond or —$[CH_2]_q$—, wherein q is 1, 2, or 3; and R is phenyl optionally substituted with 1 to 4 R';
such compounds are referred to hereafter as Formula (IIIs).

In another embodiment of the second aspect, the invention comprises the compound according to formula (IV) and (XXV),

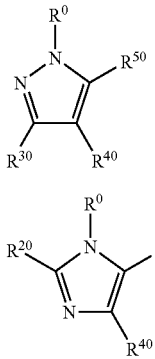

wherein $R^0$, $R^{20}$, $R^{30}$, $R^{40}$ and $R^{50}$ are as defined for formula III.

In another aspect, the invention comprises a compound of the formulae,

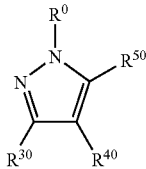

or a pharmaceutically acceptable salt thereof, wherein
one of $R^0$ and $R^{50}$ is $G^1$ and the other is $G^2$;
$R^{30}$ and $R^{40}$ are independently $R^C$;
$G^1$ is -$L^{10}$-R, wherein
  $L^{10}$ is a bond, $L^{50}$, $L^{60}$, -$L^{50}$-$L^{60}$-$L^{50}$-, or -$L^{60}$-$L^{50}$-$L^{60}$-, wherein each $L^{50}$ is independently —$[C(R^{150})_2]_m$—;
each $L^{60}$ is independently —CS—, —CO—, —$SO_2$—, —O—, —S—, —$N(R^{110})$—, —$CON(R^{110})$—, —$CONR^{11}ON(R^{110})$—, —$C(=NR^{110})$—, —$C(=NOR^{110})$—, or —$C(=N—N(R^{110})_2)$—, —$C_3$-$C_8$cycloalkyl-, or -heterocyclyl-,
wherein the cycloalkyl or heterocyclyl is optionally substituted with one to 4 $R^{140}$ groups;
or each $L^{60}$ is independently $C_2$-$C_6$ alidiyl,
wherein the alidiyl chain is optionally interrupted by —$C(R^{110})$—, —$C(R^{11})_2C(R^{110})_2$—, —$C(R^{110})$—$C(R^{110})$—, —$C(R^{110})_2O$—, —$C(R^{110})_2NR^{110}$—, —C≡C—, —O—, —S—, —$N(R^{100})CO$—, —$N(R^{100})CO_2$—, —$CON(R^{100})$—, —CO—, —$CO_2$—, —OC(=O)—, —$OC(=O)N(R^{100})$—, —$SO_2$—, —$N(R^{100})SO_2$—, or —$SO_2N(R^{100})$; and
R is aryl, heterocyclyl, heteroaryl, or —($C_3$-$C_6$)cycloalkyl, wherein R is optionally substituted with 1 to 4 R', wherein each R' is independently halogen, nitro, heterocyclyl, $C_2$-$C_6$ alkenyl, $C_2$-$C_6$ alkynyl, $C_3$-$C_8$ cycloalkyl, ($C_3$-$C_8$ cycloalkyl)-$C_1$-$C_6$ alkyl-, ($C_3$-$C_8$ cycloalkenyl)-$C_1$-$C_6$ alkyl-, ($C_3$-$C_8$ cycloalkyl)-$C_2$-$C_6$ alkenyl-, arylalkyl, aryloxy, aryl$C_{1-6}$ alkoxy, $C_1$-$C_6$ alkyl, $C_1$-$C_6$ haloalkyl, $SO_2R^{110}$, $OR^{110}$, $SR^{110}$, $N_3$, $SOR^{110}$, $COR^{110}$, $SO_2N(R^{110})_2$, $SO_2NR^{110}COR^{110}$, C≡N, $C(O)OR^{110}$, $CON(R^{110})_2$, $CON(R^{110})OR^{110}$, $OCON(R^{110})_2$, $NR^{11}COR^{110}$, $NR^{110}CON(R^{110})_2$, $NR^{110}COR^{110}$, —$C(=N—OH)R^{110}$, —$C(=S)N(R^{110})_2$, —$S(=O)N(R^{110})_2$, —$S(=O)OR^{110}$, —$N(R^{110})S(=O)_2R^{110}$, —$C(=O)N(R^{110})N(R^{110})_2$, —$OC(=O)$—$R^{110}$, —$OC(=O)$—$OR^{110}$ or $N(R^{110})_2$, wherein
each R' is optionally substituted with 1 to 4 groups which independently are -halogen, —$C_1$-$C_6$ alkyl, aryloxy $C_{0-6}$ alkyl$SO_2R^{110}$, $C_{0-6}$ alkyl$COOR^{110}$, $C_{1-6}$ alkoxyaryl, $C_1$-$C_6$ haloalkyl, —$SO_2R^{110}$, —$OR^{110}$, —$SR^{110}$, —$N_3$, —$SO_2R^{110}$, —$COR^{110}$, —$SO_2N(R^{110})_2$, —$SO_2NR^{110}COR^{110}$, —C≡N, —$C(O)OR^{110}$, —$CON(R^{110})_2$, —$CON(R^{110})OR^{110}$, —$OCON(R^{110})_2$, —$NR^{11}CR^{110}$, —$NR^{110}CON(R^{110})_2$, —$NR^{110}COOR^{110}$, or —$N(R^{110})_2$;
$G^2$ is -$L^{20}$-K', wherein
K' is aryl, heteroaryl, or heterocyclyl, each optionally substituted with one to four $R^K$ groups, wherein each $R^K$ is independently hydrogen, halogen, oxo, nitro, $CR^{110}=CR^{110}COOR^{110}$, aryloxy, aralkyloxy, aryloxyalkyl, aryl$C_0$-$C_6$ alkylcarboxy, aryl, —($C_1$-$C_6$)alkyl-aryl, heteroaryl, —($C_1$-$C_6$)alkyl-heteroaryl, heterocyclyl, —($C_1$-$C_6$)alkyl-heterocyclyl, heteroaryloxy, heterocyclyloxy, —Z, —Y—Z, or —X—Y—Z, wherein each $R^K$ is optionally substituted with 1 to 4 $R^{K'}$, wherein
each $R^{K'}$ is independently oxo, aryloxy, aralkyloxy, aryloxyalkyl, $C_1$-$C_6$ alkoxyaryl, aryl$C_0$-$C_6$ alkylcarboxy, —Z, —Y—Z, or —X—Y—Z,
or two $R^K$ bonded to the same carbon atom taken together with the carbon atom to which they are bonded form a $C_3$-$C_8$ cycloalkyl or heterocyclyl, each optionally substituted with 1 to 4 $R^{K'}$; and
$L^{20}$ is —$[C(R^{150})_2]_m$—$V^{20}$—$[C(R^{150})_2]_n$—, —$V^{20}$—$[C(R^{150})_2]_m$—$V^{20}$, —$V^{20}$—$[C(R^{150})_2]_m$—$V^{20}$—$[C(R^{150})_2]_n$; or —$V^{20}$—$[C(R^{150})_2]_m$—$V^{20}$—$[C(R^{150})_2]_n$—$V^{20}$, wherein
each $V^{20}$ is independently —$CH_2$—, —CH(Z)-, —$C(R^{110})(Z)$-, —$C(R^{110})_2$—, —$C(R^{110})_2C(R^{110})_2$—, —$C(O)C(R^{110})$=$C(R^{110})$—, —$C(R^{110})$=$C(R^{110})$—, —$C(R^{110})_2O$—, —$C(R^{110})_2NR^{110}$—, —$OC(R^{110})_2$—, —$NR^{110}C(R^{110})_2$—, —$OCH_2C(O)$—, —$OCH_2C(O)N(R^{100})$—, —C≡C—, —O—, —$N(R^{100})$—, —S—, —$SO_2$—, —N($R^{100}$)CO—, —N($R^{100}$)$CO_2$—, —CON($R^{100}$)—, —CON($R^{110}$)O—, —CO—, —CS—, —$CO_2$—, —OC(=O)—, —OC(=O)N($R^{100}$)—, —N($R^{100}$)C(=O)O—, —N($R^{100}$)$SO_2$—, —$SO_2$N($R^{100}$)—, —$NR^{100}CONR^{100}$—, or —$NR^{100}CSNR^{100}$—, or $V^{20}$ is $C_{2-6}$ alidiyl, wherein alidiyl chain is optionally interrupted by —C($R^{110}$)$_2$—, —C($R^{110}$)$_2$C($R^{110}$)$_2$—, —C($R^{110}$)=C($R^{110}$)—, —C($R^{110}$)$_2$O—, —C($R^{110}$)$_2$$NR^{110}$—, —C($R^{110}$)$NR^{110}$—, —C≡C—, —O—, —S—, —N($R^{100}$)CO—, —N($R^{100}$)$CO_2$—, —CON($R^{100}$)—, —CON($R^{110}$)—, —CON($R^{110}$)O—, —CO—, —$CO_2$—, —OC(=O)—, —OC(=O)N($R^{100}$)—, —$SO_2$—, —N($R^{100}$)$SO_2$— or —$SO_2$N($R^{100}$)—;

or $V^{20}$ is $C_3$-$C_6$cycloalkyl-, $C_3$-$C_6$cyclohaloalkyl, or heterocyclyl, each of which is optionally substituted with 1 to 4 $R^{90}$, wherein each $R^{90}$ is independently halogen, oxo, $C_1$-$C_6$ haloalkyl, $C_1$-$C_6$ alkyl, $C_1$-$C_6$ alkyloxy, $C_0$-$C_6$ alkyl or $C_1$-$C_6$ alkyl-$COOR^{110}$;

each $R^C$ is independently -$L^{30}$-$R^{70}$, wherein
each $L^{30}$ is independently a bond or —$(CH_2)_m$—$V^{10}$—$(CH_2)_n$—, wherein
$V^{10}$ is —C($R^{110}$)$_2$—, —C($R^{110}$)$_2$C($R^{110}$)$_2$—, —C($R^{111}$)=C($R^{110}$)—, —C($R^{110}$)$_2$O—, —C($R^{110}$)$_2$$NR^{110}$—, —C≡C—, —O—, —S—, —$NR^{110}$—, —N($R^{100}$)CO—, —N($R^{110}$)$CO_2$—, —OCO—, —CO—, —CS—, —$CONR^{100}$—, —C(=N—$R^{110}$)—, —C(=N—$OR^{110}$)—, —C[=N—N($R^{110}$)$_2$], —$CO_2$—, —OC(=O)—, —OC(=O)N($R^{100}$)—, —$SO_2$—, —N($R^{100}$)$SO_2$—, —$SO_2$N($R^{100}$)—, —$NR^{100}CONR^{100}$—, —$NR^{100}CSNR^{100}$—, $C_3$-$C_6$cyclo alkyl, or $C_3$-$C_6$ cyclohaloalkyl;

or each $L^{30}$ is independently $C_2$-$C_6$ alidiyl, wherein the alidiyl chain is optionally interrupted by —C($R^{110}$)$_2$—, —C($R^{110}$)$_2$C($R^{110}$)$_2$—, —C($R^{110}$)=C($R^{110}$)—, —C($R^{110}$)$_2$O—, —C($R^{110}$)$_2$$NR^{110}$—, —C≡C—, —O—, —S—, —N($R^{100}$)CO—, —N($R^{100}$)$CO_2$—, —$NR^{110}$—, —CON($R^{100}$)—, —CO—, —$CO_2$—, —OC(=O)—, —OC(=O)N($R^{100}$)—, —$SO_2$—, —N($R^{100}$)$SO_2$—, or —$SO_2$N($R^{100}$)—; and each $R^{70}$ is independently hydrogen, halogen, nitro, aryl, heteroaryl, heterocyclyl, —Z, —Y—Z, or —X—Y—Z,
wherein the aryl, heteroaryl, and heterocyclyl, are each optionally substituted with 1 to 4 $R^{70a}$, wherein each $R^{70a}$ is independently aryloxy, aralkyloxy, aryloxyalkyl, aryl$C_0$-$C_6$ alkylcarboxy, C($R^{110}$)=C($R^{110}$)—COOH, heterocyclyl, heterocyclyloxy, heteroaryloxy, oxo, —Z, —Y'—Z, or —X—Y—Z, wherein each $R^{70a}$ is optionally substituted with 1 to 4 $R^{30}$, wherein each $R^{80}$ is independently halogen, $C_1$-$C_6$ alkyl, $C_1$-$C_6$ alkoxy, $C_1$-$C_6$ haloalkyl, $C_1$-$C_6$ haloalkyl($OR^{110}$), $C_0$-$C_6$ alkyl$OR^{110}$, $C_0$-$C_6$ alkylCON($R^{110}$)$_2$, $C_0$-$C_6$ alkyl$COR^{110}$, $C_0$-$C_6$ alkyl$COOR^{110}$, or $C_0$-$C_6$ alkyl$SO_2R^{110}$, each $R^{100}$ is independently —$R^{110}$, —C(=O)$R^{110}$, —$CO_2R^{110}$, or —$SO_2R^{110}$;

each $R^{110}$ is independently -hydrogen, —$C_1$-$C_6$ alkyl, $C_2$-$C_6$ alkenyl, $C_2$-$C_6$ alkynyl, $C_3$-$C_8$ cycloalkyl, ($C_3$-$C_8$ cycloalkyl)-$C_1$-$C_6$ alkyl-, ($C_3$-$C_8$ cycloalkenyl)-$C_1$-$C_6$ alkyl-, ($C_3$-$C_8$ cycloalkyl)-$C_2$-$C_6$ alkenyl-, —$C_1$-$C_6$ haloalkyl, —N($R^{12}$)$_2$, aryl, —($C_1$-$C_6$)alkyl-aryl, heteroaryl, —($C_1$-$C_6$)alkyl-heteroaryl, heterocyclyl, or —($C_1$-$C_6$)alkyl-heterocyclyl,
wherein any of $R^{110}$ is optionally substituted with 1 to 4 radicals of $R^{120}$;

each $R^{120}$ is independently halogen, cyano, nitro, oxo, —B($OR^{130}$)$_2$, $C_0$-$C_6$ alkylN($R^{13}$)$_2$, $C_1$-$C_6$haloalkyl, $C_1$-$C_6$ alkyl, $C_1$-$C_6$ alkoxy, ($C_0$-$C_6$ alkyl)C=O($OR^{130}$), $C_0$-$C_6$ alkyl$OR^{130}$, $C_0$-$C_6$ alkyl$COR^{130}$, $C_0$-$C_6$ alkl$SO_2R^{130}$, $C_0$-$C_6$ alkylCON($R^{130}$)$_2$, $C_0$-$C_6$ alkyl$CONR^{130}OR^{130}$, $C_0$-$C_6$ alkyl$SO_2N(R^{130})_2$, $C_0$-$C_6$ alkyl$SR^{130}$, $C_0$-$C_6$ haloalkyl$OR^{130}$, $C_0$-$C_6$ alkylCN, aryloxy, aralkyloxy, aryloxyalkyl, $C_{1-6}$ alkoxyaryl, aryl$C_{0-6}$ alkylcarboxy, —$C_0$-$C_6$ alkylN($R^{130}$)$_2$, —$NR^{130}SO_2R^{130}$, or —$OC_{0-6}$ alkyl-$COOR^{130}$;

each $R^{130}$ is independently hydrogen, $C_1$-$C_6$ alkyl, $C_2$-$C_6$ alkenyl, $C_2$-$C_6$ alkynyl, $C_3$-$C_8$ cycloalkyl, ($C_3$-$C_8$ cycloalkyl)-$C_1$-$C_6$ alkyl-, ($C_3$-$C_8$ cycloalkenyl)-$C_1$-$C_6$ alkyl-, or ($C_3$-$C_8$ cycloalkyl)-$C_2$-$C_6$ alkenyl-;

each $R^{140}$ is independently $C_1$-$C_6$ alkyl, $C_1$-$C_6$ alkoxy, halogen, $C_1$-$C_6$ haloalkyl, $C_0$-$C_6$ alkylCON($R^{110}$)$_2$, $C_0$-$C_6$ alkyl$CONR^{110}OR^{110}$, $C_0$-$C_6$ alkyl$OR^{110}$, or $C_0$-$C_6$ alkyl-$COOR^{110}$; and each $R^{150}$ is independently hydrogen, halogen, $OR^{130}$, ($C_1$-$C_6$)alkyl, ($C_3$-$C_6$)cycloalkyl, or ($C_1$-$C_6$)haloalkyl, wherein
each alkyl or cycloalkyl is optionally substituted with at least one group which are each independently halogen, cyano, nitro, azido, $OR^{130}$, C(O)$R^{130}$, C(O)$OR^{130}$, C(O)N($R^{130}$)$_2$, N($R^{130}$)$_2$, N($R^{130}$)C(O)$R^{130}$, N($R^{130}$)S(O)$_2R^{130}$, OC(O)$OR^{130}$, OC(O)N($R^{130}$)$_2$, N($R^{130}$)C(O)$OR^{130}$, N($R^{130}$)C(O)N($R^{130}$), $SR^{130}$, S(O)$R^{130}$, S(O)$_2R^{130}$, or S(O)$_2$N($R^{130}$)$_2$;

X is —O—, —S—, or —N($R^{100}$)—;
each Y is independently —[C($R^{150}$)$_2$]$_p$—, —$C_2$-$C_6$ alkenyl, $C_3$-$C_8$ cycloalkyl, heterocyclyl, aryl, or heteroaryl, wherein p is 1, 2, 3, 4, 5, or 6; and the aryl, heteroaryl, cycloalkyl, or heterocyclyl is optionally substituted with 1 to 3 Z groups;

each Y' is independently —[C($R^{150}$)$_2$]$_p$—, —$C_2$-$C_6$ alkenyl, $C_3$-$C_8$ cycloalkyl, or heterocyclyl, wherein the cycloalkyl or heterocyclyl is optionally substituted with 1 to 3 Z groups; and each Z is independently —H, halogen, —$OR^{110}$, —$SR^{110}$, —C(=O)$R^{110}$, —C(=O)$OR^{110}$, —C(=O)N($R^{110}$)$_2$, —N($R^{100}$)$_2$, —$N_3$, —$NO_2$, —C(=N—OH)$R^{110}$, —C(=S)N($R^{110}$)$_2$, —CN, —S(=O)$R^{110}$, —S(=O)N($R^{110}$)$_2$, —S(=O)$OR^{110}$, —S(=O)$_2R^{110}$, S(=O)$_2$N($R^{110}$)$_2$, —$NR^{110}COR^{110}$, —N($R^{110}$)C(=O)N($R^{110}$)$_2$, —N($R^{110}$)$COOR^{110}$, —N($R^{110}$)S(=O)$_2R^{110}$, —C(=O)N($R^{110}$)N($R^{110}$)$_2$, —C(=O)N($R^{110}$)($OR^{110}$), —OC(=O)—$R^{110}$, —OC(=O)—$OR^{110}$, or —OC(=O)—N($R^{110}$)$_2$; and each m and n is independently 0, 1, 2, 3, 4, 5, or 6,
provided that the compound is not
(i) a compound of Table 1;
(ii) 4-[1-(2-chlorophenyl)-3-(trifluoromethyl)-1H-pyrazol-5-yl]-N-[3-methyl-1-(4-methylphenyl)-1H-pyrazol-5-yl]benzamide; and
(iii) 4-(1-(2-chlorophenyl)-3-(trifluoromethyl)-1H-pyrazol-5-yl)-N-(3-methyl-1-phenyl-1H-pyrazol-5-yl)benzamide.

In another aspect, the invention comprises a compound of the formulae,

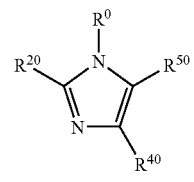

(XXVa)

or a pharmaceutically acceptable salt thereof, wherein
one of $R^0$ and $R^{20}$ is $G^1$ and the other is $G^2$;
$R^{40}$ and $R^{50}$ are independently $R^C$;
$G^1$ is -$L^{10}$-R, wherein
$L^{10}$ is a bond, $L^{50}$, $L^{60}$, -$L^{50}$-$L^{60}$-$L^{50}$-, or -$L^{60}$-$L^{50}$-$L^{60}$-, wherein
each $L^{50}$ is independently —[C($R^{150}$)$_2$]$_m$—;
each $L^{60}$ is independently —CS—, —CO—, —SO$_2$—, —O—, —S—, —N($R^{110}$)—, —CON($R^{110}$)—, —CONR$^{110}$N($R^{110}$)—, —C(=N$R^{110}$)—, —C(=NOR$^{110}$)—, or —C(=N—N($R^{110}$)$_2$)—, —C$_3$-C$_8$cycloalkyl-, or -heterocyclyl-,
wherein the cycloalkyl or heterocyclyl is optionally substituted with one to 4 $R^{140}$ groups;
or each $L^{60}$ is independently $C_2$-$C_6$ alidiyl,
wherein the alidiyl chain is optionally interrupted by —C($R^{110}$)$_2$—, —C($R^{110}$)$_2$C($R^{110}$)$_2$—, —C($R^{110}$)=C($R^{110}$)—, —C($R^{110}$)$_2$O—, —C($R^{110}$)$_2$NR$^{110}$—, —C≡C—, —O—, —S—, —N($R^{100}$)CO—, —N($R^{100}$)CO$_2$—, —CON($R^{100}$)—, —CO—, —CO$_2$—, —OC(=O)—, —OC(=O)N($R^{100}$)—, —SO$_2$—, —N($R^{100}$)SO$_2$—, or —SO$_2$N($R^{100}$); and
R is aryl, heterocyclyl, heteroaryl, or —($C_3$-$C_6$)cycloalkyl, wherein R is optionally substituted with 1 to 4 R', wherein
each R' is independently halogen, nitro, heterocyclyl, $C_2$-$C_6$ alkenyl, $C_2$-$C_6$ alkynyl, $C_3$-$C_8$ cycloalkyl, ($C_3$-$C_8$ cycloalkyl)-$C_1$-$C_6$ alkyl-, ($C_3$-$C_8$ cycloalkenyl)-$C_1$-$C_6$ alkyl-, ($C_3$-$C_8$ cycloalkyl)-$C_2$-$C_6$ alkenyl-, arylalkyl, aryloxy, arylC$_{1-6}$ alkoxy, $C_1$-$C_6$ alkyl, $C_1$-$C_6$ haloalkyl, SO$_2$R$^{110}$, OR$^{110}$, SR$^{110}$, N$_3$, SOR$^{110}$, COR$^{110}$, SO$_2$N($R^{110}$)$_2$, SO$_2$NR$^{110}$COR$^{110}$, C≡N, C(O)OR$^{110}$, CON($R^{110}$)$_2$, CON($R^{110}$)OR$^{110}$, OCON($R^{110}$)$_2$, NR$^{110}$COR$^{110}$, NR$^{110}$CON($R^{110}$)$_2$, NR$^{110}$COOR$^{110}$, —C(=N—OH)R$^{110}$, —C(=S)N($R^{110}$)$_2$, —S(=O)N($R^{110}$)$_2$, —S(=O)OR$^{110}$, —N($R^{110}$)S(=O)$_2$R$^{110}$, —C(=O)N($R^{110}$)N($R^{110}$)$_2$, —OC(=O)—R$^{110}$, —OC(=O)—OR$^{110}$ or N($R^{110}$)$_2$, wherein
each R' is optionally substituted with 1 to 4 groups which independently are -halogen, —$C_1$-$C_6$ alkyl, aryloxy $C_{0-6}$ alkylSO$_2$R$^{110}$, $C_{0-6}$ alkylCOOR$^{110}$, $C_{1-6}$ alkoxyaryl, $C_1$-$C_6$ haloalkyl, —SO$_2$R$^{110}$, —OR$^{110}$, —SR$^{110}$, —N$_3$, —SO$_2$R$^{110}$, —COR$^{110}$, —SO$_2$N($R^{110}$)$_2$, —SO$_2$NR$^{110}$COR$^{110}$, —C≡N, —C(O)OR$^{110}$, —CON($R^{110}$)$_2$, —CON($R^{110}$)OR$^{110}$, —OCON($R^{110}$)$_2$, —NR$^{11}$COR$^{110}$, —NR$^{110}$CON($R^{110}$)$_2$, —NR$^{110}$COOR$^{110}$, or —N($R^{110}$)$_2$;
$G^2$ is -$L^{20}$-K', wherein
K' is aryl, heteroaryl, or heterocyclyl, each optionally substituted with one to four $R^K$ groups, wherein each $R^K$ is independently hydrogen, halogen, oxo, nitro, CR$^{110}$=CR$^{110}$COOR$^{110}$, aryloxy, aralkyloxy, aryloxyalkyl, arylC$_0$-$C_6$ alkylcarboxy, aryl, —($C_1$-$C_6$)alkyl-aryl, heteroaryl, —($C_1$-$C_6$)alkyl-heteroaryl, heterocyclyl, —($C_1$-$C_6$)alkyl-heterocyclyl, heteroaryloxy, heterocyclyloxy, —Z, —Y—Z, or —X—Y—Z, wherein each $R^K$ is optionally substituted with 1 to 4 $R^{K'}$, wherein
each $R^{K'}$ is independently oxo, aryloxy, aralkyloxy, aryloxyalkyl, $C_1$-$C_6$ alkoxyaryl, arylC$_0$-$C_6$ alkylcarboxy, —Z, —Y—Z, or —X—Y—Z,
or two $R^K$ bonded to the same carbon atom taken together with the carbon atom to which they are bonded form a $C_3$-$C_8$ cycloalkyl or heterocyclyl, each optionally substituted with 1 to 4 $R^{K'}$; and
$L^{20}$ is —[C($R^{150}$)$_2$]$_m$—$V^{20}$—[C($R^{150}$)$_2$]$_n$—, —$V^{20}$—[C($R^{150}$)$_2$]$_m$—$V^{20}$, —$V^{20}$—[C($R^{150}$)$_2$]$_m$—$V^{20}$—[C($R^{150}$)$_2$]$_n$; or —$V^{20}$—[C($R^{150}$)$_2$]$_m$—$V^{20}$—[C($R^{150}$)$_2$]$_n$—$V^{20}$; wherein each $V^{20}$ is independently —CH$_2$—, —CH(Z)-, —C($R^{110}$)(Z)-, —C($R^{110}$)$_2$—, —C($R^{110}$)$_2$C($R^{110}$)$_2$—, —C(O)C($R^{110}$)=C($R^{110}$)—, —C($R^{110}$)=C($R^{110}$)—, —C($R^{110}$)$_2$O—, —C($R^{110}$)$_2$NR$^{110}$—, —OC($R^{110}$)$_2$—, —NR$^{110}$C($R^{110}$)$_2$—, —OCH$_2$C(O)—, —OCH$_2$C(O)N($R^{110}$)—, —C≡C—, —O—, —N($R^{100}$)—, —S—, —SO$_2$—, N($R^{100}$)CO—, —N($R^{100}$)CO$_2$—, —CON($R^{100}$)—, —CON($R^{110}$)O—, —CO—, —CS—, —CO$_2$—, —OC(=O)—, —OC(=O)N($R^{100}$)—, —N($R^{100}$)C(=O)O—, —N($R^{100}$)SO$_2$—, —SO$_2$N($R^{100}$)—, —NR$^{100}$CONR$^{100}$—, or —NR$^{100}$CSNR$^{100}$—,
or $V^{20}$ is $C_{2-6}$ alidiyl, wherein alidiyl chain is optionally interrupted by —C($R^{110}$)$_2$—, —C($R^{110}$)$_2$C($R^{110}$)$_2$—, —C($R^{110}$)=C($R^{110}$)—, —C($R^{110}$)—, —C($R^{110}$)$_2$NR$^{110}$—, —C($R^{110}$)NR$^{110}$—, —C≡C—, —O—, —S—, —N($R^{100}$)CO—, —N($R^{100}$)CO$_2$—, —CON($R^{100}$)—, —CON($R^{110}$)—, —CON($R^{110}$)O—, —CO—, —CO$_2$—, —OC(=O)—, —OC(=O)N($R^{100}$)—, —SO$_2$—, —N($R^{100}$)SO$_2$— or —SO$_2$N($R^{100}$)—;
or $V^{20}$ is $C_3$-$C_6$cycloalkyl-, $C_3$-$C_6$cyclohaloalkyl, or heterocyclyl, each of which is optionally substituted with 1 to 4 $R^{90}$, wherein
each $R^{90}$ is independently halogen, oxo, $C_1$-$C_6$ haloalkyl, $C_1$-$C_6$ alkyl, $C_1$-$C_6$ alkyloxy, $C_0$-$C_6$ alkyl or $C_1$-$C_6$ alkyl-COOR$^{110}$;
each $R^C$ is independently -$L^{30}$-$R^{70}$, wherein
each $L^{30}$ is independently a bond or —(CH$_2$)$_m$—$V^{10}$—(CH$_2$)$_n$—, wherein
$V^{10}$ is —C($R^{110}$)$_2$—, —C($R^{110}$)$_2$C($R^{110}$)$_2$—, —C($R^{110}$)=C($R^{110}$)—, —C($R^{110}$)$_2$O—, —C($R^{110}$)$_2$NR$^{110}$—, —C≡C—, —O—, —S—, —NR$^{110}$—, —N($R^{100}$)CO—, —N($R^{110}$)CO$_2$—, —OCO—, —CO—, —CS—, —CONR$^{100}$—, —C(=N—R$^{110}$)—, —C(=N—OR$^{110}$)—, —C[=N—N($R^{110}$)$_2$], —CO$_2$—, —OC(=O)—, —OC(=O)N($R^{100}$)—, —SO$_2$—, —N($R^{100}$)SO$_2$—, —SO$_2$N($R^{100}$)—, —NR$^{100}$CONR$^{100}$—, —NR$^{100}$CSNR$^{100}$—, $C_3$-$C_6$cyclo alkyl, or $C_3$-$C_6$ cyclohaloalkyl;
or each $L^{30}$ is independently $C_2$-$C_6$ alidiyl,
wherein the alidiyl chain is optionally interrupted by —C($R^{110}$)$_2$—, —C($R^{110}$)$_2$C($R^{110}$)$_2$—, —C($R^{110}$)=C($R^{110}$)—, —C($R^{110}$)$_2$O—, —C($R^{110}$)$_2$NR$^{110}$—, —C≡C—, —O—, —S—, —N($R^{100}$)CO—, —N($R^{110}$)CO$_2$—, —NR$^{110}$—, —CON($R^{100}$)—, —CO—, —CO$_2$—, —OC(=O)—, —OC(=O)N($R^{100}$)—, —SO$_2$—, —N($R^{100}$)SO$_2$—, or —SO$_2$N($R^{110}$)—; and
each $R^{70}$ is independently hydrogen, halogen, nitro, aryl, heteroaryl, heterocyclyl, —Z, —Y—Z, or —X—Y—Z, wherein the aryl, heteroaryl, and heterocyclyl, are each optionally substituted with 1 to 4 $R^{70a}$, wherein
each $R^{70a}$ is independently aryloxy, aralkyloxy, aryloxyalkyl, arylC$_0$-$C_6$ alkylcarboxy, C($R^{110}$)=C($R^{110}$)—COOH, heterocyclyl, heterocyclyloxy, heteroaryloxy, oxo, —Z, —Y'—Z, or —X—Y—Z, wherein each $R^{70a}$ is optionally substituted with 1 to 4 $R^{80}$,
wherein each $R^{80}$ is independently halogen, $C_1$-$C_6$ alkyl, $C_1$-$C_6$ alkoxy, $C_1$-$C_6$ haloalkyl, $C_1$-$C_6$ haloalkyl(OR$^{110}$), $C_0$-$C_6$ alkylOR$^{110}$, $C_0$-$C_6$ alkylCON($R^{110}$)$_2$, $C_0$-$C_6$ alkylCOR$^{110}$, $C_0$-$C_6$ alkylCOOR$^{110}$, or $C_0$-$C_6$ alkylSO$_2$R$^{110}$,
each $R^{100}$ is independently —$R^{110}$, —C(=O)R$^{110}$, —CO$_2$R$^{110}$, or —SO$_2$R$^{110}$;
each $R^{110}$ is independently -hydrogen, —$C_1$-$C_6$ alkyl, $C_2$-$C_6$ alkenyl, $C_2$-$C_6$ alkynyl, $C_3$-$C_8$ cycloalkyl, ($C_3$-$C_8$ cycloalkyl)-$C_1$-$C_6$ alkyl-, ($C_3$-$C_8$ cycloalkenyl)-$C_1$-$C_6$ alkyl-, ($C_3$-$C_8$ cycloalkyl)-$C_2$-$C_6$ alkenyl-, —$C_1$-$C_6$ haloalkyl, —N($R^{120}$)$_2$, aryl, —($C_1$-$C_6$)alkyl-aryl, heteroaryl, —($C_1$-$C_6$)alkyl-heteroaryl, heterocyclyl, or —($C_1$-$C_6$)alkyl-heterocyclyl, wherein any of $R^{110}$ is optionally substituted with 1 to 4 radicals of $R^{120}$;

each $R^{120}$ is independently halogen, cyano, nitro, oxo, —B(O$R^{130}$)$_2$, $C_0$-$C_6$ alkylN($R^{13}$)$_2$, $C_1$-$C_6$haloalkyl, $C_1$-$C_6$ alkyl, $C_1$-$C_6$ alkoxy, ($C_0$-$C_6$ alkyl)C=O(O$R^{130}$), $C_0$-$C_6$ alkylO$R^{130}$, $C_0$-$C_6$ alkylCO$R^{130}$, $C_0$-$C_6$ alklSO$_2$$R^{130}$, $C_0$-$C_6$ alkylCON($R^{130}$)$_2$, $C_0$-$C_6$ alkylCON$R^{130}$O$R^{130}$, $C_0$-$C_6$ alkylSO$_2$N($R^{30}$)$_2$, $C_0$-$C_6$ alkylS$R^{130}$, $C_0$-$C_6$ haloalkylO$R^{130}$, $C_0$-$C_6$ alkylCN, aryloxy, aralkyloxy, aryloxyalkyl, $C_{1-6}$ alkoxyaryl, aryl$C_{0-6}$ alkylcarboxy, —$C_0$-$C_6$ alkylN($R^{130}$)$_2$, —N$R^{130}$SO$_2$$R^{130}$, or —OC$_{0-6}$ alkyl-COO$R^{130}$;

each $R^{130}$ is independently hydrogen, $C_1$-$C_6$ alkyl, $C_2$-$C_6$ alkenyl, $C_2$-$C_6$ alkynyl, $C_3$-$C_8$ cycloalkyl, ($C_3$-$C_8$ cycloalkyl)-$C_1$-$C_6$ alkyl-, ($C_3$-$C_8$ cycloalkenyl)-$C_1$-$C_6$ alkyl-, or ($C_3$-$C_8$ cycloalkyl)-$C_2$-$C_6$ alkenyl-;

each $R^{140}$ is independently $C_1$-$C_6$ alkyl, $C_1$-$C_6$ alkoxy, halogen, $C_1$-$C_6$ haloalkyl, $C_0$-$C_6$ alkylCON($R^{110}$)$_2$, C≡C alkylCON$R^{110}$O$R^{110}$, $C_0$-$C_6$ alkylO$R^{110}$, or $C_0$-$C_6$ alkyl-COO$R^{110}$; and each $R^{150}$ is independently hydrogen, halogen, O$R^{130}$, ($C_1$-$C_6$)alkyl, ($C_3$-$C_6$)cycloalkyl, or ($C_1$-$C_6$)haloalkyl, wherein each alkyl or cycloalkyl is optionally substituted with at least one group which are each independently halogen, cyano, nitro, azido, O$R^{130}$, C(O)$R^{130}$, C(O)O$R^{130}$, C(O)N($R^{130}$)$_2$, N($R^{130}$)$_2$, N($R^{130}$)C(O)$R^{130}$, N($R^{130}$)S(O)$_2$$R^{130}$, OC(O)O$R^{130}$, OC(O)N($R^{130}$)$_2$, N($R^{130}$)C(O)O$R^{130}$, N($R^{130}$)C(O)N($R^{130}$), S$R^{130}$, S(O)$R^{130}$, S(O)$_2$$R^{130}$, or S(O)$_2$N($R^{130}$)$_2$;

X is —O—, —S—, or —N($R^{100}$)—;

each Y is independently —[C($R^{150}$)$_2$]$_p$—, —$C_2$-$C_6$ alkenyl, $C_3$-$C_8$ cycloalkyl, heterocyclyl, aryl, or heteroaryl, wherein p is 1, 2, 3, 4, 5, or 6 and the aryl, heteroaryl, cycloalkyl, or heterocyclyl is optionally substituted with 1 to 3 Z groups; and each $Y^1$ is independently —[C($R^{150}$)$_2$]$_p$—, —$C_2$-$C_6$ alkenyl, $C_3$-$C_8$ cycloalkyl, or heterocyclyl, wherein the cycloalkyl or heterocyclyl is optionally substituted with 1 to 3 Z groups; and each Z is independently —H, halogen, —O$R^{110}$, —S$R^{110}$, —C(=O)$R^{110}$, —C(=O)O$R^{110}$, —C(=O)N($R^{110}$)$_2$, —N($R^{100}$)$_2$, —N$_3$, —NO$_2$, —C(=N—OH)$R^{110}$, —C(=S)N($R^{110}$)$_2$, —CN, —S(=O)$R^{110}$, —S(=O)N($R^{110}$)$_2$, —S(=O)O$R^{110}$, —S(=O)$_2$$R^{110}$, —S(=O)$_2$N($R^{110}$)$_2$, —N$R^{110}$CO$R^{110}$, —N($R^{110}$)C(=O)N($R^{110}$)$_2$, —N($R^{110}$)COO$R^{110}$, —N($R^{110}$)S(=O)$_2$$R^{110}$, —C(=O)N($R^{110}$)N($R^{110}$)$_2$, —C(=O)N($R^{110}$)(O$R^{110}$), —OC(=O)—$R^{110}$, —OC(=O)—O$R^{110}$, or —OC(=O)—N($R^{110}$)$_2$; and each m and n is independently 0, 1, 2, 3, 4, 5, or 6, provided that the compound is not
(i) a compound of Table 1; and
(ii) (1-benzyl-1H-imidazol-2-yl)methyl 4-(1-(2-chlorophenyl)-3-(trifluoromethyl)-1H-pyrazol-5-yl)benzoate.

In another embodiment, the invention comprises the compound according to formula (IVa) wherein $R^0$ is $G^1$ and $R^{50}$ is $G^2$, such compounds are referred to hereafter as Formula (IVg).

In another embodiment, the invention comprises the compound according to Formula (XXVa), wherein $R^0$ is $G^1$ and $R^{20}$ is $G^2$, such compounds are referred to hereafter as Formula (XXVg).

The invention also provides the compound according to Formulae (IVa) and (IVg); and (XXVa) and (XXVg), wherein $G^2$ is -$L^{20}$-K', wherein
K' is aryl, heteroaryl, or heterocyclyl, each optionally substituted with 1 to 4 $R^K$ groups; and $L^{20}$ is —[C($R^{150}$)$_2$]$_{m'}$—$V^{20}$—[C($R^{150}$)$_2$]$_{n'}$—, —$V^{20}$—[C($R^{150}$)$_2$]$_{m'}$—$V^{20}$, or —$V^{20}$—[C($R^{150}$)$_2$]$_{m'}$—$V^{20}$—[C($R^{150}$)$_2$]$_{n'}$, wherein m' and n' are independently 0, 1, 2, 3, or 4; and $V^{20}$ is —CH(Z)-, —C($R^{110}$)(Z)-, —C($R^{110}$)$_2$—, —C($R^{110}$)$_2$C($R^{110}$)$_2$—, —C($R^{11}$)=C($R^{11}$)—, —C≡C—, —O—, —N($R^{100}$)—, —S—, —SO$_2$—, —N($R^{100}$)CO—, —N($R^{100}$)CON($R^{100}$)—, —CON($R^{100}$)—, —OCH$_2$C(O)—, —OCH$_2$C(O)N($R^{100}$)—, —CO—, —CO$_2$—, —OC(=O)—, —N($R^{100}$)SO$_2$—, or —SO$_2$N($R^{100}$)—;

such compounds are referred to hereafter as Formula (IVb) and (XXVb) respectively.

The invention also provides the compound according to Formulae (IVa) and (IVg); and (XXVa) and (XXVg), wherein $G^1$ is -$L^{10}$-R, wherein
$L^{10}$ is a bond, $L^{50}$, or $L^{60}$, wherein
$L^{50}$ is —[CH$_2$]$_q$—, wherein q is 1, 2, or 3;
$L^{60}$ is —CS—, —CO—, —SO$_2$—, or —CON($R^{110}$)—; and
R is aryl, heterocyclyl, or heteroaryl, wherein R is optionally substituted with 1 to 4 R';

such compounds are referred to hereafter as Formula (IVc) and (XXVc) respectively.

The invention also provides the compound according to Formula (IVb) and (XXVb), wherein
$G^2$ is -$L^{20}$-K', wherein
K' is aryl or heteroaryl, optionally substituted with 1 to 4 $R^K$ groups; and
$L^{20}$ is —CH$_2$—, —C($R^{110}$)$_2$—, —C($R^{110}$)$_2$C($R^{110}$)$_2$—, —C($R^{110}$)—, or —C≡C—;

such compounds are referred to hereafter as Formula (IVd) and (XXVd) respectively.

The invention also provides the compound according to Formula (IVb) and (XXVb), wherein
$G^2$ is -$L^{20}$-K', wherein
K' is aryl or heteroaryl, optionally substituted with 1 to 4 $R^K$ groups; and
$L^{20}$ is —[C($R^{150}$)$_2$]$_{m'}$—$V^{20}$—, or —$V^{20}$—[c($R^{150}$)$_2$]$_{m'}$—, wherein m' is 0, 1, 2, 3, or 4; and
$V^{20}$ is —O—, —N($R^{100}$)—, —S—, —SO$_2$—, —N($R^{100}$)CO—, —N($R^{100}$)CON($R^{100}$)—, —CON($R^{100}$)—, —CO—, —CO$_2$—, —OC(=O)—, —N($R^{100}$)SO$_2$—, or —SO$_2$N($R^{100}$)—;

such compounds are referred to hereafter as Formula (IVe) and (XXVe) respectively.

The invention also provides the compound according to Formula (IVb) and (XXVb), wherein
$G^2$ is -$L^{20}$-K', wherein
K' is aryl or heteroaryl, optionally substituted with 1 to 4 $R^K$ groups; and
L 20 is —$V^{21}$—[c($R^{150}$)$_2$]$_{m'}$—$V^{22}$—[C($R^{15}$)$_2$]$_{m'}$— or —$V^{22}$—[C($R^{150}$)$_2$]$_{m'}$—$V^{21}$—[C($R^{150}$)$_2$]$_{n'}$—,
wherein
$V^{21}$ is —O—, —N($R^{100}$)—, —S—; and
$V^{22}$ is —SO$_2$—, —N($R^{100}$)CO—, —CON($R^{100}$)—, —CO—, —CO$_2$—, —OC(=O)—, —N($R^{100}$)SO$_2$—, or —SO$_2$N($R^{100}$)—;

such compounds are referred to hereafter as Formula (IVf) and (XXVf) respectively.

The invention also provides the compounds according to Formula (III), of Formulae (V)-(XVII) and (XXVI)-(XXXVIII).

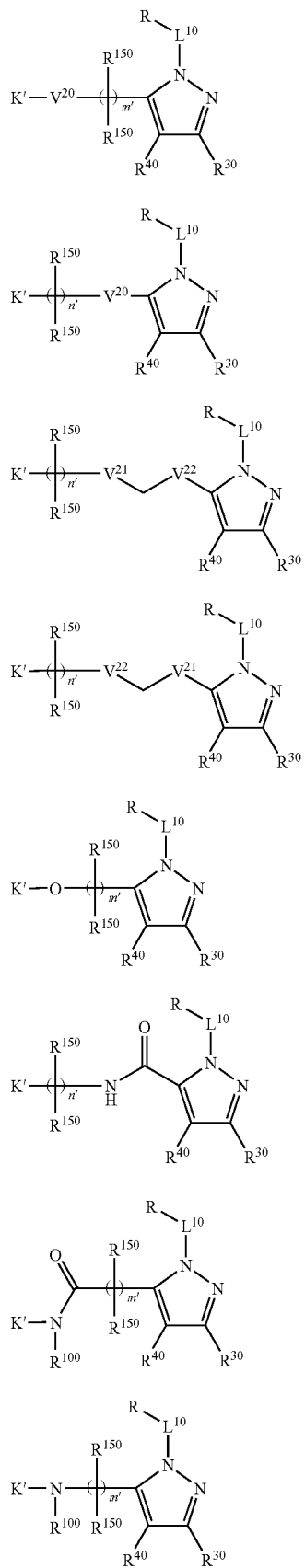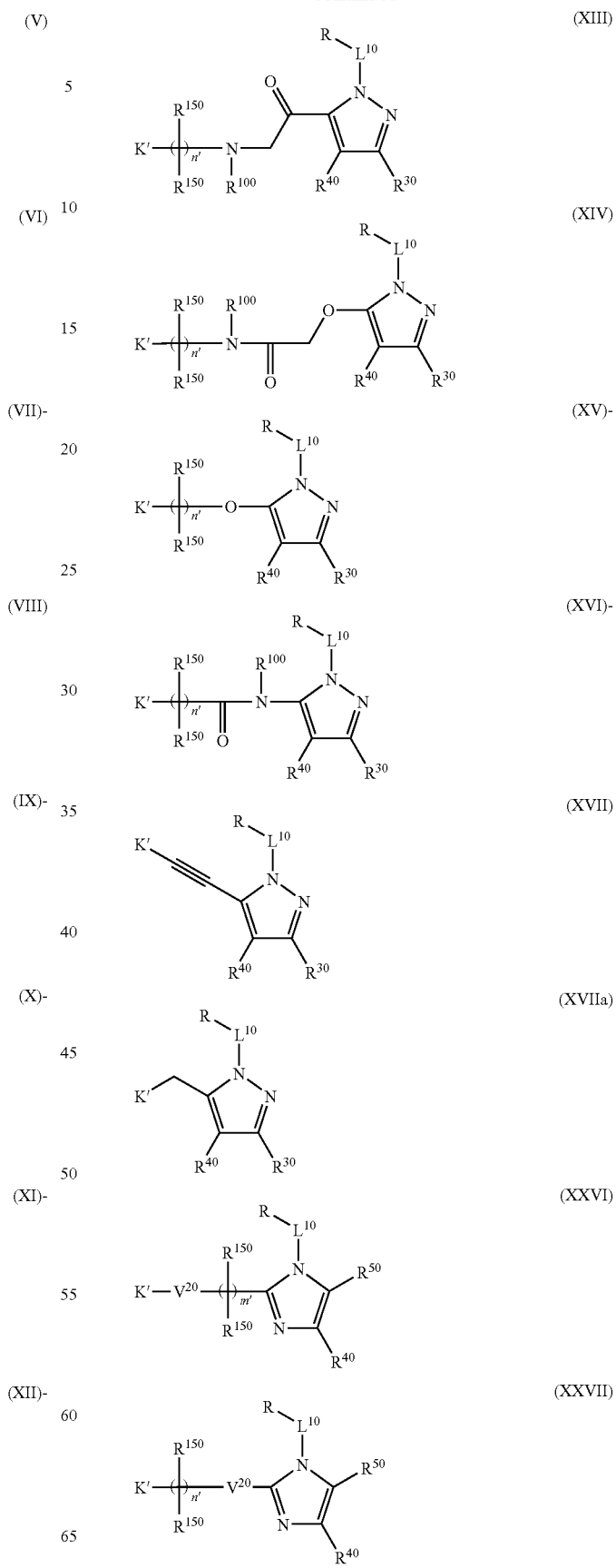

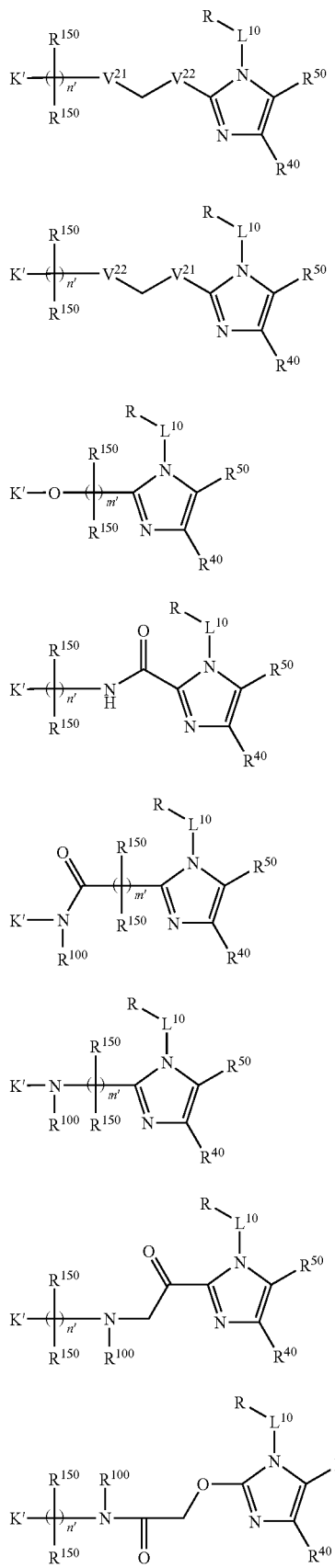
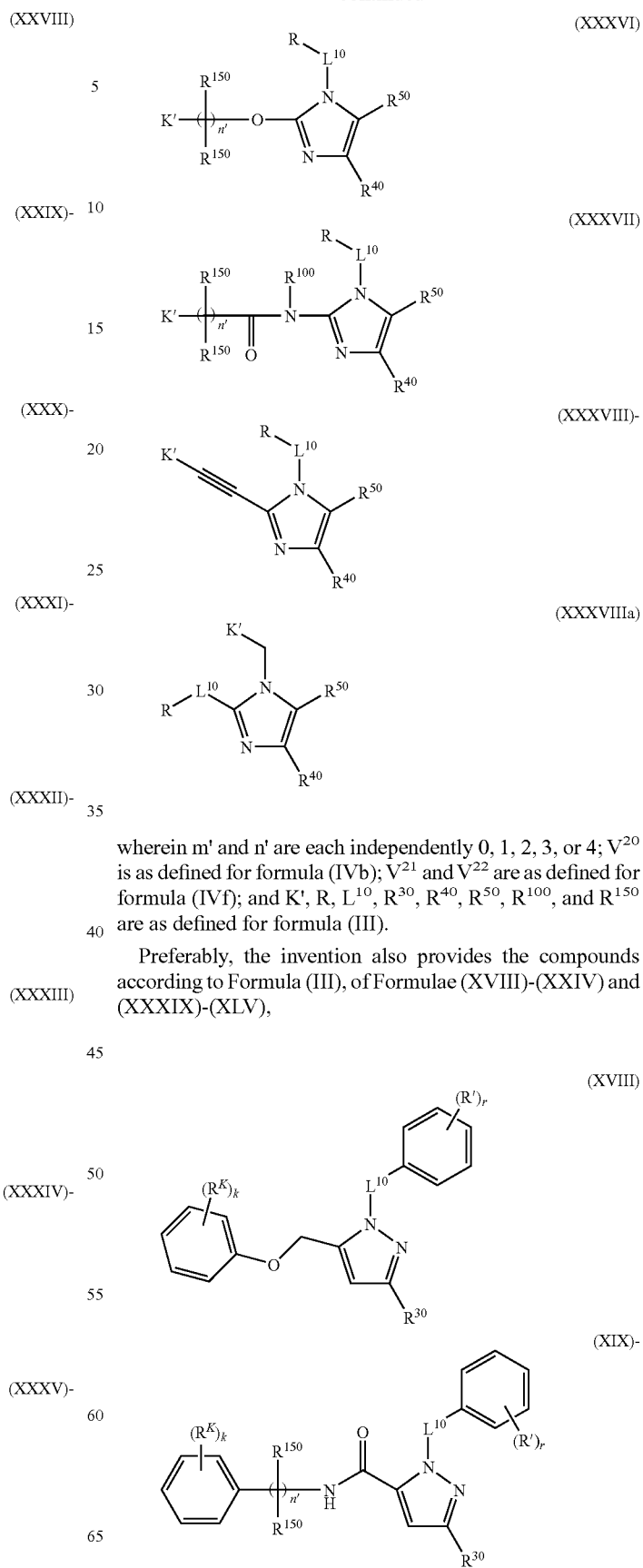
wherein m' and n' are each independently 0, 1, 2, 3, or 4; $V^{20}$ is as defined for formula (IVb); $V^{21}$ and $V^{22}$ are as defined for formula (IVf); and K', R, $L^{10}$, $R^{30}$, $R^{40}$, $R^{50}$, $R^{100}$, and $R^{150}$ are as defined for formula (III).
Preferably, the invention also provides the compounds according to Formula (III), of Formulae (XVIII)-(XXIV) and (XXXIX)-(XLV),

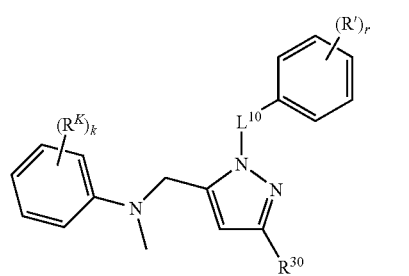
(XVIIIa)
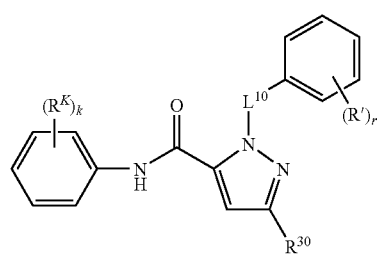
(XX)
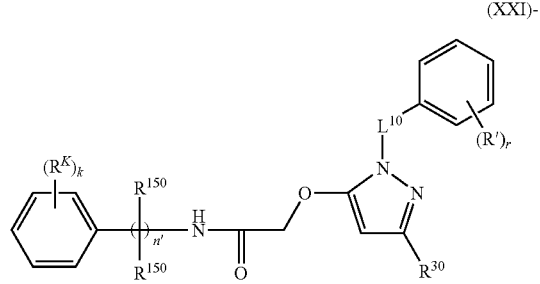
(XXI)
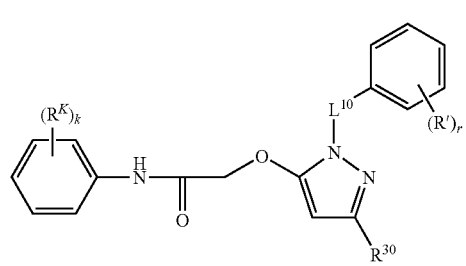
(XXII)
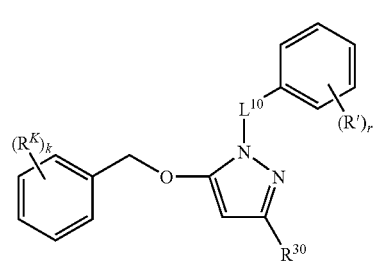
(XXIII)
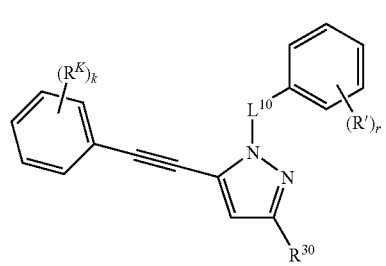
(XXIV)
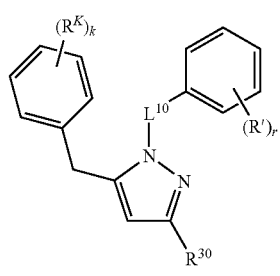
(XXIVa)
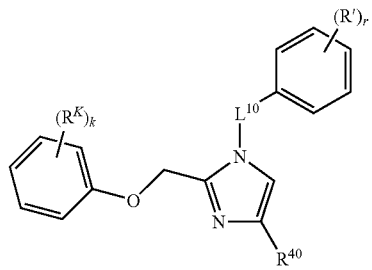
(XXXIX)
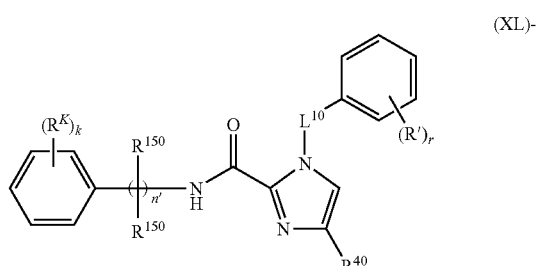
(XL)
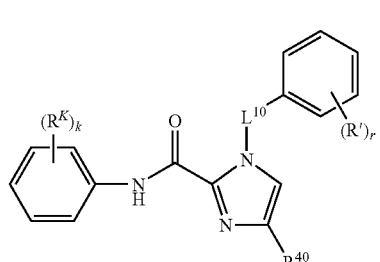
(XLI)
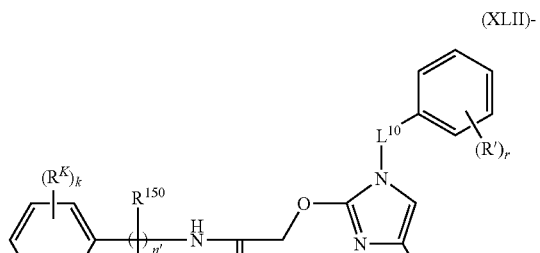
(XLII)
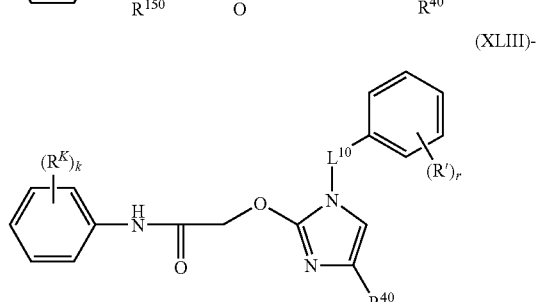
(XLIII)

-continued

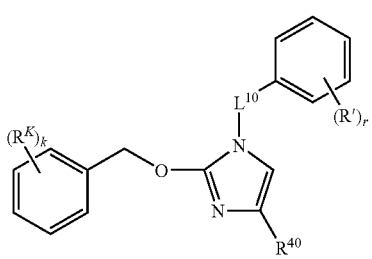

(XLIV)

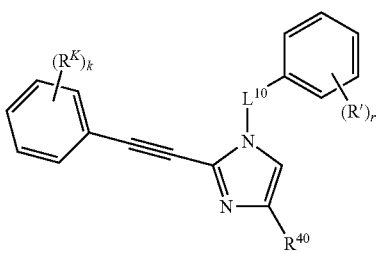

(XLV)

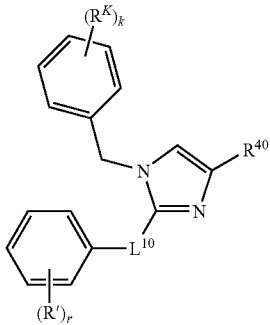

(XLVa)

wherein k and r are each independently 0, 1, 2, 3, or 4; n' is 0, 1, 2, 3 or 4; and $R^K$, R', $L^{10}$, $R^{30}$, $R^{40}$, and $R^{150}$ are as defined for formula (III).

In embodiment [1] of the second aspect, the invention comprises the compound according to formulae (III)-(XLV), (IIIa-s), (IVa-g), (XVIIa), (XXIVa), (XXXVIIIa), (XLVa) and (XXVa-g) wherein $L^{10}$ is a bond.

In embodiment [2] of the second aspect, the invention comprises the compound according to formulae (III)-(XLV), (IIIa-s), (IVa-g), (XVIIa), (XVIIIa), (XXIVa), (XXXVIIIa), (XLVa) and (XXVa-g) wherein $L^{10}$ is $L^{50}$ or $L^{60}$. Preferably, $L^{10}$ is —[C($R^{50}$)$_2$]$_m$—, —CO—, —SO$_2$—, or —C$_3$-C$_8$cycloalkyl-, wherein -m is 1, 2, 3, 4, 5, or 6. More preferably, $L^{10}$ is —[CH$_2$]$_{1-3}$—. Even more preferably, $L^{10}$ is —CH$_2$—.

In embodiment [3] of the second aspect, the invention comprises the compound according to formulae (III)-(XLV), (IIIa-s), (IVa-g), (XVIIa), (XVIIIa), (XXIVa), (XXXVIIIa), (XLVa) and (XXVa-g) wherein each R' is independently halogen, $C_1$-$C_6$ alkyl, $C_1$-$C_6$ haloalkyl, $C_3$-$C_8$cycloalkyl, —O$R^{110}$, —SO$_2R^{110}$, —CO$R^{110}$, —SO$_2$N($R^{110}$)$_2$, —C≡N, —C(O)O$R^{110}$, —CON($R^{110}$)$_2$, —N$R^{110}$CO$R^{110}$, or —N($R^{110}$)$_2$, wherein $R^{110}$ is as defined for formula (III). Preferably, each R' is independently halogen, $C_1$-$C_6$ alkyl, or $C_1$-$C_6$ haloalkyl. More preferably, each R' is fluoro, chloro, methyl, or trifluoromethyl.

In embodiment [4] of the second aspect, the invention comprises the compound according to formulae (III)-(XXIV), (IIIa-s), (XVIIa), (XVIIIa), (XXIVa), and (IVa-g), wherein $R^{30}$ is heteroaryl or heterocyclyl wherein each is optionally substituted with 1 to 4 $R^{70a}$, wherein $R^{70a}$ is as defined for formula (III).

In embodiment [5] of the second aspect, the invention comprises the compound according to formulae (III)-(XXIV), (IIIa-s), (XVIIa), (XVIIIa), (XXIVa), and (IVa-g), wherein $R^{30}$ is heteroaryl optionally substituted with 1 to 4 $R^{70a}$, wherein $R^{70a}$ is as defined for formula (III). Preferably, $R^{30}$ is a 5-membered heteroaryl optionally substituted with 1 to 4 $R^{70a}$, wherein $R^{70a}$ is as defined for formula (III). More preferably, $R^{30}$ is thienyl, furyl, pyrrolyl, oxazolyl, isoxazolyl, thiazolyl, isothiazolyl, imidazolyl, pyrazolyl, oxadiazolyl, thiadiazolyl, triazolyl, or tetrazolyl, each optionally substituted with 1 or 2 $R^{70a}$, wherein $R^{70a}$ is as defined for formula (III). More preferably, $R^{30}$ is oxazolyl, thiazolyl, imidazolyl, oxadiazolyl, or thiadiazolyl, each optionally substituted with 1 or 2 $R^{70a}$, wherein $R^{70a}$ is as defied for formula (III).

In embodiment [5a] of the second aspect, the invention comprises the compound according to formulae (III)-(XXIV), (IIIa-s), (XVIIa), (XVIIIa), (XXIVa), and (IVa-g), wherein $R^{30}$ is a 6-membered heteroaryl optionally substituted with 1 to 4 $R^{70a}$, wherein $R^{70a}$ is as defined for formula (III). More preferably, $R^{30}$ is pyridyl, pyrazinyl, or pyrimidinyl, each optionally substituted with 1 or 2 $R^{70a}$, wherein $R^{70a}$ is as defined for formula (III).

In embodiment [6] of the second aspect, the invention comprises the compound according to formulae (III)-(XXIV), (IIIa-s), (XVIIa), (XVIIIa), (XXIVa) and (IVa-g), wherein $R^{30}$ is heterocyclyl optionally substituted with 1 to 4 $R^{70a}$, wherein $R^{70a}$ is as defied for formula (III). Preferably, $R^{30}$ is a 5-membered heterocyclyl optionally substituted with 1 to 4 $R^{70a}$, wherein $R^{70a}$ is as defined for formula (III). More preferably, $R^{30}$ is tetrahydrothienyl, tetrahydrofuryl, pyrrolidinyl, dihydrothienyl, dihydrofuryl, pyrrolinyl, imidazolidinyl, pyrazolidinyl, oxazolidinyl, isoxazolidinyl, thiazolidinyl, isothiazolidinyl, dioxolanyl, oxathiolanyl, dithiolanyl, imidazolinyl, pyrazolinyl, oxazolinyl, isoxazolinyl, thiazolinyl, isothiazolinyl, 1,3-dioxolyl, 1,3-oxathiolyl, or 1,3-dithiolyl, each optionally substituted with 1 or 2 $R^{70a}$, wherein $R^{70a}$ is as defined for formula (III). Even more preferably, $R^{30}$ is imidazolidinyl, oxazolidinyl, thiazolidinyl, dioxolanyl, oxathiolanyl, dithiolanyl, imidazolinyl, oxazolinyl, thiazolinyl, 1,3-dioxolyl, 1,3-oxathiolyl, or 1,3-dithiolyl, each optionally substituted with 1 or 2 $R^{70a}$, wherein $R^{70a}$ is as defined for formula (III).

In embodiment [6a] of the second aspect, the invention comprises the compound according to formulae (III)-(XXIV), (IIIa-s), (XVIIa), (XVIIIa), (XXIVa), and (IVa-g), wherein $R^{30}$ is a 6-membered heterocyclyl optionally substituted with 1 to 4 $R^{70a}$, wherein $R^{70a}$ is as defined for formula (III). More preferably, $R^{30}$ is piperidinyl, piperazinyl, morpholinyl, thiomorpholinyl, tetrahydropyranyl, tetrahydrothiopyranyl, dioxanyl, oxathianyl, or dithianyl, each optionally substituted with 1 or 2 $R^{70a}$, wherein $R^7$ is as defined for formula (III).

In embodiment [7] of the second aspect, the invention comprises the compound according to formulae (III)-(XXIV), (IIIa-s), (XVIIa), (XVIIIa), (XXIVa), and (IVa-g), wherein $R^{30}$ is —$R^{71}$, wherein $R^{71}$ is hydrogen, halogen, —$Z^2$, or —$Y^2$—$Z^2$, wherein
$Y^2$ is —[C($R^{51}$)$_2$]$_p$—, —($C_3$-$C_6$)cycloalkyl-, or $C_2$-$C_6$alkenyl, wherein
each $R^{151}$ is independently H, halogen, —($C_3$-$C_6$)cycloalkyl-, or ($C_1$-$C_6$)alkyl; and $Z^2$ is —H, halogen, —O$R^{110}$, —N($R^{110}$)$_2$, —C(═O)$R^{110}$, —C(═O)O$R^{110}$, —C(═O)N($R^{110}$)$_2$, —C(═N—OH)$R^{110}$, or —C(═S)N($R^{110}$)$_2$, wherein $R^{110}$ is as defined for formula (III).

Preferably, $R^{71}$ is hydrogen, halogen, —$Z^2$, or —[C($R^{151}$)$_2$]$_p$—$Z^2$, wherein each $R^{151}$ is independently H, halogen, or $(C_1-C_6)$alkyl; and $Z^2$ is —H, halogen, —OR$^{110}$, or —N(R$^{110}$)$_2$ wherein R$^{110}$ is as defined for formula (III).

In embodiment [7a] of the second aspect, the invention comprises the compound according to formula (III)-(XXIV), (IIIa-s), (XVIIa), (XVIIIa), (XXIVa), and (IVa-g), wherein R$^{30}$ is —X—Y—Z, wherein X, Y, and Z are as defined for formula (III). Preferably, R$^{30}$ is —X[C(R$^{150}$)$_2$]$_p$Z, wherein p, R$^{150}$, and Z are as defined for formula (III). More preferably, R$^{30}$ is —X[C(R$^{151}$)$_2$]$_p$Z, wherein R$^{151}$ is hydrogen, halogen, $(C_1-C_2)$alkyl, or $(C_1-C_2)$haloalkyl; and p, and Z are as defined for formula (III). Even more preferably, R$^{30}$ is —O[C(R$^{151}$)$_2$]$_p$Z or —N(R$^{110}$)[C(R$^{151}$)$_2$]$_p$Z, wherein R$^{151}$ is hydrogen, halogen, $(C_1-C_2)$alkyl, or $(C_1-C_2)$haloalkyl; and p, R$^{100}$, and Z are as defined for formula (III).

In embodiment [8] of the second aspect, the invention comprises the compound according to formulae (III)-(XLV), (IIIa-s), (IVa-g), (XVIIa), (XVIIIa), (XXIVa), (XXXVIIIa), (XLVa) and (XXVa-g) wherein each R$^K$ is independently —Z, —Y—Z, phenyl, or heteroaryl, wherein the phenyl and heteroaryl are each optionally substituted with 1 to 4 R$^{K'}$, wherein each R$^{K'}$ is independently halogen, —Z$^1$, or —Y—Z$^1$, wherein Y$^1$ is —[C(R$^{150}$)$_2$]$_p$—; and Z$^1$ is —C$_1$-C$_6$alkyl, —C$_1$-C$_6$haloalkyl, halogen, —COR$^{110}$, —COOR$^{110}$, —CON(R$^{110}$)$_2$, —C≡N, —OR$^{110}$, —N(R$^{110}$)$_2$, —SO$_2$R$^{110}$, —SO$_2$N(R$^{110}$)$_2$, or —SR$^{110}$ wherein R$^{110}$ is as defined for formula (III).

In embodiment [9] of the second aspect, the invention comprises the compound according to formulae (III)-(XVII), (XXV)-(XXXVIII), (XXVa-g), (IIIa-s), (XVIIa), (XXXVIIIa), and (IVa-g), wherein K' is aryl optionally substituted with 1 to 4 R$^K$. Preferably, K' is phenyl, naphthyl, indenyl, dihydroindenyl, fluorenyl, or tetrahydronaphthyl, each optionally substituted with 1 to 4 R$^K$. Preferably, K' is phenyl optionally substituted with 1 to 4 R$^K$. More preferably, K' is phenyl substituted with 1 to 4 R$^K$, wherein only one R$^K$ is phenyl or naphthyl, each optionally substituted with 1 to 4 R$^{K'}$. More preferably, K' is phenyl substituted with 1 to 4 R$^K$, wherein only one R$^K$ is phenyl optionally substituted with 1 to 4 R$^{K'}$. Even more preferably, K' is phenyl substituted with 1 to 4 R$^K$, wherein only one R$^K$ is phenyl optionally substituted with 1 to 4 R$^{K'}$, wherein each R$^{K'}$ is independently halogen, Z$^1$, or —Y$^1$—Z$^1$, wherein Y$^1$ is —[C(R$^{50}$)$_2$]$_p$—; and Z$^1$ is —C$_1$-C$_6$alkyl, —C$_1$-C$_6$haloalkyl, halogen, —COR$^{110}$, —COOR$^{110}$, —CON(R$^{11}$)$_2$, —C≡N, —OR$^{110}$, —N(R$^{110}$)$_2$, —SO$_2$R$^{110}$, —SO$_2$N(R$^{11}$)$_2$, or —SR$^{110}$, wherein R$^{110}$ is as defined for formula (III).

In embodiment [10] of the second aspect, the invention comprises the compound according to formulae (III)-(XVII), (XXV)-(XXXVIII), (XXVa-g), (IIIa-s), (XVIIa), (XXXVIIIa), and (IVa-g), wherein K' is heteroaryl optionally substituted with 1 to 4 R$^K$ Preferably, K' is pyridyl, pyrimidinyl, pyrazinyl, furyl, thienyl, pyrrolyl, isoxazolyl, isothiazolyl, pyrazolyl, imidazolyl, oxazolyl, thiazolyl, thiadiazoyl, benzofuranyl, benzothienyl, indolyl, indazolyl, benzothiazolyl, benzoxazolyl, benzoimidazolyl, benzotriazolyl, quinolinyl, benzodioxolyl, carbazolyl, 6,7,8,9-tetrahydropyrido[2,3-b][16]naphthyridinyl, isochromanyl, or pyrazolopyrimidinyl, wherein K' is optionally substituted with R$^K$, wherein each R$^K$ is independently —X—Y—Z, —Y—Z, or —Z. Preferably, K' is pyridyl, pyrimidinyl, pyrazinyl, furyl, thienyl, pyrrolyl, isoxazolyl, isothiazolyl, pyrazolyl, imidazolyl, oxazolyl, thiazolyl, thiadiazoyl, benzofuranyl, benzothienyl, indolyl, indazolyl, benzothiazolyl, benzoxazolyl, benzoimidazolyl, benzotriazolyl, quinolinyl, benzodioxolyl, carbazolyl, 6,7,8,9-tetrahydropyrido[2,3-b][16]naphthyridinyl, isochromanyl, or pyrazolopyrimidinyl, wherein K' is optionally substituted with 1 to 4 R$^K$, each R$^K$ is independently —Z, —Y—Z, phenyl, naphthyl, or heteroaryl, wherein the phenyl and heteroaryl are each optionally substituted with 1 to 4 R$^K$, wherein each R$^{K'}$ is independently halogen, —Z$^1$, or —Y$^1$—Z$^1$, wherein Y$^1$ is —[C(R$^{150}$)$_2$]$_p$—; and Z$^1$ is —C$_1$-C$_6$alkyl, —C$_1$-C$_6$haloalkyl, halogen, —COR$^{110}$, —COOR$^{110}$, —CON(R$^{110}$)$_2$, —C≡N, —OR$^{110}$, —N(R$^{110}$)$_2$, —SO$_2$R$^{110}$, —SO$_2$N(R$^{110}$)$_2$, or —SR$^{110}$ wherein R$^{110}$ is as defined for formula (III). Even more preferably, K' is pyridyl, pyrimidinyl, pyrazinyl, furyl, thienyl, pyrrolyl, isoxazolyl, isothiazolyl, pyrazolyl, imidazolyl, oxazolyl, thiazolyl, thiadiazoyl, benzofuranyl, benzothienyl, indolyl, indazolyl, benzothiazolyl, benzoxazolyl, benzoimidazolyl, benzotriazolyl, quinolinyl, benzodioxolyl, carbazolyl, 6,7,8,9-tetrahydropyrido[2,3-b][16]naphthyridinyl, isochromanyl, or pyrazolopyrimidinyl, each substituted with 1 to 4 R$^K$, wherein only one R$^K$ is phenyl optionally substituted with 1 to 4 R$^{K'}$, wherein each R$^{K'}$ is independently halogen, Z$^1$, or Z$^1$, wherein Y$^1$ is —[C(R$^{150}$)$_2$]$_p$—; and Z$^1$ is —C$_1$-C$_6$alkyl, —C$_1$-C$_6$haloalkyl, halogen, —COR$^{110}$, —COOR$^{110}$, —CON(R$^{110}$)$_2$, —C≡N, —OR$^{110}$, —N(R$^{110}$)$_2$, —SO$_2$R$^{110}$, —SO$_2$N(R$^{110}$)$_2$, or —SR$^{110}$, wherein R$^{110}$ is as defined for formula (III).

In embodiment [11] of the second aspect, the invention comprises the compound according to formulae (III)-(XVII), (IIIa-s), (XVIIa), (XXIVa), and (IVa-g), wherein R$^{40}$ is hydrogen, halogen, nitro, cyano, C$_1$-C$_6$alkyl, or C$_1$-C$_6$haloalkyl. Preferably, R$^{40}$ is hydrogen or halogen. More preferably, R$^{40}$ is hydrogen.

In embodiment [12] of the second aspect, the invention comprises the compound according to formulae (III)-(XVII), (XXV)-(XXXVIII), (XXVa-g), (IIIa-p), (XVIIa), (XXXVIIIa), and (IVa-g), wherein R is aryl optionally substituted with 1 to 4 R'. Preferably, R is phenyl optionally substituted with 1 to 4 R'. More preferably, R is phenyl optionally substituted with 1 to 4 R', wherein each R' is independently halogen, C$_1$-C$_6$ alkyl, C$_1$-C$_6$ haloalkyl, C$_3$-C$_8$cycloalkyl, —OR$^{110}$, —SO$_2$R$^{110}$, —COR$^{110}$, —SO$_2$N(R$^{110}$)$_2$, —C≡N, —C(O)OR$^{110}$, —CON(R$^{110}$)$_2$, —NR$^{110}$COR$^{110}$, or —N(R$^{110}$)$_2$, wherein R$^{110}$ is as defined for formula (III). Even more preferably, R is phenyl optionally substituted with 1 to 4 R', wherein each R' is independently halogen, C$_1$-C$_6$ alkyl, or C$_1$-C$_6$ haloalkyl. Even more preferably, R is phenyl optionally substituted with 1 or 2 R', wherein each R' is independently fluoro, chloro, methyl, or trifluoromethyl. Even more preferably, R is phenyl optionally substituted with 1 or 2 R', wherein each R' is independently fluoro or chloro.

In embodiment [13] of the second aspect, the invention comprises the compound according to formulae (III)-(XVII), (XXV)-(XXXVIII), (XXVa-g), (IIIa-p), (XVIIa), (XXXVIIIa), and (IVa-g), wherein R is heteroaryl optionally substituted with 1 to 4 R'. Preferably, R is pyridyl, pyrazinyl, or pyrimidinyl, each optionally substituted with 1 to 4 R'. More preferably, R is pyridyl, pyrazinyl, or pyrimidinyl, each optionally substituted with 1 to 4 R', wherein each R' is independently halogen, C$_1$-C$_6$ alkyl, C$_1$-C$_6$ haloalkyl, C$_3$-C$_8$cycloalkyl, —OR$^{110}$, —SO$_2$R$^{110}$, —COR$^{110}$, —SO$_2$N(R$^{110}$)$_2$, —C≡N, —C(O)OR$^{110}$, —CON(R$^{110}$)$_2$, —NR$^{110}$COR$^{110}$, or —N(R$^{110}$)$_2$. Even more preferably, R is pyridyl, pyrazinyl, or pyrimidinyl, each optionally substituted with 1 to 4 R', wherein each R' is independently halogen, C$_1$-C$_6$ alkyl, or C$_1$-C$_6$ haloalkyl. Even more preferably, R is pyridyl, pyrazinyl, or pyrimidinyl, each optionally substituted with 1 or 2 R', wherein each R' is independently fluoro, chloro, methyl, or trifluoromethyl. Even more preferably, R is pyridyl, pyrazinyl, or pyrimidinyl, each optionally substituted with 1 or 2 R', wherein each R' is independently fluoro or chloro.

In embodiment [14] of the second aspect, the invention comprises the compound according to formulae (IIIa-s), (XXV)-(XXXVIII), (XXXVIIIa), (XLVa) and (XXVa-g), wherein $R^{50}$ is hydrogen, halogen, nitro, cyano, $C_1$-$C_6$alkyl, or $C_1$-$C_6$haloalkyl. Preferably, $R^{50}$ is hydrogen or halogen. More preferably, $R^{50}$ is hydrogen.

In embodiment [15] of the second aspect, the invention comprises the compound according to formulae (IIIa-s), (XXV)-(XLV), (XXXVIIIa), (XLVa) and (XXVa-g), wherein $R^{40}$ is heteroaryl or heterocyclyl wherein each is optionally substituted with 1 to 4 $R^{70a}$, wherein $R^{70a}$ is as defined for formula (III).

In embodiment [16] of the second aspect, the invention comprises the compound according to formulae (IIIa-s), (XXV)-(XLV), (XXXVIIIa), (XLVa) and (XXVa-g), wherein $R^{40}$ is heteroaryl optionally substituted with 1 to 4 $R^{70a}$, wherein $R^{70a}$ is as defined for formula (III). Preferably, $R^{40}$ is a 5-membered heteroaryl optionally substituted with 1 to 4 $R^{70a}$, wherein $R^{70a}$ is as defined for formula (III). More preferably, $R^{40}$ is thienyl, furyl, pyrrolyl, oxazolyl, isoxazolyl, thiazolyl, isothiazolyl, imidazolyl, pyrazolyl, oxadiazolyl, thiadiazolyl, triazolyl, or tetrazolyl, each optionally substituted with 1 or 2 $R^{70a}$, wherein $R^{70a}$ is as defined for formula (III). More preferably, $R^{40}$ is oxazolyl, thiazolyl, imidazolyl, oxadiazolyl, or thiadiazolyl, each optionally substituted with 1 or 2 $R^{70a}$, wherein $R^{70a}$ is as defined for formula (III).

In embodiment [16a] of the second aspect, the invention comprises the compound according to formulae (IIIa-s), (XXV)-(XLV), (XXXVIIIa), (XLVa) and (XXVa-g), wherein $R^{40}$ is a 6-membered heteroaryl optionally substituted with 1 to 4 $R^{70a}$, wherein $R^{70a}$ is as defined for formula (III). More preferably, $R^{40}$ is pyridinyl, pyrimidinyl, or pyrazinyl, each optionally substituted with 1 or 2 $R^{70a}$, wherein $R^{70a}$ is as defined for formula (III).

In embodiment [17] of the second aspect, the invention comprises the compound according to formulae (IIIa-s), (XXV)-(XLV), (XXXVIIIa), (XLVa) and (XXVa-g), wherein $R^{40}$ is heterocyclyl optionally substituted with 1 to 4 $R^{70a}$, wherein $R^{70a}$ is as defined for formula (III). Preferably, $R^{40}$ is a 5-membered heterocyclyl optionally substituted with 1 to 4 $R^{70a}$, wherein $R^{70a}$ is as defined for formula (III). More preferably, $R^{40}$ is tetrahydrothienyl, tetrahydrofuryl, pyrrolidinyl, dihydrothienyl, dihydrofuryl, pyrrolinyl, imidazolidinyl, pyrazolidinyl, oxazolidinyl, isoxazolidinyl, thiazolidinyl, isothiazolidinyl, dioxolanyl, oxathiolanyl, dithiolanyl, imidazolinyl, pyrazolinyl, oxazolinyl, isoxazolinyl, thiazolinyl, isothiazolinyl, 1,3-dioxolyl, 1,3-oxathiolyl, or 1,3-dithiolyl, each optionally substituted with 1 or 2 $R^{70a}$, wherein $R^{70a}$ is as defined for formula (III). Even more preferably, $R^{40}$ is imidazolidinyl, oxazolidinyl, thiazolidinyl, dioxolanyl, oxathiolanyl, dithiolanyl, imidazolinyl, oxazolinyl, thiazolinyl, 1,3-dioxolyl, 1,3-oxathiolyl, or 1,3-dithiolyl, each optionally substituted with 1 or 2 $R^{70a}$, wherein $R^{70a}$ is as defined for formula (III).

In embodiment [17a] of the second aspect, the invention comprises the compound according to formulae (IIIa-s), (XXV)-(XLV), (XXXVIIIa), (XLVa) and (XXVa-g), wherein $R^{40}$ is a 6-membered heterocyclyl optionally substituted with 1 to 4 $R^{70a}$, wherein $R^{70a}$ is as defined for formula (III). More preferably, $R^{30}$ is piperidinyl, piperazinyl, morpholinyl, thiomorpholinyl, tetrahydropyranyl, tetrahydrothiopyranyl, dioxanyl, oxathianyl, or dithianyl, each optionally substituted with 1 or 2 $R^{70a}$, wherein $R^{70a}$ is as defined for formula (III).

In embodiment [18] of the second aspect, the invention comprises the compound according to formulae (IIIa-s), (XXV)-(XLV), (XXXVIIIa), (XLVa) and (XXVa-g), wherein $R^{40}$ is —$R^{71}$, wherein $R^{71}$ is hydrogen, halogen, —$Z^2$, or —$Y^2$—$Z^2$, wherein
$Y^2$ is —[C($R^{151}$)$_2$]$_p$—, —($C_3$-$C_6$)cycloalkyl-, or $C_2$-$C_6$alkenyl, wherein
each $R^{151}$ is independently H, halogen, —($C_3$-$C_6$)cycloalkyl-, or ($C_1$-$C_6$)alkyl; and $Z^2$ is —H, halogen, —$OR^{110}$, —N($R^{110}$)$_2$, —C(=O)$R^{110}$, —C(=O)$OR^{110}$, —C(=O)N($R^{110}$)$_2$, —C(=N—OH)$R^{110}$, or —C(=S)N($R^{110}$)$_2$, wherein $R^{110}$ is as defined for formula (III).

Preferably, $R^{71}$ is hydrogen, halogen, —$Z^2$, or —[C($R^{151}$)$_2$]$_p$—$Z^2$, wherein each $R^{151}$ is independently H, halogen, or ($C_1$-$C_6$)alkyl; and $Z^2$ is —H, halogen, —$OR^{110}$, or —N($R^{110}$)$_2$ wherein $R^{110}$ is as defined for formula (III).

In embodiment [18a] of the second aspect, the invention comprises the compound according to formula (IIIa-s), (XXV)-(XLV), (XXXVIIIa), (XLVa) and (XXVa-g), wherein $R^{40}$ is —X—Y—Z, wherein X, Y, and Z are as defined for formula (III). Preferably, $R^{40}$ is —X[C($R^{150}$)$_2$]$_p$Z, wherein p, $R^{150}$, and Z are as defined for formula (III). More preferably, $R^{40}$ is —X[C($R^{151}$)$_2$]$_p$Z, wherein $R^{151}$ is hydrogen, halogen, ($C_1$-$C_2$)alkyl, or ($C_1$-$C_2$)haloalkyl; and p, and Z are as defined for formula (III). Even more preferably, $R^{40}$ is —O[C($R^{151}$)$_2$]$_p$Z or —N($R^{100}$)[C($R^{151}$)$_2$]$_p$Z, wherein $R^{151}$ is hydrogen, halogen, ($C_1$-$C_2$)alkyl, or ($C_1$-$C_2$)haloalkyl; and p, $R^{100}$, and Z are as defined for formula (III).

In a preferred embodiment, the invention comprises the compound according to formulae (III)-(XVII), (XXVI-XXXVIII), (XXVa-g), (IIIa-p), (XVIIa), (XXXVIIIa), and (IVa-g),
wherein $L^{10}$ is as defined for embodiment [1]; and R is as defined for embodiment [12].

In a preferred embodiment, the invention comprises the compound according to formulae (III)-(XVII), (XXVI-XXXVIII), (XXVa-g), (IIIa-p), (XVIIa), (XXXVIIIa), and (IVa-g),
wherein $L^{10}$ is as defined for embodiment [2]; and R is as defined for embodiment [12].

In a preferred embodiment, the invention comprises the compound according to formulae (III)-(XVII), (XXVI-XXXVIII), (XXVa-g), (IIIa-p), (XVIIa), (XXXVIIIa), and (IVa-g),
wherein $L^{10}$ is as defined for embodiment [1]; and R is as defined for embodiment [13].

In a preferred embodiment, the invention comprises the compound according to formulae (III)-(XVII), (XXVI-XXXVIII), (XXVa-g), (IIIa-p), (XVIIa), (XXXVIIIa), and (IVa-g),
wherein $L^{10}$ is as defined for embodiment [2]; and R is as defined for embodiment [13].

In a preferred embodiment, the invention comprises the compound according to formulae (III)-(XVII), (XXVI-XXXVIII), (XXVa-g), (IIIa-p), (XVIIa), (XXXVIIIa), and (IVa-g),
wherein $L^{10}$ is as defined for embodiment [1] and K' is as defined for embodiment [9].

In a preferred embodiment, the invention comprises the compound according to formulae (III)-(XVII), (XXVI-XXXVIII), (XXVa-g), (IIIa-p), (XVIIa), (XXXVIIIa), and (IVa-g),
$L^{10}$ is as defined for embodiment [1] and K' is as defined for embodiment [10].

In a more preferred embodiment, the invention comprises the compound according to formulae (III)-(XVII), (XXVI-XXXVIII), (XXVa-g), (IIIa-p), (XVIIa), (XXXVIIIa), and (IVa-g), wherein $L^{10}$ is as defined for embodiment [1], K' is as defined for embodiment [9], and R is as defined for embodiment [12].

In a more preferred embodiment, the invention comprises the compound according to formulae (III)-(XVII), (XXVI-XXXVIII), (XXVa-g), (IIIa-p), (XVIIa), (XXXVIIIa), and (IVa-g), wherein $L^{10}$ is as defined for embodiment [1], K' is as defined for embodiment [10], and R is as defined for embodiment [12].

In an even more preferred embodiment, the invention comprises the compound according to formulae (III)-(XVII), (IIIa-p), (XVIIa), and (IVa-g), wherein $L^{10}$ is as defined for embodiment [1], K' is as defined for embodiment [9], R is as defined for embodiment [12], and $R^{30}$ is as defined for embodiment [4], [5]. [5a], [6], [6a], [7] or [7a].

In an even more preferred embodiment, the invention comprises the compound according to formulae (III)-(XVII), (IIIa-p), (XVIIa), (XXXVIIIa), and (IVa-g), wherein $L^{10}$ is as defined for embodiment [1], K' is as defined for embodiment [10], R is as defined for embodiment [12], and $R^{30}$ is as defined for embodiment [4], [5]. [5a], [6], [6a], [7] or [7a].

In an even more preferred embodiment, the invention comprises the compound according to formulae (III)-(XVII), (IIIa-p), (XVIIa), and (IVa-f), wherein $L^{10}$ is as defined for embodiment [1], K' is as defined for embodiment [9], R is as defined for embodiment [12], $R^{30}$ is as defined for embodiment [4], [5]. [5a], [6], [6a], [7] or [7a], and $R^{40}$ is as defined for embodiment [11].

In an even more preferred embodiment, the invention comprises the compound according to formulae (III)-(XVII), (IIIa-p), (XVIIa), and (IVa-g), wherein $L^{10}$ is as defined for embodiment [1], K' is as defined for embodiment [10], R is as defined for embodiment [12], $R^{30}$ is as defined for embodiment [4], [5]. [5a], [6], [6a], [7] or [7a], and $R^{40}$ is as defined for embodiment [11].

In an even more preferred embodiment, the invention comprises the compound according to formulae (IIIa-p), (XXVa-g), (XXXVIIIa), and (XXVI)-(XXXVIII), wherein $L^{10}$ is as defined for embodiment [1], K' is as defined for embodiment [9], R is as defined for embodiment [12], and $R^{40}$ is as defined for embodiment [15], [16], [16a], [17], [17a], [18], or [18a].

In an even more preferred embodiment, the invention comprises the compound according to formulae (IIIa-p), (XXVa-g), (XXXVIIIa), and (XXVI)-(XXXVIII), wherein $L^{10}$ is as defined for embodiment [1], K' is as defined for embodiment [10], R is as defined for embodiment [12], and $R^{40}$ is as defined for embodiment [15], [16], [16a], [17], [17a], [18], or [18a].

In an even more preferred embodiment, the invention comprises the compound according to formulae (IIIa-p), (XXVa-g), (XXXVIIIa), and (XXVI)-(XXXVIII), wherein $L^{10}$ is as defined for embodiment [1], K' is as defined for embodiment [9], R is as defined for embodiment [12], $R^{40}$ is as defined for embodiment [15], [16], [16a], [17], [17a], [18], or [18a]; and $R^{50}$ is as defined for embodiment [14].

In an even more preferred embodiment, the invention comprises the compound according to formulae (IIIa-p), (XXVa-g), (XXXVIIIa), and (XXVI)-(XXXVIII), wherein $L^{10}$ is as defined for embodiment [1], K' is as defined for embodiment [10], R is as defined for embodiment [12], $R^{40}$ is as defined for embodiment [15], [16], [16a], [17], [17a], [18], or [18a]; and $R^{50}$ is as defined for embodiment [14].

In a preferred embodiment, the invention comprises the compound according to formulae (III)-(XVII), (XXVI-XXXVIII), (XXVa-g), (IIIa-p), (XVIIa), (XXXVIIIa), and (IVa-g), wherein $L^{10}$ is as defined for embodiment [2], and K' is as defined for embodiment [9].

In a preferred embodiment, the invention comprises the compound according to formulae (III)-(XVII), (XXVI-XXXVIII), (XXVa-g), (IIIa-p), (XVIIa), (XXXVIIIa), and (IVa-g), wherein $L^{10}$ is as defined for embodiment [2], and K' is as defined for embodiment [10].

In a more preferred embodiment, the invention comprises the compound according to formulae (III)-(XVII), (XXVI-XXXVIII), (XXVa-g), (IIIa-p), (XVIIa), (XXXVIIIa), and (IVa-g), wherein $L^{10}$ is as defined for embodiment [2], K' is as defined for embodiment [9], and R is as defined for embodiment [12].

In a more preferred embodiment, the invention comprises the compound according to formulae (III)-(XVII), (XXVI-XXXVIII), (XXVa-g), (IIIa-p), (XVIIa), (XXXVIIIa), and (IVa-g), wherein $L^{10}$ is as defined for embodiment [2], K' is as defined for embodiment [10], and R is as defined for embodiment [12].

In an even more preferred embodiment, the invention comprises the compound according to formulae (III)-(XVII), (IIIa-p), (XVIIa), and (IVa-g), wherein $L^{10}$ is as defined for embodiment [2], K' is as defined for embodiment [9], R is as defined for embodiment [12], and $R^{30}$ is as defined for embodiment [4], [5]. [5a], [6], [6a], [7] or [7a].

In an even more preferred embodiment, the invention comprises the compound according to formulae (III)-(XVII), (IIIa-p), (XVIIa), and (IVa-g), wherein $L^{10}$ is as defined for embodiment [2], K' is as defined for embodiment [10], R is as defined for embodiment [12], and $R^{30}$ is as defined for embodiment [4], [5]. [5a], [6], [6a], [7] or [7a].

In an even more preferred embodiment, the invention comprises the compound according to formulae (III)-(XVII), (IIIa-p), (XVIIa), and (IVa-g), wherein $L^{10}$ is as defined for embodiment [2], K' is as defined for embodiment [9], R is as defined for embodiment [12], $R^{30}$ is as defined for embodiment [4], [5]. [5a], [6], [6a], [7], or [7a], and $R^{40}$ is as defined for embodiment [11].

In an even more preferred embodiment, the invention comprises the compound according to formulae (III)-(XVII), (IIIa-p), (XVIIa), and (IVa-g), wherein $L^{10}$ is as defined for embodiment [2], K' is as defined for embodiment [10], R is as defined for embodiment [12], $R^{30}$ is as defined for embodiment [4], [5]. [5a], [6], [6a], [7] or [7a], and $R^{40}$ is as defined for embodiment [11].

In an even more preferred embodiment, the invention comprises the compound according to formulae (IIIa-p), (XXVa-g), (XXXVIIIa), and (XXVI)-(XXXVIII), wherein $L^{10}$ is as defined for embodiment [2], K' is as defined for embodiment [9], R is as defined for embodiment [12], and $R^{40}$ is as defined for embodiment [15], [16], [16a], [17], [17a], [18], or [18a].

In an even more preferred embodiment, the invention comprises the compound according to formulae (IIIa-p), (XXVa-g), (XXXVIIIa), and (XXVI)-(XXXVIII), wherein $L^{10}$ is as defined for embodiment [2], K' is as defined for embodiment [10], R is as defined for embodiment [12], and $R^{40}$ is as defined for embodiment [15], [16], [16a], [17], [17a], [18], or [18a].

In an even more preferred embodiment, the invention comprises the compound according to formulae (IIIa-p), (XXVa-g), (XXXVIIIa), and (XXVI)-(XXXVIII), wherein $L^{10}$ is as defined for embodiment [2], K' is as defined for embodiment [9], R is as defined for embodiment [12], $R^{40}$ is as defined for embodiment [15], [16], [16a], [17], [17a], [18], or [18a]; and $R^{50}$ is as defined for embodiment [14].

In an even more preferred embodiment, the invention comprises the compound according to formulae (IIIa-p), (XXVa-g), (XXXVIIIa), and (XXVI)-(XXXVIII),
wherein $L^{10}$ is as defined for embodiment [2], K' is as defined for embodiment [10], R is as defined for embodiment [12], $R^{40}$ is as defined for embodiment [15], [16], [16a], [17], [17a], [18], or [18a]; and $R^{50}$ is as defined for embodiment [14].

In a preferred embodiment, the invention comprises the compound according to formulae (IIIa-p), (XVIII)-(XXIV), (XVIIIa), (XXIVa), (XLVa), and (XXXIX)-(XLV), wherein $L^{10}$ is as defined for embodiment [1], and $R^K$ is as defined for embodiment [8].

In a preferred embodiment, the invention comprises the compound according to formulae (IIIa-p), (XVIII)-(XXIV), (XVIIIa), (XXIVa), (XLVa), and (XXXIX)-(XLV), wherein $L^{10}$ is as defined for embodiment [2], and $R^K$ is as defined for embodiment [8].

In a preferred embodiment, the invention comprises the compound according to formulae (IIIa-p), (XVIII)-(XXIV), (XVIIIa), (XXIVa), (XLVa), and (XXXIX)-(XLV), wherein $L^{10}$ is as defined for embodiment [1], and R' is as defined for embodiment [3].

In a preferred embodiment, the invention comprises the compound according to formulae (IIIa-p), (XVIII)-(XXIV), (XVIIIa), (XXIVa), (XLVa), and (XXXIX)-(XLV), wherein $L^{10}$ is as defined for embodiment [2], and R' is as defined for embodiment [3].

In a preferred embodiment, the invention comprises the compound according to formulae (IIIa-p), (XVIII)-(XXIV), (XVIIIa), and (XXIVa), wherein $L^{10}$ is as defined for embodiment [1], and $R^K$ is as defined for embodiment [8].

In a preferred embodiment, the invention comprises the compound according to formulae (IIIa-p), (XVIII)-(XXIV), (XVIIIa), and (XXIVa), wherein $L^{10}$ is as defined for embodiment [2], and $R^K$ is as defined for embodiment [8].

In a preferred embodiment, the invention comprises the compound according to formulae (IIIa-p), (XVIII)-(XXIV), (XVIIIa), and (XXIVa), wherein $L^{10}$ is as defined for embodiment [1], and R is as defined for embodiment [3].

In a preferred embodiment, the invention comprises the compound according to formulae (IIIa-p), (XVIII)-(XXIV), (XVIIIa), and (XXIVa) wherein $L^{10}$ is as defined for embodiment [2], and R is as defined for embodiment [3].

In a preferred embodiment, the invention comprises the compound according to formulae (IIIa-p), (XVIII)-(XXIV), (XVIIIa), and (XXIVa), wherein $L^{10}$ is as defined for embodiment [1], and $R^{30}$ is as defined for embodiment [4], [5], [5a], [6], [6a], [7] or [7a].

In a preferred embodiment, the invention comprises the compound according to formulae (IIIa-p), (XVIII)-(XXIV), (XVIIIa), and (XXIVa), wherein $L^{10}$ is as defined for embodiment [2], and $R^{30}$ is as defined for embodiment [4], [5], [5a], [6], [6a], [7] or [7a].

In a preferred embodiment, the invention comprises the compound according to formulae (IIIa-p), (XXXIX)-(XLV), and (XLVa), wherein $L^{10}$ is as defined for embodiment [1], and $R^{40}$ is as defined for embodiment [15], [16], [16a], [17], [17a], [18], or [18a]. In a preferred embodiment, the invention comprises the compound according to formulae (IIIa-p), (XXXIX)-(XLV), and (XLVa), wherein $L^{10}$ is as defined for embodiment [2], and $R^{40}$ is as defined for embodiment [15], [16], [16a], [17], [17a], [18], or [18a].

In another embodiment, the invention comprises the compound according to formula (III), of formulae (XLVI) and (XLVII),

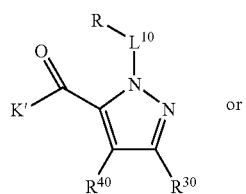

(XLVI)

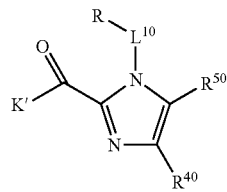

(XLVII)

wherein K' is heterocyclyl optionally substituted with one to four $R^K$ groups, and $L^{10}$, R, $R^K$, $R^{30}$, $R^{40}$, and $R^{50}$ are as defined for formula (III).

In embodiment [19], the invention comprises the compound according to formulae (XLVI) and (XLVII), wherein R is aryl optionally substituted with 1 to 4 R'. Preferably, R is phenyl optionally substituted with 1 to 4 R'. More preferably, R is phenyl optionally substituted with 1 to 4 R', wherein each R' is independently halogen, $C_1$-$C_6$ alkyl, $C_1$-$C_6$ haloalkyl, $C_3$-$C_8$cycloalkyl, —$OR^{110}$, —$SO_2R^{110}$, —$COR^{110}$, —$SO_2N(R^{110})_2$, —C≡N, —C(O)$OR^{110}$, —CON($R^{110}$)$_2$, —$NR^{110}COR^{110}$, or —N($R^{110}$)$_2$, wherein $R^{110}$ is as defined for formula (III). Even more preferably, R is phenyl optionally substituted with 1 to 4 R', wherein each R' is independently halogen, $C_1$-$C_6$ alkyl, or $C_1$-$C_6$ haloalkyl. Even more preferably, R is phenyl optionally substituted with 1 or 2 R', wherein each R' is independently fluoro, chloro, methyl, or trifluoromethyl. Even more preferably, R is phenyl optionally substituted with 1 or 2 R', wherein each R' is independently fluoro or chloro.

In a preferred embodiment, K' is a heterocyclyl group containing at least one nitrogen atom. In a more preferred embodiment, K' is a heterocyclyl group containing at least one nitrogen atom. and K' is bonded to the carbonyl group of the parent structure via a nitrogen atom.

In embodiment [20] of the second aspect, the invention comprises the compound according to formulae (XLVI) and (XLVII) wherein $L^{10}$ is a bond.

In embodiment [21] of the second aspect, the invention comprises the compound according to formulae (XLVI) and (XLVII) wherein $L^{10}$ is —[$CH_2$]$_{1-3}$—. Preferably, $L^{10}$ is —$CH_2$—.

In embodiment [22] of the second aspect, the invention comprises the compound according to formulae (XLVI) and (XLVII) wherein K' is azepanyl, diazepanyl, morpholinyl, thiomorpholinyl, piperidinyl, piperazinyl, tetrahydropyranyl, tetrahydrofuranyl, pyrrolidinyl, imidazolidinyl, oxazolidinyl, or thiazolidinyl, each optionally substituted with 1 to 4 $R^{K'}$, wherein $R^{K'}$ is as defined for formula (III). Preferably, K' is azepanyl, piperidinyl, piperazinyl, pyrrolidinyl, or morpholinyl, each optionally substituted with 1 to 4 $R^{K'}$, wherein $R^{K'}$ is as defined for formula (III).

In embodiment [23] of the second aspect, the invention comprises the compound according to formulae (XLVI) wherein $R^{30}$ is —$R^{71}$, wherein
$R^{71}$ is hydrogen, halogen, —$Z^2$, or —$Y^2$—$Z^2$, wherein
$Y^2$ is —[C($R^{151}$)$_2$]$_p$—, —($C_3$-$C_6$)cycloalkyl-, or $C_2$-$C_6$alkenyl, wherein
each $R^{151}$ is independently H, halogen, —($C_3$-$C_6$)cycloalkyl-, or ($C_1$-$C_6$)alkyl; and $Z^2$ is —H, halogen, —$OR^{110}$, —N($R^{110}$)$_2$, —C(=O)$R^{110}$, —C(=O)$OR^{110}$, —C(=O)N($R^{110}$)$_2$, —C(=N—OH)$R^{110}$, or —C(=S)N($R^{110}$)$_2$, wherein $R^{110}$ is as defined for formula (III).

In embodiment [23a] of the second aspect, the invention comprises the compound according to formula (XLVI)

wherein $R^{30}$ is heteroaryl or heterocyclyl wherein each is optionally substituted with 1 to 4 $R^{70a}$, wherein $R^{70a}$ is as defined for formula (III).

In embodiment [23b] of the second aspect, the invention comprises the compound according to formula (XLVI) wherein $R^{30}$ is heteroaryl optionally substituted with 1 to 4 $R^{70a}$, wherein $R^{70a}$ is as defined for formula (III). Preferably, $R^{30}$ is a 5-membered heteroaryl optionally substituted with 1 to 4 $R^{70a}$, wherein $R^{70a}$ is as defined for formula (III). More preferably, $R^{30}$ is thienyl, furyl, pyrrolyl, oxazolyl, isoxazolyl, thiazolyl, isothiazolyl, imidazolyl, pyrazolyl, oxadiazolyl, thiadiazolyl, triazolyl, or tetrazolyl, each optionally substituted with 1 or 2 $R^{70a}$, wherein $R^{70a}$ is as defined for formula (III). More preferably, $R^{30}$ is oxazolyl, thiazolyl, imidazolyl, oxadiazolyl, or thiadiazolyl, each optionally substituted with 1 or 2 $R^{70a}$, wherein $R^{70a}$ is as defined for formula (III).

In embodiment [23c] of the second aspect, the invention comprises the compound according to formula (XLVI) wherein $R^{30}$ is a 6-membered heteroaryl optionally substituted with 1 to 4 $R^{70a}$, wherein $R^{70a}$ is as defined for formula (III). More preferably, $R^{30}$ is pyridyl, pyrazinyl, or pyrimidinyl, each optionally substituted with 1 or 2 $R^{70a}$, wherein R is as defined for formula (III).

In embodiment [23d] of the second aspect, the invention comprises the compound according to formulae formula (XLVI), wherein $R^{30}$ is heterocyclyl optionally substituted with 1 to 4 $R^{70a}$, wherein $R^{70a}$ is as defined for formula (III). Preferably, $R^{30}$ is a 5-membered heterocyclyl optionally substituted with 1 to 4 $R^{70a}$, wherein $R^{70a}$ is as defined for formula (III). More preferably, $R^{30}$ is tetrahydrothienyl, tetrahydrofuryl, pyrrolidinyl, dihydrothienyl, dihydrofuryl, pyrrolinyl, imidazolidinyl, pyrazolidinyl, oxazolidinyl, isoxazolidinyl, thiazolidinyl, isothiazolidinyl, dioxolanyl, oxathiolanyl, dithiolanyl, imidazolinyl, pyrazolinyl, oxazolinyl, isoxazolinyl, thiazolinyl, isothiazolinyl, 1,3-dioxolyl, 1,3-oxathiolyl, or 1,3-dithiolyl, each optionally substituted with 1 or 2 $R^{70a}$, wherein $R^{70a}$ is as defined for formula (III). Even more preferably, $R^{30}$ is imidazolidinyl, oxazolidinyl, thiazolidinyl, dioxolanyl, oxathiolanyl, dithiolanyl, imidazolinyl, oxazolinyl, thiazolinyl, 1,3-dioxolyl, 1,3-oxathiolyl, or 1,3-dithiolyl, each optionally substituted with 1 or 2 $R^{70a}$, wherein $R^{70a}$ is as defined for formula (III).

In embodiment [23e] of the second aspect, the invention comprises the compound according to formula (XLVI), wherein $R^{30}$ is a 6-membered heterocyclyl optionally substituted with 1 to 4 $R^{70a}$, wherein $R^{70a}$ is as defined for formula (III). More preferably, $R^{30}$ is piperidinyl, piperazinyl, morpholinyl, thiomorpholinyl, tetrahydropyranyl, tetrahydrothiopyranyl, dioxanyl, oxathianyl, or dithianyl, each optionally substituted with 1 or 2 $R^{70a}$, wherein $R^{70a}$ is as defined for formula (III).

In embodiment [23f] of the second aspect, the invention comprises the compound according to formula (XLVI) wherein $R^{30}$ is —X—Y—Z, wherein X, Y, and Z are as defined for formula (III). Preferably, $R^{30}$ is —X[C($R^{150}$)$_2$]$_p$Z, wherein p, $R^{150}$, and Z are as defined for formula (III). More preferably, $R^{30}$ is —X[C($R^{151}$)$_2$]$_p$Z, wherein $R^{151}$ is hydrogen, halogen, (C$_1$-C$_2$)alkyl, or (C$_1$-C$_2$)haloalkyl; and p, and Z are as defined for formula (III). Even more preferably, $R^{30}$ is —O[C($R^{151}$)$_2$]$_p$Z or —N($R^{100}$)[C($R^{151}$)$_2$]$_p$Z, wherein $R^{151}$ is hydrogen, halogen, (C$_1$-C$_2$)alkyl, or (C$_1$-C$_2$)haloalkyl; and p, $R^{100}$, and Z are as defined for formula (III).

In embodiment [24] of the second aspect, the invention comprises the compound according to formulae (XLVI) wherein $R^{40}$ is hydrogen, halogen, nitro, cyano, C$_1$-C$_6$alkyl, or C$_1$-C$_6$haloalkyl. Preferably, $R^{40}$ is hydrogen or halogen. More preferably, $R^{40}$ is hydrogen.

In embodiment [25] of the second aspect, the invention comprises the compound according to formulae (XLVII) wherein $R^{40}$ is —$R^{71}$, wherein $R^{71}$ is hydrogen, halogen, —Z$^2$, or —Y$^2$—Z$^2$, wherein
Y$^2$ is —[C($R^{51}$)$_2$]$_p$—, —(C$_3$-C$_6$)cycloalkyl-, or C$_2$-C$_6$alkenyl, wherein
each $R^{151}$ is independently H, halogen, —(C$_3$-C$_6$)cycloalkyl-, or (C$_1$-C$_6$)alkyl; and Z$^2$ is —H, halogen, —OR$^{110}$, —N($R^{110}$)$_2$, —C(=O)$R^{110}$, —C(=O)OR$^{110}$, —C(=O)N($R^{110}$)$_2$, —C(=N—OH)$R^{110}$, or —C(=S)N($R^{110}$)$_2$, wherein $R^{110}$ is as defined for formula (III).

In embodiment [25a] of the second aspect, the invention comprises the compound according to formula (XLVII) wherein $R^{30}$ is heteroaryl or heterocyclyl wherein each is optionally substituted with 1 to 4 $R^{70a}$, wherein $R^{70a}$ is as defined for formula (III).

In embodiment [25b] of the second aspect, the invention comprises the compound according to formula (XLVII) wherein $R^{30}$ is heteroaryl optionally substituted with 1 to 4 $R^{70a}$, wherein $R^{70a}$ is as defined for formula (III). Preferably, $R^{30}$ is a 5-membered heteroaryl optionally substituted with 1 to 4 $R^{70a}$, wherein $R^{70a}$ is as defined for formula (III). More preferably, $R^{30}$ is thienyl, furyl, pyrrolyl, oxazolyl, isoxazolyl, thiazolyl, isothiazolyl, imidazolyl, pyrazolyl, oxadiazolyl, thiadiazolyl, triazolyl, or tetrazolyl, each optionally substituted with 1 or 2 $R^{70a}$, wherein $R^{70a}$ is as defined for formula (III). More preferably, $R^{30}$ is oxazolyl, thiazolyl, imidazolyl, oxadiazolyl, or thiadiazolyl, each optionally substituted with 1 or 2 $R^{70a}$, wherein $R^{70a}$ is as defined for formula (III).

In embodiment [25c] of the second aspect, the invention comprises the compound according to formula (XLVII) wherein $R^{30}$ is a 6-membered heteroaryl optionally substituted with 1 to 4 $R^{70a}$, wherein $R^{70a}$ is as defined for formula (III). More preferably, $R^{30}$ is pyridyl, pyrazinyl, or pyrimidinyl, each optionally substituted with 1 or 2 $R^{70a}$, wherein $R^{70a}$ is as defined for formula (III).

In embodiment [25d] of the second aspect, the invention comprises the compound according to formulae formula (XLVII), wherein $R^{30}$ is heterocyclyl optionally substituted with 1 to 4 $R^{70a}$, wherein $R^{70a}$ is as defined for formula (III). Preferably, $R^{30}$ is a 5-membered heterocyclyl optionally substituted with 1 to 4 $R^{70a}$, wherein $R^{70a}$ is as defined for formula (III). More preferably, $R^{30}$ is tetrahydrothienyl, tetrahydrofuryl, pyrrolidinyl, dihydrothienyl, dihydrofuryl, pyrrolinyl, imidazolidinyl, pyrazolidinyl, oxazolidinyl, isoxazolidinyl, thiazolidinyl, isothiazolidinyl, dioxolanyl, oxathiolanyl, dithiolanyl, imidazolinyl, pyrazolinyl, oxazolinyl, isoxazolinyl, thiazolinyl, isothiazolinyl, 1,3-dioxolyl, 1,3-oxathiolyl, or 1,3-dithiolyl, each optionally substituted with 1 or 2 $R^{70a}$, wherein $R^{70a}$ is as defined for formula (III). Even more preferably, $R^{30}$ is imidazolidinyl, oxazolidinyl, thiazolidinyl, dioxolanyl, oxathiolanyl, dithiolanyl, imidazolinyl, oxazolinyl, thiazolinyl, 1,3-dioxolyl, 1,3-oxathiolyl, or 1,3-dithiolyl, each optionally substituted with 1 or 2 $R^{70a}$, wherein $R^{70a}$ is as defined for formula (III).

In embodiment [25e] of the second aspect, the invention comprises the compound according to formula (XLVII), wherein $R^{30}$ is a 6-membered heterocyclyl optionally substituted with 1 to 4 $R^{70a}$, wherein $R^{70a}$ is as defined for formula (III). More preferably, $R^{30}$ is piperidinyl, piperazinyl, morpholinyl, thiomorpholinyl, tetrahydropyranyl, tetrahydrothiopyranyl, dioxanyl, oxathianyl, or dithianyl, each optionally substituted with 1 or 2 $R^{70a}$, wherein $R^{70a}$ is as defined for formula (III).

In embodiment [25f] of the second aspect, the invention comprises the compound according to formula (XLVII) wherein $R^{30}$ is —X—Y—Z, wherein X, Y, and Z are as defined for formula (III). Preferably, $R^{30}$ is —X[C($R^{150}$)$_2$]$_p$Z, wherein p, $R^{150}$, and Z are as defined for formula (III). More preferably, $R^{30}$ is —X[C($R^{151}$)$_2$]$_p$Z, wherein $R^{151}$ is hydrogen, halogen, ($C_1$-$C_2$)alkyl, or ($C_1$-$C_2$)haloalkyl; and p, and Z are as defined for formula (III). Even more preferably, $R^{30}$ is —O[C($R^{151}$)$_2$]$_p$Z or —N($R^{100}$)[C($R^{151}$)$_2$]$_p$Z, wherein $R^{151}$ is hydrogen, halogen, ($C_1$-$C_2$)alkyl, or ($C_1$-$C_2$)haloalkyl; and p, $R^{100}$, and Z are as defined for formula (III).

In embodiment [26] of the second aspect, the invention comprises the compound according to formulae (XLVII) wherein $R^{50}$ is hydrogen, halogen, nitro, cyano, $C_1$-$C_6$alkyl, or $C_1$-$C_6$haloalkyl. Preferably, $R^{50}$ is hydrogen or halogen. More preferably, $R^{50}$ is hydrogen.

In a preferred embodiment, the invention comprises the compound according to formulae (XLVI) and (XLVII), wherein $L^{10}$ is defined as in embodiment [20], and R is defined as in embodiment [19]

In a preferred embodiment, the invention comprises the compound according to formulae (XLVI) and (XLVII), wherein $L^{10}$ is defined as in embodiment [21], and R is defined as in embodiment [19]

In a preferred embodiment, the invention comprises the compound according to formulae (XLVI) and (XLVII), wherein $L^{10}$ is defined as in embodiment [20]; R is defined as in embodiment [19]; and K' is defined as in embodiment [22]

In a preferred embodiment, the invention comprises the compound according to formulae (XLVI) and (XLVII), wherein $L^{10}$ is defined as in embodiment [21]; R is defined as in embodiment [19]; and K' is defined as in embodiment [22].

In a preferred embodiment, the invention comprises the compound according to formulae (XLVI) and (XLVII), wherein $L^{10}$ is defined as in embodiment [20]; R is defined as in embodiment [19]; and K' is defined as in embodiment [22].

In a preferred embodiment, the invention comprises the compound according to formulae (XLVI) and (XLVII), wherein $L^{10}$ is defined as in embodiment [21]; R is defined as in embodiment [19]; and K' is defined as in embodiment [22].

In a preferred embodiment, the invention comprises the compound according to formula (XLVI) wherein $L^{10}$ is defined as in embodiment [20]; R is defined as in embodiment [19]; K' is defined as in embodiment [22]; and $R^{30}$ is defined as in any one of embodiments [23] and [23a-f].

In a preferred embodiment, the invention comprises the compound according to formula (XLVI) wherein $L^{10}$ is defined as in embodiment [21]; R is defined as in embodiment [19]; K' is defined as in embodiment [22]; and $R^{30}$ is defined as in any one of embodiments [23] and [23a-f].

In a preferred embodiment, the invention comprises the compound according to formula (XLVII) wherein $L^{10}$ is defined as in embodiment [20]; R is defined as in embodiment [19]; K' is defined as in embodiment [22]; and $R^{40}$ is defined as in any one of embodiments [25] and [25a-f].

In a preferred embodiment, the invention comprises the compound according to formula (XLVII) wherein $L^{10}$ is defined as in embodiment [21]; R is defined as in embodiment [19]; K' is defined as in embodiment [22]; and $R^{40}$ is defined as in any one of embodiments [25] and [25a-f].

In a preferred embodiment, the invention comprises the compound according to formula (XLVI) wherein $L^{10}$ is defined as in embodiment [20]; R is defined as in embodiment [19]; K' is defined as in embodiment [22]; $R^{30}$ is defined as in any one of embodiments [23] and [23a-f]; and $R^{40}$ is defined as in embodiment [24].

In a preferred embodiment, the invention comprises the compound according to formula (XLVI) wherein $L^{10}$ is defined as in embodiment [21]; R is defined as in embodiment [19]; K' is defined as in embodiment [22]; $R^{30}$ is defined as in any one of embodiments [23] and [23a-f]; and $R^{40}$ is defined as in embodiment [24].

In a preferred embodiment, the invention comprises the compound according to formula (XLVII) wherein $L^{10}$ is defined as in embodiment [20]; R is defined as in embodiment [19]; K' is defined as in embodiment [22]; $R^{40}$ is defined as in any one of embodiments [25] and [25a-f]; and $R^{50}$ is defined as in embodiment [26].

In a preferred embodiment, the invention comprises the compound according to formula (XLVII) wherein $L^{10}$ is defined as in embodiment [21]; R is defined as in embodiment [19]; K' is defined as in embodiment [22]; $R^{40}$ is defined as in any one of embodiments [25] and [25a-f]; and $R^{50}$ is defined as in embodiment [26].

In another aspect, the present invention comprises a compound according to Formula (LX),

(LX)

or a pharmaceutically acceptable salt thereof, wherein
$J^{11}$ is —N= or —C$R^{200}$—, provided that (i) when $J^{11}$ is N, then $J^{21}$ is —C$R^{300}$—; and (ii) when $J^{11}$ is —C$R^{200}$—, then $J^{21}$ is =N—;
$R^{00}$ is $G^1$, $G^{21}$, or $R^N$;
$R^{200}$ is $G^1$, $G^{21}$, or $R^C$;
$R^{300}$ and $R^{400}$ are independently $R^C$ or Q, provided one and only one of $R^{300}$, $R^{400}$, and $R^{500}$ is Q,
  wherein Q is heteroaryl or heterocyclyl, each optionally substituted with 1 to 4 $R^Q$, or
  Q is —X—Y—Z;
$R^{500}$ is $G^1$, $G^{21}$, Q, or $R^C$;
provided that only one of $R^{00}$, $R^{200}$, and $R^{500}$ is $G^1$ and only one of $R^{00}$, $R^{200}$, and $R^{500}$ is $G^{21}$;
$G^{21}$ is -$J^0$-$K^0$, wherein
$J^0$ and $K^0$ are independently aryl or heteroaryl, each optionally substituted with one to four $R^K$ groups;
and $G^1$, $R^Q$ is $R^{70a}$, $R^N$, $R^K$, $R^C$, X, Y, and Z are as defined for Formula (III).

In another aspect, the present invention comprises a compound according to Formula (LXg),

(LXg)

or a pharmaceutically acceptable salt thereof, wherein:
$J^{11}$ is —N= or —C$R^{200}$—, provided that (i) when $J^{11}$ is N, then $J^{21}$ is —C$R^{300}$—; and (ii) when $J^{11}$ is —C$R^{200}$—, then $J^{21}$ is =N—;

$R^{00}$ is $G^1$, $G^{21}$, or $R^N$;

$R^{200}$ is $G^1$, $G^{21}$, or $R^C$;

$R^{300}$ and $R^{400}$ are independently $R^C$ or Q, provided one and only one of $R^{300}$, $R^{400}$, and $R^{500}$ is Q;

Q is $C_{3-6}$ cycloalkyl, heteroaryl or heterocyclyl, each optionally substituted with 1 to 4 $R^Q$, or Q is —X—Y—Z; wherein each $R^Q$ is independently aryloxy, aralkyloxy, aryloxyalkyl, aryl$C_0$-$C_6$alkylcarboxy, $C(R^{110})$=$C(R^{110})$—COOH, oxo, =S, —Z, —Y'—Z, or —X—Y—Z, wherein each $R^Q$ is optionally substituted with 1 to 4 $R^{80}$;

$R^{500}$ is $G^1$, $G^{21}$, Q, or $R^C$;

provided that only one of $R^{00}$, $R^{200}$, and $R^{500}$ is $G^1$ and only one of $R^{00}$, $R^{200}$, and $R^{500}$ is $G^{21}$;

$G^{21}$ is -$J_0$-$K^0$, wherein $J^0$ and $K^0$ are independently aryl or heteroaryl, each optionally substituted with one to four $R^K$ groups;

each $R^K$ is independently hydrogen, halogen, $CR^{110}$=$CR^{110}COOR^{110}$, nitro, —Z, —Y—Z, or —X—Y—Z;

$G^1$ is -$L^{10}$-R, wherein $L^{10}$ is a bond $L^{50}$, $L^{60}$, -$L^{50}$-$L^{60}$-$L^{50}$-, or -$L^{60}$-$L^{50}$-$L^{60}$-, wherein each $L^{50}$ is independently —[$C(R^{150})_2$]$_m$—;

each $L^{60}$ is independently —CS—, —CO—, —SO$_2$—, —O—, —CON($R^{110}$)—, —CONR$^{110}$N($R^{110}$)—, —C(=N$R^{110}$)—, —C(=NOR$^{110}$)—, or —C(=N—N($R^{110}$)$_2$)—, —$C_3$-$C_8$cycloalkyl-, or -heterocyclyl-, wherein the cycloalkyl or heterocyclyl is optionally substituted with one to 4 $R^{140}$ groups;

or each $L^{60}$ is independently $C_2$-$C_6$ alidiyl, wherein the alidiyl chain is optionally interrupted by —$C(R^{110})_2$—, —$C(R^{11})_2C(R^{110})_2$—, —$C(R^{110})$=$C(R^{110})$—, —$C(R^{110})_2O$—, —$C(R^{110})_2NR^{110}$—, —C≡C—, —O—, —S—, —N($R^{110}$)CO—, —N($R^{100}$)CO$_2$—, —CON($R^0$)—, —CO—, —CO$_2$—, —OC(=O)—, —OC(=O)N$R^{100}$—, —SO$_2$—, —N(O$R^{100}$)SO$_2$—, or —SO$_2$N($R^{100}$);

R is aryl, heterocyclyl, heteroaryl or —($C_3$-$C_6$)cycloalkyl, wherein R is optionally substituted with 1 to 4 $R^A$, wherein each $R^A$ is independently halogen, nitro, heterocyclyl, $C_1$-$C_6$ alkyl, $C_2$-$C_6$ alkenyl, $C_2$-$C_6$ alkynyl, $C_3$-$C_8$ cycloalkyl, ($C_3$-$C_8$ cycloalkyl)-$C_1$-$C_6$ alkyl-, ($C_3$-$C_8$ cycloalkenyl)-$C_1$-$C_6$ alkyl-, ($C_3$-$C_8$ cycloalkyl)-$C_2$-$C_6$ alkenyl-, arylalkyl, aryloxy, aryl$C_{1-6}$ alkoxy, $C_1$-$C_6$ haloalkyl, SO$_2R^{110}$, OR$^{110}$, SR$^{110}$, N$_3$, SOR$^{110}$, COR$^{100}$)$_2$, SO$_2$N($R^{110}$)$_2$, SO$_2$NR$^{110}$COR$^{110}$, C≡N, C(O)OR$^{110}$, CON($R^{110}$), CON($R^{110}$)OR$^{110}$, OCON($R^{11}$)$_2$, NR$^{110}$COR$^{110}$, NR$^{110}$CON($R^{11}$)$_2$, NR$^{110}$COOR$^{110}$, —C(=N—OH)R$^{110}$, —C(=S)N($R^{110}$)$_2$, —S(=O)N($R^{110}$)$_2$, —S(=O)OR$^{110}$, —N($R^{110}$)S(=O)$_2$R$^{110}$, —C(=O)N($R^{110}$)N($R^{110}$)$_2$, —OC(=O)—R$^{110}$, —OC(=O)—OR$^{110}$ or N($R^{110}$)$_2$, wherein each $R^A$ is optionally substituted with 1 to 4 groups which independently are -halogen, —$C_1$-$C_6$ alkyl, aryloxy, $C_{0-6}$ alkylSO$_2R^{110}$, $C_{0-6}$ alkylCOOR$^{110}$, $C_{1-6}$ alkoxyaryl, $C_1$-$C_6$ haloalkyl, —SO$_2R^{110}$, —OR$^{110}$, —SR$^{110}$, —N$_3$, —SO$_2R^{110}$, —COR$^{110}$, —SO$_2$N($R^{110}$)$_2$, —SO$_2$NR$^{110}$COR$^{110}$, —C≡N, —C(O)OR$^{110}$, —CON($R^{110}$)$_2$, —CON($R^{110}$)OR$^{110}$, —OCON($R^{110}$)$_2$, —NR$^{110}$COR$^{110}$, —NR$^{110}$CON($R^{110}$)$_2$, —NR$^{110}$COOR$^{110}$, or —N($R^{110}$)$_2$;

$R^N$ is -L 31-$R^{60}$ wherein $L^{31}$ is a bond, —$X^3$—(CH$_2$)$_n$—$X^3$—, —(CH$_2$)$_m$—$X^3$—(CH$_2$)$_n$— or —(CH$_2$)$_{1+w}$—$Y^3$—(CH$_2$)$_w$—, wherein each w is independently 0-5; and each $X^3$ is independently a bond, —$C(R^{110})_2$—, —$C(R^{110})_2$ $C(R^{110})_2$—, —$C(R^{110})$=$C(R^{110})$—, —C≡C—, —CO—, —CS—, —CONR$^{100}$—, —C(=N)(R$^{110}$)—, —C(=N—OR$^{110}$)—, —C[=N—N($R^{110}$)$_2$], —CO$_2$—, —SO$_2$—, or —SO$_2$N($R^{110}$)—; and $Y^3$ is —O—, —S—, —NR$^{70}$—, —N($R^{100}$)CO—, —N($R^{100}$)CO$_2$—, —OCO—, —OC(=O)N($R^{100}$)—, —NR$^{100}$CONR$^{100}$—, —N($R^{110}$)SO$_2$—, or —NR$^{100}$CSNR$^{100}$;

or $L^{31}$ is $C_{2-6}$ alidiyl chain wherein the alidiyl chain is optionally interrupted by —$C(R^{110})_2$—, —$C(R^{110})_2C(R^{110})_2$—, —$C(R^{110})$=$C(R^{110})$—, —$C(R^{110})_2O$—, —$C(R^{110})_2NR^{110}$—, —C≡C—, —O—, —S—, —N($R^{100}$)CO—, —N($R^{100}$)CO$_2$—, —CON($R^{100}$)—, —CO—, —CO$_2$—, —OC(=O)—, —OC(=O)N($R^{100}$)—, —SO$_2$—, —N($R^{100}$)SO$_2$—, or —SO$_2$N($R^{110}$); and $R^{60}$ is $C_1$-$C_6$ alkyl, $C_1$-$C_6$ haloalkyl, aryl, $C_3$-$C_8$ cycloalkyl, heteroaryl, heterocyclyl, —CN, —C(=O)R$^{110}$, —C(=O)OR$^{110}$, —C(=O)N($R^{110}$)$_2$, —N($R^{110}$)$_2$, —SO$_2R^{110}$, —S(=O)$_2$N($R^{110}$)$_2$, —C(=O)N($R^{110}$)N($R^{110}$)$_2$, or —C(=O)N($R^{110}$)(OR$^{110}$), wherein the aryl, heteroaryl, cycloalkyl, or heterocyclyl is optionally substituted with 1 to 4 $R^{60a}$, wherein each $R^{60a}$ is independently —Z, —Y'—Z, or —X—Y—Z;

each $R^C$ is independently -$L^{30}$-$R^{70}$, wherein each $L^{30}$ is independently a bond or —(CH$_2$)$_m$—$V^{10}$—(CH$_2$)$_n$—, wherein $V^{10}$ is —$C(R^{110})_2$—, —$C(R^{110})_2C(R^{110})_2$—, —$C(R^{111})$=$C(R^{110})$—, —$C(R^{110})_2O$—, —$C(R^{110})_2NR^{110}$—, —C≡C— —O—, —S—, —NR$^{110}$N($R^{110}$)CO$_2$—, —N($R^{100}$)CO$_2$—, —OCO—, —CO—, —CS—, —CON R$^{100}$—, —C(=N—R$^{110}$)—, —C(=N—OR$^{110}$)—, —C[=N—N($R^{110}$)$_2$], —CO$_2$—, —OC(=O)—, —OC(=O)N($R^{100}$)—, —SO$_2$—, —N($R^{100}$)SO$_2$—, —SO$_2$N($R^{110}$)—, —NR$^{100}$CONR$^{100}$—, —NR$^{100}$CSNR$^{100}$—, $C_3$-$C_6$cyclo alkyl, or $C_3$-$C_6$ cyclohaloalkyl;

or each $L^{30}$ is independently $C_2$-$C_6$ alidiyl, wherein the alidiyl chain is optionally interrupted by —$C(R^{110})_2$—, —$C(R^{110})_2C(R^{110})_2$—, —$C(R^{110})$=CR$^{110}$)—, —$C(R^{110})_2O$—, —$C(R^{110})_2NR^{110}$—, —C≡C—, —O—, —S—, —N($R^{100}$)CO—, —N($R^{100}$)CO$_2$—, —NR$^{110}$—, —CON($R^{100}$)—, —CO—, —CO$_2$—, —OC(=O)—, —OC(=O)N($R^{110}$)—, —SO$_2$—, —N($R^{110}$)SO$_2$—, or —SO$_2$N($R^{100}$)—;

each $R^{70}$ is independently hydrogen, halogen, nitro, aryl, heteroaryl, heterocyclyl, —Z, —Y—Z, or —X—Y—Z, wherein the aryl, heteroaryl, and heterocyclyl, are each optionally substituted with 1 to 4 $R^{70a}$, wherein each $R^{70a}$ is independently aryloxy, aralkyloxy, aryloxyalkyl, aryl$C_0$-$C_6$alkylcarboxy, $C(R^{110})$=$C(R^{110})$—COOH, oxo, —Z, —Y'—Z, or —X—Y—Z, wherein each $R^{70a}$ is optionally substituted with 1 to 4 $R^{80}$, and wherein each $R^{80}$ is independently halogen, $C_1$-$C_6$ alkyl, $C_1$-$C_6$ alkoxy, $C_1$-$C_6$ haloalkyl, $C_1$-$C_6$ haloalkyl (OR$^{110}$), $C_0$-$C_6$ alkylOR$^{110}$, $C_0$-$C_6$ alkylCON($R^{110}$)$_2$, $C_0$-$C_6$ alkylCOR$^{110}$, $C_0$-$C_6$ alkylCOOR$^{110}$, or $C_0$-$C_6$ alkylSO$_2R^{110}$;

each $R^{100}$ is independently —R$^{110}$, —C(=O)R$^{110}$, —CO$_2R^{110}$, or —SO$_2R^{110}$;

each $R^{110}$ is independently -hydrogen, —$C_1$-$C_6$ alkyl, $C_2$-$C_6$ alkenyl, $C_2$-$C_6$ alkynyl, —$C_1$-$C_6$ haloalkyl, or —N(R$^{12}$)$_2$, wherein any of $R^{110}$ is optionally substituted with 1 to 4 radicals of $R^{120}$;

each $R^{120}$ is independently halogen, cyano, nitro, oxo, —B(OR$^{130}$)$_2$, $C_0$-$C_6$ alkylN(R$^{130}$)$_2$, $C_1$-$C_6$haloalkyl, $C_1$-$C_6$ alkyl, $C_1$-$C_6$ alkoxy, ($C_0$-$C_6$ alkyl)C=O(OR$^{130}$), $C_0$-$C_6$ alkylOR$^{130}$, $C_0$-$C_6$ alkylCOR$^{130}$, $C_0$-$C_6$alkylSO$_2$R$^{130}$, $C_0$-$C_6$alkylCON(R$^{130}$)$_2$, $C_0$-$C_6$alkylCONR$^{130}$OR$^{130}$, $C_0$-$C_6$alkylSO$_2$N(R$^{13}$)$_2$, $C_0$-$C_6$alkylSR$^{130}$, $C_0$-$C_6$ haloalkylOR$^{130}$, $C_0$-$C_6$alkylCN, —$C_0$-$C_6$alkylN(R$^{130}$)$_2$, —NR$^{130}$SO$_2$R$^{130}$, or —OC$_{0-6}$ alkylCOOR$^{130}$;

each $R^{130}$ is independently hydrogen, $C_1$-$C_6$ alkyl, $C_2$-$C_6$ alkenyl, or $C_2$-$C_6$ alkynyl;

each $R^{140}$ is independently $C_1$-$C_6$ alkyl, $C_1$-$C_6$ alkoxy, halogen, $C_1$-$C_6$ haloalkyl, $C_0$-$C_6$ alkylCON(R$^{110}$)$_2$, $C_0$-$C_6$ alkylCONR$^{110}$OR$^{110}$, $C_0$-$C_6$ alkylOR$^{110}$, or $C_0$-$C_6$ alkyl-COOR$^{110}$; and each $R^{150}$ is independently hydrogen, halogen, OR$^{130}$, ($C_1$-$C_6$)alkyl, or ($C_1$-$C_6$)haloalkyl, wherein each alkyl is optionally substituted with at least one group which are each independently halogen, cyano, nitro, azido, OR$^{130}$, C(O)R$^{130}$, C(O)OR$^{130}$, C(O)N(R$^{130}$)$_2$, N(R$^{130}$)$_2$, N(R$^{130}$)C(O)R$^{130}$, N(R$^{130}$)S(O)$_2$R$^{130}$, OC(O)OR$^{130}$, OC(O)N(R$^{130}$)$_2$, N(R$^{130}$)C(O)OR$^{130}$, N(R$^{130}$)C(O)N(R$^{130}$), SR$^{130}$, S(O)R$^{130}$, S(O)$_2$R$^{130}$, or S(O)$_2$N(R$^{130}$)$_2$;

each X is independently —O—, —S—, or —N(R$^{100}$)—;
each Y is independently —[C(R$^{150}$)$_2$]$_p$—, or —$C_2$-$C_6$ alkenyl, wherein p is 1, 2, 3, 4, 5, or 6;

each Y' is independently —[C(R$^{150}$)$_2$]$_p$—, —$C_2$-$C_6$ alkenyl, $C_3$-$C_8$ cycloalkyl, or heterocyclyl, wherein the cycloalkyl or heterocyclyl is optionally substituted with 1 to 3 Z groups;

each Z is independently —H, halogen, —OR$^{110}$, —SR$^{110}$, —C(=O)R$^{110}$, —C(=O)OR$^{110}$, —C(=O)N(R$^{110}$)$_2$, —N(R$^{100}$)$_2$, —N$_3$, —NO$_2$, —C(=N—OH)R$^{110}$, —C(=S)N(R$^{110}$)$_2$, —CN, —S(=O)R$^{110}$, —S(=O)N(R$^{110}$)$_2$, —S(=O)OR$^{110}$, —S(=O)$_2$R$^{110}$, S(=O)$_2$N(R$^{110}$)$_2$, —NR$^{110}$COR$^{110}$, —N(R$^{110}$)C(=O)N(R$^{110}$)$_2$, —N(R$^{110}$)COOR$^{110}$, —N(R$^{110}$)S(=O)$_2$R$^{110}$, —C(=O)N(R$^{110}$)N(R$^{110}$)$_2$, —C(=O)N(R$^{110}$)(OR$^{110}$), —OC(=O)—R$^{110}$, —OC(=O)—OR$^{110}$, or —OC(=O)—N(R$^{110}$)$_2$; and each m and n is independently 0, 1, 2, 3, 4, 5, or 6.

In another aspect, the present invention comprises a compound according to Formula (LX) wherein Q is heteroaryl or heterocyclyl, each optionally substituted with 1 to 4 R$^Q$.

In another aspect, the present invention comprises a compound according to Formula (LXg), of Formula (LXh),

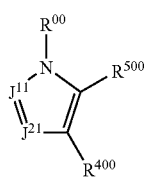

(LXh)

or a pharmaceutically acceptable salt thereof, wherein:
$J^{11}$ is —N= or —CR$^{200}$—, provided that
 (i) when $J^{11}$ is —N=, then $J^{21}$ is —CR$^{300}$—; and
 (ii) when $J^{11}$ is —CR$^{200}$—, then $J^{21}$ is =N—;
$R^{00}$ is $G^1$ or $G^{21}$, provided one and only one of $R^{00}$ and $R^{500}$ is $G^{21}$;
$R^{200}$ is $G^1$ or $R^C$, provided that only one of $R^{00}$ and $R^{200}$ is $G^1$;

$R^{300}$ is Q;
$R^{400}$ is $R^C$ or Q, provided one and only one of $R^{300}$ and $R^{400}$ is Q;
$R^{500}$ is $G^1$, $G^{21}$ or $R^C$, provided one and only one of $R^{400}$ and $R^{500}$ is $R^C$;
Q is $C_{3-6}$ cycloalkyl, heteroaryl or heterocyclyl, each optionally substituted with 1 to 4 R$^Q$;
R$^Q$ is independently C(R$^{110}$)=C(R$^{110}$)—COOH, oxo, =S, —Z, —Y—Z, or —X—Y—Z;
$G^{21}$ is -J$^0$-K$^0$, wherein
 J$^0$ and K$^0$ are independently aryl or heteroaryl, each optionally substituted with one to four R$^K$ groups;
 each R$^K$ is independently hydrogen, halogen, nitro, —Z, —Y—Z, or —X—Y—Z;
$G^1$ is -L$^{10}$-R, wherein
 $L^{10}$ is a bond or —[C(R$^{150}$)$_2$]$_m$—;
 R is aryl or heteroaryl, wherein R is optionally substituted with 1 to 4 R$^A$, wherein
  each R$^A$ is independently halogen, nitro, $C_1$-$C_6$ alkyl, $C_2$-$C_6$ alkenyl, $C_2$-$C_6$ alkynyl, $C_1$-$C_6$ haloalkyl, SO$_2$R$^{110}$, OR$^{110}$, SR$^{110}$, SOR$^{110}$, COR$^{110}$, SO$_2$N(R$^{11}$)$_2$, SO$_2$NR$^{110}$, OR$^{110}$, C=N, C(O)OR$^{110}$, CON(R$^{110}$)$_2$, CON(R$^{110}$)OR$^{110}$, OCON(R$^{110}$)$_2$, NR$^{110}$COR$^{110}$, NR$^{110}$CON(R$^{110}$)$_2$, NR$^{110}$COOR$^{110}$, —C(=N—OH)R$^{110}$, —C(=S)N(R$^{110}$)$_2$, —S(=O)N(R$^{110}$)$_2$, —S(=O)OR$^{110}$, —N(R$^{110}$)S(=O)$_2$R$^{110}$, —C(=O)N(R$^{110}$)N(R$^{110}$)$_2$, —OC(=O)—R$^{110}$, —OC(=O)—OR$^{110}$ or N(R$^{110}$);
R$^C$ is —Z, or —Y—Z;
each R$^{100}$ is independently —R$^{110}$, —C(=O)R$^{110}$, —CO$_2$R$^{110}$, or —SO$_2$R$^{110}$;
each R$^{110}$ is independently -hydrogen, —$C_1$-$C_6$ alkyl, $C_2$-$C_6$ alkenyl, $C_2$-$C_6$ alkynyl, —$C_1$-$C_6$ haloalkyl, or —N(R$^{12}$)$_2$, wherein any of R$^{110}$ is optionally substituted with 1 to 4 radicals of R$^{120}$;
each R$^{120}$ is independently halogen, cyano, nitro, oxo, $C_0$-$C_6$ alkylN(R$^{130}$)$_2$, $C_1$-$C_6$haloalkyl, $C_1$-$C_6$ alkyl, $C_1$-$C_6$ alkoxy, ($C_0$-$C_6$ alkyl)C=O(OR$^{130}$), $C_0$-$C_6$ alkylOR$^{130}$, $C_0$-$C_6$ alkylCOR$^{130}$, $C_0$-$C_6$alkylSO$_2$R$^{130}$, $C_0$-$C_6$alkylCON(R$^{130}$, $C_0$-$C_6$alkylCONR$^{1300}$R$^{130}$, $C_0$-$C_6$alkylSO$_2$N(R$^{130}$, $C_0$-$C_6$ alkylSR$^{130}$, $C_0$-$C_6$ haloalkylOR$^{130}$, $C_0$-$C_6$ alkylCN, —$C_0$-$C_6$ alkylN(R$^{130}$), —NR$^{130}$SO$_2$R$^{13}$, or —OC$_{0-6}$ alkyl-COOR$^{130}$;

each R$^{130}$ is independently hydrogen, $C_1$-$C_6$ alkyl, $C_2$-$C_6$ alkenyl, or $C_2$-$C_6$ alkynyl;

each R$^{150}$ is independently hydrogen, halogen, OR$^{130}$, ($C_1$-$C_6$)alkyl, or ($C_1$-$C_6$)haloalkyl;

or two R$^{150}$ (bonded to the same or different atoms) together with the carbon(s) to which they are bonded form a $C_{3-6}$ cycloalkyl;

each X is independently —O—, —S—, or —N(R$^{100}$)—;
each Y is independently —[C(R$^{150}$)$_2$]$_p$—, or —$C_2$-$C_6$ alkenyl, wherein p is 1, 2, 3, 4, 5, or 6;
each Z is independently —H, halogen, —OR$^{110}$, —SR$^{110}$, —C(=O)R$^{110}$, —C(=O)OR$^{110}$, —C(=O)N(R$^{110}$)$_2$, —N(R$^{100}$)$_2$, —N$_3$, —NO$_2$, —C(=N—OH)R$^{110}$, —C(=S)N(R$^{110}$)$_2$, —CN, —S(=O)R$^{110}$, —S(=O)N(R$^{110}$)$_2$, —S(=O)OR$^{110}$, —S(=O)$_2$R$^{110}$, S(=O)$_2$N(R$^{110}$)$_2$, —NR$^{110}$COR$^{110}$, —N(R$^{110}$)C(=O)N(R$^{110}$)$_2$, —N(R$^{110}$)COOR$^{110}$, —N(R$^{110}$)S(=O)$_2$R$^{110}$, —C(=O)N(R$^{110}$)N(R$^{110}$)$_2$, —C(=O)N(R$^{110}$)(OR$^{110}$), —OC(=O)—R$^{110}$, —OC(=O)—OR$^{110}$, or —OC(=O)—N(R$^{110}$)$_2$; and each m is independently 0, 1, 2, 3, 4, 5, or 6.

In another aspect, the present invention comprises a compound according to Formula (LXh) wherein:
Q is $C_{3-6}$ cycloalkyl; 5 or 6 membered heteroaryl or 5 or 6 membered heterocyclyl, each optionally substituted with one or two $R^Q$;
  each $R^Q$ is independently halogen, $C_{1-6}$ alkyl, $CF_3$, CN, oxo, =S, $C_{0-6}$ alkyl$OR^{110}$, $C(O)R^{110}$, $CON(R^{110})_2$, or —C(=O)$OR^{110}$;
$G^{21}$ is -$J^0$-$K^0$, wherein
  $J^0$ and $K^0$ are phenyl, each optionally substituted with one or two $R^K$ groups; wherein
  each $R^K$ is independently halogen or —S(=O)$_2R^{110}$;
$G^1$ is -$L^{10}$-R, wherein
  $L^{10}$ is a bond or —$[C(R^{15})_2]$—;
  R is phenyl, wherein R is optionally substituted with one or two $R^A$ groups, wherein
  each $R^A$ is halogen or $C_1$-$C_6$ haloalkyl;
$R^C$ is $C_1$-$C_6$ alkyl, $C_1$-$C_6$ haloalkyl, or —Z;
each $R^{110}$ is independently hydrogen or —$C_1$-$C_6$ alkyl;
each $R^{150}$ is independently hydrogen, halogen, or ($C_1$-$C_6$) alkyl;
or two $R^{150}$ (bonded to the same or different carbon) together with the carbon(s) to which they are bonded form a $C_{3-6}$ cycloalkyl.

In one embodiment of compounds according to Formula (LXh), $R^C$ is Z.

In another embodiment of compounds according to Formula (LXh), each $R^{150}$ is independently hydrogen, halogen, or ($C_1$-$C_6$)alkyl In another embodiment of compounds according to Formula (LXh), each $R^Q$ is independently halogen, $C_{1-6}$ alkyl, $CF_3$, CN, oxo, =S, $C_{0-6}$ alkyl$OR^{110}$, $C(O)R^{110}$, or —C(=O)$OR^{110}$.

In another aspect, the present invention comprises a compound according to Formula (LX), of Formulae (LXa) and (LXb)

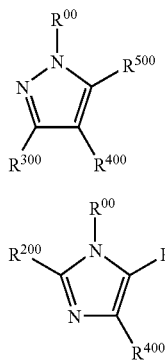

(LXa)

(LXb)

wherein $R^{00}$, $R^{200}$, $R^{300}$, $R^{400}$, and $R^{500}$ are as defined for Formula (LX).

In another embodiment, the invention comprises the compound according to Formula (LXa), wherein one of $R^{00}$ and $R^{500}$ is $G^1$ and the other is $G^{21}$, such compounds are referred to hereafter as Formula (LXc). Preferably, $R^{00}$ is $G^1$ and $R^{500}$ is $G^{21}$, such compounds are referred to hereafter as Formula (LXd).

In another embodiment, the invention comprises the compound according to Formula (LXb), wherein one of $R^{00}$ and $R^{200}$ is $G^1$ and the other is $G^{21}$, such compounds are referred to hereafter as Formula (LXe). Preferably, $R^{00}$ is $G^1$ and $R^{200}$ is $G^{21}$, such compounds are referred to hereafter as Formula (LXf).

In another aspect, the present invention comprises a compound according to Formula (LXg), of Formulae (LXi) and (LXj)

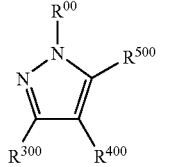

(LXi)

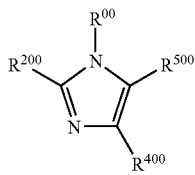

(LXj)

wherein $R^{00}$, $R^{200}$, $R^{300}$, $R^{400}$, and $R^{500}$ are as defined for Formula (LXg).

In another embodiment, the invention comprises the compound according to Formula (LXi), wherein one of $R^{00}$ and $R^{500}$ is $G^1$ and the other is $G^{21}$, such compounds are referred to hereafter as Formula (LXk). Preferably, $R^{00}$ is $G^1$ and $R^{500}$ is $G^{21}$, such compounds are referred to hereafter as Formula (LXm).

In another embodiment, the invention comprises the compound according to Formula (LXj), wherein one of $R^{00}$ and $R^{200}$ is $G^1$ and the other is $G^{21}$, such compounds are referred to hereafter as Formula (LXn). Preferably, $R^{00}$ is $G^{21}$ and $R^{200}$ is $G^1$, such compounds are referred to hereafter as Formula (LXp).

In another aspect, the present invention comprises a compound according to Formula (LXh), of Formulae (LXq) and (LXr)

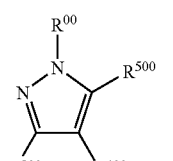

(LXq)

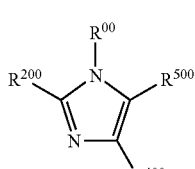

(LXr)

wherein $R^{00}$, $R^{200}$, $R^{300}$, $R^{400}$, and $R^{500}$ are as defined for Formula (LXh).

In another embodiment, the invention comprises the compound according to Formula (LXq), wherein one of $R^{00}$ and $R^{500}$ is $G^1$ and the other is $G^{21}$, such compounds are referred to hereafter as Formula (LXs). Preferably, $R^{00}$ is $G^1$ and $R^{500}$ is $G^{21}$, such compounds are referred to hereafter as Formula (LXt).

In another embodiment, the invention comprises the compound according to Formula (LXr), wherein one of $R^{00}$ and $R^{200}$ is $G^1$ and the other is $G^{21}$, such compounds are referred to hereafter as Formula (LXu). Preferably, $R^{00}$ is $G^{21}$ and $R^{200}$ is $G^1$, such compounds are referred to hereafter as Formula (LXv).

In a preferred embodiment, the present invention comprises the compounds according to Formula (LX), of Formulae (LXI)-(LXIV),

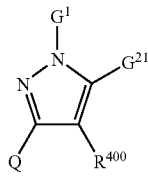
(LXI)

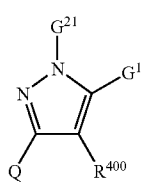
(LXII)

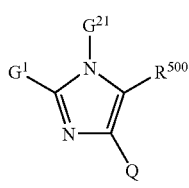
(LXIII)

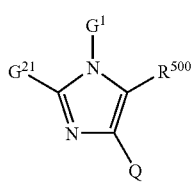
(LXIV)

wherein $G^1$, $G^{21}$, Q, $R^{400}$, and $R^{500}$ are as defined for Formula (LX).

In a preferred embodiment, the present invention comprises the compounds according to Formula (LXg), of Formulae (LXIg)-(LXIVg),

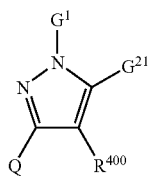
(LXIg)

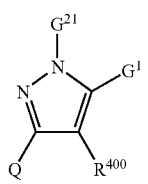
(LXIIg)

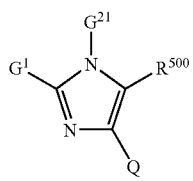
(LXIIIg)

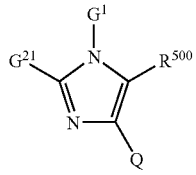
(LXIVg)

wherein $G^1$, $G^{21}$, Q, $R^{400}$, and $R^{500}$ are as defined for Formula (LXg).

In a preferred embodiment, the present invention comprises the compounds according to Formula (LXh), of Formulae (LXIh)-(LXIVh),

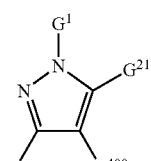
(LXIh)

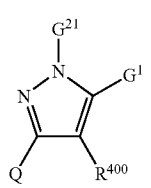
(LXIIh)

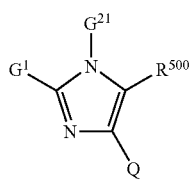
(LXIIIh)

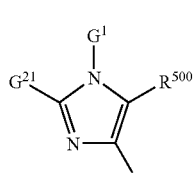
(LXIVh)

wherein $G^1$, $G^{21}$, Q, $R^{400}$, and $R^{500}$ are as defined for Formula (LXh).

In another embodiment, the invention comprises the compound according to Formulae (LXI)-(LXIV), (LXIg)-(LXIVg) and (LXIh)-(LXIVh), wherein $R^{400}$, when present, is $R^C$.

In another embodiment, the invention comprises the compound according to Formulae (LXI)-(LXIV), (LXIg)-(LXIVg) and (LXIh)-(LXIVh), wherein $R^{400}$, when present, is hydrogen.

In another embodiment, the invention comprises the compound according to Formulae (LXI)-(LXIV), (LXIg)-(LXIVg) and (LXIh)-(LXIVh), wherein $R^{500}$, when present, is $R^C$.

In another embodiment, the invention comprises the compound according to Formulae (LXI)-(LXIV), (LXIg)-(LXIVg) and (LXIh)-(LXIVh), wherein $R^{500}$, when present, is hydrogen.

In another embodiment, the invention comprises the compound according to Formulae (LX), (LXa-v), (LXIg)-(LXIVg), and (LXIh)-(LXIVh), wherein each $R^K$ is independently halogen, $C_1$-$C_6$ alkyl, $C_1$-$C_6$ haloalkyl, —$OR^{110}$, —$SO_2R^{110}$, —$COR^{110}$, —$SO_2N(R^{110})_2$, —C≡N, —C(O)$OR^{110}$, —$CON(R^{110})_2$, —$NR^{110}COR^{110}$, or $N(R^{110})_2$.

In another embodiment, the invention comprises the compound according to Formulae (LX), (LXa-v), (LXIg)-(LXIVg), and (LXIh)-(LXIVh), wherein each $R^K$ is independently halogen, cyano, $C_1$-$C_6$ alkyl, $C_1$-$C_6$ haloalkyl, —$OR^{110}$, —$SO_2R^{110}$, —$COR^{110}$, or —$C(O)OR^{110}$.

In another embodiment, the invention comprises the compound according to Formulae (LX), (LXa-v), (LXIg)-(LXIVg), and (LXIh)-(LXIVh), wherein, when present, at least one $R^K$ is —$SO_2R^{110}$.

In another embodiment, the invention comprises the compound according to Formulae (LX), (LXa-v), (LXIg)-(LXIVg), and (LXIh)-(LXIVh), wherein, each $R^K$ is independently halogen, cyano, $C_1$-$C_6$ alkyl, $C_1$-$C_6$ haloalkyl, —$OR^{110}$, —$SO_2R^{110}$, —$COR^{110}$, or —$C(O)OR^{110}$ provided that when present, at least one R is —$SO_2R^{110}$.

In another embodiment, the invention comprises the compound according to Formulae (LX)-(LXIV), (LXIg)-(LXIVg), (LXIh)-(LXIVh) and (LXa-v), wherein $G^{21}$ is -$J^O$-$K^O$, wherein
- $J^O$ and $K^O$ are independently thienyl, pyrrolyl, furyl, oxazolyl, oxazolyl, imidazolyl, pyrazolyl, isoxazolyl, isothiazolyl, phenyl, pyridyl, pyrazinyl, or pyrmidinyl, each optionally substituted with one to four $R^K$ groups.

In another embodiment, the invention comprises the compound according to Formulae (LX)-(LXIV), (LXIg)-(LXIVg), (LXIh)-(LXIVh) and (LXa-v), wherein $G^{21}$ is -$J^O$-$K^O$, wherein
- $J^O$ and $K^O$ are independently thienyl, pyrrolyl, furyl, oxazolyl, oxazolyl, imidazolyl, pyrazolyl, isoxazolyl, isothiazolyl, phenyl, pyridyl, pyrazinyl, or pyrmidinyl, each optionally substituted with one or two $R^K$ groups.

In another embodiment, the invention comprises the compound according to Formulae (LX)-(LXIV), (LXg)-(LXIVg), (LXIh)-(LXIVh) and (LXa-v), wherein $G^{21}$ is -$J^O$-$K^O$, wherein
- $J^O$ is thienyl, phenyl, or pyridyl each optionally substituted with one or two $R^K$ groups; and
- $K^O$ is phenyl, pyridyl, pyrazinyl, or pyrimidinyl, each optionally substituted with one to four $R^K$ groups.

In another embodiment, the invention comprises the compound according to Formulae (LX)-(LXIV), (LXIg)-(LXIVg), (LXIh)-(LXIVh) and (LXa-v), wherein $G^{21}$ is -$J^O$-$K^O$, wherein
- $J^O$ is thienyl optionally substituted with one or two $R^K$ groups; and
- $K^O$ is phenyl, pyridyl, pyrazinyl, or pyrimidinyl, each optionally substituted with one to four $R^K$ groups.

In another embodiment, the invention comprises the compound according to Formulae (LX)-(LXIV), (LXIg)-(LXIVg), (LXIh)-(LXIVh) and (LXa-v), wherein $G^{21}$ is -$J^O$-$K^O$, wherein
- $J^O$ is thienyl optionally substituted with one or two $R^K$ groups; and
- $K^O$ is phenyl optionally substituted with one to four $R^K$ groups.

In another embodiment, the invention comprises the compound according to Formulae (LX)-(LXIV), (LXIg)-(LXIVg), (LXIh)-(LXIVh) and (LXa-v), wherein $G^{21}$ is -$J^O$-$K^O$, wherein
- $J^O$ is phenyl optionally substituted with one or two $R^K$ groups; and
- $K^O$ is phenyl optionally substituted with one to four $R^K$ groups.

In another embodiment, the invention comprises the compound according to Formulae (LX)-(LXIV), (LXIg)-(LXIVg), (LXIh)-(LXIVh) and (LXa-v), wherein $G^{21}$ is -$J^O$-$K^O$, wherein
- $J^O$ is phenyl optionally substituted with one or two $R^K$ groups; and
- $K^O$ is phenyl optionally substituted with one to three $R^K$ groups.

In another embodiment, the invention comprises the compound according to Formulae (LX)-(LXIV), (LXIg)-(LXIVg), (LXIh)-(LXIVh) and (LXa-v), wherein $G^{21}$ is -$J^O$-$K^O$, wherein
- $J^O$ is phenyl optionally substituted with one or two $R^K$ groups; and
- $K^O$ is phenyl optionally substituted with one to three $R^K$ groups, provided that when present, at least one R is $S(=O(C_{1-6}$ alkyl).

In another embodiment, the invention comprises the compound according to Formulae (LX)-(LXIV), (LXIg)-(LXIVg), (LXIh)-(LXIVh) and (LXa-v), wherein $G^{21}$ is -$J^O$-$K^O$, wherein
- $J^O$ is phenyl optionally substituted with one or two halogen groups; and
- $K^O$ is phenyl optionally substituted with one to three $R^K$ groups.

In another embodiment, the invention comprises the compound according to Formulae (LX)-(LXIV), (LXIg)-(LXIVg), (LXIh)-(LXIVh) and (LXa-v), wherein $G^{21}$ is -$J^O$-$K^O$, wherein
- $J^O$ is phenyl optionally substituted with one or two halogen groups; and
- $K^O$ is phenyl optionally substituted with one to three $R^K$ groups, provided that when present. at least one R is $S(=O(C_{1-6}$ alkyl).

In another embodiment, the invention comprises the compound according to Formulae (LX)-(LXIV), (LXIg)-(LXIVg), (LXIh)-(LXIVh) and (LXa-v), wherein $G^{21}$ is -$J^O$-$K^O$, wherein
- $J^O$ is phenyl optionally substituted with one or two chloro groups; and
- $K^O$ is phenyl optionally substituted with one to three $R^K$ groups.

In another embodiment, the invention comprises the compound according to Formulae (LX)-(LXIV), (LXIg)-(LXIVg), (LXIh)-(LXIVh) and (LXa-v), wherein $G^{21}$ is -$J^O$-$K^O$, wherein
- $J^O$ is phenyl optionally substituted with one or two chloro groups; and $K^0$ is phenyl optionally substituted with one to three $R^K$ groups, provided that when present. at least one R is $S(=O(C_{1-6}$ alkyl)).

In another embodiment, the invention comprises the compound according to Formulae (LX)-(LXIV), (LXIg)-(LXIVg), (LXIh)-(LXIVh) and (LXa-v), wherein $G^{21}$ is -$J^0$-$K^0$, wherein $J^0$ is phenyl optionally substituted with one or two $R^K$ groups; and $K^0$ is phenyl optionally substituted with one to three $R^K$ groups, wherein each $R^K$ is independently halogen, $C_1$-$C_6$ alkyl, $C_1$-$C_6$ haloalkyl, —$OR^{110}$, —$SO_2R^{110}$, —$COR^{110}$, —$SO_2N(R^{110})_2$, —C≡N, —$C(O)OR^{110}$, —$CON(R^{110})_2$, —$NR^{110}COR^{110}$, or —$N(R^{110})_2$.

In another embodiment, the invention comprises the compound according to Formulae (LX)-(LXIV), (LXIg)-(LXIVg), (LXIh)-(LXIVh) and (LXa-v), wherein $G^{21}$ is -$J^0$-$K^0$, wherein $J^0$ is phenyl optionally substituted with one or two halogen groups; and $K^0$ is phenyl optionally substituted with one to three $R^K$ groups, wherein each $R^K$ is independently halogen, $C_1$-$C_6$ alkyl, $C_1$-$C_6$ haloalkyl, —$OR^{110}$, —$SO_2R^{110}$, —$COR^{110}$, —$SO_2N(R^{110})_2$, —C≡N, —$C(O)OR^{110}$, —$CON(R^{110})_2$, —$NR^{110}COR^{110}$, or —$N(R^{110})_2$.

In another embodiment, the invention comprises the compound according to Formulae (LX)-(LXIV), (LXIg)-(LXIVg), (LXIh)-(LXIVh) and (LXa-v), wherein $G^{21}$ is -$J^0$-$K^0$, wherein $J^0$ is phenyl optionally substituted with one or two halogen groups; and $K^0$ is phenyl optionally substituted with one to three $R^K$ groups, wherein each $R^K$ is independently halogen, $C_1$-$C_6$ alkyl, $C_1$-$C_6$ haloalkyl, —$OR^{110}$, —$SO_2R^{110}$, —$COR^{110}$, —$SO_2N(R^{110})_2$, —C≡N, —$C(O)OR^{110}$, —$CON(R^{110})_2$, —$NR^{110}COR^{110}$, or —$N(R^{110})_2$, provided that when present. at least one $R^K$ is $S(=O(C_{1-6}$ alkyl)).

In another embodiment, the invention comprises the compound according to Formulae (LX)-(LXIV), (LXIg)-(LXIVg), (LXIh)-(LXIVh) and (LXa-v), wherein $G^{21}$ is -$J^0$-$K^0$, wherein $J^0$ is phenyl optionally substituted with one or two chloro groups; and $K^0$ is phenyl optionally substituted with one to three $R^K$ groups, wherein each $R^K$ is independently halogen, $C_1$-$C_6$ alkyl, $C_1$-$C_6$ haloalkyl, —$OR^{110}$, —$SO_2R^{110}$, —$COR^{110}$, —$SO_2N(R^{110})_2$, —C≡N, —$C(O)OR^{110}$, —$CON(R^{110})_2$, —$NR^{110}COR^{110}$, or —$N(R^{110})_2$.

In another embodiment, the invention comprises the compound according to Formulae (LX)-(LXIV), (LXIg)-(LXIVg), (LXIh)-(LXIVh) and (LXa-v), wherein $G^{21}$ is -$J^0$-$K^0$, wherein $J^0$ is phenyl optionally substituted with one or two chloro groups; and $K^0$ is phenyl optionally substituted with one to three $R^K$ groups, wherein each $R^K$ is independently halogen, $C_1$-$C_6$ alkyl, $C_1$-$C_6$ haloalkyl, —$OR^{110}$, —$SO_2R^{110}$, —$COR^{110}$, —$SO_2N(R^{110})_2$, —C≡N, —$C(O)OR^{110}$, —$CON(R^{110})_2$, —$NR^{110}COR^{110}$, or —$N(R^{110})_2$, provided that when present. at least one $R^K$ is $S(=O)_2(C_{1-6}$ alkyl)).

In another embodiment, the invention comprises the compound according to Formulae (LX)-(LXIV), (LXa-v), (LXIg)-(LXIVg), and (LXIh)-(LXIVh), wherein each $R^K$ is independently halogen, cyano, $C_1$-$C_6$ alkyl, $C_1$-$C_6$ haloalkyl, —$OR^{110}$, —$SO_2R^{110}$, —$COR^{110}$, or —$C(O)OR^{110}$.

In another embodiment, the invention comprises the compound according to Formulae (LX)-(LXIV), (LXa-v), (LXIg)-(LXIVg), and (LXIh)-(LXIVh), wherein, when present, at least one R is —$SO_2R^{110}$.

In another embodiment, the invention comprises the compound according to Formulae (LX)-(LXIV), (LXa-v), (LXIg)-(LXIVg), and (LXIh)-(LXIVh), wherein, each $R^K$ is independently halogen, cyano, $C_1$-$C_6$ alkyl, $C_1$-$C_6$ haloalkyl, —$OR^{110}$, —$SO_2R^{110}$, —$COR^{110}$, or —$C(O)OR^{110}$, provided that when present, at least one R is —$SO_2R^{110}$.

In another embodiment, the invention comprises the compound according to Formulae (LX)-(LXIV), (LXIg)-(LXIVg), (LXIh)-(LXIVh) and (LXa-v), wherein $G^{21}$ is -$J^0$-$K^0$, wherein $J^0$ is thienyl optionally substituted with one or two $R^K$ groups; and $K^0$ is pyridyl optionally substituted with one to four $R^K$ groups.

In another embodiment, the invention comprises the compound according to Formulae (LX)-(LXIV), (LXIg)-(LXIVg), (LXIh)-(LXIVh) and (LXa-v), wherein $G^{21}$ is -$J^0$-$K^0$, wherein $J^0$ is phenyl each optionally substituted with one or two $R^K$ groups; and $K^0$ is pyridyl optionally substituted with one to four $R^K$ groups.

In another embodiment, the invention comprises the compound according to Formulae (LX)-(LXIV), (LXIg)-(LXIVg) and (LXa-p), wherein $G^1$ is -$L^{10}$-R, wherein $L^{10}$ is a bond, —$[C(R^{15})_2]_m$—, —CO—, —$SO_2$—, or —$C_3$-$C_8$cycloalkyl-, wherein m is 1, 2, 3, 4, 5, or 6; and R and $R^{150}$ are as defined for Formulae (III) and (LXg), respectively.

In another embodiment, the invention comprises the compound according to Formulae (LX)-(LXIV), (LXIg)-(LXIVg) and (LXa-p), wherein $G^1$ is -$L^{10}$-R', wherein $L^{10}$ is a bond or —$[C(R^{150})_2]_m$—, wherein m is 1, 2, 3, 4, 5, or 6; and R and $R^{150}$ are as defined for Formulae (III) and (LXg), respectively. Preferably, $L^{10}$ is a bond or —$[C(R^{150})_2]_m$—, and R is phenyl optionally substituted with 1 to 4 $R^A$; and $R^A$ and $R^{150}$ are as defined for Formula (III) and (LXg), respectively. Preferably, $L^{10}$ is a bond or —$[CH_2]_{1-3}$-; and R is phenyl optionally substituted with 1 to 4 $R^A$; and $R^A$ is as defined for Formula (III) and (LXg), respectively. More preferably, $L^{10}$ is a bond or —$[CH_2]_{1-3}$-; and R is phenyl optionally substituted with 1 to 4 $R^A$, wherein each $R^A$ is independently halogen, $C_1$-$C_6$ alkyl, $C_1$-$C_6$ haloalkyl, $C_3$-$C_8$cycloalkyl, —$OR^{110}$, —$SR^{110}$, —$SO_2R^{110}$, —$COR^{110}$, —$SO_2N(R^{110})_2$, —C≡N, —$C(O)OR^{110}$, —$CON(R^{110})_2$, —$NR^{110}COR^{110}$, $N(R^{110})CON(R^{110})_2$, or —$N(R^{110})_2$, wherein $R^{110}$ is as defined for Formula (III) and (LXg), respectively. Even more preferably, $L^{10}$ is a bond or —$[CH_2]_{1-3}$—; and R is phenyl optionally substituted with 1 to 4 $R^A$, wherein each $R^A$ is independently halogen, $C_1$-$C_6$ alkyl, $C_1$-$C_6$ haloalkyl, $N(R^{110})_2$, $N(R^{110})CON(R^{110})_2$, CON$(R^{110})_2$, —$OR^{110}$, —$SR^{110}$, —$SO_2R^{110}$, or —$C(O)OR^{110}$. Even more preferably, $L^{10}$ is a bond or —$[CH_2]_{1-3}$—; and R is phenyl optionally substituted with 1 to 4 $R^A$, wherein each $R^A$ is independently fluoro, chloro, methyl, or trifluoromethyl. Even more preferably, $L^{10}$ is a bond or —$[CH_2]_{1-3}$-; and R is phenyl optionally substituted with 1 to 2 $R^A$, wherein each $R^A$ is independently fluoro or chloro, or $R^A$ is trifluoromethyl. Preferably R is phenyl and is substituted with at least one halogen, preferably, with at least one chloro group, or R is substituted with at least one trifluoromethyl group.

In another embodiment, the invention comprises the compound according to Formulae (LX)-(LXIV), (LXIg)-(LXIVg), (LXIh)-(LXIVh) and (LXa-v), wherein $G^1$ is -$L^{10}$-R, wherein $L^{10}$ is a bond; and R is as defined for Formula (III). Preferably, $L^{10}$ is a bond; and R is phenyl optionally substituted with 1 to 4 $R^A$; and $R^A$ is as defined for Formulae (III), (LXg) and (LXh), respectively. More preferably, with respect to Formulae (LX) and (LXg), $L^{10}$ is a bond; and R is phenyl optionally substituted with 1 to 4 $R^A$, wherein each $R^A$ is independently halogen, $C_1$-$C_6$ alkyl, $C_1$-$C_6$ haloalkyl, $C_3$-$C_8$cycloalkyl, —$OR^{110}$, —$SR^{110}$, —$SO_2R^{110}$, —$COR^{110}$, —$SO_2N(R^{110})_2$, —C≡N, —$C(O)OR^{110}$, —$CON(R^{110})_2$, —$NR^{110}COR^{110}$, or —$N(R^{110})_2$, wherein $R^{110}$ is as defined for Formulae (III) or (LXg), respectively. More preferably, with respect to Formula (LXh), $L^{10}$ is a bond; and R is phenyl optionally substituted with 1 to 4 R', wherein each $R^A$ is independently halogen, $C_1$-$C_6$ alkyl, $C_1$-$C_6$ haloalkyl, —$OR^{110}$, —$SR^{110}$, —$SO_2R^{110}$, —$COR^{110}$, —$SO_2N(R^{110})_2$, —C≡N, —$C(O)OR^{110}$, —$CON(R^{110})_2$, —$NR^{110}COR^{110}$, or —$N(R^{110})_2$, wherein $R^{110}$ is as defined for Formula (LXh). Even more preferably, with respect to Formulae (LX), (LXg) and (LXh), $L^{10}$ is a bond; and R is phenyl optionally substituted with 1 to 4 $R^A$, wherein each $R^A$ is independently halogen, $C_1$-$C_6$ alkyl, or $C_1$-$C_6$ haloalkyl. Even more preferably, with respect to Formulae (LX), (LXg) and (LXh), $L^{10}$ is a bond; and R is phenyl optionally substituted with 1 to 4 $R^A$, wherein each $R^A$ is independently fluoro, chloro, methyl, trifluoromethyl, —$OR^{110}$, —$SR^{110}$, —$SO_2R^{110}$, or —$C(O)OR^{110}$. Even more preferably, with respect to Formulae (LX), (LXg) and (LXh), $L^{10}$ is a bond; and R is phenyl optionally substituted with 1 to 2 $R^A$, wherein each $R^A$ is independently fluoro or chloro, or $R^A$ is trifluoromethyl. Preferably R is phenyl and is substituted with at least one halogen, preferably, with at least one chloro group, or R is substituted with at least one trifluoromethyl group.

In another embodiment, the invention comprises the compound according to Formulae (LX)-(LXIV), (LXIg)-(LXIVg) and (LXa-p), wherein $G^1$ is -$L^{10}$-R, wherein $L^{10}$ is —[C($R^{150}$)$_2$]$_m$—, —CO—, —$SO_2$—, or —$C_3$-$C_8$cycloalkyl-, wherein m is 1, 2, 3, 4, 5, or 6; and R and $R^{150}$ are as defined for Formulae (III) and (LXg), respectively.

In another embodiment, the invention comprises the compound according to Formulae (LX)-(LXIV), (LXIg)-(LXIVg) and (LXa-p), wherein $G^1$ is -$L^{10}$-R', wherein $L^{10}$ is —[C($R^{150}$)$_2$]$_m$—, wherein m is 1, 2, 3, 4, 5, or 6; and R and $R^{150}$ are as defined for Formulae (III) and (LXg), respectively. Preferably, $L^{10}$ is —[C($R^{150}$)$_2$]$_m$—, and R is phenyl optionally substituted with 1 to 4 $R^A$; and $R^A$ and $R^{150}$ are as defined for Formula (III) and (LXg), respectively. Preferably, $L^{10}$ is —[CH$_2$]$_{1-3}$—; and R is phenyl optionally substituted with 1 to 4 $R^A$; and $R^A$ is as defined for Formula (III) and (LXg), respectively. More preferably, $L^{10}$ is —[CH$_2$]$_{1-3}$—; and R is phenyl optionally substituted with 1 to 4 $R^A$, wherein each $R^A$ is independently halogen, $C_1$-$C_6$ alkyl, $C_1$-$C_6$ haloalkyl, $C_3$-$C_8$cycloalkyl, —$OR^{110}$, —$SR^{110}$, —$SO_2R^{110}$, —$COR^{110}$, —$SO_2N(R^{110})_2$, —C≡N, —$C(O)OR^{110}$, —$CON(R^{110})_2$, —$NR^{110}COR^{110}$, $N(R^{110})CON(R^{110})_2$, or —$N(R^{110})_2$, wherein $R^{110}$ is as defined for Formula (III) and (LXg), respectively. Even more preferably, $L^{10}$ is —[CH$_2$]$_{1-3}$—; and R is phenyl optionally substituted with 1 to 4 $R^A$, wherein each $R^A$ is independently halogen, $C_1$-$C_6$ alkyl, $C_1$-$C_6$ haloalkyl, $N(R^{110})_2$, $N(R^{110})CON(R^{110})_2$, CON($R^{110}$)$_2$, —$OR^{110}$, —$SR^{110}$, —$SO_2R^{110}$, or —$C(O)OR^{110}$. Even more preferably, $L^{10}$ is —[CH$_2$]$_{1-3}$—; and R is phenyl optionally substituted with 1 to 4 R', wherein each $R^A$ is independently fluoro, chloro, methyl, or trifluoromethyl. Even more preferably, $L^{10}$ is —[CH$_2$]$_{1-3}$—; and R is phenyl optionally substituted with 1 to 2 $R^A$, wherein each $R^1$ is independently fluoro or chloro, or $R^A$ is trifluoromethyl. Preferably R is phenyl and is substituted with at least one halogen, preferably, with at least one chloro group, or R is substituted with at least one trifluoromethyl group.

In another embodiment, the invention comprises the compound according to Formulae (LXIh)-(LXIVh) and (LXq-v), wherein $G^1$ is -$L^{10}$-R', wherein $L^{10}$ is —[CH$_2$]$_{1-3}$—; and R is phenyl optionally substituted with 1 to 4 $R^1$. More preferably, $L^{10}$ is —[CH$_2$]$_{1-3}$—; and R is phenyl optionally substituted with 1 to 4 R', or 1 to 3 R', or 1 to 2 $R^A$, wherein each $R^1$ is independently halogen, $C_1$-$C_6$ alkyl, $C_1$-$C_6$ haloalkyl, —$OR^{110}$, —$SR^{110}$, —$SO_2R^{110}$, —$COR^{110}$, —$SO_2N(R^{110})_2$, —C≡N, —$C(O)OR^{110}$, —$CON(R^{110})_2$, —$NR^{110}COR^{110}$, $N(R^{110})CON(R^{110})_2$, or —$N(R^{110})_2$. Even more preferably, $L^{10}$ is —[CH$_2$]$_{1-3}$—; and R is phenyl optionally substituted with 1 to 4 $R^A$, or 1 to 3 $R^A$, or 1 to 2 $R^A$, wherein each $R^A$ is independently halogen, $C_1$-$C_6$ alkyl, $C_1$-$C_6$ haloalkyl, $N(R^{110})_2$, $N(R^{110})CON(R^{110})_2$, CON($R^{110}$)$_2$, —$OR^{110}$, —$SR^{110}$, —$SO_2R^{110}$, or —$C(O)OR^{110}$. Even more preferably, $L^{10}$ is —[CH$_2$]$_{1-3}$—; and R is phenyl optionally substituted with 1 to 4 R', or 1 to 3 R', or 1 to 2 $R^A$, wherein each $R^A$ is independently fluoro, chloro, methyl, or trifluoromethyl. Even more preferably, $L^{10}$ is —[CH$_2$]$_{1-3}$—; and R is phenyl optionally substituted with 1 to 2 $R^A$, wherein each $R^A$ is independently fluoro or chloro, or each $R^A$ is independently chloro or trifluoromethyl. Even more preferably, $L^{10}$ is —[CH$_2$]$_{1-3}$—; and $R^A$ is phenyl substituted with at least one chloro group or R is substituted with at least one trifluoromethyl group.

In another embodiment, the invention comprises the compound according to Formulae (LX)-(LXIV) and (LXa-v), wherein $G^1$ is -$L^{10}$-R', wherein $L^{10}$ is —[C($R^{15}$)$_2$]$_m$—, —CO—, —$SO_2$—, or —$C_3$-$C_8$cycloalkyl-, wherein -m is 1, 2, 3, 4, 5, or 6; and R is pyridyl, pyrazinyl, or pyrimidinyl, each optionally substituted with 1 to 4 $R^A$; and $R^A$ and $R^{150}$ are as defined for Formula (III). Preferably, $G^1$ is -$L^{10}$-R, wherein $L^{10}$ is —[C($R^{150}$)$_2$]$_m$—, and R is pyridyl, pyrazinyl, or pyrimidinyl, each optionally substituted with 1 to 4 $R^A$; and $R^A$ and $R^{150}$ are as defined for Formula (III). Preferably, $G^1$ is -$L^{10}$-R', wherein $L^{10}$ is —[CH$_2$]$_{1-3}$—, and R is pyridyl, pyrazinyl, or pyrimidinyl, each optionally substituted with 1 to 4 $R^A$; and $R^A$, $R^{150}$, and m are as defined for Formula (III). Preferably, $L^{10}$ is —[CH$_2$]$_{1-3}$—; and R is pyridyl, pyrazinyl, or pyrimidinyl, each optionally substituted with 1 to 4 $R^A$, wherein each $R^A$ is independently halogen, $C_1$-$C_6$ alkyl, $C_1$-$C_6$ haloalkyl, $C_3$-$C_8$cycloalkyl, —$OR^{110}$, —$SR^{110}$, —$SO_2R^{110}$, —$COR^{110}$, —$SO_2N(R^{110})_2$, —C≡N, —$C(O)OR^{110}$, —$CON(R^{110})_2$, —$NR^{110}COR^{110}$, or —$N(R^{110})_2$, wherein $R^{110}$ is as defined for Formula (III). More preferably, $L^{10}$ is —[CH$_2$]$_{1-3}$—; and R is pyridyl, pyrazinyl, or pyrimidinyl, each optionally substituted with 1 to 4 R', wherein each $R^A$ is independently halogen, $C_1$-$C_6$ alkyl, $C_1$-$C_6$ haloalkyl, —$OR^{110}$, —$SR^{110}$, —$SO_2R^{110}$, or —$C(O)OR^{110}$.

In another embodiment, the present invention comprises the compounds according to Formulae (LX) and (LXg), of Formulae (LXV)-(LXXII) and Formulae (LXVg)-(LXXIIg), respectively:

(LXV)
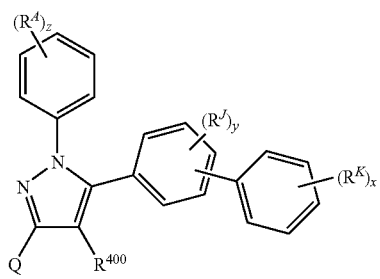

(LXVI)
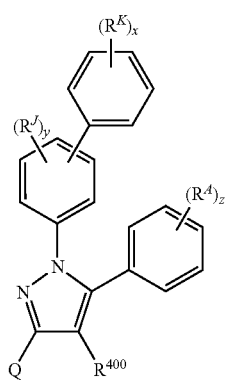

(LXVII)
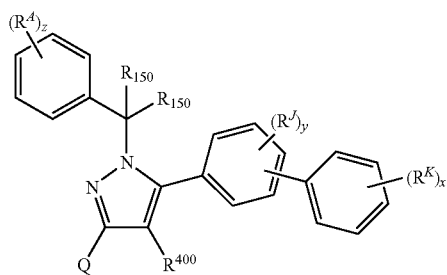

(LXVIII)
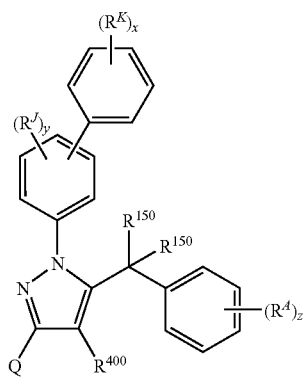

(LXIX) (LXIXg)
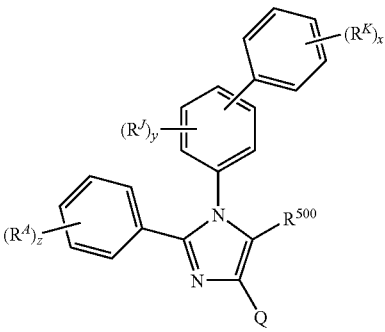

(LXX) (LXXg)
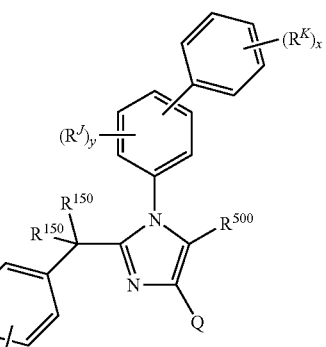

(LXXI) (LXXIg)
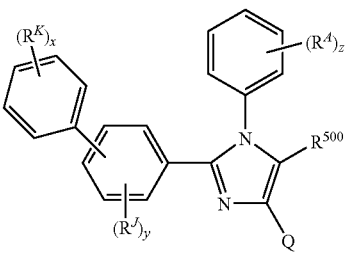

(LXXII) (LXXIIg)
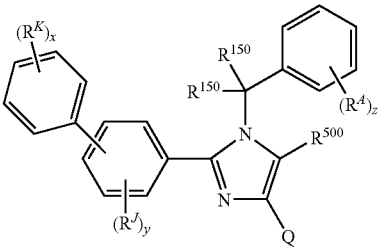

(LXVg)
(LXVIg)
(LXVIIg)
(LXVIIIg)

wherein x and z are independently 0, 1, 2, 3, or 4; y is 0, 1, 2, or 3;

each $R^J$ is independently halogen, $C_1$-$C_6$ alkyl, $C_1$-$C_6$ haloalkyl, —$OR^{110}$, —$SO_2R^{110}$, —$COR^{110}$, —$SO_2N(R^{110})_2$, —C≡N, —$C(O)OR^{110}$, —$CON(R^{110})_2$, —$NR^{11}COR^{110}$, or —$N(R^{110})_2$ and $R^{400}$, $R^{500}$, $R^A$, $R^K$, $R^{110}$, $R^{150}$, and Q are as defined for Formulae (III) and (LXg), respectively. Compounds of Formulae (LXV), (LXVII), (LXf), and (LXX) are preferred. Also preferred are compounds of Formulae (LXVg), (LXVIIg), (LXLXg), and (LXXg). Also preferred are compounds of Formulae (LXV), (LXVII), (LXVg), and (LXVIIg). Also preferred are compounds of Formulae (LXIX), (LXX), (LXIXg), and (LXXg).

In another embodiment, the invention comprises the compound according to Formulae (LXV)-(LXXII) and (LXVg)-(LXXIIg), wherein each $R^J$ is independently halogen, $C_1$-$C_6$ alkyl, or $C_1$-$C_6$ haloalkyl. Preferably, each $R^J$ is independently fluoro, chloro, methyl, or trifluoromethyl.

In another embodiment, the invention comprises the compound according to Formulae (LXV)-(LXXII) and (LXVg)-(LXXIIg), wherein each $R^K$ is independently —Z or —Y—Z; wherein Y and Z are as defined for Formula (LXg). Preferably, each $R^K$ is independently —Z, wherein Z is as defined for Formula (LXg), respectively. More preferably, each $R^K$ is independently halogen, $C_1$-$C_6$ alkyl, $C_1$-$C_6$ haloalkyl, —$OR^{110}$, —$SO_2R^{110}$, —$COR^{110}$, —$SO_2N(R^{110})_2$, —C≡N, —C(O)$OR^{110}$, —CON($R^{110}$)$_2$, —$NR^{110}COR^{110}$, or —N($R^{110}$)$_2$. More preferably, when present, at least one R is —$SO_2$($C_{1-6}$alkyl).

In another embodiment, the invention comprises the compound according to Formulae (LXV)-(LXXII) and (LXVg)-(LXXIIg), wherein each $R^J$ is independently halogen, $C_1$-$C_6$ alkyl, or $C_1$-$C_6$ haloalkyl; and each $R^K$ is independently —Z or —Y—Z; wherein Y and Z are as defined for Formula (LXg).

In another embodiment, the invention comprises the compound according to Formulae (LXV)-(LXXII) and (LXVg)-(LXXIIg), wherein each $R^J$ is independently halogen, $C_1$-$C_6$ alkyl, or $C_1$-$C_6$ haloalkyl; and each $R^K$ is independently halogen, $C_1$-$C_6$ alkyl, $C_1$-$C_6$ haloalkyl, —$OR^{110}$, —$SO_2R^{110}$, —$COR^{110}$, —$SO_2N(R^{110})_2$, —C≡N, —C(O)$OR^{110}$, —CON($R^{11}$)$_2$, —$NR^{11}COR^{110}$, or —N($R^{110}$)$_2$.

In another embodiment, the invention comprises the compound according to Formulae (LXV)-(LXXII) and (LXVg)-(LXXIIg), wherein each $R^J$ is independently halogen, $C_1$-$C_6$ alkyl, or $C_1$-$C_6$ haloalkyl; and each $R^K$ is independently halogen, $C_1$-$C_6$ alkyl, $C_1$-$C_6$ haloalkyl, —$OR^{110}$, —$SO_2R^{110}$, —$COR^{110}$, —$SO_2N(R^{110})_2$, —C≡N, —C(O)$OR^{110}$, —CON($R^{11}$)$_2$, —$NR^{11}COR^{110}$, or —N($R^{110}$)$_2$, provided that when present, at least one R is —$SO_2$($C_{1-6}$ alkyl).

In another embodiment, the invention comprises the compound according to Formulae (LXV)-(LXXII) and (LXVg)-(LXXIIg), wherein each $R^J$ is independently fluoro, chloro, methyl, or trifluoromethyl; and each $R^K$ is independently —Z or —Y—Z; wherein Y and Z are as defined for Formula (LXg).

In another embodiment, the invention comprises the compound according to Formulae (LXV)-(LXXII) and (LXVg)-(LXXIIg), wherein each $R^J$ is independently fluoro, chloro, methyl, or trifluoromethyl; and each $R^K$ is independently halogen, $C_1$-$C_6$ alkyl, $C_1$-$C_6$ haloalkyl, —$OR^{110}$, —$SO_2R^{110}$, —$COR^{110}$, —$SO_2N(R^{110})_2$, —C≡N, —C(O)$OR^{110}$, —CON($R^{110}$)$_2$, —$NR^{110}COR^{110}$, or —N($R^{110}$)$_2$.

In another embodiment, the invention comprises the compound according to Formulae (LXV)-(LXXII) and (LXVg)-(LXXIIg), wherein each $R^J$ is independently fluoro, chloro, methyl, or trifluoromethyl; and each $R^K$ is independently halogen, $C_1$-$C_6$ alkyl, $C_1$-$C_6$ haloalkyl, —$OR^{110}$, —$SO_2R^{110}$, —$COR^{110}$, —$SO_2N(R^{110})_2$, —C≡N, —C(O)$OR^{110}$, —CON($R^{110}$)$_2$, —$NR^{110}COR^{110}$, or —N($R^{110}$)$_2$, provided that when present, at least one R is —$SO_2$($C_{1-6}$ alkyl).

In another embodiment, the present invention comprises the compounds according to Formula (LXh), of Formulae (LXVh), (LXVIIh), (LXIXh), (LXXh):

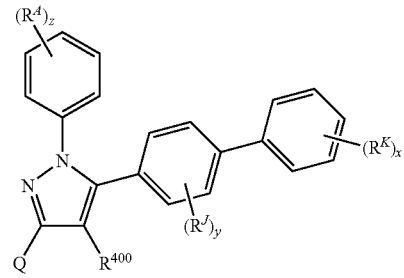
(LXVh)

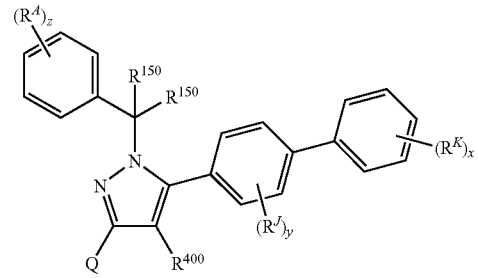
(LXVIIh)

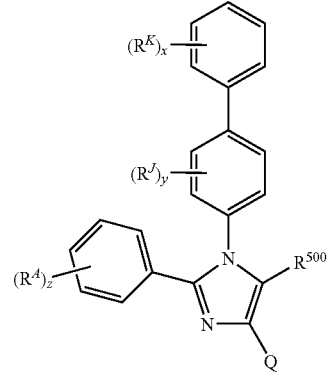
(LXIXh)

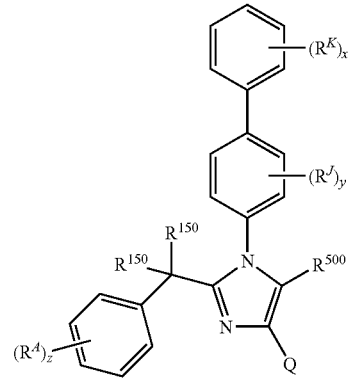
(LXXh)

wherein x and z are independently 0, 1, 2, 3, or 4; y is 0, 1, 2, or 3;
each $R^J$ is independently halogen, $C_1$-$C_6$ alkyl, $C_1$-$C_6$ haloalkyl, —$OR^{110}$, —$SO_2R^{110}$, —$COR^{110}$, —$SO_2N(R^{110})$, —C≡N, —C(O)$OR^{110}$, —CON($R^{110}$)$_2$, —$NR^{110}COR^{110}$, or —N($R^{110}$)$_2$; and
$R^{400}$, $R^{500}$, $R^A$, $R^K$, $R^{110}$, $R^{150}$, and Q are as defined for Formula (LXh). Also preferred are compounds of Formulae (LXVh) and (LXVIIh).

In another embodiment, the invention comprises the compound according to Formulae (LXVh)-(LXXh), wherein each $R^A$ is independently halogen, $C_1$-$C_6$ alkyl, $C_1$-$C_6$ haloalkyl, —OR$^{110}$, —SO$_2$R$^{110}$, —COR$^{110}$, —SO$_2$N(R$^{110}$)$_2$, —C≡N, —C(O)OR$^{110}$, —CON(R$^{110}$)$_2$, —NR$^{110}$COR$^{110}$, or —N(R$^{110}$)$_2$— More preferably, R$^A$ is independently halogen, C$_1$-C$_6$ alkyl, or C$_1$-C$_6$ haloalkyl. More preferably, each R$^A$ is independently fluoro, chloro, bromo, methyl, or trifluoromethyl. More preferably, R$^A$ is chloro or R$^A$ is trifluoromethyl.

In another embodiment, the invention comprises the compound according to Formulae (LXVh)-(LXXh), wherein each R$^J$ is independently halogen, C$_1$-C$_6$ alkyl, or C$_1$-C$_6$ haloalkyl.

In another embodiment, the invention comprises the compound according to Formulae (LXVh)-(LXXh), wherein each R$^J$ is independently fluoro, chloro, methyl, or trifluoromethyl.

In another embodiment, the invention comprises the compound according to Formulae (LXVh)-(LXXh), wherein each R$^K$ is independently —Z or —Y—Z; wherein Y and Z are as defined for Formula (LXh). Preferably, each R$^K$ is independently —Z, wherein Z is as defined for Formula (III) and (LXg), respectively. More preferably, each R$^K$ is independently halogen, C$_1$-C$_6$ alkyl, C$_1$-C$_6$ haloalkyl, —OR$^{110}$, —SO$_2$R$^{110}$, —COR$^{110}$, —SO$_2$N(R$^{110}$)$_2$, —C≡N, —C(O)OR$^{110}$, —CON(R$^{11}$)$_2$, —NR$^{110}$COR$^{110}$, or —N(R$^{11}$)$_2$. More preferably, when present, at least one R is —SO$_2$(C$_{1-6}$ alkyl).

In another embodiment, the invention comprises the compound according to Formulae (LXVh)-(LXXh), wherein each R$^J$ is independently halogen, C$_1$-C$_6$ alkyl, or C$_1$-C$_6$ haloalkyl; and each R$^K$ is independently —Z or —Y—Z; wherein Y and Z are as defined for Formula (LXh).

In another embodiment, the invention comprises the compound according to Formulae (LXVh)-(LXXh), wherein each R$^J$ is independently halogen, C$_1$-C$_6$ alkyl, or C$_1$-C$_6$ haloalkyl; and each R$^K$ is independently halogen, C$_1$-C$_6$ alkyl, C$_1$-C$_6$ haloalkyl, —OR$^{110}$, —SO$_2$R$^{110}$, —COR$^{110}$, —SO$_2$N(R$^{110}$)$_2$, —C≡N, —C(O)OR$^{100}$, —CON(R$^{110}$)$_2$, —NR$^{110}$COR$^{110}$ or —N(R$^{110}$)$_2$.

In another embodiment, the invention comprises the compound according to Formulae (LXVh)-(LXXh), wherein each R$^J$ is independently halogen, C$_1$-C$_6$ alkyl, or C$_1$-C$_6$ haloalkyl; and each R$^K$ is independently halogen, C$_1$-C$_6$ alkyl, C$_1$-C$_6$ haloalkyl, —OR$^{110}$, —SO$_2$R$^{110}$, —COR$^{110}$, —SO$_2$N(R$^{110}$)$_2$, —C≡N, —C(O)OR$^{110}$, —CON(R$^{110}$)$_2$, —NR$^{110}$COR$^{110}$, or —N(R$^{110}$)$_2$, provided that when present, at least one R$^K$ is —SO$_2$(C$_{1-6}$ alkyl).

In another embodiment, the invention comprises the compound according to Formulae (LXVh)-(LXXh), wherein each R$^J$ is independently fluoro, chloro, methyl, or trifluoromethyl; and each R$^K$ is independently —Z or —Y—Z; wherein Y and Z are as defined for Formula (LXh).

In another embodiment, the invention comprises the compound according to Formulae (LXVh)-(LXXh), wherein each R$^J$ is independently fluoro, chloro, methyl, or trifluoromethyl; and each R$^K$ is independently halogen, C$_1$-C$_6$ alkyl, C$_1$-C$_6$ haloalkyl, —OR$^{110}$, —SO$_2$R$^{110}$, —COR$^{110}$, —SO$_2$N(R$^{110}$)$_2$, —C≡N, —C(O)OR$^{110}$, —CON(R$^{11}$)$_2$, —NR$^{110}$COR$^{110}$, or —N(R$^{110}$)$_2$.

In another embodiment, the invention comprises the compound according to Formulae (LXVh)-(LXXh), wherein each R$^J$ is independently fluoro, chloro, methyl, or trifluoromethyl; and each R$^K$ is independently halogen, C$_1$-C$_6$ alkyl, C$_1$-C$_6$ haloalkyl, —OR$^{110}$, —SO$_2$R$^{110}$, —COR$^{110}$, —SO$_2$N(R$^{110}$)$_2$, —C≡N, —C(O)OR$^{110}$, —CON(R$^{110}$)$_2$, —NR$^{110}$COR$^{110}$ or —N(R$^{1100}$ provided that when present, at least one R is —SO$_2$(C$_{1-6}$ alkyl).

In another embodiment, the invention comprises the compound according to Formulae (LXVh)-(LXXh), wherein each R$^{400}$ and R$^{500}$, when present, are each R$^C$. Preferably, each R$^{400}$ and R$^{500}$, when present, are each Z. More preferably, each R$^{400}$ and R$^{500}$, when present, are each H, halogen, cyano, —OR$^{110}$, —C(=O)R$^{110}$, —C(=O)OR$^{110}$, or —S(=O)$_2$R$^{110}$.

In another embodiment, the invention comprises the compound according to Formulae (LXVh)-(LXXh), wherein each R$^{400}$ and R$^{500}$ are each hydrogen.

In another embodiment, the present invention comprises the compounds according to Formula (LX), (LXg), and (LXh), of Formulae (XCVIa-d), (XCVIa-d), (XCVIIa-d), and (XCIXa-d):

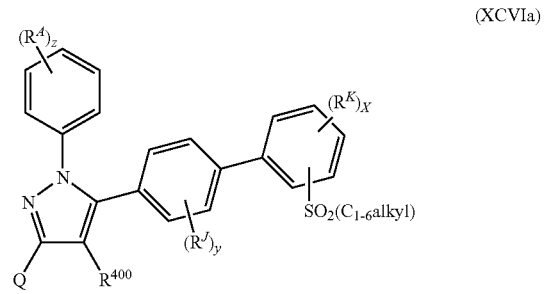
(XCVIa)

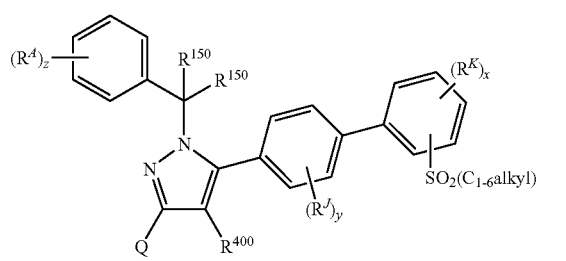
(XCVIIa)

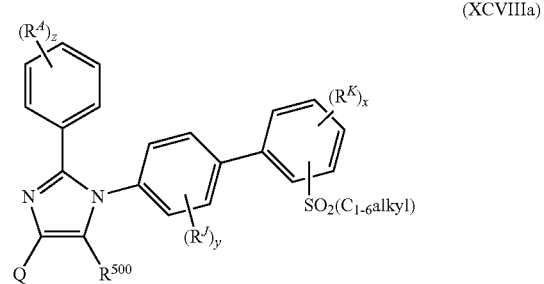
(XCVIIIa)

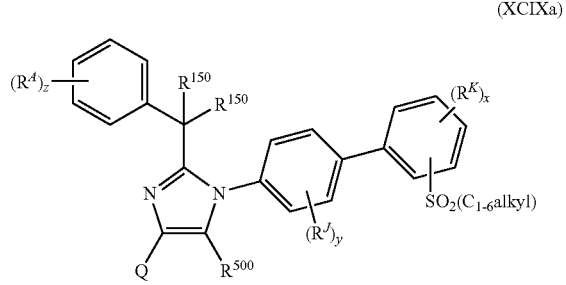
(XCIXa)

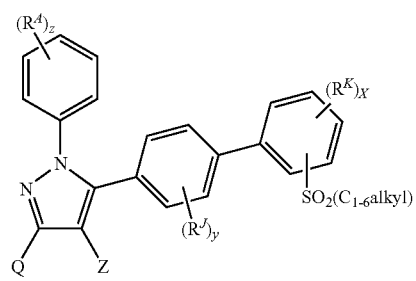
(XCVIb)
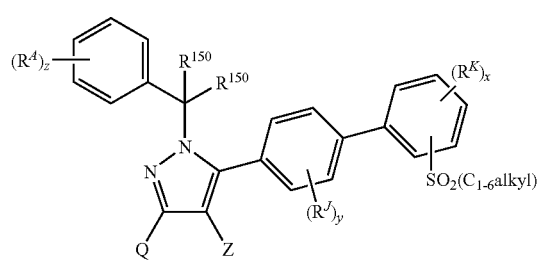
(XCVIIb)
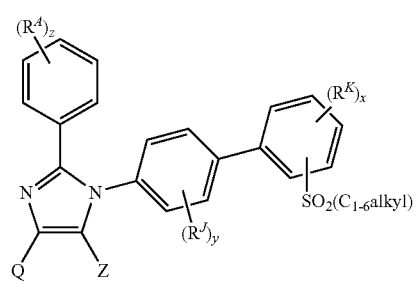
(XCVIIIb)
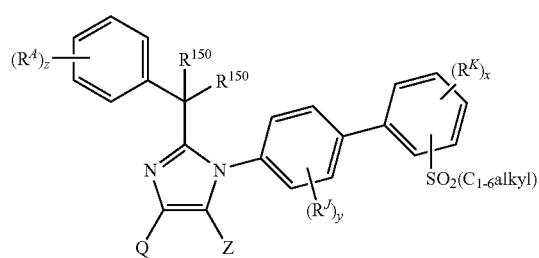
(XCIXb)
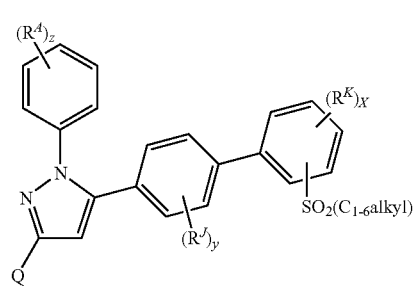
(XCVIc)
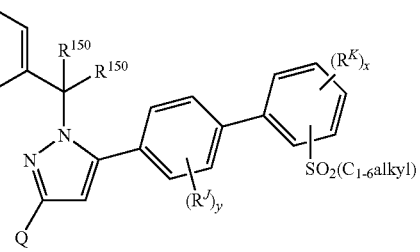
(XCVIIc)
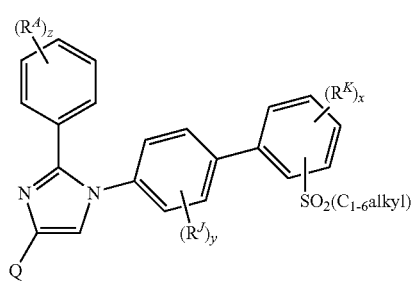
(XCVIIIc)
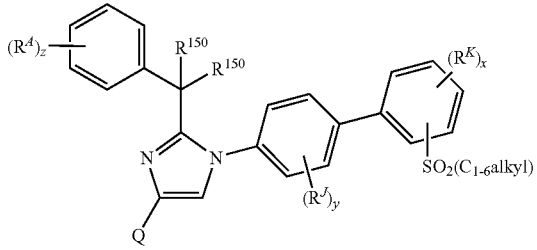
(XCIXc)
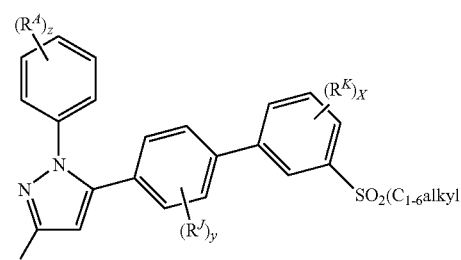
(XCVId)
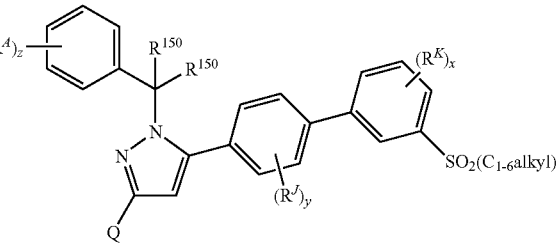
(XCVIId)

-continued (XCVIIId)

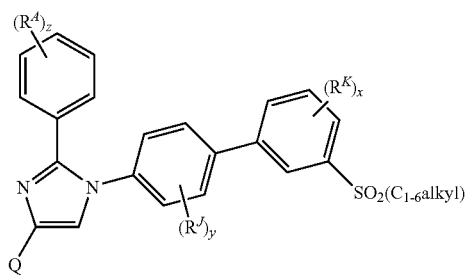

(CI)

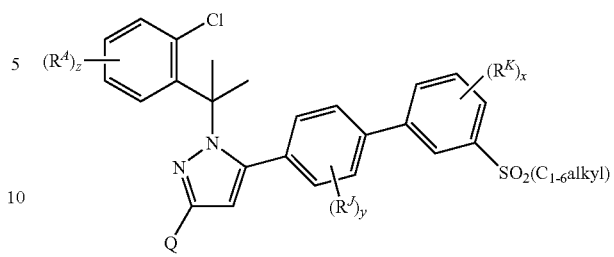

(XCIXd)

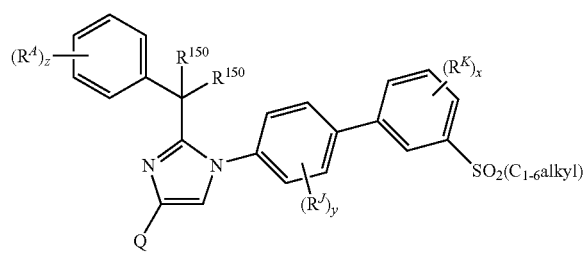

(CII)

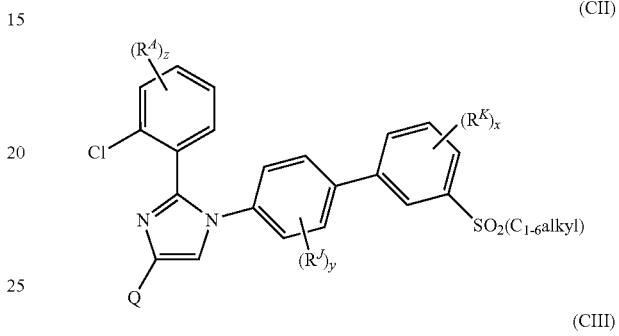

(CIII)

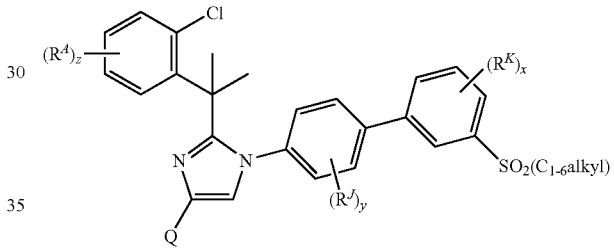

wherein
x and z are independently 0, 1, 2, or 3; y is 0, 1, or 2; and each $R^K$ and $R^J$ is independently halogen, $C_1$-$C_6$ alkyl, $C_1$-$C_6$ haloalkyl, —$OR^{110}$, —$SO_2R^{110}$, —$COR^{110}$, —$SO_2N(R^{110})_2$, —C≡N, —C(O)$OR^{110}$, —CON$(R^{110})_2$, —$NR^{110}COR^{110}$ or —$N(R^{110})_2$.

In another embodiment, the invention comprises the compound according to Formulae (XCVIa-d)-(XCIXa-d), wherein each $R^A$ is independently halogen, $C_1$-$C_6$ alkyl, $C_1$-$C_6$ haloalkyl, —$OR^{110}$, —$SO_2R^{110}$, —$COR^{110}$, —$SO_2N(R^{110})_2$, —C≡N, —C(O)$OR^{110}$, —CON$(R^{110})_2$, —$NR^{110}COR^{110}$, or —$N(R^{110})_2$— More preferably, $R^A$ is independently halogen, $C_1$-$C_6$ alkyl, or $C_1$-$C_6$ haloalkyl. More preferably, each $R^A$ is independently fluoro, chloro, bromo, methyl, or trifluoromethyl. More preferably, $R^A$ is chloro or $R^A$ is trifluoromethyl.

In another embodiment, the invention comprises the compound according to Formulae (XCVIa-d)-(XCIXa-d), wherein each $R^J$ is independently fluoro, chloro, methyl, or trifluoromethyl.

In another embodiment, the present invention comprises the compounds according to Formula (LX), (LXg), and (LXh), of Formulae (C), (CI), (CII), and (CIII):

(C)

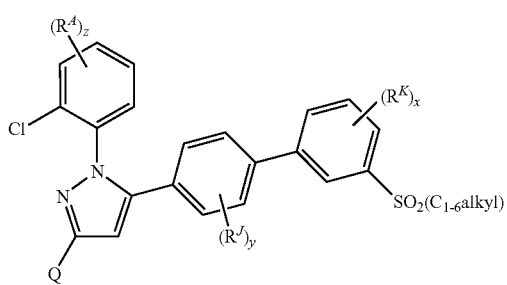

wherein
x and z are independently 0 or 1;
y is 0, 1, or 2;
each $R^K$ and $R^J$ is independently halogen, $C_1$-$C_6$ alkyl, $C_1$-$C_6$ haloalkyl, —$OR^{110}$, —$SO_2R^{110}$, —$COR^{110}$, —$SO_2N(R^{110})_2$, —C≡N, —C(O)$OR^{110}$, —CON$(R^{110})_2$, —$NR^{110}COR^{110}$, or —$N(R^{110})_2$.

In another embodiment, the invention comprises the compound according to Formulae (C)-(CIII), wherein each $R^A$ is independently halogen, $C_1$-$C_6$ alkyl, $C_1$-$C_6$ haloalkyl, —$OR^{110}$, —$SO_2R^{110}$, —$COR^{110}$, —$SO_2N(R^{110})_2$, —C≡N, —C(O)$OR^{110}$, —CON$(R^{110})_2$, —$NR^{110}COR^{110}$, or —$N(R^{110})_2$. More preferably, $R^A$ is independently halogen, $C_1$-$C_6$ alkyl, or $C_1$-$C_6$ haloalkyl. More preferably, each $R^A$ is independently fluoro, chloro, bromo, methyl, or trifluoromethyl. More preferably, $R^A$ is chloro or $R^A$ is trifluoromethyl.

In another embodiment, the invention comprises the compound according to Formulae (XCVI)-(XCIX), wherein each $R^J$ is independently fluoro, chloro, methyl, or trifluoromethyl.

In another embodiment, the invention comprises the compound according to Formulae (LX)-(LXXII), (LXg)-(LXXIIg), (LXh)-(LXXh), (LXa-v), (XCVI)-(CIII), wherein Q is heteroaryl or heterocyclyl, each optionally substituted with 1 to 4 $R^Q$.

In another embodiment, the invention comprises the compound according to Formulae (LX)-(LXXII), (LXg)-(LXXIIg), (LXh)-(LXXh), (LXa-v), (XCVI)-(CIII), wherein Q is heteroaryl optionally substituted with 1 to 4 $R^Q$. Preferably, Q is a 5-membered heteroaryl optionally substituted with 1 to 4 $R^Q$. More preferably, Q is thienyl, furyl, pyrrolyl, oxazolyl, isoxazolyl, thiazolyl, isothiazolyl, imidazolyl, pyrazolyl, oxadiazolyl, thiadiazolyl, triazolyl, or tetrazolyl, each optionally substituted with 1 to 4 $R^Q$. More preferably, Q is thienyl, furyl, pyrrolyl, oxazolyl, isoxazolyl, thiazolyl, imidazolyl, pyrazolyl, oxadiazolyl, thiadiazolyl, triazolyl, or tetrazolyl, each optionally substituted with 1 or 2 $R^Q$. More preferably, Q is Q is 1,3-thiazolyl; 1,2,4-oxadiazolyl; 1,2,5-oxadiazolyl; 1,3,4-oxadiazolyl; 1,3,5-oxadiazolyl; pyrrolyl; thienyl; pyrazolyl; imidazolyl; furyl; isoxazolyl; or 1,3,5-thiadiazolyl, each optionally substituted with 1 or 2 $R^Q$. More preferably, Q is oxazolyl, thiazolyl, imidazolyl, oxadiazolyl, thiadiazolyl, triazolyl, or tetrazolyl, each optionally substituted with 1 or 2 $R^Q$. wherein $R^Q$ is as defined for Formula (III) and $R^Q$ is as defined in Formula (LXh). In another embodiment, the invention comprises the compound according to Formulae (LX)-(LXXII), (LXg)-(LXXIIg), (LXh)-(LXXh), (LXa-v), (XCVI)-(CIII), wherein Q is oxazolyl, thiazolyl, imidazolyl, oxadiazolyl, thiadiazolyl, triazolyl, or tetrazolyl, each optionally substituted with 1 or 2 $R^Q$ wherein $R^Q$ is as defined for Formulae (III) and (LXh), respectively; and each $R^4$ is independently fluoro, chloro, bromo, methyl, trifluoromethyl, $N(R^{110})_2$, $N(R^{110})CON(R^{110})_2$, CON$(R^{110})_2$, $-OR^{110}$, $-SR^{110}$, $-SO_2R'$, or $-C(O)OR^{110}$; and m, $R^{110}$, and Z are as defined for Formulae (III) and (LXh), respectively.

In another embodiment, the invention comprises the compound according to Formulae (LX)-(LXXII), (LXg)-(LXXIIg), (LXh)-(LXXh), (LXa-v), (XCVI)-(CIII), wherein Q is a 6-membered heteroaryl optionally substituted with 1 to 4 $R^Q$. More preferably, Q is pyridyl, pyrazinyl, or pyrimidinyl, each optionally substituted with 1 or 4 $R^Q$. Even more preferably, Q is pyridyl, pyrazinyl, or pyrimidinyl, each optionally substituted with 1 or 2 $R^Q$.

In another embodiment, the invention comprises the compound according to Formulae (LX)-(LXXII), (LXg)-(LXXIIg), (LXh)-(LXXh), (LXa-v), (XCVI)-(CIII), wherein Q is pyridyl, pyrazinyl, or pyrimidinyl, each optionally substituted with 1 or 2 $R^Q$, wherein $R^Q$ is as defined for Formulae (III) and (LXh), respectively; and each $R^4$ is independently fluoro, chloro, bromo, methyl, trifluoromethyl, $N(R^{110})_2$, $N(R^{110})CON(R^{110})_2$, $CON(R^{110})_2$, $-OR^{110}$, $-SR^{110}$, $-SO_2R^{110}$, or $-C(O)OR^{110}$; and m, $R^{110}$, and Z are as defined for Formula (III) and (LXh), respectively.

In another embodiment, the invention comprises the compound according to Formulae (LX)-(LXXII), (LXg)-(LXXIIg), (LXh)-(LXXh), (LXa-v), (XCVI)-(CIII), wherein Q is heterocyclyl optionally substituted with 1 to 4 $R^Q$. Preferably, Q is a 5-membered heterocyclyl optionally substituted with 1 to 4 $R^Q$. More preferably, Q is tetrahydrothienyl, tetrahydrofuryl, pyrrolidinyl, dihydrothienyl, dihydrofuryl, pyrrolinyl, imidazolidinyl, pyrazolidinyl, oxazolidinyl, isoxazolidinyl, thiazolidinyl, isothiazolidinyl, dioxolanyl, oxathiolanyl, dithiolanyl, imidazolinyl, pyrazolinyl, oxazolinyl, isoxazolinyl, thiazolinyl, isothiazolinyl, 1,3-dioxolyl, 1,3-oxathiolyl, or 1,3-dithiolyl, each optionally substituted with 1 to 4 $R^Q$. More preferably, Q is tetrahydrothienyl, tetrahydrofuryl, pyrrolidinyl, dihydrothienyl, dihydrofuryl, pyrrolinyl, imidazolidinyl, pyrazolidinyl, oxazolidinyl, isoxazolidinyl, thiazolidinyl, isothiazolidinyl, dioxolanyl, oxathiolanyl, dithiolanyl, imidazolinyl, pyrazolinyl, oxazolinyl, isoxazolinyl, thiazolinyl, isothiazolinyl, 1,3-dioxolyl, 1,3-oxathiolyl, or 1,3-dithiolyl, each optionally substituted with 1 or 2 $R^Q$. Even more preferably, Q is pyrrolidinyl, imidazolidinyl, oxazolidinyl, thiazolidinyl, dioxolanyl, oxathiolanyl, dithiolanyl, imidazolinyl, oxazolinyl, thiazolinyl, 1,3-dioxolyl, 1,3-oxathiolyl, or 1,3-dithiolyl, each optionally substituted with 1 or 2 $R^Q$, wherein $R^Q$ is as defined for Formulae (III) and (LXh), respectively. Even more preferably, Q is 4,5-dihydro-1,3-oxazolyl; 4,5-dihydro-1,3-thiazolyl; 4,5-dihydro-1H, 1'H-2,4'-imidazolyl; pyrrolidinyl; piperidinyl; tetrahydropyranyl; 3,4-dihydro-2H-pyranyl; oxetanyl, or azetidinyl, each optionally substituted with 1 or 2 $R^Q$.

In another embodiment, the invention comprises the compound according to Formulae (LX)-(LXXII), (LXg)-(LXXIIg), (LXh)-(LXXh), (LXa-v), (XCVI)-(CIII), wherein Q is pyrrolidinyl, imidazolidinyl, oxazolidinyl, thiazolidinyl, dioxolanyl, oxathiolanyl, dithiolanyl, imidazolinyl, oxazolinyl, thiazolinyl, 1,3-dioxolyl, 1,3-oxathiolyl, or 1,3-dithiolyl, each optionally substituted with 1 or 2 $R^Q$, wherein $R^Q$ is as defined for Formulae (III) and (LXh), respectively; and each $R^4$ is independently fluoro, chloro, bromo, methyl, trifluoromethyl, $N(R^{110})_2$, $N(R^{110})CON(R^{110})_2$, $CON(R^{110})_2$, $-OR^{110}$, $-SR^{110}$, $-SO_2R'$, or $-C(O)R^{110}$; and m, $R^{110}$, and Z are as defined for Formulae (III) and (LXh), respectively.

In another embodiment, the invention comprises the compound according to Formulae (LX)-(LXXII), (LXg)-(LXXIIg), (LXh)-(LXXh), (LXa-v), (XCVI)-(CIII), wherein Q is a 6-membered heterocyclyl optionally substituted with 1 to 4 $R^Q$. More preferably, Q is piperidinyl, piperazinyl, morpholinyl, thiomorpholinyl, tetrahydropyranyl, tetrahydrothiopyranyl, dioxanyl, oxathianyl, or dithianyl, each optionally substituted with 1 to 4 $R^Q$. Even more preferably, Q is piperidinyl, piperazinyl, morpholinyl, thiomorpholinyl, tetrahydropyranyl, tetrahydrothiopyranyl, dioxanyl, oxathianyl, or dithianyl, each optionally substituted with 1 or 2 $R^Q$.

In another embodiment, the invention comprises the compound according to Formulae (LX)-(LXXII), (LXg)-(LXXIIg), (LXh)-(LXXh), (LXa-v), (XCVI)-(CIII), wherein Q is piperidinyl, piperazinyl, morpholinyl, thiomorpholinyl, tetrahydropyranyl, tetrahydrothiopyranyl, dioxanyl, oxathianyl, or dithianyl, each optionally substituted with 1 or 2 $R^Q$; and each $R^4$ is independently fluoro, chloro, bromo, methyl, trifluoromethyl, $N(R^{110})_2$, $N(R^{110})CON(R^{110})_2$, $CON(R^{110})_2$, $-OR^{110}$, $-SR^{110}$, $-SO_2R'$, or $-C(O)R^{110}$; and m, $R^{110}$, and Z are as defined for Formulae (III) and (LXh), respectively.

In another embodiment, the invention comprises the compound according to Formulae (LXg)-(LXXIIg), (LXh)-(LXXh), (LXi-v), (XCVI)-(CIII), wherein Q is a $C_{3-6}$ cycloalkyl optionally substituted with 1 to 4 $R^Q$. More preferably, Q is cyclopropyl, or Q is cyclopentyl, or Q is cyclohexyl, each optionally substituted with 1 to 4 $R^Q$. More preferably, Q is $C_{3-6}$ cycloalkyl optionally substituted with 1 or 2 $R^Q$. Even more preferably, Q is $C_{3-6}$ cycloalkyl substituted with CN, OH or $OC_{1-6}$ alkyl. Even more preferably, Q is cyclopropyl or cyclopentyl substituted with CN, OH or $OC_{1-6}$ alkyl.

In another embodiment, the invention comprises the compound according to Formulae (LX)-(LXXII), (LXg)-(LXXIIg), and (LXa-p), wherein Q is —X—Y—Z, wherein X, Y, and Z are as defined for Formula (III). Preferably, Q is $-X[C(R^{110})_2]_pZ$, wherein p, $R^{150}$, and Z are as defined for Formula (III). More preferably, Q is $-X[C(R^{151})_2]_pZ$, wherein $R^{151}$ is hydrogen, halogen, $(C_1-C_2)$alkyl, or $(C_1-C_2)$haloalkyl; and p, and Z are as defined for Formula (III). Even more preferably, Q is $-O[C(R^{151})_2]_pZ$ or $-N(R^{100})[C(R^{151})_2]Z$, wherein $R^{151}$ is hydrogen, halogen, $(C_1-C_2)$alkyl, or $(C_1-C_2)$haloalkyl; and p, $R^{100}$, and Z are as defined for Formula (III).

In another embodiment, the invention comprises the compound according to Formulae (LX)-(LXXII), (LXg)-(LXXIIg), and (LXa-p), wherein Q is $-O[C(R^{151})_2]_pZ$, wherein $R^{151}$ is hydrogen, halogen, $(C_1-C_2)$alkyl, or $(C_1-C_2)$haloalkyl; each $R^4$ is independently fluoro, chloro, bromo, methyl, trifluoromethyl, $N(R^{110})_2$, $N(R^{110})CON(R^{110})_2$, $CON(R^{110})_2$, $-OR^{110}$, $-SR^{110}$, $-SO_2R^{110}$, or $-C(O)OR^{110}$; and p, $R^{110}$, and Z are as defined for Formula (III).

In another embodiment, the present invention comprises a compound according to Formulae (LX)-(LXXII), (LXg)-(LXXIIg), (LXh)-(LXXh), (LXa-v), (XCVI)-(CIII), wherein $R^{400}$ and $R^{500}$ are hydrogen, halogen, cyano, nitro, $C_1$-$C_6$ alkyl, or $C_1$-$C_6$ haloalkyl. Preferably, $R^{400}$ and $R^{500}$ are hydrogen, halogen, $C_1$-$C_3$ alkyl, or $C_1$-$C_3$ haloalkyl. More preferably, $R^{400}$ and $R^{500}$ are hydrogen, fluoro, chloro, bromo, methyl, or trifluoromethyl. Even more preferably, $R^{400}$ and $R^{500}$ are hydrogen.

In another embodiment, the invention comprises the compound according to Formulae (LX)-(LXXII), (LXg)-(LXXIIg), (LXh)-(LXXh), (LXa-v), (XCVI)-(CIII), wherein each $R^A$ is independently halogen, $C_1$-$C_6$ alkyl, $C_1$-$C_6$ haloalkyl, $C_3$-$C_8$cycloalkyl, $-OR^{110}$, $-SO_2R^{110}$, $-COR^{110}$, $-SO_2N(R^{110})_2$, $-C\equiv N$, $-C(O)OR^{110}$, $-CON(R^{110})_2$, $-NR^{110}COR^{110}$, or $-N(R^{110})_2$, wherein $R^{110}$ is as defined for Formulae (III), (LXg) and (LXh), respectively. Preferably, each $R^A$ is independently halogen, $C_1$-$C_6$ alkyl, or $C_1$-$C_6$ haloalkyl. More preferably, each $R^A$ is independently fluoro, chloro, bromo, methyl, or trifluoromethyl. More preferably, $R^A$ is chloro.

In another embodiment, the invention comprises the compound according to Formulae (LX)-(LXXII), (LXg)-(LXXIIg), (LXh)-(LXXh), (LXa-v), (XCVI)-(CIII), wherein each $R^Q$ is independently halogen, $C_1$-$C_6$ alkyl, $C_1$-$C_6$ haloalkyl, $-OR^{110}$, $(C_{1-6}$ alkyl)$OR^{110}$, $-SO_2R^{110}$, $-COR^{110}$, $-SO_2N(R^{110})_2$, $-C\equiv N$, $-C(O)OR^{110}$, $-CON(R^{110})$, $-NR^{110}COR^{110}$, or $-N(R^{110})_2$ More preferably, $R^Q$ is $C_1$-$C_6$ alkyl, $C_1$-$C_6$ haloalkyl, $-OR^{110}$, $(C_{1-6}$ alkyl)$OR^{110}$, $-SO_2R^{110}$, $-COR^{110}$, $-C\equiv N$, or $-C(O)OR^{110}$ Even more preferably, $R^Q$ is $C_1$-$C_6$ alkyl, trifluoromethyl, OH, $OC_{1-6}$ alkyl, $CH_2OH$, $SO_2(C_{1-6}$ alkyl), $-CO(C_{1-16}$ alkyl), $-C\equiv N$, or $-CO_2(C_{1-6}$ alkyl).

In a third aspect, the invention comprises a pharmaceutical composition comprising a compound of any of formulae Ia-d or IIa-d, or a pharmaceutically acceptable derivative thereof, in a pharmaceutically acceptable carrier.

In another embodiment, the invention comprises a pharmaceutical composition comprising a compound of formula III, or a pharmaceutically acceptable derivative thereof, in a pharmaceutically acceptable carrier.

In another embodiment, the invention comprises a pharmaceutical composition comprising a compound of formula LX, or a pharmaceutically acceptable derivative thereof, in a pharmaceutically acceptable carrier.

In a fourth aspect, the invention comprises a kit, comprising a packaging material and a compound of any of formula Ia-d or IIa-d, or a pharmaceutically acceptable derivative thereof, which is effective for modulating the activity of a nuclear receptor or for treatment, prevention, inhibition, or amelioration of one or more symptoms of nuclear receptor mediated diseases or disorders.

In another embodiment, the invention comprises a kit, comprising a packaging material, a compound of formula III, or a pharmaceutically acceptable derivative thereof, which is effective for modulating the activity of a nuclear receptor or for treatment, prevention, inhibition, or amelioration of one or more symptoms of nuclear receptor mediated diseases or disorders, further comprising a label that indicates that the compound of formula III, or pharmaceutically acceptable derivative thereof, is used for modulating the activity of a nuclear receptor or for treatment, prevention or amelioration of one or more symptoms of nuclear receptor mediated diseases or disorders, or diseases or disorders in which nuclear receptor activity is implicated.

In another embodiment, the invention comprises a kit, comprising a packaging material, a compound of formula LX, or a pharmaceutically acceptable derivative thereof, which is effective for modulating the activity of a nuclear receptor or for treatment, prevention, inhibition, or amelioration of one or more symptoms of nuclear receptor mediated diseases or disorders, further comprising a label that indicates that the compound of formula III, or pharmaceutically acceptable derivative thereof, is used for modulating the activity of a nuclear receptor or for treatment, prevention or amelioration of one or more symptoms of nuclear receptor mediated diseases or disorders, or diseases or disorders in which nuclear receptor activity is implicated.

In a sixth aspect, the invention comprises a method of treating, preventing, inhibiting, or ameliorating the symptoms of a disease or disorder that is modulated or otherwise affected by nuclear receptor activity or in which nuclear receptor activity is implicated, comprising administering to a subject in need thereof a therapeutically effective amount of a compound of any of formula Ia-d or IIa-d.

In another embodiment of the sixth aspect, the invention comprises a method of treating, preventing, inhibiting, or ameliorating the symptoms of a disease or disorder that is modulated or otherwise affected by nuclear receptor activity or in which nuclear receptor activity is implicated, comprising administering to a subject in need thereof a therapeutically effective amount of a compound according formula III.

In another embodiment of the sixth aspect, the invention comprises a method of treating, preventing, inhibiting, or ameliorating the symptoms of a disease or disorder that is modulated or otherwise affected by nuclear receptor activity or in which nuclear receptor activity is implicated, comprising administering to a subject in need thereof a therapeutically effective amount of a compound according formula LX.

In a preferred embodiment of the sixth aspect, the invention comprises the method wherein the disease or disorder is hypercholesterolemia, hyperlipoproteinemia, hypertriglyceridemia, lipodystrophy, hyperglycemia, diabetes mellitus, dyslipidemia, atherosclerosis, gallstone disease, acne vulgaris, acneiform skin conditions, diabetes, Parkinson's disease, cancer, Alzheimer's disease, inflammation, immunological disorders, lipid disorders, obesity, conditions characterized by a perturbed epidermal barrier function, conditions of disturbed differentiation or excess proliferation of the epidermis or mucous membrane, or cardiovascular disorders.

In a seventh aspect, the invention comprises a method of reducing cholesterol levels in a subject in need thereof, comprising administering an effective cholesterol level-reducing amount of a compound of any of formula Ia-d or IIa-d.

In a seventh aspect, the invention comprises a method of reducing cholesterol levels in a subject in need thereof, comprising administering an effective cholesterol level-reducing amount of a compound of formula III.

In a seventh aspect, the invention comprises a method of reducing cholesterol levels in a subject in need thereof, comprising administering an effective cholesterol level-reducing amount of a compound of formula LX.

In an eighth aspect, the invention comprises a method of treating, preventing, or ameliorating one or more symptoms of a disease or disorder which is affected by cholesterol, triglyceride, or bile acid levels, comprising administering to a subject in need thereof a therapeutically effective amount of a compound of any of formula Ia-d or IIa-d.

In another embodiment of the eighth aspect, the invention comprises a method of treating, preventing, or ameliorating one or more symptoms of a disease or disorder which is affected by cholesterol, triglyceride, or bile acid levels, comprising administering to a subject in need thereof a therapeutically effective amount of a compound of formula III.

In another embodiment of the eighth aspect, the invention comprises a method of treating, preventing, or ameliorating one or more symptoms of a disease or disorder which is affected by cholesterol, triglyceride, or bile acid levels, comprising administering to a subject in need thereof a therapeutically effective amount of a compound of formula LX.

In a ninth aspect, the invention comprises a method of modulating nuclear receptor activity, comprising contacting the nuclear receptor with a compound of any of formula Ia-d or IIa-d.

In another embodiment of the ninth aspect, the invention comprises a method of modulating nuclear receptor activity, comprising contacting the nuclear receptor with a compound of formula III.

In another embodiment of the ninth aspect, the invention comprises a method of modulating nuclear receptor activity, comprising contacting the nuclear receptor with a compound of formula LX.

In an embodiment of the ninth aspect, the invention comprises the method wherein the nuclear receptor is an orphan nuclear receptor.

In an embodiment of the ninth aspect, the invention comprises the method wherein the nuclear receptor is a liver X receptor.

In a preferred embodiment of the ninth aspect, the invention comprises the method wherein the nuclear receptor is a liver X receptor, wherein the liver X receptor is $LXR_\alpha$ or $LXR_\beta$.

In an eleventh aspect, the invention comprises a method of modulating cholesterol metabolism, comprising administering an effective cholesterol metabolism-modulating amount of a compound of any of formula Ia-d or IIa-d.

In another embodiment of the eleventh aspect, the invention comprises a method of modulating cholesterol metabolism, comprising administering an effective cholesterol metabolism-modulating amount of a compound of formula III.

In another embodiment of the eleventh aspect, the invention comprises a method of modulating cholesterol metabolism, comprising administering an effective cholesterol metabolism-modulating amount of a compound of formula LX.

In a twelfth aspect, the invention comprises a method of treating, preventing or ameliorating one or more symptoms of hypocholesterolemia in a subject in need thereof, comprising administering a therapeutically effective amount of a compound of any of formula Ia-d or IIa-d.

In another embodiment of the twelfth aspect, the invention comprises a method of treating, preventing or ameliorating one or more symptoms of hypocholesterolemia in a subject in need thereof, comprising administering a therapeutically effective amount of a compound of formula III.

In another embodiment of the twelfth aspect, the invention comprises a method of treating, preventing or ameliorating one or more symptoms of hypocholesterolemia in a subject in need thereof, comprising administering a therapeutically effective amount of a compound of formula LX.

In a thirteenth aspect, the invention comprises a method of increasing cholesterol efflux from cells of a subject, comprising administering an effective cholesterol efflux-increasing amount of a compound of any of formula Ia-d or IIa-d.

In another embodiment of the thirteenth aspect, the invention comprises a method of increasing cholesterol efflux from cells of a subject, comprising administering an effective cholesterol efflux-increasing amount of a compound of formula III.

In another embodiment of the thirteenth aspect, the invention comprises a method of increasing cholesterol efflux from cells of a subject, comprising administering an effective cholesterol efflux-increasing amount of a compound of formula LX.

In a fourteenth aspect, the invention comprises a method of increasing the expression of ATP-Binding Cassette (ABC1) in the cells of a subject, comprising administering an effective ABC1 expression-increasing amount of a compound of any of formula Ia-d or IIa-d.

In another embodiment of fourteenth aspect, the invention comprises a method of increasing the expression of ATP-Binding Cassette (ABC1) in the cells of a subject, comprising administering an effective ABC1 expression-increasing amount of a compound of formula III.

In another embodiment of fourteenth aspect, the invention comprises a method of increasing the expression of ATP-Binding Cassette (ABC1) in the cells of a subject, comprising administering an effective ABC1 expression-increasing amount of a compound of formula LX.

In a fifteenth aspect, the invention comprises the compound of Formula (XC) and (XCI),

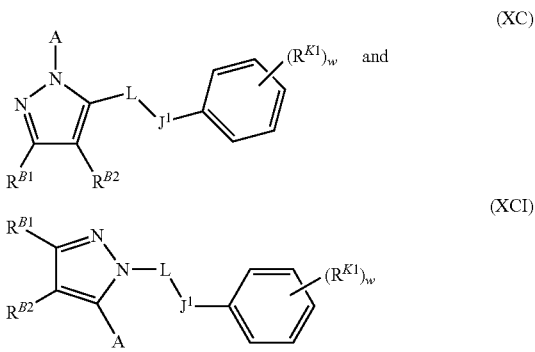

wherein, w is 0, 1 or 2;

A is phenyl or pyridyl, each optionally substituted by 1 to 5 groups which are independently halogen, $C_1$-$C_3$ alkyl, or $C_1$-$C_3$ haloalkyl;

L is a bond or —($CH_2O$)—;

$J^1$ is thienyl, pyrrolyl, furanyl, phenyl, or pyridyl, each optionally substituted by $R^{J1}$, wherein $R^{J1}$ is hydrogen, halogen, or methyl;

$R^{B1}$ is —[C($R^{B5}$)$_2$)$_v$]($R^{B4}$), wherein v is 0, 1, 2, 3, 4, 5, or 6;

$R^{B4}$ is hydrogen, $C_1$-$C_6$ alkyl, or $C_1$-$C_6$ haloalkyl, halogen, —$OR^{110}$, wherein $R^{110}$ is defined as for formula (III); and each $R^{B5}$ is independently hydrogen, halogen, $C_1$-$C_6$ alkyl, or $C_1$-$C_6$ haloalkyl, or two $R^{B5}$ attached to the same carbon taken together are oxo;

$R^{B2}$ is hydrogen or halogen;

each $R^{K'}$ is independently —S(O)$R^{K2}$, —S(O)$_2R^{K2}$, halogen, or —C(O)$OR^3$, wherein $R^{K2}$ is $C_1$-$C_6$ alkyl or $C_1$-$C_6$ haloalkyl;

$R^{K3}$ is hydrogen or $R^{K2}$.

Preferred formulae of the fifteenth aspect include formulae (XCII-XCV),

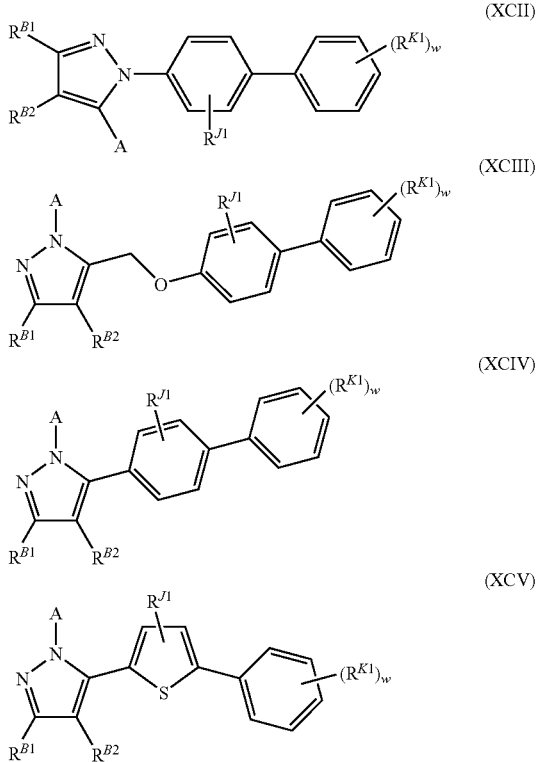

(XCII)
(XCIII)
(XCIV)
(XCV)

wherein A, $R^{B1}$, $R^{B2}$, $R^{J1}$, $R^{K1}$, and w are as defined for formulae XC and XCI.

In an embodiment [27] of the fifteenth aspect, the invention comprises compounds of formulae (XC-XCV) wherein A is phenyl optionally substituted by 1 to 5 groups which are independently halogen, $C_1$-$C_3$ alkyl, or $C_1$-$C_3$ haloalkyl. Preferred compounds of the embodiment are those where A is phenyl substituted by 1 or 2 groups which are independently halogen, $C_1$-$C_3$ alkyl, or $C_1$-$C_3$ haloalkyl. More preferred compounds of the embodiment are those where A is phenyl substituted by two groups, at the 2 and 6 positions of the phenyl ring, which are independently halogen. Even more preferred compounds of the embodiment are those where A is phenyl substituted by two groups, at the 2 and 6 positions of the phenyl ring, which are independently fluoro or chloro.

In an embodiment [28] of the fifteenth aspect, the invention comprises compounds of formulae (XC-XCV) wherein $R^{B1}$ is $R^{B1}$ is —[$CH_2$]$_u$C($R^{B5}$)$_2$($R^{B4}$), wherein u is 0, 1, 2, 3, 4, or 5. Preferred compounds of the embodiment are those where $R^{B1}$ is iPr, $CF_3$, —[$CH_2$]$_u$ C(O)$R^{B4}$, or —[$CH_2$]$_u$ C($CH_3$)$_2$OH. More preferred compounds of the embodiment are those where $R^{B1}$ is —C($CH_3$)$_2$OH.

In an embodiment [29] of the fifteenth aspect, the invention comprises compounds of formulae (XC-XCV) wherein $R^{B2}$ is hydrogen or chloro.

In an embodiment [30] of the fifteenth aspect, the invention comprises compounds of formulae (XC-XCV) wherein each $R^{K1}$ is independently —S(O)$_2$$R^{K2}$, halogen, —C(O)OH, —C(O)N($R^{K2}$)$_2$, or —C(O)O$R^{K2}$, wherein $R^{K2}$ is $C_1$-$C_6$ alkyl. Preferred compounds of the embodiment are those where each $R^{K1}$ is independently —S(O)$_2$$R^{K2}$, halogen, or —C(O)OH, wherein $R^{K2}$ is $C_1$-$C_3$ alkyl.

In an embodiment [31] of the fifteenth aspect, the invention comprises compounds of formulae (XC-XCV) wherein $R^{J1}$ is hydrogen, chloro, or methyl.

In another embodiment of the fifteenth aspect, the invention comprises the compounds of formulae (XC-XCV), wherein A is defined as for embodiment [27], and $R^{B1}$ is defined as for embodiment [28].

In another embodiment of the fifteenth aspect, the invention comprises the compounds of formulae (XC-XCV), wherein A is defined as for embodiment [27], $R^{B1}$ is defined as for embodiment [28]; and $R^{B2}$ is defined as for embodiment [29].

In another embodiment of the fifteenth aspect, the invention comprises the compounds of formulae (XC-XCV), wherein A is defined as for embodiment [27]; $R^{B1}$ is defined as for embodiment [28]; $R^{B2}$ is defined as for embodiment [29]; and $R^{K'}$ is defined as for embodiment [30].

In another embodiment of the fifteenth aspect, the invention comprises the compounds of formulae (XC-XCV), wherein A is defined as for embodiment [27]; $R^{B1}$ is defined as for embodiment [28]; $R^{B2}$ is defined as for embodiment [29]; $R^{K1}$ is defined as for embodiment [30]; and $R^{J1}$ is defined as for embodiment [31].

In another embodiment of the fifteenth aspect, the invention comprises the compounds of formulae (XC-XCV), wherein A is defined as for embodiment [27], and $R^{K1}$ is defined as for embodiment [30].

In another embodiment of the fifteenth aspect, the invention comprises the compounds of formulae (XC-XCV), wherein A is defined as for embodiment [27]; $R^{K1}$ is defined as for embodiment [30]; and $R^{J1}$ is defined as for embodiment [31].

In another embodiment of the fifteenth aspect, the invention comprises the compounds of formulae (XC-XCV), wherein A is defined as for embodiment [27]; $R^{B1}$ is defined as for embodiment [28]; $R^{K'}$ is defined as for embodiment 30]; and $R^{J1}$ is defined as for embodiment [31].

In a preferred embodiment of the fifteenth aspect, the invention comprises the compounds listed in Tables 17 and 18.

In a preferred embodiment of all the preceding formulae (III-XCV and those noted a, b, c, etc.), $R^{110}$ is not substituted by any $R^{120}$ groups.

In another preferred embodiment of all the preceding formulae (III-XCV and those noted a, b, c, etc.), $R^{K}$ is not substituted by any $R^{K'}$ groups.

In a sixteenth aspect, the invention comprises a method for regulating the lipid level in a mammal comprising administering to said mammal an effective lipid level-regulating amount of a dual LXR/FXR agonist. wherein the dual LXR/FXR agonist is a compound of formula any of formulae (XC-XCV).

DEFINITIONS

The following definitions apply to the terms used herein, unless expressly stated to the contrary. So, for example, "alkyl" is defined hereinbelow as containing from 1 to 12 carbon atoms, but a substituent defined as $C_{1-6}$ alkyl is limited to an alkyl moiety of from 1 to 6 carbons. All selections of any variables in connection with any of the general structures or formulae herein are understood to be proper only when said selection yields a stable chemical structure as recognized by one skilled in the art.

When particular embodiments are referred to by structure only, all otherwise unnamed chemical groups making up that structure are as defined in each individual embodiment of that structure. So, for example, when it is stated, "In another embodiment, the invention comprises the compound according to any one of formulae Ia-d, wherein K is phenyl or pyridyl," it is meant that another embodiment of the invention comprises each embodiment of any one of formulae Ia-d described in the specification in which K is phenyl or pyridyl and all other moieties are as defined in the particular embodiments.

For simplicity, chemical moieties are defined and referred to throughout primarily as univalent chemical moieties (e.g., alkyl, aryl, etc.). Nevertheless, such terms are also used to convey corresponding multivalent moieties under the appropriate structural circumstances clear to those skilled in the art. For example, while an "alkyl" moiety generally refers to a monovalent radical (e.g. $CH_3$—$CH_2$—), in certain circumstances a bivalent linking moiety can be "alkyl," in which case those skilled in the art will understand the alkyl to be a divalent radical (e.g., —$CH_2$—$CH_2$—), which is equivalent to the term "alkylene." (Similarly, in circumstances in which a divalent moiety is required and is stated as being "aryl," those skilled in the art will understand that the term "aryl" refers to the corresponding divalent moiety, arylene). All atoms are understood to have their normal number of valences for bond formation (i.e., 4 for carbon, 3 for N, 2 for O, and 2, 4, or 6 for S, depending on the oxidation state of the S). On occasion a moiety may be defined, for example, as $(A)_a$-B—, wherein a is 0 or 1. In such instances, when a is 0 the moiety is B— and when a is 1 the moiety is A-B—. Similarly, $C_{0-6}$ alkyl$OR^{11}$ includes both —$OR^{11}$ and $C_1$-$C_6$—$OR^{11}$, and —$[C(R^{15})_2]_m$— is a bond when m is 0. In the instances when a moiety is a divalent radical, there is no implied limitation on the location of the two bonds connecting the linking radical to its two supporting chemical units. For example, for a divalent cyclohexyl radical, the cyclohexyl can be connected either through two separate chemical bonds to two distinct carbons atoms within the ring; or the two bonds can be connected to the same carbon atom in the ring. In an illustrative example, if a divalent cyclopropyl radical connects two phenyl rings together, this definition encompasses both 1,2-diphenylcyclopropyl and 1,1-diphenylcyclopropyl units.

In a similar vein, for simplicity, on occasion a substituent of a moiety is defined as including both monovalent (e.g., halo) and divalent (e.g., oxo or spiro) groups when the moiety is defined as including moieties incapable of accepting a divalent substituent. For example, "A is cycloalkyl or aryl, each optionally substituted with halo or oxo." Those skilled in the art will understand that the divalent substituent is intended to be a substituent on only atoms having two hydrogens for substitution. Accordingly, in the above example, it will be understood that the optional oxo substituent is intended only for the cycloalkyl moiety and not the aryl moiety.

As used herein the singular forms "a", "an", and "the" include plural referents unless the context clearly dictates otherwise. For example, "a compound" refers to one or more of such compounds, while "the enzyme" includes a particular enzyme as well as other family members and equivalents thereof as known to those skilled in the art. As used in the specification and appended claims, unless specified to the contrary, the following terms have the meaning indicated.

When considering a divalent radical which connects two other radicals, such as —$CONR^{110}$—, it is understood that the divalent radical may connect the two radicals in either directionality. For example, if the other two radicals connected by the divalent radical are 'A' and 'B' respectively, then both A-$CONR^{110}$—B and B—$CONR^{110}$-A are both encompassed.

The term "absent" as used herein means the group is replaced by a single bond. If replacing the group with a bond results in two connected moieties both defined as bonds, then -bond-bond-groups are understood to reduce to a single bond.

The term "$C_0$" refers to a bond. For example, the term "$C_{0-6}$ alkyl" includes a bond and $C_{1-6}$ alkyl groups, as defined herein. For further illustration, the term "aryl$C_0$-$C_6$alkylcarboxy" includes both an aryl group and an aryl$C_{1-6}$ alkyl group, as defined herein, appended to the parent molecule through a carboxy group, as defined herein.

The term "interrupted by" as used herein means the group specified is inserted at any point within the specified chain, but not at the termini. For example, if a $C_3$-alkyl chain, as defined herein, is interrupted by —O—, then the following groups would be encompassed: —$CH_2$—O—$CH_2CH_2$—, —$CH_2CH_2$—O—$CH_2$, —$CH(CH_3)$—O—$CH_2$—, and —$CH_2$—O—$CH(CH_3)$—.

The terms "aliphatic" and "aliphatic group" as used herein means straight-chain, branched or cyclic $C_1$-$C_{12}$ (unless stated otherwise) hydrocarbon radicals which are completely saturated or which contain one or more units of unsaturation but which are not aromatic. For example, suitable aliphatic groups include substituted or unsubstituted linear, branched or cyclic alkyl, alkenyl, alkynyl groups and hybrids thereof such as (cycloalkyl)alkyl, (cycloalkenyl)alkyl or (cycloalkyl) alkenyl.

The terms "alkyl", "alkoxy", "hydroxyalkyl", "alkoxyalkyl", and "alkoxycarbonyl", used alone or as part of a larger moiety include both straight and branched chains containing one to twelve carbon atoms, unless otherwise specified The terms "alkenyl" and "alkynyl" used alone or as part of a larger moiety include both straight and branched chains containing two to twelve carbon atoms.

The term "alkoxy" refers to an —O-alkyl radical, where alkyl is defined herein.

"Alkyl" refers to a straight or branched hydrocarbon chain radical consisting solely of carbon and hydrogen atoms, containing no unsaturation, having from one to twelve carbon atoms, preferably one to eight, and which is attached to the rest of the molecule by a single bond, e.g., methyl, ethyl, n-propyl, 1-methylethyl (iso-propyl), n-butyl, n-pentyl, 1,1-dimethylethyl (t-butyl), and the like.

"Alkenyl" refers to a straight or branched hydrocarbon chain radical consisting solely of carbon and hydrogen atoms, containing at least one double bond, having from two to eight carbon atoms, and which is attached to the rest of the molecule by a single bond or a double bond, e.g., ethenyl, prop-1-enyl, but-1-enyl, pent-1-enyl, penta-1,4-dienyl, and the like.

"Aryl" refers to aromatic monocyclic or multicyclic ring system containing from 6 to 19 carbon atoms, where the ring system is optionally partially or fully saturated. Aryl groups include, but are not limited to groups such as fluorenyl, phenyl, tetrahydronaphthyl, indenyl, indanyl, phenanthrenyl, 1,2,3,4,4a,9,10,10a-octahydrophenanthrenyl, and naphthyl. The term "alkoxyaryl" as used herein means an aryl group, as defined herein, substituted with one or more alkoxy groups, as defined herein. Examples of alkoxyaryl groups include, but are not limited to, methoxyphenyl, butyloxyphenyl, and dimethoxynaphthyl.

"Aralkyl" or "arylalkyl" refers to a radical of the formula —$R^aR^b$ where $R^a$ is an alkyl radical as defined above and $R^b$ is one or more aryl radicals as defined above, e.g., benzyl, diphenylmethyl and the like.

The term "aralkyloxy" or "arylalkoxy" as used herein, means an aralkyl group, as defined herein, appended to the parent molecule through a oxygen atom. Examples of aralkyloxy include, but are not limited to, benzyloxy, 2-phenylethoxy, 4-phenylbutoxy, 9-fluorenylmethoxy, and the like.

The term "arylalkylcarboxy" as used herein, means an arylalkyl group, as defined herein, appended to the parent molecule through a carboxy group, as defined herein. The carboxy group can be bonded in either sense; either with the carbonyl carbon bonded to the arylalkyl group and the oxygen bonded to the parent molecule; or the carbonyl bonded to the parent molecule and the oxygen bonded to the arylalkyl group. Examples of arylalkylcarboxy groups include, but are not limited to, benzylacetoxy, (benzyloxy)carbonyl, (2-phenylethoxy)carbonyl, phenyl-acetyloxy, and 1-oxo-5-phenylpentyloxy.

The term "aryloxy" as used herein, means an aryl group, as defined herein, appended to a parent molecule through an oxygen atom. Examples of "aryloxy" groups include, but are not limited to phenoxy, 1-naphthyloxy, and 2-naphthyloxy.

The term "aryloxyalkyl" as used herein, means an aryloxy group, as defined herein, appended to a parent molecule through an alkyl group, as defined herein. Examples of "aryloxy" groups include, but are not limited to phenoxymethyl, 1-naphthyloxyethyl, and 2-(2-naphthyloxy)propyl.

The term "alkoxyaryl" as used herein, means an alkoxy group, as defined herein, appended to a parent molecule through an aryl group, as defined herein. Examples of "alkoxyaryl" groups include, but are not limited to methoxyphenyl, isopropoxynapthyl, 4-methoxyphenyl, and 2-isopropoxynaphthyl.

"Alkylene" and "alkylene chain" refer to a straight or branched divalent hydrocarbon chain, linking the rest of the molecule to a radical group, consisting solely of carbon and hydrogen, containing no unsaturation and having from one to twelve carbon atoms, preferably having from one to eight carbons, e.g., methylene, ethylene, propylene, n-butylene, and the like. The alkylene chain may be attached to the rest of the molecule and to the radical group through one carbon within the chain or through any two carbons within the chain.

"Alkenylene" and "alkenylene chain" refer to a straight or branched divalent hydrocarbon chain linking the rest of the molecule to a radical group, consisting solely of carbon and hydrogen, containing at least one double bond and having from two to twelve carbon atoms, e.g., ethenylene, propenylene, n-butenylene, and the like. The alkenylene chain is attached to the rest of the molecule through a single bond and to the radical group through a double bond or a single bond. The points of attachment of the alkenylene chain to the rest of the molecule and to the radical group can be through one carbon or any two carbons within the chain. The term "aryloxyalkyl" as used herein, means an alkyl group appended to the parent molecule, wherein the alkyl group is substituted with one aryloxy group, as defined herein. Examples of aryloxyalkyl groups include, but are not limited to phenoxymethyl, naphthyloxybutyl, and phenoxyhexyl.

The term "aryloxyaryl" as used herein, means an aryl group appended to the parent molecule, wherein the aryl group is substituted with one aryloxy group, as defined herein. Examples of aryloxyaryl groups include, but are not limited to phenoxyphenyl, naphthyloxyphenyl, and phenoxynaphthyl.

The term "carbonyl" as used herein, means a —C(=O)— group.

The term "carboxy" as used herein, means a —C(=O)O— group.

"Cycloalkyl" refers to a stable monovalent monocyclic or bicyclic hydrocarbon radical consisting solely of carbon and hydrogen atoms, having from three to ten carbon atoms (unless stated otherwise), and which is saturated or includes one more unsaturated units (but is not aromatic) and is attached to the rest of the molecule by a single bond, e.g., cyclopropyl, cyclobutyl, cyclopentyl, cylcopent-1-enyl, cyclohexyl, cyclohex-2,4-dienyl, decalinyl and the like.

"Cycloalkylalkyl" refers to a radical of the formula —$R^a R^d$ where $R^a$ is an alkyl radical as defined above and $R^d$ is a cycloalkyl radical as defined above.

The term "cyclohaloalkyl" as used herein means a cycloalkyl group, as defined herein which is substituted by one or more halo groups, as defined herein. Examples of "cyclohaloalkyl" groups include, but are not limited to, bromocyclohexyl, trifluorocyclopentyl, dichlorocyclohexyl and the like.

"Halo" or "Halogen" refers to bromo, chloro, fluoro or iodo.

"Haloalkyl" refers to an alkyl radical, as defined above, that is substituted by one or more halo radicals, as defined above, e.g., trifluoromethyl, difluoromethyl, trichloromethyl, 2,2,2-trifluoroethyl, 1-fluoromethyl-2-fluoroethyl, 3-bromo-2-fluoropropyl, 1-bromomethyl-2-bromoethyl, and the like.

"Haloalkenyl" refers to an alkenyl radical, as defined above, that is substituted by one or more halo radicals, as defined above, e.g., 2-bromoethenyl, 3-bromoprop-1-enyl, and the like.

The term "haloaryl" as used herein, means an aryl group, as defined herein, substituted with one or more halo groups. Examples of haloaryl groups include, but are not limited to, bromophenyl, fluorophenyl, pentafluorophenyl, chloronaphthyl, chloro-iodophenyl, and the like.

"Heterocyclyl" refers to a stable 3- to 18-membered non-aromatic ring radical which consists of carbon atoms and from one to five heteroatoms selected from the group consisting of nitrogen, oxygen and sulfur. For purposes of this invention, the heterocyclyl radical may be a monocyclic, bicyclic, tricyclic or tetracyclic ring system, which may include fused or bridged ring systems; and the nitrogen, carbon or sulfur atoms in the heterocyclyl radical is optionally oxidized; the nitrogen atom is optionally quaternized; and the heterocyclyl radical may be partially or fully saturated. Examples of such heterocyclyl radicals include, but are not limited to, dioxolanyl, decahydroisoquinolyl, imidazolinyl, imidazolidinyl, isothiazolidinyl, isoxazolidinyl, morpholinyl, octahydroindolyl, octahydroisoindolyl, 2-oxopiperazinyl, 2-oxopiperidinyl, 2-oxopyrrolidinyl, oxazolidinyl, piperidinyl, piperazinyl, 4-piperidonyl, pyrrolidinyl, pyrazolidinyl, thiazolidinyl, tetrahydrofuranyl, trithianyl, tetrahydropyranyl, thiomorpholinyl, thiamorpholinyl, 1-oxo-thiomorpholinyl, and 1,1-dioxo-thiomorpholinyl.

"Heterocyclylalkyl" refers to a radical of the formula —$R^a R^e$ where $R^a$ is an alkyl radical as defined above and $R^e$ is a heterocyclyl radical as defined above, and if the heterocyclyl is a nitrogen-containing heterocyclyl, the heterocyclyl may be attached to the alkyl radical at the nitrogen atom.

The term "heterocyclyloxy" as used herein, means a heterocyclyl group, as defined herein, appended to a parent molecule through an oxygen atom. Examples of "heterocyclyloxy" groups include, but are not limited to piperidinyloxy, tetrahydrofuranyloxy, tetrahydrotheinyloxy tetrahydropyranyloxy, dihydropyranyloxy, pyrrolidinyloxy, oxetanyloxy, and oxiranyloxy.

"Heteroaryl" refers to a 3- to 18-membered aromatic ring radical which consists of carbon atoms and from one to five heteroatoms selected from the group consisting of nitrogen, oxygen and sulfur. For purposes of this invention, the heteroaryl radical may be a monocyclic, bicyclic, tricyclic or tetracyclic ring system, which may include fused or bridged ring systems; and the nitrogen, carbon or sulfur atoms in the heteroaryl radical is optionally oxidized; the nitrogen atom is optionally quaternized. Examples include, but are not limited to, azepinyl, acridinyl, benzimidazolyl, benzthiazolyl, benzindolyl, benzothiadiazolyl, benzonaphthofuranyl, benzoxazolyl, benzodioxolyl, benzodioxinyl, benzopyranyl, benzopyranonyl, benzofuranyl, benzofuranonyl, benzothienyl (benzothiophenyl), benzotriazolyl, benzo[4,6]imidazo[1,2-a]pyridinyl, carbazolyl, cinnolinyl, dibenzofuranyl, furanyl, furanonyl, isothiazolyl, imidazolyl, indolyl, indazolyl, isoindolyl, indolinyl, isoindolinyl, indolizinyl, isoxazolyl, naphthyridinyl, oxadiazolyl, 2-oxoazepinyl, oxazolyl, oxiranyl, phenazinyl, phenothiazinyl, phenoxazinyl, phthalazinyl, phthalimidyl pteridinyl, purinyl, pyrrolyl, pyrazolyl, pyridinyl, pyrazinyl, pyrimdinyl, pyridazinyl, quinazolinyl, quinoxalinyl, quinolinyl, quinuclidinyl, isoquinolinyl, thiazolyl, thiadiazolyl, triazolyl, tetrazolyl, triazinyl, and thiophenyl. The term "heteroaryloxy" as used herein, means a heteroaryl group, as defined herein, appended to a parent molecule through an oxygen atom. Examples of "heteroaryloxy" groups include, but are not limited to pyridyloxy, indolyloxy, and quinolyloxy.

"Heteroarylalkyl" refers to a radical of the formula —$R_aR_f$— where $R_a$ is an alkyl radical as defined above and $R_f$ is a heteroaryl radical as defined above, and if the heteroaryl is a nitrogen-containing heteroaryl, the heteroaryl may be attached to the alkyl radical at the nitrogen atom.

The term "alidyl" or "alidiyl chain" refers to a straight or branched carbon chain that may be fully saturated or have one or more units of unsaturation. Alidiyl chain used herein may include alidiyl chains containing 0-4 fluorine substituents.

An "agonist for a nuclear receptor" is an agent that, when bound to the nuclear receptor, activates nuclear receptor activity to activate or repress gene function. In some cases, nuclear receptors can act through second messenger signaling pathways, and the invention would apply to these actions as well. The activation can be similar in degree to that provided by a natural hormone for the receptor, or can be stronger (optionally referred to as a "strong agonist"), or can be weaker (optionally referred to as a "weak agonist" or "partial agonist"). An example of a hormone for a nuclear receptor is thyroid hormone, which is a natural hormone for the thyroid receptor. A "putative agonist" is an agent to be tested for agonist activity.

Partial agonists or partial antagonists bind to receptors and yield a response less than that of a full agonist at saturating ligand concentrations. A partial agonist will block binding of a full agonist and suppress receptor activity to the level induced by the partial agonist alone. For example, partial agonists bind to receptors and induce only part of the changes in the receptors that are induced by agonists. The differences can be qualitative or quantitative. Thus, a partial agonist can induce some of the conformation changes induced by agonists, but not others, or it may only induce certain changes to a limited extent. Some of these compounds are naturally produced. For example, many plant estrogens (phytoestrogens), such as genistein, can behave as partial estrogen receptor agonists.

An "antagonist for a nuclear receptor" is an agent that reduces or blocks activity mediated by the receptor in response to an agonist of the receptor. The activity of the antagonist can be mediated, e.g., by blocking binding of the agonist to the receptor, or by altering receptor configuration and/or activity of the receptor. A "putative antagonist" is an agent to be tested for antagonist activity.

A "nuclear receptor" is a receptor that activates or represses transcription of one or more genes in the nucleus (but can also have second messenger signaling actions), typically in conjunction with other transcription factors. The nuclear receptor is activated by the natural cognate ligand for the receptor. Nuclear receptors are ordinarily found in the cytoplasm or nucleus, rather than being membrane-bound.

Nuclear receptor is a member of a superfamily of regulatory proteins that are receptors for, e.g., steroids, retinoids, vitamin D and thyroid hormones. These proteins bind to cis-acting elements in the promoters of their target genes and modulate gene expression in response to a ligand therefore. Nuclear receptors may be classified based on their DNA binding properties. For example, the glucocorticoid, estrogen, androgen, progestin and mineralocorticoid receptors bind as homodimers to hormone response elements (HREs) organized as inverted repeats. Another example are receptors, including those activated by retinoic acid, thyroid hormone, vitamin $D_3$, fatty acids/peroxisome proliferators and ecdysone, that bind to HREs as heterodimers with a common partner, the retinoid X receptor (RXR). Among the latter receptors is LXR.

As used herein, an orphan nuclear receptor is a nuclear receptor for which the natural ligand is unknown.

As used herein, liver X receptor or LXR refers to a nuclear receptor implicated in cholesterol biosynthesis. As used herein, the term LXR refers to both $LXR_\alpha$ and $LXR_\beta$, two forms of the protein found in mammals. Liver X receptor-α. or $LXR_\alpha$ refers to the receptor described in U.S. Pat. Nos. 5,571,696, 5,696,233 and 5,710,004, and Willy et al. (1995) Gene Dev. 9(9):1033-1045. Liver X receptor-β or $LXR_\beta$ refers to the receptor described in Peet et al. (1998) Curr. Opin. Genet. Dev. 8(5):571-575; Song et al. (1995) Ann. N.Y. Acad. Sci. 761:38-49; Alberti et al. (2000) Gene 243(1-2):93-103; and references cited therein; and in U.S. Pat. Nos. 5,571, 696, 5,696,233 and 5,710,004.

As used herein, compounds which are "commercially available" may be obtained from standard commercial sources including Acros Organics (Pittsburgh Pa.), Aldrich Chemical (Milwaukee Wis., including Sigma Chemical and Fluka), Apin Chemicals Ltd. (Milton Park UK), Avocado Research (Lancashire U.K.), BDH Inc. (Toronto, Canada), Bionet (Cornwall, U.K.), Chemservice Inc. (West Chester Pa.), Crescent Chemical Co. (Hauppauge N.Y.), Eastman Organic Chemicals, Eastman Kodak Company (Rochester N.Y.), Fisher Scientific Co. (Pittsburgh Pa.), Fisons Chemicals (Leicestershire UK), Frontier Scientific (Logan Utah), ICN Biomedicals, Inc. (Costa Mesa Calif.), Key Organics (Comwafl U.K.), Lancaster Synthesis (Windham N.H.), Maybridge Chemical Co. Ltd. (Cornwall U.K.), Parish Chemical Co. (Orem Utah), Pfaltz & Bauer, Inc. (Waterbury Conn.), Polyorganix (Houston Tex.), Pierce Chemical Co. (Rockford Ill.), Riedel de Haen AG (Hannover, Germany), Spectrum Quality Product, Inc. (New Brunswick, N.J.), TCI America (Portland Oreg.), Trans World Chemicals, Inc. (Rockville Md.), and Wako Chemicals USA, Inc. (Richmond Va.).

As used herein, "suitable conditions" for carrying out a synthetic step are explicitly provided herein or may be discerned by reference to publications directed to methods used in synthetic organic chemistry. The reference books and treatise set forth above that detail the synthesis of reactants useful in the preparation of compounds of the present invention, will also provide suitable conditions for carrying out a synthetic step according to the present invention.

As used herein, "methods known to one of ordinary skill in the art" may be identified though various reference books and databases. Suitable reference books and treatise that detail the synthesis of reactants useful in the preparation of compounds of the present invention, or provide references to articles that describe the preparation, include for example, "Synthetic Organic Chemistry", John Wiley & Sons, Inc., New York; S. R. Sandler et al., "Organic Functional Group Preparations," 2nd Ed., Academic Press, New York, 1983; H. O. House, "Modern Synthetic Reactions", 2nd Ed., W. A. Benjamin, Inc. Menlo Park, Calif. 1972; T. L. Gilchrist, "Heterocyclic Chemistry", 2nd Ed., John Wiley & Sons, New York, 1992; J. March, "Advanced Organic Chemistry: Reactions, Mechanisms and Structure", 4th Ed., Wiley-Interscience, New York, 1992. Specific and analogous reactants may also be identified through the indices of known chemicals prepared by the Chemical Abstract Service of the American Chemical Society, which are available in most public and university libraries, as well as through on-line databases (the American Chemical Society, Washington, D.C. may be contacted for more details). Chemicals that are known but not commercially available in catalogs may be prepared by custom chemical synthesis houses, where many of the standard chemical supply houses (e.g., those listed above) provide custom synthesis services.

"Prodrugs" is meant to indicate a compound that may be converted under physiological conditions or by solvolysis to a biologically active compound of the invention. Thus, the term "prodrug" refers to a metabolic precursor of a compound of the invention that is pharmaceutically acceptable. A prodrug may be inactive when administered to a subject in need thereof, but is converted in vivo to an active compound of the invention. Prodrugs are typically rapidly transformed in vivo to yield the parent compound of the invention, for example, by hydrolysis in blood. The prodrug compound often offers advantages of solubility, tissue compatibility or delayed release in a mammalian organism (see, Bundgard, H., *Design of Prodrugs* (1985), pp. 7-9, 21-24 (Elsevier, Amsterdam). A discussion of prodrugs is provided in Higuchi, T., et al., "Pro-drugs as Novel Delivery Systems," A.C.S. Symposium Series, Vol. 14, and in Bioreversible Carriers in Drug Design, ed. Edward B. Roche, American Pharmaceutical Association and Pergamon Press, 1987, both of which are incorporated in full by reference herein. The term "prodrug" is also meant to include any covalently bonded carriers which release the active compound of the invention in vivo when such prodrug is administered to a mammalian subject. Prodrugs of a compound of the invention may be prepared by modifying functional groups present in the compound of the invention in such a way that the modifications are cleaved, either in routine manipulation or in vivo, to the parent compound of the invention. By virtue of knowledge of pharmacodynamic processes and drug metabolism in vivo, those of skill in this art, once a pharmaceutically active compound is known, can design prodrugs of the compound (see, e.g., Nogrady (1985) *Medicinal Chemistry A Biochemical Approach*, Oxford University Press, New York, pages 388-392). Prodrugs include compounds of the invention wherein a hydroxy, amino or mercapto group is bonded to any group that, when the prodrug of the compound of the invention is administered to a mammalian subject, cleaves to form a free hydroxy, free amino or free mercapto group, respectively. Examples of prodrugs include, but are not limited to, acetate, formate and benzoate derivatives of alcohol and amine functional groups in the compounds of the invention and the like.

"Polymorph" refers to the different crystal forms of a compound, resulting from the possibility of at least two different arrangements of the molecules of the compound in the solid state. Polymorphs of a given compound will be different in crystal structure but identical in liquid or vapor states. Different polymorphic forms of a given substance may differ from each other with respect to one or more physical properties, such as solubility and dissociation, true density, crystal shape, compaction behavior, flow properties, and/or solid state stability.

"Stable compound" and "stable structure" are meant to indicate a compound that is sufficiently robust to survive isolation to a useful degree of purity from a reaction mixture, and formulation into an efficacious therapeutic agent.

"Mammal" includes humans and domestic animals, such as cats, dogs, swine, cattle, sheep, goats, horses, rabbits, and the like.

"Optional" or "optionally" means that the subsequently described event of circumstances may or may not occur, and that the description includes instances where said event or circumstance occurs and instances in which it does not. For example, "optionally substituted aryl" means that the aryl radical may or may not be substituted and that the description includes both substituted aryl radicals as defined herein and aryl radicals having no substitution.

"Pharmaceutically acceptable carrier, diluent or excipient" includes without limitation any adjuvant, carrier, excipient, glidant, sweetening agent, diluent, preservative, dye/colorant, flavor enhancer, surfactant, wetting agent, dispersing agent, suspending agent, stabilizer, isotonic agent, solvent, or emulsifier which has been approved by the United States Food and Drug Administration as being acceptable for use in humans or domestic animals.

"Pharmaceutically acceptable salt" includes both acid and base addition salts.

"Pharmaceutically acceptable acid addition salt" refers to those salts which retain the biological effectiveness and properties of the free bases, which are not biologically or otherwise undesirable, and which are formed with inorganic acids such as hydrochloric acid, hydrobromic acid, sulfuric acid, nitric acid, phosphoric acid and the like, and organic acids such as acetic acid, trifluoroacetic acid, propionic acid, glycolic acid, pyruvic acid, oxalic acid, maleic acid, malonic acid, succinic acid, fumaric acid, tartaric acid, citric acid, benzoic acid, cinnamic acid, mandelic acid, methanesulfonic acid, ethanesulfonic acid, p-toluenesulfonic acid, salicylic acid, and the like.

"Pharmaceutically acceptable base addition salt" refers to those salts which retain the biological effectiveness and properties of the free acids, which are not biologically or otherwise undesirable. These salts are prepared from addition of an inorganic base or an organic base to the free acid. Salts derived from inorganic bases include, but are not limited to, the sodium, potassium, lithium, ammonium, calcium, magnesium, iron, zinc, copper, manganese, aluminum salts and the like. Preferred inorganic salts are the ammonium, sodium, potassium, calcium, and magnesium salts. Salts derived from organic bases include, but are not limited to, salts of primary, secondary, and tertiary amines, substituted amines including naturally occurring substituted amines, cyclic amines and basic ion exchange resins, such as isopropylamine, trimethylamine, diethylamine, triethylamine, tripropylamine, ethanolamine, 2-dimethylaminoethanol, 2-diethylaminoethanol, dicyclohexylamine, lysine, arginine, histidine, caffeine, procaine, hydrabamine, choline, betaine, ethylenediamine, glucosamine, methylglucamine, theobromine, purines, piperazine, piperidine, N-ethylpiperidine, polyamine resins and the like. Particularly preferred organic bases are isopropylamine, diethylamine, ethanolamine, trimethylamine, dicyclohexylamine, choline and caffeine.

"Pharmaceutically acceptable derivative" refers to pharmaceutically acceptable salts as defined herein and also includes esters, prodrugs, solvates and polymorphs of the compounds of the invention.

"Therapeutically effective amount" refers to that amount of a compound of the invention which, when administered to a mammal, preferably a human, is sufficient to effect treatment, as defined below, for a disease-state associated with nuclear receptor activity. The amount of a compound of the invention which constitutes a "therapeutically effective amount" will vary depending on the compound, the condition and its severity, and the age of the mammal to be treated, but can be determined routinely by one of ordinary skill in the art having regard to his own knowledge and to this disclosure.

"Modulating" or "modulate" refers to the treating, prevention, suppression, enhancement or induction of a function or condition. For example, the compounds of the present invention can modulate hyperlipidemia by lowering cholesterol in a human, thereby suppressing hyperlipidemia.

"Treating" or "treatment" as used herein covers the treatment of a disease or condition associated with the nuclear receptor activity as disclosed herein, in a mammal, preferably a human, and includes:

i. Preventing a disease or condition associated with the nuclear receptor activity from occurring in a mammal, in particular, when such mammal is predisposed to the disease or condition but has not yet been diagnosed as having it;

ii. inhibiting a disease or condition associated with the nuclear receptor activity, i.e., arresting its development; or iii. relieving a disease or condition associated with the nuclear receptor activity, i.e., causing regression of the condition.

Preferably, the term "treating" or "treatment" as used herein covers the treatment of a disease or condition associated with the nuclear receptor activity as disclosed herein, in a mammal, preferably a human, and includes:

i. inhibiting a disease or condition associated with the nuclear receptor activity, i.e., arresting its development; or ii. relieving a disease or condition associated with the nuclear receptor activity, i.e., causing regression of the condition.

The various compounds described herein, or their pharmaceutically acceptable salts, may contain one or more asymmetric centers and may thus give rise to enantiomers, diastereomers, and other stereoisomeric forms that may be defined, in terms of absolute stereochemistry, as (R)- or (S)- or, as (D)- or (L)- for amino acids. The present invention is meant to include all such possible isomers, as well as, their racemic and optically pure forms. Optically active (+) and (−), (R)- and (S)-, or (D)- and (L)-isomers may be prepared using chiral synthons or chiral reagents, or resolved using conventional techniques, such as reverse phase HPLC. When the compounds described herein contain olefinic double bonds or other centers of geometric asymmetry, and unless specified otherwise, it is intended that the compounds include both E and Z geometric isomers. It will be apparent to one skilled in the art that certain compounds of this invention may exist in tautomeric forms, all such tautomeric forms of the compounds being within the scope of the invention. Unless otherwise stated, structures depicted herein are also meant to include all stereochemical forms of the structure; i.e., the R and S configurations for each asymmetric center. Therefore, single stereochemical isomers as well as enantiomeric and diastereomeric mixtures of the present compounds are within the scope of the invention. Unless otherwise stated, structures depicted herein are also meant to include compounds which differ only in the presence of one or more isotopically enriched atoms. For example, compounds having the present structure except for the replacement of a hydrogen atom by a deuterium or tritium, or the replacement of a carbon atom by a $^{13}$C- or $^{14}$C-enriched carbon are within the scope of this invention.

The chemical naming protocol and structure diagrams used herein employ and rely on the chemical naming features as utilized by the ChemDraw program (available from Cambridgesoft Corp., Cambridge, Mass.). In particular, the compound names were derived from the structures using the Autonom program as utilized by Chemdraw Ultra or ISIS base (MDL Corp.).

The term "atherosclerosis" refers to process whereby atherosclerotic plaques form within the inner lining of the artery wall leading to atherosclerotic cardiovascular diseases. Atherosclerotic cardiovascular diseases can be recognized and understood by physicians practicing in the relevant fields of medicine, and include without limitation, restenosis, coronary heart disease (also known as coronary artery heart disease or ischemic heart disease), cerebrovascular disease including ischemic stroke, multi-infarct dementia, and peripheral vessel disease, including intermittent claudication, and erectile dysfunction.

The term "dyslipidemia" refers to abnormal levels of lipoproteins in blood plasma including both depressed and/or elevated levels of lipoproteins (e.g., elevated levels of Low Density Lipoprotein, (LDL), Very Low Density Lipoprotein (VLDL) and depressed levels of High Density Lipoprotein (HDL) (less than 40 mg/dL)).

As used herein, "$EC_{50}$" refers to a dosage, concentration or amount of a particular test compound that elicits a dose-dependent response at 50% of maximal expression of a particular response that is induced, provoked or potentiated by the particular test compound.

The term "cholesterol" refers to a steroid alcohol that is an essential component of cell membranes and myelin sheaths and, as used herein, incorporates its common usage. Cholesterol also serves as a precursor for steroid hormones and bile acids.

The term "triglyceride(s)" ("TGs"), as used herein, incorporates its common usage. TGs consist of three fatty acid molecules esterified to a glycerol molecule and serve to store fatty acids which are used by muscle cells for energy production or are taken up and stored in adipose tissue.

The term "hyperlipidemia" refers to the presence of an abnormally elevated level of lipids in the blood. Hyperlipidemia can appear in at least three for MS (ES): (1) hypercholesterolemia, i.e., an elevated LDL cholesterol level (120 mg/dL and above); (2) hypertriglyceridemia, i.e., an elevated triglyceride level; (150 mg/dL and above) and (3) combined hyperlipidemia, i.e., a combination of hypercholesterolemia and hypertriglyceridemia.

Exemplary Primary Hyperlipidemia includes, but is not limited to, the following:

(1) Familial Hyperchylomicronemia, a rare genetic disorder which causes a deficiency in an enzyme, LP lipase, that breaks down fat molecules. The LP lipase deficiency can cause the accumulation of large quantities of fat or lipoproteins in the blood;

(2) Familial Hypercholesterolemia, a relatively common genetic disorder caused where the underlying defect is a series of mutations in the LDL receptor gene that result in malfunctioning LDL receptors and/or absence of the LDL receptors. This brings about ineffective clearance of LDL by the LDL receptors resulting in elevated LDL and total cholesterol levels in the plasma;

(3) Familial Combined Hyperlipidemia, also known as multiple lipoprotein-type hyperlipidemia; an inherited disorder where patients and their affected first-degree relatives can at various times manifest high cholesterol and high triglycerides. Levels of HDL cholesterol are often moderately decreased;

(4) Familial Defective Apolipoprotein B-100 is a relatively common autosomal dominant genetic abnormality. The defect is caused by a single nucleotide mutation that produces a substitution of glutamine for arginine which can cause reduced affinity of LDL particles for the LDL receptor. Consequently, this can cause high plasma LDL and total cholesterol levels.

Familial Dysbetalipoproteinemia, also referred to as Type III Hyperlipoproteinemia, is an uncommon inherited disorder resulting in moderate to severe elevations of serum triglyceride (TG) and cholesterol levels with abnormal apolipoprotein E function. HDL levels are usually normal; and Familial Hypertriglyceridemia, is a common inherited disorder in which the concentration of plasma VLDL is elevated. This can cause mild to moderately elevated triglyceride levels (and usually not cholesterol levels) and can often be associated with low plasma HDL levels.

Risk factors in exemplary Secondary Hyperlipidemia include, but are not limited to, the following: (1) disease risk factors, such as a history of type 1 diabetes, type 2 diabetes, Cushing's syndrome, hypothyroidism and certain types of renal failure; (2) drug risk factors, which include, birth control pills; hormones, such as estrogen, and corticosteroids; certain diuretics; and various beta. blockers; (3) dietary risk factors include dietary fat intake per total calories greater than 40%; saturated fat intake per total calories greater than 10%; cholesterol intake greater than 300 mg per day; habitual and excessive alcohol use; and obesity; and (4) non-genetic dyslipidemias.

The methods of the present invention can be used effectively in combination with one or more additional active diabetes agents depending on the desired target therapy (see, e.g., Turner, N. et al. Prog. Drug Res. (1998) 51:33-94; Haffner, S. Diabetes Care (1998) 21: 160-178; and DeFronzo, R. et al. (eds.), Diabetes Reviews (1997) Vol. 5 No. 4). A number of studies have investigated the benefits of combination therapies with oral agents (see, e.g., Mahler, R., J. Clin. Endocrinol. Metab. (1999)84:1165-71; United Kingdom Prospective Diabetes Study Group: UKPDS 28, Diabetes Care (1998)21:87-92; Bardin, C. W.(ed.), CURRENT THERAPY IN ENDOCRINOLOGY AND METABOLISM, 6th Edition (Mosby—Year Book, Inc., St. Louis, Mo. 1997); Chiasson, J. et al., Ann. Intern. Med. (1994) 121: 928-935; Coniff, R. et al., Clin. Ther. (1997) 19: 16-26; Coniff, R. et al., Am. J. Med. (1995) 98: 443-451; and Iwamoto, Y. et al, Diabet. Med. (1996)13: 365-370; Kwiterovich, P. Am. J. Cardiol (1998) 82(12A):3U-17U). These studies indicate that diabetes and hyperlipidemia modulation can be further improved by the addition of a second agent to the therapeutic regimen. As used herein, "$IC_{50}$" refers to an amount, concentration or dosage of a particular test compound that achieves a 50% inhibition of a maximal response, such as modulation of nuclear receptor, including the $LXR_\alpha$ or $LXR_\beta$ activity, in an assay that measures such response.

As used herein, "$LXR_\alpha$" (LXR alpha) refers to all mammalian forms of such receptor including, for example, alternative splice isoforms and naturally occurring isoforms. Representative LXR, species include, without limitation the rat (Genbank Accession NM_031627), mouse (Genbank Accession BC012646), and human (GenBank Accession No. U22662) forms of the receptor.

As used herein, "$LXR_\beta$" (LXR beta) refers to all mammalian forms of such receptor including, for example, alternative splice isoforms and naturally occurring isoforms. Representative $LXR_\beta$ species include, without limitation the rat (GenBank Accession NM_031626), mouse (Genbank Accession NM_009473), and human (GenBank Accession No. U07132) forms of the receptor.

As used herein "LXR" or "LXRs" refers to both $LXR_\alpha$ and $LXR_\beta$.

The terms "obese" and "obesity" refers to a Body Mass Index (BMI) greater than 27.8 kg/m$^2$ for men and 27.3 kg/m$^2$ for women (BMI equals weight (kg)/(height)$^2$(m$^2$).

Use of the Compounds of the Invention

The compounds of the invention exhibit valuable pharmacological properties in mammals, and are particularly useful as selective LXR agonists, antagonists, inverse agonists, partial agonists and antagonists, as well as LXR/FXR dual agonists, for the treatment, or prevention of diseases associated with, or symptoms arising from the complications of, altered cholesterol transport, cholesterol reverse transport, fatty acid metabolism, cholesterol absorption, cholesterol re-absorption, cholesterol secretion, cholesterol excretion, or cholesterol metabolism.

These diseases include, for example, hyperlipidemia, dyslipidemia, hypercholesterolemia, atherosclerosis, atherosclerotic cardiovascular diseases, hyperlipoproteinemia, (see, e.g., International Patent Application Publication Nos. WO 00/57915 and WO 00/37077), hyperglycemia, insulin resistance, diabetes, lipodystrophy, obesity, syndrome X (US Patent Application Publication No. 20030073614, International Patent Application Publication No. WO 01/82917), excess lipid deposition in peripheral tissues such as skin (xanthomas) (see, e.g., U.S. Pat. Nos. 6,184,215 and 6,187,814), stroke, peripheral occlusive disease, memory loss (*Brain Research* (1997), Vol. 752, pp. 189-196), optic nerve and retinal pathologies (i.e., macular degeneration, retintis pigmentosa), repair of traumatic damage to the central or peripheral nervous system (*Trends in Neurosciences* (1994), Vol. 17, pp. 525-530), prevention of the degenerative process due to aging (*American Journal of Pathology* (1997), Vol. 151, pp. 1371-1377), Parkinson's disease or Alzheimer's disease (see, e.g., International Patent Application Publication No. WO 00/17334; *Trends in Neurosciences* (1994), Vol. 17, pp. 525-530), prevention of degenerative neuropathies occurring in diseases such as diabetic neuropathies (see, e.g., International Patent Application Publication No. WO 01/82917), multiple sclerosis (*Annals of Clinical Biochem.* (1996), Vol. 33, No. 2, pp. 148-150), and autoimmune diseases (*J. Lipid Res.* (1998), Vol. 39, pp. 1740-1743).

Also provided, are methods of increasing the expression of ATP-Binding Cassette (ABCA1), (see, e.g., International Patent Application Publication No. WO 00/78972) thereby increasing reverse cholesterol transport in mammalian cells using the claimed compounds and compositions.

Accordingly in another aspect, the invention also includes methods to remove cholesterol from tissue deposits such as atherosclerotic plaques or xanthomas in a patient with atherosclerosis or atherosclerotic cardiovascular disease manifest by clinical signs of such disease, wherein the methods comprise administering to the patient a therapeutically effective amount of a compound or composition of the present invention. Additionally, the instant invention also provides a method for preventing or reducing the risk of a first or subsequent occurrence of an atherosclerotic cardiovascular disease event including ischemic heart disease, ischemic stroke, multi-infarct dementia, and intermittent claudication comprising the administration of a prophylactically effective amount of a compound or composition of the present invention to a patient at risk for such an event. The patient may already have atherosclerotic cardiovascular disease at the time of administration, or may be at risk for developing it. Risk factors for developing atherosclerotic cardiovascular disease events include increasing age (65 and over), male gender, a family history of atherosclerotic cardiovascular disease events, high blood cholesterol (especially LDL or "bad" cholesterol over 100 mg/dL), cigarette smoking and exposure to tobacco smoke, high blood pressure, diabetes, obesity and physical inactivity.

Also contemplated herein is the use of a compound of the invention, or a pharmaceutically acceptable derivative thereof, in combination with one or more of the following therapeutic agents in treating atherosclerosis: antihyperlipidemic agents, plasma HDL-raising agents, antihypercholesterolemic agents, cholesterol biosynthesis inhibitors (such as NMG CoA reductase inhibitors, such as lovastatin, simvastatin, pravastatin, fluvastatin, atorvastatin and rivastatin), acyl-coenzyme A:cholesterol acytransferase (ACAT) inhibitors, probucol, raloxifene, nicotinic acid, niacinamide, cholesterol absorption inhibitors, bile acid sequestrants (such as anion exchange resins, or quaternary amines (e.g., cholestyramine or colestipol)), low density lipoprotein receptor inducers, clofibrate, fenofibrate, benzofibrate, cipofibrate, gemfibrizol, vitamin $B_6$, vitamin $B_{12}$, anti-oxidant vitamins, β-blockers, anti-diabetes agents, angiotensin TI antagonists, angiotensin converting enzyme inhibitors, platelet aggregation inhibitors, fibrinogen receptor antagonists, aspirin or fibric acid derivatives.

In one embodiment compounds of the invention are used in combination with a cholesterol biosynthesis inhibitor, particularly an HMG-CoA reductase inhibitor. The term RMG-CoA reductase inhibitor is intended to include all pharmaceutically acceptable salt, ester, free acid and lactone forms of compounds which have RMG-CoA reductase inhibitory activity and, therefore, the use of such salts, esters, free acids and lactone forms is included within the scope of this invention. Compounds which have inhibitory activity for RMG-CoA reductase can be readily identified using assays well-known in the art. For instance, suitable assays are described or disclosed in U.S. Pat. No. 4,231,938 and WO 84/02131. Examples of suitable RMG-CoA reductase inhibitors include, but are not limited to, lovastatin (MEVACOR®; see, U.S. Pat. No. 4,231,938); simvastatin (ZOCOR®; see, U.S. Pat. No. 4,444,784); pravastatin sodium (PRAVACHOL®; see, U.S. Pat. No. 4,346,227); fluvastatin sodium (LESCOL®; see, U.S. Pat. No. 5,354,772); atorvastatin calcium (LIPITOR®; see, U.S. Pat. No. 5,273,995) andrivastatin (also known as cerivastatin; see, U.S. Pat. No. 5,177,080). The structural formulae of these and additional HMG-CoA reductase inhibitors that can be used in combination with the compounds of the invention are described at page 87 of M. Yalpani, "Cholesterol Lowering Drugs," *Chemistry & Industry*, pp. 85-89 (5 Feb. 1996). In presently preferred embodiments, the RMG-CoA reductase inhibitor is selected from lovastatin and simvastatin.

The compounds of the present invention can also be used in methods for decreasing hyperglycemia and insulin resistance, i.e., in methods for treating diabetes (International Patent Application Publication No. WO 01/82917), and in methods of treatment prevention, or amelioration of disorders related to, or arising as complications of diabetes, hyperglycemia or insulin resistance including the cluster of disease states, conditions or disorders that make up "Syndrome X" (See US Patent Application 20030073614) comprising the administration of a therapeutically effective amount of a compound or composition of the present invention to a patient in need of such treatment. Additionally, the instant invention also provides a method for preventing or reducing the risk of developing hyperglycemia, insulin resistance, diabetes or syndrome X in a patient, comprising the administration of a prophylactically effective amount of a compound or composition of the present invention to a patient at risk for such an event.

Diabetes mellitus, commonly called diabetes, refers to a disease process derived from multiple causative factors and characterized by elevated levels of plasma glucose, referred to as hyperglycemia. See, e.g., LeRoith, D. et al., (eds.), DIABETES MELLITUS (Lippincott-Raven Publishers, Philadelphia, Pa. U.S.A. 1996). According to the American Diabetes Association, diabetes mellitus is estimated to affect approximately 6% of the world population. Uncontrolled hyperglycemia is associated with increased and premature mortality due to an increased risk for macrovascular and macrovascular diseases, including nephropathy, neuropathy, retinopathy, hypertension, cerebrovascular disease and coronary heart disease. Therefore, control of glucose homeostasis is a critically important approach for the treatment of diabetes.

There are two major forms of diabetes: type 1 diabetes (formerly referred to as insulin-dependent diabetes or IDEM); and type 2 diabetes (formerly referred to as noninsulin dependent diabetes or NIDDM). Type 2 diabetes is a disease characterized by insulin resistance accompanied by relative, rather than absolute, insulin deficiency. Type 2 diabetes can range from predominant insulin resistance with relative insulin deficiency to predominant insulin deficiency with some insulin resistance. Insulin resistance is the diminished ability of insulin to exert its biological action across a broad range of concentrations. In insulin resistant individuals, the body secretes abnormally high amounts of insulin to compensate for this defect. When inadequate amounts of insulin are present to compensate for insulin resistance and adequate control of glucose, a state of impaired glucose tolerance develops. In a significant number of individuals, insulin secretion declines further and the plasma glucose level rises, resulting in the clinical state of diabetes. Type 2 diabetes can be due to a profound resistance to insulin stimulating regulatory effects on glucose and lipid metabolism in the main insulin-sensitive tissues: muscle, liver and adipose tissue. This resistance to insulin responsiveness results in insufficient insulin activation of glucose uptake, oxidation and storage in muscle and inadequate insulin repression of lipolysis in adipose tissue and of glucose production and secretion in liver. In Type 2 diabetes, free fatty acid levels are often elevated in obese and some non-obese patients and lipid oxidation is increased.

Premature development of atherosclerosis and increased rate of cardiovascular and peripheral vascular diseases are characteristic features of patients with diabetes. Hyperlipidemia is an important precipitating factor for these diseases. Hyperlipidemia is a condition generally characterized by an abnormal increase in serum lipids, e.g., cholesterol and triglyceride, in the bloodstream and is an important risk factor in developing atherosclerosis and heart disease. For a review of disorders of lipid metabolism, see, e.g., Wilson, J. et al., (ed.), Disorders of Lipid Metabolism, Chapter 23, Textbook of Endocrinology, 9th Edition, (W. B. Sanders Company, Philadelphia, Pa. U.S.A. 1998). Hyperlipidemia is usually classified as primary or secondary hyperlipidemia. Primary hyperlipidemia is generally caused by genetic defects, while secondary hyperlipidemia is generally caused by other factors, such as various disease states, drugs, and dietary factors. Alternatively, hyperlipidemia can result from both a combination of primary and secondary causes of hyperlipidemia. Elevated cholesterol levels are associated with a number of disease states, including coronary artery disease, angina pectoris, carotid artery disease, strokes, cerebral arteriosclerosis, and xanthoma.

Dyslipidemia, or abnormal levels of lipoproteins in blood plasma, is a frequent occurrence among diabetics, and has been shown to be one of the main contributors to the increased incidence of coronary events and deaths among diabetic subjects (see, e.g., Joslin, E. Ann. Chim. Med. (1927), Vol. 5, pp. 1061-1079). Epidemiological studies since then have confirmed the association and have shown a several-fold increase in coronary deaths among diabetic subjects when compared with non-diabetic subjects (see, e.g., Garcia, M. J. et al., Diabetes (1974), Vol. 23, pp. 105-11 (1974); and Laakso, M. and Lehto, S., Diabetes Reviews (1997), Vol. 5, No. 4, pp. 294-315). Several lipoprotein abnormalities have been described among diabetic subjects (Howard B., et al., Arteriosclerosis (1978), Vol. 30, pp. 153-162).

The compounds of the invention can also be used effectively in combination with one or more additional active diabetes agents depending on the desired target therapy (see, e.g., Turner, N. et al., Prog. Drug Res. (1998), Vol. 51, pp. 33-94; Hafffier, S., Diabetes Care (1998), Vol. 21, pp. 160-178; and DeFronzo, R. et al. (eds.), Diabetes Reviews (1997), Vol. 5, No. 4). A number of studies have investigated the benefits of combination therapies with oral agents (see, e.g., Mahler, R., J. Clin. Endocriinol. Metab. (1999), Vol. 84, pp. 1165-71; United Kingdom Prospective Diabetes Study Group: UKPDS 28, Diabetes Care (1998), Vol. 21, pp. 87-92; Bardin, C. W.(ed.), CURRENT THERAPY IN ENDOCRINOLOGY AND METABOLISM, 6th Edition (Mosby—Year Book, Inc., St. Louis, Mo. 1997); Chiasson, J. et al., Ann. Intern. Med. (1994), Vol. 121, pp. 928-935; Coniff, R. et al., Clin. Ther. (1997), Vol. 19, pp. 16-26; Coniff, R. et al., Am. J. Med. (1995), Vol. 98, pp. 443-451; Iwamoto, Y. et al., Diabet. Med. (1996), Vol. 13, pp. 365-370; Kwiterovich, P., Am. J. Cardiol (1998), Vol. 82 (12A), pp. 3U-117U). These studies indicate that diabetes and hyperlipidemia modulation can be further improved by the addition of a second agent to the therapeutic regimen.

Accordingly, the compounds of the invention may be used in combination with one or more of the following therapeutic agents in treating diabetes: sulfonylureas (such as chlorpropamide, tolbutamide, acetohexamide, tolazamide, glyburide, gliclazide, glynase, glimepiride, and glipizide), biguanides (such as metformin), thiazolidinediones (such as ciglitazone, pioglitazone, troglitazone, and rosiglitazone), and related insulin sensitizers, such as selective and non-selective activators of PPARα, PPARβ and PPARγ; dehydroepiandrosterone (also referred to as DHEA or its conjugated sulphate ester, DHEA-SO$_4$); antiglucocorticoids; TNFαinhibitors; α-glucosidase inhibitors (such as acarbose, miglitol, and voglibose), pramlintide (a synthetic analog of the human hormone amylin), other insulin secretogogues (such as repaglinide, gliquidone, and nateglinide), insulin, as well as the therapeutic agents discussed above for treating atherosclerosis.

Further provided by this invention are methods of using the compounds of the invention to treat obesity, as well as the complications of obesity. Obesity is linked to a variety of medical conditions including diabetes and hyperlipidemia. Obesity is also a known risk factor for the development of type 2 diabetes (See, e.g., Barrett-Conner, E., Epidemol. Rev. (1989), Vol. 11, pp. 172-181; and Knowler, et al., Am. J. Clin. Nutr. (1991), Vol. 53, pp. 1543-1551).

In addition, the compounds of the invention can be used in combination with agents used in treated obesity or obesity-related disorders. Such agents, include, but are not limited to, phenylpropanolamine, phentermine, diethylpropion, mazindol, fenfluramine, dexfenfluramine, phentiramine, β$_3$ adrenoceptor agonist agents; sibutramine, gastrointestinal lipase inhibitors (such as orlistat), and leptins. Other agents used in treating obesity or obesity-related disorders include neuropeptide Y, enterostatin, cholecytokinin, bombesin, amylin, histamine H$_3$ receptors, dopamine D$_2$ receptor modulators, melanocyte stimulating hormone, corticotrophin releasing factor, galanin and gamma amino butyric acid (GABA).

Evaluation of the Use of the Compounds of the Invention

Standard physiological, pharmacological and biochemical procedures are available for testing the compounds to identify those that possess biological activities that modulate the activity or nuclear receptors, including the LXRs (LXR$_\alpha$ and LXR$_\beta$) and FXR. Such assays include, for example, biochemical assays such as binding assays, fluorescence polarization assays, FRET based coactivator recruitment assays (see, generally, Glickman et al., J. Biomolecular Screening (2002), Vol. 7, No. 1, pp. 3-10, as well as cell based assays including the co-transfection assay, the use of LBD-Gal 4 chimeras and protein-protein interaction assays, (see, Lehmann. et al., J. Biol. Chem. (1997), Vol. 272, No. 6, pp. 3137-3140.

High throughput screening systems are commercially available (see, e.g., Zymark Corp., Hopkinton, Mass.; Air Technical Industries, Mentor, Ohio; Beckman Instruments Inc., Fullerton, Calif.; Precision Systems, Inc., Natick, Mass.) that enable these assays to be run in a high throughput mode. These systems typically automate entire procedures, including all sample and reagent pipetting, liquid dispensing timed incubations, and final readings of the microplate in detector (s) appropriate for the assay. These configurable systems provide high throughput and rapid start up as well as a high degree of flexibility and customization. The manufacturers of such systems provide detailed protocols for various high throughput systems. Thus, for example, Zymark Corp. provides technical bulletins describing screening systems for detecting the modulation of gene transcription, ligand binding, and the like.

Assays that do not require washing or liquid separation steps are preferred for such high throughput screening systems and include biochemical assays such as fluorescence polarization assays (see, for example, Owicki, J., Biomol. Screen (2000 October), Vol. 5, No. 5, pp. 297), scintillation proximity assays (SPA) (see, for example, Carpenter et al., Methods Mol. Biol. (2002), Vol 190, pp. 3149) and fluorescence resonance energy transfer energy transfer (FRET) or time resolved FRET based coactivator recruitment assays (Mukheijee et al., J. Steroid Biochem. Mol. Biol. (2002 July); Vol. 81, No. 3, pp. 217-25; (Zhou et al., Mol. Endocrinol. (1998 October), Vol. 12, No. 10, pp. 1594-604). Generally such assays can be preformed using either the full length receptor, or isolated ligand binding domain (LBD). In the case of LXR$_\alpha$, the LBD comprises amino acids 188-447, for LXR$_\beta$ the LDB comprises amino acids 198-461, and for FXR, the LBD comprises amino acids 244 to 472 of the full length sequence.

If a fluorescently labeled ligand is available, fluorescence polarization assays provide a way of detecting binding of compounds to the nuclear receptor of interest by measuring changes in fluorescence polarization that occur as a result of the displacement of a trace amount of the label ligand by the compound. Additionally this approach can also be used to monitor the ligand dependent association of a fluorescently labeled coactivator peptide to the nuclear receptor of interest to detect ligand binding to the nuclear receptor of interest.

The ability of a compound to bind to a receptor, or heterodimer complex with RXR, can also be measured in a homogeneous assay format by assessing the degree to which the compound can compete off a radiolabelled ligand with known affinity for the receptor using a scintillation proximity assay (SPA). In this approach, the radioactivity emitted by a radiolabelled compound (for example, [$^3$H] 24,25 Epoxycholesterol) generates an optical signal when it is brought into close proximity to a scintillant such as a YSI-copper containing bead, to which the nuclear receptor is bound. If the radiolabelled compound is displaced from the nuclear receptor the amount of light emitted from the nuclear receptor bound scintillant decreases, and this can be readily detected using standard microplate liquid scintillation plate readers such as, for example, a Wallac MicroBeta reader.

The heterodimerization of LXR with RXR, can also be measured by fluorescence resonance energy transfer (FRET), or time resolved FRET, to monitor the ability of the compounds provided herein to bind to LXR or other nuclear receptors. Both approaches rely upon the fact that energy transfer from a donor molecule to an acceptor molecule only occurs when donor and acceptor are in close proximity. Typically the purified LBD of the nuclear receptor of interest is labeled with biotin then mixed with stoichiometric amounts of europium labeled streptavidin (Wallac Inc.), and the purified LBD of $RXR_\alpha$ is labeled with a suitable fluorophore such as CY5™. Equimolar amounts of each modified LBD are mixed together and allowed to equilibrate for at least 1 hour prior to addition to either variable or constant concentrations of the sample for which the affinity is to be determined. After equilibration, the time-resolved fluorescent signal is quantitated using a fluorescent plate reader. The affinity of the compound can then be estimated from a plot of fluorescence versus concentration of compound added.

This approach can also be exploited to measure the ligand dependent interaction of a co-activator peptide with a nuclear receptor in order to characterize the agonist or antagonist activity of the compounds disclosed herein. Typically the assay in this case involves the use a recombinant Glutathione-S-transferase (GST)-nuclear receptor ligand binding domain (LBD) fusion protein and a synthetic biotinylated peptide sequenced derived from the receptor interacting domain of a co-activator peptide such as the steroid receptor coactivator 1 (SRC-1). Typically GST-LBD is labeled with a europium chelate (donor) via a europium-tagged anti-GST antibody, and the coactivator peptide is labeled with allophycocyanin via a streptavidin-biotin linkage.

In the presence of an agonist for the nuclear receptor, the peptide is recruited to the GST-LBD bringing europium and allophycocyanin into close proximity to enable energy transfer from the europium chelate to the allophycocyanin. Upon excitation of the complex with light at 340 nm excitation energy absorbed by the europium chelate is transmitted to the allophycocyanin moiety resulting in emission at 665 nm. If the europium chelate is not brought in to close proximity to the allophycocyanin moiety there is little or no energy transfer and excitation of the europium chelate results in emission at 615 nm. Thus the intensity of light emitted at 665 nm gives an indication of the strength of the protein-protein interaction. The activity of a nuclear receptor antagonist can be measured by determining the ability of a compound to competitively inhibit (i.e., $IC_{50}$) the activity of an agonist for the nuclear receptor In addition, a variety of cell based assay methodologies may be successfully used in screening assays to identify and profile the specificity of compounds of the present invention. These approaches include the co-transfection assay, translocation assays, complementation assays and the use of gene activation technologies to over express endogenous nuclear receptors.

Three basic variants of the co-transfection assay strategy exist, co-transfection assays using full-length nuclear receptor, co transfection assays using chimeric nuclear receptors comprising the ligand binding domain of the nuclear receptor of interest fused to a heterologous DNA binding domain, and assays based around the use of the mammalian two hybrid assay system.

The basic co-transfection assay is based on the co-transfection into the cell of an expression plasmid to express the nuclear receptor of interest in the cell with a reporter plasmid comprising a reporter gene whose expression is under the control of DNA sequence that is capable of interacting with that nuclear receptor (see, for example, U.S. Pat. Nos. 5,071, 773; 5,298,429 and 6,416,957). Treatment of the transfected cells with an agonist for the nuclear receptor increases the transcriptional activity of that receptor which is reflected by an increase in expression of the reporter gene which may be measured by a variety of standard procedures.

For those receptors that function as heterodimers with RXR, such as the LXRs and FXR, the co-transfection assay typically includes the use of expression plasmids for both the nuclear receptor of interest and RXR. Typical co-transfection assays require access to the full length nuclear receptor and suitable response elements that provide sufficient screening sensitivity and specificity to the nuclear receptor of interest.

Typically, the expression plasmid comprises: (1) a promoter, such as an SV40 early region promoter, HSV tk promoter or phosphoglycerate kinase (pgk) promoter, CMV promoter, $Sr\alpha$ promoter or other suitable control elements known in the art, (2) a cloned polynucleotide sequence, such as a cDNA encoding a receptor, co-factor, or fragment thereof, ligated to the promoter in sense orientation so that transcription from the promoter will produce a RNA that encodes a functional protein, and (3) a polyadenylation sequence. For example and not limitation, an expression cassette of the invention may comprise the cDNA expression cloning vectors, or other preferred expression vectors known and commercially available from vendors such as Invitrogen, (CA), Stratagene, (CA) or Clontech, (CA). Alternatively expression vectors developed by academic groups such as the pCMX vectors originally developed in the Evans lab (Willey et al. Genes & Development 9 1033-1045 (1995)) may also be used.

The transcriptional regulatory sequences in an expression cassette are selected by the practitioner based on the intended application; depending upon the specific use, transcription regulation can employ inducible, repressible, constitutive, cell-type specific, developmental stage-specific, sex-specific, or other desired type of promoter or control sequence.

Alternatively, the expression plasmid may comprise an activation sequence to activate or increase the expression of an endogenous chromosomal sequence. Such activation sequences include for example, a synthetic zinc finger motif (for example, see U.S. Pat. Nos. 6,534,261 and 6,503,7171) or a strong promoter or enhancer sequence together with a targeting sequence to enable homologous or non-homologous recombination of the activating sequence upstream of the gene of interest.

Genes encoding the following full-length previously described proteins, which are suitable for use in the co-transfection studies and profiling the compounds described herein, include human LXR, (accession U22662), human $LXR_\beta$ (accession U07132), rat FXR (accession U18374), human $FXR_\alpha$ (accession NM 005123), human $RXR\alpha$ (accession NM_002957), human RXR$_\beta$ (accession XM_042579), human RXRγ (accession XM_053680), human PPARα (accession X57638) and human PPARδ (accession U10375). All accession numbers in this application refer to GenBank accession numbers.

Reporter plasmids may be constructed using standard molecular biological techniques by placing cDNA encoding for the reporter gene downstream from a suitable minimal promoter. For example luciferase reporter plasmids may be constructed by placing cDNA encoding firefly luciferase (typically with SV40 small t intron and poly-A tail, (de Wet et al., (1987) *Mol. Cell. Biol.* 7 725-735) down stream from the herpes virus thymidine kinase promoter (located at nucleotides residues-105 to +51 of the thymidine kinase nucleotide sequence, obtained for example, from the plasmid pBLCAT2 (Luckow & Schutz (1987) Nucl. Acid. Res. 15 5490-5494)) which is linked in turn to the appropriate response element (RE).

The choice of hormone response element is dependent upon the type of assay to be used. In the case of the use of the full-length LXR$_\alpha$ or LXR$_\beta$ a reporter plasmid comprising a known LXR RE would typically be used, such as for example in a reporter plasmid such as LXRExl-tk-luciferase, (see U.S. Pat. No. 5,747,661, which is hereby incorporated by reference). In the case of a LXR$_\alpha$ or LXR$_\beta$-LBD-Gal4 fusion, GAL4 Upstream Activating Sequences (UAS) would be used. Typically the GAL4 UAS would comprise the sequence 5'CGGRNNRCYNYNCNCCG-3', where Y=C or T, R=A or G, and N=A, C, T or G, and would be present as a tandem repeat of 4 copies.

Numerous methods of co-transfecting the expression and reporter plasmids are known to those of skill in the art and may be used for the co-transfection assay to introduce the plasmids into a suitable cell type. Typically such a cell will not endogenously express nuclear receptors that interact with the response elements used in the reporter plasmid.

Numerous reporter gene systems are known in the art and include, for example, alkaline phosphatase (see, Berger, J., et al., Gene (1988), Vol. 66, pp. 1-10; and Kain, S. R., Methods. Mol. Biol. (1997), Vol. 63, pp. 49-60), β-galactosidase (See, U.S. Pat. No. 5,070,012, issued Dec. 3, 1991 to Nolan et al., and Bronstein, I., et al., J. Chemilum. Biolum. (1989), Vol. 4, pp. 99-111), chloramphenicol acetyltransferase (See, Gonnan et al., Mol. Cell. Biol. (1982), Vol. 2, pp. 1044-51), β-glucuronidase, peroxidase, β-lactamase (U.S. Pat. Nos. 5,741,657 and 5,955,604), catalytic antibodies, luciferases (U.S. Pat. Nos. 5,221,623; 5,683,888; 5,674,713; 5,650,289; and 5,843,746) and naturally fluorescent proteins (Tsien, R. Y., Annu. Rev. Biochem. (1998), Vol. 67, pp. 509-44).

The use of chimeras comprising the ligand binding domain (LBD) of the nuclear receptor of interest to a heterologous DNA binding domain (DBD) expands the versatility of cell based assays by directing activation of the nuclear receptor in question to defined DNA binding elements recognized by defined DNA binding domain (see WO95/18380). This assay expands the utility of cell based co-transfection assays in cases where the biological response or screening window using the native DNA binding domain is not satisfactory.

In general the methodology is similar to that used with the basic co-transfection assay, except that a chimeric construct is used in place of the full length nuclear receptor. As with the full length nuclear receptor, treatment of the transfected cells with an agonist for the nuclear receptor LBD increases the transcriptional activity of the heterologous DNA binding domain which is reflected by an increase in expression of the reporter gene as described above. Typically for such chimeric constructs, the DNA binding domains from defined nuclear receptors, or from yeast or bacterially derived transcriptional regulators such as members of the GAL 4 and Lex A/Umud super families are used.

A third cell based assay of utility for screening compounds of the present invention is a mammalian two-hybrid assay that measures the ability of the nuclear hormone receptor to interact with a cofactor in the presence of a ligand (see, for example, U.S. Pat. Nos. 5,667,973, 5,283,173 and 5,468,614). The basic approach is to create three plasmid constructs that enable the interaction of the nuclear receptor with the interacting protein to be coupled to a transcriptional readout within a living cell. The first construct is an expression plasmid for expressing a fusion protein comprising the interacting protein, or a portion of that protein containing the interacting domain, fused to a GAL4 DNA binding domain. The second expression plasmid comprises DNA encoding the nuclear receptor of interest fused to a strong transcription activation domain such as VP16, and the third construct comprises the reporter plasmid comprising a reporter gene with a minimal promoter and GAL4 upstream activating sequences.

Once all three plasmids are introduced into a cell, the GAL4 DNA binding domain encoded in the first construct allows for specific binding of the fusion protein to GAL4 sites upstream of a minimal promoter. However because the GAL4 DNA binding domain typically has no strong transcriptional activation properties in isolation, expression of the reporter gene occurs only at a low level. In the presence of a ligand, the nuclear receptor-VP16 fusion protein can bind to the GAL4-interacting protein fusion protein bringing the strong transcriptional activator VP16 in close proximity to the GAL4 binding sites and minimal promoter region of the reporter gene. This interaction significantly enhances the transcription of the reporter gene which can be measured for various reporter genes as described above. Transcription of the reporter gene is thus driven by the interaction of the interacting protein and nuclear receptor of interest in a ligand dependent fashion.

Any compound which is a candidate for activation of LXR$_\alpha$ or LXR$_\beta$ may be tested by these methods. Generally, compounds are tested at several different concentrations to optimize the chances that activation of the receptor will be detected and recognized if present. Typically assays are performed in triplicate and vary within experimental error by less than 15%. Each experiment is typically repeated three or more times with similar results.

Activity of the reporter gene can be conveniently normalized to the internal control and the data plotted as fold activation relative to untreated cells. A positive control compound (agonist) may be included along with DMSO as high and low controls for normalization of the assay data. Similarly, antagonist activity can be measured by determining the ability of a compound to competitively inhibit the activity of an agonist.

Additionally the compounds and compositions can be evaluated for their ability to increase or decrease the expression of genes known to be modulated by LXR$_\alpha$ or LXR$_\beta$ and other nuclear receptors in vivo, using Northern-blot, RT PCR or oligonucleotide microarray analysis to analyze RNA levels. Western-blot analysis can be used to measure expression of proteins encoded by LXR target genes. Genes that are known to be regulated by the LXRs include the ATP binding cassette transporters ABCA1, ABCG1, ABCG5, ABCG8, the sterol response element binding protein 1c (SREBP1c) gene, stearoyl CoA desaturase 1 (SCD-1) and the apolipoprotein apoE gene (ApoE).

Established animal models exist for a number of diseases of direct relevance to the claimed compounds and these can be used to further profile and characterize the claimed compounds. These model systems include diabetic dislipidemia using Zucker (fa/fa) rats or (db/db) mice, spontaneous hyperlipidemia using apolipoprotein E deficient mice (ApoE$^{-/-}$), diet-induced hyperlipidemia, using low density lipoprotein receptor deficient mice (LDLW) and atherosclerosis using both the Apo E($^{-/-}$) and LDLR($^{-/-}$) mice fed a western diet. (21% fat, 0.05% cholesterol). Additionally LXR or FXR animal models (e.g., knockout mice) can be used to further evaluate the present compounds and compositions in vivo (see, for example, Peet, et al., Cell (1998), Vol. 93, pp. 693-704, and Sinal, et al., Cell (2000), Vol. 102, pp. 731-744).

Administration of the Compounds of the Invention

Administration of the compounds of the invention, or their pharmaceutically acceptable salts, in pure form or in an appropriate pharmaceutical composition, can be carried out via any of the accepted modes of administration of agents for serving similar utilities. The pharmaceutical compositions of the invention can be prepared by combining a compound of the invention with an appropriate pharmaceutically acceptable carrier, diluent or excipient, and may be formulated into preparations in solid, semi-solid, liquid or gaseous forms, such as tablets, capsules, powders, granules, ointments, solutions, suppositories, injections, inhalants, gels, microspheres, and aerosols. Typical routes of administering such pharmaceutical compositions include, without limitation, oral, topical, transdermal, inhalation, parenteral, sublingual, rectal, vaginal, and intranasal. The term parenteral as used herein includes subcutaneous injections, intravenous, intramuscular, intrasternal injection or infusion techniques.

Pharmaceutical compositions of the invention are formulated so as to allow the active ingredients contained therein to be bioavailable upon administration of the composition to a patient. Compositions that will be administered to a subject or patient take the form of one or more dosage units, where for example, a tablet may be a single dosage unit, and a container of a compound of the invention in aerosol form may hold a plurality of dosage units. Actual methods of preparing such dosage forms are known, or will be apparent, to those skilled in this art; for example, see Remington's Pharmaceutical Sciences, 18th Ed., (sack Publishing Company, Easton, Pa., 1990). The composition to be administered will, in any event, contain a therapeutically effective amount of a compound of the invention, or a pharmaceutically acceptable salt thereof, for treatment of a disease-state associated with the activity of a nuclear receptor in accordance with the teachings of this invention.

A pharmaceutical composition of the invention may be in the form of a solid or liquid. In one aspect, the carrier(s) are particulate, so that the compositions are, for example, in tablet or powder form. The carrier(s) may be liquid, with the compositions being, for example, an oral syrup, injectable liquid or an aerosol, which is useful in, e.g., inhalatory administration.

When intended for oral administration, the pharmaceutical composition is preferably in either solid or liquid form, where semi-solid, semi-liquid, suspension and gel forms are included within the forms considered herein as either solid or liquid.

As a solid composition for oral administration, the pharmaceutical composition may be formulated into a powder, granule, compressed tablet, pill, capsule, chewing gum, wafer or the like form. Such a solid composition will typically contain one or more inert diluents or edible carriers. In addition, one or more of the following may be present: binders such as carboxymethylcellulose, ethyl cellulose, microcrystalline cellulose, gum tragacanth or gelatin; excipients such as starch, lactose or dextrins, disintegrating agents such as alginic acid, sodium alginate, Primogel, corn starch and the like; lubricants such as magnesium stearate or Sterotex; glidants such as colloidal silicon dioxide; sweetening agents such as sucrose or saccharin; a flavoring agent such as peppermint, methyl salicylate or orange flavoring; and a coloring agent.

When the pharmaceutical composition is in the form of a capsule, e.g., a gelatin capsule, it may contain, in addition to materials of the above type, a liquid carrier such as polyethylene glycol or oil.

The pharmaceutical composition may be in the form of a liquid, e.g., an elixir, syrup, solution, emulsion or suspension. The liquid may be for oral administration or for delivery by injection, as two examples.

When intended for oral administration, preferred composition contain, in addition to the present compounds, one or more of a sweetening agent, preservatives, dye/colorant and flavor enhancer. In a composition intended to be administered by injection, one or more of a surfactant, preservative, wetting agent, dispersing agent, suspending agent, buffer, stabilizer and isotonic agent may be included.

The liquid pharmaceutical compositions of the invention, whether they be solutions, suspensions or other like form, may include one or more of the following adjuvants: sterile diluents such as water for injection, saline solution, preferably physiological saline, Ringer's solution, isotonic sodium chloride, fixed oils such as synthetic mono or diglycerides which may serve as the solvent or suspending medium, polyethylene glycols, glycerin, propylene glycol or other solvents; antibacterial agents such as benzyl alcohol or methyl paraben; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. The parenteral preparation can be enclosed in ampoules, disposable syringes or multiple dose vials made of glass or plastic. Physiological saline is a preferred adjuvant. An injectable pharmaceutical composition is preferably sterile.

A liquid pharmaceutical composition of the invention intended for either parenteral or oral administration should contain an amount of a compound of the invention such that a suitable dosage will be obtained. Typically, this amount is at least 0.01% of a compound of the invention in the composition. When intended for oral administration, this amount may be varied to be between 0.1 and about 70% of the weight of the composition. Preferred oral pharmaceutical compositions contain between about 4% and about 50% of the compound of the invention. Preferred pharmaceutical compositions and preparations according to the present invention are prepared so that a parenteral dosage unit contains between 0.01 to 1% by weight of the compound of the invention.

The pharmaceutical composition of the invention may be intended for topical administration, in which case the carrier may suitably comprise a solution, emulsion, ointment or gel base. The base, for example, may comprise one or more of the following: petrolatum, lanolin, polyethylene glycols, bee wax, mineral oil, diluents such as water and alcohol, and emulsifiers and stabilizers. Thickening agents may be present in a pharmaceutical composition for topical administration. If intended for transdermal administration, the composition may include a transdermal patch or iontophoresis device. Topical formulations may contain a concentration of the compound of the invention from about 0.1 to about 10% w/v (weight per unit volume).

The pharmaceutical composition of the invention may be intended for rectal administration, in the form, e.g., of a suppository, which will melt in the rectum and release the drug. The composition for rectal administration may contain an oleaginous base as a suitable nonirritating excipient. Such bases include, without limitation, lanolin, cocoa butter and polyethylene glycol.

The pharmaceutical composition of the invention may include various materials, which modify the physical form of a solid or liquid dosage unit. For example, the composition may include materials that form a coating shell around the active ingredients. The materials that form the coating shell are typically inert and may be selected from, for example, sugar, shellac, and other enteric coating agents. Alternatively, the active ingredients may be encased in a gelatin capsule.

The pharmaceutical composition of the invention in solid or liquid form may include an agent that binds to the compound of the invention and thereby assists in the delivery of the compound. Suitable agents that may act in this capacity include a monoclonal or polyclonal antibody, a protein or a liposome.

The pharmaceutical composition of the invention may consist of dosage units that can be administered as an aerosol. The term aerosol is used to denote a variety of systems ranging from those of colloidal nature to systems consisting of pressurized packages. Delivery may be by a liquefied or compressed gas or by a suitable pump system that dispenses the active ingredients. Aerosols of compounds of the invention may be delivered in single phase, bi-phasic, or tri-phasic systems in order to deliver the active ingredient(s). Delivery of the aerosol includes the necessary container, activators, valves, subcontainers, and the like, which together may form a kit. One skilled in the art without undue experimentation may determine preferred aerosols.

The pharmaceutical compositions of the invention may be prepared by methodology well known in the pharmaceutical art. For example, a pharmaceutical composition intended to be administered by injection can be prepared by combining a compound of the invention with sterile, distilled water so as to form a solution. A surfactant may be added to facilitate the formation of a homogeneous solution or suspension. Surfactants are compounds that non-covalently interact with the compound of the invention so as to facilitate dissolution or homogeneous suspension of the compound in the aqueous delivery system.

The compounds of the invention, or their pharmaceutically acceptable salts, are administered in a therapeutically effective amount, which will vary depending upon a variety of factors including the activity of the specific compound employed; the metabolic stability and length of action of the compound; the age, body weight, general health, sex, and diet of the patient; the mode and time of administration; the rate of excretion; the drug combination; the severity of the particular disorder or condition; and the subject undergoing therapy. Generally, a therapeutically effective daily dose is from about 0.1 mg to about 20 mg/kg of body weight per day of a compound of the invention, or a pharmaceutically acceptable salt thereof; preferably, from about 0.1 mg to about 10 mg/kg of body weight per day; and most preferably, from about 0.1 mg to about 7.5 mg/kg of body weight per day.

Compounds of the invention, or pharmaceutically acceptable derivatives thereof, may also be administered simultaneously with, prior to, or after administration of one or more of the therapeutic agents described above in the Utility of the Compounds of the Invention. Such combination therapy includes administration of a single pharmaceutical dosage formulation which contains a compound of the invention and one or more additional active agents, as well as administration of the compound of the invention and each active agent in its own separate pharmaceutical dosage formulation. For example, a compound of the invention and an RMG-CoA reductase inhibitor can be administered to the patient together in a single oral dosage composition such as a tablet or capsule, or each agent administered in separate oral dosage formulations. Where separate dosage formulations are used, the compounds of the invention and one or more additional active agents can be administered at essentially the same time, i.e., concurrently, or at separately staggered times, i.e., sequentially; combination therapy is understood to include all these regimens.

Dosage information for RMG-CoA reductase inhibitors is well known in the art, since several RMG-CoA reductase inhibitors are marketed in the U.S. In particular, the daily dosage amounts of the RMG-CoA reductase inhibitor may be the same or similar to those amounts which are employed for anti-hypercholesterolemic treatment and which are described in the Physicians' Desk Reference (PDR). For example, see the 50th Ed. of the PDR', 1996 (Medical Economics Co); in particular, see at page 216 the heading "Hypolipidemics," sub-heading "HMG-CoA Reductase Inhibitors," and the reference pages cited therein. Preferably, the oral dosage amount of RMG-CoA reductase inhibitor is from about 1 to 200 mg/day and, more preferably, from about 5 to 160 mg/day. However, dosage amounts will vary depending on the potency of the specific RMG-CoA reductase inhibitor used as well as other factors as noted above. An RMG-CoA reductase inhibitor which has sufficiently greater potency may be given in sub-milligram daily dosages.

As examples, the daily dosage amount for simvastatin may be selected from 5 mg, 10 mg, 20 mg, 40 mg, 80 mg and 160 mg for lovastatin, 10 mg, 20 mg, 40 mg and 80 mg; for fluvastatin sodium, 20 mg, 40 mg and 80 mg; and for pravastatin sodium, 10 mg, 20 mg, and 40 mg. The daily dosage amount for atorvastatin calcium may be in the range of from 1 mg to 160 mg and, more particularly, from 5 mg to 80 mg. Oral administration may be in a single or divided doses of two, three, or four times daily, although a single daily dose of the RMG-CoA reductase inhibitor is preferred.

Preparation of the Compounds of the Invention

It is understood that in the following description, combinations of substituents and/or variables of the depicted formulae are permissible only if such contributions result in stable compounds.

It will also be appreciated by those skilled in the art that in the processes described below the functional groups of intermediate compounds may need to be protected by suitable protecting groups. Such functional groups include hydroxy, amino, mercapto and carboxylic acid. Suitable protecting groups for hydroxy include trialkylsilyl or diarylalkylsilyl (e.g., t-butyldimethylsilyl, t-butyldiphenylsilyl or trimethylsilyl), tetrahydropyranyl, benzyl, and the like. Suitable protecting groups for 1,2-dihydroxys include ketal- and acetal-forming groups. Suitable protecting groups for amino, amidino and guanidino include t-butoxycarbonyl, benzyloxycarbonyl, and the like. Suitable protecting groups for mercapto include —C(O)—R (where R is alkyl, aryl or aralkyl), p-methoxybenzyl, trityl and the like. Suitable protecting groups for carboxylic acid include alkyl, aryl or aralkyl esters.

Protecting groups may be added or removed in accordance with standard techniques, which are well-known to those skilled in the art and as described herein. The use of protecting groups is described in detail in Green, T. W. and P. G. M. Wutz, Protective Groups in Organic Synthesis (1999), 3rd Ed., Wiley-Interscience. The protecting group may also be a polymer resin such as a Wang resin or a 2-chlorotrityl chloride resin.

It will also be appreciated by those skilled in the art, although such protected derivatives of compounds of the invention, as described above in the First aspect of the invention, may not possess pharmacological activity as such, they may be administered to a mammal having a disease associated with defects in cholesterol transport, glucose metabolism, fatty acid metabolism and cholesterol metabolism, and thereafter metabolized in the body to form compounds of the invention which are pharmacologically active. Such derivatives may therefore be described as "prodrugs". All prodrugs of compounds of the invention are included within the scope of the invention.

It is understood that one of ordinary skill in the art would be able to make the compounds of the invention not specifically prepared herein in light of the following disclosure, including the Preparations and Examples, and information known to those of ordinary skill in the chemical synthesis field.

Starting materials in the synthesis examples provided herein are either available from commercial sources or via literature procedures or by methods disclosed herein. All commercially available compounds were used without further purification unless otherwise indicated. Deuterated solvents such as DMSO-$d_6$ or $CDCl_3$ (99.8% D, Cambridge Isotope Laboratories) were used in all experiments as indicated. $^1$H NMR spectra were recorded on a Bruker Avance 400 MHz NMR spectrometer. Significant peaks are tabulated and typically include: number of protons, multiplicity (s, singlet; d, double; t, triplet; q, quartet; m, multiplet; br s, broad singlet) and coupling constant(s) in Hertz. Chemical shifts are reported as parts per million (δ) relative to tetramethylsilane. Mass spectra were recorded on a Perkin-ELmer SCIEX HPLCAMS instrument using reverse-phase conditions (acetonitrile/water, 0.05% trifluoroacetic acid) and electrospray (ES) ionization. Abbreviations used in the examples below have their accepted meanings in the chemical literature. For example, $CH_2Cl_2$ (dichloromethane), $C_6H_6$ (benzene), TFA (trifluoroacetic acid), EtOAc (Ethyl Acetate), $Et_2O$ (diethyl ether), DMAP (4-dimethylaminopyridine), DMF (N,N-dimethylformamide) and THF (tetrahydrofuran). Flash chromatography was performed using Merck Silica Gel 60 (230-400 mesh).

For purposes of illustration only, most of the formulae in the following Reaction Schemes are directed to specific embodiments of the compounds of invention. However, one of ordinary skiff in the art, in view of the teachings of this specification would reasonably be expected to be able to prepare aft the compounds of the invention in the First aspect of the invention utilizing the appropriately-substituted starting materials and methods known to one skilled in the art.

In the general descriptions immediately following each Reaction Scheme, the phrase "standard isolation procedures" is meant to include one or more of the following techniques familiar to one schooled in the art of organic chemistry: organic extraction, washing of organic solutions with dilute aqueous acid or base, use of drying agents, filtration, concentration in vacuo, followed by purification using distillation, crystallization, or solid-liquid phase chromatography. The phrase "elevated temperature" refers to a temperature above ambient temperature and the phrase "reduced temperature" refers to a temperature below ambient temperature.

The following specific Preparations (for intermediates) and Examples (for compounds, pharmaceutical compositions and methods of use of the invention) are provided as a guide to assist in the practice of the invention, and are not intended as a limitation on the scope of the invention. Without further description, it is believed that one of ordinary skill in the art can, using the preceding description and the following illustrative examples, make and utilize the compounds of the present invention and practice the claimed methods. It should be understood that the foregoing discussion and examples merely present a detailed description of certain preferred embodiments. It will be apparent to one of ordinary skill in the art that various modifications and equivalents can be made without departing from the spirit and scope of the invention.

Unless otherwise indicated, all compounds associated with NMR and/or mass spectra data were prepared and the NMR and mass spectra measured.

Synthesis

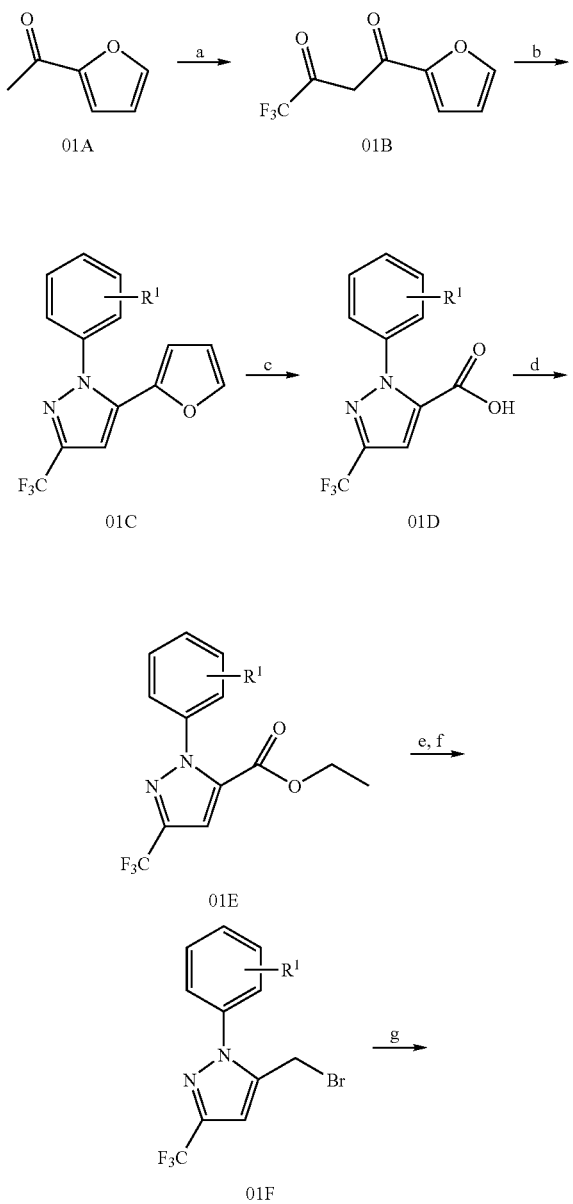

Scheme 1
Preparation of N-Aryl-pyrazole analogs

-continued

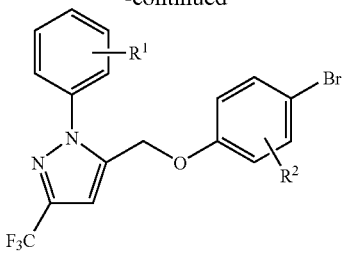

01G a) LiHMDS, THF, Ethyl trifluoroacetate, 0-3° C.;
b) Arylhydrazine hydrochloride, HOAc, 80° C.;
c) NaClO₂, H₃CCN—H₂O, NaH₂PO₄, 25° C.;
d) EDCI, DMAP, EtOH, CH₂Cl₂, 25° C.;
e) DIBAL-H, THF, 0-3° C.;
f) Ph₃PBr₂, CH₂Cl₂, 25° C.;
g) 4-Bromophenol, K₂CO₃, DMF-H₃CCN, 80° C.

As depicted in Scheme 1,5-pyrazolemethyl phenyl ether 01G was prepared from 2-acetylfuran 01A. 01A was converted to diketone 01B under well precedented conditions. Diketone 01B was condensed with an aryl hydrazine in a regioselective reaction to provide N-aryl pyrazole 01C as a single isomer. Oxidation of the furan ring of 01C using sodium chlorite afforded acid 01D in good yields. The acid was then converted to ester 01E, reduced to alcohol, which was converted to bromide 01F using triphenylphosphonium dibromide. The pyrazolemethyl bromide 01F reacted with a variety of phenol to afford ether 01G.

Example 1

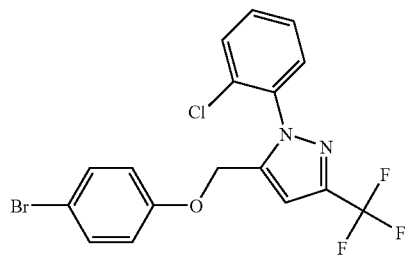

5-(4-Bromophenoxymethyl)-1-(2-chlorophenyl)-3-trifluoromethyl-1H-pyrazole

Example 1a

Preparation of 1-(2-Chlorophenyl)-5-furan-2-yl-3-trifluoromethyl-1H-pyrazole

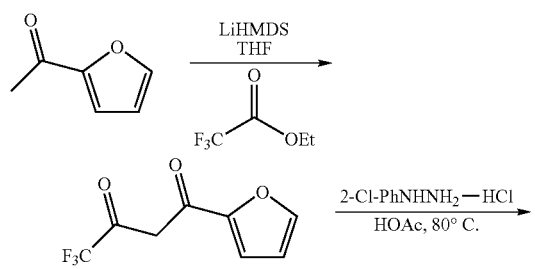

-continued

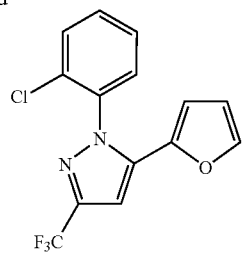

Into a 500 mL flask was weighed 20.0 g (181.6 mmol) of 2-acetylfuran, 50 mL of THF, and 24 mL of ethyl trifluoroacetate. The resulting solution was cooled to 0-3° C. in an ice bath and 1.0 M LiHMDS was added (200 mL). The reaction was allowed to warm to room temperature where it remained overnight. The reaction was then concentrated in vacuo to remove THF and the residue was washed into a separatory funnel with ethyl acetate and 1.0 M HCl. The ethyl acetate was separated, washed with brine, dried (Na₂SO₄), and concentrated in vacuo. The resulting 4,4,4-trifluoro-1-furan-2-yl-butane-1,3-dione was recovered as a brown semisolid, yield: 32.5 g (100+%).

Into a 500 mL flask was weighed 25.0 g (139.6 mmol) of 2-chlorophenylhydrazine hydrochloride, 27.4 g (153 mmol) of 4,4,4-trifluoro-1-furan-2-yl-butane-1,3-dione, and 200 mL of acetic acid. The resulting solution was heated at 80° C. for 18 h then was cooled and was washed into a separatory funnel with 1.0 M NaOH and ethyl acetate. The ethyl acetate was separated, washed with 1.0 M NaOH, brine, dried (Na₂SO₄), and was concentrated in vacuo. The residue was filtered through a short column of silica gel affording 1-(2-chlorophenyl)-5-furan-2-yl-3-trifluoromethyl-1H-pyrazole as a brown oil, yield: 37.31 g (85%); MS (ES): 313 [M+H]⁺.

Example 1B

Preparation of 2-(2-Chlorophenyl)-5-trifluoromethyl-2H-pyrazole-3-carboxylic acid

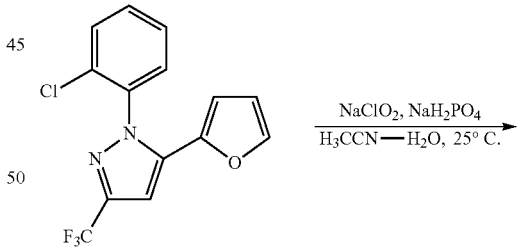

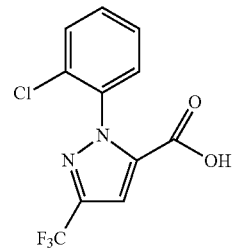

A 2 L flask was charged with 37.31 g of 1-(2-chlorophenyl)-5-furan-2-yl-3-trifluoromethyl-1H-pyrazole (119 mmol), 470 mL of acetonitrile, then a solution of NaH₂PO₄ (71.49 g in 174 mL of water) was added. The resulting solution was cooled to 0-30C in an ice bath and a NaClO₂ solution (80%, 107.84 g in 391 mL of water) was added portionwise. The resulting solution was allowed to warm to room temperature where it remained for 42 h. The reaction was then concentrated in vacuo to remove acetonitrile. The residue was washed into a separatory funnel with 525 mL of 2.0 M NaOH and CH₂Cl₂. The CH₂Cl₂ was separated and was washed twice with 2.0 M NaOH. The NaOH washings were combined, acidified with concentrated HCl, and were extracted with CH₂Cl₂. The CH₂Cl₂ was then concentrated in vacuo and the crude acid was precipitated from CH₂Cl₂ with hexanes. 2-(2-chlorophenyl)-5-trifluoromethyl-2H-pyrazole-3-carboxylic acid was recovered as a tan solid, yield: 20.1 g (58%); ¹H NMR (400 MHz, DMSO-d₆): δ 14.1 (s, 1H), 7.86-7.90 (m, 2H), 7.80 (dt, J=1.5, 7.5 Hz, 1H), 7.76 (s, 1H), 7.73 (dt, J=1.5, 7.5 Hz, 1H); MS (ES): 291 [M+H]⁺.

Example 1c

Preparation of 2-(2-Chlorophenyl)-5-trifluoromethyl-2H-pyrazole-3-carboxylic acid ethyl ester

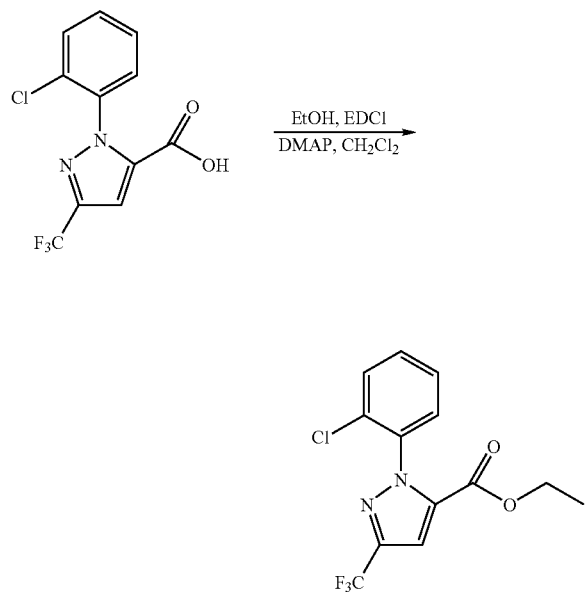

Into a 500 mL flask was weighed 11.5 g (39.6 mmol) of 2-(2-chlorophenyl)-5-trifluoromethyl-2H-pyrazole-3-carboxylic acid, 8.95 g (46.7 mmol) of EDCI, 530 mg (4.34 mmol) of DMAP, and 200 mL of CH₂Cl₂. Ethanol (8.6 mL) was then added to the stirred solution which was maintained at room temperature for 3 h. The reaction was then concentrated in vacuo to remove CH₂Cl₂. The residue was washed into a separatory funnel with ethyl acetate and 1.0 M sodium carbonate. The ethyl acetate was separated, washed with brine, dried (Na₂SO₄), and concentrated in vacuo. The residue was purified by silica gel flash chromatography (Jones Flashmaster, 2×70 g Silica gel, gradient elution from 100% hexanes to 40% ethyl acetate over 30 minutes). Appropriate fractions were combined and concentrated in vacuo affording 2-(2-chlorophenyl)-5-trifluoromethyl-2H-pyrazole-3-carboxylic acid ethyl ester as a viscous yellow oil, yield: 10.0 g (79.3%); ¹H NMR (400 MHz, CDCl₃): δ 7.32-7.46 (m, 4H), 7.19 (d, J=6 Hz, 1H), 4.16 (q, J=7 Hz, 2H), 1.13 (t, J=7 Hz, 3H); MS (ES): 319 [M+H]⁺.

Example 1d

Preparation of [2-(2-Chlorophenyl)-5-trifluoromethyl-2H-pyrazol-3-yl]-methanol

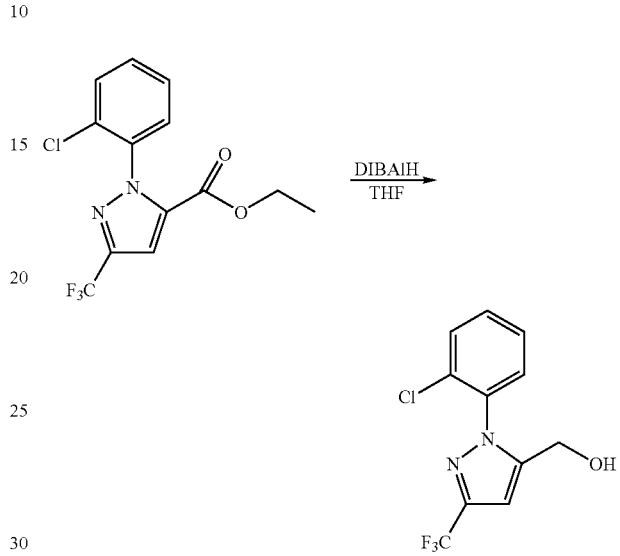

Into a 500 mL flask was weighed 3.84 g (12.6 mmol) of 2-(2-chlorophenyl)-5-trifluoromethyl-2H-pyrazole-3-carboxylic acid methyl ester and 50 mL of anhydrous THF. The solution was cooled to approximately −10° C. in an ice-methanol bath and 1.0 M DIBAL-H in THF was added (50 mL). The reaction was allowed to warm to room temperature over 30 minutes and remained at room temperature for another 1 h. The reaction was concentrated in vacuo to remove THF then was washed into a separatory funnel with ethyl acetate and saturated sodium potassium tartrate. The ethyl acetate was separated, washed with brine, dried (Na₂SO₄), and concentrated in vacuo. The crude [2-(2-chloro-phenyl)-5-trifluoromethyl-2H-pyrazol-3-yl]-methanol was recovered as a colorless oil, yield: 3.54 g; ¹H NMR (400 MHz, CDCl₃): δ 7.33-7.50 (m, 4H), 6.64 (s, 1H), 4.45 (s, 2H); MS (ES): 277 [M+H]⁺.

Example 1e

Preparation of 5-Bromomethyl-1-(2-chlorophenyl)-3-trifluoromethyl-1H-pyrazole

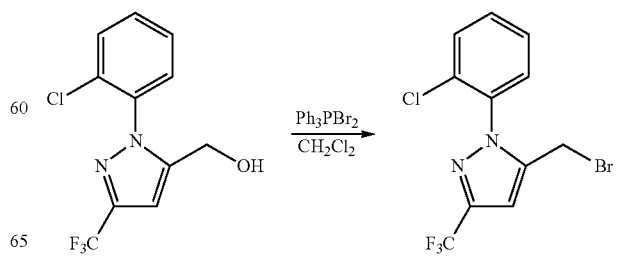

A dry 250 mL flask was charged with triphenylphosphonium dibromide (6.3 g, 14.9 mmol) and a solution of [2-(2-chlorophenyl)-5-trifluoromethyl-2H-pyrazol-3-yl]-methanol (3.54 g in 100 mL of $CH_2Cl_2$) was added portionwise. The reaction was stirred at room temperature for 2 h then was washed into a separatory funnel with water and $CH_2Cl_2$. The $CH_2Cl_2$ was separated, dried ($MgSO_4$), and concentrated in vacuo. The crude bromide was purified by silica gel flash chromatography (Jones Flashmaster, 70 g Silica gel, gradient elution from 100% hexanes to 10% ethyl acetate over 30 minutes). Appropriate fractions were combined and concentrated in vacuo to afford 5-bromomethyl-1-(2-chlorophenyl)-3-trifluoromethyl-1H-pyrazole as a colorless oil, yield: 2.74 g (64% for both steps); $^1$H NMR (400 MHz, $CDCl_3$): δ 7.35-7.55 (m, 4H), 6.70 (s, 1H), 4.21 (br s, 2H).

Example 1f

Preparation of 5-(4-Bromophenoxymethyl)-1-(2-chlorophenyl)-3-trifluoromethyl-1H-pyrazole

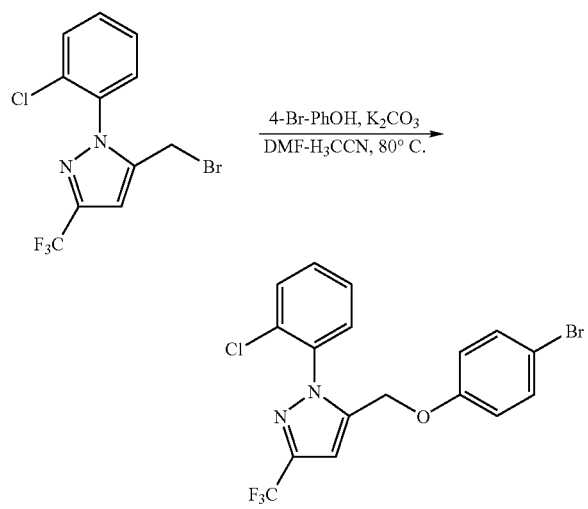

Into a 25 mL flask was weighed 1.52 g (4.48 mmol) of 5-bromomethyl-1-(2-chlorophenyl)-3-trifluoromethyl-1H-pyrazole, 854 mg of 4-bromophenol, 584 mg of sodium carbonate, then 5 mL of DMF, and 5 mL of acetonitrile were added. The resulting suspension was stirred and heated at 80-85°C for 20 h then was washed into a separatory funnel with ethyl acetate and water. The ethyl acetate was separated, washed with brine, dried ($Na_2SO_4$), and concentrated in vacuo. The residue was purified by silica gel flash chromatography (Biotage, 80 g Silica gel, gradient elution from 100% hexanes to 40% ethyl acetate over 30 minutes). Appropriate fractions were combined and concentrated in vacuo to afford the product as a colorless solid, yield: 1.917 g (99%); $^1$H NMR (400 MHz, DMSO-$d_6$): δ 7.82 (m, 2H), 7.70 (dt, J=1.5, 7.5 Hz, 1H), 7.62 (dt, J=1.5, 7.5 Hz, 1H), 7.49 (d, J=9 Hz, 2H), 7.27 (s, 1H), 6.92 (d, J=9 Hz, 2H), 5.12 (s, 2H); MS (ES): 431 [M+H]$^+$.

The following compounds are prepared essentially according to the previous examples:

(E)-3-{4-[2-(2-chlorophenyl)-5-trifluoromethyl-2H-pyrazol-3-ylmethoxy]-phenyl}-acrylic acid ethyl ester; $^1$H-NMR ($CDCl_3$): δ 7.60 (d, J=16 Hz, 1H), 7.55 (dd, J=1.5, 8 Hz, 1H), 7.38-7.50 (m, 5H), 6.80 (d, J=6 Hz, 2H), 6.77 (s, 1H), 6.30 (d, J=16 Hz, 1H), 4.95 (br s, 2H), 4.25 (q, J=7 Hz, 2H), 1.32 (t, J=7 Hz, 3H); MS (ES): 451 [M+H]$^+$;

5-(Biphenyl-3-yloxymethyl)-1-(2-chlorophenyl)-3-trifluoromethyl-1H-pyrazole; $^1$H-NMR ($CDCl_3$): δ 7.59-7.28 (10H, m), 7.20 (1H, m), 6.99 (1H, m), 6.84 (1H, s), 6.78 (1H, m), 4.98 (2H, s). MS (ES): 429 [M+H]$^+$;

5-(Biphenyl-4-yloxymethyl)-1-(2-chlorophenyl)-3-trifluoromethyl-1H-pyrazole; $^1$H-NMR ($CDCl_3$): δ 7.59-7.37 (10H, m), 7.31 (1H, m), 6.89-6.80 (3H, m), 4.96 (2H, s). MS (ES): 429 [M+H]$^+$;

Benzoic acid 3-[2-(2-chlorophenyl)-5-trifluoromethyl-2H-pyrazol-3-ylmethoxy]-phenyl ester; $^1$H-NMR ($CDCl_3$): δ 8.24-8.12 (2H, m), 7.64 (1H, m), 7.59-7.34 (6H, m), 7.29 (1H, t), 6.88-6.78 (2H, m), 6.76-6.62 (2H, m), 4.92 (2H, s). MS (ES): 473 [M+H]$^+$;

5-(4-Benzyloxy-phenoxymethyl)-1-(2-chlorophenyl)-3-trifluoromethyl-1H-pyrazole; $^1$H-NMR ($CDCl_3$): δ 7.58-7.28 (9H, m), 6.89-6.80 (2H, m), 6.78 (1H, s), 6.74-6.65 (2H, m), 5.00 (2H, s), 4.86 (2H, s). MS (ES): 459 [M+H]$^+$;

5-(3-Benzyloxy-phenoxymethyl)-1-(2-chlorophenyl)-3-trifluoromethyl-1H-pyrazole; $^1$H-NMR ($CDCl_3$): δ 7.57-7.30 (9H, m), 7.14 (1H, t), 6.80 (1H, s), 6.61 (1H, m), 6.46-6.35 (2H, m), 5.01 (2H, s), 4.88 (2H, s). MS (ES): 459 [M+H]$^+$;

{4-[2-(2-Chlorophenyl)-5-trifluoromethyl-2H-pyrazol-3-ylmethoxy]-phenyl}-phenyl-methanone; $^1$H-NMR ($CDCl_3$): δ 7.83-7.66 (4H, m), 7.62-7.36 (7H, m), 6.90-6.77 (3H, m), 5.01 (2H, s). MS (ES): 457 [M+H]$^+$;

4-[2-(2-Chlorophenyl)-5-trifluoromethyl-2H-pyrazol-3-ylmethoxy]-benzoic acid benzyl ester; $^1$H-NMR ($CDCl_3$): δ 8.03-7.93 (2H, m), 7.58-7.30 (9H, m), 6.85-6.74 (3H, m), 5.33 (2H, s), 4.97 (2H, s). MS (ES): 487 [M+H]$^+$;

1-(2-chlorophenyl)-5-({[4-(1H-pyrrol-1-yl)phenyl]oxy}methyl)-3-(trifluoromethyl)-1H-pyrazole; $^1$H NMR (DMSO-$d_6$): δ 7.80 (m, 2H), 7.68 (t, 1H, 6 Hz), 7.62 (t, 1H, 7 Hz), 7.49 (d, 2H, 9 Hz) 7.29 (t, 2H, 2 Hz), 7.25 (s, 1H), 6.97 (d, 2H, 9 Hz), 6.26 (s, 2H), 5.11 (s, 2H); MS (ES): 418 [M+H]$^+$;

5-({[1-(2-Chlorophenyl)-3-(trifluoromethyl)-1H-pyrazol-5-yl]methyl}oxy)-1H-indole-2-carboxylic acid; MS (ES): 436 [M+H]$^+$;

7-({[1-(2-Chlorophenyl)-3-(trifluoromethyl)-1H-pyrazol-5-yl]methyl}oxy)-6-(methyloxy)-3,4-dihydroisoquinoline; MS (ES): 436 [M+H]$^+$;

[2-({[1-(2-Chlorophenyl)-3-(trifluoromethyl)-1H-pyrazol-5-yl]methyl}oxy)phenyl](phenyl)methanone; MS (ES): 457 [M+H]$^+$;

4'-({[1-(2-Chlorophenyl)-3-(trifluoromethyl)-1H-pyrazol-5-yl]methyl}oxy)biphenyl-4-carboxylic acid; MS (ES): 473 [M+H]$^+$;

(2R)-2-{[4-({[1-(2-Chlorophenyl)-3-(trifluoromethyl)-1H-pyrazol-5-yl]methyl}oxy)phenyl]oxy}propanoic acid; MS (ES): 441 [M+H]$^+$;

4-{[4-({[1-(2-Chlorophenyl)-3-(trifluoromethyl)-1H-pyrazol-5-yl]methyl}oxy)-3-methylphenyl]sulfonyl}-2-methylphenol; MS (ES): 537 [M+H]$^+$;

[3-({[1-(2-Chlorophenyl)-3-(trifluoromethyl)-1H-pyrazol-5-yl]methyl}oxy)phenyl](phenyl)methanone; MS (ES): 457 [M+H]$^+$;

7-({[1-(2-Chlorophenyl)-3-(trifluoromethyl)-1H-pyrazol-5-yl]methyl}oxy)quinoline; MS (ES): 404 [M+H]$^+$;

5-({[3,4-Bis(methyloxy)phenyl]oxy}methyl)-1-(2-chlorophenyl)-3-(trifluoromethyl)-1H-pyrazole; MS (ES): 413 [M+H]$^+$;

4-{[4-({[1-(2-Chlorophenyl)-3-(trifluoromethyl)-1H-pyrazol-5-yl]methyl}oxy)phenyl]oxy}phenol; MS (ES): 461 [M+H]$^+$;

7-({[1-(2-Chlorophenyl)-3-(trifluoromethyl)-1H-pyrazol-5-yl]methyl}oxy)isoquinoline; MS (ES): 404 [M+H]+;

5-({[1-(2-Chlorophenyl)-3-(trifluoromethyl)-1H-pyrazol-5-yl]methyl}oxy)quinoline; MS (ES): 404 [M+H]+;

7-({[1-(2-Chlorophenyl)-3-(trifluoromethyl)-1H-pyrazol-5-yl]methyl}oxy)-2H-chromen-2-one; MS (ES): 421 [M+H]+;

1-[4-({[1-(2-Chlorophenyl)-3-(trifluoromethyl)-1H-pyrazol-5-yl]methyl}oxy)phenyl]-1H-1,2,4-triazole; MS (ES): 420 [M+H]+;

4-({[1-(2-Chlorophenyl)-3-(trifluoromethyl)-1H-pyrazol-5-yl]methyl}oxy)-6-fluoro-2-methylquinoline; MS (ES): 436 [M+H]+;

4-({[1-(2-Chlorophenyl)-3-(trifluoromethyl)-1H-pyrazol-5-yl]methyl}oxy)-8-fluoroquinoline; MS (ES): 422 [M+H]+;

5-[2-({[1-(2-Chlorophenyl)-3-(trifluoromethyl)-1H-pyrazol-5-yl]methyl}oxy)phenyl]isoxazole; MS (ES): 420 [M+H]+;

(2E)-3-[3-({[1-(2-Chlorophenyl)-3-(trifluoromethyl)-1H-pyrazol-5-yl]methyl}oxy)phenyl]prop-2-enoic acid; MS (ES): 423 [M+H]+;

1-(2-Chlorophenyl)-5-({[4-(1H-imidazol-1-yl)phenyl]oxy}methyl)-3-(trifluoromethyl)-1H-pyrazole; MS (ES): 419 [M+H]+;

1-[3-({[1-(2-Chlorophenyl)-3-(trifluoromethyl)-1H-pyrazol-5-yl]methyl}oxy)phenyl]ethanone; MS (ES): 395 [M+H]+;

2-{[4-({[1-(2-Chlorophenyl)-3-(trifluoromethyl)-1H-pyrazol-5-yl]methyl}oxy)phenyl]amino}-1,3-thiazol-4(5H)-one; MS (ES): 467 [M+H]+;

4-({[1-(2-Chlorophenyl)-3-(trifluoromethyl)-1H-pyrazol-5-yl]methyl}oxy)-2-methylquinoline; MS (ES): 418 [M+H]+;

6-({[1-(2-Chlorophenyl)-3-(trifluoromethyl)-1H-pyrazol-5-yl]methyl}oxy)quinoline; MS (ES): 404 [M+H]+;

7-({[1-(2-Chlorophenyl)-3-(trifluoromethyl)-1H-pyrazol-5-yl]methyl}oxy)-4-[(methyloxy)methyl]-2H-chromen-2-one; MS (ES): 465 [M+H]+;

7-({[1-(2-Chlorophenyl)-3-(trifluoromethyl)-1H-pyrazol-5-yl]methyl}oxy)-4-methyl-2H-chromen-2-one; MS (ES): 435 [M+H]+;

2-({[1-(2-Chlorophenyl)-3-(trifluoromethyl)-1H-pyrazol-5-yl]methyl}oxy)-9H-fluoren-9-one; MS (ES): 455 [M+H]+;

Ethyl 4-({[1-(2-chlorophenyl)-3-(trifluoromethyl)-1H-pyrazol-5-yl]methyl}oxy)benzoate; MS (ES): 425 [M+H]+;

5-({[1-(2-Chlorophenyl)-3-(trifluoromethyl)-1H-pyrazol-5-yl]methyl}oxy)-2-methyl-1,3-benzothiazole; MS (ES): 424 [M+H]+;

Ethyl 5-({[1-(2-chlorophenyl)-3-(trifluoromethyl)-1H-pyrazol-5-yl]methyl}oxy)-2-methyl-1H-indole-3-carboxylate; MS (ES): 478 [M+H]+;

Ethyl 5-({[1-(2-chlorophenyl)-3-(trifluoromethyl)-1H-pyrazol-5-yl]methyl}oxy)-1H-indole-2-carboxylate; MS (ES): 464 [M+H]+;

8-({[1-(2-Chlorophenyl)-3-(trifluoromethyl)-1H-pyrazol-5-yl]methyl}oxy)-2-methylquinoline; MS (ES): 418 [M+H]+;

4-{[4-({[1-(2-Chlorophenyl)-3-(trifluoromethyl)-1H-pyrazol-5-yl]methyl}oxy)phenyl]thio}phenol; MS (ES): 477 [M+H]+;

2-({[1-(2-Chlorophenyl)-3-(trifluoromethyl)-1H-pyrazol-5-yl]methyl}oxy)-1,3-benzothiazole; MS (ES): 410 [M+H]+;

5-({[1-(2-Chlorophenyl)-3-(trifluoromethyl)-1H-pyrazol-5-yl]methyl}oxy)isoquinoline; MS (ES): 404 [M+H]+;

1-(2-Chlorophenyl)-5-({[4-(methylsulfonyl)phenyl]oxy}methyl)-3-(trifluoromethyl)-1H-pyrazole; MS (ES): 431 [M+H]+.

Scheme 2

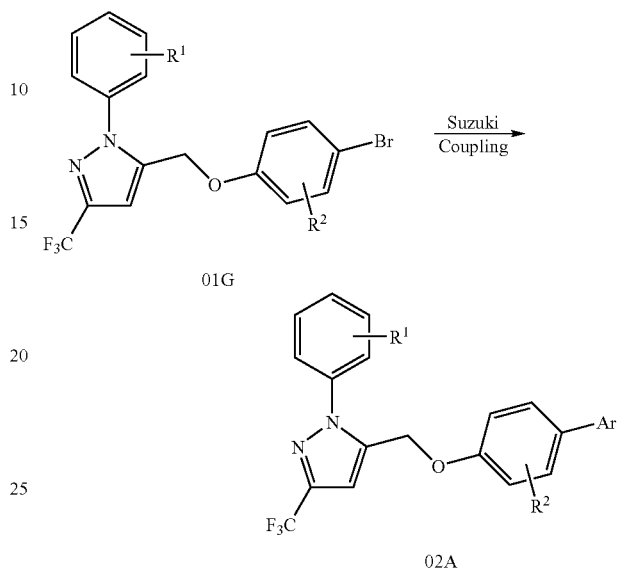

As depicted in Scheme 2, phenylbromide 01G was submitted to Suzuki coupling to afford arylphenyl ether 02A.

Example 2

1-(2-Chlorophenyl)-5-(3'-methanesulfonylbiphenyl-4-yloxymethyl)-3-trifluoromethyl-1H-pyrazole

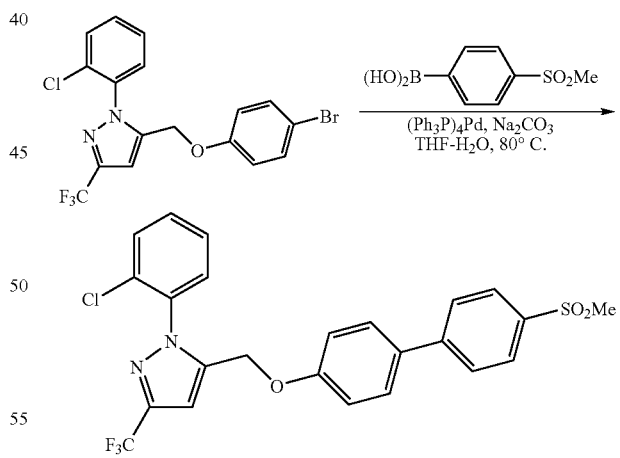

Into a 25 mL flask was weighed 151.2 mg (350 μmol) of 5-(4-bromophenoxymethyl)-1-(2-chlorophenyl)-3-trifluoromethyl-1H-pyrazole (Example 1f, 204 mg, 1.02 μmol) of 3-methylsulfonylboronic acid, and 5 mL of THF was then added. The resulting solution was stirred and heated at 80-85° C. and 50 mg of tetrakistriphenylphosphine palladium (0) was added followed by 500 μL of 1.0 M Na₂CO₃. The resulting solution was maintained at 80-85° C. for 3 h then was washed into a separatory funnel with ethyl acetate and 1.0 M Na₂CO₃. The ethyl acetate was separated, washed with brine, dried (Na₂SO₄), and concentrated in vacuo. The residue was purified by silica gel flash chromatography (Jones Flashmaster, 50 g Silica gel, gradient elution from 100% hexanes to 40% ethyl acetate over 30 minutes). Appropriate fractions were combined and concentrated in vacuo to afford the product as a colorless semisolid, yield: 26 mg (15%); ¹H NMR (400 MHz, CDCl₃): δ 8.08 (1H, m), 7.87 (1H, m), 7.79 (1H, m), 7.64-7.41 (7H, m), 6.93-6.85 (2H, m), 6.83 (1H, s), 4.98 (2H, s), 3.09 (3H, s). MS (ES): 507 [M+H]⁺.

The following compounds are prepared essentially according to the previous examples:

1-(2-Chlorophenyl)-5-(4'-methanesulfonyl-biphenyl-4-yloxymethyl)-3-trifluoromethyl-1H-pyrazole; ¹H-NMR (CDCl₃): δ 8.01-7.93 (2H, m), 7.74-7.66 (2H, m), 7.60-7.38 (6H, m), 6.93-6.86 (2H, m), 6.83 (1H, s), 4.98 (2H, s), 3.08 (3H, s). MS (ES): 507 [M+H]⁺;

2-{4'-[2-(2-Chlorophenyl)-5-trifluoromethyl-2H-pyrazol-3-ylmethoxy]-biphenyl-3-yl}-2-methyl-propionic acid. ¹H NMR (400 MHz, CDCl₃): δ 7.36-7.55 (m, 10H), 6.83-6.86 (m, 3H), 4.96 (br s, 2H), 1.64 (s, 6H); MS (ES): 515 [M+H]⁺.

{4'-[2-(2-Chlorophenyl)-5-trifluoromethyl-2H-pyrazol-3-ylmethoxy]-biphenyl-3-yl}-acetic acid; ¹H NMR (400 MHz, CDCl₃): δ 9.45 (br s, 1H), 7.55 (dd, J=1.5, 8 Hz, 1H), 7.51 (dd, J=1.5, 8 Hz, 1H), 7.35-7.49 (m, 7H), 7.23 (d, J=7.5 Hz, 1H), 6.85 (s, 1H), 6.83 (d, J=3 Hz, 2H), 4.96 (br s, 2H), 3.70 (s, 2H); MS (ES): 487 [M+H]⁺;

{4'-[2-(2-Chlorophenyl)-5-trifluoromethyl-2H-pyrazol-3-ylmethoxy]-biphenyl-4-yl}-acetic acid; ¹H NMR (400 MHz, CDCl₃) δ: 9.0 (br s, 1H), 7.56 (dd, J=1.5, 8 Hz, 1H), 7.37-7.54 (m, 7H), 7.33 (d, J=8 Hz, 2H), 6.86 (s, 1H), 6.83 (d, J=3 Hz, 2H), 4.96 (br s, 2H), 3.69 (s, 2H); MS (ES): 487 [M+H]⁺.

3-{4-[2-(2-Chlorophenyl)-5-trifluoromethyl-2H-pyrazol-3-ylmethoxy]-phenyl}-acrylic acid; ¹H NMR (400 MHz, DMSO-d₆): δ 7.75 (dd, J=1.5, 8 Hz, 1H), 7.69 (dd, J=1.5, 8 Hz, 1H), 7.61 (dt, J=1.5, 8 Hz, 1H), 7.53 (dt, J=1.5, 8 Hz, 1H), 7.35 (d, J=8.5 Hz, 2H), 7.18 (s, 1H), 7.04 (d, J=16 Hz, 1H), 6.80 (d, J=8.5 Hz, 2H), 6.24 (d, J=16 Hz, 1H); 4.98 (s, 2H); MS (ES): 423 [M+H]⁺.

1-(2-chlorophenyl)-5-(3-fluoro-3'-meyhanesulfonylbiphenyl-4-yloxymethyl)-3-trifluoromethyl-1H-pyrazole. MS (ESI): 525 [M+H]⁺.

1-(2-chlorophenyl)-5-(2-chloro-3'-meyhanesulfonylbiphenyl-4-yloxymethyl)-3-trifluoromethyl-1H-pyrazole. MS (ESI): 541 [M+H]⁺.

1-(2-chlorophenyl)-5-(2-methyl-3'-meyhanesulfonylbiphenyl-4-yloxymethyl)-3-trifluoromethyl-1H-pyrazole. MS (ESI): 521 [M+H]⁺.

1-(2-chlorophenyl)-5-(2-fluoro-3'-meyhanesulfonylbiphenyl-4-yloxymethyl)-3-trifluoromethyl-1H-pyrazole. MS (ESI): 525 [M+H]⁺.

1-(2-chlorophenyl)-5-(2-cyano-3'-meyhanesulfonylbiphenyl-4-yloxymethyl)-3-trifluoromethyl-1H-pyrazole. MS (ESI): 532 [M+H]⁺.

1-(2-chlorophenyl)-5-(3-methyl-3'-meyhanesulfonylbiphenyl-4-yloxymethyl)-3-trifluoromethyl-1H-pyrazole. MS (ESI): 521 [M+H]⁺.

1-(2-chlorophenyl)-5-(3,5-dimethyl-3'-meyhanesulfonylbiphenyl-4-yloxymethyl)-3-trifluoromethyl-1H-pyrazole. MS (ESI): 535 [M+H]⁺.

1-(2-Chlorophenyl)-5-({[5'-fluoro-2'-(methyloxy)biphenyl-4-yl]oxy}methyl)-3-(trifluoromethyl)-1H-pyrazole; MS (ES): 477 [M+H]⁺;

[4'-({[1-(2-Chlorophenyl)-3-(trifluoromethyl)-1H-pyrazol-5-yl]methyl}oxy)biphenyl-3-yl]methanol; MS (ES): 459 [M+H]⁺;

4'-({[1-(2-Chlorophenyl)-3-(trifluoromethyl)-1H-pyrazol-5-yl]methyl}oxy)-N,N-dimethylbiphenyl-4-amine; MS (ES): 472 [M+H]⁺;

1-(2-Chlorophenyl)-5-({[3'-(methyloxy)biphenyl-4-yl]oxy}methyl)-3-(trifluoromethyl)-1H-pyrazole; MS (ES): 459 [M+H]⁺;

1-(2-Chlorophenyl)-5-({[2'-(methyloxy)biphenyl-4-yl]oxy}methyl)-3-(trifluoromethyl)-1H-pyrazole; MS (ES): 459 [M+H]⁺;

5-({[3',4'-Bis(methyloxy)biphenyl-4-yl]oxy}methyl)-1-(2-chlorophenyl)-3-(trifluoromethyl)-1H-pyrazole; MS (ES): 489 [M+H]⁺;

4'-({[1-(2-Chlorophenyl)-3-(trifluoromethyl)-1H-pyrazol-5-yl]methyl}oxy)-N,N-dimethylbiphenyl-3-sulfonamide; MS (ES): 536 [M+H]⁺;

5-[4-({[1-(2-Chlorophenyl)-3-(trifluoromethyl)-1H-pyrazol-5-yl]methyl}oxy)phenyl]pyrimidine; MS (ES): 431 [M+H]⁺;

1-(2-Chlorophenyl)-5-({[2'-fluoro-5'-(trifluoromethyl)biphenyl-4-yl]oxy}methyl)-3-(trifluoromethyl)-1H-pyrazole; MS (ES): 515 [M+H]⁺;

[4'-({[1-(2-Chlorophenyl)-3-(trifluoromethyl)-1H-pyrazol-5-yl]methyl}oxy)biphenyl-4-yl]methanol; MS (ES): 459 [M+H]⁺;

4'-({[1-(2-Chlorophenyl)-3-(trifluoromethyl)-1H-pyrazol-5-yl]methyl}oxy)biphenyl-4-carbonitrile; MS (ES): 454 [M+H]⁺;

5-({[2',5'-Bis(methyloxy)biphenyl-4-yl]oxy}methyl)-1-(2-chlorophenyl)-3-(trifluoromethyl)-1H-pyrazole; MS (ES): 489 [M+H]⁺;

5-({[2',4'-Bis(methyloxy)biphenyl-4-yl]oxy}methyl)-1-(2-chlorophenyl)-3-(trifluoromethyl)-1H-pyrazole; MS (ES): 489 [M+H]⁺;

5-({[4-(1,3-Benzodioxol-5-yl)phenyl]oxy}methyl)-1-(2-chlorophenyl)-3-(trifluoromethyl)-1H-pyrazole; MS (ES): 473 [M+H]⁺;

1-(2-Chlorophenyl)-5-({[2'-fluoro-6'-(methyloxy)biphenyl-4-yl]oxy}methyl)-3-(trifluoromethyl)-1H-pyrazole; MS (ES): 477 [M+H]⁺;

1-(2-Chlorophenyl)-5-({[4-(2,3-dihydro-1,4-benzodioxin-6-yl)phenyl]oxy}methyl)-3-(trifluoromethyl)-1H-pyrazole; MS (ES): 487 [M+H]⁺;

4'-({[1-(2-Chlorophenyl)-3-(trifluoromethyl)-1H-pyrazol-5-yl]methyl}oxy)biphenyl-3-carbonitrile; MS (ES): 454 [M+H]⁺;

2-Chloro-5-[4-({[1-(2-chlorophenyl)-3-(trifluoromethyl)-1H-pyrazol-5-yl]methyl}oxy)phenyl]pyridine; MS (ES): 464 [M+H]⁺;

5-[4-({[1-(2-Chlorophenyl)-3-(trifluoromethyl)-1H-pyrazol-5-yl]methyl}oxy)phenyl]-1H-indole; MS (ES): 468 [M+H]⁺;

1-[4'-({[1-(2-Chlorophenyl)-3-(trifluoromethyl)-1H-pyrazol-5-yl]methyl}oxy)biphenyl-4-yl]ethanone; MS (ES): 471 [M+H]⁺;

1-(2-Chlorophenyl)-5-({[4'-(methyloxy)biphenyl-4-yl]oxy}methyl)-3-(trifluoromethyl)-1H-pyrazole; MS (ES): 459 [M+H]⁺;

1-[4'-({[1-(2-Chlorophenyl)-3-(trifluoromethyl)-1H-pyrazol-5-yl]methyl}oxy)biphenyl-2-yl]ethanone; MS (ES): 471 [M+H]⁺;

5-[4-({[1-(2-Chlorophenyl)-3-(trifluoromethyl)-1H-pyrazol-5-yl]methyl}oxy)phenyl]-2-(methyloxy)pyridine; MS (ES): 460 [M+H]⁺;

1-(2-Chlorophenyl)-5-({[5'-methyl-2'-(methyloxy)biphenyl-4-yl]oxy}methyl)-3-(trifluoromethyl)-1H-pyrazole; MS (ES): 473 [M+H]+;

4'-({[1-(2-Chlorophenyl)-3-(trifluoromethyl)-1H-pyrazol-5-yl]methyl}oxy)biphenyl-4-amine; MS (ES): 444 [M+H]+;

1-[4'-({[1-(2-Chlorophenyl)-3-(trifluoromethyl)-1H-pyrazol-5-yl]methyl}oxy)biphenyl-3-yl]ethanone; MS (ES): 471 [M+H]+;

Methyl 4'-({[1-(2-chlorophenyl)-3-(trifluoromethyl)-1H-pyrazol-5-yl]methyl}oxy)biphenyl-3-carboxylate; MS (ES): 487 [M+H]+;

1-(2-Chlorophenyl)-5-{[(2',5'-difluorobiphenyl-4-yl)oxy]methyl}-3-(trifluoromethyl)-1H-pyrazole; MS (ES): 465 [M+H]+;

N-[4'-({[1-(2-Chlorophenyl)-3-(trifluoromethyl)-1H-pyrazol-5-yl]methyl}oxy)biphenyl-4-yl]acetamide; MS (ES): 486 [M+H]+;

5-({[2',3'-Bis(methyloxy)biphenyl-4-yl]oxy}methyl)-1-(2-chlorophenyl)-3-(trifluoromethyl)-1H-pyrazole; MS (ES): 489 [M+H]+;

1-(2-Chlorophenyl)-5-{[(3'-nitrobiphenyl-4-yl)oxy]methyl}-3-(trifluoromethyl)-1H-pyrazole; MS (ES): 474 [M+H]+;

3-Chloro-4'-({[1-(2-chlorophenyl)-3-(trifluoromethyl)-1H-pyrazol-5-yl]methyl}oxy)-N-cyclopropylbiphenyl-4-carboxamide; MS (ES): 546 [M+H]+;

Methyl N-{[4'-({[1-(2-chlorophenyl)-3-(trifluoromethyl)-1H-pyrazol-5-yl]methyl}oxy)biphenyl-4-yl]carbonyl}glycinate; MS (ES): 544 [M+H]+;

4'-({[1-(2-Chlorophenyl)-3-(trifluoromethyl)-1H-pyrazol-5-yl]methyl}oxy)-N,N-diethylbiphenyl-3-carboxamide; MS (ES): 528 [M+H]+;

4-{[4'-({[1-(2-Chlorophenyl)-3-(trifluoromethyl)-1H-pyrazol-5-yl]methyl}oxy)biphenyl-3-yl]carbonyl}thiomorpholine; MS (ES): 558 [M+H]+;

4'-({[1-(2-Chlorophenyl)-3-(trifluoromethyl)-1H-pyrazol-5-yl]methyl}oxy)-N-ethylbiphenyl-3-carboxamide; MS (ES): 500 [M+H]+;

4'-({[1-(2-Chlorophenyl)-3-(trifluoromethyl)-1H-pyrazol-5-yl]methyl}oxy)-5-fluorobiphenyl-3-carboxylic acid; MS (ES): 491 [M+H]+;

3-Chloro-4'-({[1-(2-chlorophenyl)-3-(trifluoromethyl)-1H-pyrazol-5-yl]methyl}oxy)-N-(phenylmethyl)biphenyl-4-carboxamide; MS (ES): 596 [M+H]+;

4'-({[1-(2-Chlorophenyl)-3-(trifluoromethyl)-1H-pyrazol-5-yl]methyl}oxy)-N,N-diethylbiphenyl-4-carboxamide; MS (ES): 528 [M+H]+;

4'-({[1-(2-Chlorophenyl)-3-(trifluoromethyl)-1H-pyrazol-5-yl]methyl}oxy)-N-methylbiphenyl-4-carboxamide; MS (ES): 486 [M+H]+;

1-(2-Chlorophenyl)-5-({[4'-fluoro-2'-(methyloxy)biphenyl-4-yl]oxy}methyl)-3-(trifluoromethyl)-1H-pyrazole; MS (ES): 477 [M+H]+;

1-(2-Chlorophenyl)-5-({[2'-fluoro-3'-(methyloxy)biphenyl-4-yl]oxy}methyl)-3-(trifluoromethyl)-1H-pyrazole; MS (ES): 477 [M+H]+;

1-(2-Chlorophenyl)-5-({[3'-(pyrrolidin-1-ylcarbonyl)biphenyl-4-yl]oxy}methyl)-3-(trifluoromethyl)-1H-pyrazole; MS (ES): 526 [M+H]+;

Methyl [4'-({[1-(2-chlorophenyl)-3-(trifluoromethyl)-1H-pyrazol-5-yl]methyl}oxy)biphenyl-4-yl]carbamate; MS (ES): 502 [M+H]+;

1-(2-Chlorophenyl)-5-({[4'-(ethylsulfonyl)biphenyl-4-yl]oxy}methyl)-3-(trifluoromethyl)-1H-pyrazole; MS (ES): 521 [M+H]+;

4-{[3-Chloro-4'-({[1-(2-chlorophenyl)-3-(trifluoromethyl)-1H-pyrazol-5-yl]methyl}oxy)biphenyl-4-yl]carbonyl}morpholine; MS (ES): 576 [M+H]+;

1-{[3-Chloro-4'-({[1-(2-chlorophenyl)-3-(trifluoromethyl)-1H-pyrazol-5-yl]methyl}oxy)biphenyl-4-yl]carbonyl}piperidine; MS (ES): 574 [M+H]+;

1-(2-Chlorophenyl)-5-[({2'-[(1-methylethyl)oxy]-5'-(trifluoromethyl)biphenyl-4-yl}oxy)methyl]-3-(trifluoromethyl)-1H-pyrazole; MS (ES): 555 [M+H]+.

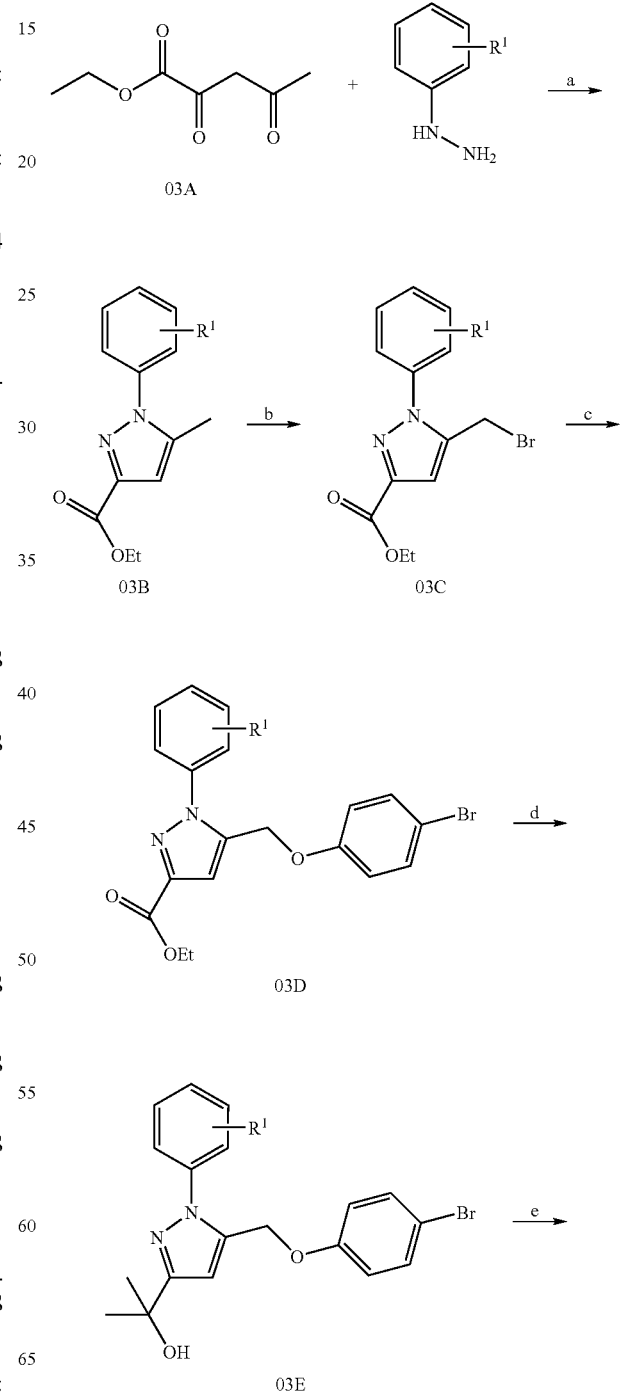

Scheme 3
Preparation of N-Aryl-pyrazole analogs

-continued

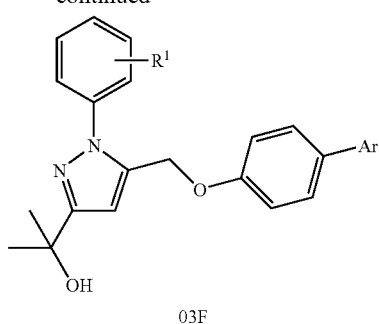

03F a) AcOH, Ethanol 80° C.;
b) NBS, Benzoyl Peroxide CCl₄;
c) 4-Bromohenol, K₂CO₃, H₃CCN;
d) MeMgBr, THF 0° C.;
e) Pd (dppf), K₂CO₃, DME:H₂O As depicted in Scheme 3, 3-carbinol moiety was introduced onto the pyrazole ring. 03A was condensed with an aryl hydrazine to provide the N-aryl pyrazole 03B as a mixture of isomers which were separable by crystallization. Bromination of 03B with NBS provided pyrazole-5-ylmethyl bromide 03C, which reacted with a phenol in the presence of a base to afford bromophenoxy ether 03D. The ester group of 03D was converted to the carbinol group to afford 03E with methyl magnesiumbromide. 03E was submitted to Suzuki coupling to afford arylphenyl ether 03F.

Example 3

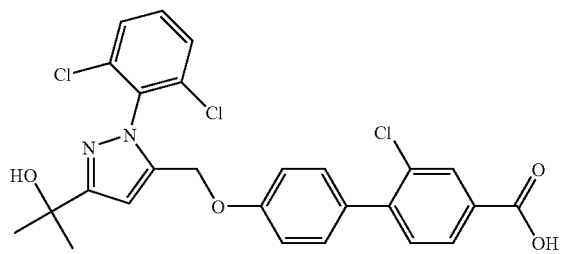

2-Chloro-4'-[2-(2,6-dichloro-phenyl)-5-(1-hydroxy-1-methyl-ethyl)-2H-pyrazol-3-ylmethoxy]-biphenyl-4-carboxylic acid Example 3a Preparation of 1-(2,6-Dichlorophenyl)-5-methyl-1H-pyrazole-3-carboxylic acid ethyl ester

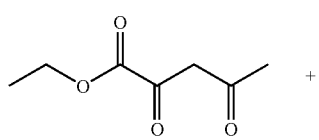 +

-continued

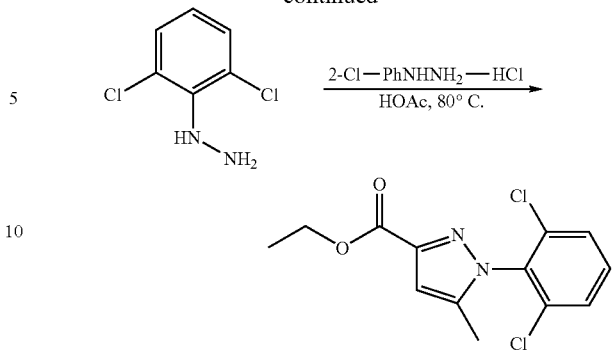

Into a 2000 mL flask was weighed 35.33 g (223.5 mmol) of 2,4-dioxopentanoic acid ethyl ester, 50 g (234.7 mmol) of 2,6-dichlorophenyl hydrazine, 400 mL of acetic acid and 400 mL of ethanol. The resulting solution was heated at 80° C. for 18 h and was then cooled and was washed into a separatory funnel with 1.0 M aq. NaOH and ethyl acetate. The organic layer was separated, washed with sat. aq. NaHCO₃, brine, dried over Na₂SO₄, and was concentrated in vacuo. The residue was recrystallized from EtOH-heptanes to afford 1-(2,6-dichlorophenyl)-5-methyl-1H-pyrazole-3-carboxylic acid ethyl ester (44.6 g, 60%); $^1$H NMR (400 MHz, DMSO-d₆): δ 7.67 (d J=7.67 Hz, 2H), 7.57 (m, 1H), 4.17 (q, J=7.07 Hz 2H), 1.97 (s, 3H); 1.18 (t, J=7.07 Hz 3H), MS (ES): 321 [M+Na]⁺.

Example 3b

Preparation of 5-Bromomethyl-1-(2,6-dichlorophenyl)-1H-pyrazole-3-carboxylic acid ethyl ester

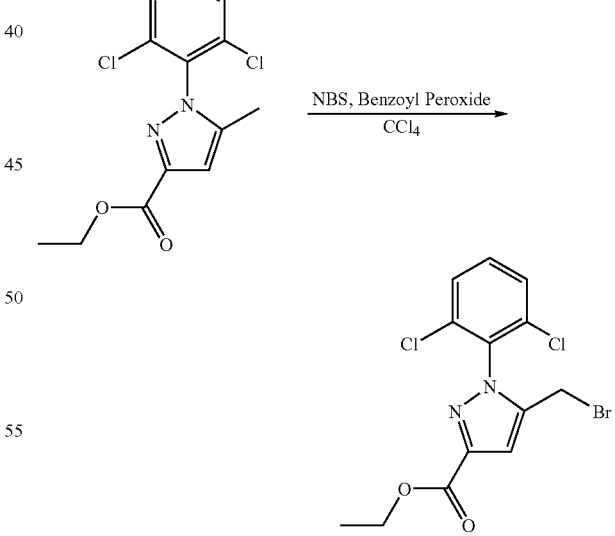

A 2 L flask was charged with 44.6 g of 1-(2,6-dichlorophenyl)-5-methyl-1H-pyrazole-3-carboxylic acid ethyl ester (133 mmol), 28.43 g of N-bromosuccinimide, 0.80 g of benzoyl peroxide and 1 L of carbon tetrachloride. The resulting solution was placed under a high intensity lamp for 2 hours. The resulting solution was allowed to cool to room temperature, filtered through a pad of celite. The filtrate was then concentrated in vacuo and the crude bromide was passed through a plug of silica using 40% EtOAc:hexane and recrystallized from heptane-ethanol to afford 5-bromomethyl-1-(2,6-dichlorophenyl)-1H-pyrazole-3-carboxylic acid ethyl ester was recovered as a tan solid (19.3 g, 38%); $^1$H NMR (400 MHz, CDCl$_3$): δ 7.45 (m, 4H), 7.05 (s, 1H), 6.77 (s 0.2H starting material), 4.43 (q, J=7.07 Hz 2H), 4.27 (s, 2.16H), 2.14 (s, 0.6H starting material); 1.41 (t, J=7.07 Hz 3H), MS (ES): 399 [M+Na]$^+$.

Example 3c

Preparation of 5-(4-Bromophenoxymethyl)-1-(2,6-dichlorophenyl)-1H-pyrazole-3-carboxylic acid ethyl ester

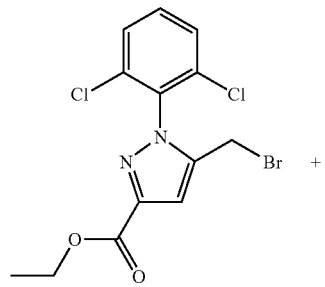

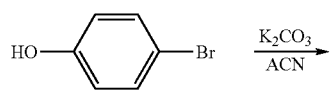

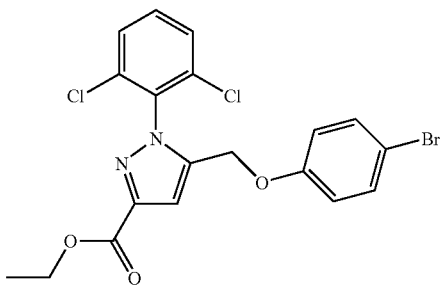

Into a 500 mL flask was weighed 19.3 g (53 mmol) of 5-bromomethyl-1-(2,6-dichloro-phenyl)-1H-pyrazole-3-carboxylic acid ethyl ester, 13.7 g (79 mmol) of 4-bromophenol, 10.9 mg (79 mmol) of potassium carbonate, and 100 mL of ACN. The reaction mixture was heated to reflux for 4 h. After cooling, the crude reaction mixture was washed into a separatory funnel with ethyl acetate and water. The organic layer was separated, washed with brine, dried (Na$_2$SO$_4$), and concentrated in vacuo. The residue was purified by column chromatography on silica eluting with DCM-methanol (100:0 to 98:2) to afford 5-(4-bromophenoxymethyl)-1-(2,6-dichlorophenyl)-1H-pyrazole-3-carboxylic acid ethyl ester as an off white solid (25.3 g, 100%); $^1$H NMR (400 MHz, CDCl$_3$): δ 7.45 (m, 6H), 7.06 (s, 1H), 6.67 (d J=8.8 Hz 2H), 4.88 (s, 2H), 4.43 (q, J=7.07 Hz 2H), 1.41 (t, J=7.07 Hz 3H), MS (ES): 491 [M+Na]$^+$.

Example 3d

Preparation of 2-[5-(4-Bromo-phenoxymethyl)-1-(2,6-dichlorophenyl)-1H-pyrazol-3-yl]-propan-2-ol

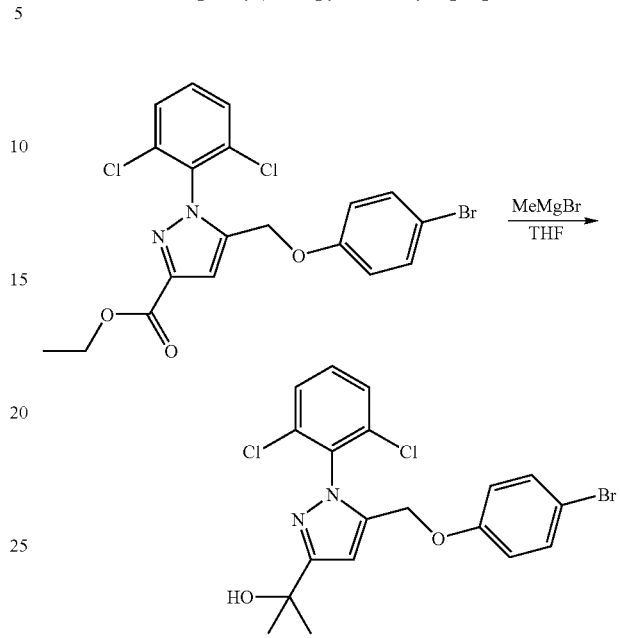

Into a 2000 mL flask was added 135 ml (188 mmol) of methyl magnesium bromide in THF (1.4M). The solution was cooled to 0° C. under argon. 5-(4-bromophenoxymethyl)-1-(2,6-dichlorophenyl)-1H-pyrazole-3-carboxylic acid ethyl ester, 25.3 g (53.8 mmol) was added as a solution in (400 ml of THF) over 10 min. The reaction mixture was allowed to warm to room temperature. After 1 h the crude reaction was concentrated in vacuo, washed into a separatory funnel with ethyl acetate and aq. NH$_4$Cl. The organic layer was separated, washed with brine, dried over Na$_2$SO$_4$, and concentrated in vacuo. The residue was recrystallized from EtOH to afford 2-[5-(4-bromophenoxymethyl)-1-(2,6-dichlorophenyl)-1H-pyrazol-3-yl]-propan-2-ol as an off white solid (5.53 g, 23%); $^1$H NMR (400 MHz, CDCl$_3$): δ 7.44 (m, 1H), 7.42 (s, 1H), 7.33 (m, 1H), 7.31 (d J=9.1 Hz 2H), 6.67 (d J=9.1 Hz 2H), 6.49 (s, 1H), 4.83 (s, 2H), 4.43 (q, J=7.07 Hz 2H), 2.52 (s, 1H), 1.64 (s 6H), MS (ES): 477 [M+Na]$^+$.

Example 3e

Preparation of 2-Chloro-4'-[2-(2,6-dichlorophenyl)-5-(1-hydroxy-1-methyl-ethyl)-2H-pyrazol-3-yl-methoxy]-biphenyl-4-carboxylic acid

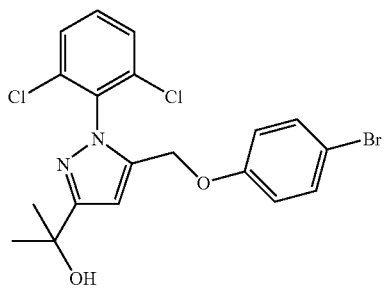

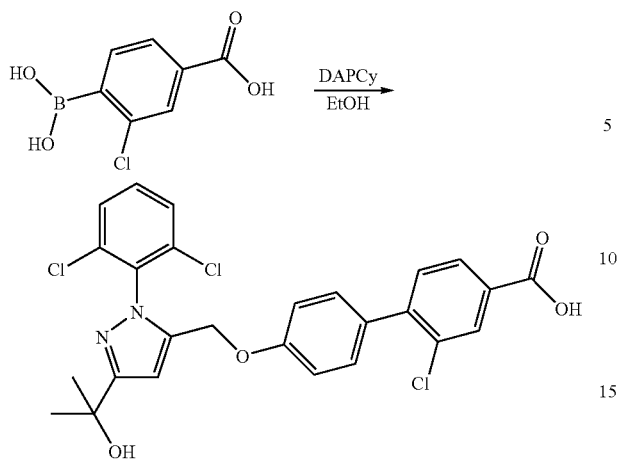

Into a 8 mL flask was added 256 mg (0.56 mmol) of 2-[5-(4-bromo-phenoxymethyl)-1 (2,6-dichloro-phenyl)-1H-pyrazol-3-yl]-propan-2-ol, 134 mg (0.67 mmol) of (4-carboxy-2-chlorophenyl)boronic acid, 200 mg of potassium carbonate (1.68 mmol), 10 mg (0.017 mmol) of dicyclohexyl palladium acetate and 2 mL of ethanol. The reaction mixture was heated to 80° C. for 4 h. After cooling, the crude reaction mixture was filtered through a pad of celite, concentrated in vacuo, and purified on a reverse phase HPLC-MS to afford 2-chloro-4'-[2-(2,6-dichloro-phenyl)-5-isopropyl-2H-pyrazol-3-ylmethoxy]-biphenyl-4-carboxylic acid as an off white solid (34 mg, 11%); $^1$H NMR (400 MHz, CDCl$_3$): δ 8.16 (m, 1H), 7.98 (d, J=8.1 Hz, 1H), 7.45 (d, J=7.83 Hz, 2H) 7.35 (m, 4H), 6.88 (d, J=8.84 Hz, 2H), 6.54 (s, 1H), 4.92 (s, 2H), 1.66 (s 6H), MS (ES): 531 [M+H]$^+$.

Scheme 4

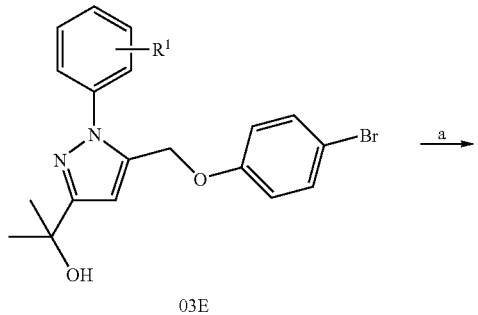

03E

↓ a

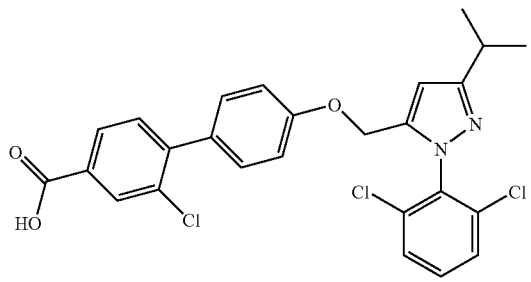

04A

-continued

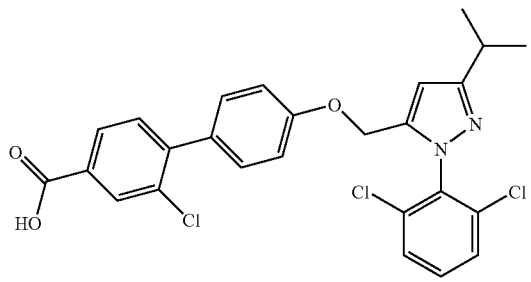

04B a) Triethylsilane, TFA b) Pd (dppf), K$_2$CO$_3$, DME:H$_2$O

As depicted in Scheme 4, isopropyl group can be introduced via dehydroxylation of a carbinol moiety. The hydroxyl group of alcohol 03E was removed with triethylsilane in trifluoroacetic acid to afford isopropyl pyrazole 04A, which was submitted to Suzuki coupling to afford arylphenyl ether 04B Example 4

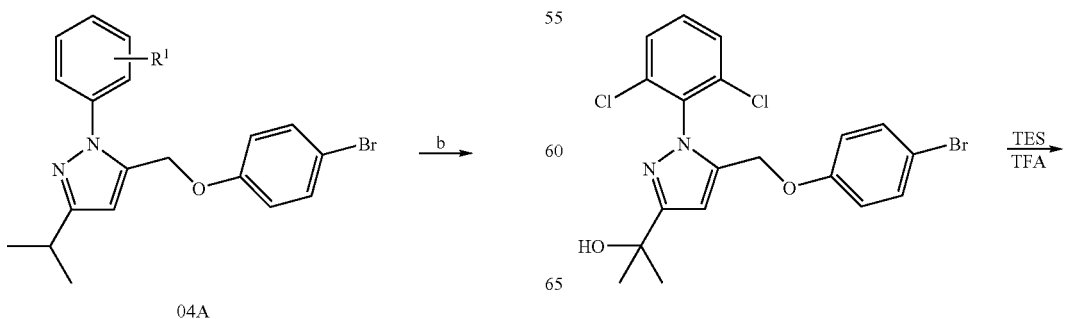

2-Chloro-4'-[2-(2,6-dichlorophenyl)-5-isopropyl-2H-pyrazol-3-ylmethoxy]-biphenyl-4-carboxylic acid Example 4a Preparation of 5-(4-Bromophenoxymethyl)-1-(2,6-dichlorophenyl)-3-isopropyl-1H-pyrazole -continued

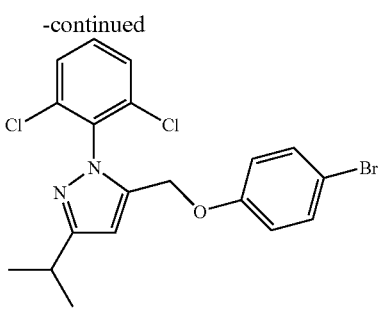

Into a 25 mL flask was added 527 mg (1.16 mmol) of 2-[5-(4-bromophenoxymethyl)-1 (2,6-dichlorophenyl)-1H-pyrazol-3-yl]-propan-2-ol, 278 μL (1.74 mmol) Triethylsilane and 2 mL of Trifluoroacetic acid. After 1 h the crude reaction was concentrated in vacuo, washed into a separatory funnel with ethyl acetate and NaHCO₃. The ethyl acetate was separated, washed with brine, dried (Na₂SO₄), and concentrated in vacuo to afford 5-(4-bromophenoxymethyl)-1-(2,6-dichlorophenyl)-3-isopropyl-1H-pyrazole as an off white solid (450 mg, 99%); $^1$H NMR (400 MHz, CDCl₃): δ 7.42 (m, 1H), 7.41 (s, 1H), 7.33 (m, 1H), 7.31 (d J=9.1 Hz 2H), 6.67 (d J=9.1 Hz 2H), 6.36 (s, 1H), 4.82 (s, 2H), 4.43 (q, J=7.07 Hz 2H), 1.58 (s, 6H), MS (ES): 439 [M+H]⁺.

Example 4b

Preparation of 2-Chloro-4'-[2-(2,6-dichlorophenyl)-5-isopropyl-2H-pyrazol-3-ylmethoxy]-biphenyl-4-carboxylic acid

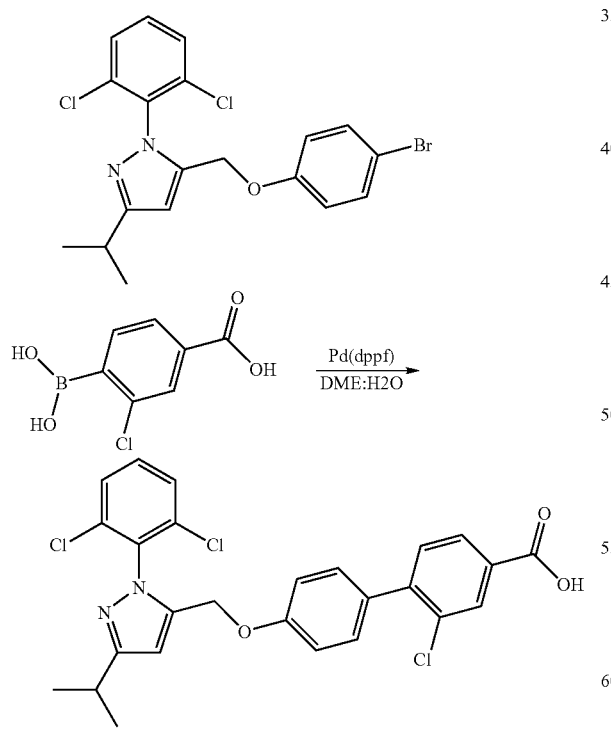

Into a 8 mL flask was added 200 mg (0.454 mmol) of 5-(4-bromophenoxymethyl)-1-(2,6-dichlorophenyl)-3-isopropyl-1H-pyrazole, 108 mg (0.54 mmol) of (4-carboxy-2-chlorophenyl)boronic acid, 186 mg of potassium carbonate (1.36 mmol) and 2 mL of 9:1 DME-water. The solution was sparged under argon and 6.5 mg (0.01 mmol) of palladium dppf was added. The reaction mixture was heated to 80° C. for 4 h. After cooling, the crude reaction was filtered through a pad of celite, concentrated in vacuo, and purified directly on a reverse phase HPLC-MS to afford 2-chloro-4'-[2-(2,6-dichlorophenyl)-5-isopropyl-2H-pyrazol-3-ylmethoxy]-biphenyl-4-carboxylic acid as an off white solid, yield (80.1 mg, 34%); $^1$H NMR (400 MHz, DMSO-d₆): δ 13.37 (s, 1H), 8.04 (m, 1H), 7.96 (dd, J=8.1 (1.77) Hz, 1H), 7.73 (d J=8.1 Hz, 2H) 7.61 (m, 1H), 7.55 (d, J=7.83 Hz, 1H), 7.41 (d, J=8.84 Hz, 2H), 6.98 (d, J=9.09 Hz, 2H), 6.61 (s, 1H), 5.01 (s, 1H), 4.83 (s, 2H), 3.02 (m 1H), 2.52 (s, 1H), 1.31 (d J=6.82 Hz 6H), MS (ES): 515 [M+H]⁺.

Scheme 5
Preparation of N-Aryl-imidazole analogs

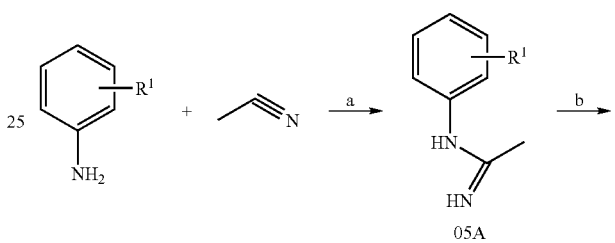

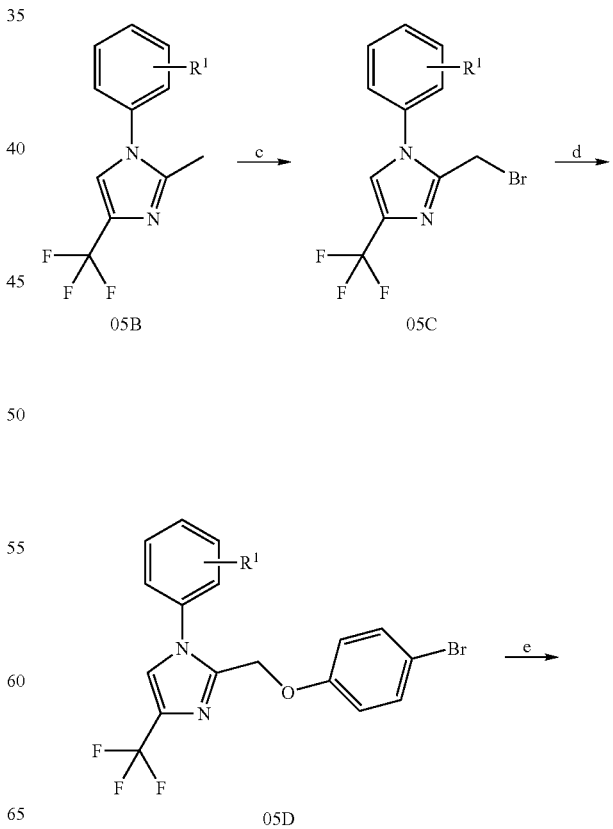

-continued

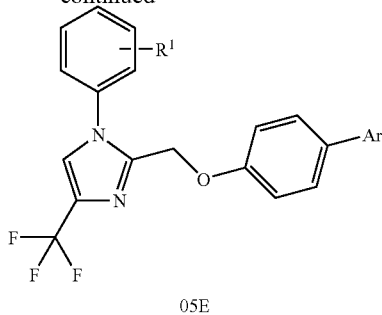

05E a) Me₃Al, Toluene
b) CF₃COCH₂Br/NaHCO₃, Ethanol 80° C., p-TsOH;
c) NBS Benzoyl Peroxide CCl₄;
d) 4-Bromohenol, K₂CO₃, H₃CCN;
e) Pd (dppf), K₂CO₃, DME:H₂O As depicted in Scheme 5,2-phenoxymethyl-1-phenyl-4-trifluoromethyl-1H-imidazole 05E was prepared starting from aniline and acetonitrile. Aniline was condensed with acetonitrile in the presence of trimethylaluminum to afford N-aryl-acetamidine 05A. N-aryl-acetamidine 05A was condensed with 1-bromo-3,3,3-trifluoroacetone in a two step reaction sequence with Na₂CO₃ and then with p-toluenesulfonic acid to afford regioselectively N-aryl imidazole 05B. Bromination of 05B with NBS afforded bromomethylimidazole 05C. Bromophenol reacted with bromomethylimidazole 05C in the presence of a base to afforded imidazole aryl bromide 05D, which was then submitted to Suzuki coupling to afford imidazole arylphenyl ether 05E.

Example 5

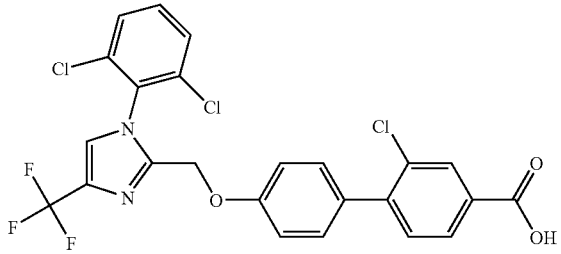

2-Chloro-4'-[1-(2,6-dichlorophenyl)-4-trifluoromethyl-1H-imidazol-2-ylmethoxy]-biphenyl-4-carboxylic acid Example 5a Preparation of N-(2,6-Dichlorophenyl)acetamidine

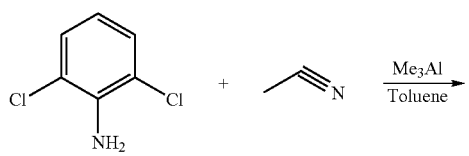

-continued

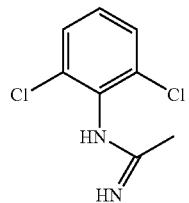

Into a 2000 mL flask was weighed 25 g (154 mmol) of 2,6-dichloroaniline, 200 mL of anhydrous toluene. The resulting solution was cooled to 0° C. under nitrogen. 84 mL (170 mmol) of trimethylaluminum was added dropwise and the reaction was allowed to warm to room temperature. After 1 h 7.6 g (185 mmol) was added and the flask heated to 80° C. for 3 hours. The reaction mixture was cooled and quenched with 100 g of silica gel followed by 500 mL of chloroform-methanol (3:1). After 30 minutes the crude reaction was filtered and concentrated in vacuo to give the crude product, which was recrystallized from ether-heptane to afford N-(2,6-dichlorophenyl)acetamidine as a white solid (15.8 g, 51%); GC/MS: 202 [M⁺].

Example 5b

Preparation of 1-(2,6-Dichlorophenyl)-2-methyl-4-trifluoromethyl-1H-imidazole

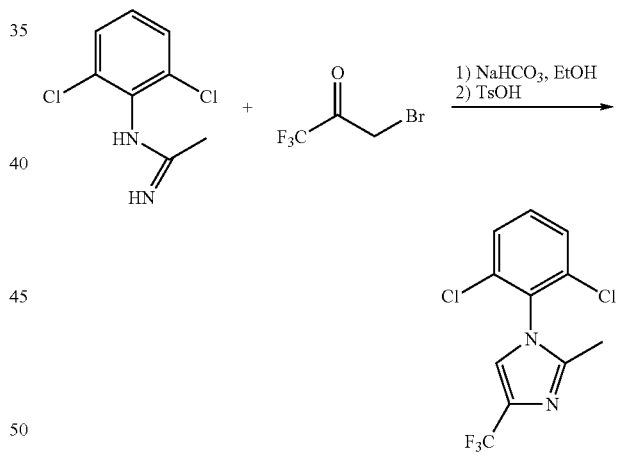

A 500 mL flask was charged with 4.8 g (24 mmol) of N-(2,6-dichlorophenyl)acetamidine, sodium bicarbonate 4.03 g (48 mmol) and 250 mL anhydrous ethanol. 5 g (26.2 mmol) of 3-bromo-1,1,1-trifluoro-propan-2-one was added dropwise. After 1 h solid was filtered off and the filtrate was evaporated in vacuo to give a crude. A mixture of the crude and p-toluenesulfonic acid (668 mg, 3.5 mmol) in toluene was heated to 105° C. for 15 hours. The crude reaction mixture was washed into a separatory funnel with ethyl acetate and water. The organic layer was separated, washed with brine, dried (Na₂SO₄), and concentrated in vacuo to give the crude product, which was then purified by column chromatography on silica eluting with EtOAc-Hexane (10:0 to 3:2) to afford 1-(2,6-dichloro-phenyl)-2-methyl-4-trifluoromethyl-1H- imidazole as a tan solid (0.9, 43%); ¹H NMR (400 MHz, CDCl₃): δ 7.52 (m, 2H), 7.43 (m, 1H), 7.19 (m, 1H), 2.2 (s, 3H); MS (ES): 295 [M+H]⁺.

Example 5c

Preparation of 5-Bromomethyl-1-(2,6-dichloro-phenyl)-3-trifluoromethyl-1H-pyrazole

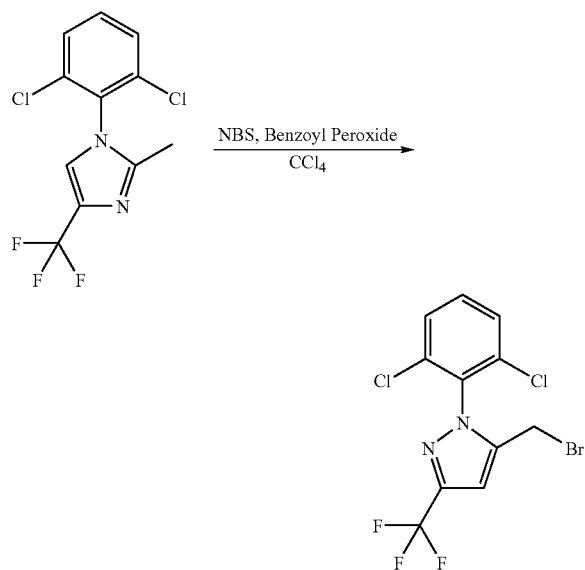

A 250 mL flask was charged with 900 mg (3.05 mmol) of 1-(2,6-dichlorophenyl)-2-methyl-4-trifluoromethyl-1H-imidazole, 651 mg (3.6 mmol), N-bromosuccinimide, 22 mg (0.09 mmol) benzoyl peroxide and 50 mL of carbon tetrachloride. The resulting solution was placed under a high intensity lamp for 2 hours. The resulting solution was allowed to cool to room temperature and filtered through a pad of celite. The filtrate was then concentrated in vacuo to give the crude product, which was then purified by column chromatography on silica eluting with EtOAc-Hexane (3:1) to afford 5-bromomethyl-1-(2,6-dichlorophenyl)-3-trifluoromethyl-1H-pyrazole as a tan solid (570 mg, 50%); ¹H NMR (400 MHz, CDCl₃): δ 7.53 (m, 3H), 7.29 (m, 1H), 4.3 (s, 2H), MS (ES): 399 [M+Na]⁺.

Example 5d

Preparation of 2-(4-Bromophenoxymethyl)-1-(2,6-dichlorophenyl)-4-trifluoromethyl-1H-imidazole

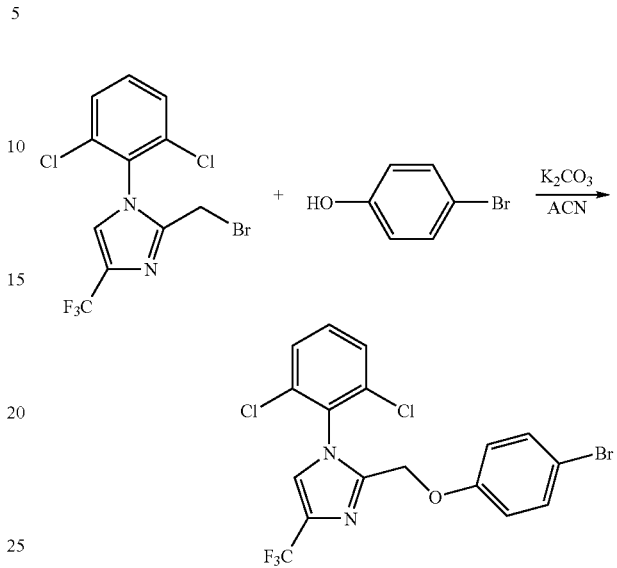

Into a 250 mL flask was weighed 570 mg (1.52 mmol) of 2-Bromomethyl-1-(2,6-dichlorophenyl)-4-trifluoromethyl-1H-imidazole, 394 mg (2.25 mmol) of 4-bromophenol, 310 mg (2.25 mmol) of potassium carbonate, and 20 mL of acetonitrile. The flask was heated in an oil bath to reflux for 4 h. The crude reaction was washed into a separatory funnel with ethyl acetate and water. The organic layer was separated, washed with brine, dried (Na₂SO₄), and concentrated in vacuo. The residue was purified by silica gel flash chromatography by column chromatography eluting with MeOH-DCM (0:100 to 2:98) to afford 2-(4-Bromophenoxymethyl)-1-(2,6-dichlorophenyl)-4-trifluoromethyl-1H-imidazole as an off white solid (417 mg, 59%); ¹H NMR (400 MHz, CDCl₃): δ 7.96 (d J=8.6 Hz 2H), 7.68 (d J=8.3 Hz 2H), 7.46 (m, 5H), 7.32 (m, 1H), 6.88 (d J=8.84 Hz 2H), 5.10 (s, 2H), 3.08 (s, 3H), MS (ES): 465 [M+H]⁺.

Example 5e

Preparation of 1-(2,6-Dichlorophenyl)-2-(4'-methanesulfonyl-biphenyl-4-yloxymethyl)-4-trifluoromethyl-1H-imidazole

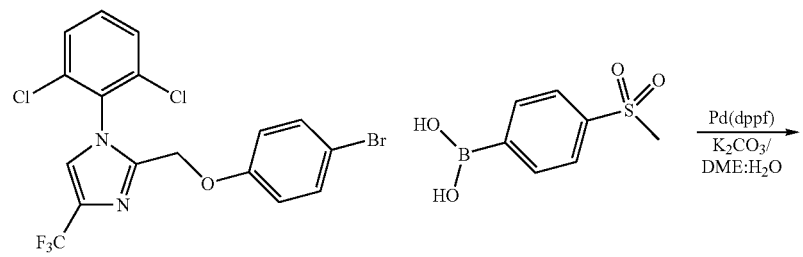

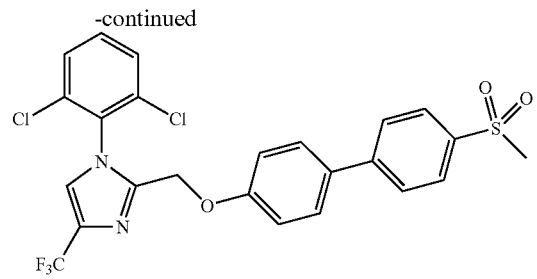

Into a 8 mL flask was added 96 mg (0.20 mmol) of 2-(4-bromophenoxymethyl)-1-(2,6-dichlorophenyl)-4-trifluoromethyl-1H-imidazole, 45.1 mg (0.23 mmol) of [(4-methylsulfonyl)phenyl]boronic acid, 70 mg of potassium carbonate (0.51 mmol), 2.9 mg (0.004 mmol) of palladium DPPF and 2 mL of DME:H$_2$O (9:1). The reaction mixture was heated to 80° C. for 4 h. After cooling, the crude reaction mixture was filtered through a pad of celite and the filtrate was concentrated in vacuo. The residue was purified by column chromatography on silica gel eluting with DCM-acetonitrile (10:0 to 8:2, with 1% acetic acid) to afford 1-(2,6-Dichlorophenyl)-2-(4'-methanesulfonylbiphenyl-4-yloxymethyl)-4-trifluoromethyl-1H-imidazole as an off white solid (22.9 mg, 21%); $^1$H NMR (400 MHz, CDCl$_3$): δ 8.16 (m, 1H), 7.98 (d, J=8.1 Hz, 1H), 7.45 (d J=7.83 Hz, 2H) 7.35 (m, 4H), 6.88 (d, J=8.84 Hz, 2H), 6.54 (s, 1H), 4.92 (s, 2H), 1.66 (s 6H), MS (ES): 541 [M+H]$^+$.

The following compounds are prepared essentially according to the previous examples:

1-(2,6-Dichlorophenyl)-2-(3'-methanesulfonyl-biphenyl-4-yloxymethyl)-4-trifluoromethyl-1H-imidazole (MS (ES): 541 [M+H]$^+$.

2-Chloro-4'-[1-(2,6-dichlorophenyl)-4-trifluoromethyl-1H-imidazol-2-ylmethoxy]-biphenyl-4-carboxylic acid (MS (ES): 541 [M+H]$^+$.

Scheme 6

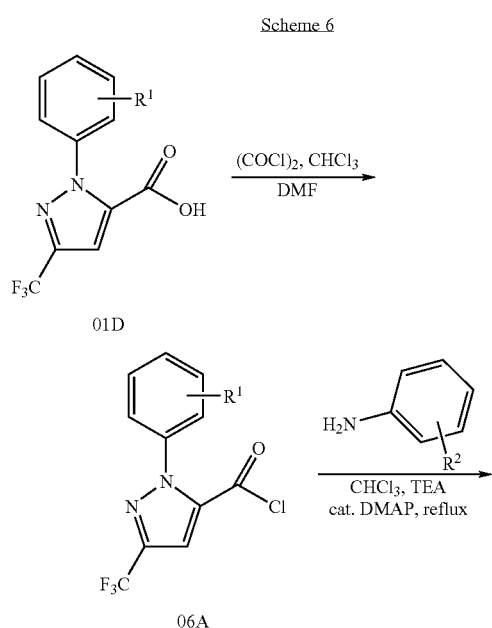

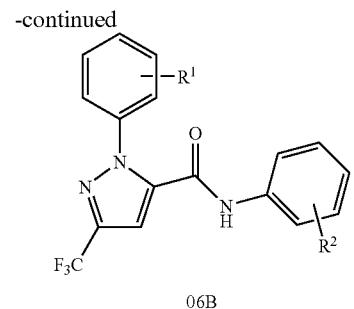

As depicted in Scheme 6,5-pyrazoleamide 06B can be prepared by using well known acid chloride or amide coupling methodology. The amino moiety of the resulting amide products may be derived from aliphatic amines or anilines. Pyrazole acid 01D reacted with an excess of oxalyl chloride in an anhydrous solvent such as chloroform or dichloromethane to afford acid chloride 06A, which can be used without further purification to prepare the 5-pyrazole-amides 06B. In a typical reaction, the acid chloride 06A was combined with amine or aniline and TEA in anhydrous CHCl$_3$ to afford pyrazole-amide analogue 06B.

Example 6

2-(2-Chloro-phenyl)-5-trifluoromethyl-2H-pyrazole-3-carboxylic acid 3-methanesulfonyl-benzylamide Example 6a Preparation of 2-(2-Chloro-phenyl)-5-trifluoromethyl-2H-pyrazole-3-carbonyl chloride

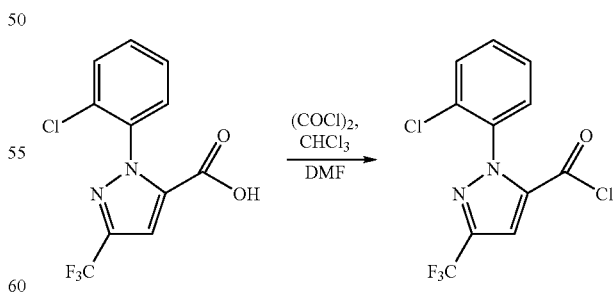

To a N$_2$ purged round bottom flask was added 2-(2-chlorophenyl)-5-trifluoromethyl-2H-pyrazole-3-carboxylic acid (2.10 g, 7.20 mmol) and anhydrous CHCl$_3$ (30 mL). The solution was cooled to 0° C. prior to the addition of oxalyl chloride (1.3 mL, 14 mmol) and anhydrous DMF (1 mL). The reaction solution was stirred 1 h under N$_2$. The solution was concentrated under reduced pressure on the rotavapor to afford 2.4 g crude product. The crude acid chloride was used without further purification in the next reaction step.

Example 6b

Preparation of 2-(2-Chlorophenyl)-5-trifluoromethyl-2H-pyrazole-3-carboxylic acid 3-methanesulfonyl-benzylamide

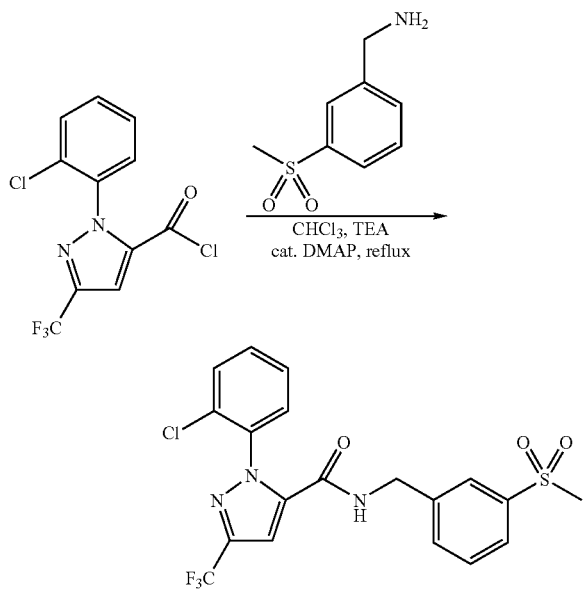

To a round bottom flask was added 2-(2-chlorophenyl)-5-trifluoromethyl-2H-pyrazole-3-carbonyl chloride (160 mg, 0.520 mmol) in a solution of anhydrous CHCl$_3$ (10 mL). To the reaction solution was added 3-methylsulfonyl benzylamine (122 mg, 0.661 mmol), TEA (150 µL, 1.10 mmol), and DMAP (67 mg, 0.549 mmol). The reaction solution was allowed to stir at 60° C. for 5 hrs. The reaction solution was diluted with EtOAc (150 mL), poured into a separatory funnel and washed with aq. NH$_4$Cl. The partitioned organic phase was dried over Na$_2$SO$_4$, filtered, and concentrated under reduced pressure on the rotavapor. The crude material was chromatographed through a silica gel column using a solvent gradient of 100% hexane to 30% EtOAc to afford 50 mg of title compound (20%). $^1$H NMR (CDCl$_3$): δ 7.83 (m, 1H), 7.79 (s, 1H), 7.48-7.58 (m, 4H), 7.42-7.46 (m, 2H), 7.05 (s, 1H), 6.66 (t, J=6 Hz, 1H), 4.58 (d, J=6 Hz, 2H), 3.03 (s, 3H); MS (ES): 458.1 [M+H]$^+$.

Following the procedures set forth above in the foregoing preparations and examples, the following compounds of the invention were prepared by substituting the appropriate reagents.

2-(2,5-Dichloro-phenyl)-5-trifluoromethyl-2H-pyrazole-3-carboxylic acid (3-methanesulfonyl-phenyl)-amide; MS (ES): 478.3, 480.3 [M+H]$^+$.

2-(2,5-Dichloro-phenyl)-5-trifluoromethyl-2H-pyrazole-3-carboxylic acid 3-trifluoromethyl-benzylamide; MS (ES): 482.1, 484.1 [M+H]$^+$.

2-(2,5-Dichloro-phenyl)-5-trifluoromethyl-2H-pyrazole-3-carboxylic acid 4-methanesulfonyl-benzylamide; MS (ES): 492.1, 494.1 [M+H]$^+$.

2-(2,5-Dichloro-phenyl)-5-trifluoromethyl-2H-pyrazole-3-carboxylic acid 3-chloro-benzylamide; MS (ES): 448.3, 450.3, 452.3 [M+H]$^+$.

2-(2-Chloro-phenyl)-5-trifluoromethyl-2H-pyrazole-3-carboxylic acid (3-methanesulfonyl-phenyl)-amide; MS (ES): 444.1 [M+H]$^+$.

2-(2-Chloro-phenyl)-5-trifluoromethyl-2H-pyrazole-3-carboxylic acid 3-trifluoromethyl-benzylamide; MS (ES): 448.2 [M+H]$^+$.

2-(2-Isopropoxy-phenyl)-5-trifluoromethyl-2H-pyrazole-3-carboxylic acid 3-trifluoromethyl-benzylamide; MS (ES): 472.3 [M+H]$^+$.

2-(2-Chloro-phenyl)-5-trifluoromethyl-2H-pyrazole-3-carboxylic acid (2-fluoro-5-methanesulfonyl-phenyl)-amide; MS (ES): 462.1 [M+H]$^+$.

Scheme 7 Preparation of N-arylpyrazole-5-carboxamides

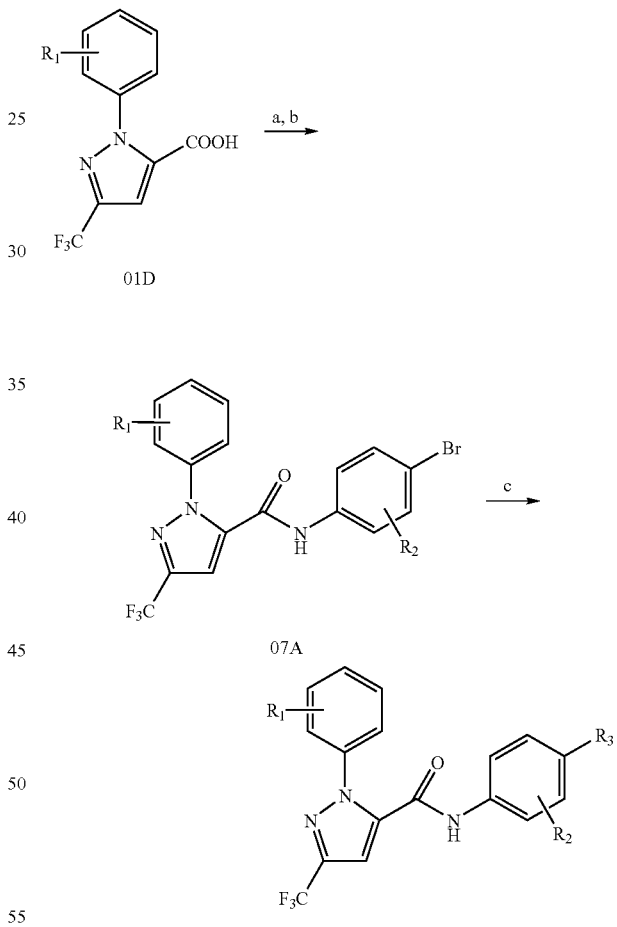

a) oxalyl chloride, DMF (cat), CH$_2$Cl$_2$;
b) bromoaniline (or substituted bromoaniline), DIPEA, DMAP CH$_2$Cl$_2$;
c) Aryl- (or alkyl-) boronic acid, DAPCy, Cs$_2$CO$_3$, EtOH, 80° C.

As depicted in Scheme 7, (N-arylpyrazole-5-yl)-carboxamides 07B were prepared from N-arylpyrazole-5-carboxylic acid 01D. N-arylpyrazole-5-carboxylic acid 01D was converted to its acid chloride and coupled with bromoanilines to afford carboxamides 07A. Coupling of the aryl bromide with aryl or alkyl boronic acids under Suzuki coupling conditions afforded carboxamides 07B

Example 7

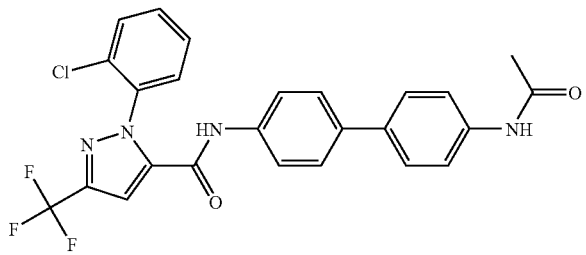

2-(2-Chloro-phenyl)-5-trifluoromethyl-2H-pyrazole-3-carboxylic acid (4'-acetylamino-biphenyl-4-yl)-amide

Example 7a

Preparation of N-(4-bromophenyl)-1-(2-chlorophenyl)-3-(trifluoromethyl)-1H-pyrazole-5-carboxamide

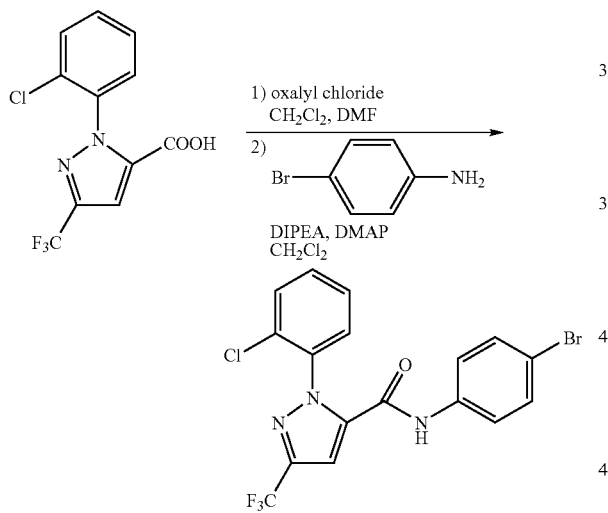

To a solution of 13.8 g crude 1-(2-chlorophenyl)-3-(trifluoromethyl)-1H-pyrazole-5-carboxylic acid (47 mmol) was added 0.1 mL of dry DMF followed by dropwise addition of 6.5 mL of oxalyl chloride (75 mmol). The resulting dark solution was allowed to stir at room temperature overnight. The dark solution was then concentrated in vacuo to afford a brown oil that was taken up in toluene and concentrated in vacuo to remove any residual oxalyl chloride. The crude 1-(2-chlorophenyl)-3-(trifluoromethyl)-1H-pyrazole-5-carbonyl chloride was carried on to the acylation without purification.

In a 500 mL round bottom flask crude 1-(2-chlorophenyl)-3-(trifluoromethyl)-1H-pyrazole-5-carbonyl chloride (47 mmol) was dissolved in 200 mL CH$_2$Cl$_2$ to afford a dark solution. To this solution was added 8.2 g of 4-bromoaniline (47 mmol) and a few pellets of 4-(dimethylamino)pyridine. The resulting slurry was treated with 20 mL of N,N-diisopropylethylamine (115 mmol) to afford a dark solution. After stirring for 2 hours at room temperature the reaction was quenched by the addition of H$_2$O and diluted with additional CH$_2$Cl$_2$. The organic layer was washed with 1N HCl, saturated NaHCO$_3$ solution, dried (Na$_2$SO$_4$), filtered, and concentrated in vacuo to afford crude N-(4-bromophenyl)-1-(2-chlorophenyl)-3-(trifluoromethyl)-1H-pyrazole-5-carboxamide as a dark brown syrup. The crude product was purified by silica gel flash chromatography on a 300 g column using gradient elution from 0% to 30% EtOAc/hexane. Most of the product-containing fractions were impure. All product-containing fractions were combined and concentrated in vacuo to afford a sticky orange foam. This material was further purified by silica gel flash chromatography on a 160 g column using gradient elution from 0% to 20% EtOAc/hexane. Appropriate fractions were combined and concentrated in vacuo to afford N-(4-bromophenyl)-1-(2-chlorophenyl)-3-(trifluoromethyl)-1H-pyrazole-5-carboxamide as a pale orange foam that was broken up to a powder. The material is not completely pure. Yield: 2.61 g (12% yield); $^1$H NMR (400 MHz, CDCl$_3$): δ 7.64 (br s, 1H), 7.56-7.55 (impurity), 7.54-7.53 (m, 1H), 7.52-7.51 (m, 1H), 7.50-7.49 (impurity), 7.48-7.44 (m, 3H), 7.43-7.41 (m, 1H), 7.38-7.36 (m, 1H), 7.36-7.34 (m, 1H), 7.11 (s, 1H); GC/MS (EI, 70 eV) 445, 443.

Example 7b

Preparation of 2-(2-Chloro-phenyl)-5-trifluoromethyl-2H-pyrazole-3-carboxylic acid (4'-acetylamino-biphenyl-4-yl)-amide

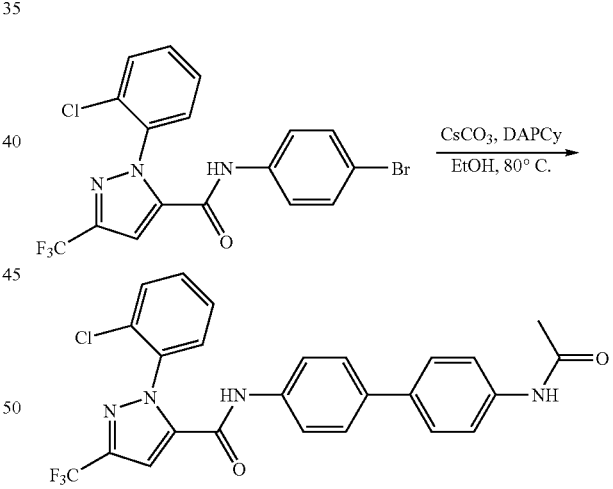

In a 4 ml vial was added 22.3 mg (0.125 mmol) of (4-acetylaminophenyl)boronic acid, 11 mg (0.025 mmol) of N-(4-bromophenyl)-1-(2-chlorophenyl)-3-(trifluoromethyl)-1H-pyrazole-5-carboxamide, 200 μL of a saturated CsCO$_3$ solution of ethanol and 10 μg of DAPCy. The vial was sealed and heated to 60° C. overnight. The crude product was dissolved up in 200 μL of DMSO and injected directly on a reverse phase LCMS preparative instrument. The relevant fraction was collected dried to afford 2-(2-Chloro-phenyl)-5-trifluoromethyl-2H-pyrazole-3-carboxylic acid (4'-acetylamino-biphenyl-4-yl)-amide (4.3 mg, 0.0086 mmol: 34% yield as an off white solid. MS (ESI) m/z 499 [M+H]$^+$.

187

Scheme 8 Preparation of N-arylpyrazol-5-ylacetic acid

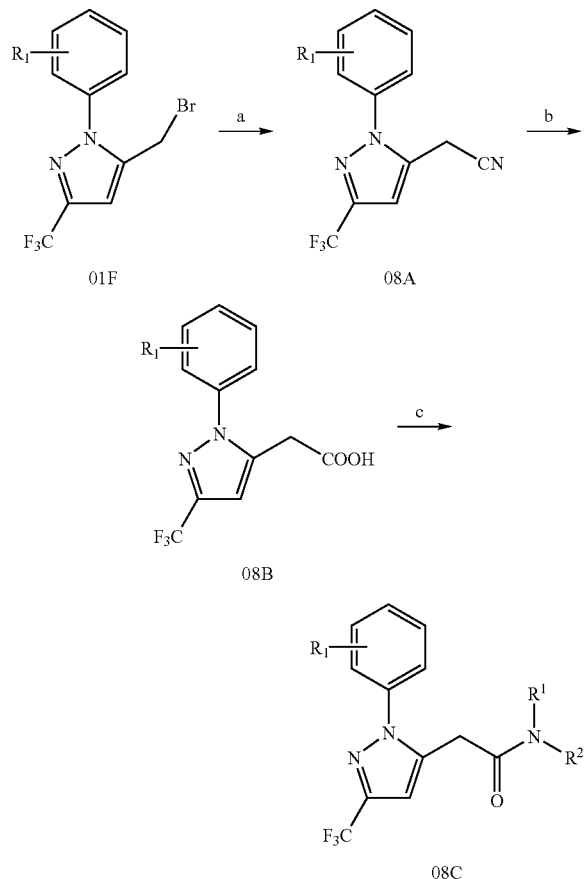

a) NaCN, DMF, 50° C.;
b) KOH, EtOH, reflux;
c) i) oxalyl chloride, DMF (cat.), CH₂Cl₂; ii) Amines, DIPEA, DMAP CH₂Cl₂.

As depicted in Scheme 8, N-arylpyrazol-5-yl acetic acid was prepared from 5-(bromomethyl)-N-arylpyrazole 01F. 5-(bromomethyl)-N-arylpyrazole 01F was treated with sodium cyanide in DMF to afford N-aryl-5-(cyanomethyl) pyrazole 08A. The nitrile was converted to the acid by basic hydrolysis with KOH in refluxing ethanol to afford N-arylpyrazol-5-yl acetic acid 08B, which is transformed into amides 08C.

Example 8

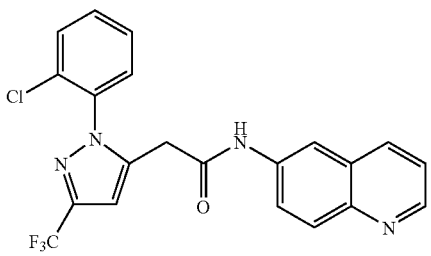

188

2-[2-(2-Chloro-phenyl)-5-trifluoromethyl-2H-pyra-zol-3-yl]-N-quinolin-6-yl-acetamide

Example 8a

Preparation of 2-(1-(2-chlorophenyl)-3-(trifluorom-ethyl)-1H-pyrazol-5-yl)acetic acid

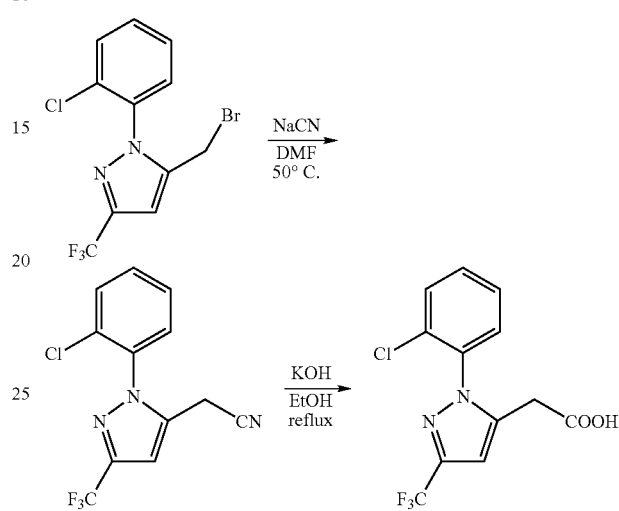

Into a 250 mL flask was weighed 11.3 g of 5-(bromom-ethyl)-1-(2-chlorophenyl)-3-(trifluoromethyl)-1H-pyrazole (33 mmol) which was then dissolved in 40 mL of dry DMF. The resulting solution was treated with 2.5 g of sodium cyanide (52 mmol). The resulting suspension was heated to 50° C. After 4 hours at 50° C., heating was discontinued and the reaction was allowed to cool to room temperature. After standing at room temperature for 2 days the reaction was diluted with ether and H₂O. The layers were separated and the aqueous layer was extracted with ether (4×). The combined organic layers were washed with H₂O (3×), then brine (2×), dried (Na₂SO₄), filtered and concentrated in vacuo to afford crude 2-(1-(2-chlorophenyl)-3-(trifluoromethyl)-1H-pyra-zol-5-yl)acetonitrile as a red oil, yield 8.2 g (86%), ¹H NMR (400 MHz, CDCl₃): δ 7.62-7.46 (m, 4H), 6.82 (s, 1H), 3.9-3.4 (broad hump, 2H).

Into a 250 mL round bottom flask was weighed 2.3 g of crude 2-(1-(2-chlorophenyl)-3-(trifluoromethyl)-1H-pyra-zol-5-yl)acetonitrile (8.0 mmol). To this was added 40 mL of ethanol and 2.5 g of KOH (44 mmol). The resulting mixture was heated to reflux. After 17 hours at reflux the reaction was cooled and concentrated in vacuo to remove most of the ethanol. The resulting dark oil was taken up in H₂O and EtOAc and acidified by the addition of 3N aqueous HCl. The acidic aqueous was extracted with EtOAc (3×), the combined organic extracts were washed with brine, dried (Na₂SO₄), filtered and concentrated in vacuo to afford the crude acid as a dark oil. The crude product was purified by silica gel flash chromatography on an 80 g column using gradient elution from 0% to 40% acetonitrile/CH₂Cl₂ and collected by monitoring the UV response at 240 nm. Appropriate fractions were combined and concentrated in vacuo to afford 2-(1-(2-chlo-rophenyl)-3-(trifluoromethyl)-1H-pyrazol-5-yl)acetic acid as a dark glass. The product was not completely pure and was taken up in 1N NaOH and Et₂O. The ether layer was extracted with 1N NaOH (1×) and the combined basic aqueous layers were extracted with Et$_2$O (1×). The basic layer was acidified by the addition of concentrated HCl and was extracted with EtOAc (3×). The combined EtOAc extracts were washed with brine, dried (Na$_2$SO$_4$), filtered and concentrated in vacuo to afford 2-(1-(2-chlorophenyl)-3-(trifluoromethyl)-1H-pyrazol-5-yl)acetic acid as a yellow oil that partially solidified after standing under vacuum overnight: yield 1.5 g (61% yield); $^1$H NMR (400 MHz, CDCl$_3$): δ 7.58-7.54 (m, 1H), 7.52-7.39 (m, 3H), 6.73 (s, 1H), 3.80-3.45 (broad hump, 2H); MS (ESI) m/z 305.0 [M+H]$^+$.

Example 8b

Preparation of 2-[2-(2-Chloro-phenyl)-5-trifluoromethyl-2H-pyrazol-3-yl]-N-quinolin-6-yl-acetamide

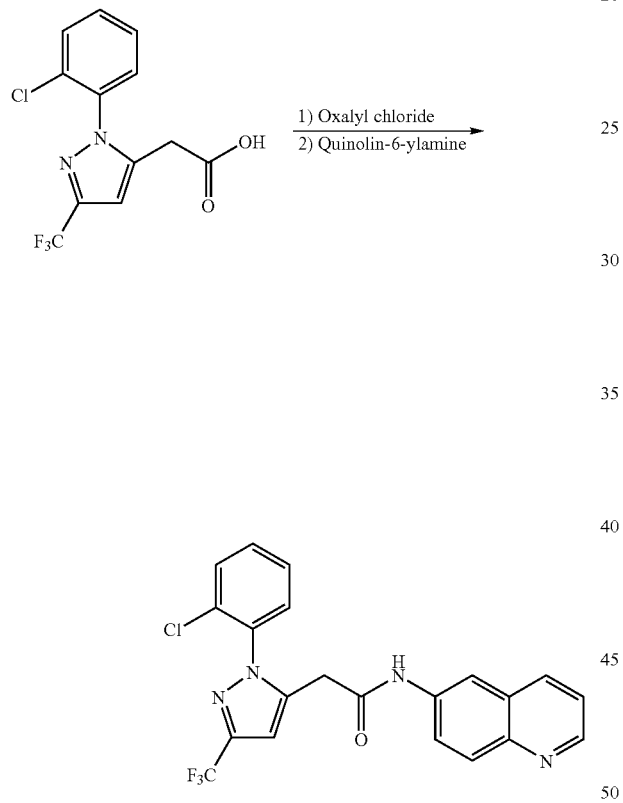

Into a 250 mL round bottom flask under nitrogen was added 1.5 g (4.9 mmol) of 8B, 100 mL of anhydrous THF, 2.2 mL (24.5 mmol) of Oxalyl chloride and 50 μL of DMF. After stirring for 30 min the solvent was removed in vacuo and the solid was dried from DCM 3 times. The crude product was used directly in the next step. In a 4 ml vial was added 7 mg (0.050 mmol) of Quinolin-6-ylamine, 8 mg (0.025 mmol) of the acid chloride 300 μL of ACN and 60 μL (0.080 mmol) of DIEA. The vial was sealed and heated to 60° C. overnight. The crude product was dissolved up in 200 μL of DMSO and injected directly on a reverse phase LCMS preparative instrument. The relevant fraction was collected dried to afford 2-[2-(2-Chloro-phenyl)-5-trifluoromethyl-2H-pyrazol-3-yl]-N-quinolin-6-yl-acetamide (2.0 mg, 0.046 mmol: 24% yield as an off white solid. MS (ESI) m/z 431 [M+H]$^+$.

Scheme 9
Preparation of (N-Aryl)-(N-arylpyrazole-5-yl)-methylamines

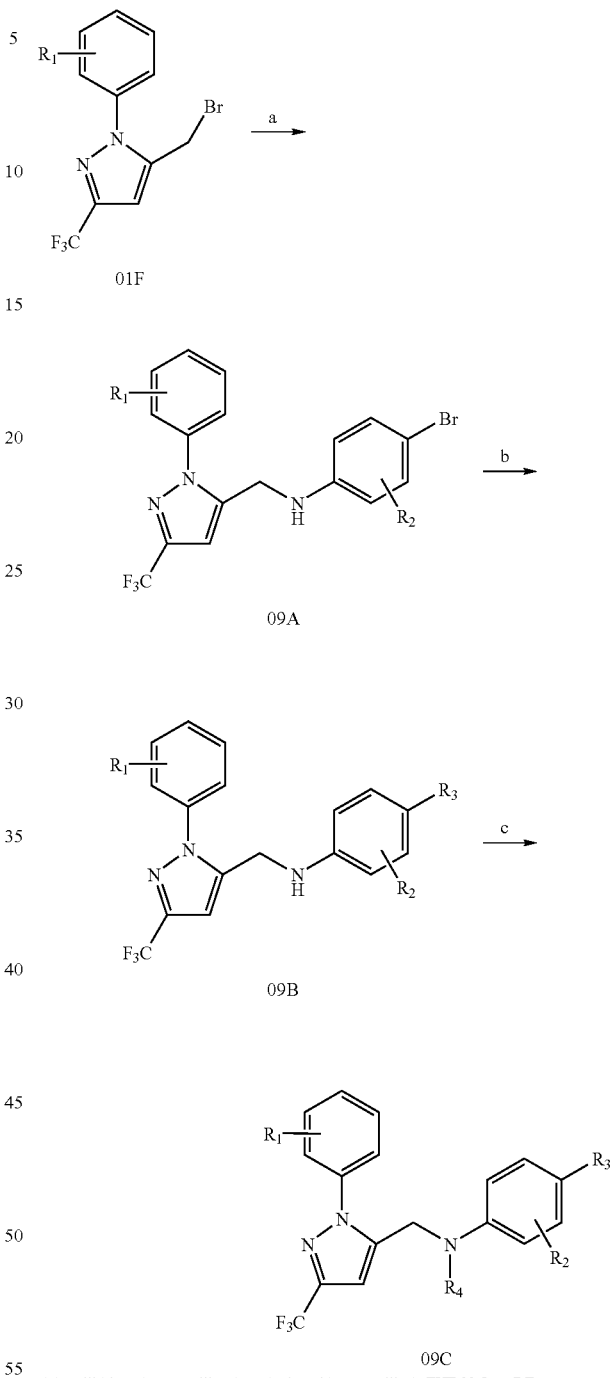

a) butyllithium, bromoaniline (or substituted bromoaniline), THF 0° C. to RT;
b) Aryl- (or alkyl-) boronic acid, palladium catalyst, K$_2$CO$_3$, aqueous DME, 80° C. (or 140° C. μwave heating);
c) Aldehyde, NaCNBH$_3$, HOAc/MeOH.

As depicted in Scheme 9, (N-aryl)-(N-arylpyrazole-5-yl)-methylamine 09C was prepared from 5-(bromomethyl)-N-arylpyrazoles 01F. 5-(Bromomethyl)-N-arylpyrazole 01F was treated with a metallated halo-aniline to afford the 5-(N-arylamino)methyl-N-arylpyrazole 09A. Coupling of the aryl bromide with aryl or alkyl boronic acids under Suzuki coupling conditions afforded the 5-(N-arylamino)methyl-N- arylpyrazole 09B. Alkylation of the amino group with an aldehyde under reductive amination conditions afforded the alkylated amine 09C.

Example 9

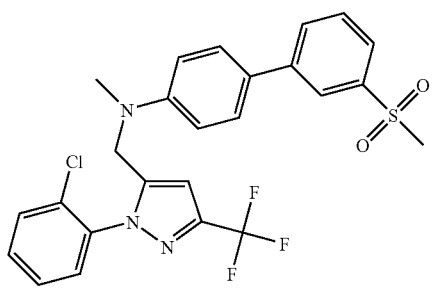

N-((1-(2-chlorophenyl)-3-(trifluoromethyl)-1H-pyrazol-5-yl)methyl)-N-methyl-3'-(methylsulfonyl)biphenyl-4-amine

Example 9a

Preparation of 4-bromo-N-((1-(2-chlorophenyl)-3-(trifluoromethyl)-1H-pyrazol-5-yl)methyl)aniline

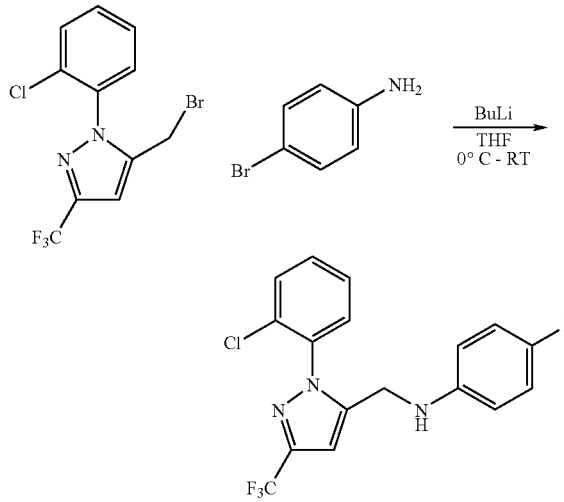

Into a dry, nitrogen-flushed 250 mL round-bottom flask was placed 4.0 g of 4-bromoaniline (23 mmol). After addition of THF (30 mL), the resulting solution was cooled in an ice bath. 14 mL of a 1.6 M solution in hexane of butyllithium (22 mmol) was added dropwise to the 4-bromoaniline solution to afford a beige suspension. After 10 minutes stirring, the cold suspension was treated with 6.0 g of 5-(bromomethyl)-1-(2-chlorophenyl)-3-(trifluoromethyl)-1H-pyrazole (18 mmol) as a solution in THF (30 mL) via cannula. The flask and cannula were then rinsed with additional THF (10 mL) to insure complete transfer of the bromide. After 1 hour stirring at 0° C., LC/MS analysis showed no remaining 5-(bromomethyl)-1-(2-chlorophenyl)-3-(trifluoromethyl)-1H-pyrazole, and showed a large peak for the desired product. After 100 min., the reaction was quenched by the addition of 1 mL of acetic acid (18 mmol). The resulting pale suspension was concentrated in vacuo to afford a pale brown foam. The crude product was purified by silica gel flash chromatography using gradient elution from 0% to 70% EtOAc/hexane. Many of the column fractions were impure. Pure fractions were concentrated in vacuo to afford 4-bromo-N-((1-(2-chlorophenyl)-3-(trifluoromethyl)-1H-pyrazol-5-yl)methyl)aniline as a pale yellow oil, yield: 2.35 g (31%); $^1$H NMR (400 MHz, CDCl$_3$): δ 7.59-7.55 (m, 1H), 7.52-7.45 (m, 1H), 7.44-7.40 (m, 2H), 7.25-7.21 (m, 2H), 6.63 (s, 1H), 6.41-6.37 (m, 2H), 4.20 (br s, 2H), 3.90 (br s, 1H); MS (ESI) m/z 432.0 [M+H]$^+$.

Example 9b

Preparation of N-((1-(2-chlorophenyl)-3-(trifluoromethyl)-1H-pyrazol-5-yl)methyl)-3'-(methylsulfonyl)biphenyl-4-amine

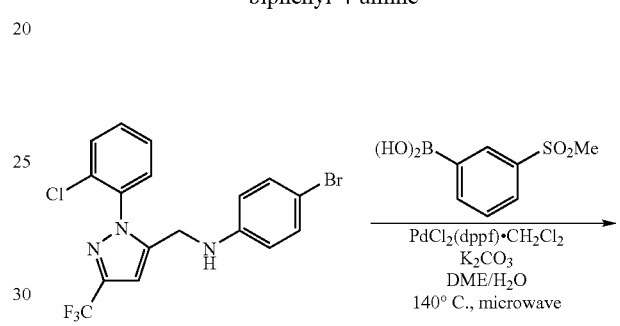

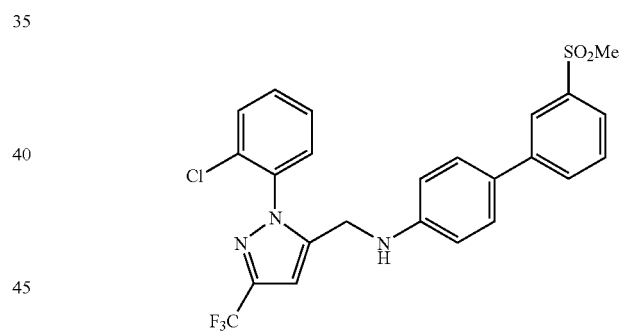

A mixture of 225 mg of 4-bromo-N-((1-(2-chlorophenyl)-3-(trifluoromethyl)-1H-pyrazol-5-yl)methyl)aniline (0.52 mmol), 160 mg of 3-(methylsulfonyl)phenylboronic acid (0.82 mmol), 27 mg of PdCl$_2$(dppf).CH$_2$Cl$_2$ (33 µmol), and 0.5 mL of 3.5 M aqueous K$_2$CO$_3$ (1.75 mmol) in DME (2.5 mL) was placed in a 5 mL microwave reaction vial and heated to 140° C. for 10 minutes in the Biotage Initiator microwave reactor. After cooling to room temperature the vial was opened and the lower aqueous layer was removed by means of a glass pipet. The resulting dark organic solution was diluted with EtOAc, treated with Na$_2$SO$_4$ filtered and concentrated in vacuo to afford a dark oil. The crude product was purified by silica gel flash chromatography on a 12 g column using gradient elution from 0% to 90% EtOAc/hexane. Appropriate fractions were combined and concentrated in vacuo to afford N-((1-(2-chlorophenyl)-3-(trifluoromethyl)-1H-pyrazol-5-yl)methyl)-3'-(methylsulfonyl)biphenyl-4-amine as a white foam, yield 150 mg (57%): $^1$H NMR (400 MHz, CDCl$_3$): δ

8.10-8.06 (m, 1H), 7.83-7.77 (m, 2H), 7.61-7.55 (m, 2H), 7.52-7.41 (m, 5H), 7.67 (s, 1H), 6.64-6.59 (m, 2H); MS (ESI) m/z 506.1 [M+H]⁺.

Example 9c

Preparation of N-((1-(2-chlorophenyl)-3-(trifluoromethyl)-1H-pyrazol-5-yl)methyl)-N-methyl-3'-(methylsulfonyl)biphenyl-4-amine

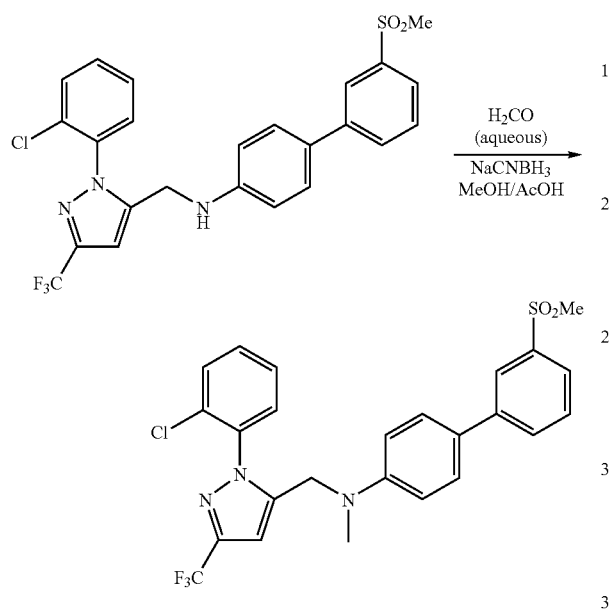

Into an 8 mL vial was weighed 215 mg of N-((1-(2-chlorophenyl)-3-(trifluoromethyl)-1H-pyrazol-5-yl)methyl)-3'-(methylsulfonyl)biphenyl-4-amine (0.42 mmol). Addition of 2 mL of methanol followed by 0.5 mL of acetic acid, and 150 µL of 37% aqueous formaldehyde solution afforded a solution that was treated with 40 mg of sodium cyanoborohydride (0.64 mmol). After 30 min. at room temperature the reaction was quenched by the addition of 6N HCl (aq.). After gas evolution had subsided, the reaction mixture was diluted with EtOAc and the aqueous was made basic by the addition of saturated aqueous NaHCO₃. The basic aqueous was extracted with EtOAc (3×) and the combined organic extracts were washed with brine, dried (Na₂SO₄), filtered, and concentrated in vacuo to afford a colorless film. The crude product was purified by silica gel flash chromatography on a 12 g column using gradient elution from 0% to 100% EtOAc/hexane. Appropriate fractions were combined and concentrated in vacuo to afford N-((1-(2-chlorophenyl)-3-(trifluoromethyl)-1H-pyrazol-5-yl)methyl)-N-methyl-3'-(methylsulfonyl)biphenyl-4-amine as a colorless film. This material was impure by NMR analysis and was further purified by preparative reverse phase HPLC eluting with a gradient from 30% to 100% MeCN in H₂O (each with 0.05% trifluoroacetic acid). The appropriate fractions were made basic by addition of saturated aqueous NaHCO₃ solution and concentrated in vacuo to remove most of the acetonitrile. The resulting basic aqueous was extracted with CH₂Cl₂ (4×). The combined organic extracts were dried (Na₂SO₄), filtered and concentrated in vacuo to afford N-((1-(2-chlorophenyl)-3-(trifluoromethyl)-1H-pyrazol-5-yl)methyl)-N-methyl-3'-(methylsulfonyl)biphenyl-4-amine as a brittle foam that was broken up into a white powder, yield 126 mg (57% yield): ¹H NMR (400 MHz, CDCl₃): δ 8.11-8.08 (m, 1H, 7.84-7.79 (m, 2H, 7.62-7.56 (m, 2H, 7.52-7.40 (m, 5H), 6.72-6.67 (m, 2H), 6.52 (s, 1H), 4.43 (br s, 1H), 3.09 (s, 3H), 2.94 (S, 3H); MS (ESI) m/z 520.3 [M+H]⁺.

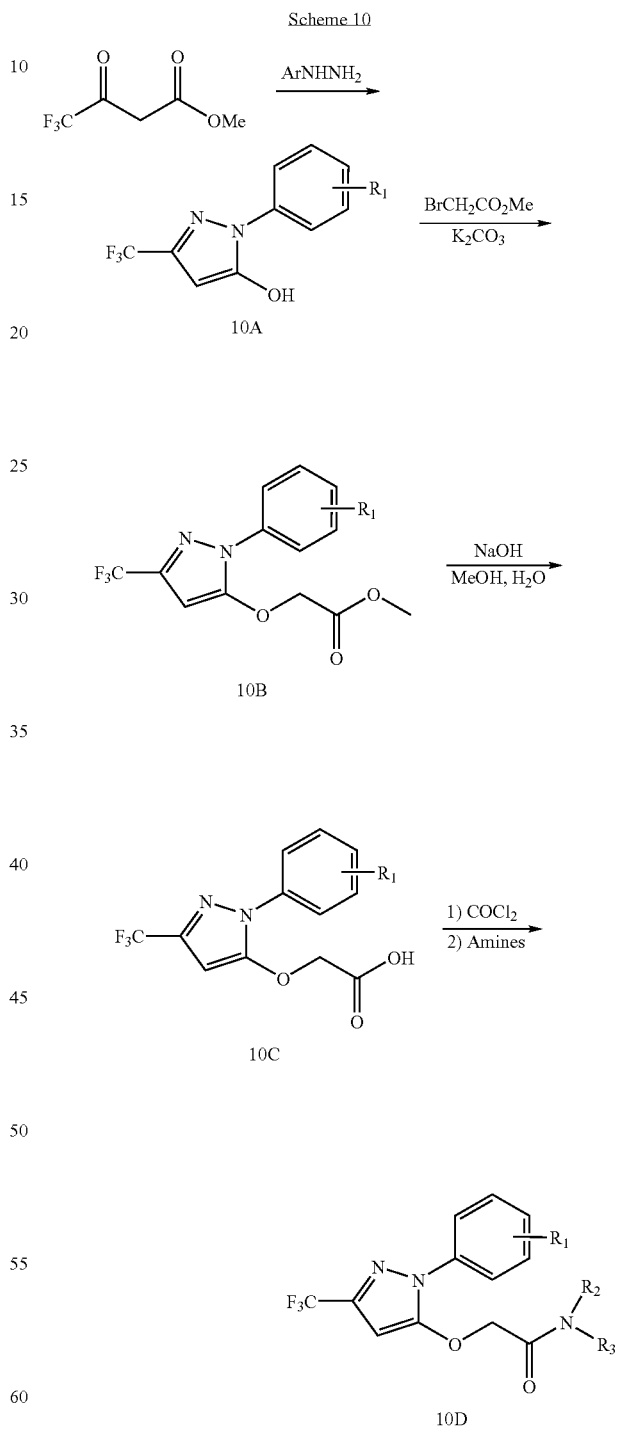

As depicted in Scheme 10, 1H-pyrazol-5-ol 10A was alkylated to introduce carboxamide. 1H-Pyrazol-5-ol 10A was treated with bromoacetate in the presence of a base to afford ether 10B, which was hydrolyzed to afford acid 10C. Acid 10C was treated with oxalyl chloride to form acid chlorides and then amines to form amides 10D.

Example 10

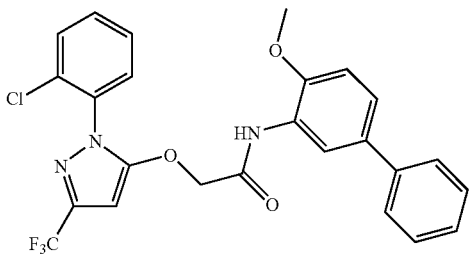

2-[2-(2-Chloro-phenyl)-5-trifluoromethyl-2H-pyrazol-3-yloxy]-N-(4-methoxy-biphenyl-3-yl)-acetamide

Example 10a

Preparation of 1-(2-chlorophenyl)-3-(trifluoromethyl)-1H-pyrazol-5-ol

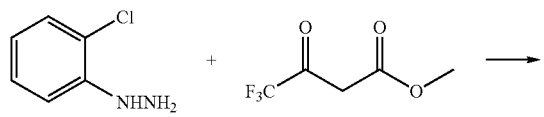

Into a 250 mL flask was weighed 5.01 g of 4,4,4-trifluoro-3-oxo-butyric acid ethyl ester, 4.88 g of 2-chlorophenylhydrazine hydrochloride, and 100 mL of ethanol. The resulting solution was heated at 90-95°C for 18 h then was concentrated in vacuo to remove ethanol. The residue was washed into a separatory funnel with ethyl acetate and 1 M HCl. The ethyl acetate was separated, washed with brine, was dried, and concentrated in vacuo. The residue was partially purified by silica gel flash chromatography (Jones Flashmaster, 70 g Silica gel, gradient elution from 100% hexanes to 20% ethyl acetate over 30 minutes). Appropriate fractions were combined and concentrated and product was precipitated by addition of excess hexanes. The solid precipitate was collected by filtration and was dried under high vacuum to afford the intermediate 2-(2-Chlorophenyl)-5-trifluoromethyl-2H-pyrazol-3-ol as a tan powder, yield: 3.73 g (52%). $^1$H NMR (DMSO-d$_6$): δ 12.25 (br s, 1H), 7.72 (d, J=8 Hz, 1H), 7.5-7.65 (m, 3H), 5.94 (s, 1H).

Example 10b

Preparation of methyl {[1-(2-chlorophenyl)-3-(trifluoromethyl)-1H-pyrazol-5-yl]oxy}acetate

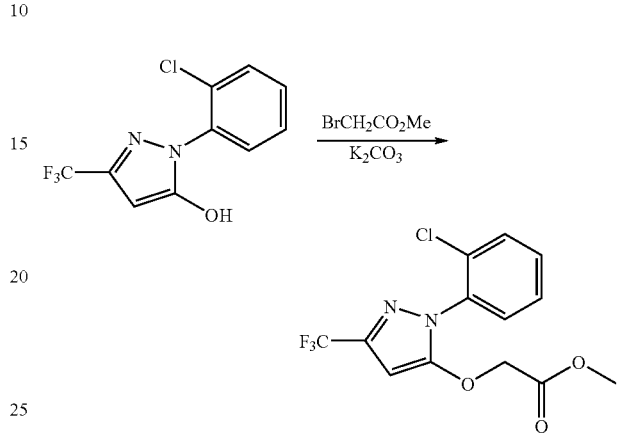

A mixture of 1-(2-chlorophenyl)-3-(trifluoromethyl)-1H-pyrazol-5-ol (0.26 g, 1 mmol), methyl bromoacetate (0.195 mL, 2 mmol) and K$_2$CO$_3$ (276 mg, 2 mmol) in acetonitrile (2 mL) was shaken overnight at 85° C. After cooling, solid was removed by filtration and washed with acetonitrile. The filtrate was evaporated to give a crude, which was purified by chromatography on silica gel eluting with EtOAc-Hexane (1:4) to give methyl {[1-(2-chlorophenyl)-3-(trifluoromethyl)-1H-pyrazol-5-yl]oxy}acetate (180 mg). $^1$H-NMR (CDCl$_3$): δ 7.52 (2H, m), 7.42 (2H, m), 5.91 (1H, s), 4.67 (2H, s), 3.80 (3H, s). MS (ES): 335 [M+H]+

Example 10c

Preparation of [2-(2-chloro-phenyl)-5-trifluoromethyl-2-H-pyrazol-3-yloxy]-acetic acid

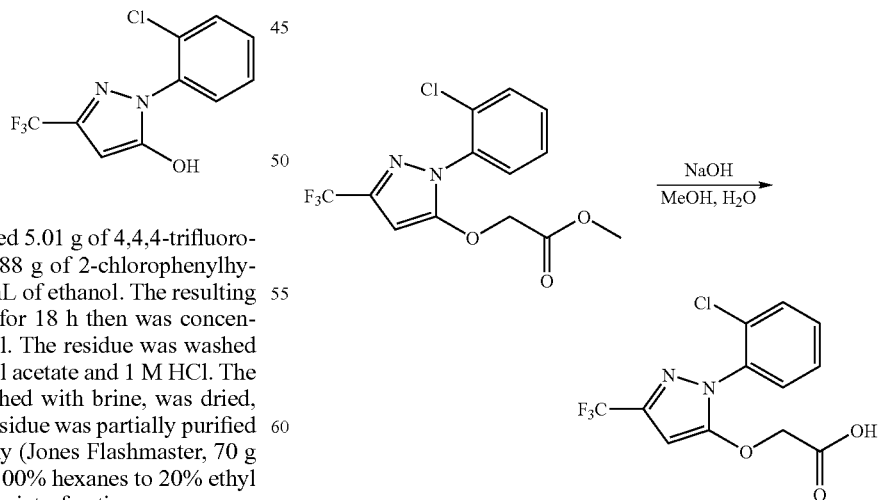

To a solution of methyl {[1-(2-chlorophenyl)-3-(trifluoromethyl)-1H-pyrazol-5-yl]oxy}acetate (17.90 g, 53.48 mmol) in MeOH (120 mL) cooled with an ice/water bath was added a solution of NaOH (4.28 g, 106.95 mmol) in water (120 mL). The reaction mixture was stirred at 0° C. for 10 minutes and stirred at room temperature for 2 hours. The solvent methanol was evaporated and the reaction mixture was acidified with 6.0M HCl and was then extracted with DCM (30 mL×3). The organic phase was separated and dried over anhydrous Na$_2$SO$_4$. Evaporation of the solvent resulted in the product carboxylic acid (15.81 g, yield 92%). NMR (CDCl$_3$): δ 7.76 (br, 1H), 7.55-7.33 (m, 4H), 5.91 (s, 1H), 4.67 (s, 2H). MS (ES): 321[M+H]$^+$.

Example 10d

Preparation of 2-[2-(2-Chloro-phenyl)-5-trifluoromethyl-2H-pyrazol-3-yloxy]-N-(4-methoxy-biphenyl-3-yl)-acetamide

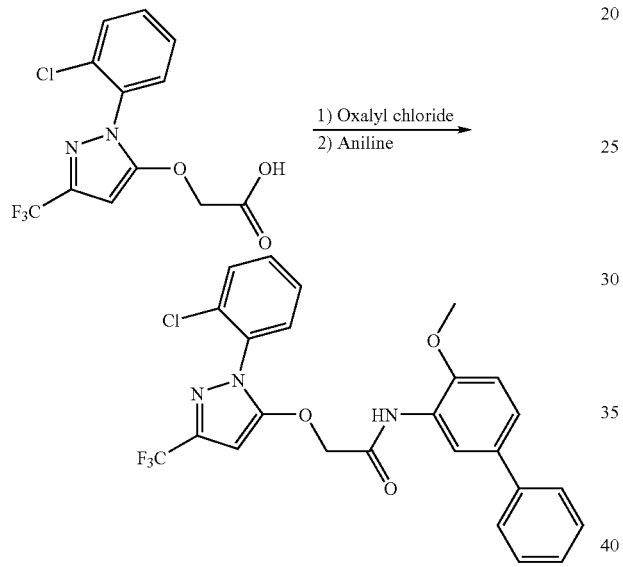

Into a 250 mL round bottom flask under nitrogen was added 1.5 g (4.7 mmol) of 8B, 100 mL of anhydrous THF, 2.1 mL (23.5 mmol) of Oxalyl chloride and 50 μL of DMF. After stirring for 30 min the solvent was removed in vacuo and the solid was dried from DCM 3 times. The crude product was used directly in the next step. In a 4 ml vial was added 7 mg (0.050 mmol) of (4-Methoxy-biphenyl-3-yl)-methyl-amine, 8 mg (0.025 mmol) of the acid chloride 300 μL of ACN and 60 μL (0.080 mmol) of DIEA. The vial was sealed and heated to 60° C. overnight. The crude product was dissolved up in 200 μL of DMSO and injected directly on a reverse phase LCMS preparative instrument. The relevant fraction was collected dried to afford 2-[2-(2-Chloro-phenyl)-5-trifluoromethyl-2H-pyrazol-3-yloxy]-N-(4-methoxy-biphenyl-3-yl)-acetamide (2.0 mg, 0.040 mmol: 16% yield as an off white solid. MS (ESI) m/z 502 [M+H]$^+$.

Scheme 11

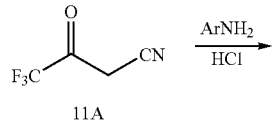

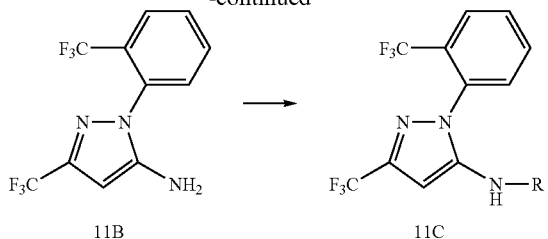

As depicted in Scheme 11, aminopyrazole was prepared and derivatized. Cyanoketone 11A condensed with aryl hydrazines to afford aminopyrazole 11B, which was treated with acyl chlorides, chloroformates isocyanates and sulfonyl chlorides to afford amides, carbamates, ureas and sulfonamides 11C.

Example 11

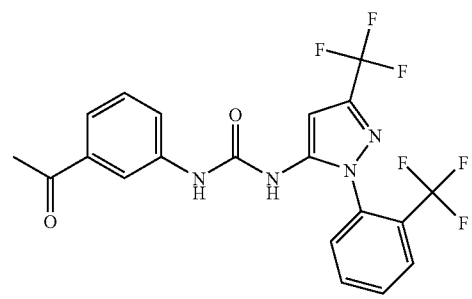

1-(3-acetyl-phenyl)-3-[5-trifluoromethyl-2-(2-trifluoromethyl-phenyl)-2H-pyrazol-3-yl]-urea Example 11a Preparation of 5-trifluoromethyl-2-(2-trifluoromethyl-phenyl)-2H-pyrazol-3-ylamine

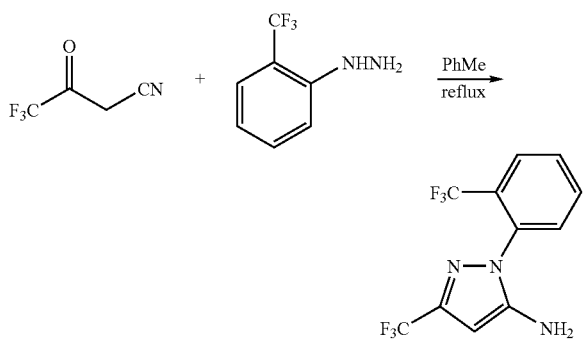

A solution of 2-trifluoromethyl-phenylhydrazine (1.1 g, 6.3 mmol) and 4,4,4-trifluoro-3-oxobutyronitrile (0.82 g, 6.0 mmol) in toluene (3 mL, anhyd.) was heated at reflux. After 5 h the reaction mixture was allowed to cool, concentrated and purified by chromatography (silica, EtOAc/Hex, 0:100 to 25:75) to yield the title compound (1.1 g, 61%) as an amber liquid. ¹H-NMR (CD₂Cl₂): δ 8.40 (1H, br s), 7.77 (1H, d), 7.59 (2H, m), 7.17 (1H, m), 3.56 (2H, s); Rf 0.45 (20% EtOAc/Hex).

Example 11b

Preparation of 1-(3-acetyl-phenyl)-3-[5-trifluoromethyl-2-(2-trifluoromethyl-phenyl)-2H-pyrazol-3-yl]-urea

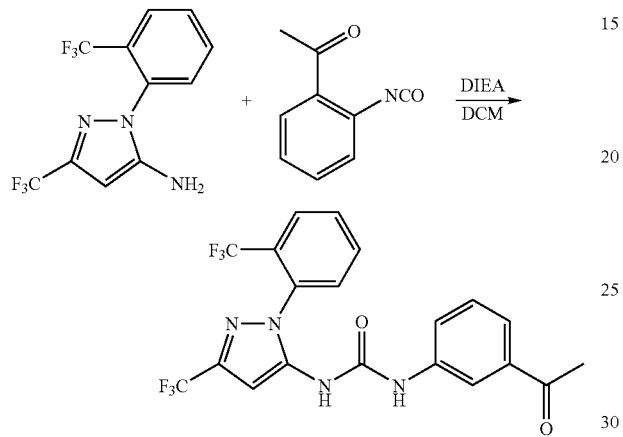

To a solution of 5-trifluoromethyl-2-(2-trifluoromethyl-phenyl)-2H-pyrazol-3-ylamine (97 mg, 0.33 mmol) and DIEA (57 µL, 0.33 mmol) in DCM (2 mL) was added 3'-isocyanato-acetophenone (41 µL, 0.30 mmol). After 15 h the reaction mixture was concentrated and purified by chromatography (silica, EtOAc/Hex, 0:100 to 50:50) to yield the title compound (36 mg). ¹H-NMR (DMSO-d₆): δ 9.67 (1H, s), 8.24 (1H, m), 7.99 (1H, d), 7.94-7.80 (3H, m), 7.69 (1H, d), 7.62 (1H, d), 7.48 (1H, t), 6.31 (2H, s), 2.57 (3H, s); MS (ES): 457 [M+H]⁺.

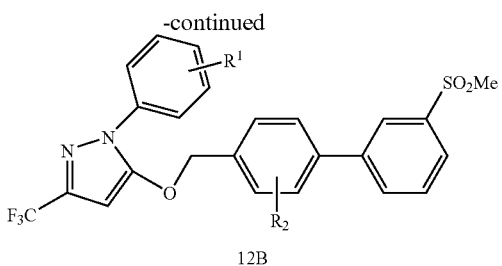

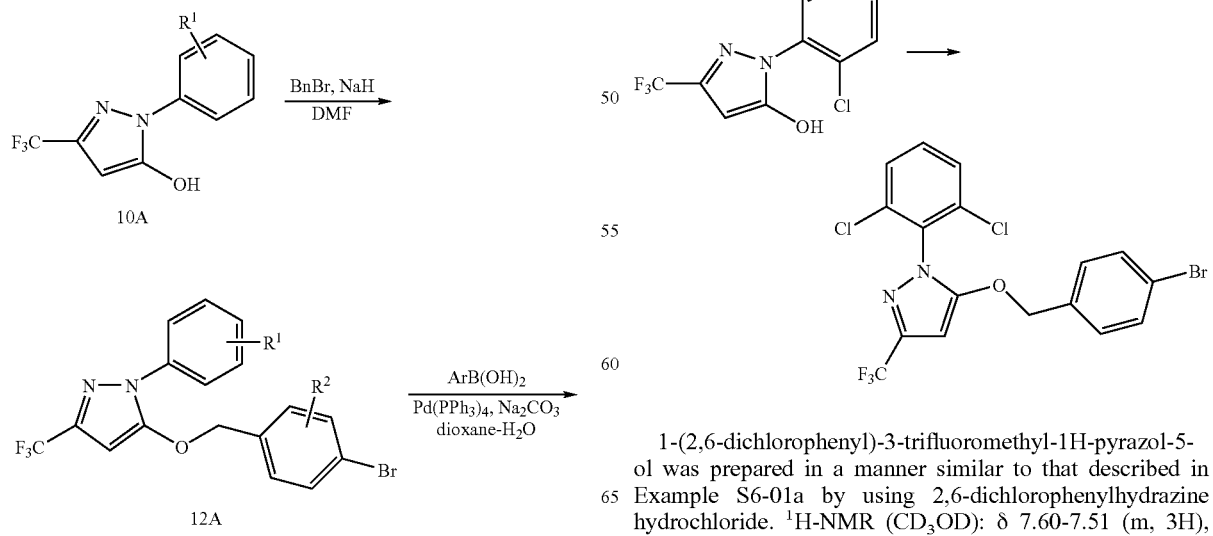

As depicted in Scheme 12, 1H-pyrazol-5-ol 10A was alkylated to afford ether 12A, which was submitted to Suzuki coupling to afford arylphenyl ether 12B.

Example 12

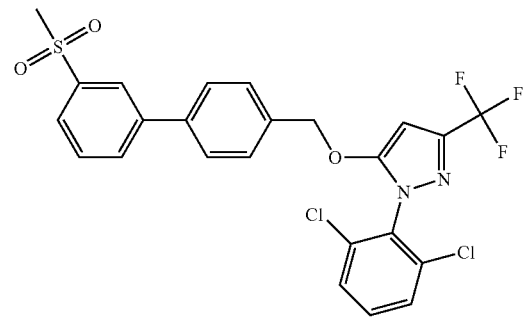

1-(2,6-dichlorophenyl)-5-(3'-methanesulfonyl-biophenyl-4-ylmethoxy)-3-trifluoromethyl-1H-pyrazole

Example 12a

Preparation of 5-(4-bromobenzyloxy)-1-(2,6-dichlorophenyl)-3-trifluoromethyl-1H-pyrazole 1-(2,6-dichlorophenyl)-3-trifluoromethyl-1H-pyrazol-5-ol was prepared in a manner similar to that described in Example S6-01a by using 2,6-dichlorophenylhydrazine hydrochloride. ¹H-NMR (CD₃OD): δ 7.60-7.51 (m, 3H), 5.86 (s, 1H). MS (ESI): 298 [M+H]⁺.

At 0° C. NaH (60%, 400 mg, 10 mmol) was added to a stirred mixture of 1-(2,6-dichlorophenyl)-3-trifluoromethyl-1H-pyrazol-5-ol (1.5 g, 5 mmol) and 4-bromobenzyl bromide (1.5 g, 6 mmol) in dry DMF (20 mL), the resulting mixture was stirred at ambient temperature for 1 h, then quenched with aqueous NH$_4$Cl at 0° C., extracted with EtOAc. The combined extracts were washed with H$_2$O and brine, dried over Na$_2$SO$_4$, and evaporated in vacuo. The crude product was purified by column chromatography (30% EtOAc/hexanes) to give 5-(4-bromobenzyloxy)-1-(2,6-dichlorophenyl)-3-trifluoromethyl-1H-pyrazole as a white solid (2.2 g, 94%). $^1$H-NMR (CDCl$_3$): δ 7.47-7.41 (m, 4H), 7.36-7.33 (m, 1H), 7.17 (d, 2H), 5.93 (s, 1H), 5.08 (s, 2H), MS (ESI): 467[M+H]$^+$.

The following compounds are prepared essentially according to the previous examples:

5-(4-bromo-2-fluorobenzyloxy)-1-(2,6-dichlorophenyl)-3-trifluoromethyl-1H-pyrazole MS (ESI): 488 [M+H]$^+$.

Example 12b

Preparation of J-(2,6-dichlorophenyl)-5-(3'-methanesulfonylbiphenyl-4-ylmethoxy)-3-trifluoromethyl-1H-pyrazole

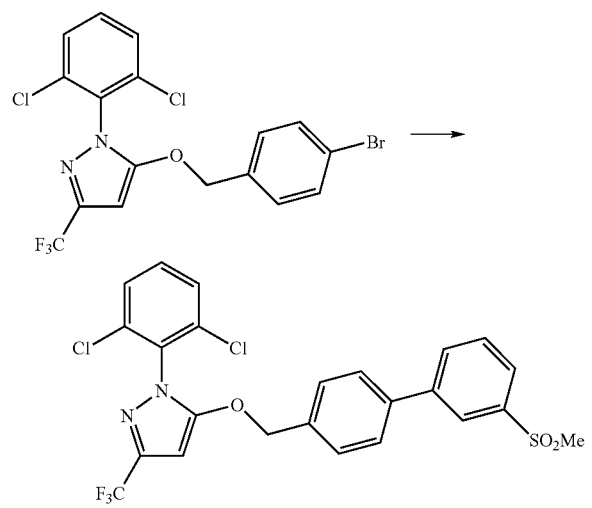

A mixture of 5-(4-bromobenzyloxy)-1-(2,6-dichlorophenyl)-3-trifluoromethyl-1H-pyrazole (940 mg, 2 mmol) 3-methylsulfonylboronic acid (600 mg, 3 mmol), Na$_2$CO$_3$ (640 mg, 6 mmol) tetrakistriphenylphosphine palladium (0) (240 mg, 0.207 mmol) in dioxane-H$_2$O (10:1, 33 mL) was stirred at 85° C. under N$_2$ for 10 h. The reaction mixture was concentrated in vacuo, and the residue was partitioned between EtOAc and H$_2$O. The organic phase was washed with brine, dried (Na$_2$SO$_4$), and concentrated in vacuo. The residue was purified by silica gel flash chromatography (40% EtOAc/hexanes) to give 1-(2,6-dichlorophenyl)-5-(3'-methanesulfonylbiphenyl-4-ylmethoxy)-3-trifluoromethyl-1H-pyrazole as a white solid (415 mg, 38%). $^1$H NMR (400 MHz, CDCl$_3$): δ 8.14 (t, 1H), 7.94-7.92 (m, 1H), 7.87-7.84 (m, 1H), 7.67-7.61 (m, 3H), 7.48-7.34 (m, 5H), 5.97 (s, 1H), 5.22 (s, 2H), 3.09 (s, 3H). MS (ESI): 541 [M+H]$^+$.

The following compounds are prepared essentially according to the previous examples:
1-(2,6-dichlorophenyl)-5-(3-fluoro-3'-methanesulfonylbiphenyl-4-ylmethoxy)-3-trifluoromethyl-1H-pyrazole MS (ESI): 559 [M+H]$^+$.

Scheme 13

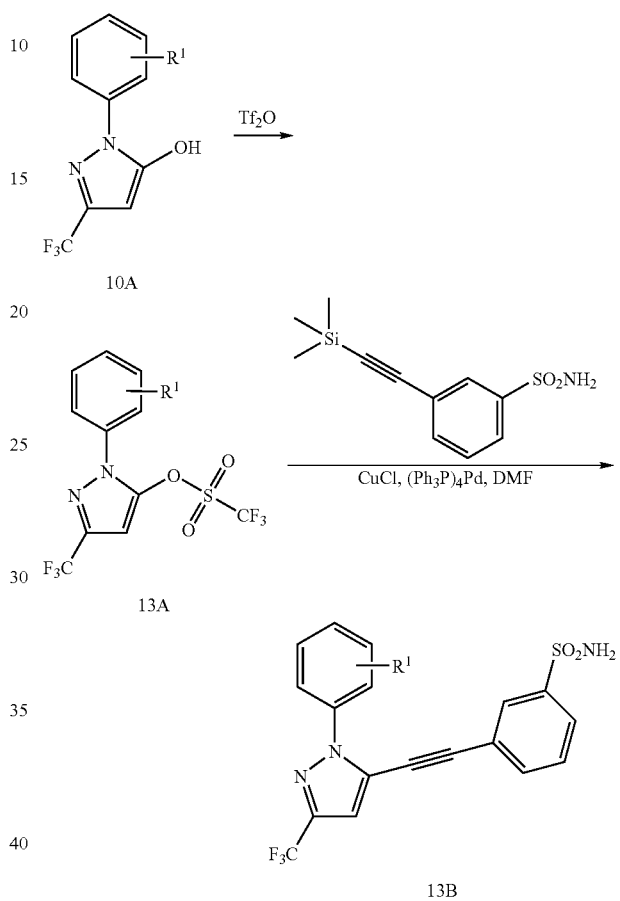

As described with Scheme 13, pyrazol-3-yl trifluoromethanesulfonate 13A can be coupled directly to TMS-alkynes under the catalysis of Cu(I) Cl and Pd(0) to introduce a triple bond in the molecule. 10A was treated with trifluoromethanesulfonic anhydride to afford trifluoromethanesulfonate 13A, which coupled with TMS-alkyne to afford aryl alkynyl pyrazole 13B.

Example 13

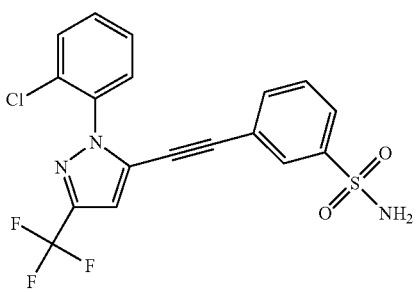

3-[2-(2-Chloro-phenyl)-5-trifluoromethyl-2H-pyrazol-3-ylethynyl]-benzenesulfonamide

Example 13a

Preparation of Trifluoromethanesulfonic acid 2-(2-chlorophenyl)-5-trifluoromethyl-2H-pyrazol-3-yl ester

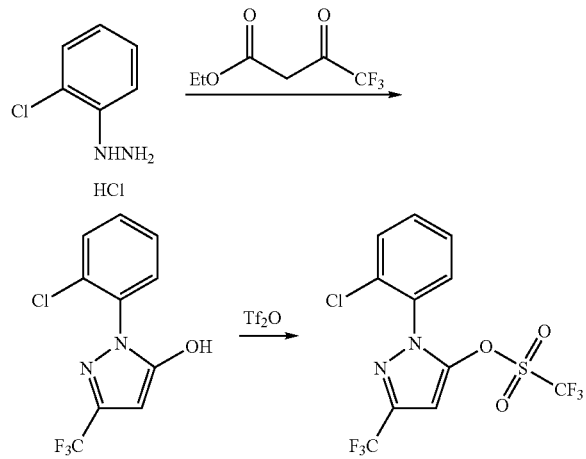

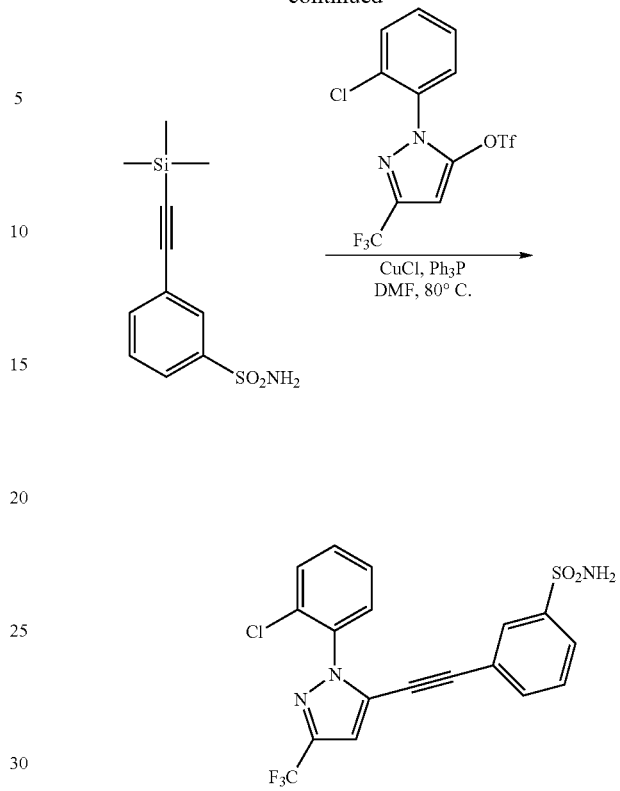

Into a 50 mL flask was weighed 1.01 g (3.84 mmol) of oxo-pyrazole, 1.06 g of 2,6-Di-tert-butyl-4-methyl-pyridine (5.16 mmol), and 10 mL of dichloromethane. The resulting solution was cooled to 0° C. in an ice bath and trifluoromethane sulfonic anhydride (800 µL) was added. The reaction was allowed to warm to room temperature and after 3 h the reaction was washed into a separatory funnel with saturated sodium bicarbonate and ethyl acetate. The ethyl acetate was separated, washed with brine, was dried (Na$_2$SO$_4$), and concentrated in vacuo. The residue was purified by silica gel flash chromatography (Jones Flashmaster, 70 g Silica gel, gradient elution from 100% hexanes to 20% ethyl acetate over 30 minutes). Appropriate fractions were combined and concentrated in vacuo to afford the product trifluoromethanesulfonic acid 2-(2-chlorophenyl)-5-trifluoromethyl-2H-pyrazol-3-yl ester as a colorless solid, yield: 662.5 mg (44%). $^1$H NMR (CDCl$_3$): δ 7.60 (d, J=8 Hz, 1H), 7.4-7.6 (m, 3H), 6.61 (s, 1H).

Example 13b

Preparation of 3-[2-(2-Chloro-phenyl)-5-trifluoromethyl-2H-pyrazol-3-ylethynyl]-benzenesulfonamide

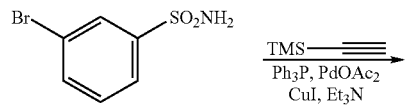

Into a sealable tube was weighed 1.24 g of 3-bromophenylsulfonamide, 112 mg of triphenylphosphine, 40 mg of palladium acetate, 32 mg of copper (I) iodide, and 5 mL of triethylamine. To this suspension was added 2.0 mL of trimethylsilylacetylene and the vessel was sealed, was set in an oil bath, and was rapidly stirred at 90-95 0C. After 1 h the reaction was cooled, unsealed, and was filtered with added ethyl acetate to remove solids. The filtrate was concentrated in vacuo and the residue was purified by silica gel flash chromatography (Jones Flashmaster, 50 g silica gel, gradient elution from 100% hexanes to 20% ethyl acetate over 30 minutes). Appropriate fractions were combined and concentrated in vacuo affording 3-trimethylsilanylethynyl-benzenesulfonamide as a faintly yellow semi-crystalline solid, yield: 908.3 mg (68%). $^1$H NMR (CDCl$_3$): δ 8.02 (s, 1H), 7.85 (d, J=8 Hz, 1H), 7.64 (d, J=8 Hz, 1H), 7.48 (t, J=8 Hz, 1H), 5.02 (br s, 2H), 0.26 (s, 9H). Into a 50 mL flask was weighed 423.7 mg of trifluoromethanesulfonic acid 2-(2-chlorophenyl)-5-trifluoromethyl-2H-pyrazol-3-yl ester (1.07 mmol), 325.6 mg (1.28 mmol) of alkyne, 26.5 mg of copper (I) chloride, and 69.3 mg (600 µmol) of triphenylphosphine, followed by 5 mL of DMF. The reaction was heated at 80-85 0C for 5 h then was quenched by addition of 3 M HCl. The reaction mixture was washed into a separatory funnel with ethyl acetate and 3.0 M HCl. The ethyl acetate was separated, washed with brine, was dried (Na$_2$SO$_4$), and concentrated in vacuo. The residue was purified by silica gel flash chromatography (Jones Flashmaster, 50 g silica gel, gradient elution from 100% hexanes to 40% ethyl acetate over 30 minutes). Appropriate fractions were combined and concentrated in vacuo affording the product as a grayish powder, yield: 78.4 mg (17%); $^1$H NMR (CDCl$_3$): δ 7.89 (m, 1H), 7.84 (s, 1H), 7.60 (d, J=8 Hz, 1H), 7.35-7.6 (m, 5H), 6.94 (s, 1H), 4.82 (s, 2H); MS (ES): 426 [M+H]$^+$.

Scheme 14

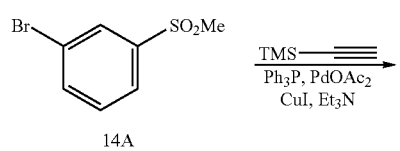

14A

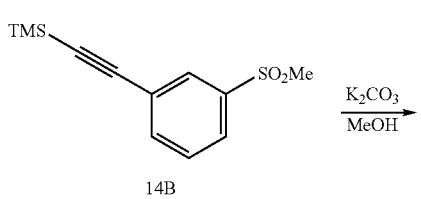

14B

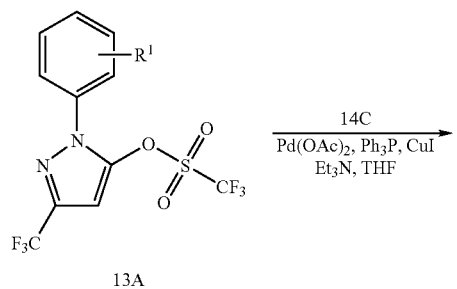

14C

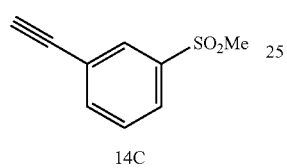

13A

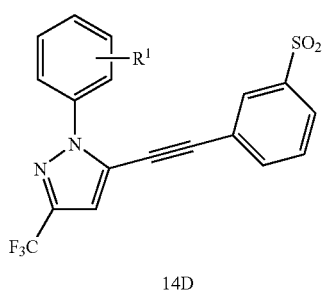

14D

As described with Scheme 14, aryl alkynyl pyrazole 14D can also be prepared via the coupling of pyrazol-3-yl trifluoromethanesulfonate 14A with terminal alkynes under the catalysis of Cu(I)I and Pd(II). Alkyne 14B was prepared via coupling of aryl bromides 14A with trimethylsilyl ethyne and the trimethylsilyl group was removed by treatment with potassium carbonate in methanol to afford terminal alkyne 14C. Coupling of triflate 13A with alkyne 14C afforded aryl alkynyl pyrazole 14D.

Example 14

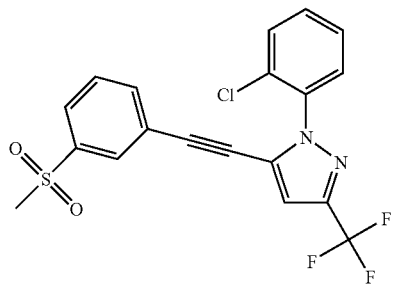

1-(2-Chloro-phenyl)-5-(3-methanesulfonyl-phenyl-ethynyl)-3-trifluoromethyl-1H-pyrazole

Example 14a

Preparation of 1-Ethynyl-3-methanesulfonyl-benzene

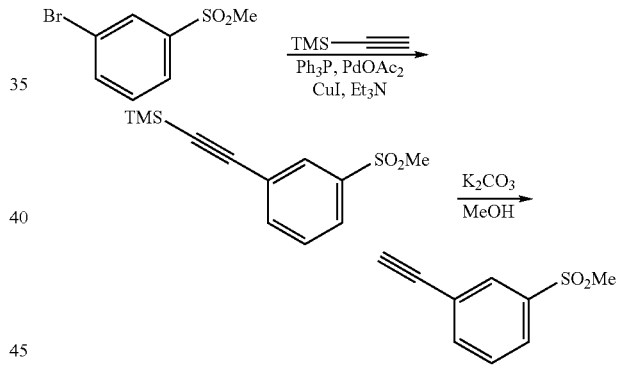

Into a sealable tube was weighed 2.06 g (8.76 mmol) of 1-bromo-3-methanesulfonyl-benzene, 93 mg of palladium acetate, 122 mg of triphenylphosphine, 79 mg of copper (I) iodide, 10.0 mL of triethylamine, and 2.0 mL of trimethylsilylacetylene. The reaction vessel was sealed and was heated at 80-85° C. for 1 h then was filtered of solids with added ethyl acetate. The filtrate was concentrated in vacuo and was purified by silica gel flash chromatography (Jones Flashmaster, 50 g Silica gel, gradient elution from 100% hexanes to 40% ethyl acetate over 30 minutes). Appropriate fractions were combined and concentrated in vacuo affording (3-methanesulfonyl-phenylethynyl)-trimethylsilane as a faintly yellow oil, yield: 1.60 g (72%). $^1$H NMR (CDCl$_3$): δ 8.04 (s, 1H), 7.88 (d, J=8 Hz, 1H), 7.71 (d, J=8 Hz, 1H), 3.05 (s, 3H), 0.27 (s, 9H).

The TMS-acetylene 1.58 g (626 μmol) was treated with 1.02 g of potassium carbonate and 10.0 mL of methanol. The resulting suspension was stirred at room temperature for 3 h then was concentrated to remove methanol. The residue was washed into a separatory funnel with ethyl acetate and water.

The ethyl acetate was separated, washed with ammonium chloride, brine, was dried (Na₂SO₄), and concentrated in vacuo. The residue was purified by silica gel flash chromatography (Jones Flashmaster, 50 g Silica gel, gradient elution from 100% hexanes to 40% ethyl acetate over 30 minutes). Appropriate fractions were combined and concentrated in vacuo affording 1-Ethynyl-3-methanesulfonyl-benzene as a cream colored solid, yield: 977 mg (86.6%). ¹H NMR (CDCl₃): δ 8.07 (s, 1H), 7.92 (d, J=8 Hz, 1H), 7.75 (d, J=8 Hz, 1H), 7.55 (t, J=8 Hz, 1H), 3.22 (s, 1H), 3.06 (s, 3H).

Example 14b

Preparation of 1-(2-Chlorophenyl)-5-(3-methanesulfonylphenylethynyl)-3-trifluoromethyl-1H-pyrazole

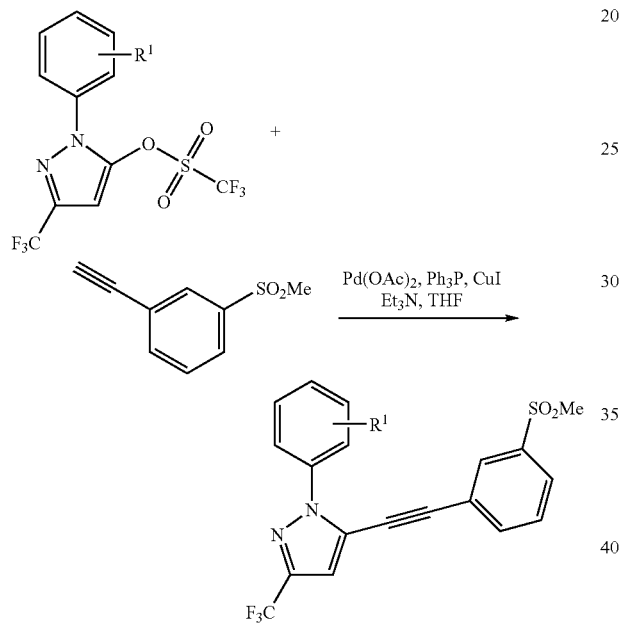

Into an 8 mL vial was weighed 428 mg of trifluoromethanesulfonic acid 2-(2-chlorophenyl)-5-trifluoromethyl-2H-pyrazol-3-yl ester (1.08 mmol), 201 mg (1.12 mmol) of acetylene, 35 mg of palladium acetate, 59.5 mg of triphenylphosphine, 31 mg of copper (I) iodide, and 3 mL of triethylamine. The resulting suspension was heated at 90° C. for 1 hr then was filtered through celite with added ethyl acetate. The filtrate was concentrated in vacuo and was purified by silica gel flash chromatography (Jones Flashmaster, 50 g Silica gel, gradient elution from 100% hexanes to 40% ethyl acetate over 40 minutes). Appropriate fractions were combined and concentrated in vacuo affording the product as a cream colored semi-solid, yield: 196.9 mg (43%); ¹H NMR (CDCl₃): δ 7.90 (d, J=8 Hz, 1H), 7.85 (s, 1H), 7.61 (d, J=8 Hz, 1H), 7.46-7.56 (m, 5H), 6.95 (s, 1H), 3.04 (s, 3H); MS (ES): 425 [M+H]⁺.

The following compounds are prepared essentially according to the previous examples:

1-(2-chlorophenyl)-5-{[4-(methylsulfonyl)phenyl]ethynyl}-3-(trifluoromethyl)-1H-pyrazole; MS (ES): 424 [M+H]⁺.

1-(2-chlorophenyl)-5-({4-[(methylsulfonyl)methyl]phenyl}ethynyl)-3-(trifluoromethyl)-1H-pyrazole; MS (ES): 439 [M+H]⁺.

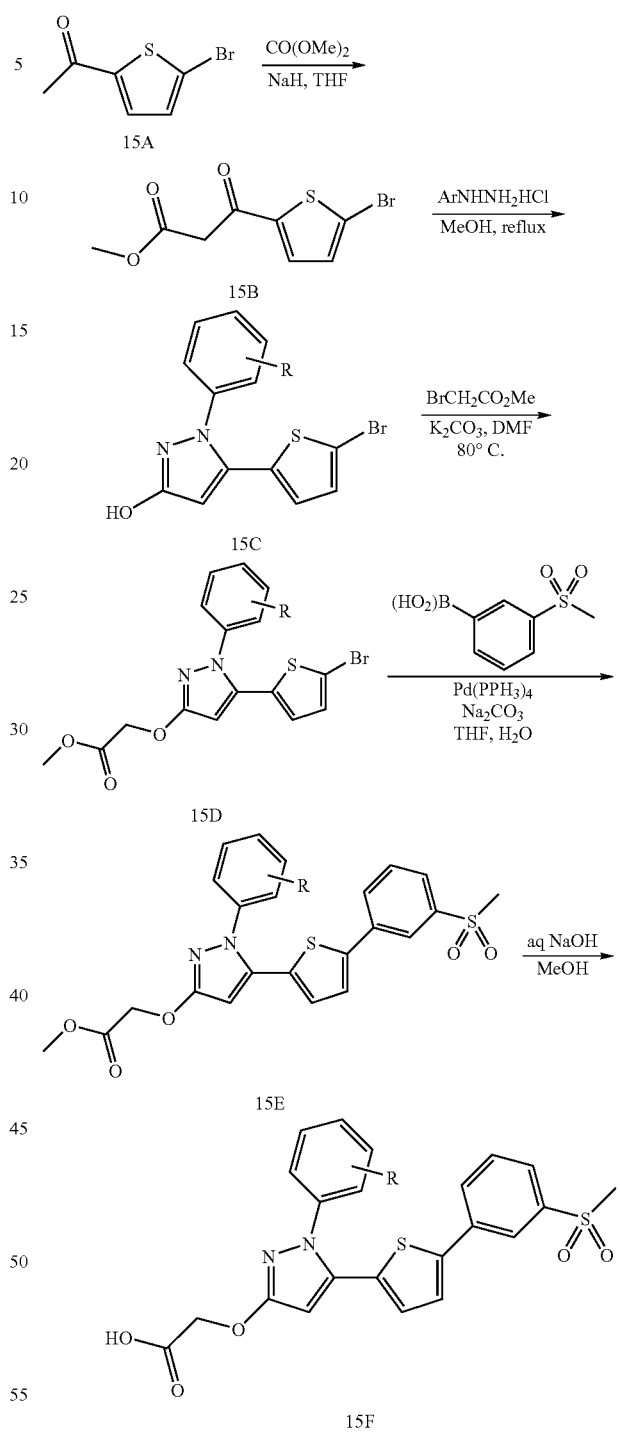

Scheme 15

As depicted in Scheme 15, pyrazole-3-ol (15C) was prepared via the condensation of ketoester 15B with a hydrazine and then was alkylated to afford ether analogs. β-ketoester 15B was prepared by treating 1-(5-bromo-thiophen-2-yl)ethanone 15A with dimethyl carbonate in the presence of NaH. The resulting O-ketoester 15B and a hydrazine hydrochloride was heated to reflux in MeOH to give a mixture of 1H-pyrazole-3-ol 15C and the corresponding 3-methoxy-1H-pyrazole, which can be separated by chromatography. 15C reacted with methyl bromoacetate in the presence of K₂CO₃ in DMF to give [1H-pyrazol-3-yloxy]-acetic acid methyl ester 15D, which was treated with 3-methanesulfonylphenylboronic acid in the presence of Pd (PPh₃)₄ and aq Na₂CO₃ in THF to give Suzuki coupling product 15E. Ester 15E was hydrolyzed with aq NaOH in MeOH to afford acid 15F.

Example 15

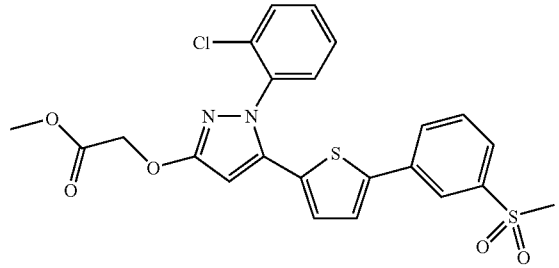

1-(2-chloro-phenyl)-5-[5-(3-methanesulfonyl-phenyl)-thiophen-2-yl]-3-methoxy-1H-pyrazole

Example 15a

Preparation of 3-(5-bromo-thiophen-2-yl-3-oxo-propionic acid methyl ester

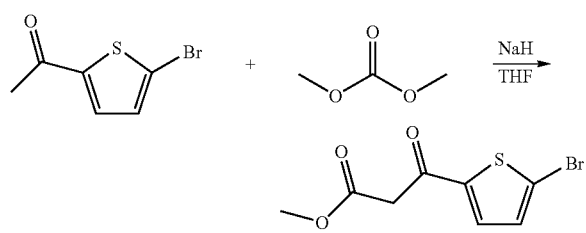

To a solution of dimethyl carbonate (33.67 mL, 400 mmol) in anhydrous THF (200 mL) was added NaH (12.0 g, 300 mmol, 60% dispersion), which was pre-washed with anhydrous hexane. A solution of 1-(5-bromo-thiophen-2-yl)ethanone (20.51 g, 10 mmol) in THF was added dropwise via an additional funnel. The reaction mixture was stirred under nitrogen atmosphere for overnight. The reaction mixture was cooled off with an ice water bath and quenched with water and acidified to pH 3 with 6.0 M HCl. The organic layer was separated from the aqueous layer, which was washed with DCM three times. The combined organic layer was dried over anhydrous Na₂SO₄ and concentrated, resulting in the product 3-(5-bromo-thiophen-2-yl-3-oxo-propionic acid methyl ester (25.8 g, 98% yield) as dark brown oil. The crude β-ketoester product was relatively pure by analysis of the ¹H NMR spectrum. ¹H-NMR (CDCl₃): δ 7.48 (d, J=4.1 Hz, 1H), 7.13 (d, J=4.1 Hz, 1H), 3.87 (s, 2H), 3.75 (S, 3H).

Example 15b

Preparation of 5-(5-bromo-thiophene-2-yl)-1-(2-chloro-phenyl)-1H-pyrazole-3-ol

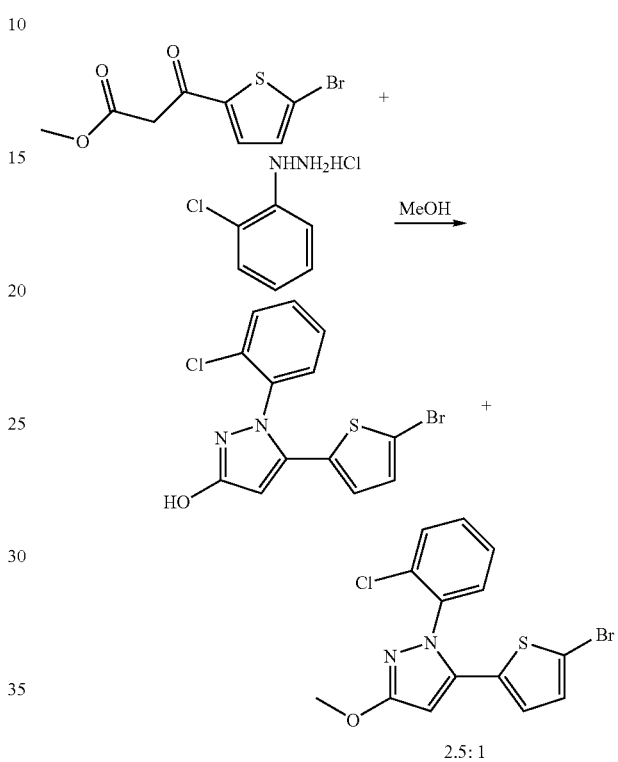

2.5 : 1

To a solution of 3-(5-bromo-thiophen-2-yl-3-oxo-propionic acid methyl ester (2.0 g, 7.60 mmol) in 1.2 M HCl in MeOH (20 mL) was added 2-chlorophenylhydrazine hydrochloride (1.43 g, 7.98 mmol). The reaction mixture was heated to reflux for 4 hours and cooled off. The solvent was evaporated and the residue was purified by flash column chromatography with 10% ethyl acetate in hexane. The product 5-(5-bromo-thiophene-2-yl)-1-(2-chloro-phenyl)-1H-pyrazole-3-ol was recovered as a white solid (1.89 g, 70% yield. MS (ES): 355 [M+H]⁺.

Example 15c

Preparation of [5-(5-bromo-thiophene-2-yl)-1-(2-chloro-phenyl)-1H-pyrazol-3-yloxy]-acetic acid methyl ester

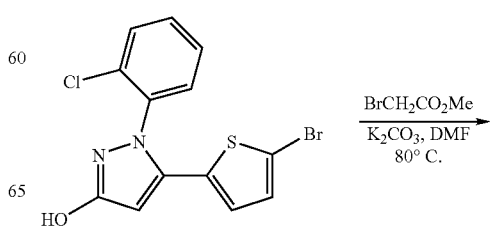

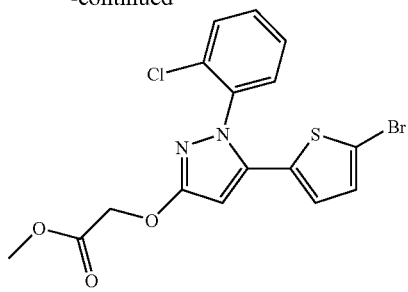

To a solution of 5-(5-bromo-thiophene-2-yl)-1-(2-chloro-phenyl)-1H-pyrazole-3-ol (2.21 g, 6.21 mmol) in anhydrous DMF was added K₂CO₃ (1.72 g, 12.43 mmol) and methyl bromoacetate (1.2 mL, 12.43 mmol). The reaction mixture was heated at 80° C. under nitrogen atmosphere overnight. Evaporate the solvent and the residue was dissolved in DCM and it was passed through a short pad of celite. The solvent was concentrated and the crude product was purified by flash column chromatography (20% ethyl acetate in hexane), resulting in the product of [5-(5-bromo-thiophen-2-yl)-1-(2-chloro-phenyl)-1H-pyrazol-3-yloxy]-acetic acid methyl ester (2.36 g, 89% yield).

Example 15d

Preparation of methyl {1-(2-chloro-phenyl)-5-[5-(3-methanesulfonyl-phenyl)-thiophen-2-yl]-1H-pyrazol-3-yloxy}acetate

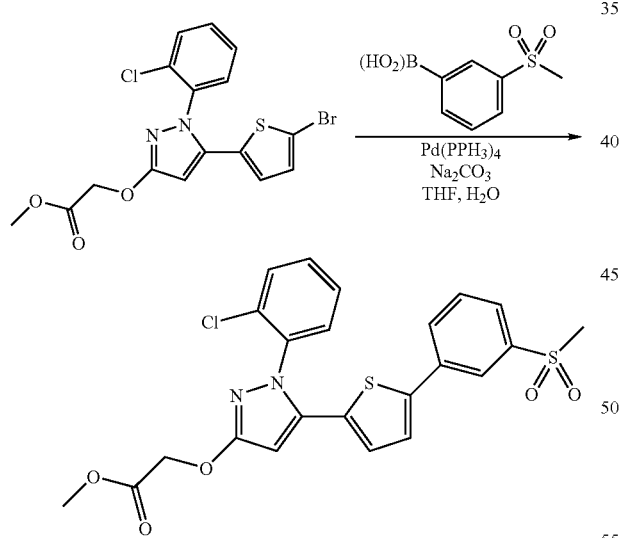

To a solution of [5-(5-bromo-thiophen-2-yl)-1-(2-chloro-phenyl)-1H-pyrazol-3-yloxy]-acetic acid methyl ester (1.43 g, 3.33 mmol) in anhydrous THF (13.0 mL) was added sequentially 3-methylsulfonylphenylboronic acid (0.80 g, 4.0 mmol), Pd(PPh₃)₄ (192 mg, 0.17 mmol), Na₂CO₃ (1.06 g, 10.0 mmol) and water (1.0 mL). The reaction mixture was heated to reflux at 70° C. for overnight. The solvent was evaporated and the crude residue was purified by flash column chromatography with 50% ethyl acetate in hexane, resulting the product methyl {1-(2-chloro-phenyl)-5-[5-(3-methanesulfonyl-phenyl)-thiophen-2-yl]-1H-pyrazol-3-yloxy}acetate (0.746 g, 45% yield). ¹H-NMR (CDCl₃): δ 8.17 (m, 1H), 7.83 (m, 2H), 7.55 (m, 3H), 7.40 (m, 3H), 7.33 (m, 1H), 5.91 (s, 1H), 4.70 (s, 2H), 3.81 (s, 3H), 3.09 (s, 3H). MS (ES): 503 [M+H]⁺.

The following compounds are prepared essentially according to the previous examples:

1-(2-chloro-phenyl)-5-[5-(3-methanesulfonyl-phenyl)-thiophen-2-yl]-3-methoxy-1H-pyrazole. ¹H-NMR (CDCl₃): δ 8.18 (m, 1H), 7.84 (m, 1H), 7.82 (m, 1H), 7.57 (m, 1H), 7.51 (m, 2H), 7.41-7.35 (m, 4H), 5.96 (s, 1H), 3.96 (s, 3H), 3.09 (s, 3H). MS (ES): 445 [M+H]⁺.

Example 16

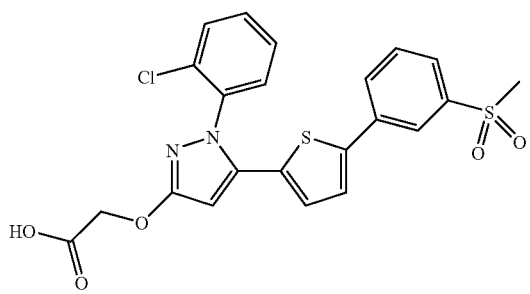

{1-(2-R-phenyl)-5-[5-(3-methanesulfonyl-phenyl)-thiophen-2-yl]-1H-pyrazole-3-yloxy}-acetic acid Preparation of {1-(2-R-phenyl)-5-[5-(3-methanesulfonyl-phenyl)-thiophen-2-yl]-1H-pyrazole-3-yloxy}-acetic acid

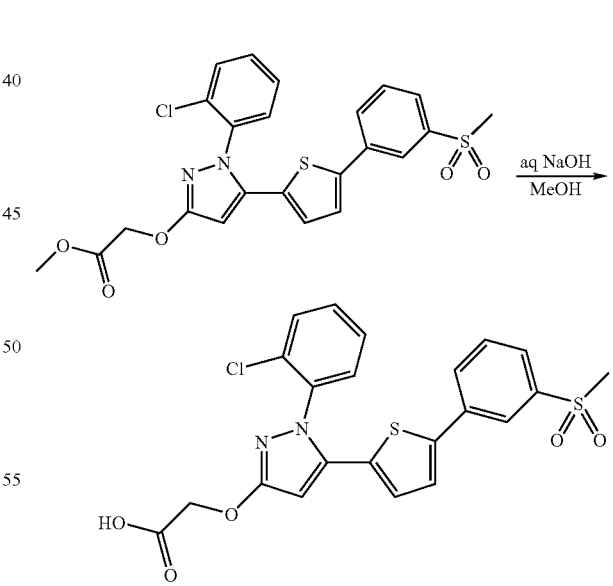

To a solution of methyl {1-(2-chloro-phenyl)-5-[5-(3-methanesulfonyl-phenyl)-thiophen-2-yl]-1H-pyrazol-3-yloxy}-acetate (90 mg, 0.18 mmol) in MeOH (8.0 mL) was added NaOH (14.3 mg, 0.36 mmol) and water (2.0 mL). The reaction mixture was stirred at room temperature for 4 hours. Evaporate the solvent and the mixture was adjust to weakly acidic with 1.0 M HCl and extract with DCM. The organic phase was separated and dried over anhydrous Na₂SO₄. Evaporation of the solvent provided the product {1-(2-R-phenyl)-5-[5-(3-methanesulfonyl-phenyl)-thiophen-2-yl]-1H-pyrazole-3-yloxy}-acetic acid (70 mg, 80% yield).). ¹H-NMR (Acetone-d6): δ 8.20 (m, 1H), 8.00 (m, 1H), 7.86 (m, 1H) 7.65 (m, 4H), 7.55 (m, 2H), 7.48 (m, 1H), 6.34 (s, 1H), 4.88 (s, 2H), 3.20 (s, 3H). MS (ES): 489 [M+H]⁺.

1-{1-(2-chloro-phenyl)-5-[5-(3-methanesulfonyl-phenyl)-thiophen-2-yl]-1H-pyrazole-3-yloxy}-2-methyl-propan-2-ol Preparation of 1-{1-(2-chloro-phenyl)-5-[5-(3-methanesulfonyl-phenyl)-thiophen-2-yl]-1H-pyrazole-3-yloxy}-2-methyl-propan-2-ol

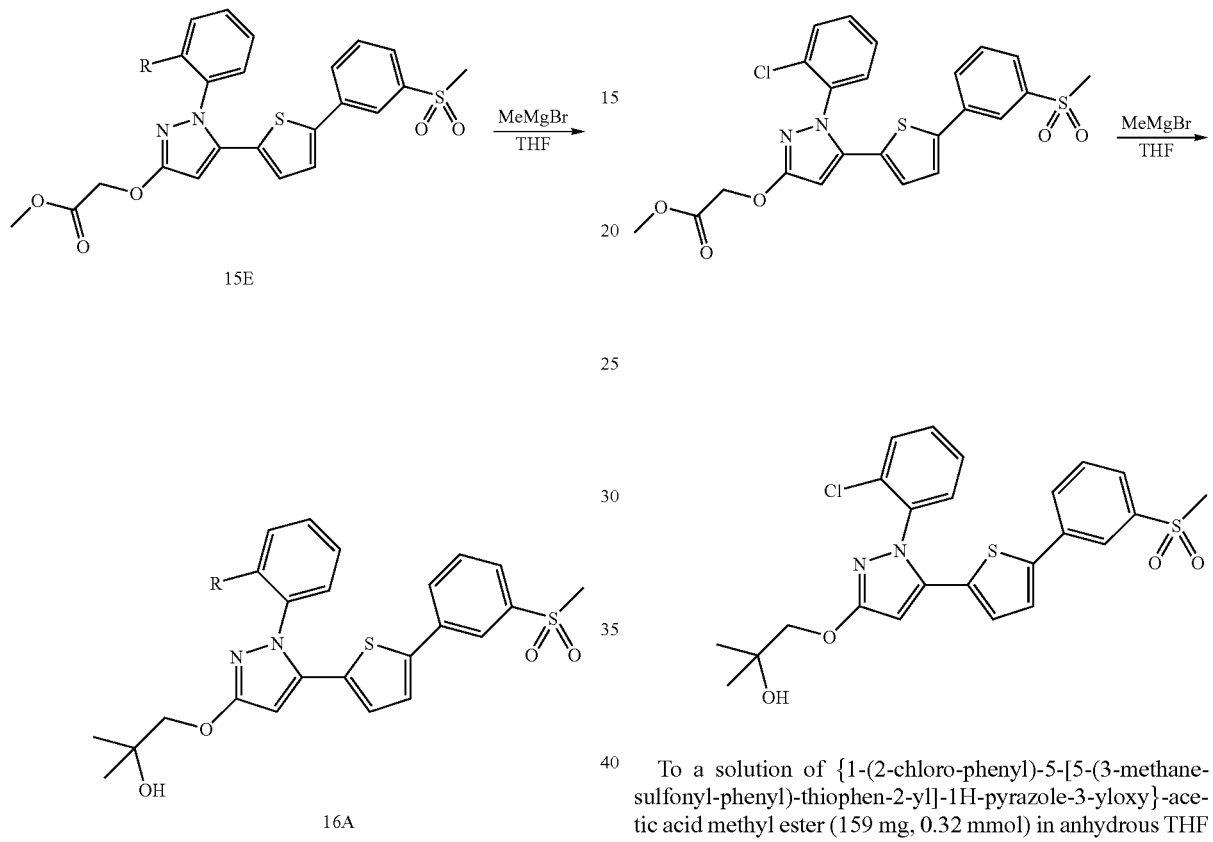

As depicted in Scheme 15, Ester 15E also treated with MeMgBr in THF to afford Carbinol 16A.

Example 17

To a solution of {1-(2-chloro-phenyl)-5-[5-(3-methanesulfonyl-phenyl)-thiophen-2-yl]-1H-pyrazole-3-yloxy}-acetic acid methyl ester (159 mg, 0.32 mmol) in anhydrous THF (5.0 mL) was added a solution of MeMgBr (0.26 mL, 3.0 M) in diethyl ether. The reaction mixture was stirred under nitrogen atmosphere for 4 hours. The mixture was quenched was aq NH₄Cl and extracted with ethyl acetate. The organic layer was separated and dried over anhydrous Na₂SO₄. Evaporation of the solvent provided 1-{1-(2-chloro-phenyl)-5-[5-(3-methanesulfonyl-phenyl)-thiophen-2-yl]-1H-pyrazole-3-yloxy}-2-methyl-propan-2-ol (92 mg, 58% yield). ¹H-NMR (CDCl₃): δ 8.07 (m, 1H), 7.87 (m, 1H), 7.73 (m, 1H), 7.59 (m, 1H), 7.49 (m, 4H), 7.40 (m, 1H), 7.34 (m, 1H), 5.49 (s, 1H), 3.89 (s, 2H), 3.59 (s, 1H), 3.07 (s, 3H), 1.06 (s, 6H). MS (ES): 503 [M+H]⁺.

-continued

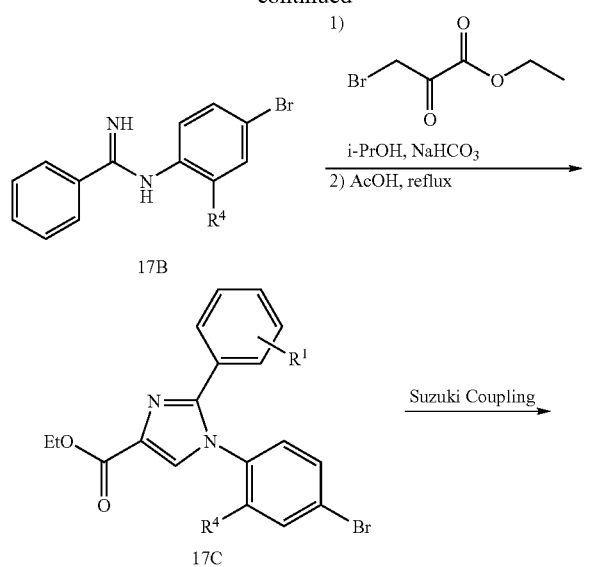

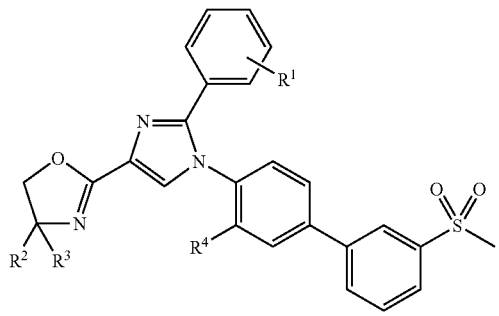

17G

As depicted in Scheme 17, imidazole-oxazolines templates 17G were prepared via cyclization of 2-hydroxyethylamide analogue 17F using known methodology. Aniline 17A was treated with trimethylaluminum followed by arylnitrile ($R^1$-PhCN) to afford amidine 17B. The resulting amidine intermediate was reacted with ethyl-bromopyruvate in the presence of a base followed by a dehydration step to form the imidazole product 17C. Suzuki coupling of 17C with a boronic acid afforded 17D. The ester group on 17D was hydrolyzed to afford the carboxylic acid derivative, which was treated with oxalyl chloride to yield acid chloride 17E. Acid chloride 17E was reacted with an ethanolamine derivative ($R^2R^3C(HN_2)CH_2OH$) to afford hydroxyethylamide 17F, which was cyclized in the presence of PPA to afford oxazoline (4,5-dihydro-oxazoles) 17G.

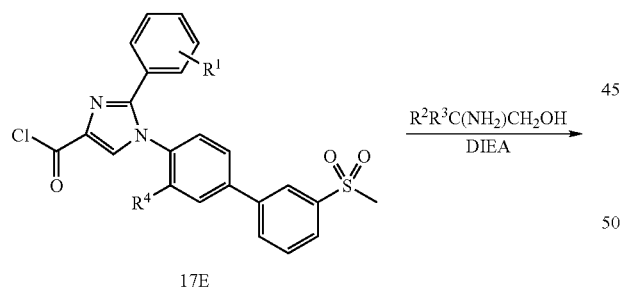

Example 18

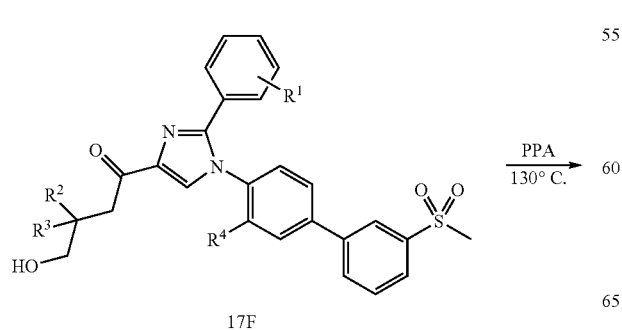

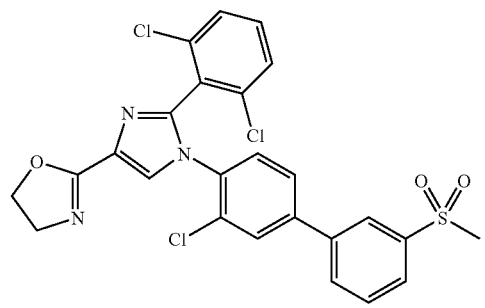

217

2-[1-(3-Chloro-3'-methanesulfonyl-biphenyl-4-yl)-2-(2,6-dichloro-phenyl)-1H-imidazol-4-yl]-4,5-dihydro-oxazole Example 18a Preparation of N-(4-Bromo-2-chloro-phenyl)-2,6-dichloro-benzamidine

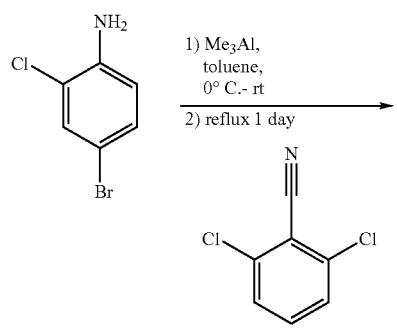

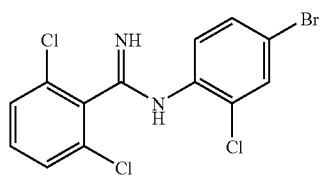

To a dry, N$_2$ purged 500 mL round bottom flask was added 4-bromo-2-choloroaniline (18.3 g, 88.6 mmol) and anhydrous toluene (100 mL). To the solution at 0° C. was added, dropwise, a 2.0 M solution of Me$_3$Al in toluene (58 mL). The solution was allowed to stir, warming to room temperature for approximately 1 hr. To the reaction solution was added 2,6-dichlorobenzonitrile (19.8 g, 115 mmol) in a toluene solution (50 mL). The reaction solution was allowed to stir at 90° C. for approximately 24 hrs. The reaction solution was allowed to cool to room temperature prior to quenching by pouring the reaction solution into an Erlenmeyer flask containing a 2:1 CHCl$_3$/MeOH solution and 200 g of silica. The slurry was allowed to stir 30 min prior to filtration into a Buchner funnel under vacuum. The filtrate was concentrated on the rotavapor and the resulting residue was reprecipitated using a 10:1 Hexane/Et$_2$O mixture. The resulting white precipitates were isolated by vacuum filtration to afford 28.3 g (84% yield) of N-(4-Bromo-2-chloro-phenyl)-2,6-dichloro-benzamidine. GCMS m/z=378, 380 [M+].

218

Example 18b

Preparation of J-(4-Bromo-2-chloro-phenyl)-2-(2,6-dichloro-phenyl)-1H-imidazole-4-carboxylic acid ethyl ester

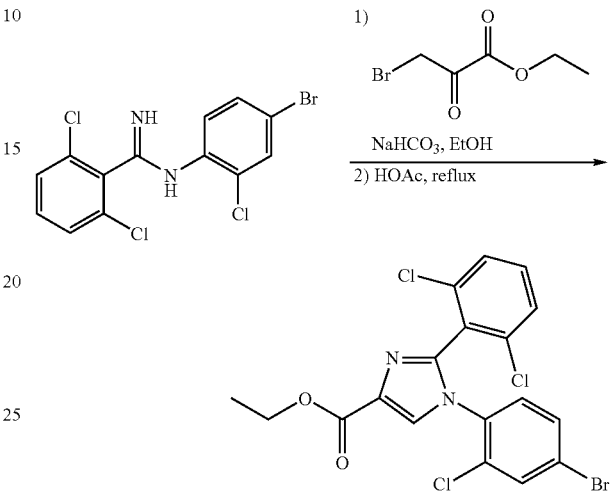

To a 500 mL round bottom flask attached with condenser was added N-(4-Bromo-2-chloro-phenyl)-2,6-dichloro-benzamidine (28.3 g, 74.7 mmol), ethyl 3-bromopyruvate (18.8 mL, 149 mmol), sodium bicarbonate (12.5 g, 149 mmol), and EtOH (180 mL). The reaction slurry was allowed to stir at reflux for 2.5 hrs. The reaction solution was decanted into a clean round bottom flask and concentrated in vacuo. The resulting residue was dissolved in acetic acid (120 mL), and the solution was allowed to stir at reflux for 1 hr. The cooled reaction solution was concentrated in vacuo, and the product residue was taken into EtOAc (250 mL) and washed with aq NaCl (200 mL×2) and aq NaHCO$_3$ (200 mL). The organic phase was partitioned, dried over Na$_2$SO$_4$, filtered, concentrated, and chromatographed through a SiO$_2$ column using a mobile gradient of 100% hexane to 70% EtOAc to afford 23.5 g (66% yield) of title compound. MS (ESI) 474.0, 476.0, 478.2 [M+H]$^+$.

Example 18c

Preparation of 1-(3-Chloro-3'-methanesulfonyl-biphenyl-4-yl)-2-(2,6-dichloro-phenyl)-1H-imidazole-4-carboxylic acid ethyl ester

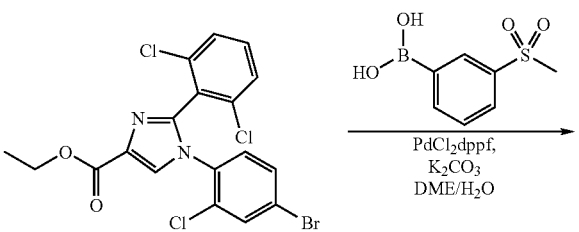

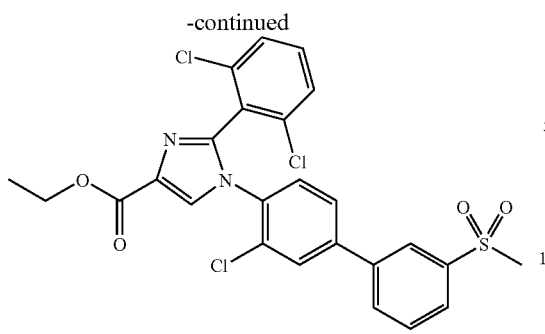

To a 2 L round bottom flask attached with condenser column and magnetic stir bar was added 1-(4-Bromo-2-chloro-phenyl)-2-(2,6-dichloro-phenyl)-1H-imidazole-4-carboxylic acid ethyl ester (21.1 g, 44.5 mmol), 3-methylsulfonylphenyl boronic acid (9.78 g, 48.9 mmol), $PdCl_2dppf$ (1.09 g, 3 mol %), $K_2CO_3$ (18.9 g, 137 mmol), 1,2-dimethoxyethane (250 mL) and $H_2O$ (50 mL). The reaction solution was allowed to stir at 80° C. for 2.5 hrs. The reaction solution was diluted with EtOAc (150 mL) and filtered through a Celite padded Buchner funnel to remove spent Pd. The filtrate was transferred to a separatory funnel and washed with aq $NH_4Cl$ (300 mL) and aq NaCl (200 mL). The organic phase was dried over $Na_2SO_4$, filtered, concentrated on the rotavapor and chromatographed through a 300 g $SiO_2$ column using a mobile phase gradient of 3% EtOAc to 100% EtOAc to afford 19.3 g (79% yield) of the title compound. MS (ESI) 549.3, 551.3, 553.3 $[M+H]^+$.

Example 18d

Preparation of 1-(3-Chloro-3'-methanesulfonyl-biphenyl-4-yl)-2-(2,6-dichloro-phenyl)-1H-imidazole-4-carboxylic acid

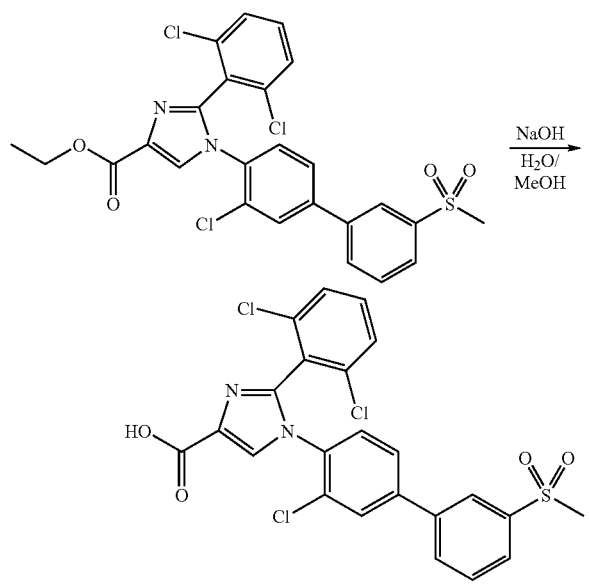

To a 250 mL round bottom flask was added 1-(3-Chloro-3'-methanesulfonyl-biphenyl-4-yl)-2-(2,6-dichloro-phenyl)-1H-imidazole-4-carboxylic acid ethyl ester (4.07 g, 7.40 mmol), MeOH (72 mL), and 2N aq NaOH (18.5 mL). The reaction solution was allowed to stir at 50° C. for 2 hr. The reaction solution was diluted with EtOAc (200 mL), neutralized by the addition of aq 1 N HCl, and poured into a separatory funnel. The organic phase was partitioned, and the aqueous phase was and extracted with EtOAc (150 mL×2). The combined organic phases were dried over $Na_2SO_4$, filtered into a round bottom flask and concentrated on the rotavapor. The crude residue was reprecipitated in an EtOAc/hexane solution and the solid precipitate was filtered under vacuum to afford 3.22 g (83% yield) of title product. MS (ESI) 521.3, 523.3, 525.3 $[M+H]^+$.

Example 18e

Preparation of 1-(3-Chloro-3'-methanesulfonyl-biphenyl-4-yl)-2-(2,6-dichloro-phenyl)-1H-imidazole-4-carboxylic acid (2-hydroxy-ethyl)-amide

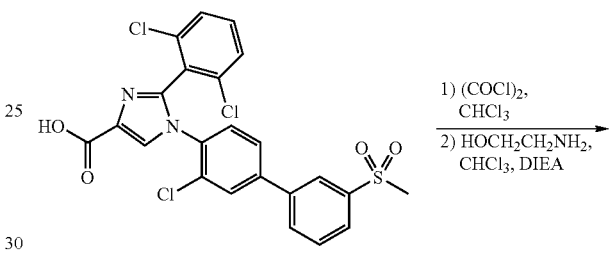

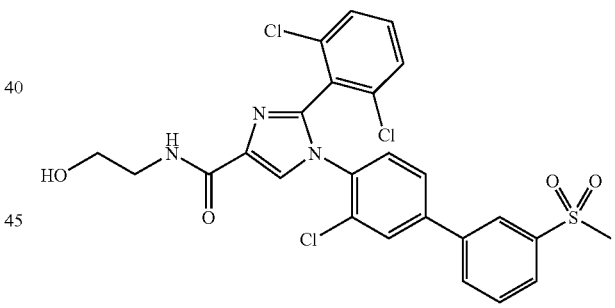

To a dry, $N_2$ purged 100 mL round bottom flask was added 1-(3-Chloro-3'-methanesulfonyl-biphenyl-4-yl)-2-(2,6-dichloro-phenyl)-1H-imidazole-4-carboxylic acid (730 mg, 1.39 mmol) and anhydrous $CHCl_3$ (15 mL). The solution was cooled to 0° C. prior to addition of oxalyl chloride (610 μL, 7.00 mmol) and several drops anhydrous DMF. The reaction solution was allowed to stir warming to r.t. over 1.5 hrs. The solvent and excess reagent was removed in vacuo. To the crude acid chloride residue was added anhydrous $CHCl_3$ (12 mL), ethanolamine (170 μL, 2.78 mmol) and DIEA (730 μL, 3.87 mmol). The reaction solution was allowed to stir at 50° C. for approx 1 hr. The reaction solution was diluted with DCM (120 mL) and transferred to a separatory funnel. The solution was washed with aq $NH_4Cl$ (50 mL×2) and with aq NaCl (50 mL). The organic phase was dried over $Na_2SO_4$, filtered, concentrated on the rotavapor and chromatographed through a 25 g $SiO_2$ column using a mobile phase gradient of

Example 18f

Preparation of 2-[1-(3-Chloro-3'-methanesulfonyl-biphenyl-4-yl)-2-(2,6-dichlorophenyl)-1H-imidazol-4-yl]-4,5-dihydro-oxazole

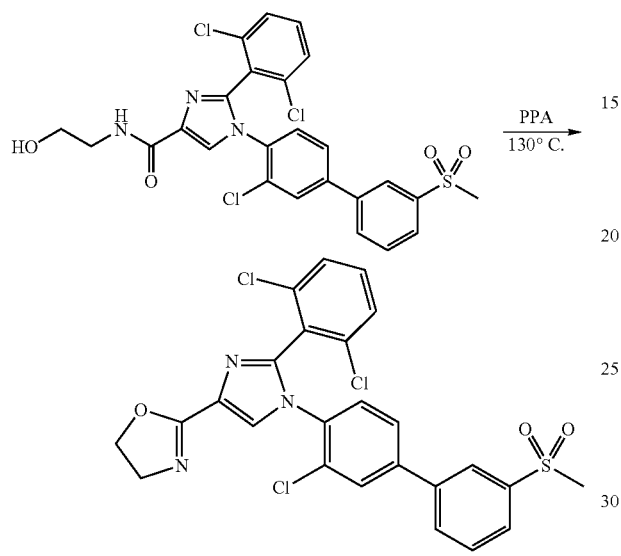

To a 40 mL glass vial containing 1-(3-Chloro-1'-methanesulfonyl-Diphenyl-4-yl)-2-(2,6-dichloro-phenyl)-1H-imidazole-4-carboxylic acid (2-hydroxy-ethyl)-amide (473 mg, 837 μmol) was added polyphosphoric acid (22.3 g, 115% $H_3PO_4$). The mixture was allowed to heat and stir at 130° C. for 2.5 hr. The reaction mixture was cooled to r.t. prior to addition of ice/$H_2O$ (400 mL). The aqueous reaction mixture was extracted with dichloromethane (50 mL×3). The organic phase was dried over $Na_2SO_4$, filtered and concentrated in vacuo. The crude product was chromatographed through a 25 g $SiO_2$ column using a gradient of 5% EtOAc to 100% EtOAc to afford 312 mg (68% yield) of title product. MS (ESI) 546.2, 548.2, 550.2 [M+H]$^+$; $^1$H NMR (400 MHz, DMSO-$d_6$): δ 8.21 (s, 2H), 8.15 (d, J=2 Hz, 1H), 8.08 (d, J=8 Hz, 1H), 7.94 (d, J=8 Hz, 1H), 7.80 (dd, J=2 Hz, $J_2$=8 Hz, 1H), 7.74 (t, J=8 Hz, 1H), 7.47-7.58 (m, 3H), 7.38 (d, J=8 Hz, 2H), 4.37 (t, J=10 Hz, 2H), 3.94 (t, J=10 Hz, 2H), 3.30 (s, 3H).

The following compounds are prepared essentially according to the previous examples:

2-[1-(3-Chloro-3'-methanesulfonyl-biphenyl-4-yl)-2-(2,6-dichloro-phenyl)-1H-imidazol-4-yl]-4,4-dimethyl-4,5-dihydro-oxazole; MS (ESI) 574.3, 576.3, 578.3 [M+H]$^+$;

2-[1-(3-Chloro-3'-ethanesulfonyl-biphenyl-4-yl)-2-(2,6-dichloro-phenyl)-1H-imidazol-4-yl]-4,4-dimethyl-4,5-dihydro-oxazole; MS (ESI) 588.2, 590.2, 592.2 [M+H]$^+$;

2-[1-(3-Chloro-3'-methanesulfonyl-biphenyl-4-yl)-2-(2,6-dichloro-phenyl)-1H-imidazol-4-yl]—, -methyl-4,5-dihydro-oxazole; MS (ESI) 560.2, 562.2, 564.2 [M+H]$^+$;

2-[1-(3-Chloro-3'-methanesulfonyl-biphenyl-4-yl)-2-(2,6-dichloro-phenyl)-1H-imidazol-4-yl]-4-methyl-4,5-dihydro-oxazole; MS (ESI) 560.2, 562.2, 564.2 [M+H]$^+$;

2-[2-(2,6-Dichloro-phenyl)-1-(3'-methanesulfonyl-biphenyl-4-yl)-1H-imidazol-4-yl]-4,4-dimethyl-4,5-dihydro-oxazole; MS (ESI) 540.2, 542.2 [M+H]$^+$;

Scheme 18

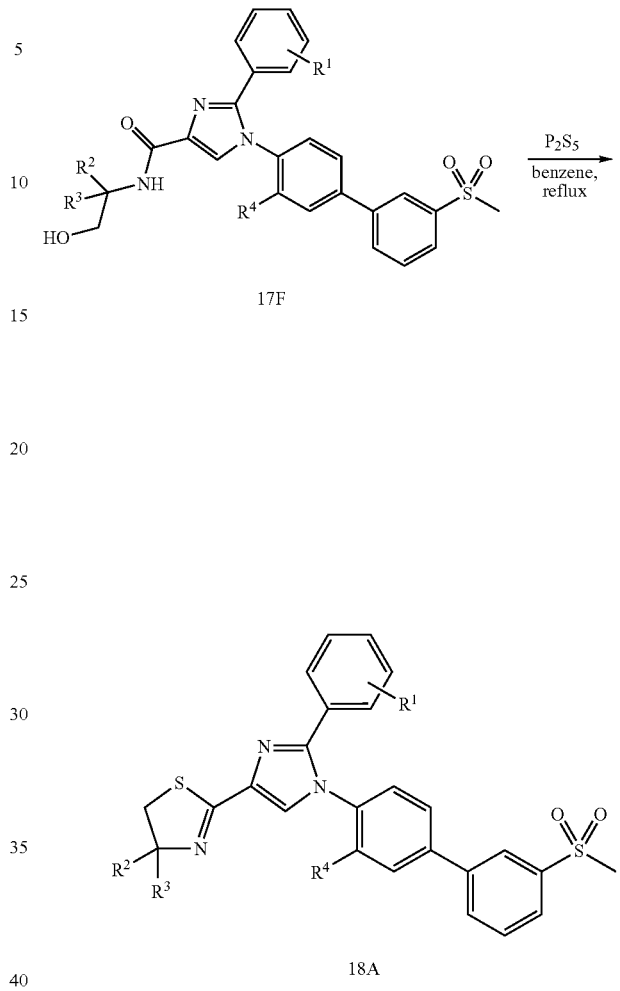

As depicted in Scheme 18, methods for the preparation of the thiazoline ring are known. By example, amide 17F was treated with phosphorus pentasulfide in refluxing benzene to synthesize the thiazoline analogue 18A.

Example 19

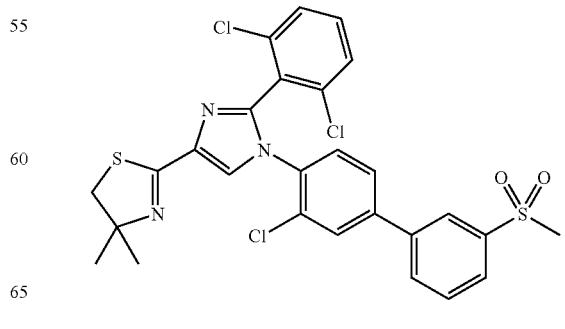

223

2-[1-(3-Chloro-3'-methanesulfonyl-biphenyl-4-yl)-2-(2,6-dichloro-phenyl)-1H-imidazol-4-yl]-4,4-dimethyl-4,5-dihydro-thiazole

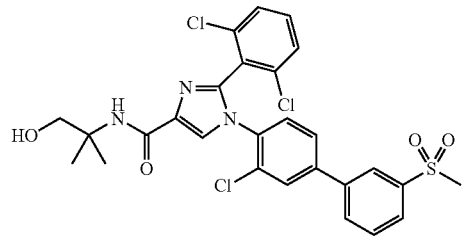

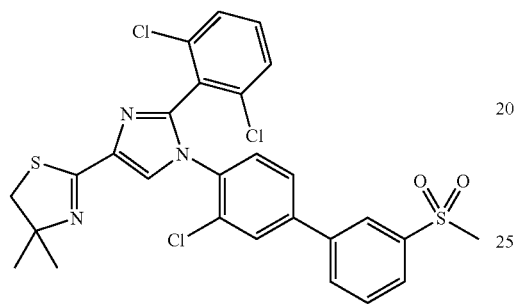

To a N₂ purged 50 mL round bottom flask attached with condenser was added 1-(3-Chloro-3'-methanesulfonyl-biphenyl-4-yl)-2-(2,6-dichloro-phenyl)-1H-imidazole-4-carboxylic acid (2-hydroxy-1,1-dimethyl-ethyl)-amide (140 mg, 236 μmol), anhydrous benzene (14 mL) and P₂S₅ (500 mg, 2.25 mmol). The reaction solution was stirred at reflux for 1 hr. The reaction solution was diluted with EtOAc (100 mL) and filtered through a Buchner funnel to remove excess P₂S₅. The filtrate was washed with aq. 0.1 N NaOH. The organic phase was partitioned, dried over Na₂SO₄, filtered, concentrated in vacuo, and chromatographed through a 25 g SiO₂ column using a gradient of 100% Hexane to 80% EtOAc to afford 24 mg (17% yield) of title compound. MS (ESI) 590.0, 592.0, 594.3 [M+H]⁺; ¹H NMR (400 MHz, DMSO-d₆) δ 8.27 (t, J=2 Hz, 1H), 8.21 (t, J=2 Hz, 1H), 8.17 (d, J=2 Hz, 1H), 8.14 (d, J=8 Hz, 1H), 8.10 (d, J=8 Hz, 1H), 7.99 (d, J=8 Hz, 1H), 7.95 (d, J=8 Hz, 1H), 7.78-7.85 (m, 2H), 7.74 (t, J=8 Hz, 1H), 7.49-7.61 (m, 3H), 7.43 (d, J=8 Hz, 1H), 3.36 (br s, 2H), 3.26 (s, 3H), 1.48 (s, 6H).

224

-continued

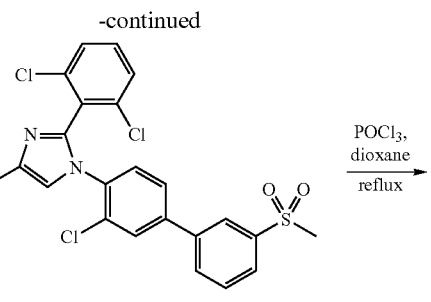

19A

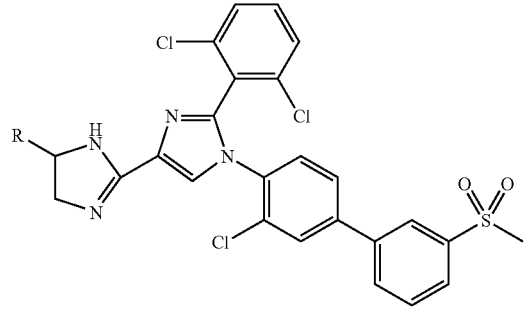

19B

As depicted in Scheme 18, methods to prepare the imidazoline ring from a precursor amide are known. By example, 2-aminoethylamide 19A, easily obtained from carboxylic acid 17E, was cyclized in the presence of phosphorous (III) oxytrichloride to synthesize the imidazoline analogue 19B.

Example 20

Scheme 19

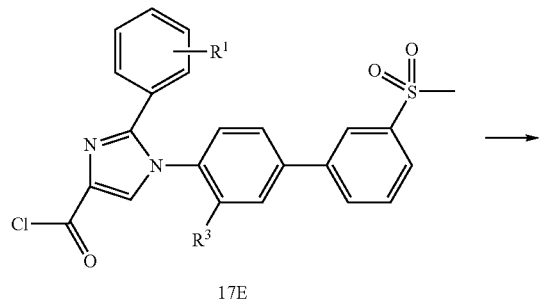

17E

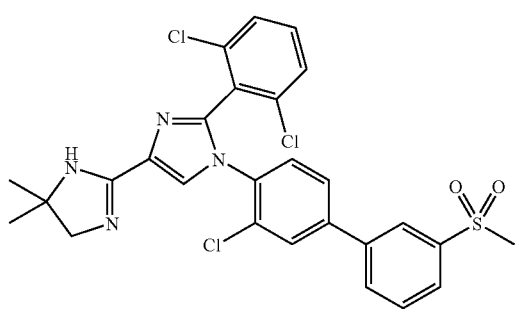

225

1'-(3-Chloro-3'-methanesulfonyl-biphenyl-4-yl)-2'-(2,6-dichloro-phenyl)-5,5-dimethyl-4,5-dihydro-1H,1'H-[2,4']biimidazolyl Preparation of 1'-(3-Chloro-3'-methanesulfonyl-biphenyl-4-yl)-2'-(2,6-dichloro-phenyl)-5,5-dimethyl-4,5-dihydro-1H,1'H-[2,4']biimidazolyl

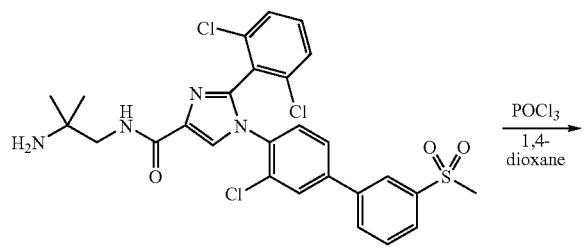

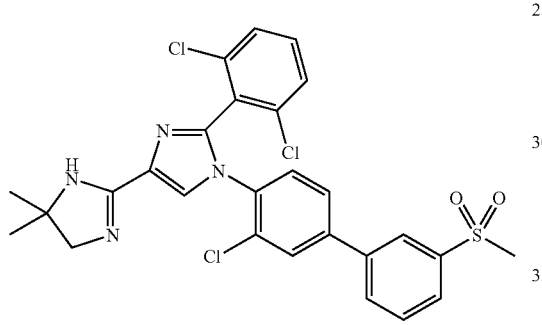

To a N₂ purged 100 mL round bottom flask attached with condenser was added 1-(3-Chloro-3'-methanesulfonyl-biphenyl-4-yl)-2-(2,6-dichloro-phenyl)-1H-imidazole-4-carboxylic acid (2-amino-2-methyl-propyl)-amide (590 mg, 1.00 mmol), POCl₃ (0.91 mL, 10 mmol) and anhydrous 1,4-dioxane (35 mL). The reaction solution was heated at reflux for 2 hrs. The cooled reaction mixture was added H₂O (50 mL) and the mixture as poured to a separatory funnel. To the mixture was added EtOAc (150 mL) and 1N aq. NaOH to raise the pH to 8. The aqueous phase was extracted with EtOAc (70 mL×2), and the combined organic layers were dried over Na₂SO₄, filtered, concentrated in vacuo, and chromatographed through a 25 g SiO₂ column using a gradient of 100% Hexane to 90% EtOAc to afford 288 mg (51% yield) of the title compound. MS (ESI) 573.3, 575.3, 577.2 [M+H]⁺; ¹H NMR (400 MHz, DMSO-d₆) δ 11.18 (s, 1H), 9.07 (s, 1H), 8.23 (t, J=2 Hz, 1H), 8.21 (d, J=2 Hz, 1H), 8.11 (d, J=8 Hz, 1H), 7.96 (d, J=8 Hz, 1H), 7.86 (dd, J₁=2 Hz, J₂=8 Hz, 1H), 7.75 (t, J=8 Hz, 1H), 7.54-7.65 (m, 3H), 7.48 (d, J=8 Hz, 1H), 3.76 (s, 2H), 3.29 (s, 3H), 1.47 (s, 6H).

The following compounds are prepared essentially according to the previous examples:

1'-(3-Chloro-3'-methanesulfonyl-biphenyl-4-yl)-2'-(2,6-dichloro-phenyl)-4,5-dihydro-1H,1'H-[2,4']biimidazolyl; MS (ESI) 545.3, 547.3, 549.3 [M+H]⁺;

2'-(2,6-Dichloro-phenyl)-1'-(3'-methanesulfonyl-biphenyl-4-yl)-5,5-dimethyl-4,5-dihydro-1H,1'H-[2,4']biimidazolyl; MS (ESI) 539.3, 541.3 [M+H]⁺;

226

Scheme 20

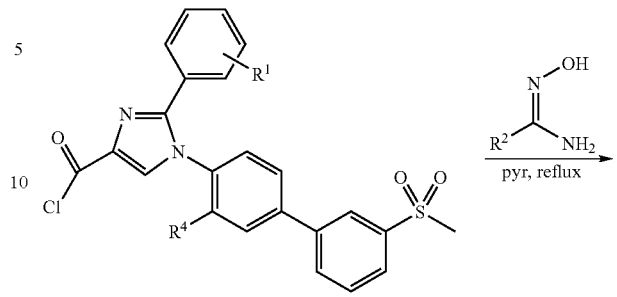

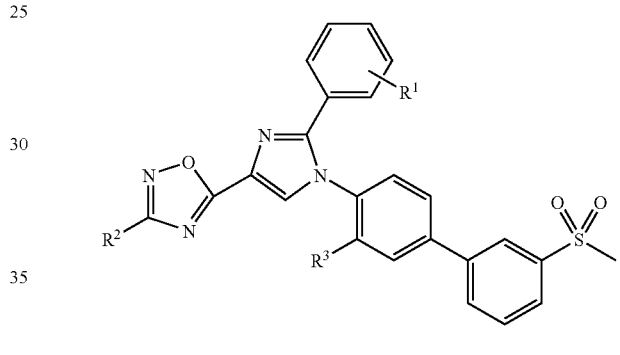

As depicted in Scheme 20, [1,2,4]-oxadiazole containing imidazole templates can be synthesized using known methods. By example, acid chloride 17E was treated with acetamide oxime in refluxing pyridine to afford [1,2,4]-oxadiazole 20A.

Example 21

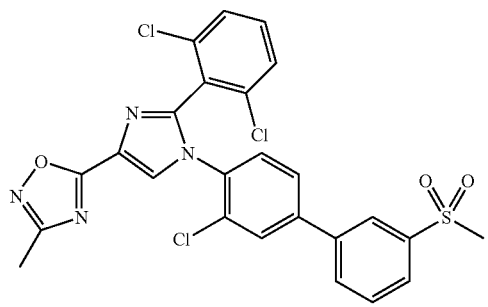

5-[1-(3-Chloro-3'-methanesulfonyl-biphenyl-4-yl)-2-(2,6-dichloro-phenyl)-1H-imidazol-4-yl]-3-methyl-[1,2,4]oxadiazole Preparation of 5-[1-(3-Chloro-3'-methanesulfonyl-biphenyl-4-yl)-2-(2,6-dichloro-phenyl)-1H-imidazol-4-yl]-3-methyl-[1,2,4]oxadiazole

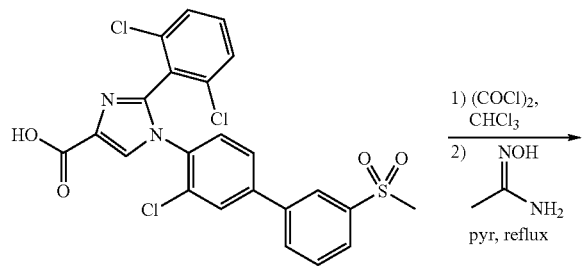

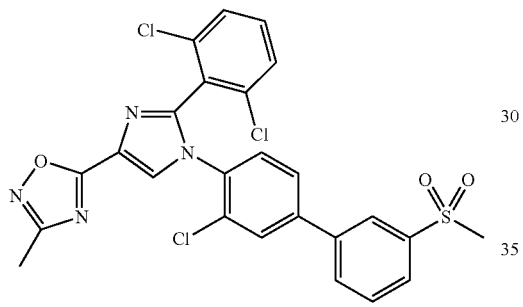

To a 100 mL round bottom flask was added 1-(3-Chloro-3'-methanesulfonyl-biphenyl-4-yl)-2-(2,6-dichloro-phenyl)-1H-imidazole-4-carboxylic acid (1.01 g, 1.93 mmol) and anhydrous $CHCl_3$ (17 mL). The reaction solution was cooled to 0° C. prior to addition of oxalyl chloride (0.90 mL, 9.70 mmol) and 1 drop of anhydrous DMF. The reaction solution was allowed to stir warming to r.t. over 1.5 h. The solution was concentrated in vacuo and the residue was dissolved anhydrous toluene (19 mL). To the reaction flask was added acetamide oxime (286 mg, 3.86 mmol) and pyridine (470 µL, 5.79 mmol). The reaction solution was allowed to reflux under $N_2$ for 16 hrs. The reaction solution was diluted with EtOAc (100 mL) and washed with sat aq. $NH_4Cl$ (150 mL×2). The organic phase was dried over $Na_2SO_4$, filtered, concentrated in vacuo, and chromatographed through a 25 g $SiO_2$ column using a 100% Hexane to 80% EtOAc gradient to yield 202 mg (18% yield) of title compound. MS (ESI) 559.0, 561.0, 563.2 $[M+H]^+$; $^1H$ NMR (400 MHz, DMSO-$d_6$) δ 8.80 (s, 1H), 8.24 (t, J=2 Hz, 1H), 8.19 (d, J=2 Hz, 1H), 8.11 (d, J=8 Hz, 1H), 7.96 (d, J=8 Hz, 1H), 7.85 (dd, $J_1$=2 Hz, $J_2$=8 Hz), 7.76 (t, J=8 Hz, 1H), 7.51-7.64 (m, 3H), 7.46 (d, J=8 Hz, 1H), 3.31 (s, 3H), 2.43 (s, 3H).

The following compound was prepared essentially according to the previous examples:

5-[2-(2,6-Dichloro-phenyl)-1-(3'-methanesulfonyl-biphenyl-4-yl)-1H-imidazol-4-yl]-3-methyl-[1,2,4]oxadiazole; MS (ESI) 525.3, 527.3 $[M+H]^+$.

Example 22

The following compounds of the invention, in Tables 2-19, were prepared according to one of the previous Examples.

TABLE 2

| # | IUPAC Name | Structure |
|---|---|---|
| 111 | 5-[(biphenyl-4-yloxy)methyl]-1-(2-chlorophenyl)-3-(trifluoromethyl)-1H-pyrazole | 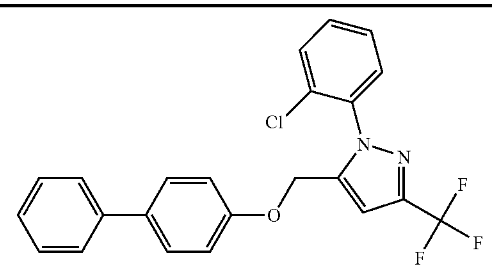 |
| 112 | 5-[(biphenyl-3-yloxy)methyl]-1-(2-chlorophenyl)-3-(trifluoromethyl)-1H-pyrazole | 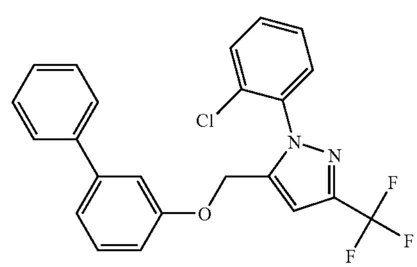 |

TABLE 3

| # | IUPAC Name | Structure |
|---|---|---|
| 113 | 2-chloro-4'-({[1-(2,6-dichlorophenyl)-4-(trifluoromethyl)-1H-imidazol-2-yl]methyl}oxy)biphenyl-4-carboxylic acid | 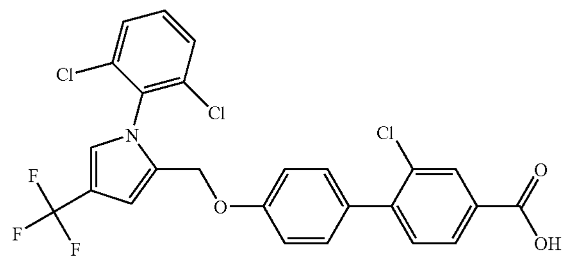 |
| 114 | 1-(2,6-dichlorophenyl)-2-({[3'-(methylsulfonyl)biphenyl-4-yl]oxy}methyl)-4-(trifluoromethyl)-1H-imidazole | 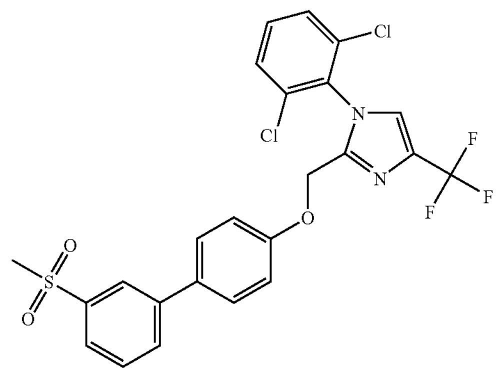 |
| 115 | 1-(2,6-dichlorophenyl)-2-({[4'-(methylsulfonyl)biphenyl-4-yl]oxy}methyl)-4-(trifluoromethyl)-1H-imidazole | 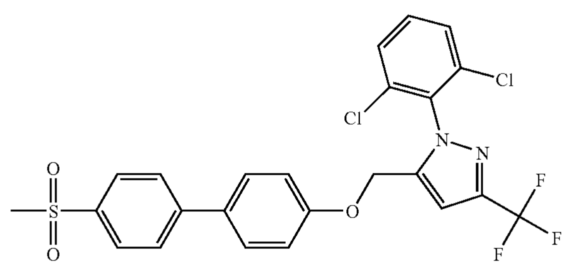 |

TABLE 4

| # | IUPAC Name | Structure |
|---|---|---|
| 116 | 1-(2,6-dichlorophenyl)-5-({[3'-(methylsulfonyl)biphenyl-4-yl]methyl}oxy)-3-(trifluoromethyl)-1H-pyrazole | 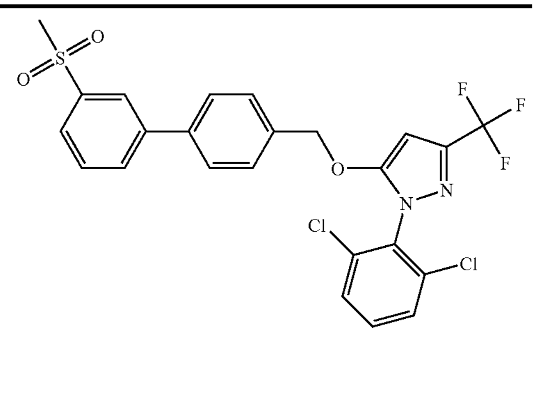 |

TABLE 4-continued

| # | IUPAC Name | Structure |
|---|---|---|
| 117 | 1-(2,6-dichlorophenyl)-5-({[3-fluoro-3'-(methylsulfonyl)biphenyl-4-yl]methyl}oxy)-3-(trifluoromethyl)-1H-pyrazole | 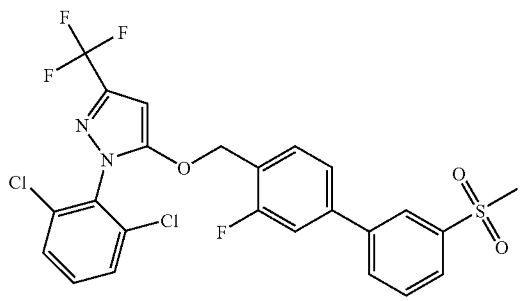 |

TABLE 5

| # | IUPAC Name | Structure |
|---|---|---|
| 118 | 2-(1-(2-chlorophenyl)-3-(trifluoromethyl)-1H-pyrazol-5-yloxy)-N-(4-methoxybiphenyl-3-yl)acetamide | 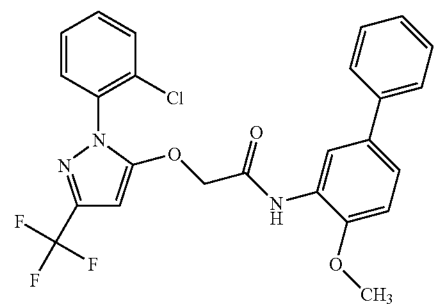 |
| 119 | N-(2-benzylphenyl)-2-(1-(2-chlorophenyl)-3-(trifluoromethyl)-1H-pyrazol-5-yloxy)acetamide | 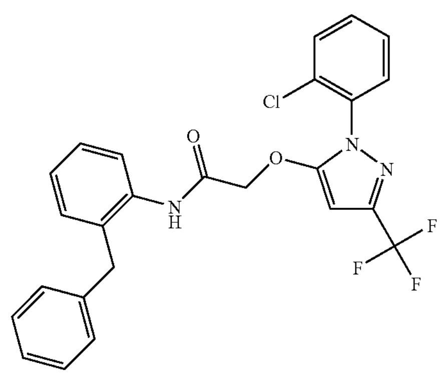 |
| 120 | N-(2-chloro-5-methylphenyl)-2-(1-(2-chlorophenyl)-3-(trifluoromethyl)-1H-pyrazol-5-yloxy)acetamide | 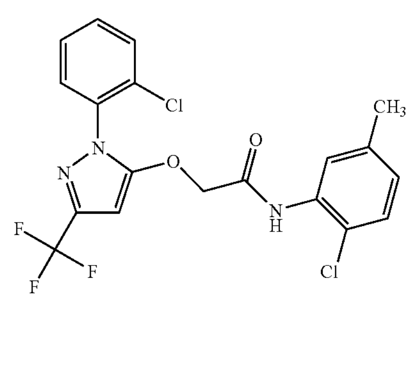 |

TABLE 5-continued

| # | IUPAC Name | Structure |
|---|---|---|
| 121 | N-(2-bromophenyl)-2-(1-(2-chlorophenyl)-3-(trifluoromethyl)-1H-pyrazol-5-yloxy)acetamide | 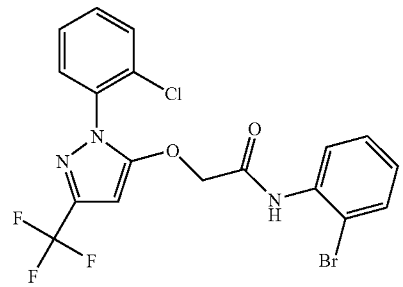 |
| 122 | 2-(1-(2-chlorophenyl)-3-(trifluoromethyl)-H-pyrazol-5-yloxy)-N-(2-methoxy-5-(trifluoromethyl)phenyl)acetamide | 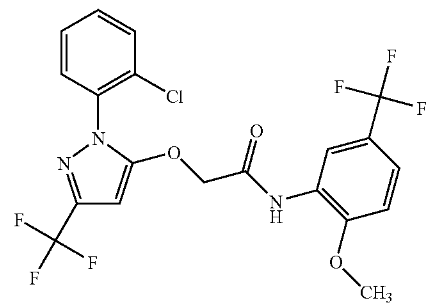 |
| 123 | N-(2-chloro-4,6-dimethylphenyl)-2-(1-(2-chlorophenyl)-3-(trifluoromethyl)-1H-pyrazol-5-yloxy)acetamide | 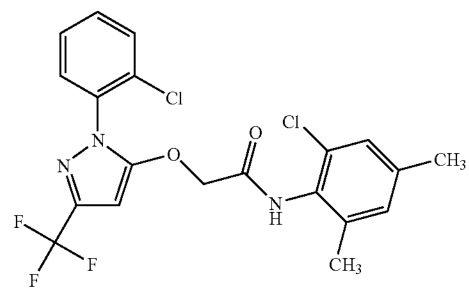 |
| 124 | 2-(1-(2-chlorophenyl)-3-(trifluoromethyl)-1H-pyrazol-5-yloxy)-N-(2,6-dichlorophenyl)acetamide | 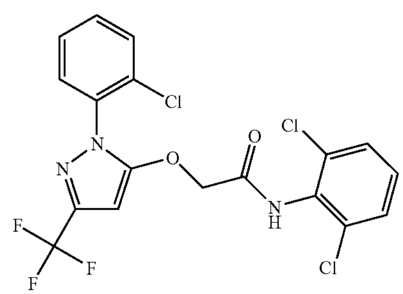 |
| 125 | 2-(1-(2-chlorophenyl)-3-(trifluoromethyl)-1H-pyrazol-5-yloxy)-N-(2,4-dimethoxyphenyl)acetamide | 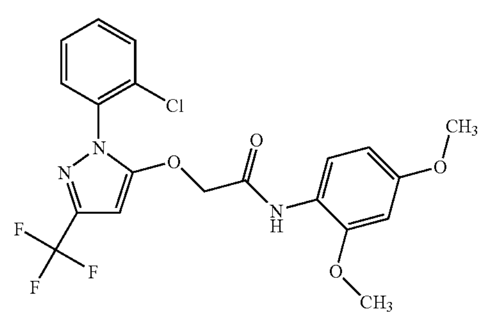 |

TABLE 5-continued

| # | IUPAC Name | Structure |
|---|---|---|
| 126 | N-(4-chloro-2-methoxy-5-methylphenyl)-2-(1-(2-chlorophenyl)-3-(trifluoromethyl)-1H-pyrazol-5-yloxy)acetamide | 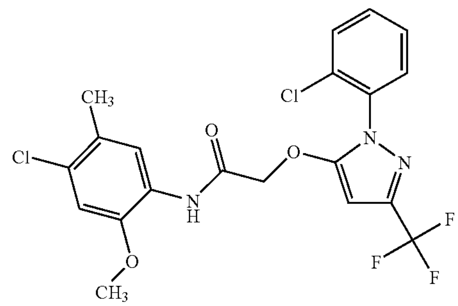 |
| 127 | N-(4-chlorophenyl)-2-(1-(2-chlorophenyl)-3-(trifluoromethyl)-1H-pyrazol-5-yloxy)acetamide | 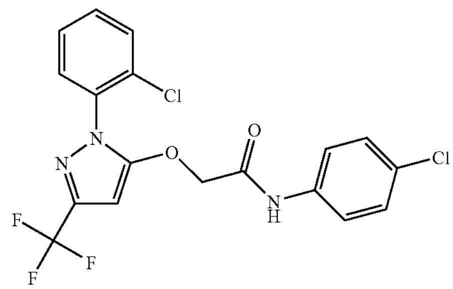 |
| 128 | 2-(1-(2-chlorophenyl)-3-(trifluoromethyl)-1H-pyrazol-5-yloxy)-N-(4-(trifluoromethyl)phenyl)acetamide | 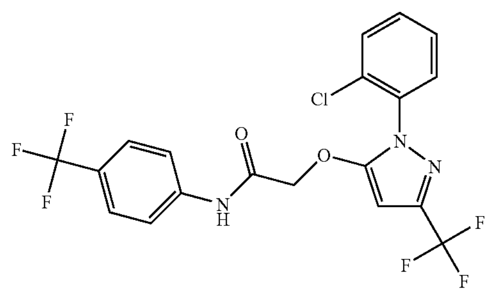 |
| 129 | 2-(1-(2-chlorophenyl)-3-(trifluoromethyl)-1H-pyrazol-5-yloxy)-N-(5-methoxy-2-methylphenyl)acetamide | 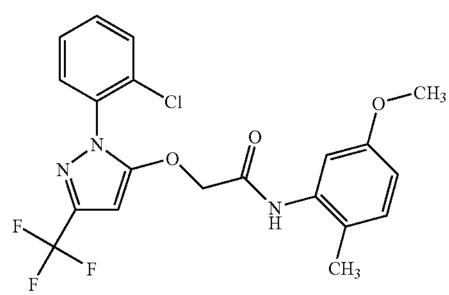 |
| 130 | 2-(1-(2-chlorophenyl)-3-(trifluoromethyl)-1H-pyrazol-5-yloxy)-N-o-tolylacetamide | 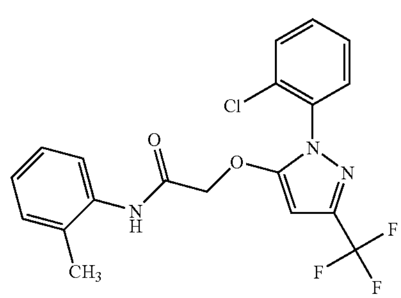 |

TABLE 5-continued

| # | IUPAC Name | Structure |
|---|---|---|
| 131 | 2-(1-(2-chlorophenyl)-3-(trifluoromethyl)-1H-pyrazol-5-yloxy)-N-(4-fluoro-2-(trifluoromethyl)phenyl)acetamide | 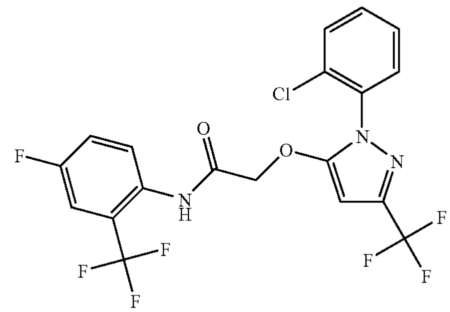 |
| 132 | N-(4-bromo-2-(trifluoromethyl)phenyl)-2-(1-(2-chlorophenyl)-3-(trifluoromethyl)-1H-pyrazol-5-yloxy)acetamide | 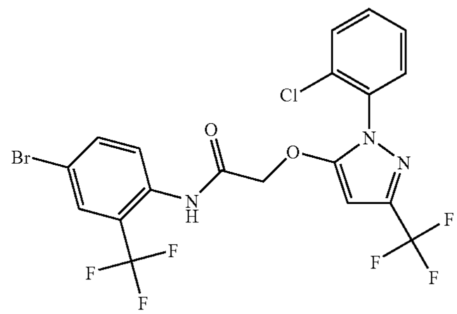 |
| 133 | N-(2-acetylphenyl)-2-(1-(2-chlorophenyl)-3-(trifluoromethyl)-1H-pyrazol-5-yloxy)acetamide | 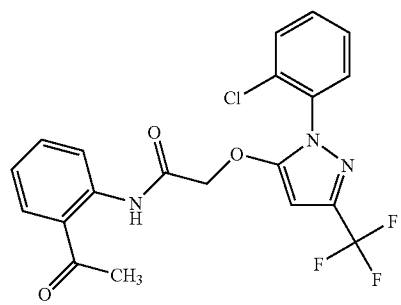 |
| 134 | 2-(1-(2-chlorophenyl)-3-(trifluoromethyl)-1H-pyrazol-5-yloxy)-N-(3,5-difluorophenyl)acetamide | 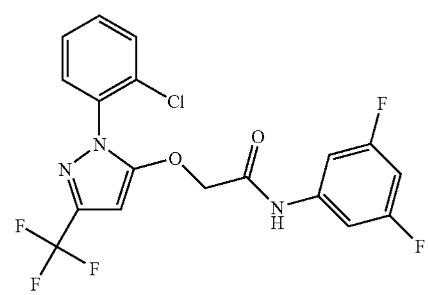 |
| 135 | N-(2-(1H-pyrrol-1-yl)phenyl)-2-(1-(2-chlorophenyl)-3-(trifluoromethyl)-1H-pyrazol-5-yloxy)acetamide | 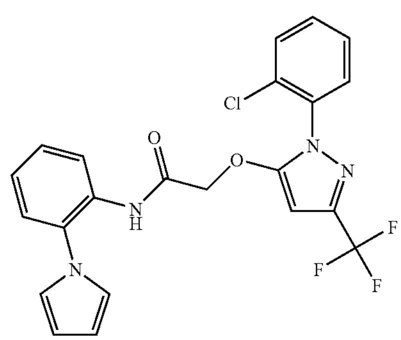 |

TABLE 5-continued

| # | IUPAC Name |
|---|---|
| 136 | N-(4-bromo-2-fluorophenyl)-2-(1-(2-chlorophenyl)-3-(trifluoromethyl)-1H-pyrazol-5-yloxy)acetamide |
| 137 | 2-(1-(2-chlorophenyl)-3-(trifluoromethyl)-1H-pyrazol-5-yloxy)-N-(4-(dimethylamino)phenyl)acetamide |
| 138 | N-(4-chloro-2-(trifluoromethyl)phenyl)-2-(1-(2-chlorophenyl)-3-(trifluoromethyl)-1H-pyrazol-5-yloxy)acetamide |
| 139 | N-(3-benzoylphenyl)-2-(1-(2-chlorophenyl)-3-(trifluoromethyl)-1H-pyrazol-5-yloxy)acetamide |
| 140 | N-(6-acetylbenzo[d][1,3]dioxol-5-yl)-2-(1-(2-chlorophenyl)-3-(trifluoromethyl)-1H-pyrazol-5-yloxy)acetamide |

TABLE 5-continued

| # | IUPAC Name | Structure |
|---|---|---|
| 141 | N-(4-chloronaphthalen-1-yl)-2-(1-(2-chlorophenyl)-3-(trifluoromethyl)-1H-pyrazol-5-yloxy)acetamide | 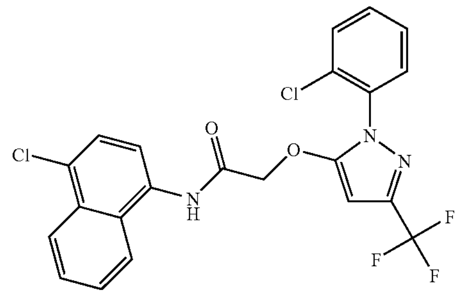 |
| 142 | 2-(1-(2-chlorophenyl)-3-(trifluoromethyl)-1H-pyrazol-5-yloxy)-N-phenylacetamide | 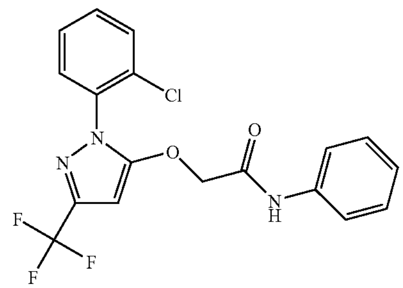 |
| 143 | N-(4-benzoylphenyl)-2-(1-(2-chlorophenyl)-3-(trifluoromethyl)-1H-pyrazol-5-yloxy)acetamide | 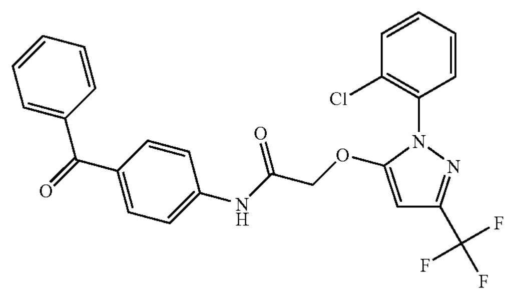 |
| 144 | 2-(2-(1-(2-chlorophenyl)-3-(trifluoromethyl)-1H-pyrazol-5-yloxy)acetamido)-6-(trifluoromethyl)benzoic acid | 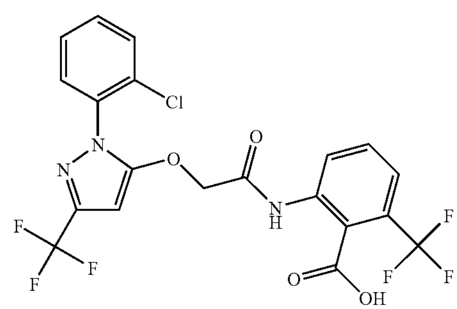 |
| 145 | 5-bromo-2-(2-(1-(2-chlorophenyl)-3-(trifluoromethyl)-1H-pyrazol-5-yloxy)acetamido)benzoic acid | 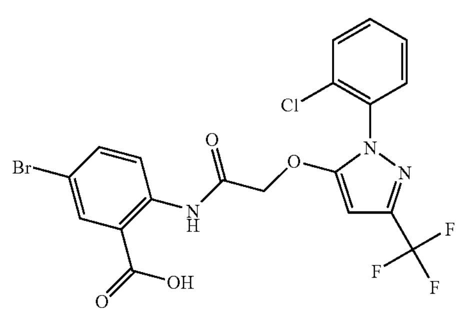 |

TABLE 5-continued

| # | IUPAC Name | Structure |
|---|---|---|
| 146 | 2-(1-(2-chlorophenyl)-3-(trifluoromethyl)-1H-pyrazol-5-yloxy)-N-(4-hydroxyphenyl)acetamide | 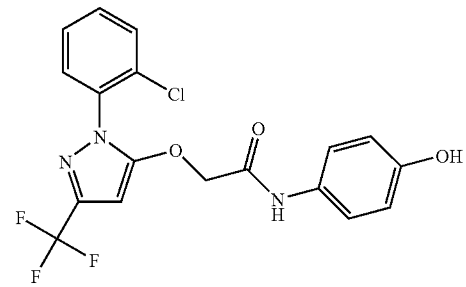 |
| 147 | 2-(1-(2-chlorophenyl)-3-(trifluoromethyl)-1H-pyrazol-5-yloxy)-N-(3,5-dibromo-4-hydroxyphenyl)acetamide | 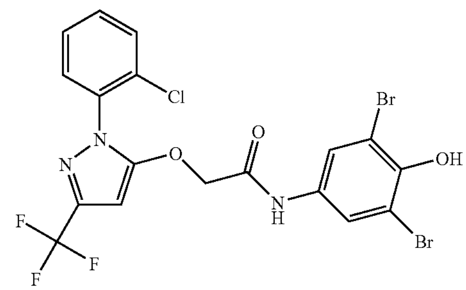 |
| 148 | 5-(2-(1-(2-chlorophenyl)-3-(trifluoromethyl)-1H-pyrazol-5-yloxy)acetamido)-2-hydroxybenzoic acid | 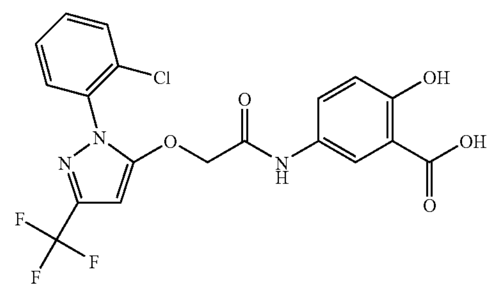 |
| 149 | 4-(2-(1-(2-chlorophenyl)-3-(trifluoromethyl)-1H-pyrazol-5-yloxy)acetamido)benzenesulfonic acid | 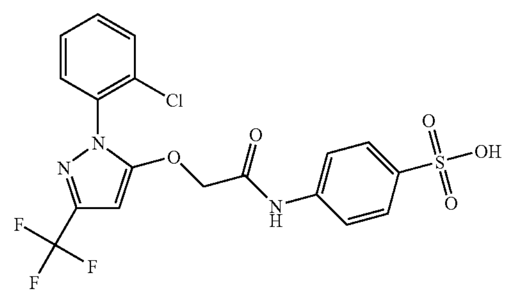 |
| 150 | 2-(1-(2-chlorophenyl)-3-(trifluoromethyl)-1H-pyrazol-5-yloxy)-N-(3-hydroxy-4-methoxyphenyl)acetamide | 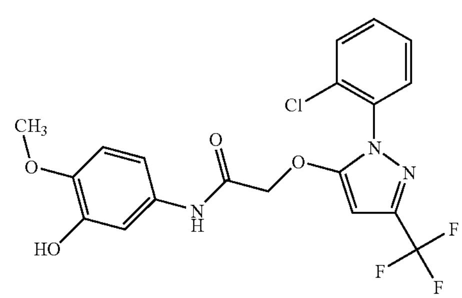 |

TABLE 5-continued

| # | IUPAC Name |
|---|---|
| 151 | 2-(1-(2-chlorophenyl)-3-(trifluoromethyl)-1H-pyrazol-5-yloxy)-N-(3-(dimethylamino)phenyl)acetamide |
| 152 | (E)-3-(4-(2-(1-(2-chlorophenyl)-3-(trifluoromethyl)-1H-pyrazol-5-yloxy)acetamido)phenyl)acrylic acid |
| 153 | 2-(1-(2-chlorophenyl)-3-(trifluoromethyl)-1H-pyrazol-5-yloxy)-N-(4-(4-methoxyphenylamino)phenyl)acetamide |
| 154 | 2-(1-(2-chlorophenyl)-3-(trifluoromethyl)-1H-pyrazol-5-yloxy)-N-(3-((diethylamino)methyl)-4-hydroxyphenyl)acetamide |
| 155 | ethyl 3-(2-(1-(2-chlorophenyl)-3-(trifluoromethyl)-1H-pyrazol-5-yloxy)acetamido)benzoate |

TABLE 5-continued

| # | IUPAC Name | Structure |
|---|---|---|
| 156 | 4-(2-(1-(2-chlorophenyl)-3-(trifluoromethyl)-1H-pyrazol-5-yloxy)acetamido)-3-hydroxybenzoic acid | 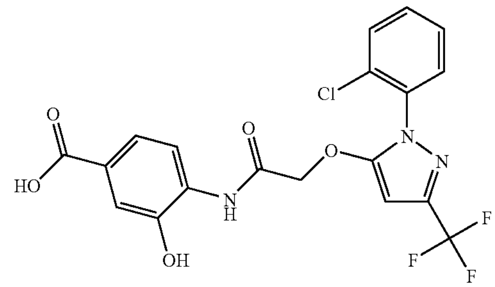 |
| 157 | N-(3-benzoylphenyl)-2-(1-(2-chlorophenyl)-3-(trifluoromethyl)-1H-pyrazol-5-yloxy)acetamide | 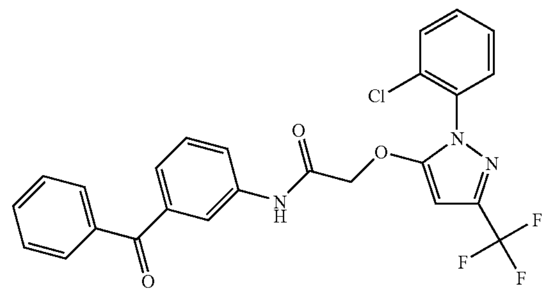 |
| 158 | 2-(1-(2-chlorophenyl)-3-(trifluoromethyl)-1H-pyrazol-5-yloxy)-N-(2-hydroxy-5-tert-pentylphenyl)acetamide | 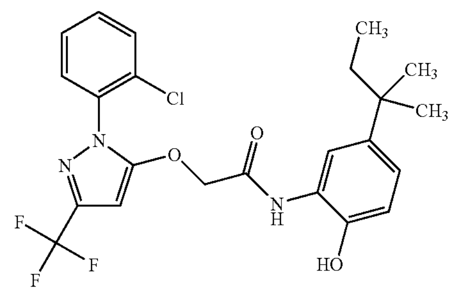 |
| 159 | 5-(2-(1-(2-chlorophenyl)-3-(trifluoromethyl)-1H-pyrazol-5-yloxy)acetamido)-2,4-dimethylbenzenesulfonic acid | 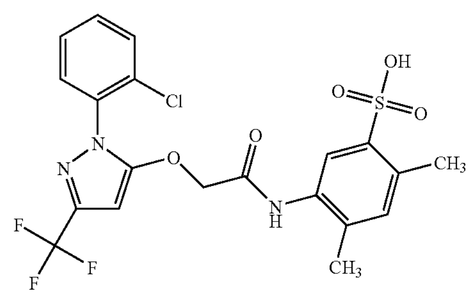 |
| 160 | 2-(1-(2-chlorophenyl)-3-(trifluoromethyl)-1H-pyrazol-5-yloxy)-N-(3,5-dichloro-2-hydroxy-4-methylphenyl)acetamide | 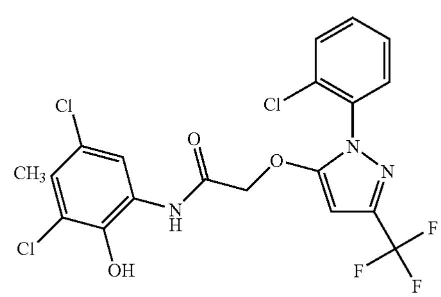 |

| # | IUPAC Name | Structure |
|---|---|---|
| 161 | 2-(1-(2-chlorophenyl)-3-(trifluoromethyl)-1H-pyrazol-5-yloxy)-N-(2-hydroxy-5-sulfamoylphenyl)acetamide | 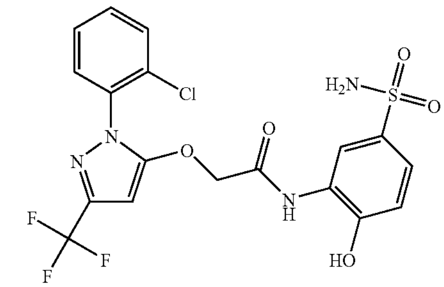 |
| 162 | 2-(1-(2-chlorophenyl)-3-(trifluoromethyl)-1H-pyrazol-5-yloxy)-N-(3-hydroxy-4-methylphenyl)acetamide | 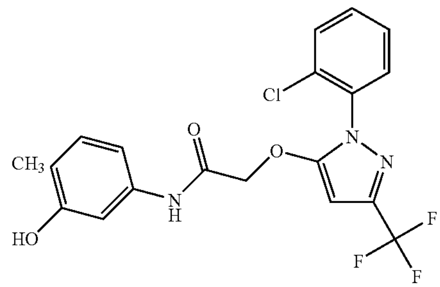 |
| 163 | 3-(2-(1-(2-chlorophenyl)-3-(trifluoromethyl)-1H-pyrazol-5-yloxy)acetamido)benzenesulfonic acid | 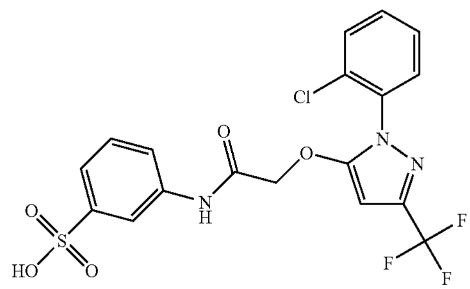 |
| 164 | N-(4-(4-aminophenylsulfonyl)phenyl)-2-(1-(2-chlorophenyl)-3-(trifluoromethyl)-1H-pyrazol-5-yloxy)acetamide | 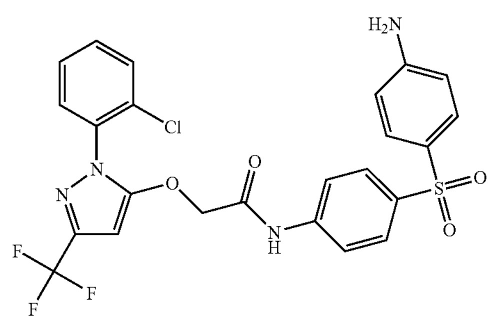 |
| 165 | 4-(2-(1-(2-chlorophenyl)-3-(trifluoromethyl)-1H-pyrazol-5-yloxy)acetamido)-N,N-dimethylbenzamide | 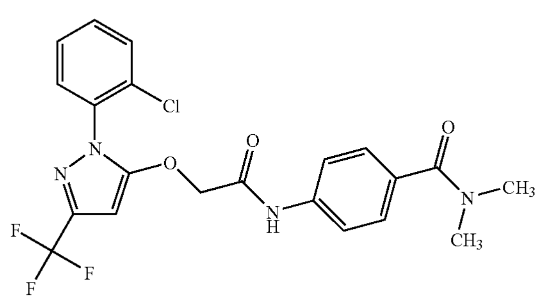 |

TABLE 5-continued

| # | IUPAC Name | Structure |
|---|---|---|
| 166 | 2-(1-(2-chlorophenyl)-3-(trifluoromethyl)-1H-pyrazol-5-yloxy)-N-(4-(N-pyrimidin-2-ylsulfamoyl)phenyl)acetamide | 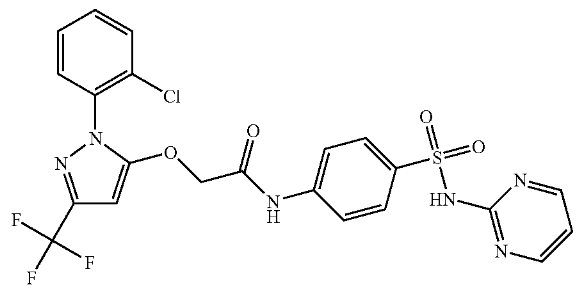 |
| 167 | 2-(1-(2-chlorophenyl)-3-(trifluoromethyl)-1H-pyrazol-5-yloxy)-N-(4-(N-thiazol-2-ylsulfamoyl)phenyl)acetamide | 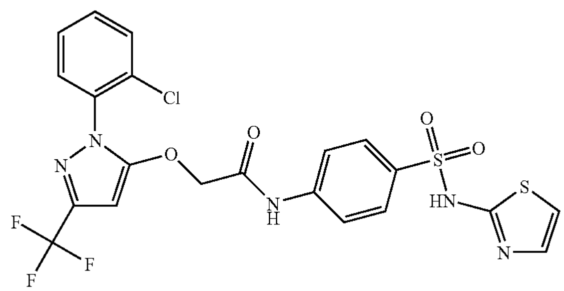 |
| 168 | N-(benzo[d][1,3]dioxol-5-yl)-2-(1-(2-chlorophenyl)-3-(trifluoromethyl)-1H-pyrazol-5-yloxy)acetamide | 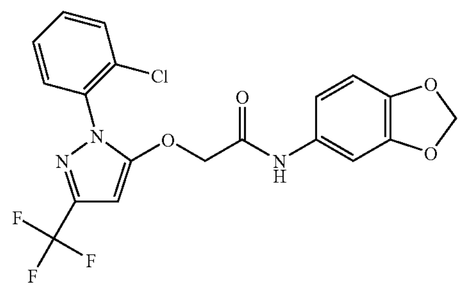 |
| 169 | ethyl 5-(2-(1-(2-chlorophenyl)-3-(trifluoromethyl)-1H-pyrazol-5-yloxy)acetamido)-1,3,4-thiadiazole-2-carboxylate | 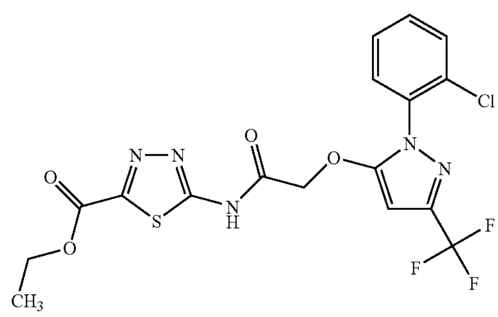 |
| 170 | 2-(1-(2-chlorophenyl)-3-(trifluoromethyl)-1H-pyrazol-5-yloxy)-N-(5-methylthiazol-2-yl)acetamide | 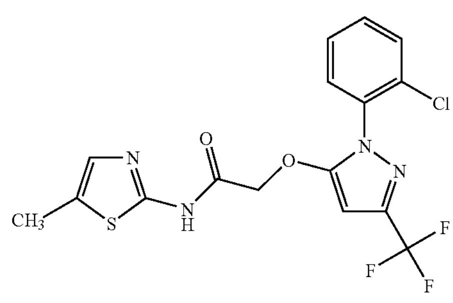 |

… TABLE 5-continued

| # | IUPAC Name | Structure |
|---|---|---|
| 171 | 2-(1-(2-chlorophenyl)-3-(trifluoromethyl)-1H-pyrazol-5-yloxy)-N-(5-(trifluoromethyl)-1,3,4-thiadiazol-2-yl)acetamide | 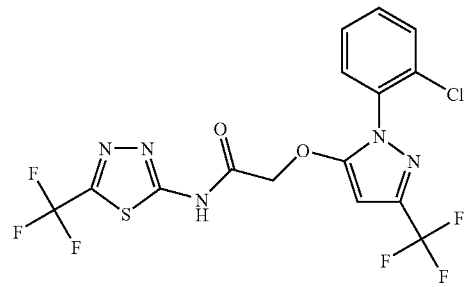 |
| 172 | 2-(1-(2-chlorophenyl)-3-(trifluoromethyl)-1H-pyrazol-5-yloxy)-N-(4,5-dimethylthiazol-2-yl)acetamide | 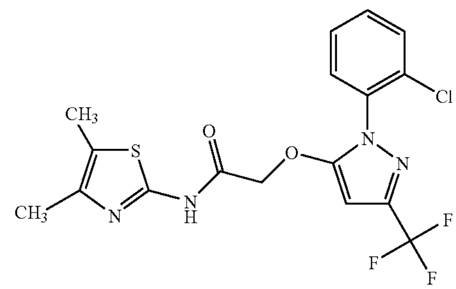 |
| 173 | 2-(1-(2-chlorophenyl)-3-(trifluoromethyl)-1H-pyrazol-5-yloxy)-N-(4,6-dihydroxy-5-methylpyrimidin-2-yl)acetamide | 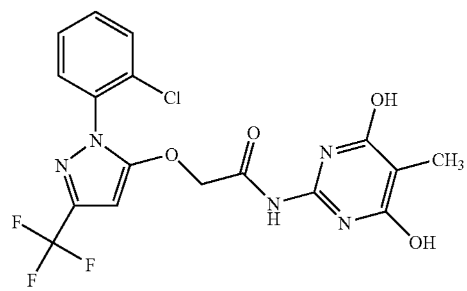 |
| 174 | 2-(1-(2-chlorophenyl)-3-(trifluoromethyl)-1H-pyrazol-5-yloxy)-N-(5-(ethylthio)-1,3,4-thiadiazol-2-yl)acetamide | 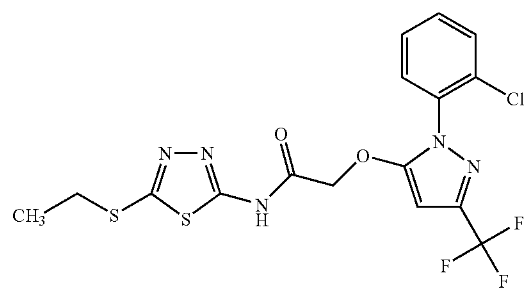 |
| 175 | 2-(1-(2-chlorophenyl)-3-(trifluoromethyl)-1H-pyrazol-5-yloxy)-N-(1-methyl-3-phenyl-1H-pyrazol-5-yl)acetamide | 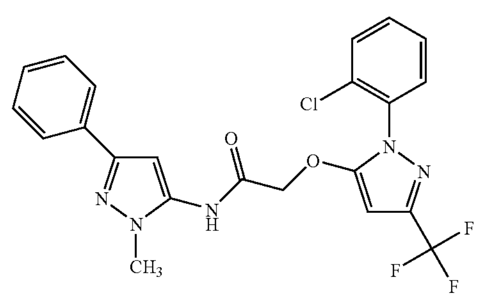 |

TABLE 5-continued

| # | IUPAC Name | Structure |
|---|---|---|
| 176 | 2-(1-(2-chlorophenyl)-3-(trifluoromethyl)-1H-pyrazol-5-yloxy)-N-(1,3-diphenyl-1H-pyrazol-5-yl)acetamide | 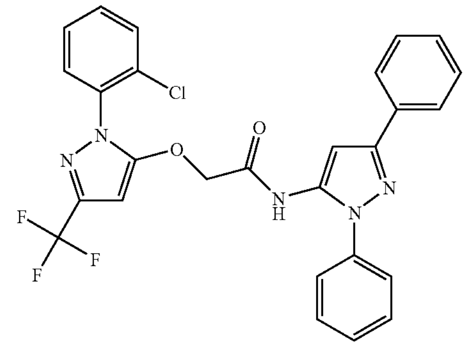 |
| 177 | 2-(1-(2-chlorophenyl)-3-(trifluoromethyl)-1H-pyrazol-5-yloxy)-N-(3-ethyl-6-methylpyridin-2-yl)acetamide | 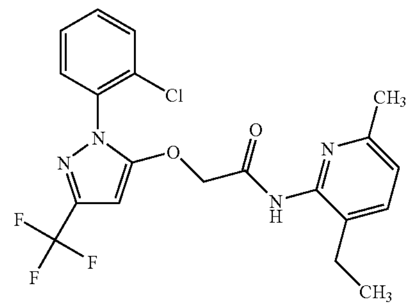 |
| 178 | methyl 3-(2-(1-(2-chlorophenyl)-3-(trifluoromethyl)-1H-pyrazol-5-yloxy)acetamido)-5-(4-fluorophenyl)thiophene-2-carboxylate | 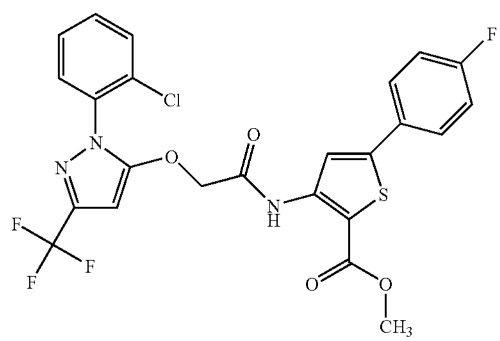 |
| 179 | 2-(1-(2-chlorophenyl)-3-(trifluoromethyl)-1H-pyrazol-5-yloxy)-N-(7-(trifluoromethyl)quinolin-4-yl)acetamide | 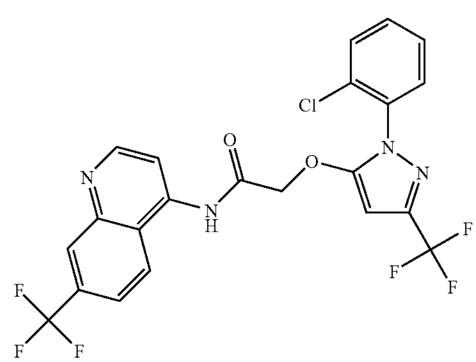 |

TABLE 5-continued

| # | IUPAC Name | Structure |
|---|---|---|
| 180 | 2-(1-(2-chlorophenyl)-3-(trifluoromethyl)-1H-pyrazol-5-yloxy)-N-(8-(trifluoromethyl)quinolin-4-yl)acetamide | 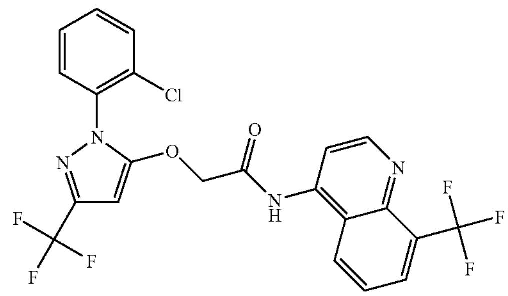 |
| 181 | 3-(2-(1-(2-chlorophenyl)-3-(trifluoromethyl)-1H-pyrazol-5-yloxy)acetamido)-1H-1,2,4-triazole-5-carboxylic acid | 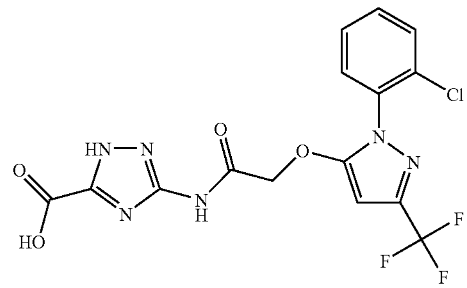 |
| 182 | 2-(1-(2-chlorophenyl)-3-(trifluoromethyl)-1H-pyrazol-5-yloxy)-N-(4-(trifluoromethyl)benzyl)acetamide | 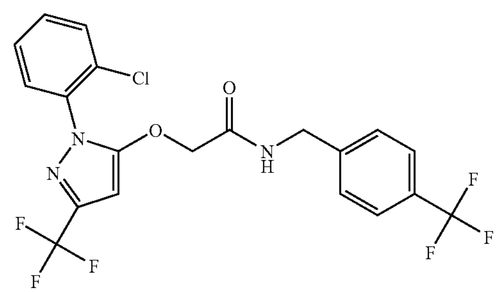 |
| 183 | N-(4-chlorophenethyl)-2-(1-(2-chlorophenyl)-3-(trifluoromethyl)-1H-pyrazol-5-yloxy)acetamide | 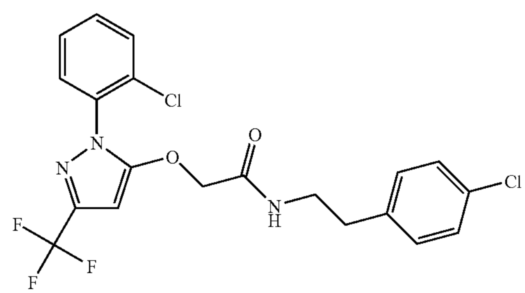 |
| 184 | 2-(1-(2-chlorophenyl)-3-(trifluoromethyl)-1H-pyrazol-5-yloxy)-N-(3-methylbenzyl)acetamide | 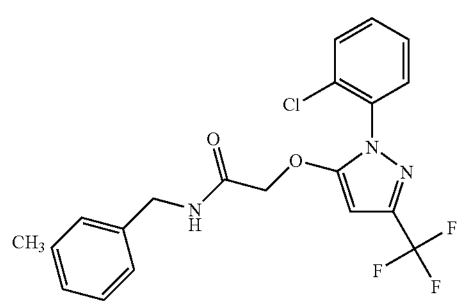 |

TABLE 5-continued

| # | IUPAC Name |
|---|---|
| 185 | N-(4-bromophenethyl)-2-(1-(2-chlorophenyl)-3-(trifluoromethyl)-1H-pyrazol-5-yloxy)acetamide |
| 186 | 2-(1-(2-chlorophenyl)-3-(trifluoromethyl)-1H-pyrazol-5-yloxy)-N-(4-methylphenethyl)acetamide |
| 187 | 2-(1-(2-chlorophenyl)-3-(trifluoromethyl)-1H-pyrazol-5-yloxy)-N-(4-phenylbutan-2-yl)acetamide |
| 188 | 2-(1-(2-chlorophenyl)-3-(trifluoromethyl)-1H-pyrazol-5-yloxy)-N-(3-methoxybenzyl)acetamide |
| 189 | 2-(1-(2-chlorophenyl)-3-(trifluoromethyl)-1H-pyrazol-5-yloxy)-N-(3-methoxyphenethyl)acetamide |

TABLE 5-continued

| # | IUPAC Name | Structure |
|---|---|---|
| 190 | 2-(1-(2-chlorophenyl)-3-(trifluoromethyl)-1H-pyrazol-5-yloxy)-N-(3,4-dimethoxybenzyl)acetamide | 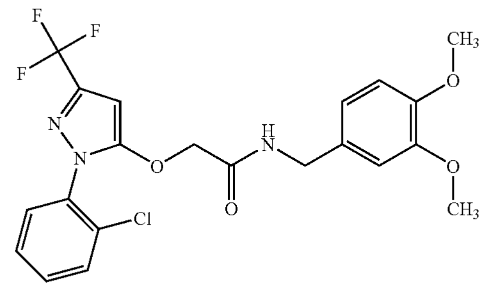 |
| 191 | 2-(1-(2-chlorophenyl)-3-(trifluoromethyl)-1H-pyrazol-5-yloxy)-N-(1-(naphthalen-1-yl)ethyl)acetamide | 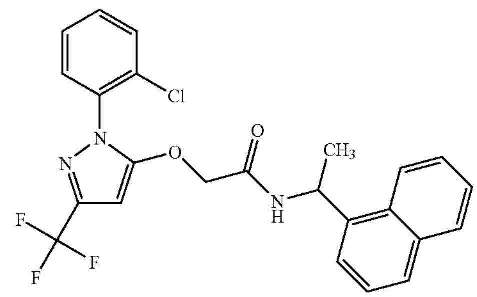 |
| 192 | 2-(1-(2-chlorophenyl)-3-(trifluoromethyl)-1H-pyrazol-5-yloxy)-N-(4-methoxyphenethyl)acetamide | 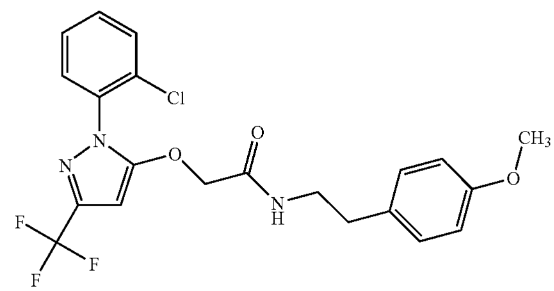 |
| 193 | 2-(1-(2-chlorophenyl)-3-(trifluoromethyl)-1H-pyrazol-5-yloxy)-N-(1-(4-chlorophenyl)ethyl)acetamide | 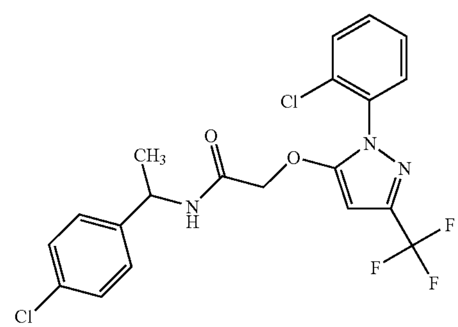 |
| 194 | 2-(1-(2-chlorophenyl)-3-(trifluoromethyl)-1H-pyrazol-5-yloxy)-N-(2,4-dichlorophenethyl)acetamide | 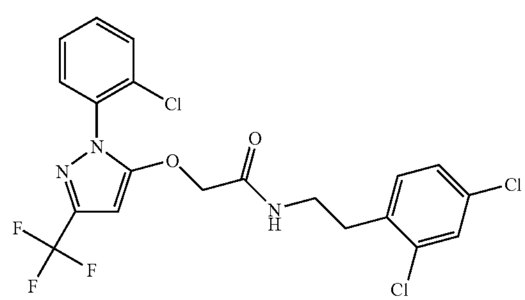 |

TABLE 5-continued

| # | IUPAC Name | Structure |
|---|---|---|
| 195 | 2-(1-(2-chlorophenyl)-3-(trifluoromethyl)-1H-pyrazol-5-yloxy)-N-(4-fluorobenzyl)acetamide | 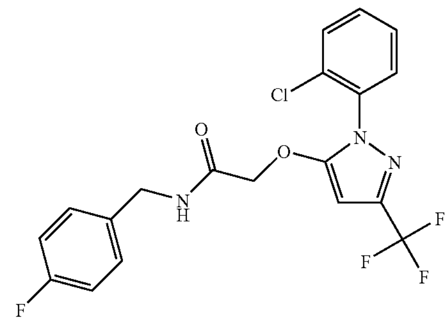 |
| 196 | 2-(1-(2-chlorophenyl)-3-(trifluoromethyl)-1H-pyrazol-5-yloxy)-N-(3-fluorobenzyl)acetamide | 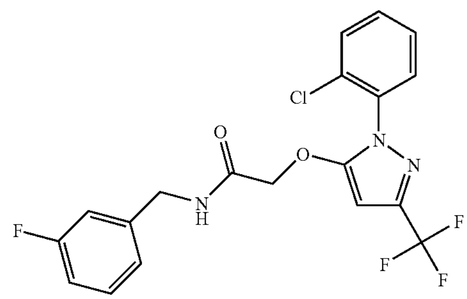 |
| 197 | 2-(1-(2-chlorophenyl)-3-(trifluoromethyl)-1H-pyrazol-5-yloxy)-N-(2-fluorobenzyl)acetamide | 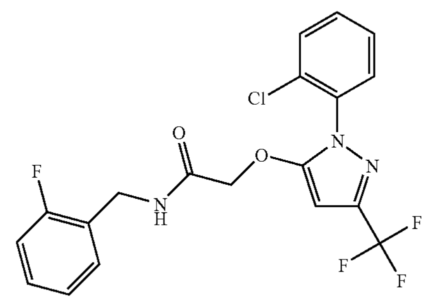 |
| 198 | 2-(1-(2-chlorophenyl)-3-(trifluoromethyl)-1H-pyrazol-5-yloxy)-N-(2,5-difluorobenzyl)acetamide | 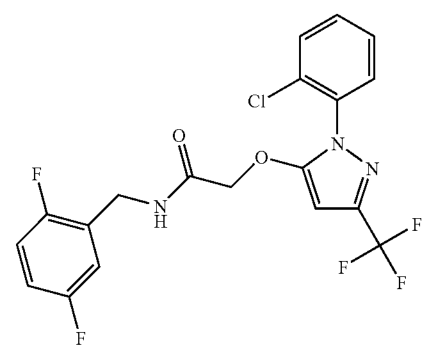 |
| 199 | N-(4-chlorobenzyl)-2-(1-(2-chlorophenyl)-3-(trifluoromethyl)-1H-pyrazol-5-yloxy)acetamide | 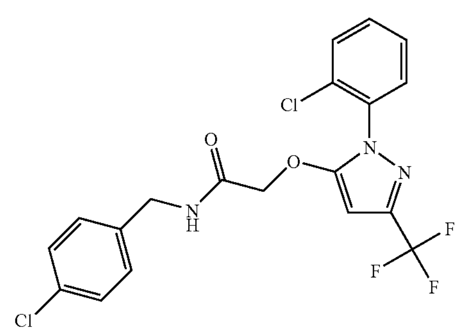 |

TABLE 5-continued

| # | IUPAC Name | Structure |
|---|---|---|
| 200 | N-(4-(1H-pyrazol-1-yl)benzyl)-2-(1-(2-chlorophenyl)-3-(trifluoromethyl)-1H-pyrazol-5-yloxy)acetamide | 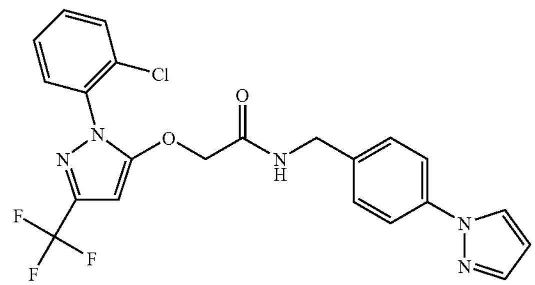 |
| 201 | N-(4-(1H-pyrrol-1-yl)benzyl)-2-(1-(2-chlorophenyl)-3-(trifluoromethyl)-1H-pyrazol-5-yloxy)acetamide | 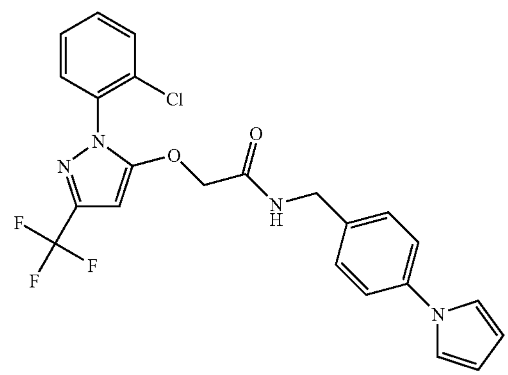 |
| 202 | 2-(1-(2-chlorophenyl)-3-(trifluoromethyl)-1H-pyrazol-5-yloxy)-N-(2,4-dimethoxybenzyl)acetamide | 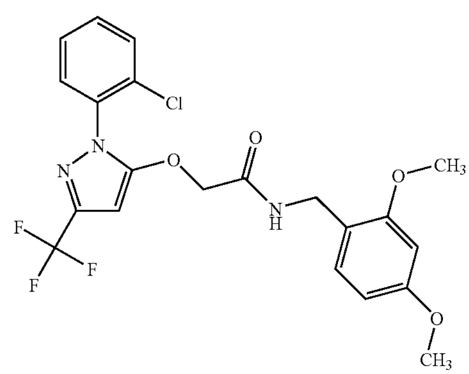 |
| 203 | 2-(1-(2-chlorophenyl)-3-(trifluoromethyl)-1H-pyrazol-5-yloxy)-N-(4-(p-tolyloxy)benzyl)acetamide | 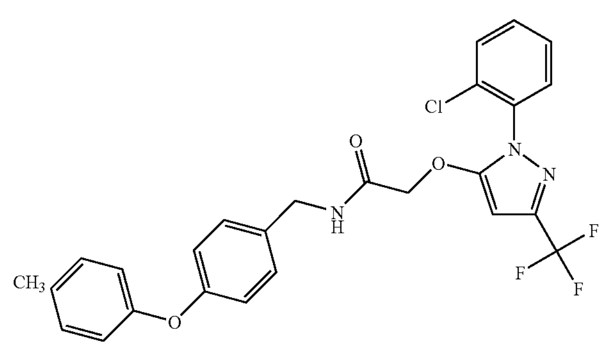 |

TABLE 5-continued

| # | IUPAC Name | Structure |
|---|---|---|
| 204 | N-((2'-chlorobiphenyl-4-yl)methyl)-2-(1-(2-chlorophenyl)-3-(trifluoromethyl)-1H-pyrazol-5-yloxy)acetamide | 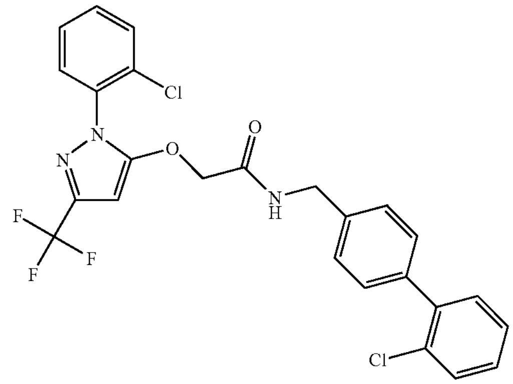 |
| 205 | 2-(1-(2-chlorophenyl)-3-(trifluoromethyl)-1H-pyrazol-5-yloxy)-N-(3-phenoxybenzyl)acetamide | 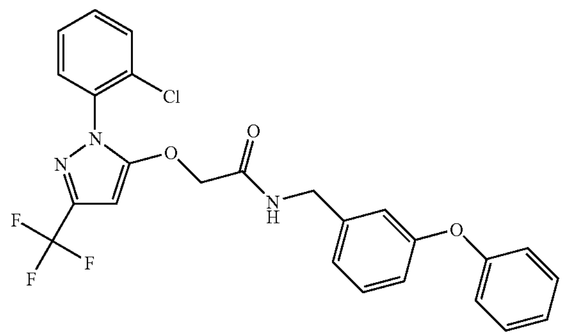 |
| 206 | 2-(1-(2-chlorophenyl)-3-(trifluoromethyl)-1H-pyrazol-5-yloxy)-N-(2,4-dimethylphenethyl)acetamide | 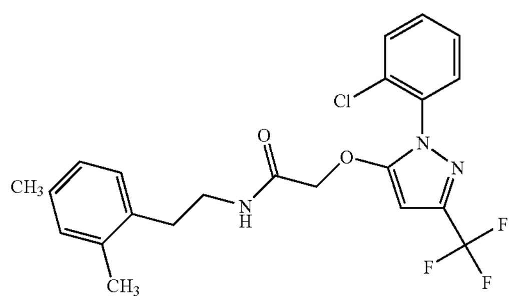 |
| 207 | 2-(1-(2-chlorophenyl)-3-(trifluoromethyl)-1H-pyrazol-5-yloxy)-N-(1-(2,6-dimethylphenoxy)propan-2-yl)acetamide | 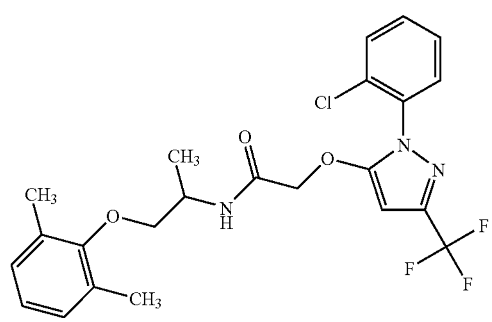 |

TABLE 5-continued

| # | IUPAC Name | Structure |
|---|---|---|
| 208 | N-(1-benzylpiperidin-4-yl)-2-(1-(2-chlorophenyl)-3-(trifluoromethyl)-1H-pyrazol-5-yloxy)acetamide | 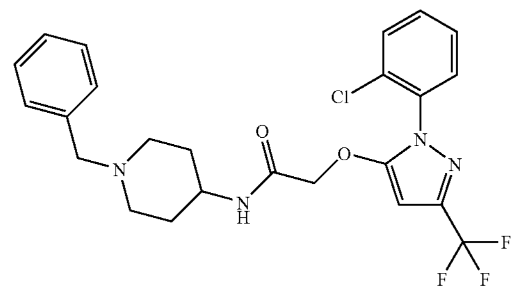 |
| 209 | 2-(1-(2-chlorophenyl)-3-(trifluoromethyl)-1H-pyrazol-5-yloxy)-1-(4-(4-chlorophenylsulfonyl)piperidin-1-yl)ethanone | 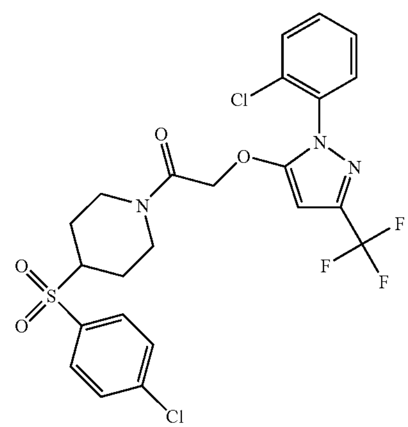 |
| 210 | 2-(1-(2-chlorophenyl)-3-(trifluoromethyl)-1H-pyrazol-5-yloxy)-N-(2-phenoxypropyl)acetamide | 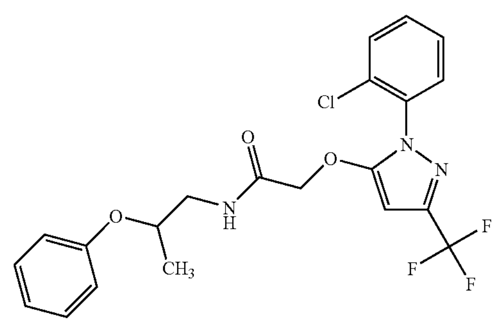 |
| 211 | 2-(1-(2-chlorophenyl)-3-(trifluoromethyl)-1H-pyrazol-5-yloxy)-N-(2-(4-methoxyphenoxy)propyl)acetamide | 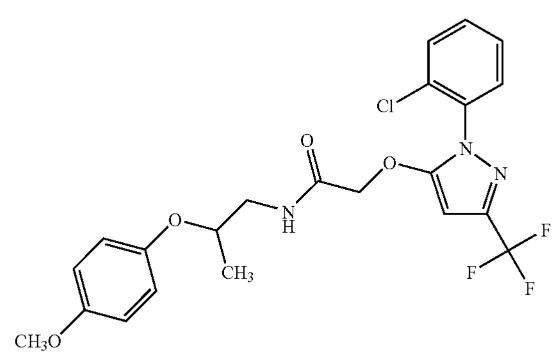 |

TABLE 5-continued

| # | IUPAC Name | Structure |
|---|---|---|
| 212 | 2-(1-(2-chlorophenyl)-3-(trifluoromethyl)-1H-pyrazol-5-yloxy)-N-(2-(p-tolyloxy)propyl)acetamide | 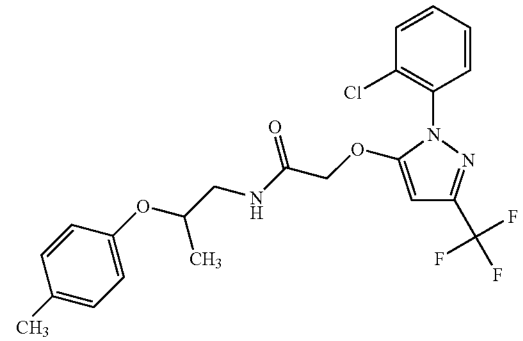 |
| 213 | 2-(1-(2-chlorophenyl)-3-(trifluoromethyl)-1H-pyrazol-5-yloxy)-N-(2-(4-(trifluoromethyl)phenoxy)propyl)acetamide | 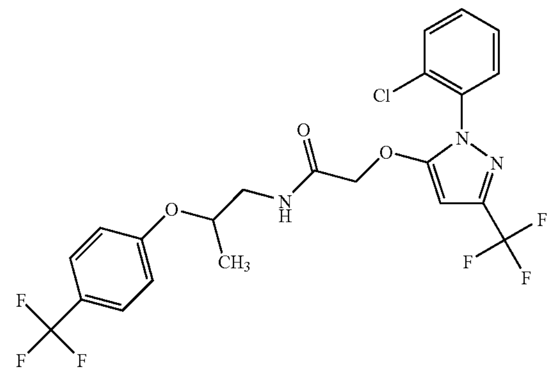 |
| 214 | 2-(1-(2-chlorophenyl)-3-(trifluoromethyl)-1H-pyrazol-5-yloxy)-N-((1-(pyrimidin-2-yl)piperidin-3-yl)methyl)acetamide | 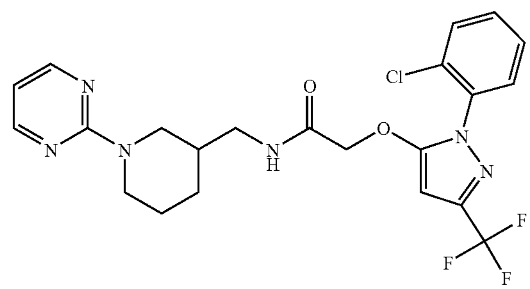 |
| 215 | 2-(1-(2-chlorophenyl)-3-(trifluoromethyl)-1H-pyrazol-5-yloxy)-N-(5-oxo-1-(2,4,6-trichlorophenyl)-4,5-dihydro-1H-pyrazol-3-yl)acetamide | 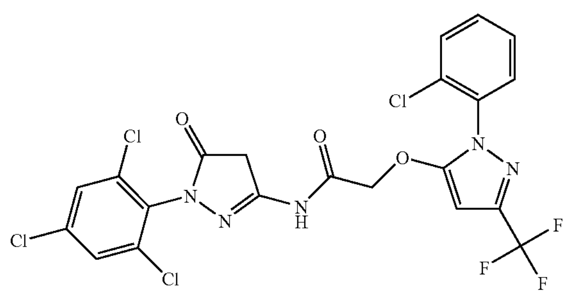 |
| 216 | (2S)-2-(2-(1-(2-chlorophenyl)-3-(trifluoromethyl)-1H-pyrazol-5-yloxy)acetamido)-3-(4-hydroxyphenyl)propanoic acid | 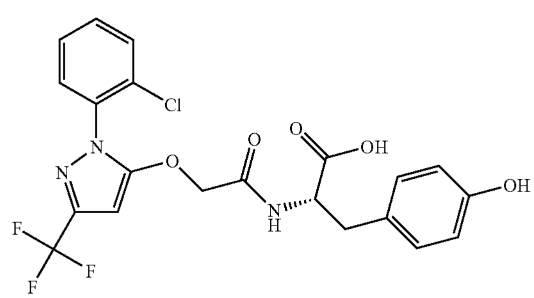 |

TABLE 5-continued

| # | IUPAC Name |
|---|---|
| 217 | 2-(1-(2-chlorophenyl)-3-(trifluoromethyl)-1H-pyrazol-5-yloxy)-N-(phenyl(pyridin-2-yl)methyl)acetamide |
| 218 | 2-(1-(2-chlorophenyl)-3-(trifluoromethyl)-1H-pyrazol-5-yloxy)-N-((1S,2S)-1,3-dihydroxy-1-(4-(methylthio)phenyl)propan-2-yl)acetamide |
| 219 | 2-(1-(2-chlorophenyl)-3-(trifluoromethyl)-1H-pyrazol-5-yloxy)-N-(2-(4-methoxyphenyl)-2-(pyrrolidin-1-yl)ethyl)acetamide |
| 220 | 2-(1-(2-chlorophenyl)-3-(trifluoromethyl)-1H-pyrazol-5-yloxy)-N-(2-(4-methoxyphenyl)-2-morpholinoethyl)acetamide |
| 221 | N-(3-(1H-imidazol-1-yl)propyl)-2-(1-(2-chlorophenyl)-3-(trifluoromethyl)-1H-pyrazol-5-yloxy)acetamide |

TABLE 5-continued

| # | IUPAC Name |
|---|---|
| 222 | 2-(1-(2-chlorophenyl)-3-(trifluoromethyl)-1H-pyrazol-5-yloxy)-N-(2-(pyridin-2-yl)ethyl)acetamide |
| 223 | 2-(1-(2-chlorophenyl)-3-(trifluoromethyl)-1H-pyrazol-5-yloxy)-N-(pyridin-4-ylmethyl)acetamide |
| 224 | 2-(1-(2-chlorophenyl)-3-(trifluoromethyl)-1H-pyrazol-5-yloxy)-N-((1-methyl-1H-benzo[d][1,2,3]triazol-5-yl)methyl)acetamide |
| 225 | N-(benzo[b]thiophen-3-ylmethyl)-2-(1-(2-chlorophenyl)-3-(trifluoromethyl)-1H-pyrazol-5-yloxy)acetamide |
| 226 | N-((1H-indol-3-yl)methyl)-2-(1-(2-chlorophenyl)-3-(trifluoromethyl)-1H-pyrazol-5-yloxy)acetamide |

TABLE 5-continued

| # | IUPAC Name | Structure |
|---|---|---|
| 227 | 2-(1-(2-chlorophenyl)-3-(trifluoromethyl)-1H-pyrazol-5-yloxy)-N-((1,5-dimethyl-1H-pyrazol-3-yl)methyl)acetamide | 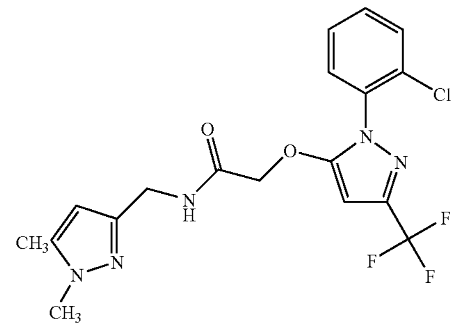 |
| 228 | N-((5-chlorobenzo[b]thiophen-3-yl)methyl)-2-(1-(2-chlorophenyl)-3-(trifluoromethyl)-1H-pyrazol-5-yloxy)acetamide | 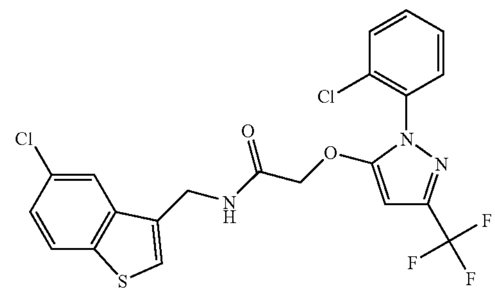 |
| 229 | 2-(1-(2-chlorophenyl)-3-(trifluoromethyl)-1H-pyrazol-5-yloxy)-N-((4,5,6,7-tetrahydrobenzo[d]thiazol-2-yl)methyl)acetamide | 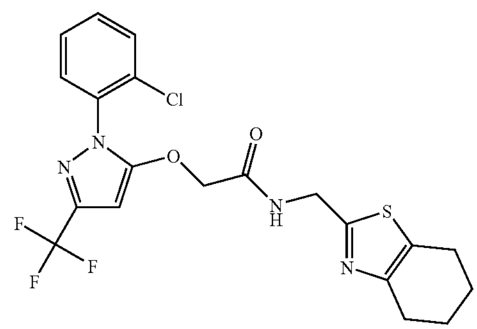 |
| 230 | 2-(1-(2-chlorophenyl)-3-(trifluoromethyl)-1H-pyrazol-5-yloxy)-N-(2-(indolin-1-yl)ethyl)acetamide | 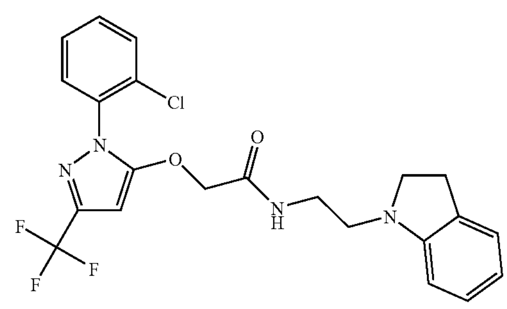 |
| 231 | 2-(1-(2-chlorophenyl)-3-(trifluoromethyl)-1H-pyrazol-5-yloxy)-N-(isochroman-1-ylmethyl)acetamide | 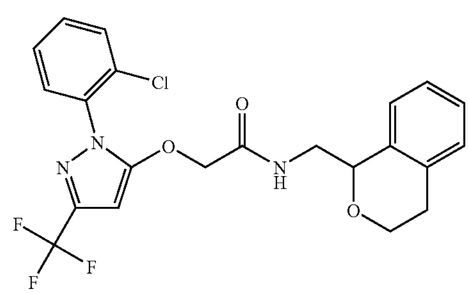 |

TABLE 5-continued

| # | IUPAC Name | Structure |
|---|---|---|
| 232 | 2-(1-(2-chlorophenyl)-3-(trifluoromethyl)-1H-pyrazol-5-yloxy)-N-(2-(4-methylthiazol-5-yl)ethyl)acetamide | 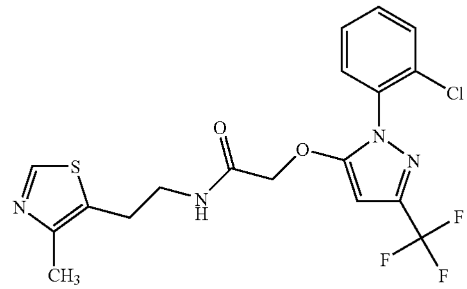 |
| 233 | 2-(1-(2-chlorophenyl)-3-(trifluoromethyl)-1H-pyrazol-5-yloxy)-N-((6-methylimidazo[1,2-a]pyridin-2-yl)methyl)acetamide | 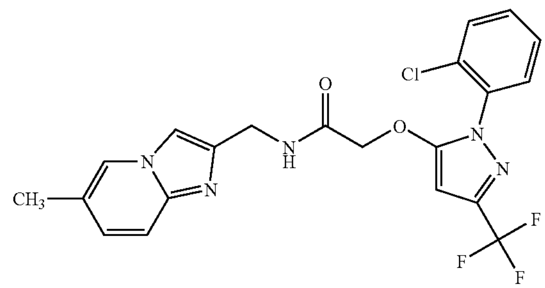 |

TABLE 6

| # | IUPAC Name | Structure |
|---|---|---|
| 234 | 2-{[1-(2-chlorophenyl)-3-(trifluoromethyl)-1H-pyrazol-5-yl]oxy}-N-[(5-methylimidazo[1,2-a]pyridin-2-yl)methyl]acetamide | 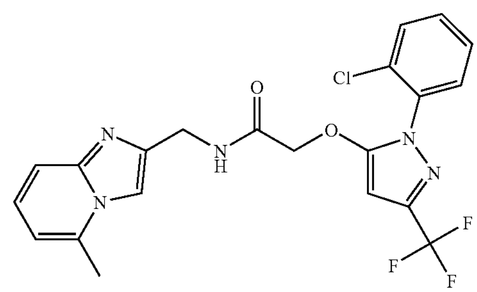 |
| 235 | 2-{[1-(2-chlorophenyl)-3-(trifluoromethyl)-1H-pyrazol-5-yl]oxy}-N-(2-furan-2-ylethyl)acetamide | 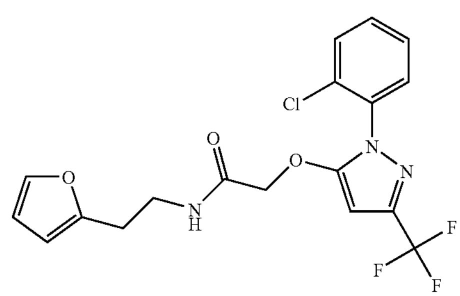 |

TABLE 6-continued

| # | IUPAC Name | Structure |
|---|---|---|
| 236 | 2-{[1-(2-chlorophenyl)-3-(trifluoromethyl)-1H-pyrazol-5-yl]oxy}-N-(1H-indol-2-ylmethyl)acetamide | 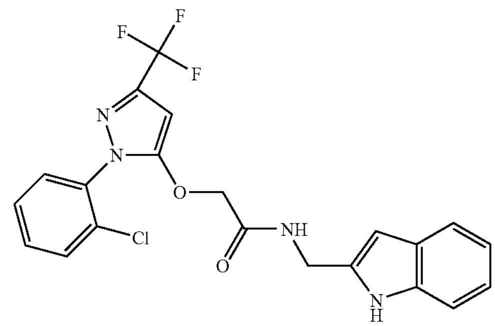 |
| 237 | 2-{[1-(2-chlorophenyl)-3-(trifluoromethyl)-1H-pyrazol-5-yl]oxy}-N-[3-(3,5-dimethyl-1H-pyrazol-1-yl)propyl]acetamide | 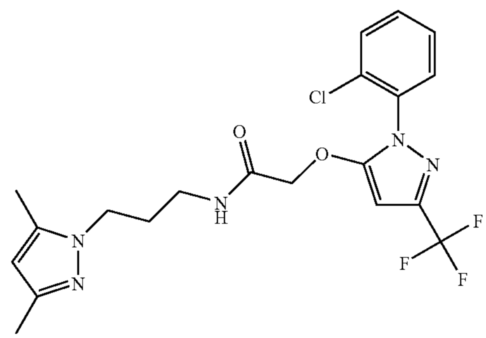 |
| 238 | 2-{[1-(2-chlorophenyl)-3-(trifluoromethyl)-1H-pyrazol-5-yl]oxy}-N-(imidazo[1,2-a]pyridin-2-ylmethyl)acetamide | 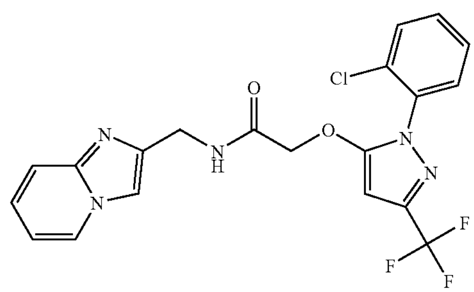 |
| 239 | 2-{[1-(2-chlorophenyl)-3-(trifluoromethyl)-1H-pyrazol-5-yl]oxy}-N-[(2-phenyl-1,3-thiazol-4-yl)methyl]acetamide | 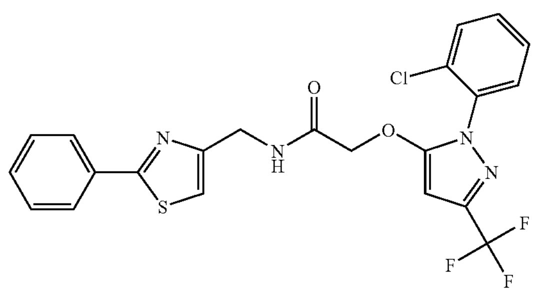 |
| 240 | 2-{[1-(2-chlorophenyl)-3-(trifluoromethyl)-1H-pyrazol-5-yl]oxy}-N-[(4-methyl-1,3-thiazol-2-yl)methyl]acetamide | 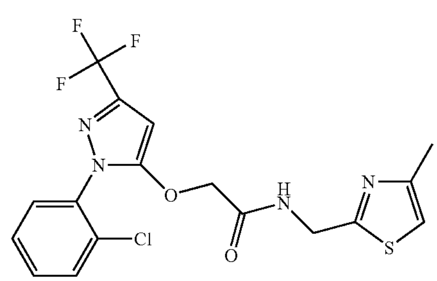 |

TABLE 6-continued

| # | IUPAC Name | Structure |
|---|---|---|
| 241 | 2-{[1-(2-chlorophenyl)-3-(trifluoromethyl)-1H-pyrazol-5-yl]oxy}-N-[phenyl(pyridin-4-yl)methyl]acetamide | 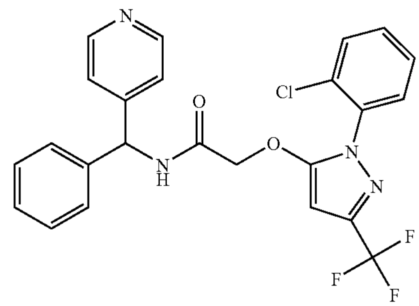 |
| 242 | 2-{[1-(2-chlorophenyl)-3-(trifluoromethyl)-1H-pyrazol-5-yl]oxy}-N-{6-[(2,4-dichlorophenyl)oxy]pyridin-3-yl}acetamide | 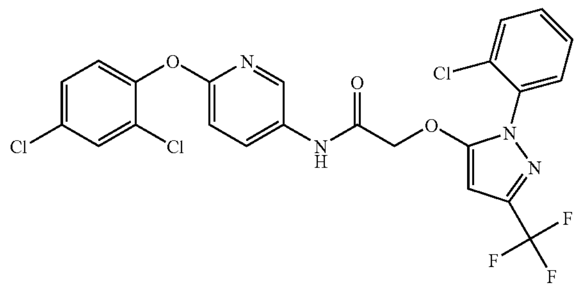 |
| 243 | 2-{[1-(2-chlorophenyl)-3-(trifluoromethyl)-1H-pyrazol-5-yl]oxy}-N-[(4'-fluorobiphenyl-3-yl)methyl]acetamide | 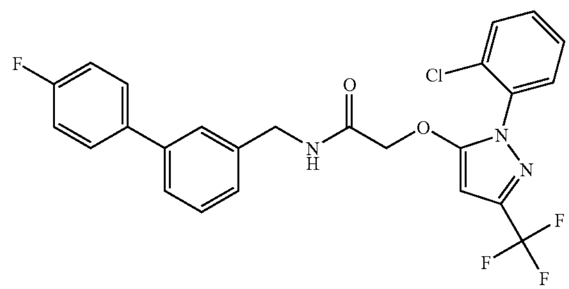 |
| 244 | 2-{[1-(2-chlorophenyl)-3-(trifluoromethyl)-1H-pyrazol-5-yl]oxy}-N-{[3-(1H-pyrazol-1-yl)phenyl]methyl}acetamide | 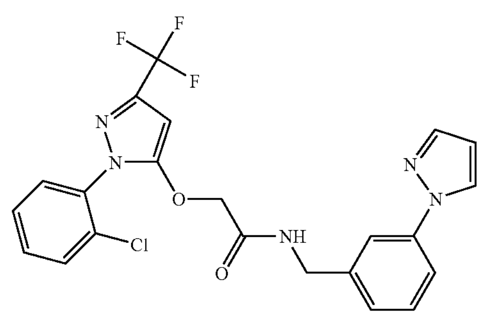 |
| 245 | methyl 2-[({[1-(2-chlorophenyl)-3-(trifluoromethyl)-1H-pyrazol-5-yl]oxy}acetyl)amino]-5-methylthiophene-3-carboxylate | 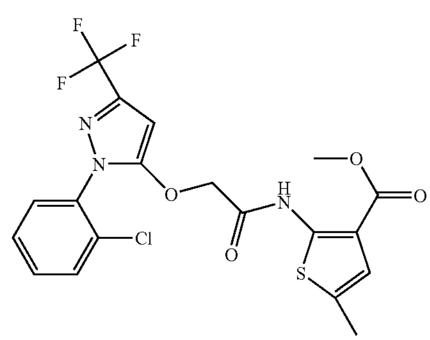 |

TABLE 6-continued

| # | IUPAC Name | Structure |
|---|---|---|
| 246 | 3-(3-chlorophenyl)-3-[({[1-(2-chlorophenyl)-3-(trifluoromethyl)-1H-pyrazol-5-yl]oxy}acetyl)amino]propanoic acid | 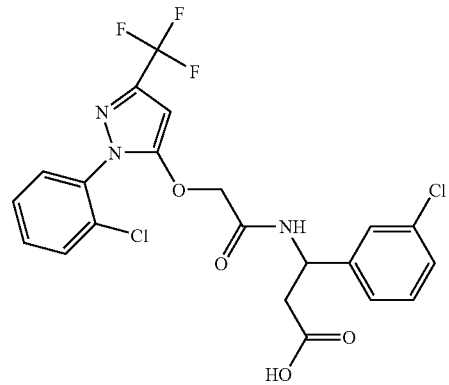 |
| 247 | 2-{[1-(2-chlorophenyl)-3-(trifluoromethyl)-1H-pyrazol-5-yl]oxy}-N-[2-(2-methyl-1-phenyl-1H-indol-3-yl)ethyl]acetamide | 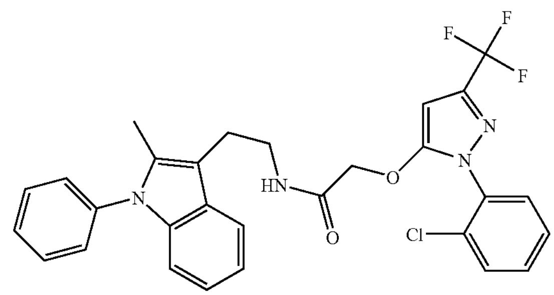 |
| 248 | 2-{[1-(2-chlorophenyl)-3-(trifluoromethyl)-1H-pyrazol-5-yl]oxy}-N-(2-methyl-1,3-benzothiazol-6-yl)acetamide | 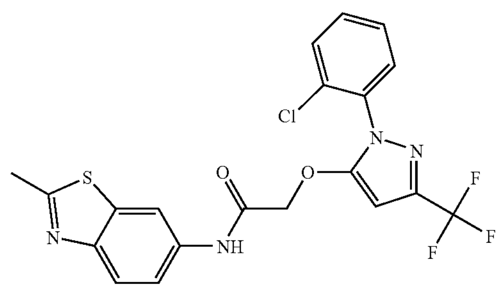 |
| 249 | 2-{[1-(2-chlorophenyl)-3-(trifluoromethyl)-1H-pyrazol-5-yl]oxy}-N-[1-(2-methyl-1,3-thiazol-4-yl)ethyl]acetamide | 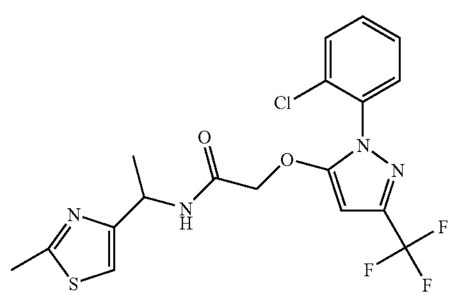 |
| 250 | 2-{[1-(2-chlorophenyl)-3-(trifluoromethyl)-1H-pyrazol-5-yl]oxy}-N-[2-(2-methyl-1H-indol-3-yl)ethyl]acetamide | 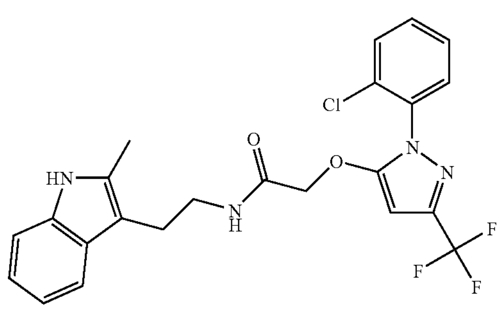 |

TABLE 6-continued

| # | IUPAC Name | Structure |
|---|---|---|
| 251 | N-[(6-chloro-1H-benzimidazol-2-yl)methyl]-2-{[1-(2-chlorophenyl)-3-(trifluoromethyl)-1H-pyrazol-5-yl]oxy}acetamide | 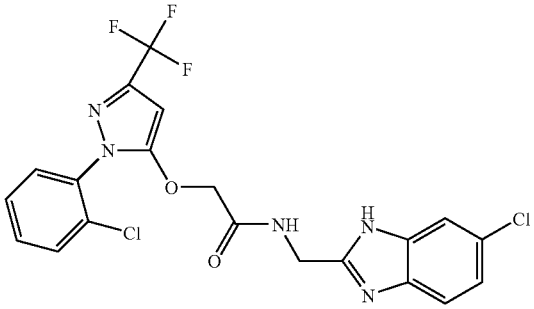 |
| 252 | 2-{[1-(2-chlorophenyl)-3-(trifluoromethyl)-1H-pyrazol-5-yl]oxy}-N-[4-(1H-pyrazol-1-yl)phenyl]acetamide | 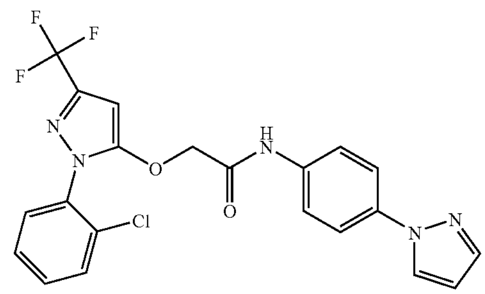 |
| 253 | 2-{[1-(2-chlorophenyl)-3-(trifluoromethyl)-1H-pyrazol-5-yl]oxy}-N-[3-(3-methyl-2-oxoimidazolidin-1-yl)phenyl]acetamide | 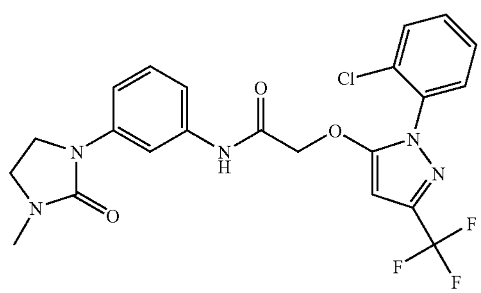 |
| 254 | N-[2-(5-chloro-1H-benzimidazol-2-yl)ethyl]-2-{[1-(2-chlorophenyl)-3-(trifluoromethyl)-1H-pyrazol-5-yl]oxy}acetamide | 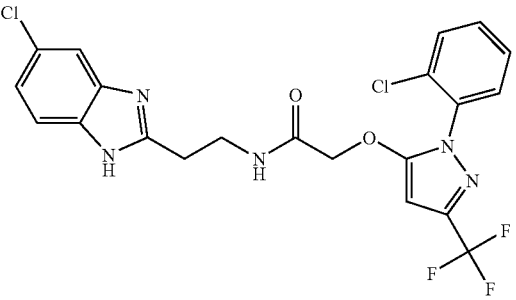 |
| 255 | 2-{[1-(2-chlorophenyl)-3-(trifluoromethyl)-1H-pyrazol-5-yl]oxy}-N-[1-(3,5-dimethyl-1H-pyrazol-4-yl)ethyl]acetamide | 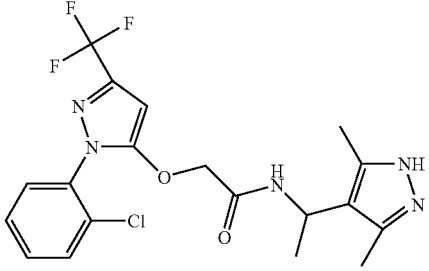 |

TABLE 6-continued

| # | IUPAC Name |
|---|---|
| 256 | 2-{[1-(2-chlorophenyl)-3-(trifluoromethyl)-1H-pyrazol-5-yl]oxy}-N-[2-(5-cyano-2-methyl-1H-indol-3-yl)ethyl]acetamide |
| 257 | 2-{[1-(2-chlorophenyl)-3-(trifluoromethyl)-1H-pyrazol-5-yl]oxy}-N-[2-(3,5-dimethyl-1H-pyrazol-1-yl)ethyl]acetamide |
| 258 | 2-{[1-(2-chlorophenyl)-3-(trifluoromethyl)-1H-pyrazol-5-yl]oxy}-N-{1-methyl-3-[4-(methyloxy)phenyl]propyl}acetamide |
| 259 | 2-{[1-(2-chlorophenyl)-3-(trifluoromethyl)-1H-pyrazol-5-yl]oxy}-N-[(4'-fluorobiphenyl-2-yl)methyl]acetamide |

TABLE 6-continued

| # | IUPAC Name |
|---|---|
| 260 | 2-{[1-(2-chlorophenyl)-3-(trifluoromethyl)-1H-pyrazol-5-yl]oxy}-N-[2-(dimethylamino)-2-phenylethyl]acetamide |
| 261 | 2-{[1-(2-chlorophenyl)-3-(trifluoromethyl)-1H-pyrazol-5-yl]oxy}-N-[3-(4-fluorophenyl)-1H-pyrazol-5-yl]acetamide |
| 262 | 2-[({[1-(2-chlorophenyl)-3-(trifluoromethyl)-1H-pyrazol-5-yl]oxy}acetyl)amino]-1,3-benzothiazole-5-carboxylic acid |
| 263 | 2-{[1-(2-chlorophenyl)-3-(trifluoromethyl)-1H-pyrazol-5-yl]oxy}-N-(2-methyl-1H-benzimidazol-6-yl)acetamide |
| 264 | 2-{[1-(2-chlorophenyl)-3-(trifluoromethyl)-1H-pyrazol-5-yl]oxy}-N-(4'-fluorobiphenyl-3-yl)acetamide |

TABLE 6-continued

| # | IUPAC Name |
|---|---|
| 265 | 2-{[1-(2-chlorophenyl)-3-(trifluoromethyl)-1H-pyrazol-5-yl]oxy}-N-{[1-(phenylmethyl)-1H-pyrazol-4-yl]methyl}acetamide |
| 266 | 2-{[1-(2-chlorophenyl)-3-(trifluoromethyl)-1H-pyrazol-5-yl]oxy}-N-[(4-oxo-3,4-dihydroquinazolin-2-yl)methyl]acetamide |
| 267 | methyl N-({[1-(2-chlorophenyl)-3-(trifluoromethyl)-1H-pyrazol-5-yl]oxy}acetyl)-L-tyrosinate |
| 268 | methyl N-({[1-(2-chlorophenyl)-3-(trifluoromethyl)-1H-pyrazol-5-yl]oxy}acetyl)-L-histidinate |
| 269 | N-[4-(acetylamino)-3-chlorophenyl]-2-{[1-(2-chlorophenyl)-3-(trifluoromethyl)-1H-pyrazol-5-yl]oxy}acetamide |

TABLE 6-continued

| # | IUPAC Name | Structure |
|---|---|---|
| 270 | N-{4-[(4-chlorophenyl)oxy]phenyl}-2-{[1-(2-chlorophenyl)-3-(trifluoromethyl)-1H-pyrazol-5-yl]oxy}acetamide | 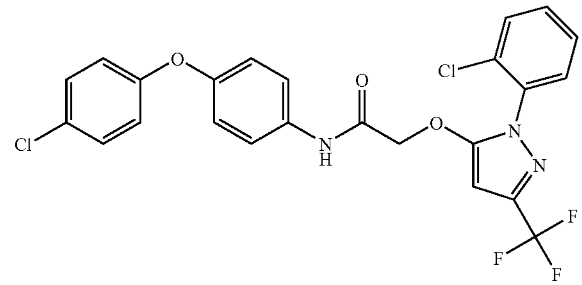 |
| 271 | 2-{[1-(2-chlorophenyl)-3-(trifluoromethyl)-1H-pyrazol-5-yl]oxy}-N-[4-(1,1-dimethylethyl)-2,6-dimethylphenyl]acetamide | 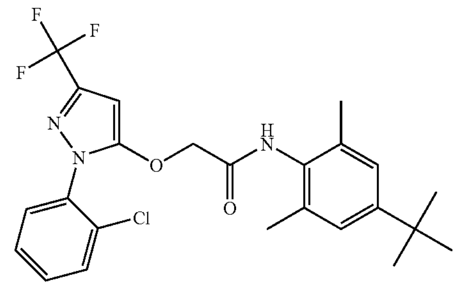 |
| 272 | N-{2-[(4-chloro-3,5-dimethylphenyl)oxy]-5-(trifluoromethyl)phenyl}-2-{[1-(2-chlorophenyl)-3-(trifluoromethyl)-1H-pyrazol-5-yl]oxy}acetamide | 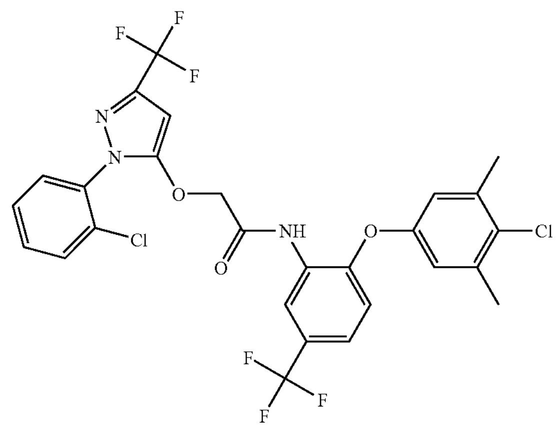 |
| 273 | 2-{[1-(2-chlorophenyl)-3-(trifluoromethyl)-1H-pyrazol-5-yl]oxy}-N-(6-{[4-(1,1-dimethylethyl)phenyl]oxy}pyridin-3-yl)acetamide | 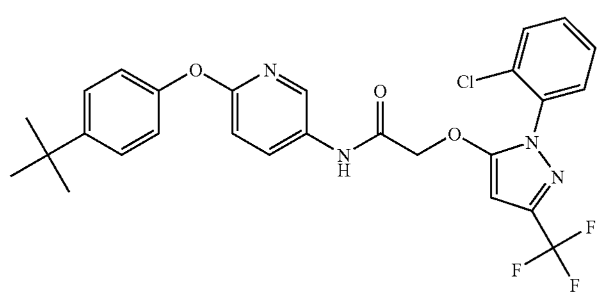 |
| 274 | 2-{[1-(2-chlorophenyl)-3-(trifluoromethyl)-1H-pyrazol-5-yl]oxy}-N-(6-{[3-(trifluoromethyl)phenyl]oxy}pyridin-3-yl)acetamide | 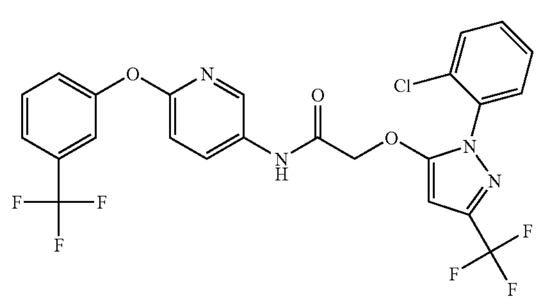 |

TABLE 6-continued

| # | IUPAC Name | Structure |
|---|---|---|
| 275 | 2-methylpropyl 2-[({[1-(2-chlorophenyl)-3-(trifluoromethyl)-1H-pyrazol-5-yl]oxy}acetyl)amino]benzoate | 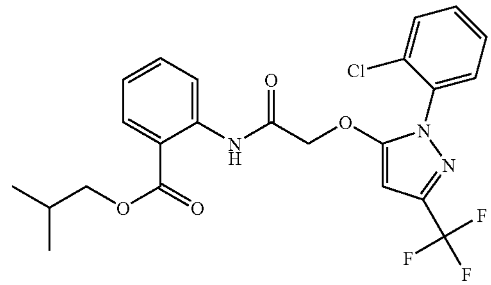 |
| 276 | methyl N-({[1-(2-chlorophenyl)-3-(trifluoromethyl)-1H-pyrazol-5-yl]oxy}acetyl)tyrosinate | 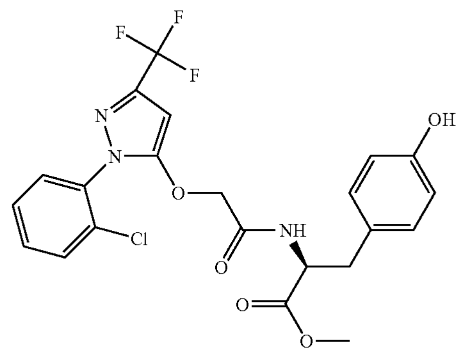 |
| 277 | 2-{[1-(2-chlorophenyl)-3-(trifluoromethyl)-1H-pyrazol-5-yl]oxy}-N-{2-[(2,4-difluorophenyl)oxy]pyridin-3-yl}acetamide | 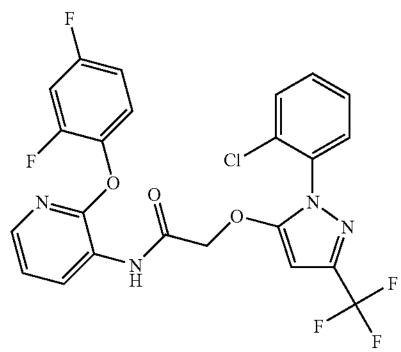 |
| 278 | methyl 3-[({[1-(2-chlorophenyl)-3-(trifluoromethyl)-1H-pyrazol-5-yl]oxy}acetyl)amino]-5-(1,1-dimethylethyl)thiophene-2-carboxylate | 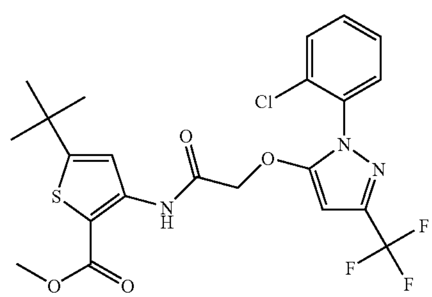 |
| 279 | 2-{[1-(2-chlorophenyl)-3-(trifluoromethyl)-1H-pyrazol-5-yl]oxy}-N-[(1R)-1-naphthalen-2-ylethyl]acetamide | 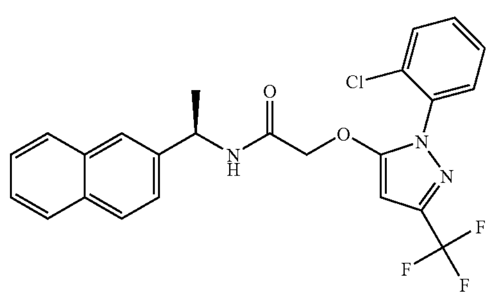 |

| # | IUPAC Name | Structure |
|---|---|---|
| 280 | 2-{[1-(2-chlorophenyl)-3-(trifluoromethyl)-1H-pyrazol-5-yl]oxy}-N-{2-[(7-methyl-2,3-dihydro-1H-inden-4-yl)oxy]pyridin-3-yl}acetamide | 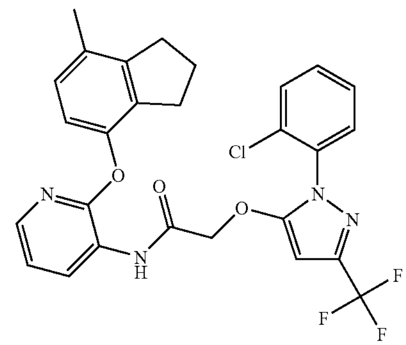 |
| 281 | N-[4-(acetylamino)-3-cyanophenyl]-2-{[1-(2-chlorophenyl)-3-trifluoromethyl)-1H-pyrazol-5-yl]oxy}acetamide | 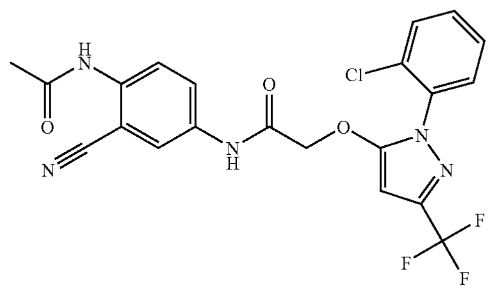 |
| 282 | ethyl 2-[({[1-(2-chlorophenyl)-3-(trifluoromethyl)-1H-pyrazol-5-yl]oxy}acetyl)amino]-4-furan-2-ylthiophene-3-carboxylate | 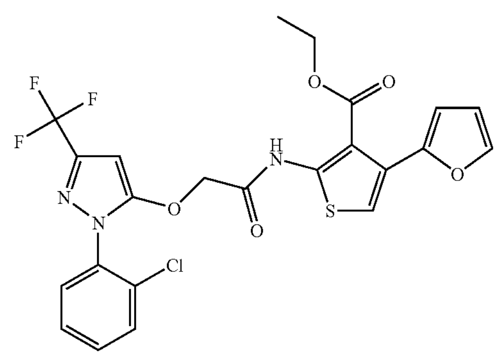 |
| 283 | 2-{[1-(2-chlorophenyl)-3-(trifluoromethyl)-1H-pyrazol-5-yl]oxy}-N-[2-methyl-4,5-bis(methyloxy)phenyl]acetamide | 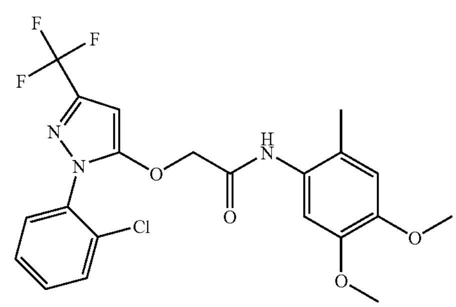 |

| # | IUPAC Name | Structure |
|---|---|---|
| 284 | 2-(1-(2-chlorophenyl)-3-(trifluoromethyl)-1H-pyrazol-5-yloxy)-N-(((1R,4aS,10aR)-7-isopropyl-1,4a-dimethyl-1,2,3,4,4a,9,10,10a-octahydrophenanthren-1-yl)methyl)acetamide | 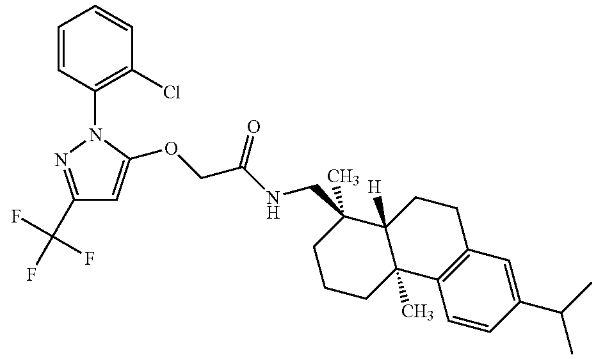 |
| 285 | methyl N-({[1-(2-chlorophenyl)-3-(trifluoromethyl)-1H-pyrazol-5-yl]oxy}acetyl)-alpha-methyltryptophanate | 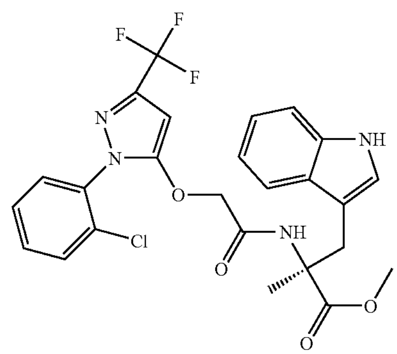 |
| 286 | 2-{[1-(2-chlorophenyl)-3-(trifluoromethyl)-1H-pyrazol-5-yl]oxy}-N-{4-chloro-2-[(trifluoromethyl)oxy]phenyl}acetamide | 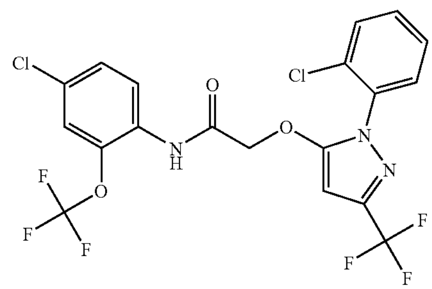 |
| 287 | methyl 2-[({[1-(2-chlorophenyl)-3-(trifluoromethyl)-1H-pyrazol-5-yl]oxy}acetyl)amino]thiophene-3-carboxylate | 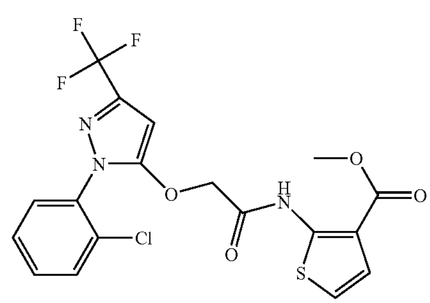 |
| 288 | 2-{[1-(2-chlorophenyl)-3-(trifluoromethyl)-1H-pyrazol-5-yl]oxy}-N-{2-[(2,3-dimethylphenyl)oxy]pyridin-3-yl}acetamide | 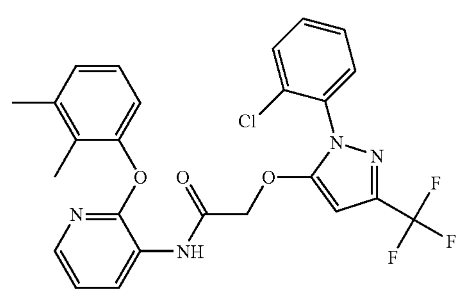 |

TABLE 6-continued

| # | IUPAC Name | Structure |
|---|---|---|
| 289 | ethyl 5-[({[1-(2-chlorophenyl)-3-(trifluoromethyl)-1H-pyrazol-5-yl]oxy}acetyl)amino]-1-(4-fluorophenyl)-1H-pyrazole-4-carboxylate | 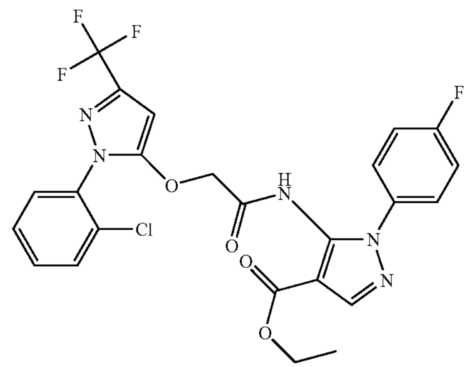 |
| 290 | N-(4-butyl-2-methylphenyl)-2-{[1-(2-chlorophenyl)-3-(trifluoromethyl)-1H-pyrazol-5-yl]oxy}acetamide | 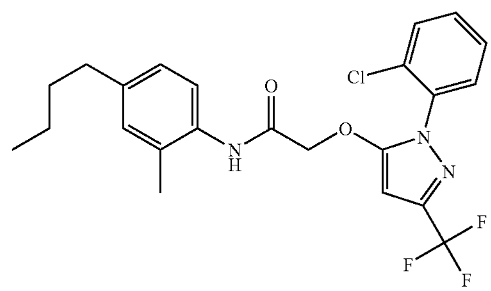 |
| 291 | N-[4-(acetylamino)-3-methylphenyl]-2-{[1-(2-chlorophenyl)-3-(trifluoromethyl)-1H-pyrazol-5-yl]oxy}acetamide | 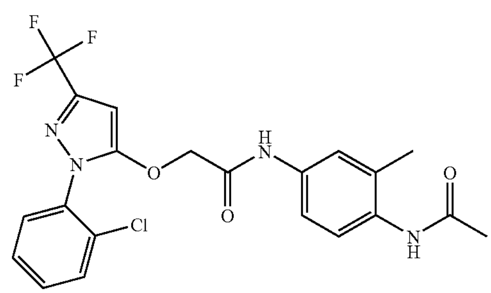 |
| 292 | 2-{[1-(2-chlorophenyl)-3-(trifluoromethyl)-1H-pyrazol-5-yl]oxy}-N-(3-cyano-5-phenylfuran-2-yl)acetamide | 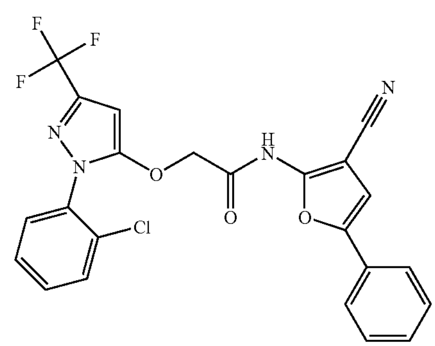 |
| 293 | N-(4-{[3,5-bis(trifluoromethyl)phenyl]oxy}phenyl)-2-{[1-(2-chlorophenyl)-3-(trifluoromethyl)-1H-pyrazol-5-yl]oxy}acetamide | 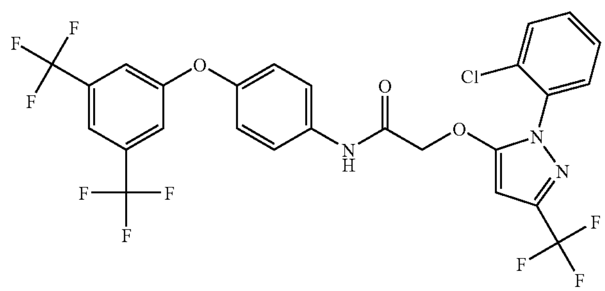 |

TABLE 6-continued

| # | IUPAC Name | Structure |
|---|---|---|
| 294 | 2-{[1-(2-chlorophenyl)-3-(trifluoromethyl)-1H-pyrazol-5-yl]oxy}-N-{(1R)-1-[3-(methyloxy)phenyl]ethyl}acetamide | 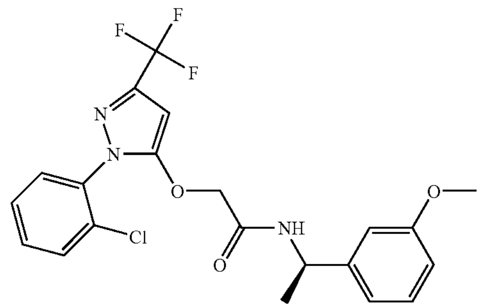 |
| 295 | N-[2-chloro-4,6-bis(methyloxy)phenyl]-2-{[1-(2-chlorophenyl)-3-(trifluoromethyl)-1H-pyrazol-5-yl]oxy}acetamide | 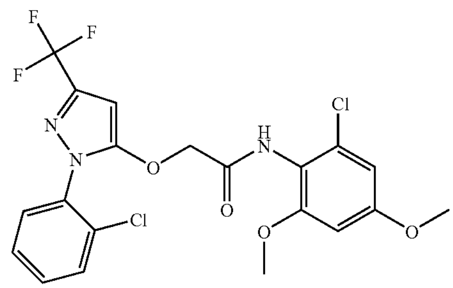 |
| 296 | 2-{[1-(2-chlorophenyl)-3-(trifluoromethyl)-1H-pyrazol-5-yl]oxy}-N-[2-(2,5-dimethylphenyl)ethyl]acetamide | 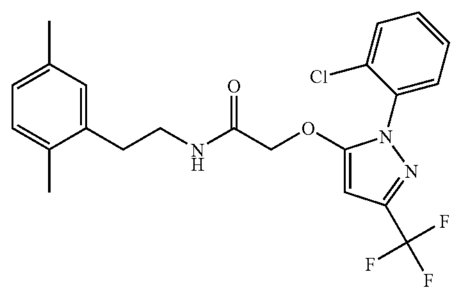 |
| 297 | 2-{[1-(2-chlorophenyl)-3-(trifluoromethyl)-1H-pyrazol-5-yl]oxy}-N-[(3-methyl-2-thienyl)methyl]acetamide | 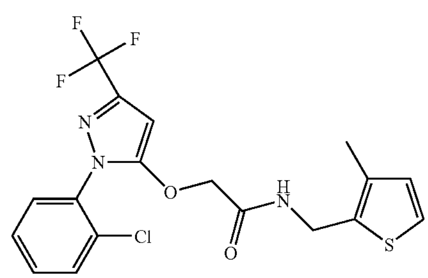 |
| 298 | 2-{[1-(2-chlorophenyl)-3-(trifluoromethyl)-1H-pyrazol-5-yl]oxy}-N-{[4-(2-thienyl)phenyl]methyl}acetamide | 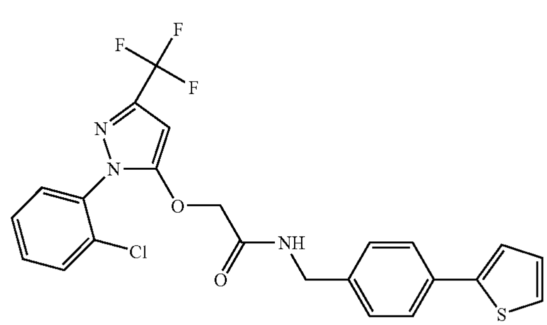 |

TABLE 6-continued

| # | IUPAC Name | Structure |
|---|---|---|
| 299 | 2-{[1-(2-chlorophenyl)-3-(trifluoromethyl)-1H-pyrazol-5-yl]oxy}-N-[2-(methyloxy)biphenyl-4-yl]acetamide | 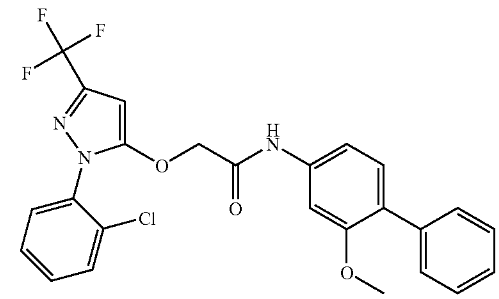 |
| 300 | 2-{[1-(2-chlorophenyl)-3-(trifluoromethyl)-1H-pyrazol-5-yl]oxy}-N-{4-[2,2,2-trifluoro-1-hydroxy-1-(trifluoromethyl)ethyl]phenyl}acetamide | 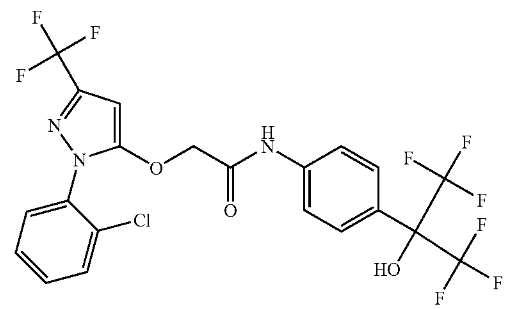 |
| 301 | 2-{[1-(2-chlorophenyl)-3-(trifluoromethyl)-1H-pyrazol-5-yl]oxy}-N-(2,6-dimethylphenyl)acetamide | 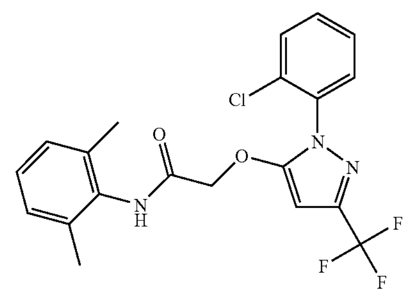 |
| 302 | 2-{[1-(2-chlorophenyl)-3-(trifluoromethyl)-1H-pyrazol-5-yl]oxy}-N-(2-phenylethyl)acetamide | 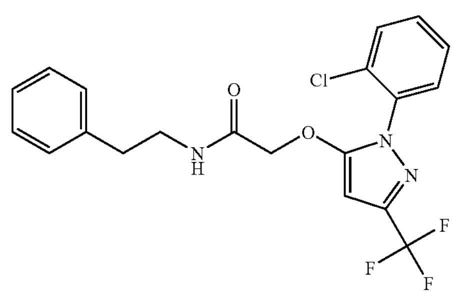 |
| 303 | 2-{[1-(2-chlorophenyl)-3-(trifluoromethyl)-1H-pyrazol-5-yl]oxy}-N-(3-methylphenyl)acetamide | 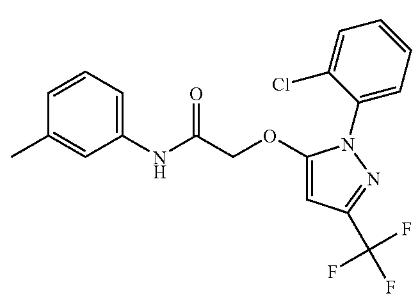 |

TABLE 6-continued

| # | IUPAC Name | Structure |
|---|---|---|
| 304 | 2-{[1-(2-chlorophenyl)-3-(trifluoromethyl)-1H-pyrazol-5-yl]oxy}-N-(2-phenylpropyl)acetamide | 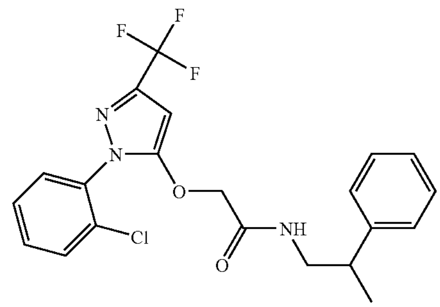 |
| 305 | 2-{[1-(2-chlorophenyl)-3-(trifluoromethyl)-1H-pyrazol-5-yl]oxy}-N-[2-(2-fluorophenyl)ethyl]acetamide | 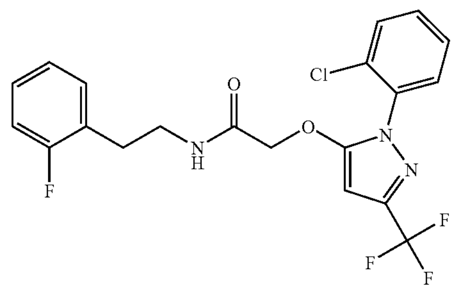 |
| 306 | 2-{[1-(2-chlorophenyl)-3-(trifluoromethyl)-1H-pyrazol-5-yl]oxy}-N-{2-[2-(methyloxy)phenyl]ethyl}acetamide | 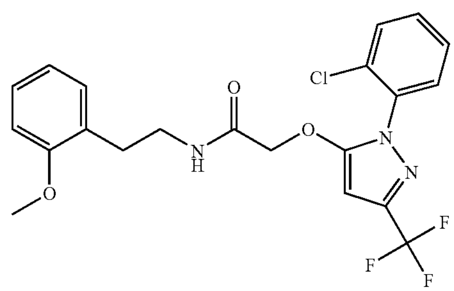 |
| 307 | 2-{[1-(2-chlorophenyl)-3-(trifluoromethyl)-1H-pyrazol-5-yl]oxy}-N-[2-(2-thienyl)ethyl]acetamide | 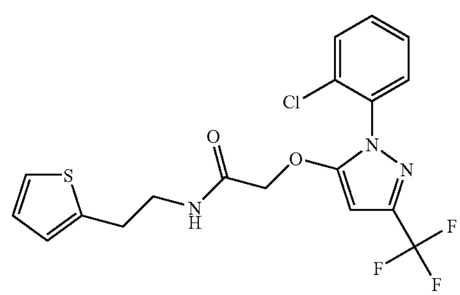 |
| 308 | 2-{[1-(2-chlorophenyl)-3-(trifluoromethyl)-1H-pyrazol-5-yl]oxy}-N-[(1S)-1-phenylethyl]acetamide | 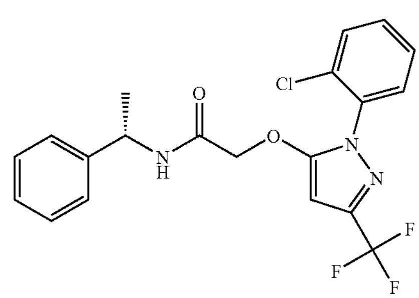 |

TABLE 6-continued

| # | IUPAC Name |
|---|---|
| 309 | 2-{[1-(2-chlorophenyl)-3-(trifluoromethyl)-1H-pyrazol-5-yl]oxy}-N-[(1R)-1-phenylethyl]acetamide |
| 310 | 2-{[1-(2-chlorophenyl)-3-(trifluoromethyl)-1H-pyrazol-5-yl]oxy}-N-[2-methyl-6-(1-methylethyl)phenyl]acetamide |
| 311 | 2-{[1-(2-chlorophenyl)-3-(trifluoromethyl)-1H-pyrazol-5-yl]oxy}-N-(4-ethylphenyl)acetamide |
| 312 | 2-{[1-(2-chlorophenyl)-3-(trifluoromethyl)-1H-pyrazol-5-yl]oxy}-N-(2,3-dimethylphenyl)acetamide |
| 313 | N-(3-chloro-4-methylphenyl)-2-{[1-(2-chlorophenyl)-3-(trifluoromethyl)-1H-pyrazol-5-yl]oxy}acetamide |

TABLE 6-continued

| # | IUPAC Name | Structure |
|---|---|---|
| 314 | N-(2-chloro-4-methylphenyl)-2-{[1-(2-chlorophenyl)-3-(trifluoromethyl)-1H-pyrazol-5-yl]oxy}acetamide | 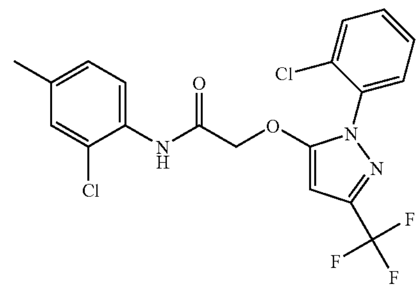 |
| 315 | N-(2-bromo-4-fluorophenyl)-2-{[1-(2-chlorophenyl)-3-(trifluoromethyl)-1H-pyrazol-5-yl]oxy}acetamide | 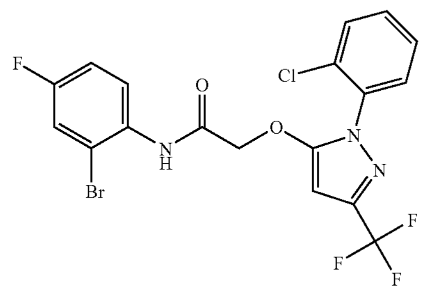 |
| 316 | N-(4-chloro-2-fluorophenyl)-2-{[1-(2-chlorophenyl)-3-(trifluoromethyl)-1H-pyrazol-5-yl]oxy}acetamide | 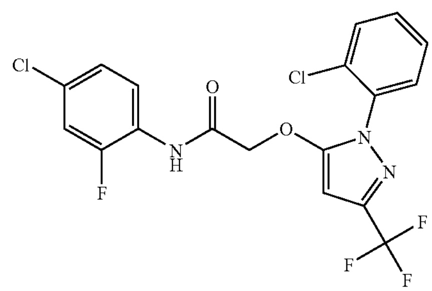 |
| 317 | 2-{[1-(2-chlorophenyl)-3-(trifluoromethyl)-1H-pyrazol-5-yl]oxy}-N-[2-fluoro-3-(trifluoromethyl)phenyl]acetamide | 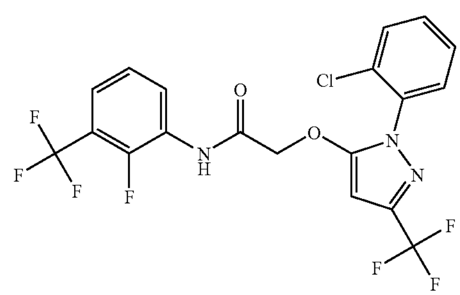 |
| 318 | N-(3-chloro-2-methylphenyl)-2-{[1-(2-chlorophenyl)-3-(trifluoromethyl)-1H-pyrazol-5-yl]oxy}acetamide | 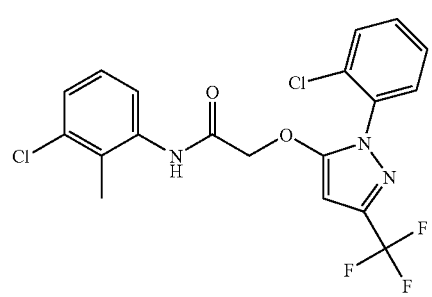 |

TABLE 6-continued

| # | IUPAC Name |
|---|---|
| 319 | 2-{[1-(2-chlorophenyl)-3-(trifluoromethyl)-1H-pyrazol-5-yl]oxy}-N-(2,5-difluorophenyl)acetamide |
| 320 | 2-{[1-(2-chlorophenyl)-3-(trifluoromethyl)-1H-pyrazol-5-yl]oxy}-N-(3-fluoro-2-methylphenyl)acetamide |
| 321 | N-(2-chloro-4-fluorophenyl)-2-{[1-(2-chlorophenyl)-3-(trifluoromethyl)-1H-pyrazol-5-yl]oxy}acetamide |
| 322 | 2-{[1-(2-chlorophenyl)-3-(trifluoromethyl)-1H-pyrazol-5-yl]oxy}-N-(2-ethyl-6-methylphenyl)acetamide |
| 323 | ethyl 2-[({[1-(2-chlorophenyl)-3-(trifluoromethyl)-1H-pyrazol-5-yl]oxy}acetyl)amino]benzoate |

TABLE 6-continued

| # | IUPAC Name |
|---|---|
| 324 | 2-{[1-(2-chlorophenyl)-3-(trifluoromethyl)-1H-pyrazol-5-yl]oxy}-N-(2,3-difluorophenyl)acetamide |
| 325 | N-(2-chloro-6-methylphenyl)-2-{[1-(2-chlorophenyl)-3-(trifluoromethyl)-1H-pyrazol-5-yl]oxy}acetamide |
| 326 | 2-{[1-(2-chlorophenyl)-3-(trifluoromethyl)-1H-pyrazol-5-yl]oxy}-N-(2,4,6-trimethylphenyl)acetamide |
| 327 | 2-{[1-(2-chlorophenyl)-3-(trifluoromethyl)-1H-pyrazol-5-yl]oxy}-N-(2,4-difluorophenyl)acetamide |
| 328 | 2-{[1-(2-chlorophenyl)-3-(trifluoromethyl)-1H-pyrazol-5-yl]oxy}-N-(2,3-dichlorophenyl)acetamide |

TABLE 6-continued

| # | IUPAC Name | Structure |
|---|---|---|
| 329 | 2-{[1-(2-chlorophenyl)-3-(trifluoromethyl)-1H-pyrazol-5-yl]oxy}-N-(4-fluoro-2-methylphenyl)acetamide | 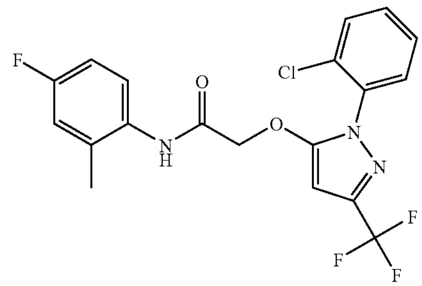 |
| 330 | N-(2-bromo-4-methylphenyl)-2-{[1-(2-chlorophenyl)-3-(trifluoromethyl)-1H-pyrazol-5-yl]oxy}acetamide | 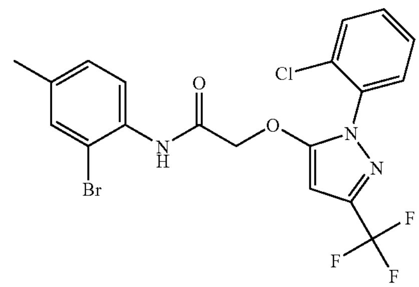 |
| 331 | 2-{[1-(2-chlorophenyl)-3-(trifluoromethyl)-1H-pyrazol-5-yl]oxy}-N-(2-ethylphenyl)acetamide | 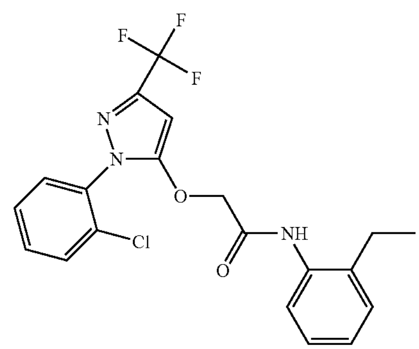 |
| 332 | 2-{[1-(2-chlorophenyl)-3-(trifluoromethyl)-1H-pyrazol-5-yl]oxy}-N-[(2,4-dimethylphenyl)methyl]acetamide | 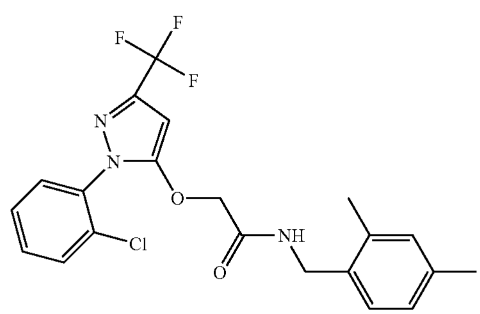 |
| 333 | 2-{[1-(2-chlorophenyl)-3-(trifluoromethyl)-1H-pyrazol-5-yl]oxy}-N-(3,5-dimethylphenyl)acetamide | 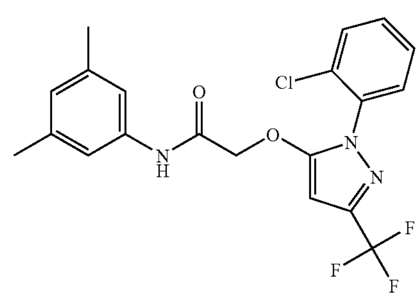 |

TABLE 6-continued

| # | IUPAC Name |
|---|---|
| 334 | 2-{[1-(2-chlorophenyl)-3-(trifluoromethyl)-1H-pyrazol-5-yl]oxy}-N-(furan-2-ylmethyl)acetamide |
| 335 | 2-{[1-(2-chlorophenyl)-3-(trifluoromethyl)-1H-pyrazol-5-yl]oxy}-N-(3-fluorophenyl)acetamide |
| 336 | 2-{[1-(2-chlorophenyl)-3-(trifluoromethyl)-1H-pyrazol-5-yl]oxy}-N-{4-[(trifluoromethyl)oxy]phenyl}acetamide |
| 337 | 2-{[1-(2-chlorophenyl)-3-(trifluoromethyl)-1H-pyrazol-5-yl]oxy}-N-[2-(trifluoromethyl)phenyl]acetamide |
| 338 | 2-{[1-(2-chlorophenyl)-3-(trifluoromethyl)-1H-pyrazol-5-yl]oxy}-N-[(2,4-difluorophenyl)methyl]acetamide |

TABLE 6-continued

| # | IUPAC Name | Structure |
|---|---|---|
| 339 | N-(3-chloro-4-fluorophenyl)-2-{[1-(2-chlorophenyl)-3-(trifluoromethyl)-1H-pyrazol-5-yl]oxy}acetamide | 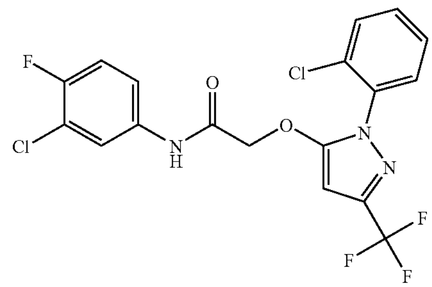 |
| 340 | N-[3-chloro-4-(methyloxy)phenyl]-2-{[1-(2-chlorophenyl)-3-(trifluoromethyl)-1H-pyrazol-5-yl]oxy}acetamide | 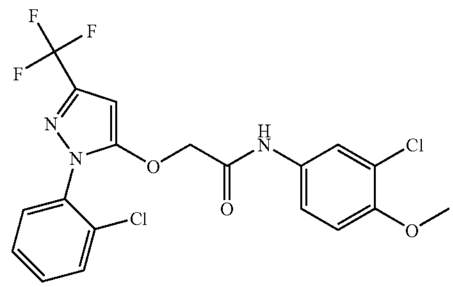 |
| 341 | 2-{[1-(2-chlorophenyl)-3-(trifluoromethyl)-1H-pyrazol-5-yl]oxy}-N-{3-[(phenylmethyl)oxy]phenyl}acetamide | 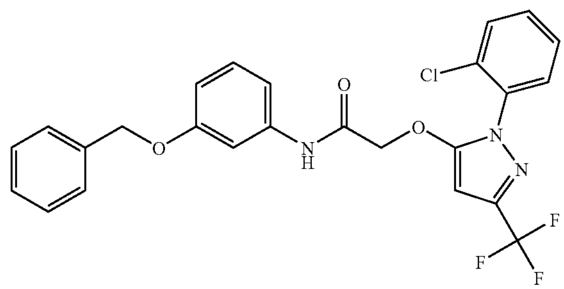 |
| 342 | 2-{[1-(2-chlorophenyl)-3-(trifluoromethyl)-1H-pyrazol-5-yl]oxy}-N-(3-phenyl-1,2,4-thiadiazol-5-yl)acetamide | 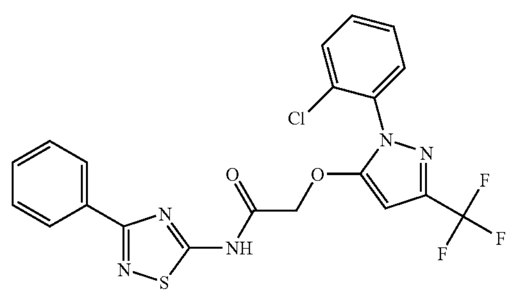 |
| 343 | N-[2,6-bis(1-methylethyl)phenyl]-2-{[1-(2-chlorophenyl)-3-(trifluoromethyl)-1H-pyrazol-5-yl]oxy}acetamide | 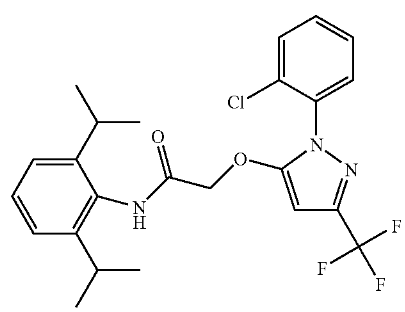 |

TABLE 6-continued

| # | IUPAC Name |
|---|---|
| 344 | 2-{[1-(2-chlorophenyl)-3-(trifluoromethyl)-1H-pyrazol-5-yl]oxy}-N-[2-methyl-4-(methyloxy)phenyl]acetamide |
| 345 | 2-{[1-(2-chlorophenyl)-3-(trifluoromethyl)-1H-pyrazol-5-yl]oxy}-N-(3-fluoro-4-methylphenyl)acetamide |
| 346 | 2-{[1-(2-chlorophenyl)-3-(trifluoromethyl)-1H-pyrazol-5-yl]oxy}-N-(5-methyl-1,3,4-thiadiazol-2-yl)acetamide |
| 347 | 2-{[1-(2-chlorophenyl)-3-(trifluoromethyl)-1H-pyrazol-5-yl]oxy}-N-[2-(1-methylpropyl)phenyl]acetamide |
| 348 | N-(3-bromo-4-methylphenyl)-2-{[1-(2-chlorophenyl)-3-(trifluoromethyl)-1H-pyrazol-5-yl]oxy}acetamide |

TABLE 6-continued

| # | IUPAC Name | Structure |
|---|---|---|
| 349 | 2-{[1-(2-chlorophenyl)-3-(trifluoromethyl)-1H-pyrazol-5-yl]oxy}-N-{2-[(trifluoromethyl)oxy]phenyl}acetamide | 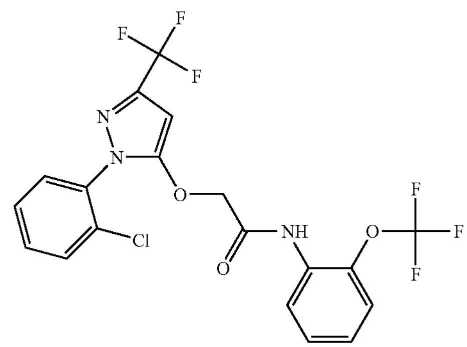 |
| 350 | N-[2,5-bis(methyloxy)phenyl]-2-{[1-(2-chlorophenyl)-3-(trifluoromethyl)-1H-pyrazol-5-yl]oxy}acetamide | 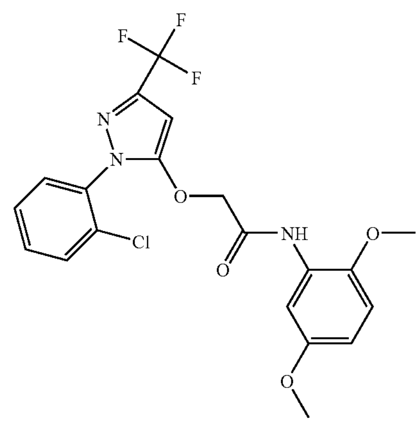 |
| 351 | 2-{[1-(2-chlorophenyl)-3-(trifluoromethyl)-1H-pyrazol-5-yl]oxy}-N-{4-[(difluoromethyl)oxy]phenyl}acetamide | 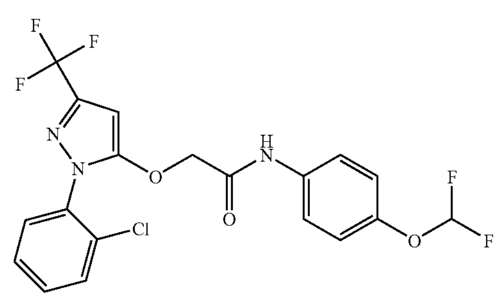 |
| 352 | 2-{[1-(2-chlorophenyl)-3-(trifluoromethyl)-1H-pyrazol-5-yl]oxy}-N-(2,3,4-trifluorophenyl)acetamide | 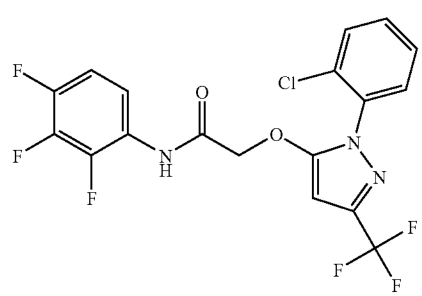 |

TABLE 6-continued

| # | IUPAC Name | Structure |
|---|---|---|
| 353 | 2-{[1-(2-chlorophenyl)-3-(trifluoromethyl)-1H-pyrazol-5-yl]oxy}-N-[2-methyl-6-(methyloxy)phenyl]acetamide | 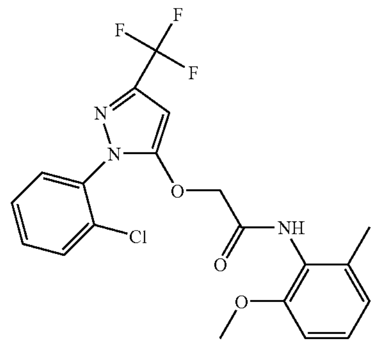 |
| 354 | 2-{[1-(2-chlorophenyl)-3-(trifluoromethyl)-1H-pyrazol-5-yl]oxy}-N-(2,4,6-trifluorophenyl)acetamide | 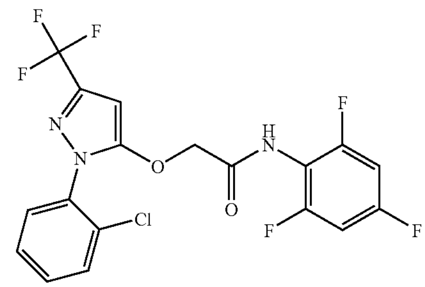 |
| 355 | 2-{[1-(2-chlorophenyl)-3-(trifluoromethyl)-1H-pyrazol-5-yl]oxy}-N-[4-(1,1-dimethylethyl)phenyl]acetamide | 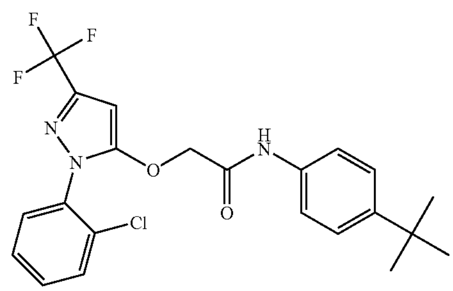 |
| 356 | 2-{[1-(2-chlorophenyl)-3-(trifluoromethyl)-1H-pyrazol-5-yl]oxy}-N-[3-(methyloxy)phenyl]acetamide | 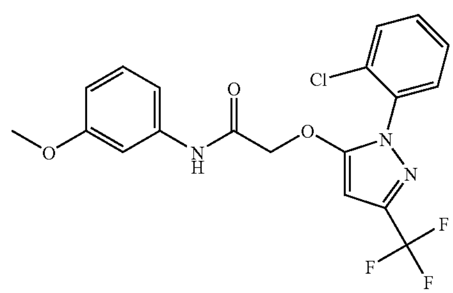 |
| 357 | 2-{[1-(2-chlorophenyl)-3-(trifluoromethyl)-1H-pyrazol-5-yl]oxy}-N-[3-(phenyloxy)phenyl]acetamide | 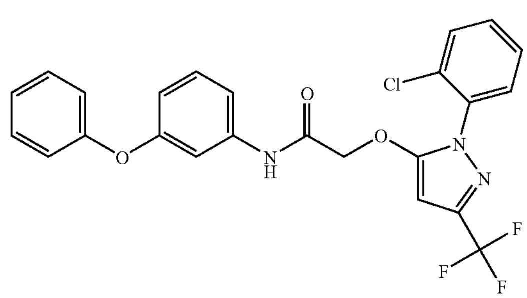 |

TABLE 6-continued

| # | IUPAC Name | Structure |
|---|---|---|
| 358 | 2-{[1-(2-chlorophenyl)-3-(trifluoromethyl)-1H-pyrazol-5-yl]oxy}-N-(2,6-diethylphenyl)acetamide | 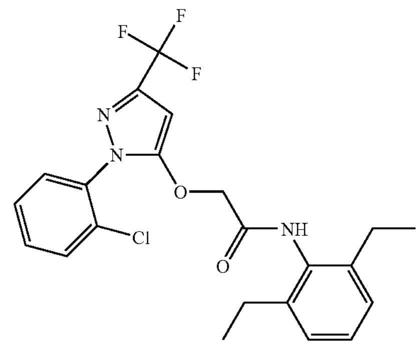 |
| 359 | N-(5-chloro-2-methylphenyl)-2-{[1-(2-chlorophenyl)-3-(trifluoromethyl)-1H-pyrazol-5-yl]oxy}acetamide | 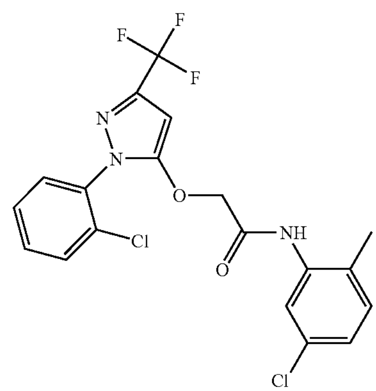 |
| 360 | 2-{[1-(2-chlorophenyl)-3-(trifluoromethyl)-1H-pyrazol-5-yl]oxy}-N-(3,4-difluorophenyl)acetamide | 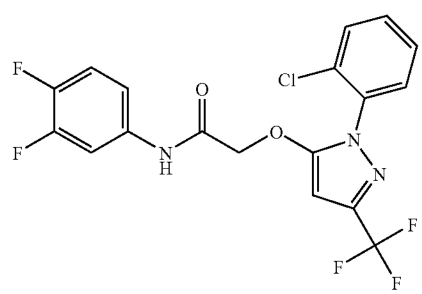 |
| 361 | 2-{[1-(2-chlorophenyl)-3-(trifluoromethyl)-1H-pyrazol-5-yl]oxy}-N-(2,3-dihydro-1H-inden-5-yl)acetamide | 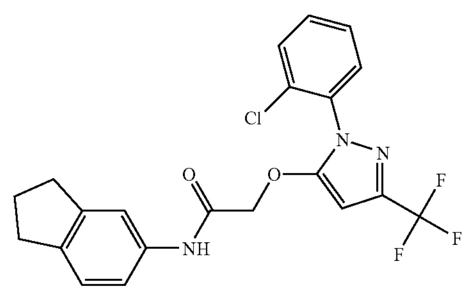 |
| 362 | 2-{[1-(2-chlorophenyl)-3-(trifluoromethyl)-1H-pyrazol-5-yl]oxy}-N-(3-ethylphenyl)acetamide | 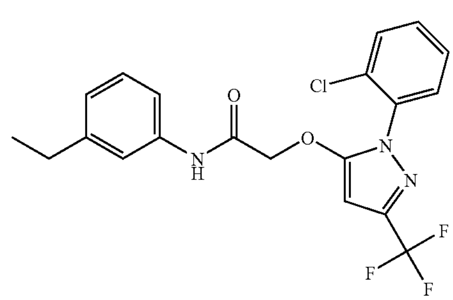 |

TABLE 6-continued

| # | IUPAC Name | Structure |
|---|---|---|
| 363 | N-(4-chloro-2-methylphenyl)-2-{[1-(2-chlorophenyl)-3-(trifluoromethyl)-1H-pyrazol-5-yl]oxy}acetamide | 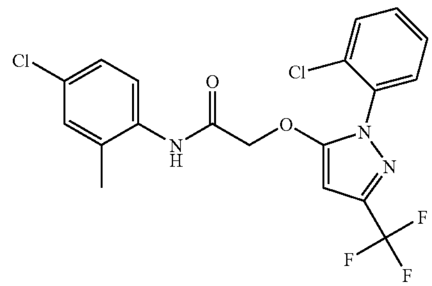 |
| 364 | 2-{[1-(2-chlorophenyl)-3-(trifluoromethyl)-1H-pyrazol-5-yl]oxy}-N-(3-methylisothiazol-5-yl)acetamide | 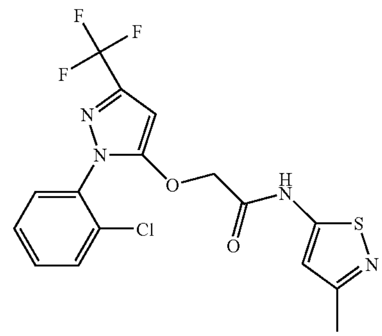 |
| 365 | 2-{[1-(2-chlorophenyl)-3-(trifluoromethyl)-1H-pyrazol-5-yl]oxy}-N-[2-chloro-5-(trifluoromethyl)phenyl]acetamide | 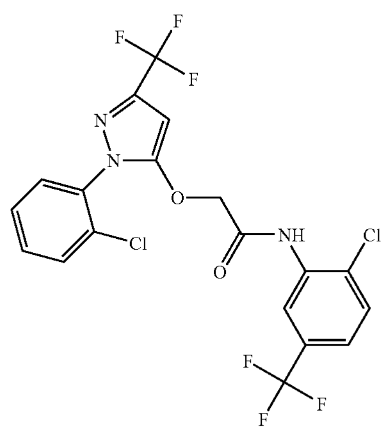 |
| 366 | N-[2-(2-chlorophenyl)ethyl]-2-{[1-(2-chlorophenyl)-3-(trifluoromethyl)-1H-pyrazol-5-yl]oxy}acetamide | 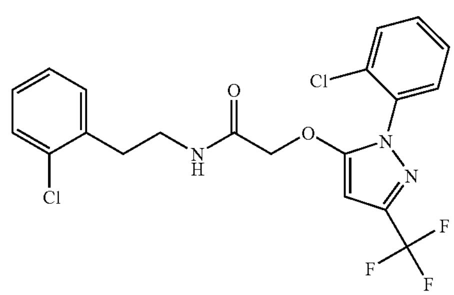 |

TABLE 6-continued

| # | IUPAC Name |
|---|---|
| 367 | 2-{[1-(2-chlorophenyl)-3-(trifluoromethyl)-1H-pyrazol-5-yl]oxy}-N-[5-methyl-2-(methyloxy)phenyl]acetamide |
| 368 | 2-{[1-(2-chlorophenyl)-3-(trifluoromethyl)-1H-pyrazol-5-yl]oxy}-N-[2-(naphthalen-1-ylamino)ethyl]acetamide |
| 369 | N-[5-chloro-2-(methyloxy)phenyl]-2-{[1-(2-chlorophenyl)-3-(trifluoromethyl)-1H-pyrazol-5-yl]oxy}acetamide |
| 370 | N-(5-bromo-2-methylphenyl)-2-{[1-(2-chlorophenyl)-3-(trifluoromethyl)-1H-pyrazol-5-yl]oxy}acetamide |
| 371 | N-1,3-benzothiazol-2-yl-2-{[1-(2-chlorophenyl)-3-(trifluoromethyl)-1H-pyrazol-5-yl]oxy}acetamide |

TABLE 6-continued

| # | IUPAC Name |
|---|---|
| 372 | 2-{[1-(2-chlorophenyl)-3-(trifluoromethyl)-1H-pyrazol-5-yl]oxy}-N-{2-[(difluoromethyl)oxy]phenyl}acetamide |
| 373 | N-[2-chloro-5-(methyloxy)phenyl]-2-{[1-(2-chlorophenyl)-3-(trifluoromethyl)-1H-pyrazol-5-yl]oxy}acetamide |
| 374 | 2-{[1-(2-chlorophenyl)-3-(trifluoromethyl)-1H-pyrazol-5-yl]oxy}-N-[2-fluoro-5-(trifluoromethyl)phenyl]acetamide |
| 375 | 2-{[1-(2-chlorophenyl)-3-(trifluoromethyl)-1H-pyrazol-5-yl]oxy}-N-(2-fluoro-5-methylphenyl)acetamide |
| 376 | 2-{[1-(2-chlorophenyl)-3-(trifluoromethyl)-1H-pyrazol-5-yl]oxy}-N-[4-(phenyloxy)phenyl]acetamide |

TABLE 6-continued

| # | IUPAC Name | Structure |
|---|---|---|
| 377 | methyl 3-[({[1-(2-chlorophenyl)-3-(trifluoromethyl)-1H-pyrazol-5-yl]oxy}acetyl)amino]benzoate | 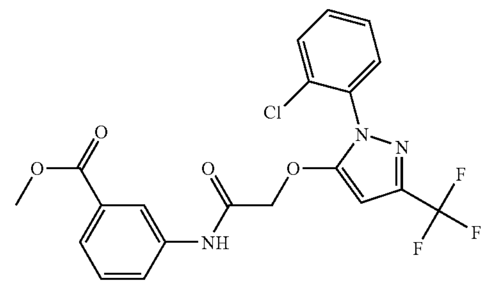 |
| 378 | 2-{[1-(2-chlorophenyl)-3-(trifluoromethyl)-1H-pyrazol-5-yl]oxy}-N-(2-cyanophenyl)acetamide | 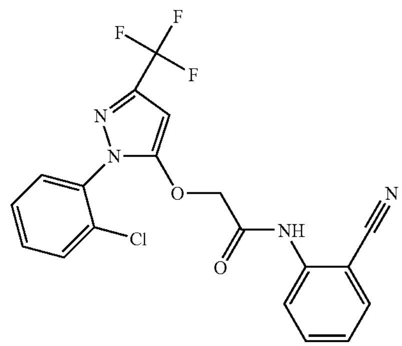 |
| 379 | 2-{[1-(2-chlorophenyl)-3-(trifluoromethyl)-1H-pyrazol-5-yl]oxy}-N-(4-phenyl-1,3-thiazol-2-yl)acetamide | 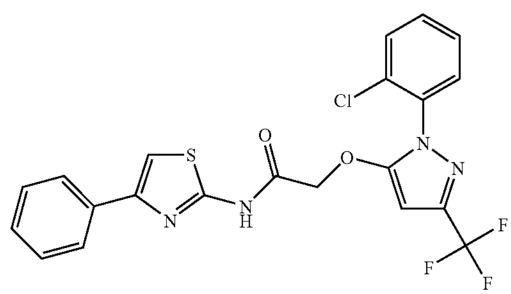 |
| 380 | 2-{[1-(2-chlorophenyl)-3-(trifluoromethyl)-1H-pyrazol-5-yl]oxy}-N-(4-methyl-1,3-thiazol-2-yl)acetamide | 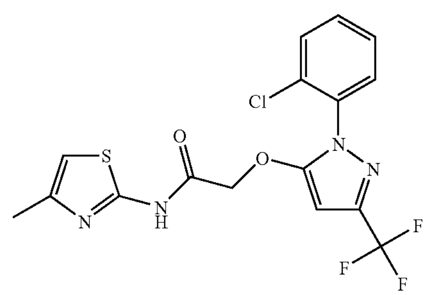 |
| 381 | 2-{[1-(2-chlorophenyl)-3-(trifluoromethyl)-1H-pyrazol-5-yl]oxy}-N-[2-(1-methylethyl)phenyl]acetamide | 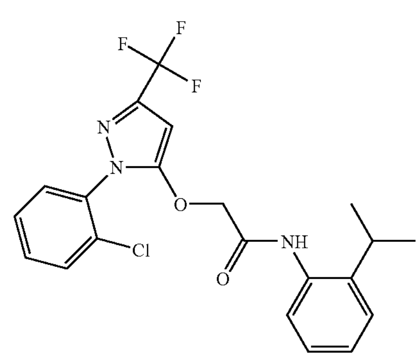 |

TABLE 6-continued
| # | IUPAC Name | Structure |
|---|---|---|
| 382 | 2-{[1-(2-chlorophenyl)-3-(trifluoromethyl)-1H-pyrazol-5-yl]oxy}-N-[2-(1H-indol-3-yl)ethyl]acetamide | 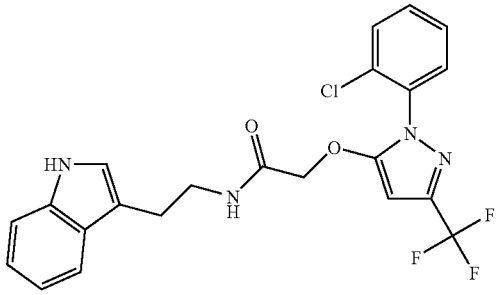 |
| 383 | 2-[({[1-(2-chlorophenyl)-3-(trifluoromethyl)-1H-pyrazol-5-yl]oxy}acetyl)amino]benzoic acid | 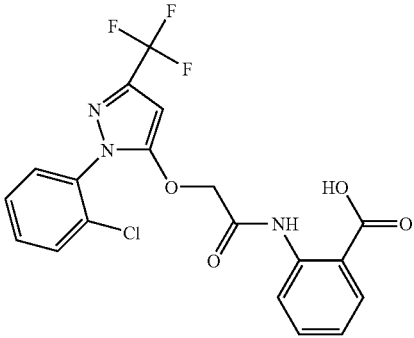 |
| 384 | 2-{[1-(2-chlorophenyl)-3-(trifluoromethyl)-1H-pyrazol-5-yl]oxy}-N-[(2-methylphenyl)methyl]acetamide | 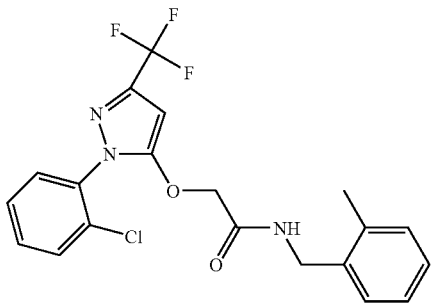 |
| 385 | N-(3-chloro-4-hydroxyphenyl)-2-{[1-(2-chlorophenyl)-3-(trifluoromethyl)-1H-pyrazol-5-yl]oxy}acetamide | 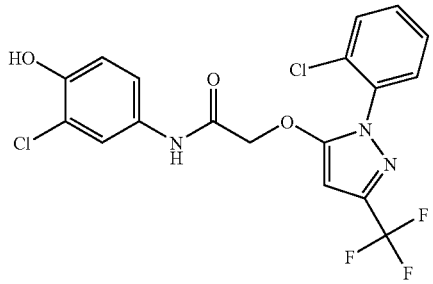 |

TABLE 6-continued

| # | IUPAC Name | Structure |
|---|---|---|
| 386 | 2-{[1-(2-chlorophenyl)-3-(trifluoromethyl)-1H-pyrazol-5-yl]oxy}-N-(1,2,3,4-tetrahydronaphthalen-1-yl)acetamide | 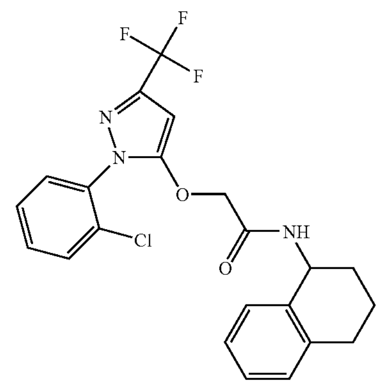 |
| 387 | 2-[({[1-(2-chlorophenyl)-3-(trifluoromethyl)-1H-pyrazol-5-yl]oxy}acetyl)amino]-5-methylbenzoic acid | 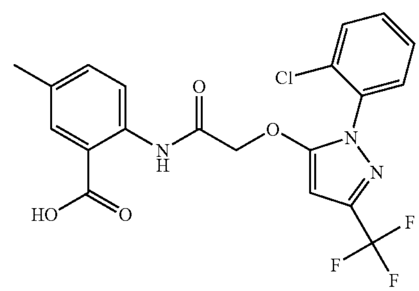 |
| 388 | 2-[({[1-(2-chlorophenyl)-3-(trifluoromethyl)-1H-pyrazol-5-yl]oxy}acetyl)amino]-4-methylbenzoic acid | 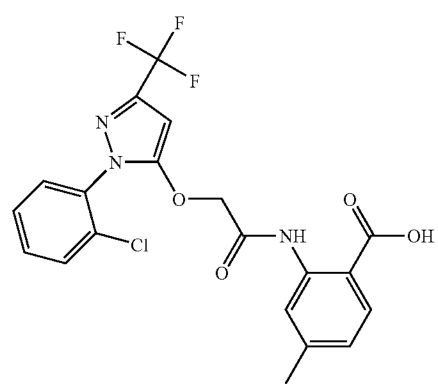 |
| 389 | 2-{[1-(2-chlorophenyl)-3-(trifluoromethyl)-1H-pyrazol-5-yl]oxy}-N-(2-piperidin-1-ylphenyl)acetamide | 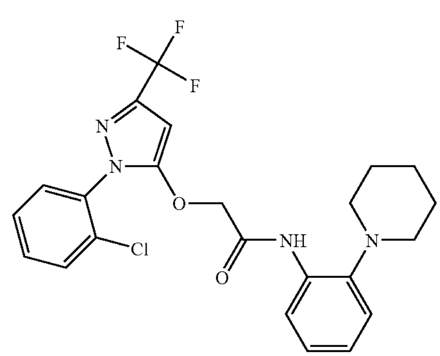 |

TABLE 6-continued

| # | IUPAC Name | Structure |
|---|---|---|
| 390 | 2-{[1-(2-chlorophenyl)-3-(trifluoromethyl)-1H-pyrazol-5-yl]oxy}-N-{4-[(phenylmethyl)oxy]phenyl}acetamide | 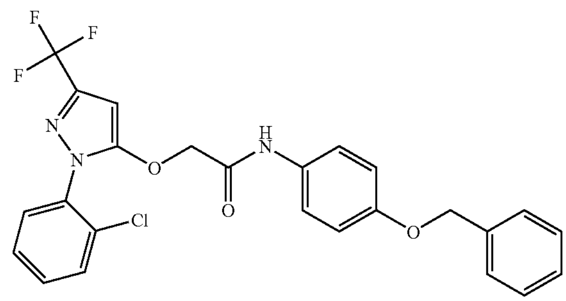 |
| 391 | methyl N-({[1-(2-chlorophenyl)-3-(trifluoromethyl)-1H-pyrazol-5-yl]oxy}acetyl)-L-phenylalaninate | 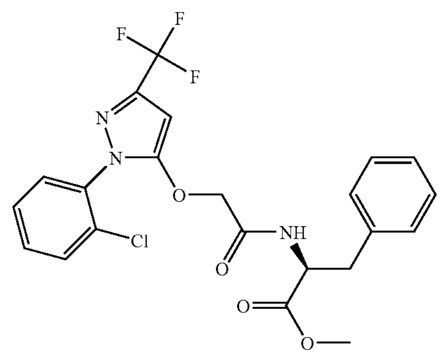 |
| 392 | 2-{[1-(2-chlorophenyl)-3-(trifluoromethyl)-1H-pyrazol-5-yl]oxy}-N-(6-methyl-1,3-benzothiazol-2-yl)acetamide | 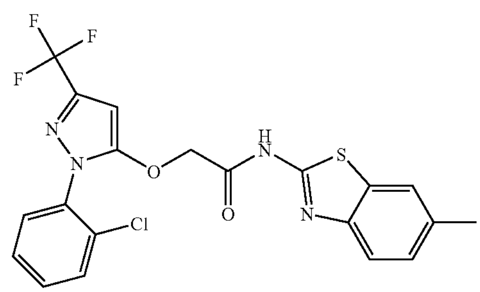 |
| 393 | 2-{[1-(2-chlorophenyl)-3-(trifluoromethyl)-1H-pyrazol-5-yl]oxy}-N-isoquinolin-5-ylacetamide | 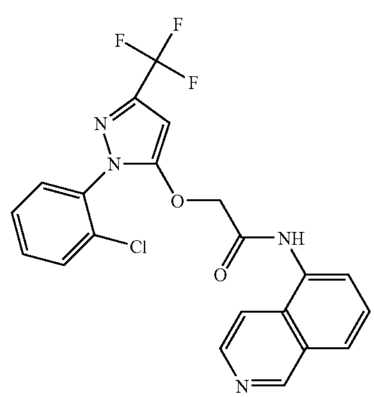 |

TABLE 6-continued

| # | IUPAC Name |
|---|---|
| 394 | 2-{[1-(2-chlorophenyl)-3-(trifluoromethyl)-1H-pyrazol-5-yl]oxy}-N-quinolin-6-ylacetamide |
| 395 | N-biphenyl-4-yl-2-{[1-(2-chlorophenyl)-3-(trifluoromethyl)-1H-pyrazol-5-yl]oxy}acetamide |
| 396 | 2-{[1-(2-chlorophenyl)-3-(trifluoromethyl)-1H-pyrazol-5-yl]oxy}-N-(1-methyl-1H-benzimidazol-2-yl)acetamide |
| 397 | 2-{[1-(2-chlorophenyl)-3-(trifluoromethyl)-1H-pyrazol-5-yl]oxy}-N-[5-(methylthio)-1,3,4-thiadiazol-2-yl]acetamide |
| 398 | 2-{[1-(2-chlorophenyl)-3-(trifluoromethyl)-1H-pyrazol-5-yl]oxy}-N-{2-[6-(methyloxy)-1H-indol-3-yl]ethyl}acetamide |

TABLE 6-continued

| # | IUPAC Name |
|---|---|
| 399 | 2-{[-(2-chlorophenyl)-3-(trifluoromethyl)-1H-pyrazol-5-yl]oxy}-N-1H-indazol-5-ylacetamide |
| 400 | 2-{[1-(2-chlorophenyl)-3-(trifluoromethyl)-1H-pyrazol-5-yl]oxy}-N-1,3,4-thiadiazol-2-ylacetamide |
| 401 | 2-{[1-(2-chlorophenyl)-3-(trifluoromethyl)-1H-pyrazol-5-yl]oxy}-N-[(5-methylisoxazol-3-yl)methyl]acetamide |
| 402 | N-[(4-bromophenyl)methyl]-2-{[1-(2-chlorophenyl)-3-(trifluoromethyl)-1H-pyrazol-5-yl]oxy}acetamide |
| 403 | 2-{[1-(2-chlorophenyl)-3-(trifluoromethyl)-1H-pyrazol-5-yl]oxy}-N-(4-fluorophenyl)acetamide |

TABLE 6-continued

| # | IUPAC Name | Structure |
|---|---|---|
| 404 | N-[(4-chloro-2-fluorophenyl)methyl]-2-{[1-(2-chlorophenyl)-3-(trifluoromethyl)-1H-pyrazol-5-yl]oxy}acetamide | 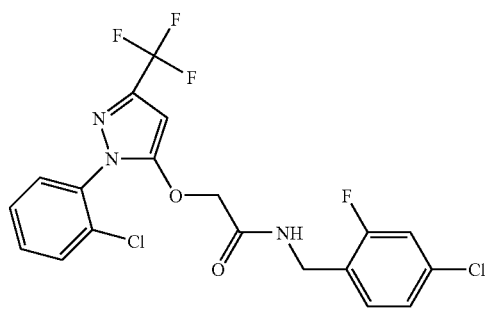 |
| 405 | 2-{[1-(2-chlorophenyl)-3-(trifluoromethyl)-1H-pyrazol-5-yl]oxy}-N-[5-(1,1-dimethylethyl)-1,3,4-thiadiazol-2-yl]acetamide | 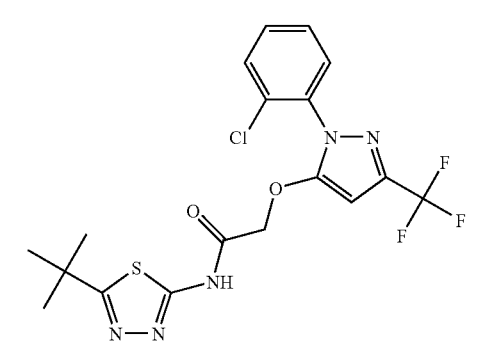 |
| 406 | 2-{[1-(2-chlorophenyl)-3-(trifluoromethyl)-1H-pyrazol-5-yl]oxy}-N-(4-cyclohexylphenyl)acetamide | 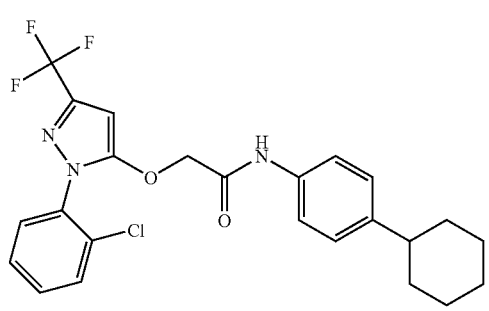 |
| 407 | methyl (2S)-[({[1-(2-chlorophenyl)-3-(trifluoromethyl)-1H-pyrazol-5-yl]oxy}acetyl)amino](phenyl)ethanoate | 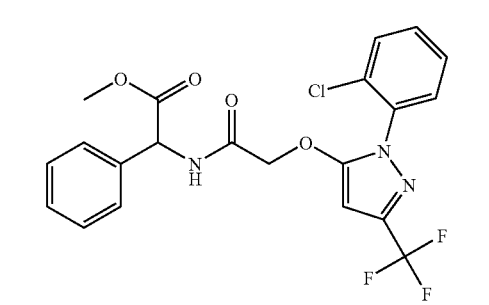 |
| 408 | 2-{[1-(2-chlorophenyl)-3-(trifluoromethyl)-1H-pyrazol-5-yl]oxy}-N-[(5-methylpyrazin-2-yl)methyl]acetamide | 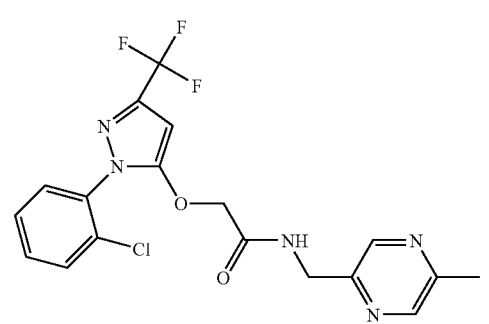 |

TABLE 6-continued

| # | IUPAC Name | Structure |
|---|---|---|
| 409 | 2-{[1-(2-chlorophenyl)-3-(trifluoromethyl)-1H-pyrazol-5-yl]oxy}-N-[4-(1H-imidazol-1-yl)phenyl]acetamide) | 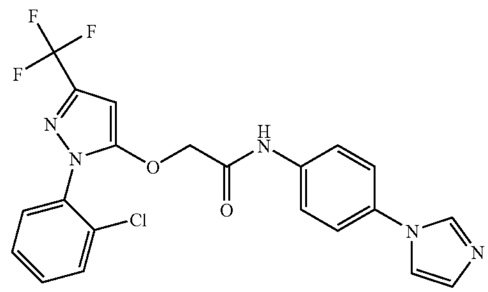 |
| 410 | 2-{[1-(2-chlorophenyl)-3-(trifluoromethyl)-1H-pyrazol-5-yl]oxy}-N-(naphthalen-1-ylmethyl)acetamide | 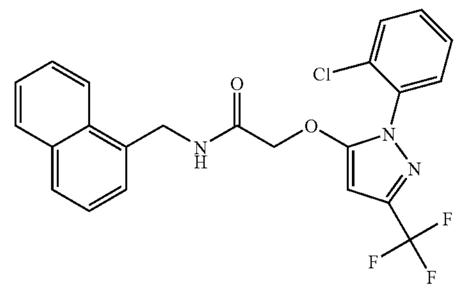 |
| 411 | 2-{[1-(2-chlorophenyl)-3-(trifluoromethyl)-1H-pyrazol-5-yl]oxy}-N-quinolin-5-ylacetamide | 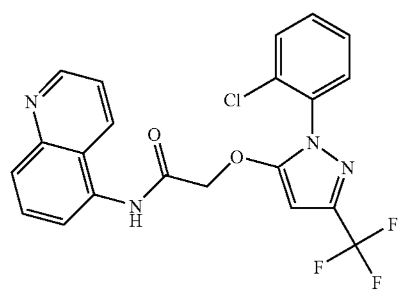 |
| 412 | 2-{[1-(2-chlorophenyl)-3-(trifluoromethyl)-1H-pyrazol-5-yl]oxy}-N-naphthalen-2-ylacetamide | 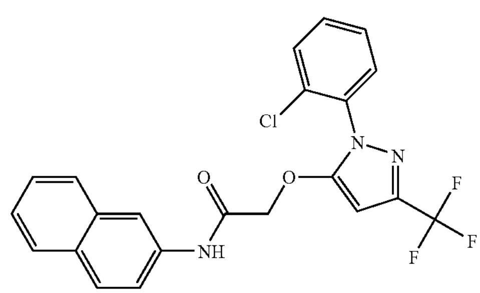 |
| 413 | 2-{[1-(2-chlorophenyl)-3-(trifluoromethyl)-1H-pyrazol-5-yl]oxy}-N-[(2,3-dimethylphenyl)methyl]acetamide | 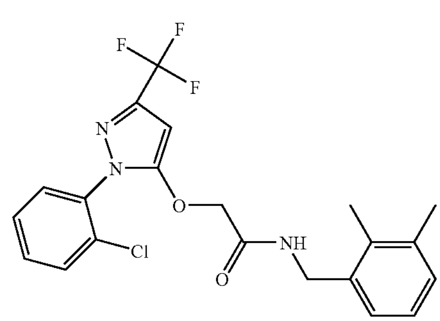 |

TABLE 6-continued

| # | IUPAC Name | Structure |
|---|---|---|
| 414 | 2-{[1-(2-chlorophenyl)-3-(trifluoromethyl)-1H-pyrazol-5-yl]oxy}-N-(4-methylphenyl)acetamide | 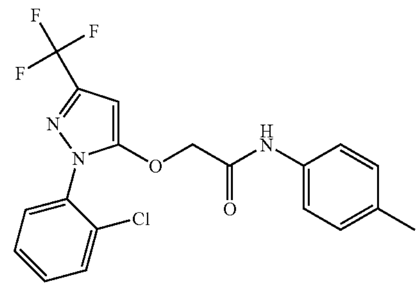 |
| 415 | 2-{[1-(2-chlorophenyl)-3-(trifluoromethyl)-1H-pyrazol-5-yl]oxy}-N-pyridin-4-ylacetamide | 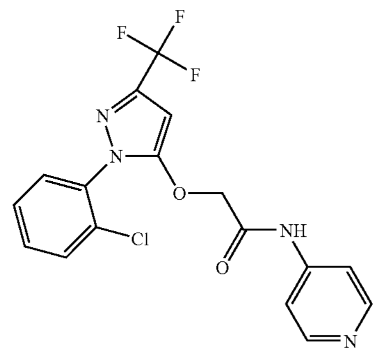 |
| 416 | 2-{[1-(2-chlorophenyl)-3-(trifluoromethyl)-1H-pyrazol-5-yl]oxy}-N-{[2-(methyloxy)phenyl]methyl}acetamide | 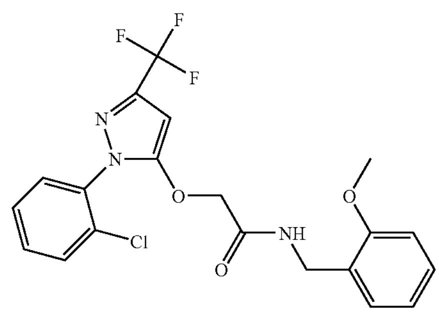 |
| 417 | 2-{[1-(2-chlorophenyl)-3-(trifluoromethyl)-1H-pyrazol-5-yl]oxy}-N-(2-thienylmethyl)acetamide | 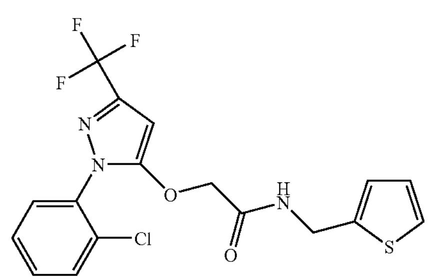 |
| 418 | 2-{[1-(2-chlorophenyl)-3-(trifluoromethyl)-1H-pyrazol-5-yl]oxy}-N-(3,4-dimethylphenyl)acetamide | 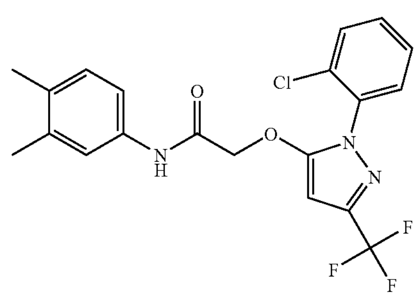 |

TABLE 6-continued

| # | IUPAC Name | Structure |
|---|---|---|
| 419 | 2-{[1-(2-chlorophenyl)-3-(trifluoromethyl)-1H-pyrazol-5-yl]oxy}-N-[(4-methylphenyl)methyl]acetamide | 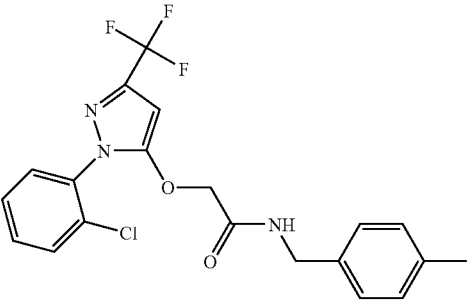 |
| 420 | 2-{[1-(2-chlorophenyl)-3-(trifluoromethyl)-1H-pyrazol-5-yl]oxy}-N-(pyridin-3-ylmethyl)acetamide | 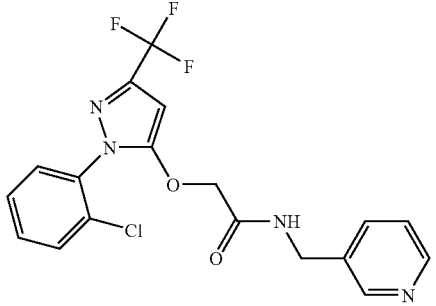 |
| 421 | 2-{[1-(2-chlorophenyl)-3-(trifluoromethyl)-1H-pyrazol-5-yl]oxy}-N-pyridin-3-ylacetamide | 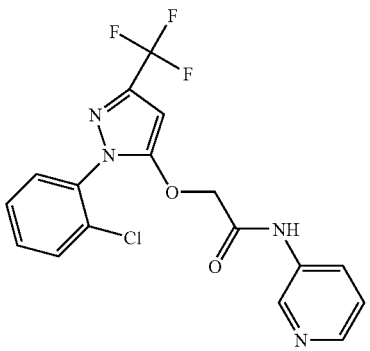 |
| 422 | 2-{[1-(2-chlorophenyl)-3-(trifluoromethyl)-1H-pyrazol-5-yl]oxy}-N-[3-(trifluoromethyl)phenyl]acetamide | 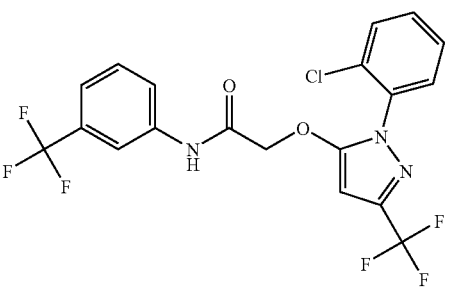 |
| 423 | N-(3-acetylphenyl)-2-{[1-(2-chlorophenyl)-3-(trifluoromethyl)-1H-pyrazol-5-yl]oxy}acetamide | 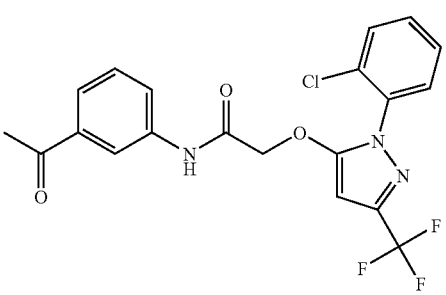 |

TABLE 6-continued

| # | IUPAC Name | Structure |
|---|---|---|
| 424 | 2-{[1-(2-chlorophenyl)-3-(trifluoromethyl)-1H-pyrazol-5-yl]oxy}-N-(5-ethyl-1,3,4-thiadiazol-2-yl)acetamide | 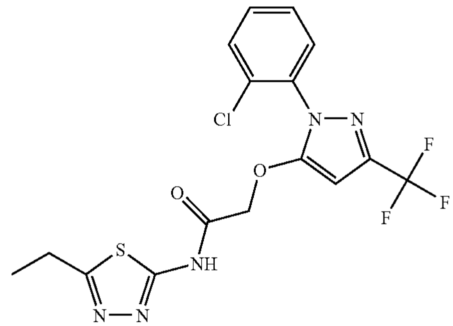 |
| 425 | 2-{[1-(2-chlorophenyl)-3-(trifluoromethyl)-1H-pyrazol-5-yl]oxy}-N-(2-propylphenyl)acetamide | 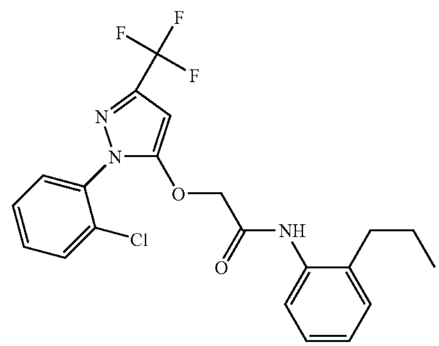 |
| 426 | 2-{[1-(2-chlorophenyl)-3-(trifluoromethyl)-1H-pyrazol-5-yl]oxy}-N-[2-(1,1-dimethylethyl)phenyl]acetamide | 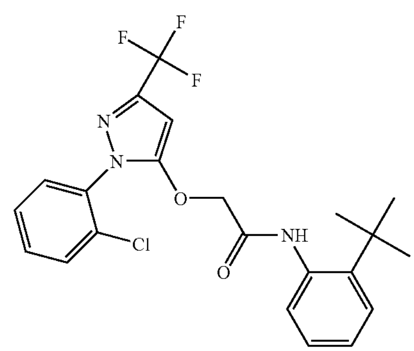 |
| 427 | 2-{[1-(2-chlorophenyl)-3-(trifluoromethyl)-1H-pyrazol-5-yl]oxy}-N-isoxazol-3-ylacetamide | 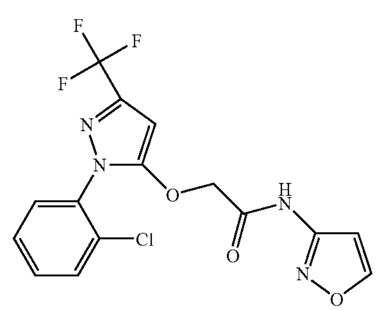 |

TABLE 6-continued

| # | IUPAC Name | Structure |
|---|---|---|
| 428 | 2-{[1-(2-chlorophenyl)-3-(trifluoromethyl)-1H-pyrazol-5-yl]oxy}-N-[(2,4-dichlorophenyl)methyl]acetamide | 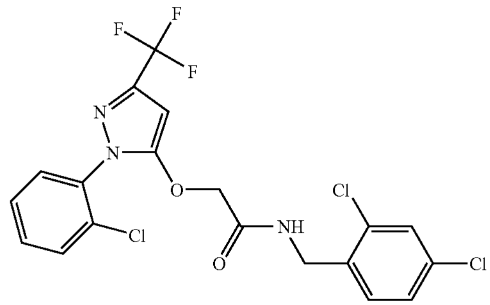 |
| 429 | N-(4-bromo-2-ethylphenyl)-2-{[1-(2-chlorophenyl)-3-(trifluoromethyl)-1H-pyrazol-5-yl]oxy}acetamide | 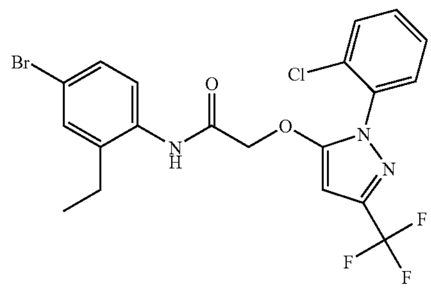 |
| 430 | 2-{[1-(2-chlorophenyl)-3-(trifluoromethyl)-1H-pyrazol-5-yl]oxy}-N-(4-piperidin-1-ylphenyl)acetamide | 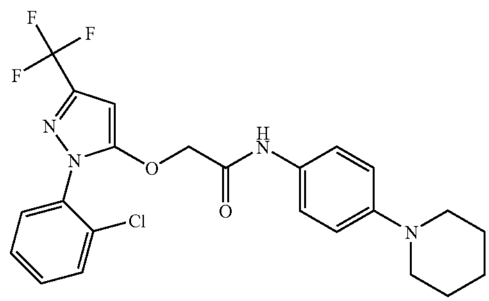 |
| 431 | 2-{[1-(2-chlorophenyl)-3-(trifluoromethyl)-1H-pyrazol-5-yl]oxy}-N-[3-(1,1-dimethylethyl)phenyl]acetamide | 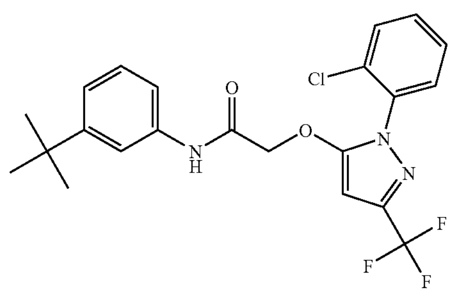 |
| 432 | 2-{[1-(2-chlorophenyl)-3-(trifluoromethyl)-1H-pyrazol-5-yl]oxy}-N-(2-{[2-(methyloxy)phenyl]oxy}ethyl)acetamide | 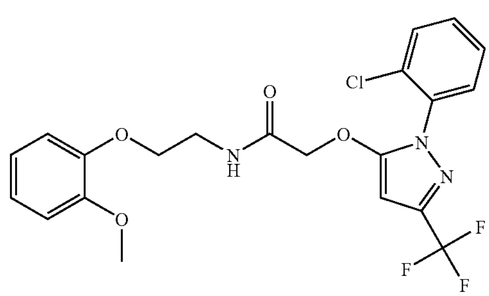 |

TABLE 6-continued

| # | IUPAC Name | Structure |
|---|---|---|
| 433 | 2-{[1-(2-chlorophenyl)-3-(trifluoromethyl)-1H-pyrazol-5-yl]oxy}-N-(1-pyridin-4-ylethyl)acetamide | 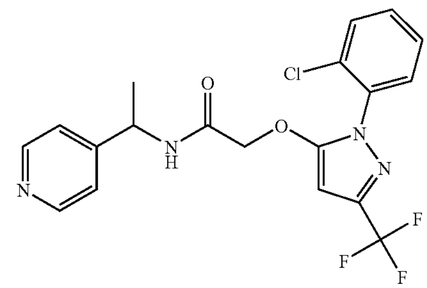 |
| 434 | 2-{[1-(2-chlorophenyl)-3-(trifluoromethyl)-1H-pyrazol-5-yl]oxy}-N-(4-hydroxybiphenyl-3-yl)acetamide | 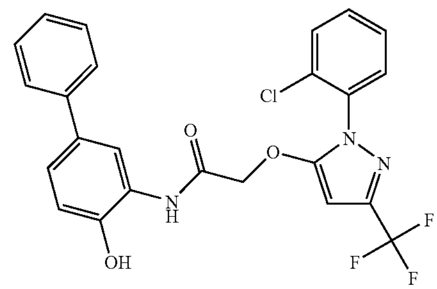 |
| 435 | 2-{[1-(2-chlorophenyl)-3-(trifluoromethyl)-1H-pyrazol-5-yl]oxy}-N-[6-(trifluoromethyl)-1,3-benzothiazol-2-yl]acetamide | 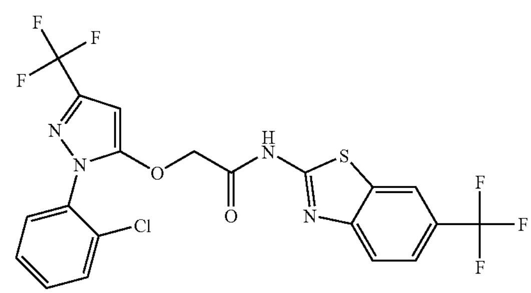 |
| 436 | N-{[4-(aminosulfonyl)phenyl]methyl}-2-{[1-(2-chlorophenyl)-3-(trifluoromethyl)-1H-pyrazol-5-yl]oxy}acetamide | 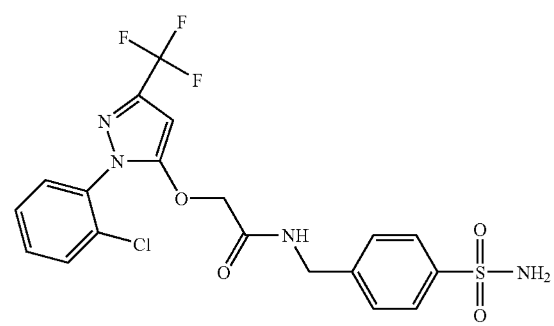 |
| 437 | 2-{[1-(2-chlorophenyl)-3-(trifluoromethyl)-1H-pyrazol-5-yl]oxy}-N-[4-(1,1-dimethylethyl)-1,3-thiazol-2-yl]acetamide | 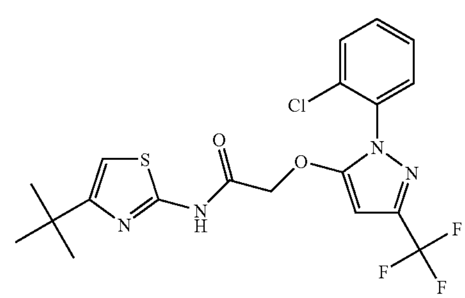 |

TABLE 6-continued

| # | IUPAC Name | Structure |
|---|---|---|
| 438 | 2-{[1-(2-chlorophenyl)-3-(trifluoromethyl)-1H-pyrazol-5-yl]oxy}-N-({3-[(difluoromethyl)oxy]phenyl}methyl)acetamide | 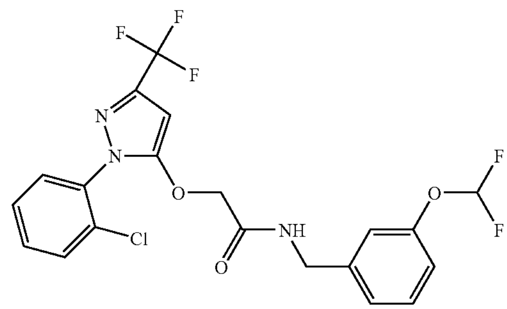 |
| 439 | N-({[1-(2-chlorophenyl)-3-(trifluoromethyl)-1H-pyrazol-5-yl]oxy}acetyl)-1-methyltryptophan | 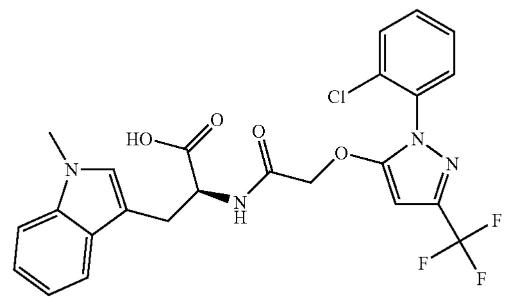 |
| 440 | [({[1-(2-chlorophenyl)-3-(trifluoromethyl)-1H-pyrazol-5-yl]oxy}acetyl)amino](2-thienyl)acetic acid | 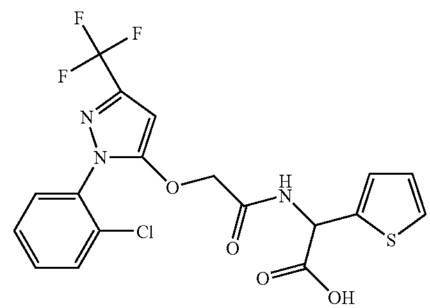 |
| 441 | 2-{[1-(2-chlorophenyl)-3-(trifluoromethyl)-1H-pyrazol-5-yl]oxy}-N-[4'-(methyloxy)biphenyl-2-yl]acetamide | 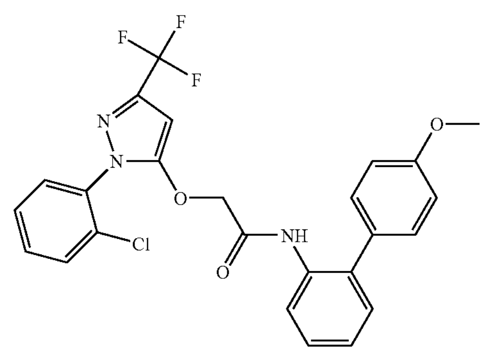 |
| 442 | 2-[({[1-(2-chlorophenyl)-3-(trifluoromethyl)-1H-pyrazol-5-yl]oxy}acetyl)amino]-N-methylbenzamide | 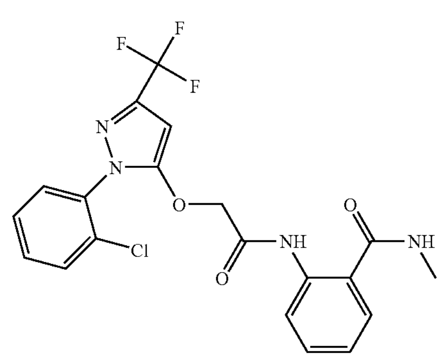 |

TABLE 6-continued

| # | IUPAC Name |
|---|---|
| 443 | 2-{[1-(2-chlorophenyl)-3-(trifluoromethyl)-1H-pyrazol-5-yl]oxy}-N-(8-hydroxyquinolin-5-yl)acetamide |
| 444 | 2-{[1-(2-chlorophenyl)-3-(trifluoromethyl)-1H-pyrazol-5-yl]oxy}-N-(8-hydroxyquinolin-5-yl)acetamide |
| 445 | N-(4-{[(2-chlorophenyl)methyl]oxy}phenyl)-2-{[1-(2-chlorophenyl)-3-(trifluoromethyl)-1H-pyrazol-5-yl]oxy}acetamide |
| 446 | 2-{[1-(2-chlorophenyl)-3-(trifluoromethyl)-1H-pyrazol-5-yl]oxy}-N-{2-[hydroxy(phenyl)methyl]phenyl}acetamide |
| 447 | N-{2-[(2-chlorophenyl)oxy]ethyl}-2-{[1-(2-chlorophenyl)-3-(trifluoromethyl)-1H-pyrazol-5-yl]oxy}acetamide |

TABLE 6-continued

| # | IUPAC Name | Structure |
|---|---|---|
| 448 | 3-chloro-2-[({[1-(2-chlorophenyl)-3-(trifluoromethyl)-1H-pyrazol-5-yl]oxy}acetyl)amino]benzoic acid | 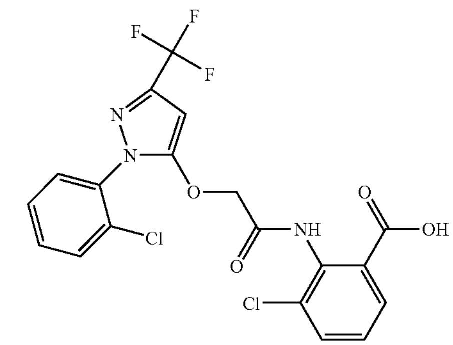 |
| 449 | 2-{[1-(2-chlorophenyl)-3-(trifluoromethyl)-1H-pyrazol-5-yl]oxy}-N-[(1R)-2-hydroxy-1-(1H-imidazol-4-ylmethyl)ethyl]acetamide | 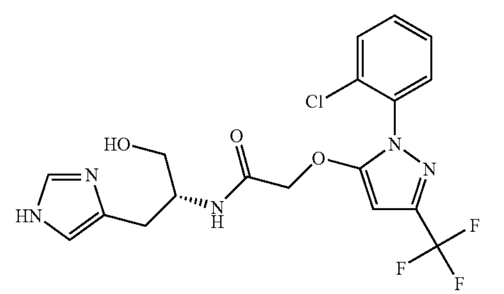 |
| 450 | {3-[({[1-(2-chlorophenyl)-3-(trifluoromethyl)-1H-pyrazol-5-yl]oxy}acetyl)amino]phenyl}acetic acid | 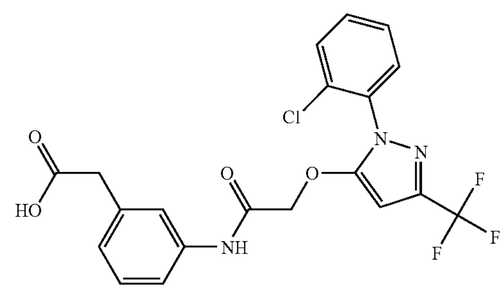 |
| 451 | 2-{[1-(2-chlorophenyl)-3-(trifluoromethyl)-1H-pyrazol-5-yl]oxy}-N-[(2-methyl-1,3-thiazol-4-yl)methyl]acetamide | 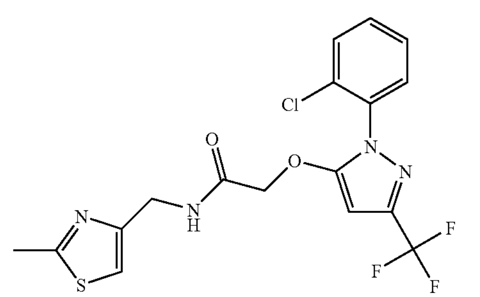 |
| 452 | 2-{[1-(2-chlorophenyl)-3-(trifluoromethyl)-1H-pyrazol-5-yl]oxy}-N-[(5-phenyl-1,3,4-oxadiazol-2-yl)methyl]acetamide | 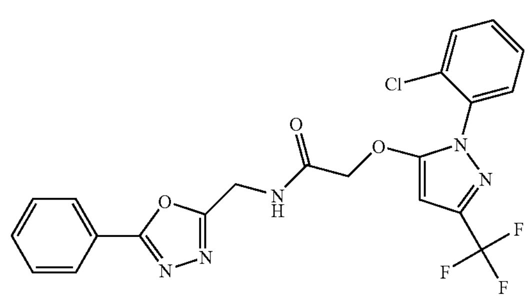 |

TABLE 6-continued

| # | IUPAC Name | Structure |
|---|---|---|
| 453 | 2-[4-({[1-(2-chlorophenyl)-3-(trifluoromethyl)-1H-pyrazol-5-yl]oxy}acetyl)-1,4-diazepan-1-yl]pyridine-3-carbonitrile | 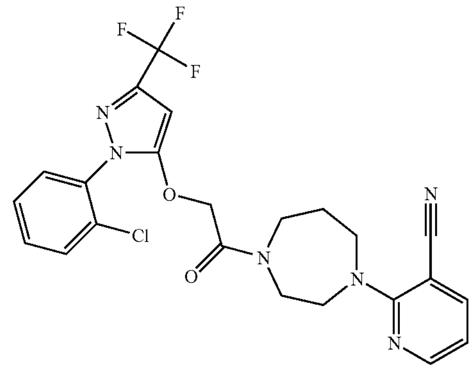 |
| 454 | 1-({[1-(2-chlorophenyl)-3-(trifluoromethyl)-1H-pyrazol-5-yl]oxy}acetyl)-4-(2,5-dimethylphenyl)piperazine | 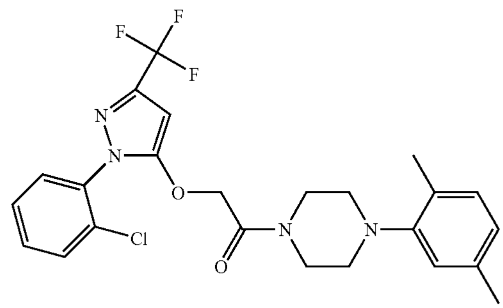 |
| 455 | 2-[4-({[1-(2-chlorophenyl)-3-(trifluoromethyl)-1H-pyrazol-5-yl]oxy}acetyl)piperazin-1-yl]pyridine-3-carbonitrile | 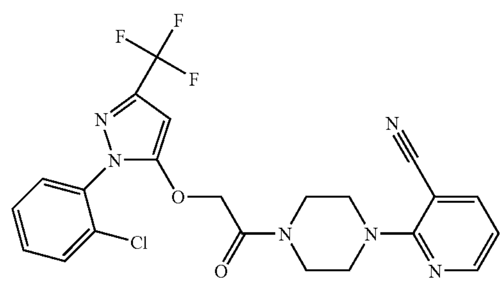 |
| 456 | 1-({[1-(2-chlorophenyl)-3-(trifluoromethyl)-1H-pyrazol-5-yl]oxy}acetyl)-4-(6-methylpyridin-2-yl)piperazine | 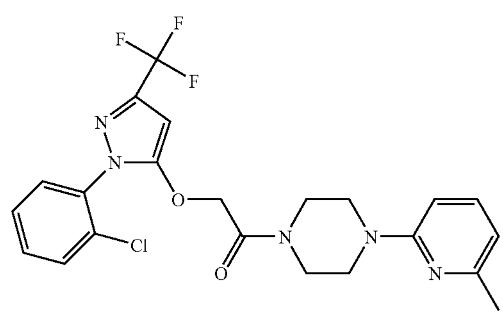 |
| 457 | 1-({[1-(2-chlorophenyl)-3-(trifluoromethyl)-1H-pyrazol-5-yl]oxy}acetyl)-4-(furan-2-ylcarbonyl)piperazine | 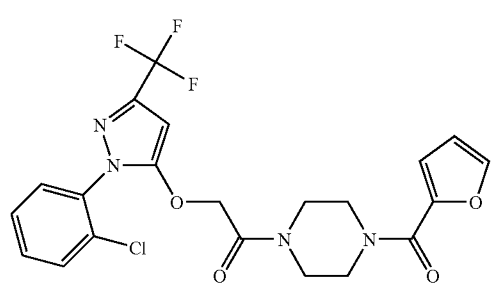 |

TABLE 6-continued

| # | IUPAC Name |
|---|---|
| 458 | 1-({[1-(2-chlorophenyl)-3-(trifluoromethyl)-1H-pyrazol-5-yl]oxy}acetyl)-4-(2-pyridin-2-ylethyl)piperazine |
| 459 | 1-({[1-(2-chlorophenyl)-3-(trifluoromethyl)-1H-pyrazol-5-yl]oxy}acetyl)-N,N-dimethyl-2,3-dihydro-1H-indole-5-sulfonamide |
| 460 | 1-({[1-(2-chlorophenyl)-3-(trifluoromethyl)-1H-pyrazol-5-yl]oxy}acetyl)-4-pyridin-2-ylpiperazine |
| 461 | 1-(1,3-benzodioxol-5-ylmethyl)-4-({[1-(2-chlorophenyl)-3-(trifluoromethyl)-1H-pyrazol-5-yl]oxy}acetyl)piperazine |
| 462 | 2-[4-({[1-(2-chlorophenyl)-3-(trifluoromethyl)-1H-pyrazol-5-yl]oxy}acetyl)piperazin-1-yl]-N-methyl-N-phenylacetamide |

TABLE 6-continued

| # | IUPAC Name | Structure |
|---|---|---|
| 463 | 1-({[1-(2-chlorophenyl)-3-(trifluoromethyl)-1H-pyrazol-5-yl]oxy}acetyl)-4-(3,5-dichlorophenyl)piperazine | 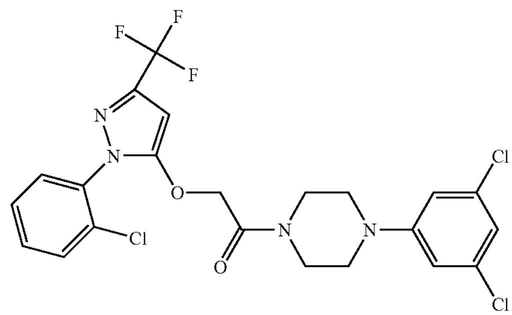 |
| 464 | 1-({[1-(2-chlorophenyl)-3-(trifluoromethyl)-1H-pyrazol-5-yl]oxy}acetyl)-4-(pyridin-2-ylmethyl)piperazine | 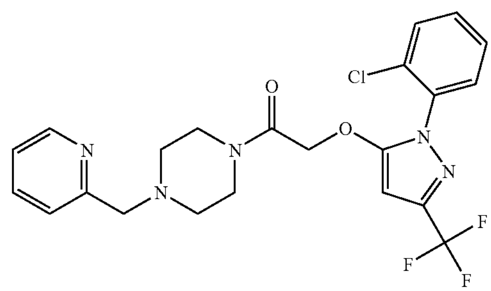 |
| 465 | 2-[4-({[1-(2-chlorophenyl)-3-(trifluoromethyl)-1H-pyrazol-5-yl]oxy}acetyl)piperazin-1-yl]phenol | 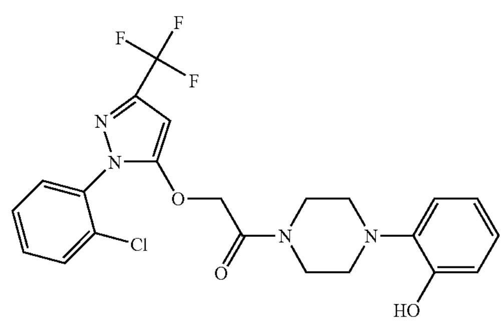 |
| 466 | 1-({[1-(2-chlorophenyl)-3-(trifluoromethyl)-1H-pyrazol-5-yl]oxy}acetyl)-4-[2-(trifluoromethyl)phenyl]piperazine | 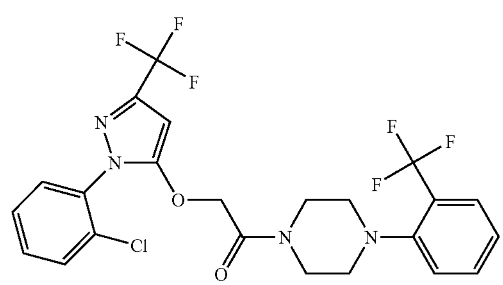 |
| 467 | 1-({[1-(2-chlorophenyl)-3-(trifluoromethyl)-1H-pyrazol-5-yl]oxy}acetyl)-4-[4-(methyloxy)phenyl]piperazine | 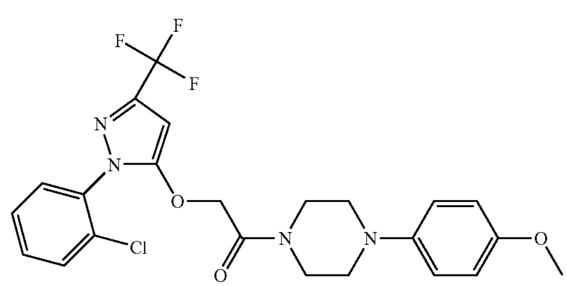 |

TABLE 6-continued

| # | IUPAC Name |
|---|---|
| 468 | 1-biphenyl-4-yl-4-({[(2-chlorophenyl)-3-(trifluoromethyl)-1H-pyrazol-5-yl]oxy}acetyl)piperazine |
| 469 | 1-[(4-chlorophenyl)methyl]-4-({[1-(2-chlorophenyl)-3-(trifluoromethyl)-1H-pyrazol-5-yl]oxy}acetyl)piperazine |
| 470 | 1-({[1-(2-chlorophenyl)-3-(trifluoromethyl)-1H-pyrazol-5-yl]oxy}acetyl)-4-(2,4-dimethylphenyl)piperazine |
| 471 | 2-[4-({[1-(2-chlorophenyl)-3-(trifluoromethyl)-1H-pyrazol-5-yl]oxy}acetyl)piperazin-1-yl]benzonitrile |
| 472 | 1-({[1-(2-chlorophenyl)-3-(trifluoromethyl)-1H-pyrazol-5-yl]oxy}acetyl)-4-(3-phenylpropyl)piperazine |

TABLE 6-continued

| # | IUPAC Name | Structure |
|---|---|---|
| 473 | 1-({[1-(2-chlorophenyl)-3-(trifluoromethyl)-1H-pyrazol-5-yl]oxy}acetyl)-4-(2,3-dichlorophenyl)piperazine | 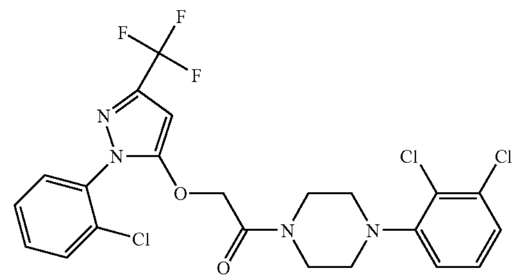 |
| 474 | 1-({[1-(2-chlorophenyl)-3-(trifluoromethyl)-1H-pyrazol-5-yl]oxy}acetyl)-4-(pyridin-4-ylmethyl)piperazine | 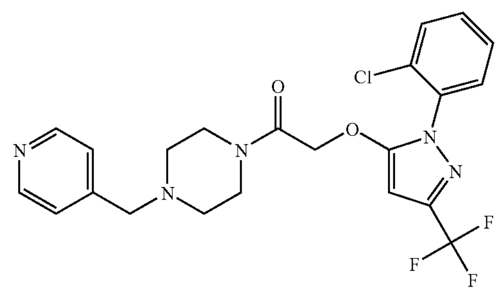 |
| 475 | 1-({[1-(2-chlorophenyl)-3-(trifluoromethyl)-1H-pyrazol-5-yl]oxy}acetyl)-4-(3,4-dichlorophenyl)piperazine | 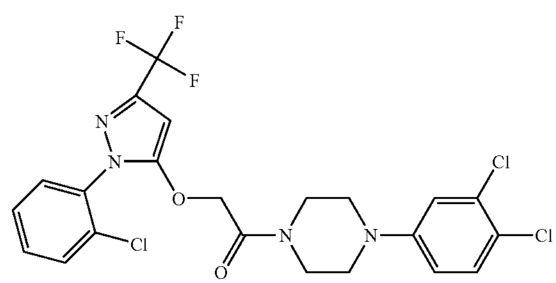 |
| 476 | 1-[5-chloro-2-(methyloxy)phenyl]-4-({[1-(2-chlorophenyl)-3-(trifluoromethyl)-1H-pyrazol-5-yl]oxy}acetyl)piperazine | 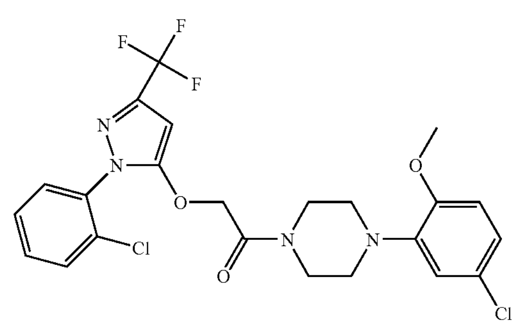 |
| 477 | 1-({[1-(2-chlorophenyl)-3-(trifluoromethyl)-1H-pyrazol-5-yl]oxy}acetyl)-4-(2-fluorophenyl)piperazine | 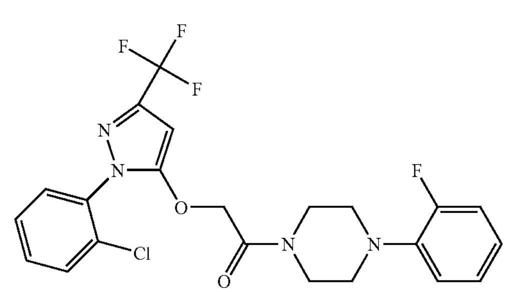 |

TABLE 6-continued

| # | IUPAC Name | Structure |
|---|---|---|
| 478 | 1-(3-chlorophenyl)-4-({[1-(2-chlorophenyl)-3-(trifluoromethyl)-1H-pyrazol-5-yl]oxy}acetyl)piperazine | 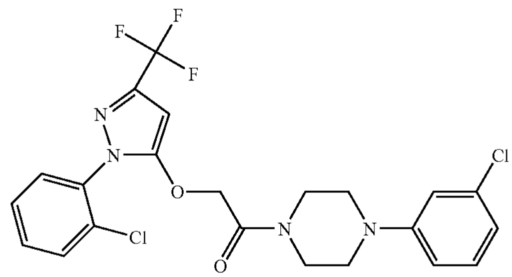 |
| 479 | 2-[4-({[1-(2-chlorophenyl)-3-(trifluoromethyl)-1H-pyrazol-5-yl]oxy}acetyl)piperazin-1-yl]pyrazine | 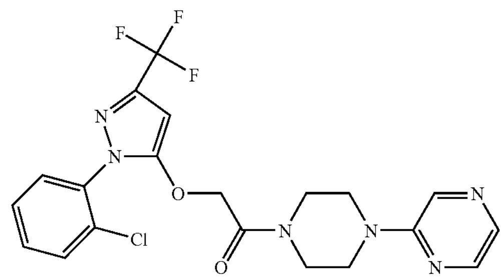 |
| 480 | 1-({[1-(2-chlorophenyl)-3-(trifluoromethyl)-1H-pyrazol-5-yl]oxy}acetyl)-4-[(2E)-3-phenylprop-2-enoyl]piperazine | 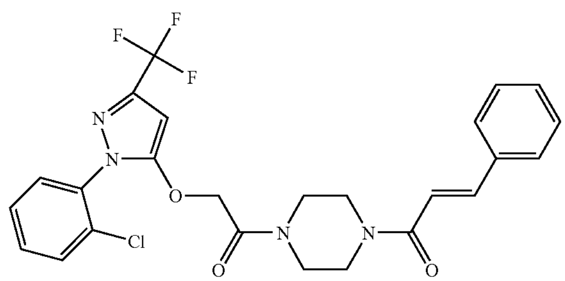 |
| 481 | 3-[({[1-(2-chlorophenyl)-3-(trifluoromethyl)-1H-pyrazol-5-yl]oxy}acetyl)amino]-3-phenylpropanoic acid | 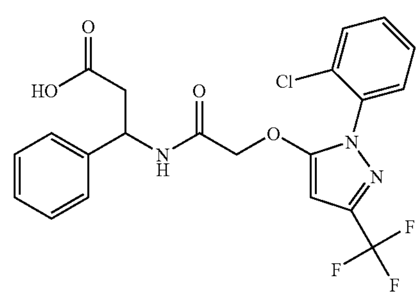 |
| 482 | 2-{[1-(2-chlorophenyl)-3-(trifluoromethyl)-1H-pyrazol-5-yl]oxy}-N-[2-(4-fluorophenyl)-1,1-dimethylethyl]acetamide | 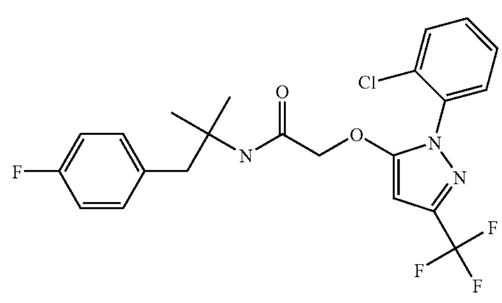 |

TABLE 6-continued

| # | IUPAC Name |
|---|---|
| 483 | 2-{[1-(2-chlorophenyl)-3-(trifluoromethyl)-1H-pyrazol-5-yl]oxy}-N-{[2-fluoro-4-(trifluoromethyl)phenyl]methyl}acetamide |
| 484 | 2-{[1-(2-chlorophenyl)-3-(trifluoromethyl)-1H-pyrazol-5-yl]oxy}-N-(4-naphthalen-2-yl-1,3-thiazol-2-yl)acetamide |
| 485 | N-[3,5-bis(trifluoromethyl)phenyl]-2-{[1-(2-chlorophenyl)-3-(trifluoromethyl)-1H-pyrazol-5-yl]oxy}acetamide |
| 486 | N-1H-benzimidazol-2-yl-2-{[1-(2-chlorophenyl)-3-(trifluoromethyl)-1H-pyrazol-5-yl]oxy}acetamide |
| 487 | 1-({[1-(2-chlorophenyl)-3-(trifluoromethyl)-1H-pyrazol-5-yl]oxy}acetyl)-4-[4-(trifluoromethyl)phenyl]piperazine |

TABLE 6-continued

| # | IUPAC Name | Structure |
|---|---|---|
| 488 | 1-({[1-(2-chlorophenyl)-3-(trifluoromethyl)-1H-pyrazol-5-yl]oxy}acetyl)-4-(pyridin-3-ylmethyl)piperazine | 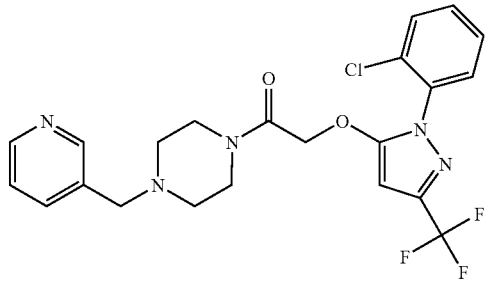 |
| 489 | 1-({[1-(2-chlorophenyl)-3-(trifluoromethyl)-1H-pyrazol-5-yl]oxy}acetyl)-4-(2,3-dimethylphenyl)piperazine | 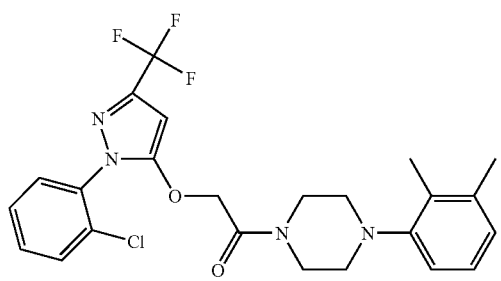 |
| 490 | 2-{[1-(2-chlorophenyl)-3-(trifluoromethyl)-1H-pyrazol-5-yl]oxy}-N-(5-phenyl-1H-pyrazol-3-yl)acetamide | 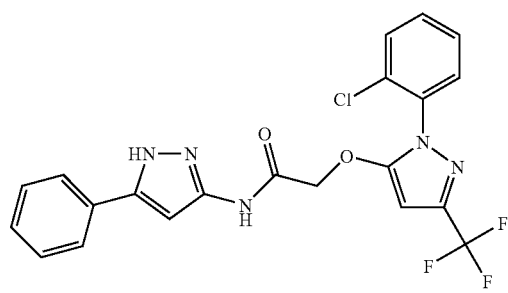 |
| 491 | 1-({[1-(2-chlorophenyl)-3-(trifluoromethyl)-1H-pyrazol-5-yl]oxy}acetyl)-4-[3-(trifluoromethyl)phenyl]piperazine | 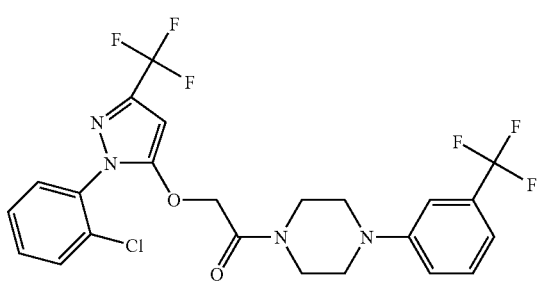 |
| 492 | 2-{[1-(2-chlorophenyl)-3-(trifluoromethyl)-1H-pyrazol-5-yl]oxy}-N-(5,6-dimethyl-1,3-benzothiazol-2-yl)acetamide | 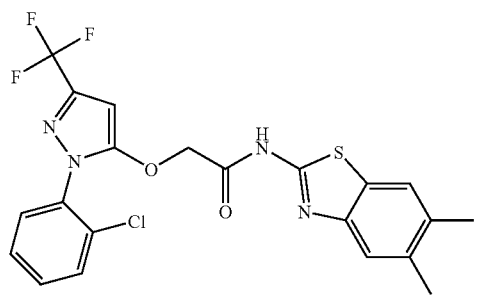 |

TABLE 6-continued

| # | IUPAC Name |
|---|---|
| 493 | 2-{[1-(2-chlorophenyl)-3-(trifluoromethyl)-1H-pyrazol-5-yl]oxy}-N-{[3-fluoro-4-(trifluoromethyl)phenyl]methyl}acetamide |
| 494 | 2-{[1-(2-chlorophenyl)-3-(trifluoromethyl)-1H-pyrazol-5-yl]oxy}-N-1H-indol-4-ylacetamide |
| 495 | 2-{[1-(2-chlorophenyl)-3-(trifluoromethyl)-1H-pyrazol-5-yl]oxy}-N-[(2S)-2-hydroxy-2-phenylethyl]acetamide |
| 496 | 2-{[1-(2-chlorophenyl)-3-(trifluoromethyl)-1H-pyrazol-5-yl]oxy}-N-(1,3-dimethyl-1H-pyrazol-5-yl)acetamide |
| 497 | 2-{[1-(2-chlorophenyl)-3-(trifluoromethyl)-1H-pyrazol-5-yl]oxy}-N-[4-(cyanomethyl)phenyl]acetamide |

TABLE 6-continued

| # | IUPAC Name | Structure |
|---|---|---|
| 498 | N-(2-bromo-4,6-difluorophenyl)-2-{[1-(2-chlorophenyl)-3-(trifluoromethyl)-1H-pyrazol-5-yl]oxy}acetamide | 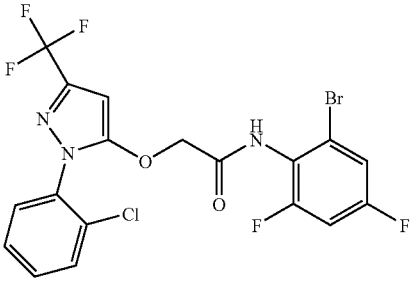 |
| 499 | 2-{[1-(2-chlorophenyl)-3-(trifluoromethyl)-1H-pyrazol-5-yl]oxy}-N-{4-[(pyridin-2-ylamino)sulfonyl]phenyl}acetamide | 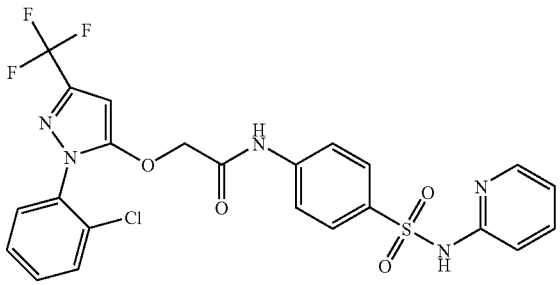 |
| 500 | 2-{[1-(2-chlorophenyl)-3-(trifluoromethyl)-1H-pyrazol-5-yl]oxy}-N-[4-(phenylmethyl)phenyl]acetamide | 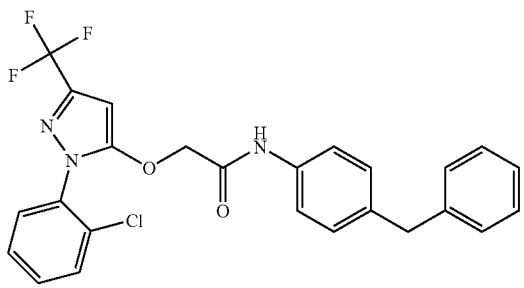 |
| 501 | 2-{[1-(2-chlorophenyl)-3-(trifluoromethyl)-1H-pyrazol-5-yl]oxy}-N-(1,1-dioxido-1-benzothien-6-yl)acetamide | 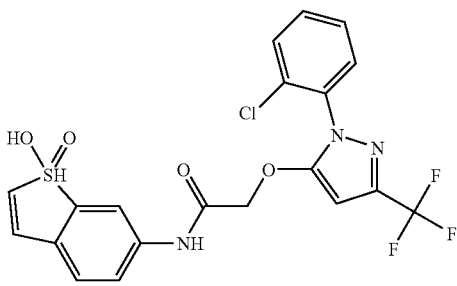 |
| 502 | 2-{[1-(2-chlorophenyl)-3-(trifluoromethyl)-1H-pyrazol-5-yl]oxy}-N-[2-(1H-pyrazol-1-yl)phenyl]acetamide | 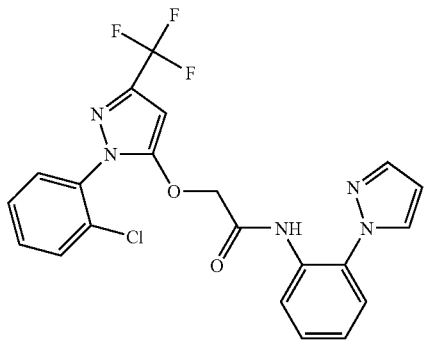 |

TABLE 6-continued

| # | IUPAC Name | Structure |
|---|---|---|
| 503 | 2-{[1-(2-chlorophenyl)-3-(trifluoromethyl)-1H-pyrazol-5-yl]oxy}-N-{4-[(1,1-dioxidothiomorpholin-4-yl)methyl]phenyl}acetamide | 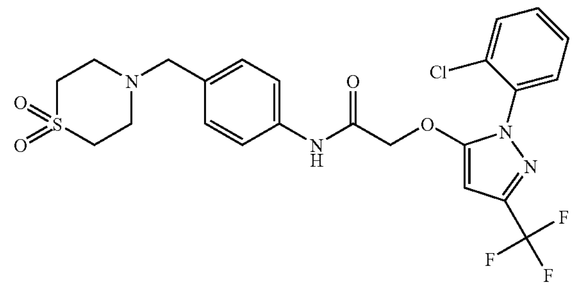 |
| 504 | N-[4-(4-chlorophenyl)-1,2,3-thiadiazol-5-yl]-2-{[1-(2-chlorophenyl)-3-(trifluoromethyl)-1H-pyrazol-5-yl]oxy}acetamide | 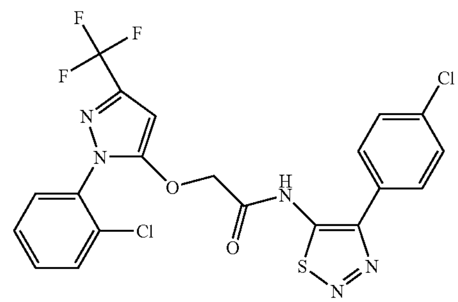 |
| 505 | 2-{[1-(2-chlorophenyl)-3-(trifluoromethyl)-1H-pyrazol-5-yl]oxy}-N-[2-(hydroxymethyl)phenyl]acetamide | 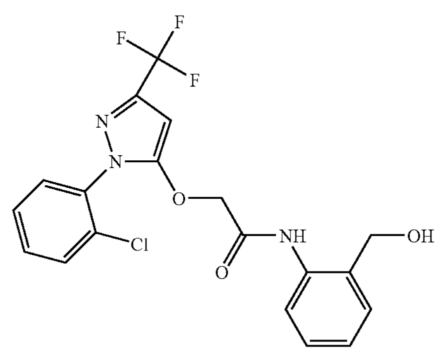 |
| 506 | methyl 3-[({[1-(2-chlorophenyl)-3-(trifluoromethyl)-1H-pyrazol-5-yl]oxy}acetyl)amino]-4-methylbenzoate | 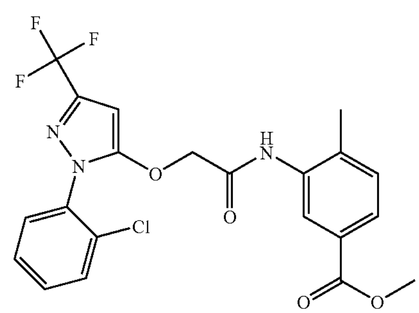 |
| 507 | 3-[({[1-(2-chlorophenyl)-3-(trifluoromethyl)-1H-pyrazol-5-yl]oxy}acetyl)amino]-5-(1,1-dimethylethyl)thiophene-2-carboxamide | 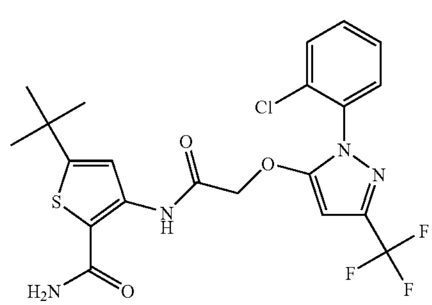 |

TABLE 6-continued

| # | IUPAC Name | Structure |
|---|---|---|
| 508 | 2-{[1-(2-chlorophenyl)-3-(trifluoromethyl)-1H-pyrazol-5-yl]oxy}-N-(4-{[(5-methyl-1,3,4-thiadiazol-2-yl)amino]sulfonyl}phenyl)acetamide | 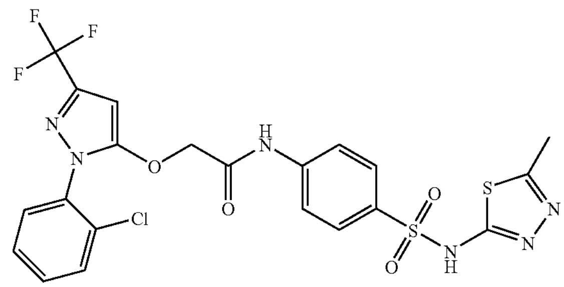 |
| 509 | 2-{[1-(2-chlorophenyl)-3-(trifluoromethyl)-1H-pyrazol-5-yl]oxy}-N-{4-[4-(methyloxy)phenyl]-1,2,3-thiadiazol-5-yl}acetamide | 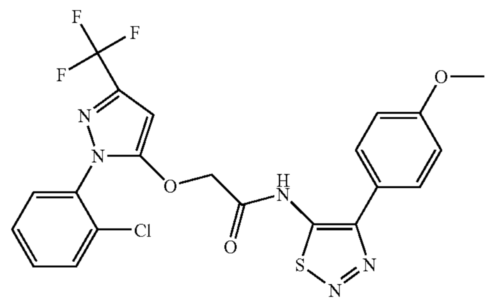 |
| 510 | N-[(2-bromophenyl)methyl]-2-{[1-(2-chlorophenyl)-3-(trifluoromethyl)-1H-pyrazol-5-yl]oxy}acetamide | 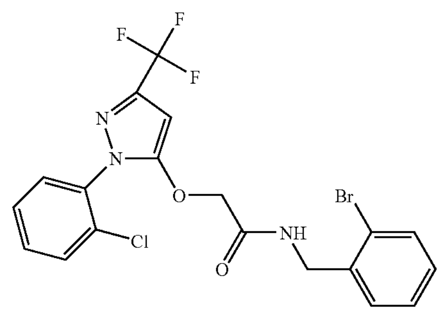 |
| 511 | 2-{[1-(2-chlorophenyl)-3-(trifluoromethyl)-1H-pyrazol-5-yl]oxy}-N-[4-(1H-1,2,4-triazol-1-yl)phenyl]acetamide | 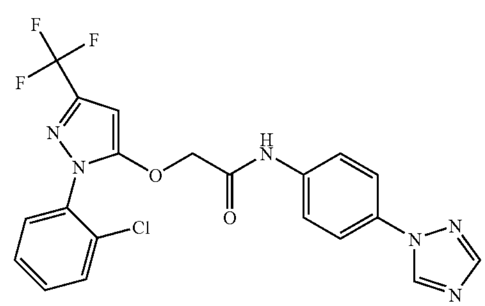 |
| 512 | 2-{[1-(2-chlorophenyl)-3-(trifluoromethyl)-1H-pyrazol-5-yl]oxy}-N-{2-[4-(methyloxy)phenyl]-oxoethyl}acetamide | 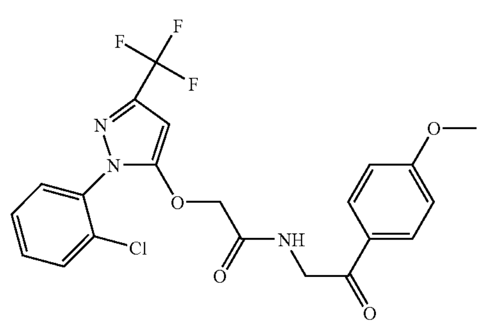 |

TABLE 6-continued

| # | IUPAC Name |
|---|---|
| 513 | 2-{[1-(2-chlorophenyl)-3-(trifluoromethyl)-1H-pyrazol-5-yl]oxy}-N-[2-(2-methylphenyl)ethyl]acetamide |
| 514 | 2-{[1-(2-chlorophenyl)-3-(trifluoromethyl)-1H-pyrazol-5-yl]oxy}-N-{4-[4-(trifluoromethyl)phenyl]-1,2,3-thiadiazol-5-yl}acetamide |
| 515 | N-[3-(acetylamino)phenyl]-2-{[1-(2-chlorophenyl)-3-(trifluoromethyl)-1H-pyrazol-5-yl]oxy}acetamide |
| 516 | 2-{[1-(2-chlorophenyl)-3-(trifluoromethyl)-1H-pyrazol-5-yl]oxy}-N-1H-1,2,4-triazol-3-ylacetamide |
| 517 | 2-{[1-(2-chlorophenyl)-3-(trifluoromethyl)-1H-pyrazol-5-yl]oxy}-N-[2-hydroxy-1-(hydroxymethyl)-2-phenylethyl]acetamide |

TABLE 6-continued

| # | IUPAC Name |
|---|---|
| 518 | 2-{[1-(2-chlorophenyl)-3-(trifluoromethyl)-1H-pyrazol-5-yl]oxy}-N-(3-{[ethyl(phenyl)amino]sulfonyl}-methylphenyl)acetamide |
| 519 | 2-{[1-(2-chlorophenyl)-3-(trifluoromethyl)-1H-pyrazol-5-yl]oxy}-N-(5,6-dimethyl-1H-benzimidazol-2-yl)acetamide |
| 520 | 2-{[1-(2-chlorophenyl)-3-(trifluoromethyl)-1H-pyrazol-5-yl]oxy}-N-(4-methylbiphenyl-3-yl)acetamide |
| 521 | (2S)-2-[({[1-(2-chlorophenyl)-3-(trifluoromethyl)-1H-pyrazol-5-yl]oxy}acetyl)amino]-4-phenylbutanoic acid |
| 522 | 2-{[1-(2-chlorophenyl)-3-(trifluoromethyl)-1H-pyrazol-5-yl]oxy}-N-[(3S)-1-(phenylmethyl)pyrrolidin-3-yl]acetamide |

TABLE 6-continued

| # | IUPAC Name | Structure |
|---|---|---|
| 523 | 2-{[1-(2-chlorophenyl)-3-(trifluoromethyl)-1H-pyrazol-5-yl]oxy}-N-[(2-morpholin-4-ylphenyl)methyl]acetamide | 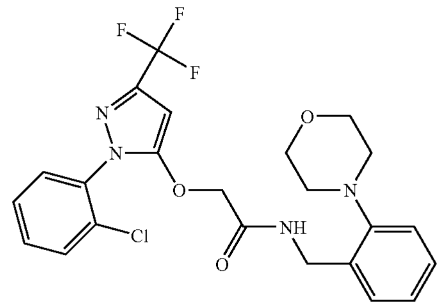 |
| 524 | N-(4-bromo-2-cyanophenyl)-2-{[1-(2-chlorophenyl)-3-(trifluoromethyl)-1H-pyrazol-5-yl]oxy}acetamide | 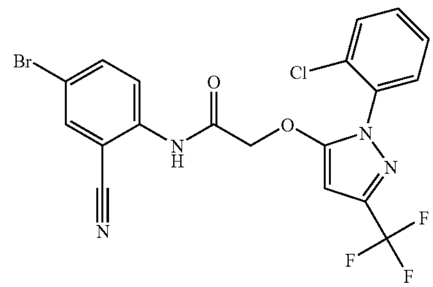 |
| 525 | (2S)-(2-chlorophenyl)[({[1-(2-chlorophenyl)-3-(trifluoromethyl)-1H-pyrazol-5-yl]oxy}acetyl)amino]ethanoic acid | 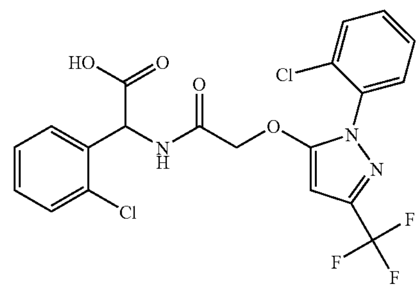 |
| 526 | N-(5-bromo-1,3-thiazol-2-yl)-2-{[1-(2-chlorophenyl)-3-(trifluoromethyl)-1H-pyrazol-5-yl]oxy}acetamide | 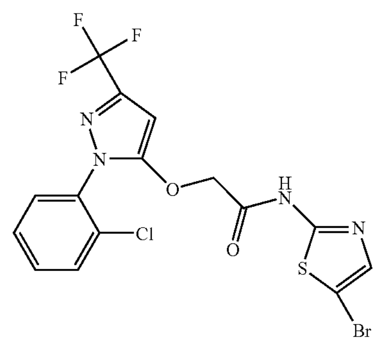 |
| 527 | N-[3-(4-chlorophenyl)-1-methyl-1H-pyrazol-5-yl]-2-{[1-(2-chlorophenyl)-3-(trifluoromethyl)-1H-pyrazol-5-yl]oxy}acetamide | 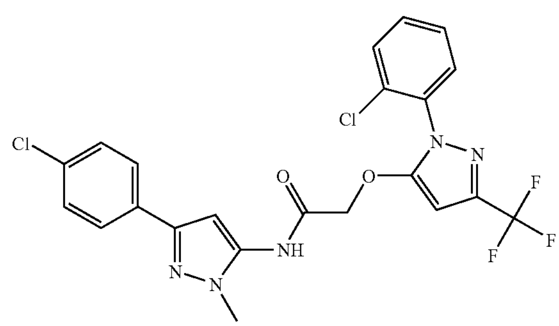 |

TABLE 6-continued

| # | IUPAC Name | Structure |
|---|---|---|
| 528 | 2-{[1-(2-chlorophenyl)-3-(trifluoromethyl)-1H-pyrazol-5-yl]oxy}-N-[(1-methyl-1H-pyrrol-2-yl)methyl]acetamide | 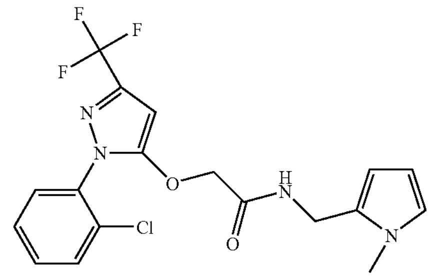 |
| 529 | 2-{[1-(2-chlorophenyl)-3-(trifluoromethyl)-1H-pyrazol-5-yl]oxy}-N-{[4-(4-methylpiperazin-1-yl)phenyl]methyl}acetamide | 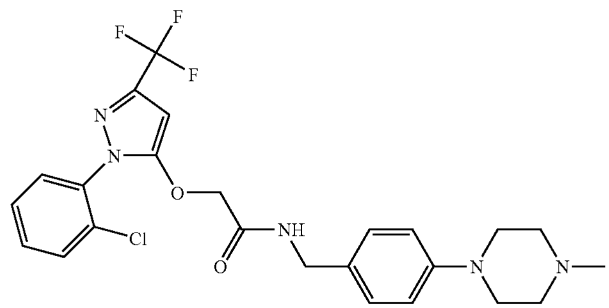 |
| 530 | 2-[({[1-(2-chlorophenyl)-3-(trifluoromethyl)-1H-pyrazol-5-yl]oxy}acetyl)amino]-6-methylbenzoic acid | 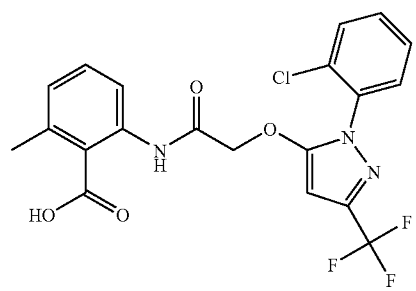 |
| 531 | N-(5-chloro-2-hydroxyphenyl)-2-{[1-(2-chlorophenyl)-3-(trifluoromethyl)-1H-pyrazol-5-yl]oxy}acetamide | 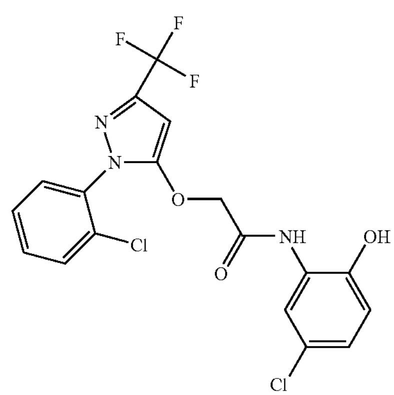 |
| 532 | N-[(2-chloro-4-fluorophenyl)methyl]-2-{[1-(2-chlorophenyl)-3-(trifluoromethyl)-1H-pyrazol-5-yl]oxy}acetamide | 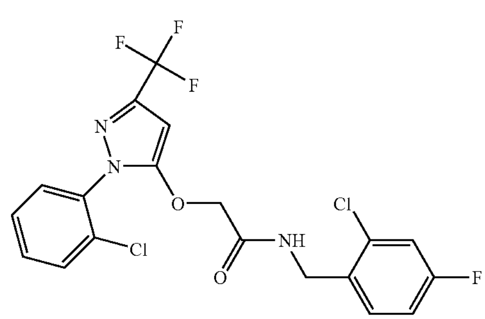 |

TABLE 6-continued

| # | IUPAC Name | Structure |
|---|---|---|
| 533 | 2-{[1-(2-chlorophenyl)-3-(trifluoromethyl)-1H-pyrazol-5-yl]oxy}-N-pyrimidin-2-ylacetamide | 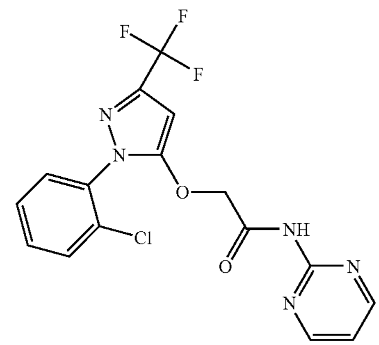 |
| 534 | 2-[({[1-(2-chlorophenyl)-3-(trifluoromethyl)-1H-pyrazol-5-yl]oxy}acetyl)amino]-3-methylbenzoic acid | 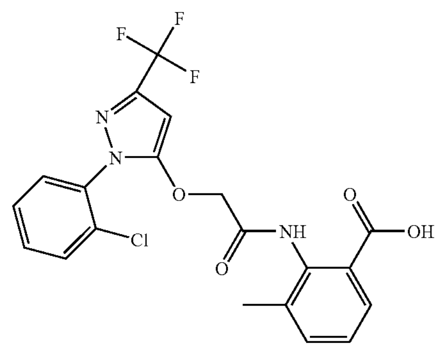 |
| 535 | N-({[1-(2-chlorophenyl)-3-(trifluoromethyl)-1H-pyrazol-5-yl]oxy}acetyl)-5-(methyloxy)tryptophan | 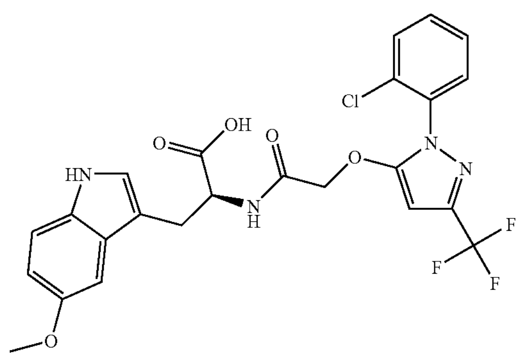 |
| 536 | N-[2-(aminosulfonyl)phenyl]-2-{[1-(2-chlorophenyl)-3-(trifluoromethyl)-1H-pyrazol-5-yl]oxy}acetamide | 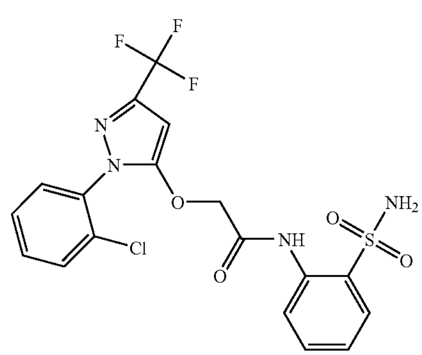 |

TABLE 6-continued

| # | IUPAC Name | Structure |
|---|---|---|
| 537 | 2-{[1-(2-chlorophenyl)-3-(trifluoromethyl)-1H-pyrazol-5-yl]oxy}-N-1,3-thiazol-2-ylacetamide | 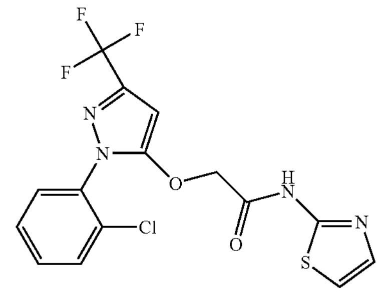 |
| 538 | methyl N-({[1-(2-chlorophenyl)-3-(trifluoromethyl)-1H-pyrazol-5-yl]oxy}acetyl)-D-tryptophanate | 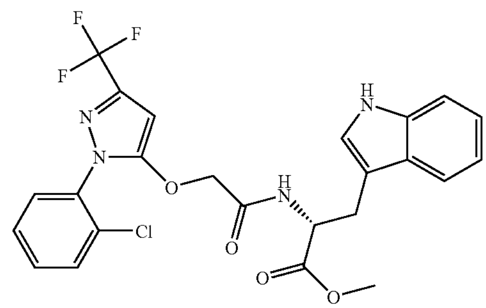 |
| 539 | N-[4-(butyloxy)phenyl]-2-{[1-(2-chlorophenyl)-3-(trifluoromethyl)-1H-pyrazol-5-yl]oxy}acetamide | 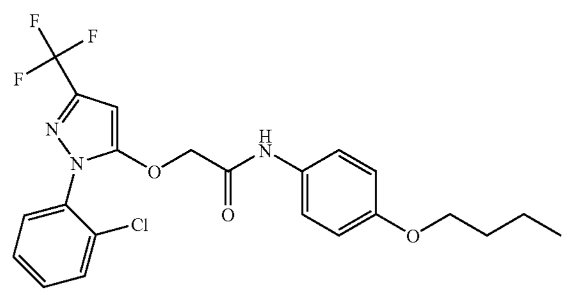 |
| 540 | N-(2-bromo-6-chloro-4-fluorophenyl)-2-{[1-(2-chlorophenyl)-3-(trifluoromethyl)-1H-pyrazol-5-yl]oxy}acetamide | 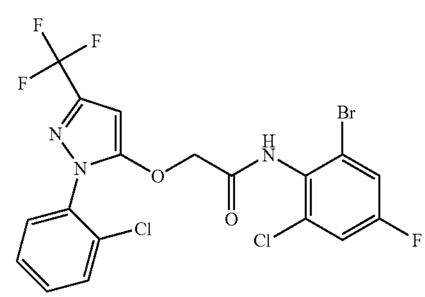 |
| 541 | 2-{[1-(2-chlorophenyl)-3-(trifluoromethyl)-1H-pyrazol-5-yl]oxy}-N-[3-(2-methylphenyl)-1H-pyrazol-5-yl]acetamide | 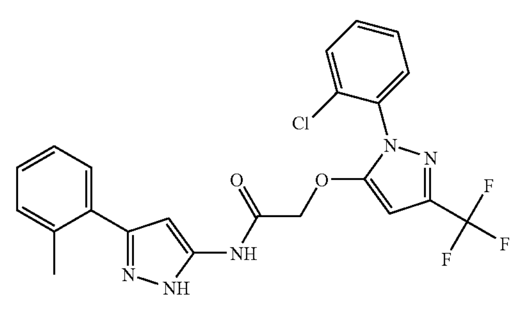 |

TABLE 6-continued

| # | IUPAC Name | Structure |
|---|---|---|
| 542 | N-({[1-(2-chlorophenyl)-3-(trifluoromethyl)-1H-pyrazol-5-yl]oxy}acetyl)-7-methyltryptophan | 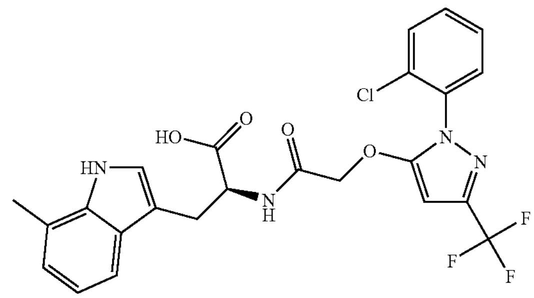 |
| 543 | 2-{[1-(2-chlorophenyl)-3-(trifluoromethyl)-1H-pyrazol-5-yl]oxy}-N-[(4-cyanophenyl)methyl]acetamide | 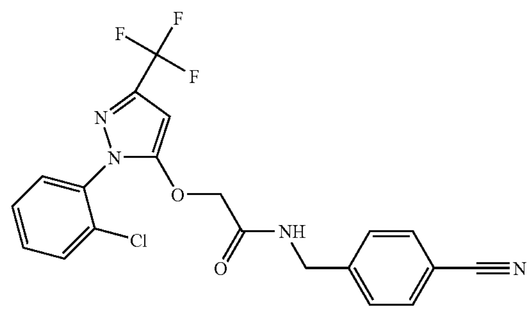 |
| 544 | 2-{[1-(2-chlorophenyl)-3-(trifluoromethyl)-1H-pyrazol-5-yl]oxy}-N-(5-cyclobutyl-1H-pyrazol-3-yl)acetamide | 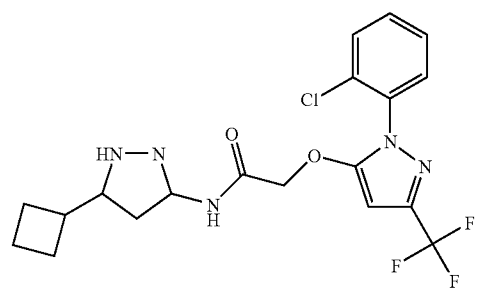 |
| 545 | 2-{[1-(2-chlorophenyl)-3-(trifluoromethyl)-1H-pyrazol-5-yl]oxy}-N-(3-cyano-4-fluorophenyl)acetamide | 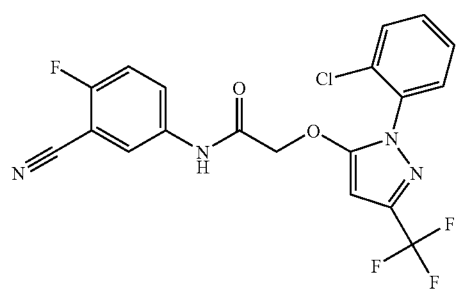 |
| 546 | 2-{[1-(2-chlorophenyl)-3-(trifluoromethyl)-1H-pyrazol-5-yl]oxy}-N-[2-(2-fluorophenyl)-1-methylethyl]acetamide | 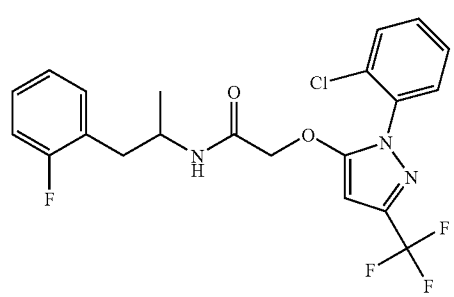 |

TABLE 6-continued

| # | IUPAC Name |
|---|---|
| 547 | 2-{[1-(2-chlorophenyl)-3-(trifluoromethyl)-1H-pyrazol-5-yl]oxy}-N-(5-propyl-1H-pyrazol-3-yl)acetamide |
| 548 | 2-{[1-(2-chlorophenyl)-3-(trifluoromethyl)-1H-pyrazol-5-yl]oxy}-N-{2-[(4-fluorophenyl)oxy]ethyl}acetamide |
| 549 | 2-{[1-(2-chlorophenyl)-3-(trifluoromethyl)-1H-pyrazol-5-yl]oxy}-N-[2-(4-fluorophenyl)-1-methylethyl]acetamide |
| 550 | 2-{[1-(2-chlorophenyl)-3-(trifluoromethyl)-1H-pyrazol-5-yl]oxy}-N-(5-ethyl-1H-pyrazol-3-yl)acetamide |
| 551 | 2-{[1-(2-chlorophenyl)-3-(trifluoromethyl)-1H-pyrazol-5-yl]oxy}-N-[1-(3-methylpyridin-2-yl)piperidin-4-yl]acetamide |

TABLE 6-continued

| # | IUPAC Name | Structure |
|---|---|---|
| 552 | 2-{[1-(2-chlorophenyl)-3-(trifluoromethyl)-1H-pyrazol-5-yl]oxy}-N-(1-pyridin-2-ylpiperidin-4-yl)acetamide | 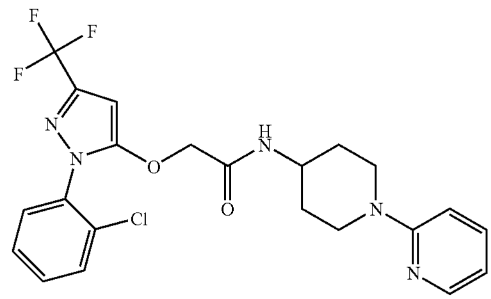 |
| 553 | 2-[4-({[1-(2-chlorophenyl)-3-(trifluoromethyl)-1H-pyrazol-5-yl]oxy}acetyl)piperazin-1-yl]pyridine-3-carboxamide | 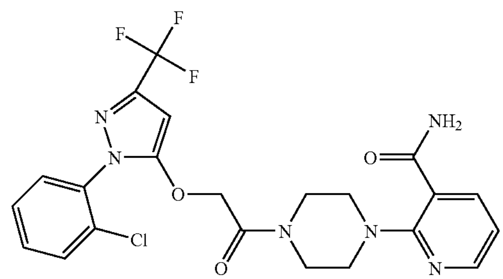 |
| 554 | 2-{[1-(2-chlorophenyl)-3-(trifluoromethyl)-1H-pyrazol-5-yl]oxy}-N-{1-[3-(methyloxy)pyridin-2-yl]piperidin-4-yl}acetamide | 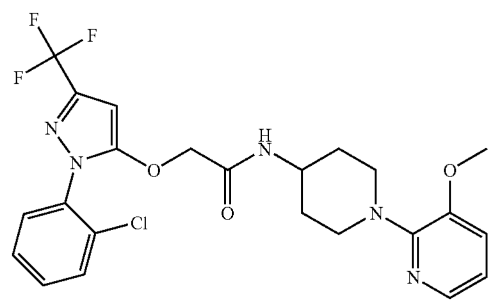 |
| 555 | 4-{[1-({[1-(2-chlorophenyl)-3-(trifluoromethyl)-1H-pyrazol-5-yl]oxy}acetyl)piperidin-4-yl]oxy}benzamide | 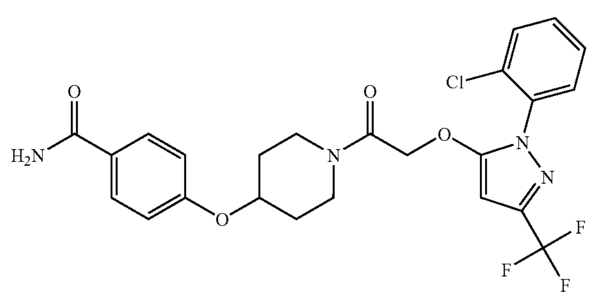 |
| 556 | 2-{[1-(2-chlorophenyl)-3-(trifluoromethyl)-1H-pyrazol-5-yl]oxy}-N-[(1-methyl-1H-imidazol-2-yl)methyl]acetamide | 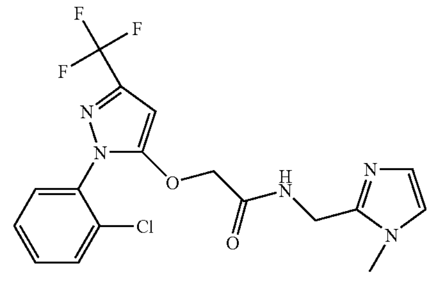 |

TABLE 6-continued

| # | IUPAC Name |
|---|---|
| 557 | 2-{[1-(2-chlorophenyl)-3-(trifluoromethyl)-1H-pyrazol-5-yl]oxy}-N-[2-(3-methylphenyl)ethyl]acetamide |
| 558 | 3-[({[1-(2-chlorophenyl)-3-(trifluoromethyl)-1H-pyrazol-5-yl]oxy}acetyl)amino]pyridine-4-carboxylic acid |
| 559 | 2-{[1-(2-chlorophenyl)-3-(trifluoromethyl)-1H-pyrazol-5-yl]oxy}-N-[1-(3-chloropyridin-2-yl)piperidin-4-yl]acetamide |
| 560 | 2-{[1-(2-chlorophenyl)-3-(trifluoromethyl)-1H-pyrazol-5-yl]oxy}-N-[3-(hydroxymethyl)pyridin-4-yl]acetamide |
| 561 | 2-{[1-(2-chlorophenyl)-3-(trifluoromethyl)-1H-pyrazol-5-yl]oxy}-N-(3-hydroxypyridin-4-yl)acetamide |

TABLE 6-continued

| # | IUPAC Name |
|---|---|
| 562 | (2E)-3-{4-[({[1-(2-chlorophenyl)-3-(trifluoromethyl)-1H-pyrazol-5-yl]oxy}acetyl)amino]pyridin-3-yl}prop-2-enoic acid |
| 563 | 2-{[1-(2-chlorophenyl)-3-(trifluoromethyl)-1H-pyrazol-5-yl]oxy}-N-{3-methyl-4-[4-(methyloxy)phenyl]isoxazol-5-yl}acetamide |
| 564 | 3-[({[1-(2-chlorophenyl)-3-(trifluoromethyl)-1H-pyrazol-5-yl]oxy}acetyl)amino]-2-methylbenzoic acid |
| 565 | 2-[({[1-(2-chlorophenyl)-3-(trifluoromethyl)-1H-pyrazol-5-yl]oxy}acetyl)amino]-6-fluorobenzoic acid |
| 566 | 2-{[1-(2-chlorophenyl)-3-(trifluoromethyl)-1H-pyrazol-5-yl]oxy}-N-{4-[(phenyloxy)methyl]-1,3-thiazol-2-yl}acetamide |

TABLE 6-continued

| # | IUPAC Name |
|---|---|
| 567 | N-[4-(acetylamino)phenyl]-2-{[1-(2-chlorophenyl)-3-(trifluoromethyl)-1H-pyrazol-5-yl]oxy}acetamide |
| 568 | N-{[2,5-bis(methyloxy)phenyl]methyl}-2-{[1-(2-chlorophenyl)-3-(trifluoromethyl)-1H-pyrazol-5-yl]oxy}acetamide |
| 569 | 2-{[1-(2-chlorophenyl)-3-(trifluoromethyl)-1H-pyrazol-5-yl]oxy}-N-[4-(2-hydroxyethyl)phenyl]acetamide |
| 570 | 2-{[1-(2-chlorophenyl)-3-(trifluoromethyl)-1H-pyrazol-5-yl]oxy}-N-[(1S,2S)-2-hydroxy-1-(hydroxymethyl)-2-(4-nitrophenyl)ethyl]acetamide |
| 571 | 4-{[({[1-(2-chlorophenyl)-3-(trifluoromethyl)-1H-pyrazol-5-yl]oxy}acetyl)amino]methyl}benzoic acid |

TABLE 6-continued

| # | IUPAC Name | Structure |
|---|---|---|
| 572 | N-[3-(4-bromo-1-methyl-1H-pyrazol-3-yl)phenyl]-2-{[1-(2-chlorophenyl)-3-(trifluoromethyl)-1H-pyrazol-5-yl]oxy}acetamide | 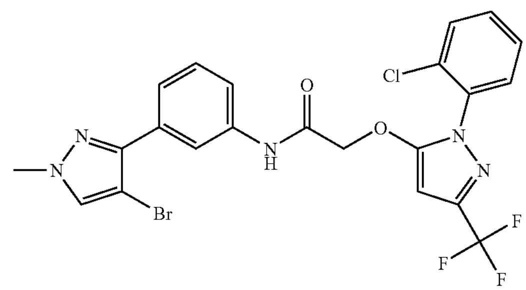 |
| 573 | methyl 3-[({[1-(2-chlorophenyl)-3-(trifluoromethyl)-1H-pyrazol-5-yl]oxy}acetyl)amino]-4-cyanothiophene-2-carboxylate | 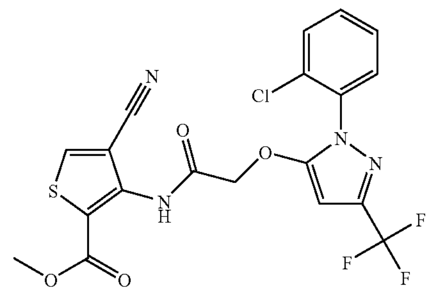 |
| 574 | 2-{[1-(2-chlorophenyl)-3-(trifluoromethyl)-1H-pyrazol-5-yl]oxy}-N-{(1S)-1-[hydroxy(diphenyl)methyl]-2-methylpropyl}acetamide | 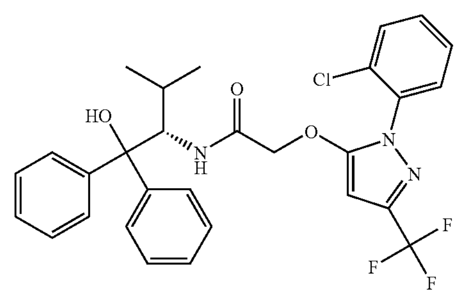 |
| 575 | 2-{[1-(2-chlorophenyl)-3-(trifluoromethyl)-1H-pyrazol-5-yl]oxy}-N-(5-phenyl-1,3,4-thiadiazol-2-yl)acetamide | 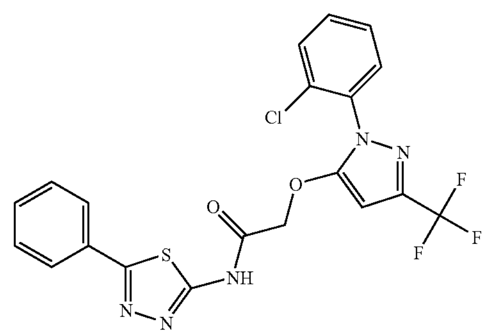 |
| 576 | 2-[({[1-(2-chlorophenyl)-3-(trifluoromethyl)-1H-pyrazol-5-yl]oxy}acetyl)amino]-5-fluorobenzoic acid | 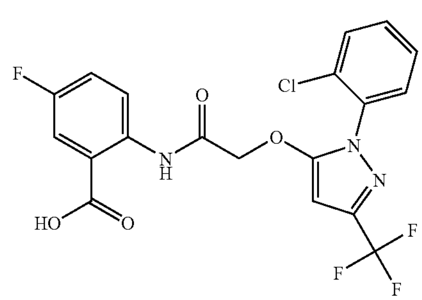 |

TABLE 6-continued

| # | IUPAC Name | Structure |
|---|---|---|
| 577 | 2-{[1-(2-chlorophenyl)-3-(trifluoromethyl)-1H-pyrazol-5-yl]oxy}-N-[2-(2-hydroxyethyl)phenyl]acetamide | 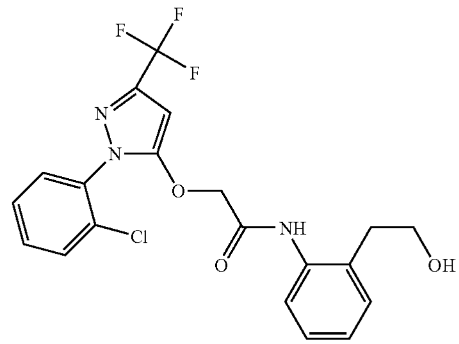 |
| 578 | 3,6-dichloro-2-[({[1-(2-chlorophenyl)-3-(trifluoromethyl)-1H-pyrazol-5-yl]oxy}acetyl)amino]benzoic acid | 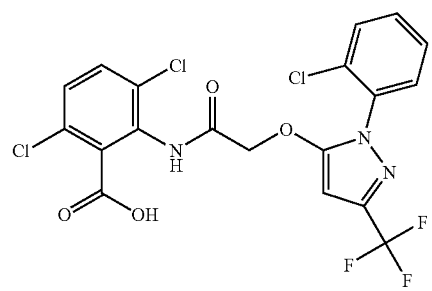 |
| 579 | 2-{[1-(2-chlorophenyl)-3-(trifluoromethyl)-1H-pyrazol-5-yl]oxy}-N-{5-[(dimethylamino)sulfonyl]-2-methylphenyl}acetamide | 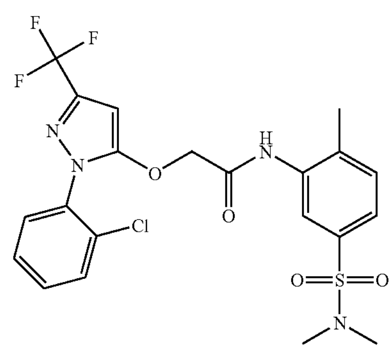 |
| 580 | 3-[({[1-(2-chlorophenyl)-3-(trifluoromethyl)-1H-pyrazol-5-yl]oxy}acetyl)amino]-4-(methyloxy)benzenesulfonic acid | 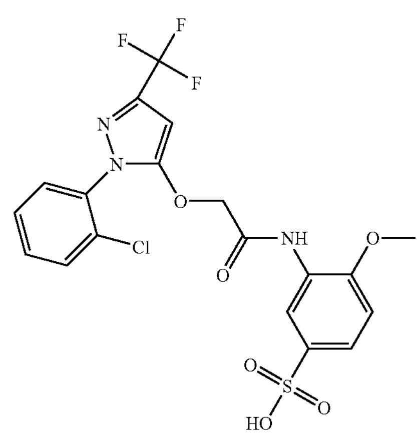 |

TABLE 6-continued

| # | IUPAC Name | Structure |
|---|---|---|
| 581 | 2-[({[1-(2-chlorophenyl)-3-(trifluoromethyl)-1H-pyrazol-5-yl]oxy}acetyl)amino]-4-fluorobenzoic acid | 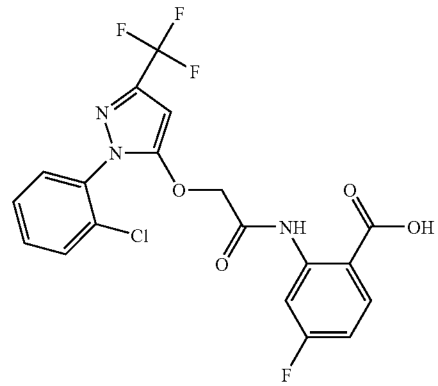 |
| 582 | 2-{[1-(2-chlorophenyl)-3-(trifluoromethyl)-1H-pyrazol-5-yl]oxy}-N-[2-oxo-4-(trifluoromethyl)-2H-chromen-7-yl]acetamide | 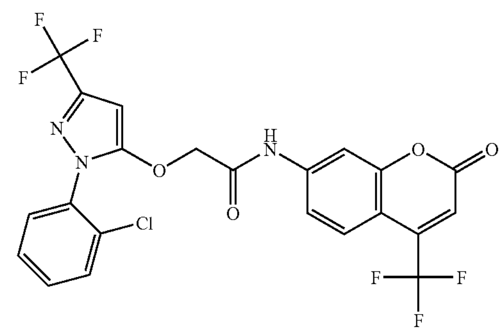 |
| 583 | 3-chloro-N-({[1-(2-chlorophenyl)-3-(trifluoromethyl)-1H-pyrazol-5-yl]oxy}acetyl)-L-tyrosine | 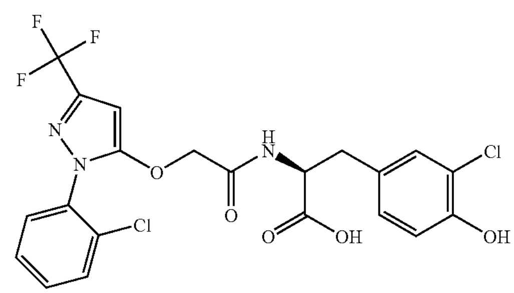 |
| 584 | 3,5-dichloro-4-[({[1-(2-chlorophenyl)-3-(trifluoromethyl)-1H-pyrazol-5-yl]oxy}acetyl)amino]-N-cyclopropylbenzamide | 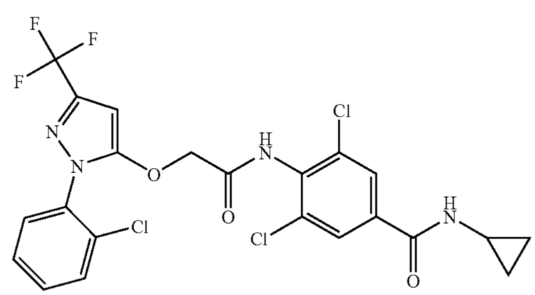 |
| 585 | N-[2,5-bis(1,1-dimethylethyl)phenyl]-2-{[1-(2-chlorophenyl)-3-(trifluoromethyl)-1H-pyrazol-5-yl]oxy}acetamide | 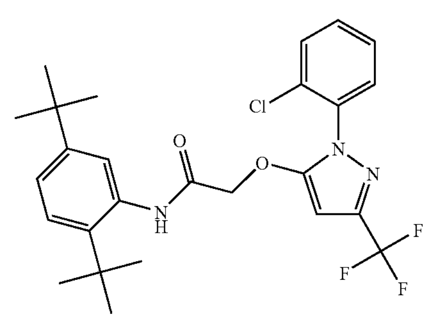 |

TABLE 6-continued

| # | IUPAC Name | Structure |
|---|---|---|
| 586 | 5-(acetylamino)-2-[({[1-(2-chlorophenyl)-3-(trifluoromethyl)-1H-pyrazol-5-yl]oxy}acetyl)amino]benzoic acid | 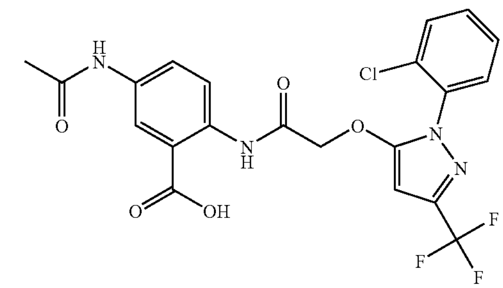 |
| 587 | N-[2,5-bis(trifluoromethyl)phenyl]-2-{[1-(2-chlorophenyl)-3-(trifluoromethyl)-1H-pyrazol-5-yl]oxy}acetamide | 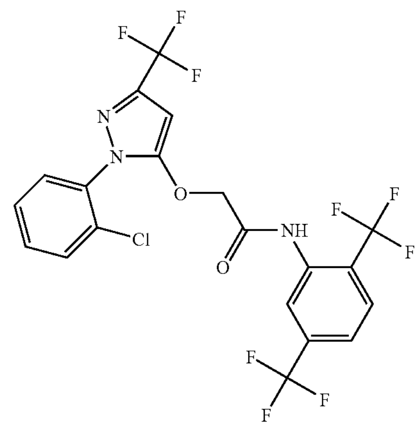 |
| 588 | 2-{[1-(2-chlorophenyl)-3-(trifluoromethyl)-1H-pyrazol-5-yl]oxy}-N-(2,6-dibromo-4-methylphenyl)acetamide | 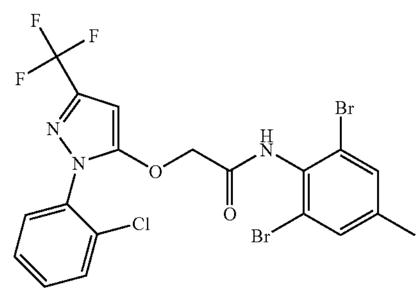 |
| 589 | 1,1-dimethylethyl 3-[({[1-(2-chlorophenyl)-3-(trifluoromethyl)-1H-pyrazol-5-yl]oxy}acetyl)amino]benzoate | 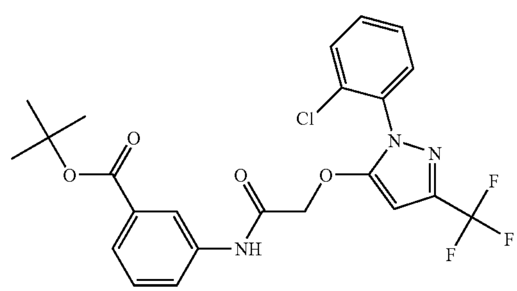 |
| 590 | 2-[1-(2-chlorophenyl)-3-(trifluoromethyl)-1H-pyrazol-5-yl]oxy}-N-(5-hydroxynaphthalen-1-yl)acetamide | 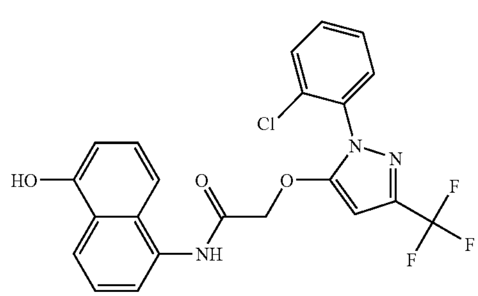 |

TABLE 6-continued

| # | IUPAC Name |
|---|---|
| 591 | methyl 3-[({[1-(2-chlorophenyl)-3-(trifluoromethyl)-1H-pyrazol-5-yl]oxy}acetyl)amino]-2-methylbenzoate |
| 592 | N-({[1-(2-chlorophenyl)-3-(trifluoromethyl)-1H-pyrazol-5-yl]oxy}acetyl)-3-hydroxy-L-tyrosine |
| 593 | 3-{4-[({[1-(2-chlorophenyl)-3-(trifluoromethyl)-1H-pyrazol-5-yl]oxy}acetyl)amino]phenyl}propanoic acid |
| 594 | 2-{[1-(2-chlorophenyl)-3-(trifluoromethyl)-1H-pyrazol-5-yl]oxy}-N-[4-(hydroxymethyl)phenyl]acetamide |
| 595 | N-[2-(2-bromophenyl)ethyl]-2-{[1-(2-chlorophenyl)-3-(trifluoromethyl)-1H-pyrazol-5-yl]oxy}acetamide |

TABLE 6-continued

| # | IUPAC Name | Structure |
|---|---|---|
| 596 | N-[4-chloro-2-(hydroxymethyl)phenyl]-2-{[1-(2-chlorophenyl)-3-(trifluoromethyl)-1H-pyrazol-5-yl]oxy}acetamide | 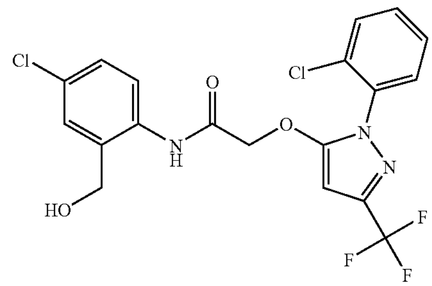 |

TABLE 7

| # | IUPAC Name | Structure |
|---|---|---|
| 597 | N-(4-sec-butylphenyl)-1-(2-chlorophenyl)-3-(trifluoromethyl)-1H-pyrazole-5-carboxamide | 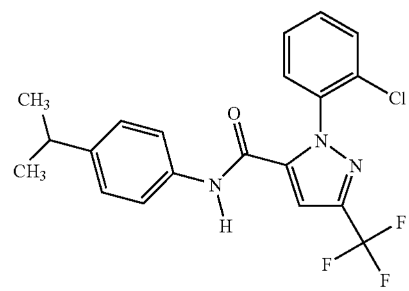 |
| 598 | 1-(2-chlorophenyl)-N-(4-isopropylphenyl)-3-(trifluoromethyl)-1H-pyrazole-5-carboxamide | 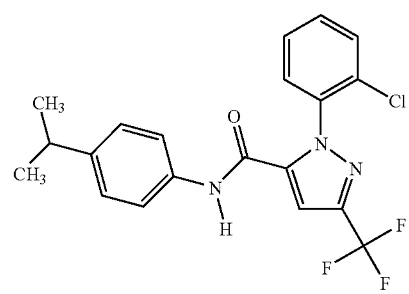 |
| 599 | N-(2-sec-butylphenyl)-1-(2-chlorophenyl)-3-(trifluoromethyl)-1H-pyrazole-5-carboxamide | 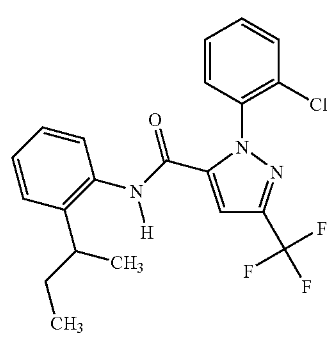 |

TABLE 7-continued

| # | IUPAC Name |
|---|---|
| 600 | 1-(2-chlorophenyl)-N-(2,3-dihydro-1H-inden-5-yl)-3-(trifluoromethyl)-1H-pyrazole-5-carboxamide |
| 601 | 1-(2-chlorophenyl)-N-(2,3-dihydro-1H-inden-1-yl)-3-(trifluoromethyl)-1H-pyrazole-5-carboxamide |
| 602 | 1-(2-chlorophenyl)-N-((1R,2S)-2-hydroxy-2,3-dihydro-1H-inden-1-yl)-3-(trifluoromethyl)-1H-pyrazole-5-carboxamide |
| 603 | 1-(2-chlorophenyl)-N-(4-(dimethylamino)phenyl)-3-(trifluoromethyl)-1H-pyrazole-5-carboxamide |
| 604 | N-(2-carbamoyl-4-chlorophenyl)-1-(2-chlorophenyl)-3-(trifluoromethyl)-1H-pyrazole-5-carboxamide |

TABLE 7-continued

| # | IUPAC Name |
|---|---|
| 605 | 1-(2-chlorophenyl)-N-(9H-fluoren-9-yl)-3-(trifluoromethyl)-1H-pyrazole-5-carboxamide |
| 606 | 1-(2-chlorophenyl)-N-(5,6,7,8-tetrahydronaphthalen-1-yl)-3-(trifluoromethyl)-1H-pyrazole-5-carboxamide |
| 607 | N-(5-chloro-2,4-dimethoxyphenyl)-1-(2-chlorophenyl)-3-(trifluoromethyl)-1H-pyrazole-5-carboxamide |
| 608 | 1-(2-chlorophenyl)-N-(2-(hydroxymethyl)-4-methylphenyl)-3-(trifluoromethyl)-1H-pyrazole-5-carboxamide |
| 609 | 1-(2-chlorophenyl)-N-(9H-fluoren-2-yl)-3-(trifluoromethyl)-1H-pyrazole-5-carboxamide |

TABLE 7-continued

| # | IUPAC Name | Structure |
|---|---|---|
| 610 | 3-(1-(2-chlorophenyl)-3-(trifluoromethyl)-1H-pyrazole-5-carboxamido)-4-methoxybenzoic acid | 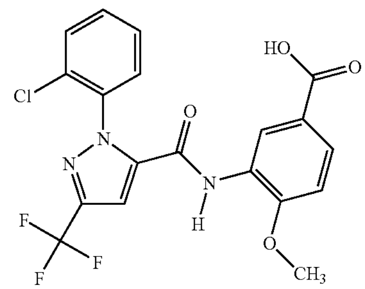 |
| 611 | 1-(2-chlorophenyl)-N-[3-(methylsulfonyl)phenyl]-3-(trifluoromethyl)-1H-pyrazole-5-carboxamide | 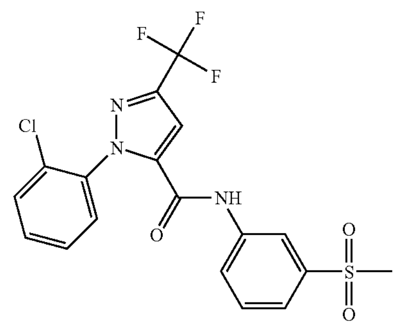 |
| 612 | ethyl 5-(1-(2-chlorophenyl)-3-(trifluoromethyl)-1H-pyrazole-5-carboxamido)-1,3,4-thiadiazole-2-carboxylate | 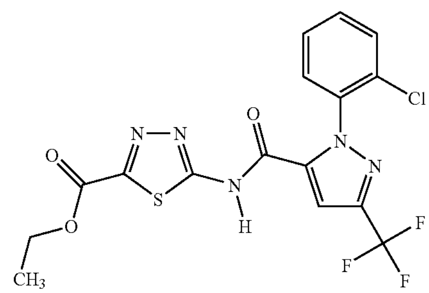 |
| 613 | 1-(2-chlorophenyl)-N-(2-methylquinolin-4-yl)-3-(trifluoromethyl)-1H-pyrazole-5-carboxamide | 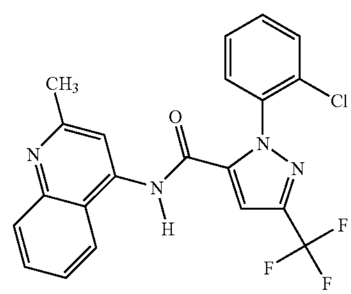 |
| 614 | 1-(2-chlorophenyl)-N-(3-methylisothiazol-5-yl)-3-(trifluoromethyl)-1H-pyrazole-5-carboxamide | 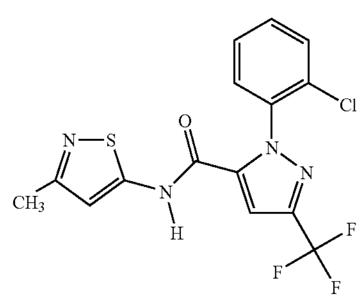 |

TABLE 7-continued

| # | IUPAC Name | Structure |
|---|---|---|
| 615 | 1-(2-chlorophenyl)-N-(5-ethyl-1,3,4-thiadiazol-2-yl)-3-(trifluoromethyl)-1H-pyrazole-5-carboxamide | 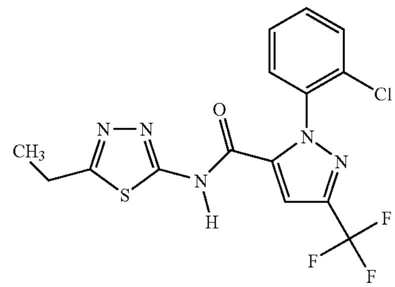 |
| 616 | 1-(2-chlorophenyl)-N-(5-methylisoxazol-3-yl)-3-(trifluoromethyl)-1H-pyrazole-5-carboxamide | 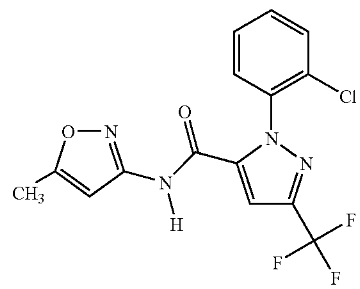 |
| 617 | N-(benzo[d][1,3]dioxol-5-yl)-1-(2-chlorophenyl)-3-(trifluoromethyl)-1H-pyrazole-5-carboxamide | 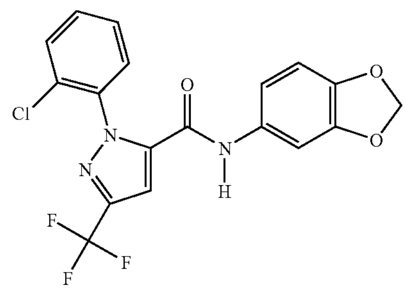 |
| 618 | 1-(2-chlorophenyl)-N-(quinolin-8-yl)-3-(trifluoromethyl)-1H-pyrazole-5-carboxamide | 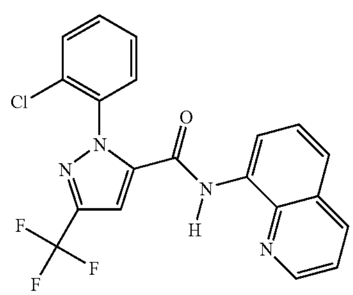 |
| 619 | 1-(2-chlorophenyl)-N-(pyridin-3-yl)-3-(trifluoromethyl)-1H-pyrazole-5-carboxamide | 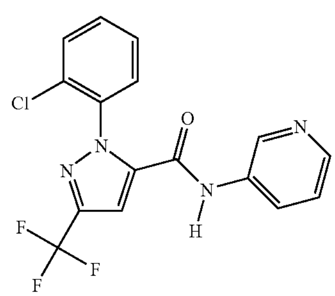 |

TABLE 7-continued

| # | IUPAC Name | Structure |
|---|---|---|
| 620 | N-(benzo [d]thiazol-2-yl)-1-(2-chlorophenyl)-3-(trifluoromethyl)-1H-pyrazole-5-carboxamide | 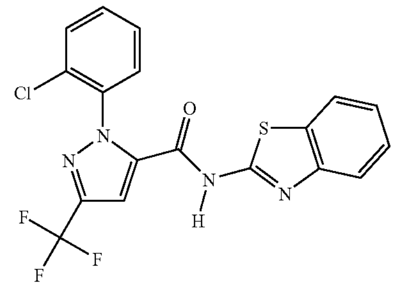 |
| 621 | 1-(2-chlorophenyl)-N-(pyridin-4-yl)-3-(trifluoromethyl)-1H-pyrazole-5-carboxamide | 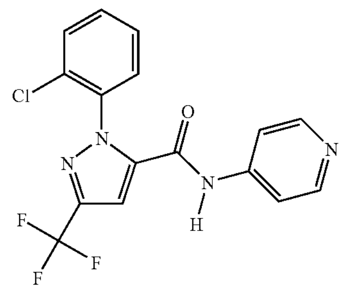 |
| 622 | 1-(2-chlorophenyl)-N-(5-methyl-1,3,4-thiadiazol-2-yl)-3-(trifluoromethyl)-1H-pyrazole-5-carboxamide | 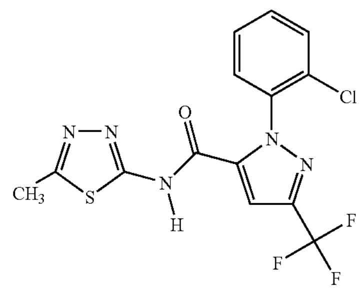 |
| 623 | N-(6-acetylbenzo[d][1,3]dioxol-5-yl)-1-(2-chlorophenyl)-3-(trifluoromethyl)-1H-pyrazole-5-carboxamide | 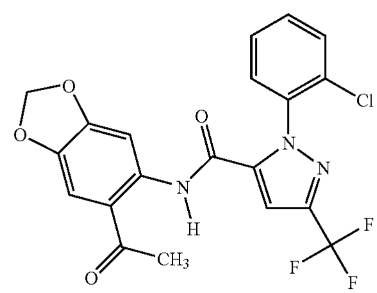 |
| 624 | 1-(2-chlorophenyl)-N-(4-methoxybenzo [d]thiazol-2-yl)-3-(trifluoromethyl)-1H-pyrazole-5-carboxamide | 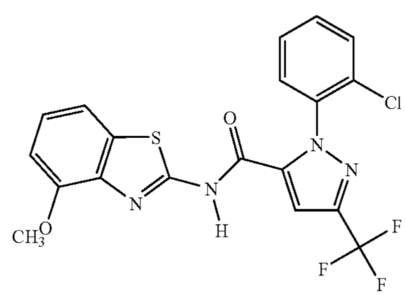 |

TABLE 7-continued

| # | IUPAC Name | Structure |
|---|---|---|
| 625 | N-(5-chlorobenzo[d]oxazol-2-yl)-1-(2-chlorophenyl)-3-(trifluoromethyl)-1H-pyrazole-5-carboxamide | 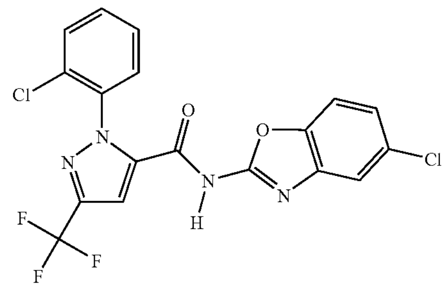 |
| 626 | N-(5-tert-butyl-1,3,4-thiadiazol-2-yl)-1-(2-chlorophenyl)-3-trifluoromethyl)-1H-pyrazole-5-carboxamide | 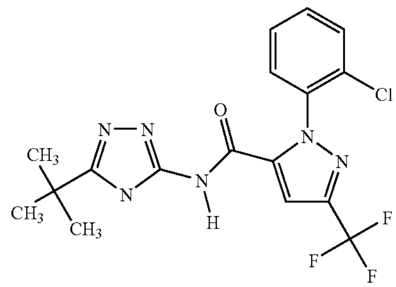 |
| 627 | 1-(2-chlorophenyl)-N-(4-methylthiazol-2-yl)-3-(trifluoromethyl)-1H-pyrazole-5-carboxamide | 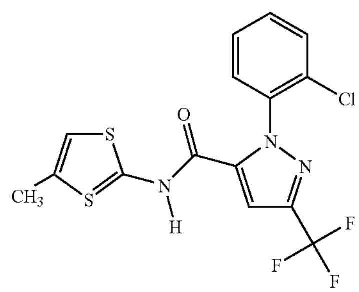 |
| 628 | 1-(2-chlorophenyl)-N-(1H-indazol-6-yl)-3-(trifluoromethyl)-1H-pyrazole-5-carboxamide | 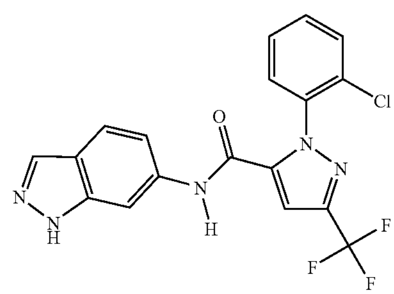 |
| 629 | 3-(1-(2-chlorophenyl)-3-(trifluoromethyl)-1H-pyrazole-5-carboxamido)pyrazine-2-carboxylic acid | 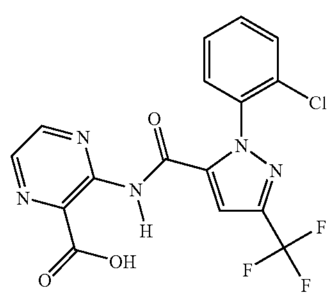 |

TABLE 7-continued

| # | IUPAC Name |
|---|---|
| 630 | 1-(2-chlorophenyl)-N-(9-ethyl-9H-carbazol-3-yl)-3(trifluoromethyl)-1H-pyrazole-5-carboxamide |
| 631 | 1-(2-chlorophenyl)-N-(4-(4-chlorophenyl)thiazol-2-yl)-3-(trifluoromethyl)-1H-pyrazole-5-carboxamide |
| 632 | 1-(2-chlorophenyl)-N-(1-phenyl-1H-pyrazolo[3,4-d]pyrimidin-4-yl)-3-(trifluoromethyl)-1H-pyrazole-5-carboxamide |
| 633 | 1-(2-chlorophenyl)-N-(3-methyl-1-phenyl-1H-pyrazol-5-yl)-3-(trifluoromethyl)-1H-pyrazole-5-carboxamide |
| 634 | 1-(2-chlorophenyl)-N-(4-(naphthalen-1-yl)thiazol-2-yl)-3-(trifluoromethyl)-1H-pyrazole-5-carboxamide |

TABLE 7-continued

| # | IUPAC Name | Structure |
|---|---|---|
| 635 | 1-(2-chlorophenyl)-N-(4-cyano-1-phenyl-1H-pyrazol-5-yl)-3-(trifluoromethyl)-1H-pyrazole-5-carboxamide | 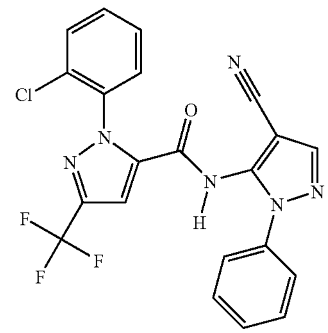 |
| 636 | N-(2-benzylphenyl)-1-(2-chlorophenyl)-3-(trifluoromethyl)-1H-pyrazole-5-carboxamide | 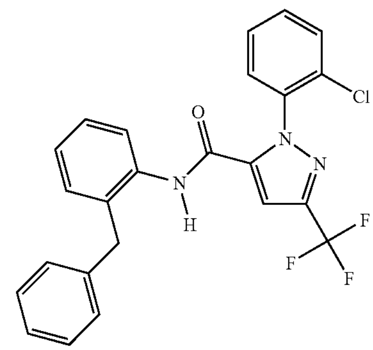 |
| 637 | N-(2-benzoylphenyl)-1-(2-chlorophenyl)-3-(trifluoromethyl)-1H-pyrazole-5-carboxamide | 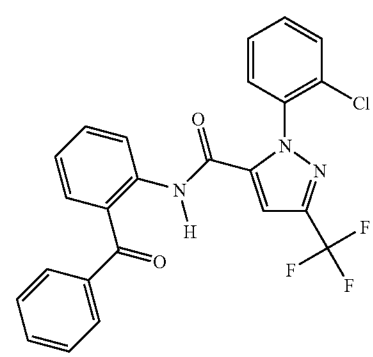 |
| 638 | 1-(2-chlorophenyl)-N-(2-(4-methylbenzoyl)phenyl)-3-trifluoromethyl)-1H-pyrazole-5-carboxamide | 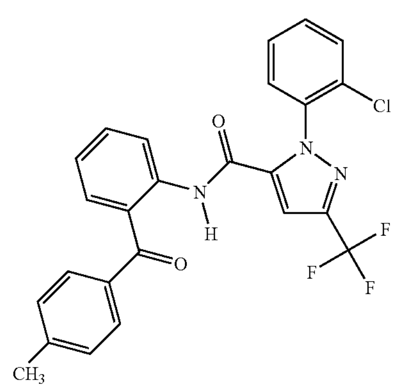 |

TABLE 7-continued

| # | IUPAC Name | Structure |
|---|---|---|
| 639 | N-(2-benzylphenyl)-1-(2-chlorophenyl)-3-(trifluoromethyl)-1H-pyrazole-5-carboxamide | 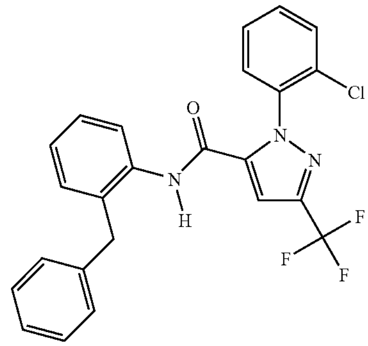 |
| 640 | N-(2-benzoyl-5-methylphenyl)-1-(2-chlorophenyl)-3-(trifluoromethyl)-1H-pyrazole-5-carboxamide | 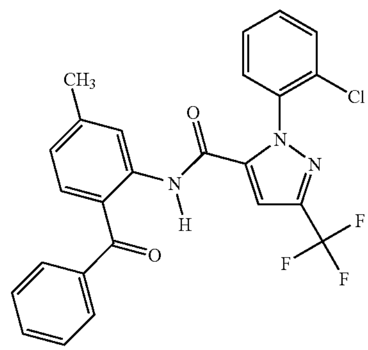 |
| 641 | N-(4-chloro-2-(2-chlorobenzoyl)phenyl)-1-(2-chlorophenyl)-3-(trifluoromethyl)-1H-pyrazole-5-carboxamide | 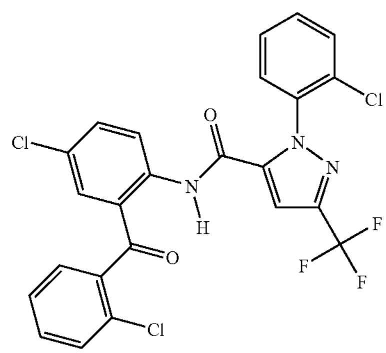 |
| 642 | 1-(2-chlorophenyl)-N-(2-phenoxyphenyl)-3-(trifluoromethyl)-1H-pyrazole-5-carboxamide | 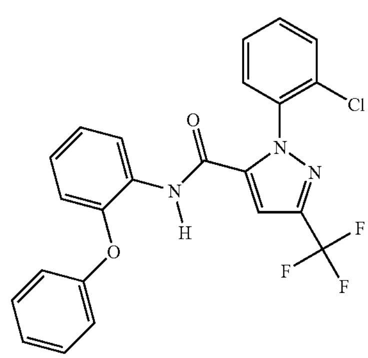 |

TABLE 7-continued

| # | IUPAC Name | Structure |
|---|---|---|
| 643 | N-(4-benzamido-2-methoxy-5-methylphenyl)-1-(2-chlorophenyl)-3-(trifluoromethyl)-1H-pyrazole-5-carboxamide | 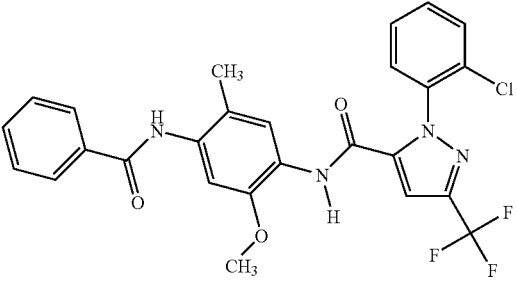 |
| 644 | N-(2-(1H-pyrrol-1-yl)phenyl)-1-(2-chlorophenyl)-3-(trifluoromethyl)-1H-pyrazole-5-carboxamide | 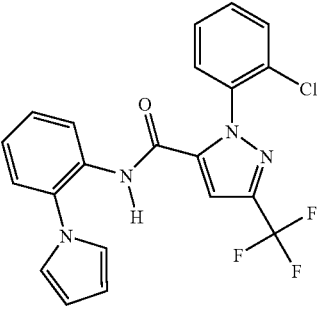 |
| 645 | N-(2-(1H-pyrrol-1-yl)phenyl)-1-(2-chlorophenyl)-3-(trifluoromethyl)-1H-pyrazole-5-carboxamide | 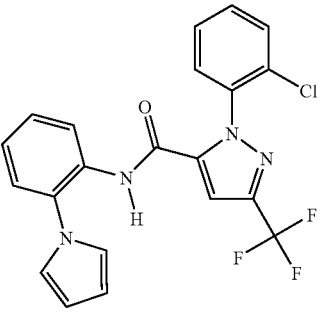 |
| 646 | 1-(2-chlorophenyl)-N-(2-(naphthalen-1-ylamino)ethyl)-(trifluoromethyl)-1H-pyrazole-5-carboxamide | 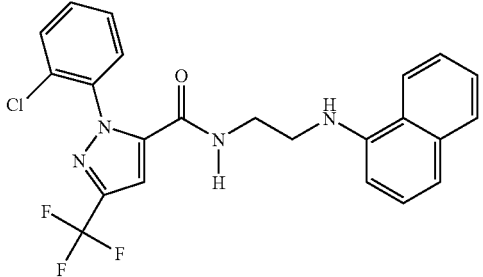 |
| 647 | 1-(2-chlorophenyl)-N-(phenyl(pyridin-2-yl)methyl)-3-(trifluoromethyl)-1H-pyrazole-5-carboxamide | 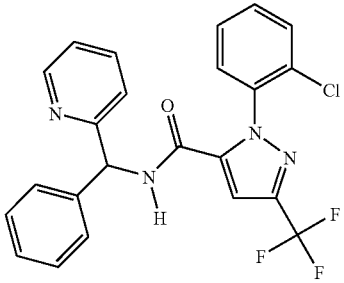 |

TABLE 7-continued

| # | IUPAC Name | Structure |
|---|---|---|
| 648 | N-(1-benzylpiperidin-4-yl)-1-(2-chlorophenyl)-3-(trifluoromethyl)-1H-pyrazole-5-carboxamide | 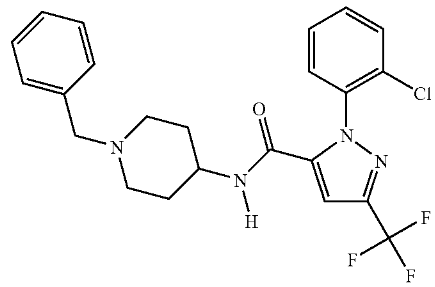 |
| 649 | 1-(2-chlorophenyl)-N-(1-(2,6-dimethylphenoxy)propan-2-yl)-3-(trifluoromethyl)-1H-pyrazole-5-carboxamide | 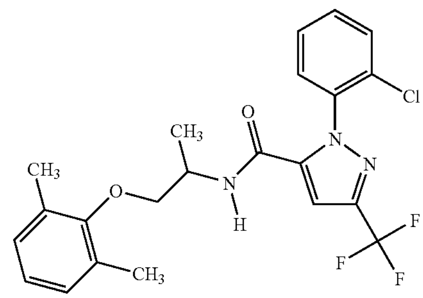 |
| 650 | 1-(2-chlorophenyl)-N-(2-(pyridin-3-yl)-2-(pyrrolidin-1-yl)ethyl)-3-(trifluoromethyl)-1H-pyrazole-5-carboxamide | 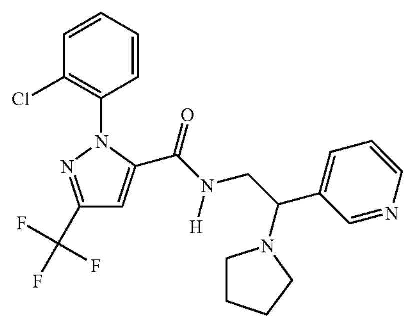 |
| 651 | N-(2-(4-benzylpiperazin-1-yl)ethyl)-1-(2-chlorophenyl)-3-(trifluoromethyl)-1H-pyrazole-5-carboxamide | 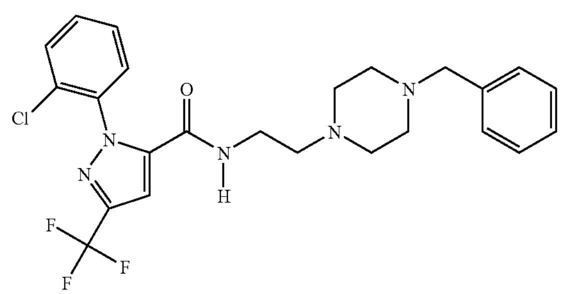 |
| 652 | 1-(2-chlorophenyl)-N-((1S,2S)-1-hydroxy-3-methoxy-1-phenylpropan-2-yl)-3-(trifluoromethyl)-1H-pyrazole-5-carboxamide | 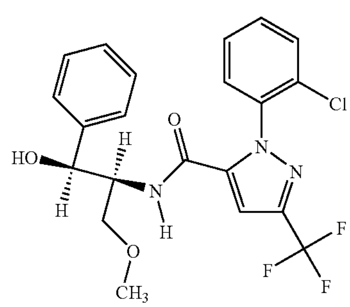 |

TABLE 7-continued

| # | IUPAC Name | Structure |
|---|---|---|
| 653 | 1-(2-chlorophenyl)-N-(1-(4-chlorophenyl)-3-hydroxypropan-2-yl)-3-(trifluoromethyl)-1H-pyrazole-5-carboxamide | 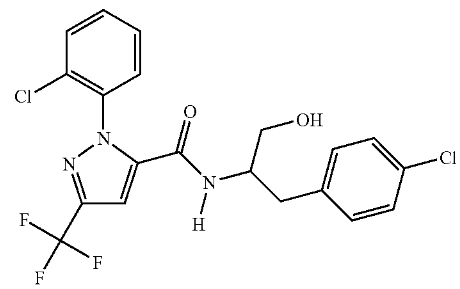 |
| 654 | methyl 3-(4-chlorophenyl)-2-(1-(2-chlorophenyl)-3-(trifluoromethyl)-1H-pyrazole-5-carboxamido)propanoate | 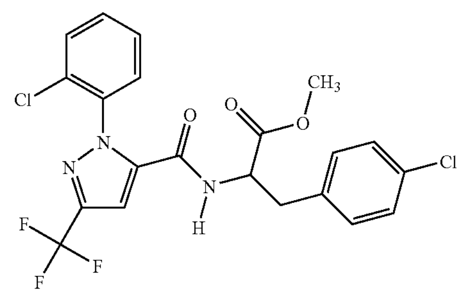 |
| 655 | (2S)-benzyl 2-(1-(2-chlorophenyl)-3-(trifluoromethyl)-1H-pyrazole-5-carboxamido)propanoate | 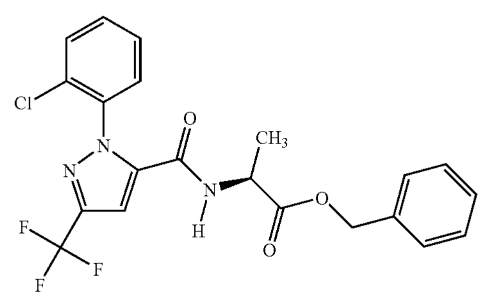 |
| 656 | N-(2-(benzylthio)etthyl)-1-(2-chlorophenyl)-3-(trifluoromethyl)-1H-pyrazole-5-carboxamide | 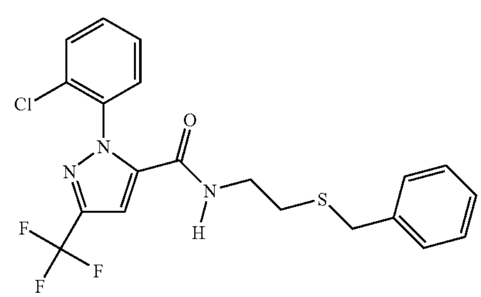 |
| 657 | 1-(2-chlorophenyl)-N-(1-(2,6-dimethylphenoxy)propan-2-yl)-3-(trifluoromethyl)-1H-pyrazole-5-carboxamide | 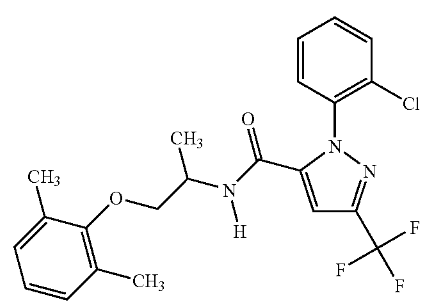 |

TABLE 7-continued

| # | IUPAC Name | Structure |
|---|---|---|
| 658 | N-(benzo[d][1,3]dioxol-5-ylmethyl)-1-(2-chlorophenyl)-3-(trifluoromethyl)-1H-pyrazole-5-carboxamide | 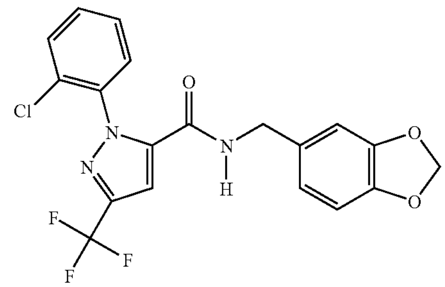 |
| 659 | 1-(2-chlorophenyl)-N-(pyridin-3-ylmethyl)-3-(trifluoromethyl)-1H-pyrazole-5-carboxamide | 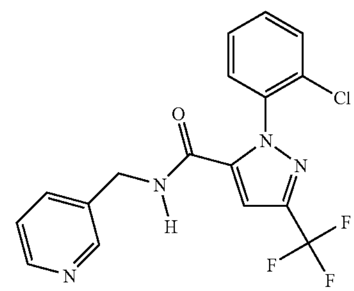 |
| 660 | 1-(2-chlorophenyl)-N-(thiophen-2-ylmethyl)-3-(trifluoromethyl)-1H-pyrazole-5-carboxamide | 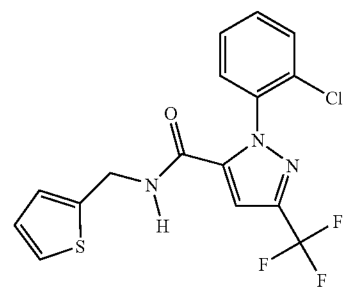 |
| 661 | N-(2-(1H-indol-3-yl)ethyl)-1-(2-chlorophenyl)-3-(trifluoromethyl)-1H-pyrazole-5-carboxamide | 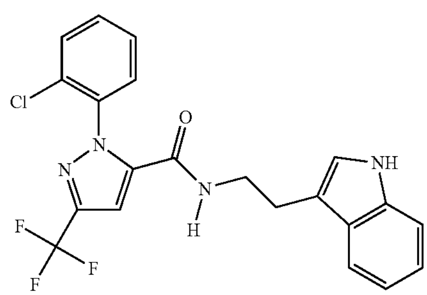 |
| 662 | 1-(2-chlorophenyl)-N-(furan-2-ylmethyl)-3-(trifluoromethyl)-1H-pyrazole-5-carboxamide | 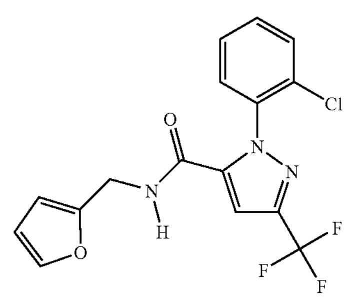 |

TABLE 7-continued

| # | IUPAC Name | Structure |
|---|---|---|
| 663 | 1-(2-chlorophenyl)-N-((1,5-dimethyl-1H-pyrazol-3-yl)methyl)-3-(trifluoromethyl)-1H-pyrazole-5-carboxamide | 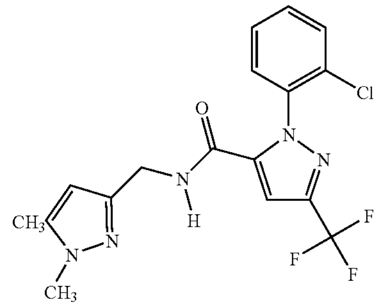 |
| 664 | 1-(2-chlorophenyl)-N-((2,5-dimethylfuran-3-yl)methyl)-3-(trifluoromethyl)-1H-pyrazole-5-carboxamide | 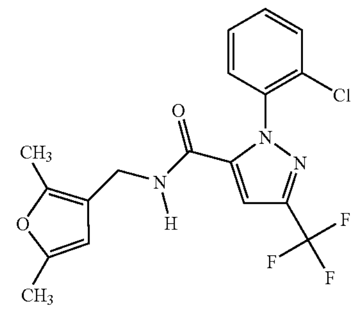 |
| 665 | 1-(2-chlorophenyl)-N-(pyridin-2-ylmethyl)-3-(trifluoromethyl)-1H-pyrazole-5-carboxamide | 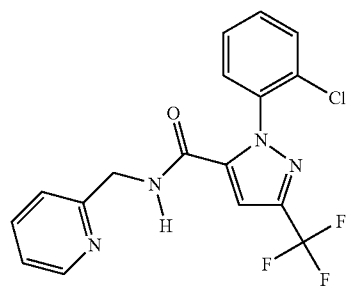 |
| 666 | 1-(2-chlorophenyl)-N-((1-methyl-1H-benzo[d][1,2,3]triazol-5-yl)methyl)-3-trifluoromethyl)-1H-pyrazole-5-carboxamide | 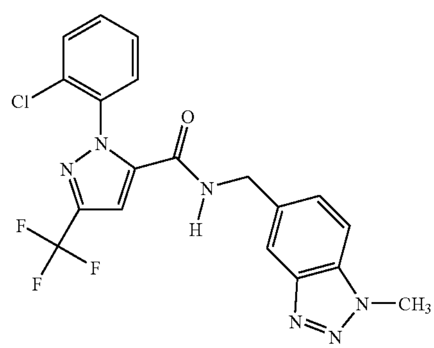 |
| 667 | 1-(2-chlorophenyl)-N-(pyridin-4-ylmethyl)-3-(trifluoromethyl)-1H-pyrazole-5-carboxamide | 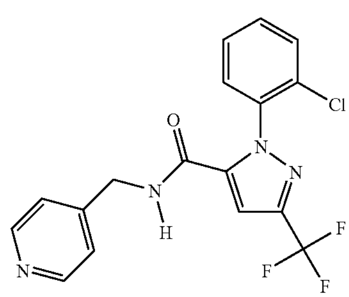 |

TABLE 7-continued

| # | IUPAC Name | Structure |
|---|---|---|
| 668 | 1-(2-chlorophenyl)-N-(2-(thiophen-2-yl)ethyl)-3-(trifluoromethyl)-1H-pyrazole-5-carboxamide | 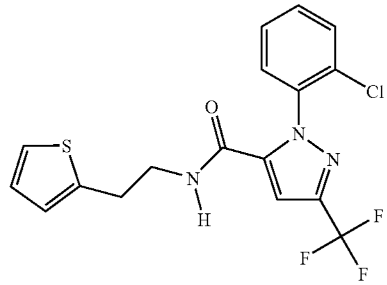 |
| 669 | 1-(2-chlorophenyl)-N-(2-(5-methyl-1H-indol-3-yl)ethl)-3-(trifluoromethl)-1H-prazole-5-carboxamide | 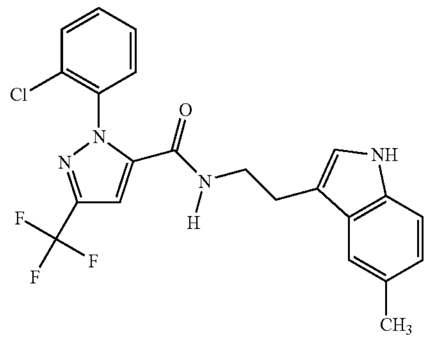 |
| 670 | 1-(2-chlorophenyl)-N-(2-(thiophen-2-yl)ethyl)-3-(trifluoromethyl)-1H-pyrazole-5-carboxamide | 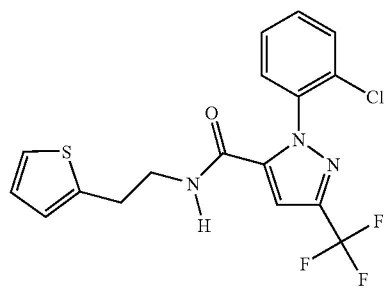 |
| 671 | 1-(2-chlorophenyl)-N-((5-methylfuran-2-yl)methyl)-3-(trifluoromethyl)-1H-pyrazole-5-carboxamide | 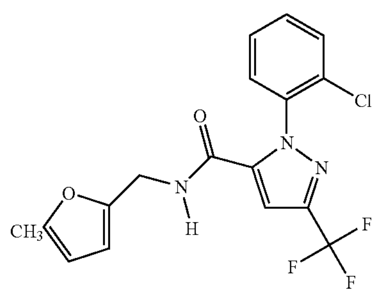 |
| 672 | N-(benzo[d][1,3]dioxol-5-ylmethyl)-1-(2-chlorophenyl)-3-(trifluoromethyl)-1H-pyrazole-5-carboxamide | 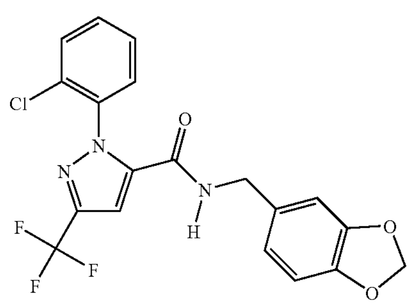 |

TABLE 7-continued

| # | IUPAC Name |
|---|---|
| 673 | 1-(2-chlorophenyl)-N-(3-methoxyphenethyl)-3-(trifluoromethyl)-1H-pyrazole-5-carboxamide |
| 674 | 1-(2-chlorophenyl)-N-(1-(4-chlorophenyl)ethyl)-3-(trifluoromethyl)-1H-pyrazole-5-carboxamide |
| 675 | 1-(2-chlorophenyl)-N-((R)-1-phenylethyl)-3-(trifluoromethyl)-1H-pyrazole-5-carboxamide |
| 676 | 1-(2-chlorophenyl)-N-(4-methoxyphenethyl)-3-(trifluoromethyl)-1H-pyrazole-5-carboxamide |
| 677 | 1-(2-chlorophenyl)-N-(4-methylphenethyl)-3-(trifluoromethyl)-1H-pyrazole-5-carboxamide |

TABLE 7-continued

| # | IUPAC Name | Structure |
|---|---|---|
| 678 | 1-(2-chlorophenyl)-N-(1-(4-fluorophenyl)ethyl)-3-(trifluoromethyl)-1H-pyrazole-5-carboxamide | 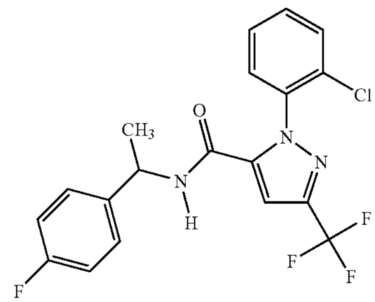 |
| 679 | methyl 4-((1-(2-chlorophenyl)-3-(trifluoromethyl)-1H-pyrazole-5-carboxamido)methyl)benzoate | 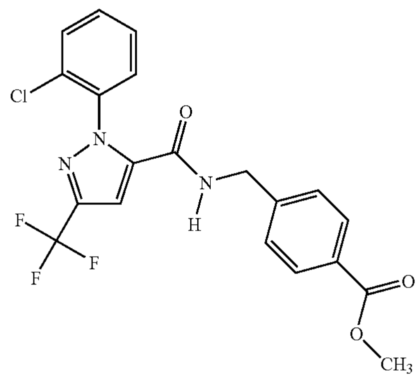 |
| 680 | N-(2-chlorophenethyl)-1-(2-chlorophenyl)-3-(trifluoromethyl)-1H-pyrazole-5-carboxamide | 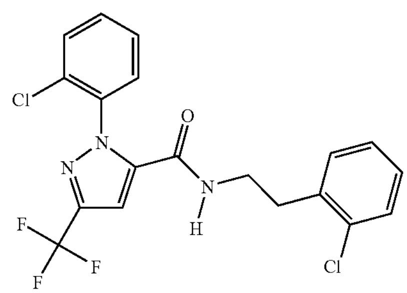 |
| 681 | 1-(2-chlorophenyl)-N-((S)-1-phenylethyl)-3-(trifluoromethyl)-1H-pyrazole-5-carboxamide | 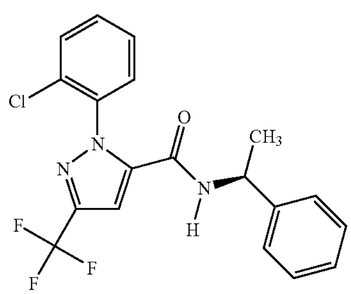 |
| 682 | 1-(2-chlorophenyl)-N-(4-methylbenzyl)-3-(trifluoromethyl)-1H-pyrazole-5-carboxamide | 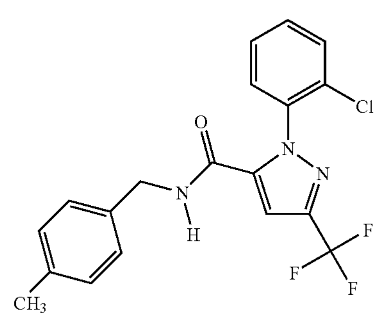 |

TABLE 7-continued

| # | IUPAC Name | Structure |
|---|---|---|
| 683 | 1-(2-chlorophenyl)-N-(1-phenylpropyl)-3-(trifluoromethyl)-1H-pyrazole-5-carboxamide | 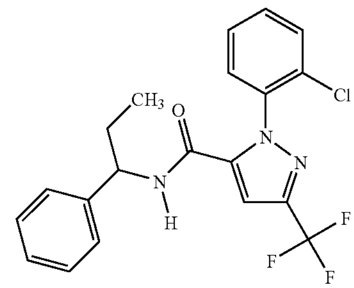 |
| 684 | 1-(2-chlorophenyl)-N-(4-phenylbutan-2-yl)-3-(trifluoromethyl)-1H-pyrazole-5-carboxamide | 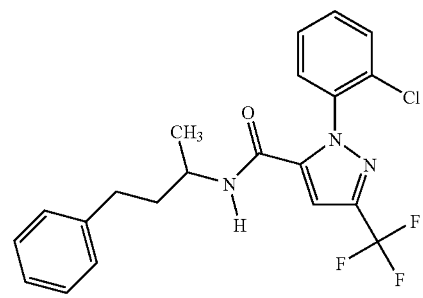 |
| 685 | 1-(2-chlorophenyl)-N-(4-fluorobenzyl)-3-(trifluoromethyl)-1H-pyrazole-5-carboxamide | 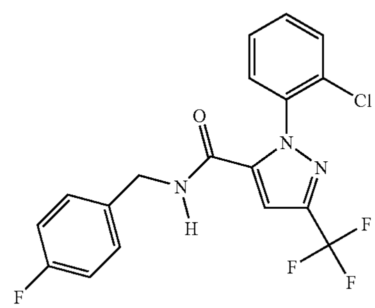 |
| 686 | 1-(2-chlorophenyl)-N-(2-methoxyphenethyl)-3-(trifluoromethyl)-1H-pyrazole-5-carboxamide | 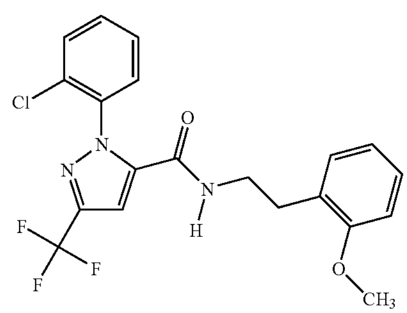 |
| 687 | N-(4-(1H-pyrazol-1-yl)benzyl)-1-(2-chlorophenyl)-3-(trifluoromethyl)-1H-pyrazole-5-carboxamide | 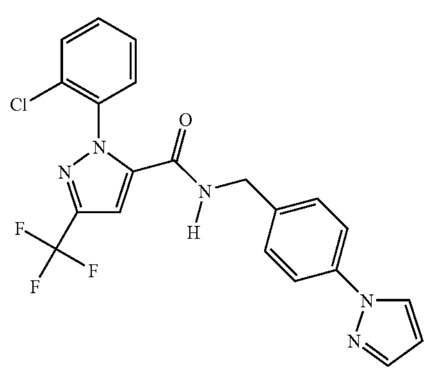 |

TABLE 7-continued

| # | IUPAC Name | Structure |
|---|---|---|
| 688 | 1-(2-chlorophenyl)-N-(2,5-difluorobenzyl)-3-(trifluoromethyl)-1H-pyrazole-5-carboxamide | 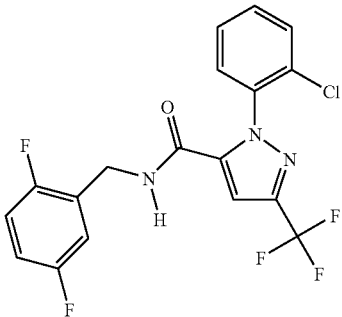 |
| 689 | 1-(2-chlorophenyl)-N-(3,4-dimethoxyphenethyl)-3-(trifluoromethyl)-1H-pyrazole-5-carboxamide | 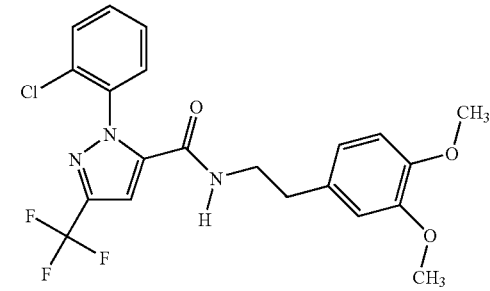 |
| 690 | 1-(2-chlorophenyl)-3-(trifluoromethyl)-N-(2-(trifluoromethyl)benzyl)-1H-pyrazole-5-carboxamide | 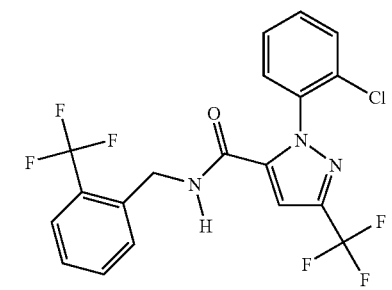 |
| 691 | 1-(2-chlorophenyl)-N-(2-fluorobenzyl)-3-(trifluoromethyl)-1H-pyrazole-5-carboxamide | 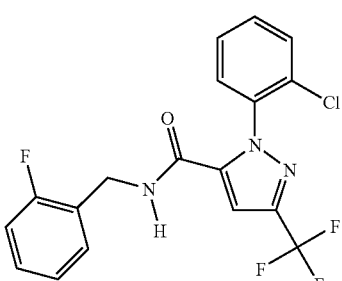 |
| 692 | 1-(2-chlorophenyl)-N-(2-phenylpropyl)-3-(trifluoromethyl)-1H-pyrazole-5-carboxamide | 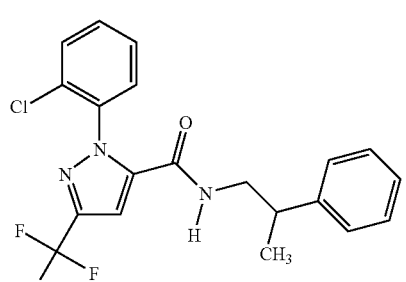 |

TABLE 7-continued

| # | IUPAC Name | Structure |
|---|---|---|
| 693 | 1-(2-chlorophenyl)-N-(3-fluorophenethyl)-3-(trifluoromethyl)-1H-pyrazole-5-carboxamide | 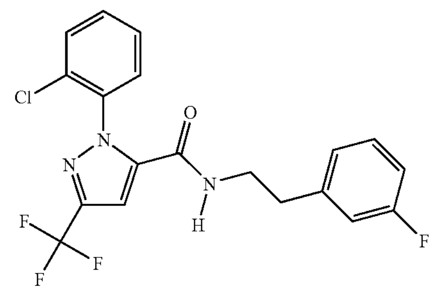 |
| 694 | 1-(2-chlorophenyl)-N-(4-fluorophenethyl)-3-(trifluoromethyl)-1H-pyrazole-5-carboxamide | 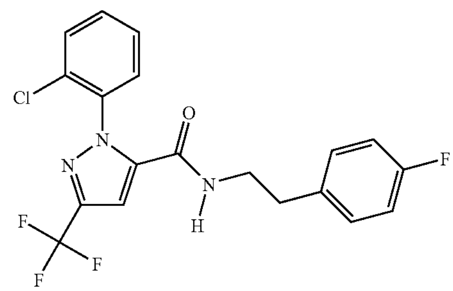 |
| 695 | 1-(2-chlorophenyl)-N-(4-phenylbutan-2-yl)-3-(trifluoromethyl)-1H-pyrazole-5-carboxamide | 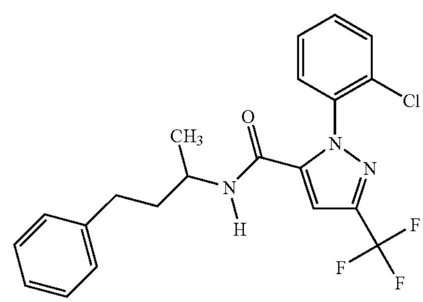 |
| 696 | 1-(2-chlorophenyl)-N-(3-(trifluoromethoxy)benzyl)-3-(trifluoromethyl)-1H-pyrazole-5-carboxamide | 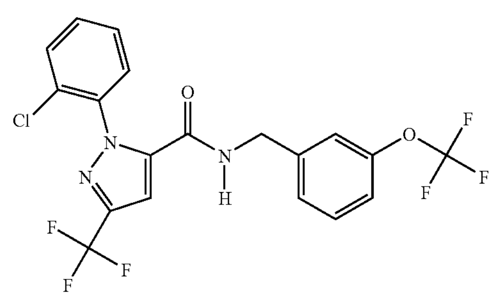 |
| 697 | N-(4-tert-butylbenzyl)-1-(2-chlorophenyl)-3-(trifluoromethyl)-1H-pyrazole-5-carboxamide | 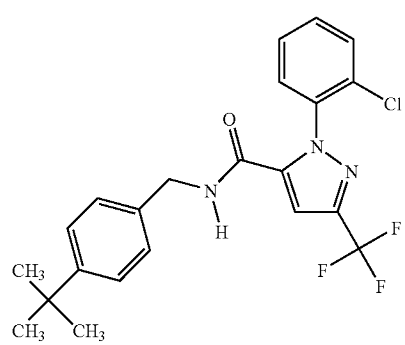 |

TABLE 7-continued

| # | IUPAC Name | Structure |
|---|---|---|
| 698 | N-(biphenyl-2-ylmethyl)-1-(2-chlorophenyl)-3-(trifluoromethyl)-1H-pyrazole-5-carboxamide | 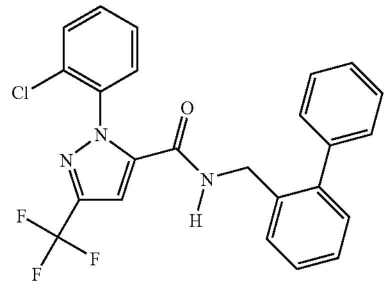 |
| 699 | 1-(2-chlorophenyl)-N-(4-phenoxyphenethyl)-3-(trifluoromethyl)-1H-pyrazole-5-carboxamide | 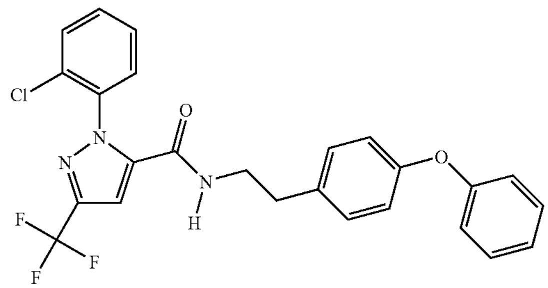 |
| 700 | 1-(2-chlorophenyl)-N-(2-(4-chlorophenyl)propyl)-3-(trifluoromethyl)-1H-pyrazole-5-carboxamide | 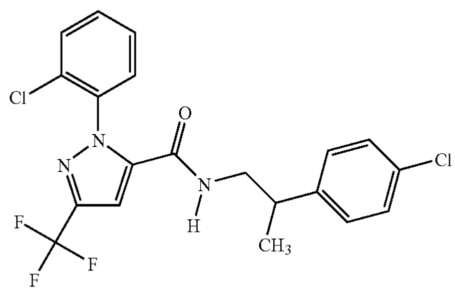 |
| 701 | 1-(2-chlorophenyl)-N-(4-isopropylbenzyl)-3-(trifluoromethyl)-1H-pyrazole-5-carboxamide | 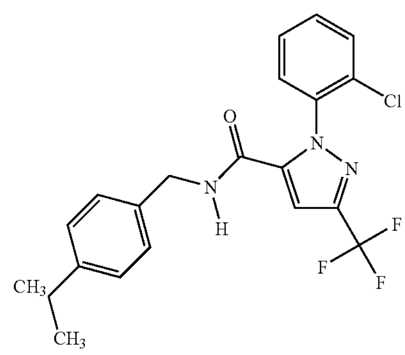 |
| 702 | 1-(2-chlorophenyl)-N-((S)-1-(naphthalen-1-yl)ethyl)-3-(trifluoromethyl)-1H-pyrazole-5-carboxamide | 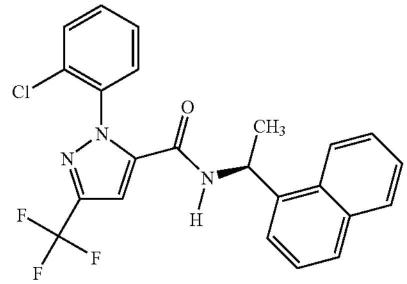 |

TABLE 8

| # | IUPAC Name | Structure |
|---|---|---|
| 703 | 1-{[1-(2-chlorophenyl)-3-(trifluoromethyl)-1H-pyrazol-5-yl]carbonyl}-4-[2-(2-thienyl)ethyl]piperazine | 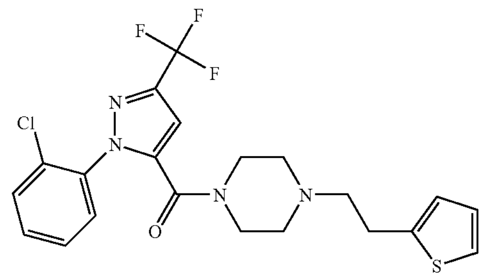 |
| 704 | 8-{[1-(2-chlorophenyl)-3-(trifluoromethyl)-1H-pyrazol-5-yl]carbonyl}-1,4-dioxa-8-azaspiro[4.5]decane | 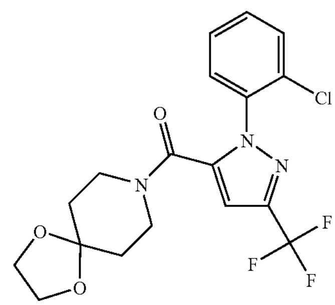 |
| 705 | 1-{[1-(2-chlorophenyl)-3-(trifluoromethyl)-1H-pyrazol-5-yl]carbonyl}-4-(1-methylpiperidin-4-yl)piperazine | 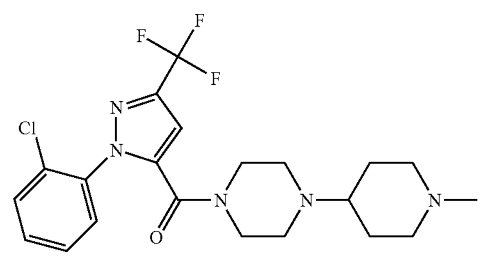 |
| 706 | 1-{[1-(2-chlorophenyl)-3-(trifluoromethyl)-1H-pyrazol-5-yl]carbonyl}-4-(pyridin-2-ylmethyl)piperazine | 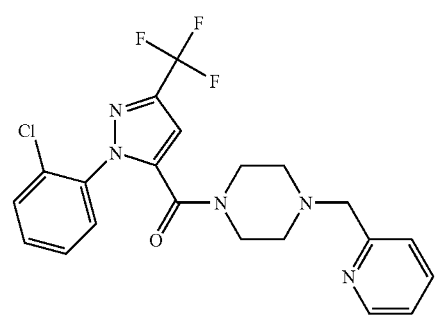 |
| 707 | 1-{[1-(2-chlorophenyl)-3-(trifluoromethyl)-1H-pyrazol-5-yl]carbonyl}-4-(2-piperidin-1-ylethyl)piperazine | 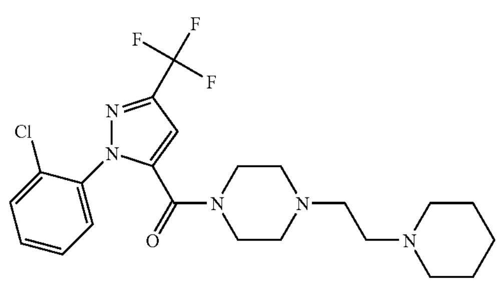 |

TABLE 8-continued

| # | IUPAC Name |
|---|---|
| 708 | 2-(4-{[1-(2-chlorophenyl)-3-(trifluoromethyl)-1H-pyrazol-5-yl]carbonyl}-1,4-diazepan-1-yl)pyridine-3-carbonitrile |
| 709 | 1-{[1-(2-chlorophenyl)-3-(trifluoromethyl)-1H-pyrazol-5-yl]carbonyl}-4-(tetrahydrofuran-2-ylmethyl)piperazine |
| 710 | ethyl 1-{[1-(2-chlorophenyl)-3-(trifluoromethyl)-1H-pyrazol-5-yl]carbonyl}piperidine-3-carboxylate |
| 711 | 2-(4-{[1-(2-chlorophenyl)-3-(trifluoromethyl)-1H-pyrazol-5-yl]carbonyl}piperazin-1-yl)pyrimidine |
| 712 | 2-(4-{[1-(2-chlorophenyl)-3-(trifluoromethyl)-1H-pyrazol-5-yl]carbonyl}piperazin-1-yl)pyridine-3-carbonitrile |

TABLE 8-continued

| # | IUPAC Name | Structure |
|---|---|---|
| 713 | 7-{[1-(2-chlorophenyl)-3-(trifluoromethyl)-1H-pyrazol-5-yl]carbonyl}-6,7,8,9-tetrahydroprido[2,3,-b]-1,6-naphthyridine | 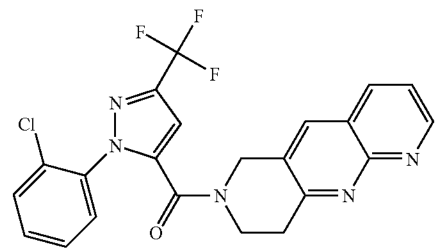 |
| 714 | 1-{[1-(2-chlorophenyl)-3-(trifluoromethyl)-1H-pyrazol-5-yl]carbonyl}-4-(2-oxo-2-pyrrolidin-1-ylethyl)piperazine | 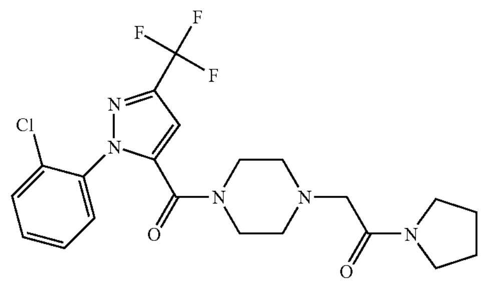 |
| 715 | ethyl 4-{[1-(2-chlorophenyl)-3-(trifluoromethyl)-1H-pyrazol-5-yl]carbonyl}piperazine-1-carboxylate | 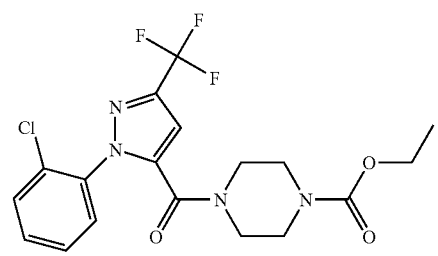 |
| 716 | 1-{[1-(2-chlorophenyl)-3-(trifluoromethyl)-1H-pyrazol-5-yl]carbonyl}-4-methylpiperidine | 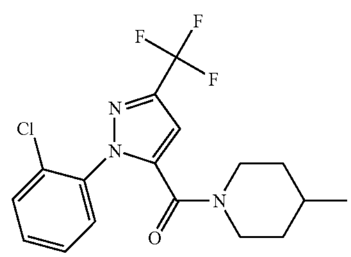 |
| 717 | ethyl 1-{[1-(2-chlorophenyl)-3-trifluoromethyl)-1H-pyrazol-5-yl]carbonyl}piperidine-2-carboxylate | 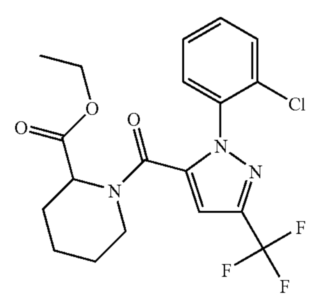 |
| 718 | 1-{[1-(2-chlorophenyl)-3-(trifluoromethyl)-1H-pyrazol-5-yl]carbonyl}-4-pyridin-4-ylpiperazine | 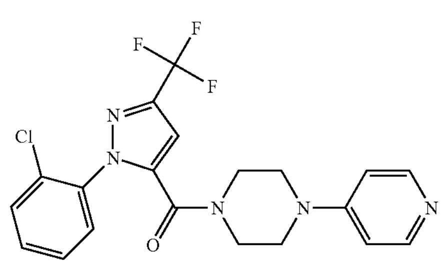 |

TABLE 8-continued

| # | IUPAC Name | Structure |
|---|---|---|
| 719 | 1-(2-chlorophenyl)-N-{3-[(furan-2-ylmethyl)oxy]-2-hydroxypropyl}-N-methyl-3-(trifluoromethyl)-1H-pyrazole-5-carboxamide | 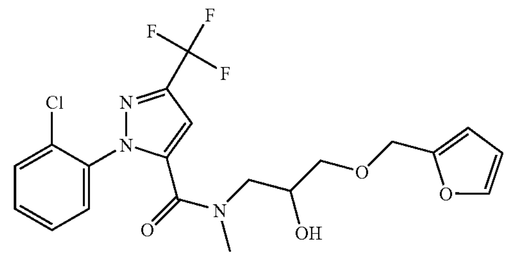 |
| 720 | 1-(2-chlorophenyl)-N-methyl-N-(pyridin-3-ylmethyl)-3-(trifluoromethyl)-1H-pyrazole-5-carboxamide | 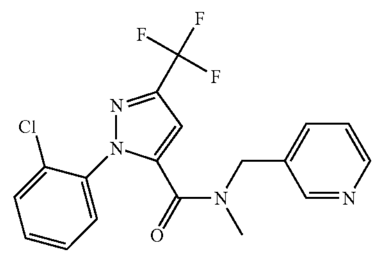 |
| 721 | 1-{[1-(2-chlorophenyl)-3-(triffluoromethyl)pyrazol-5-yl]carbonyl}-4-[5-trifluoromethyl)pyridin-2-yl]piperazine | 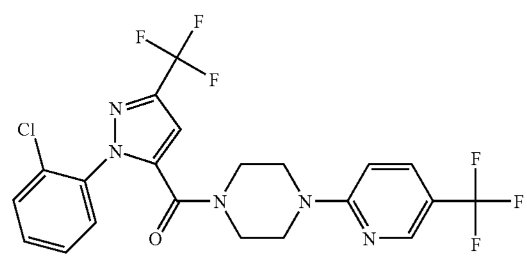 |
| 722 | 1-(2-chlorophenyl)-N-[3-(dimethylamino)propyl]-N-methyl-3-(trifluoromethyl)-1H-pyrazole-5-carboxamide | 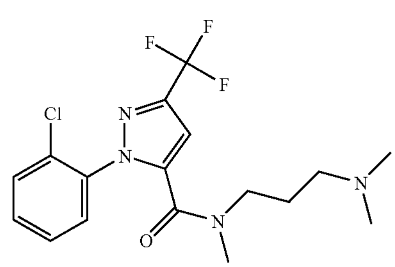 |
| 723 | 1-{[1-(2-chlorophenyl)-3-(trifluoromethyl)-1H-pyrazol-5-yl]carbonyl}-4-[2-(methyloxy)ethyl]piperazine | 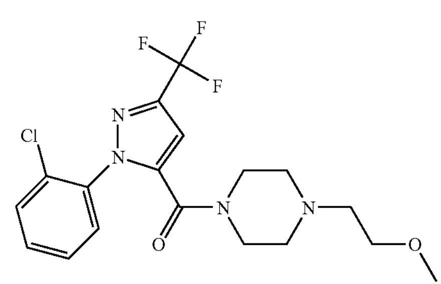 |

TABLE 8-continued

| # | IUPAC Name | Structure |
|---|---|---|
| 724 | 4-[(4-{[1-(2-chlorophenyl)-3-(trifluoromethyl)-1H-pyrazol-5-yl]carbonyl}piperazin-1-yl)acetyl]morpholine | 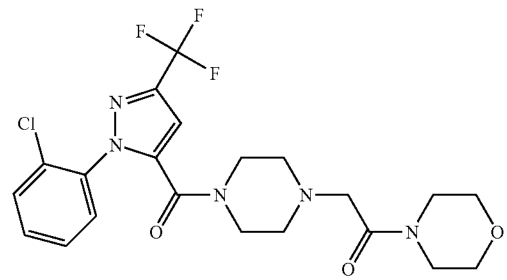 |
| 725 | 1-{[1-(2-chlorophenyl)-3-(trifluoromethyl)-1H-pyrazol-5-yl]carbonyl}-4-(2-pyrrolidin-1-ylethyl)piperazine | 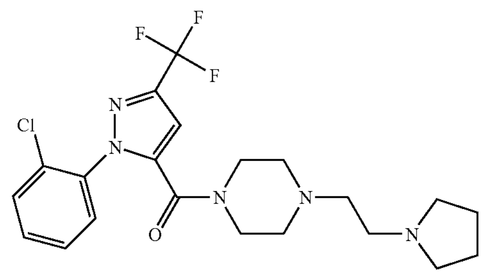 |
| 726 | 1-{[1-(2-chlorophenyl)-3-(trifluoromethyl)-1H-pyrazol-5-yl]carbonyl}-4-pyridin-2-ylpiperazine | 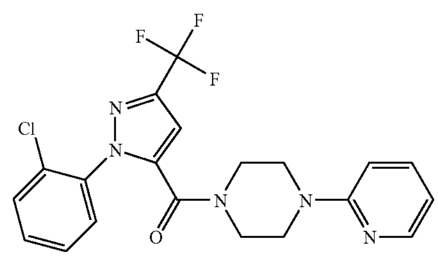 |
| 727 | 1-{[1-(2-chlorophenyl)-3-(trifluoromethyl)-1H-pyrazol-5-yl]carbonyl}-4-methyl-1,4-diazepane | 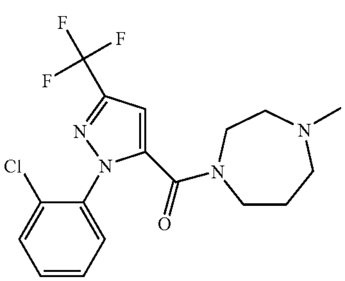 |
| 728 | 1-{[1-(2-chlorophenyl)-3-(trifluoromethyl)-1H-pyrazol-5-yl]carbonyl}-4-(2-pyridin-2-ylethyl)piperazine | 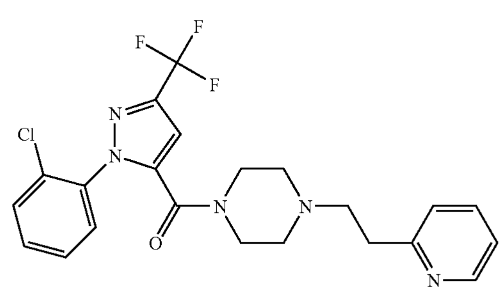 |

TABLE 8-continued

| # | IUPAC Name | Structure |
|---|---|---|
| 729 | 1-{[1-(2-chlorophenyl)-3-(trifluoromethyl)-1H-pyrazol-5-yl]carbonyl}-4-(ethylsulfonyl)piperazine | 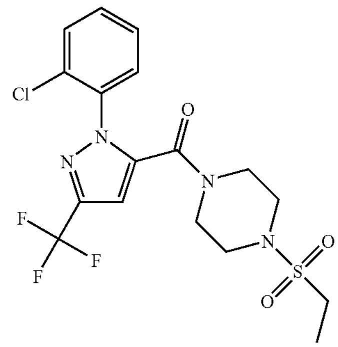 |
| 730 | 1-{[1-(2-chlorophenyl)-3-(trifluoromethyl)-1H-pyrazol-5-yl]carbonyl}-4-[(1-methylpiperidin-3-yl)methyl]piperazine | 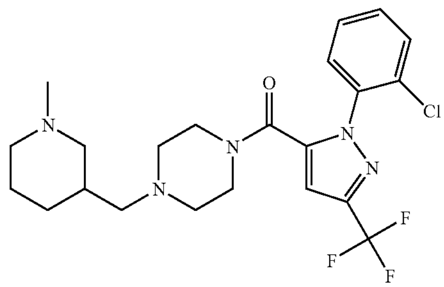 |
| 731 | 1-{[1-(2-chlorophenyl)-3-(trifluoromethyl)-1H-pyrazol-5-yl]carbonyl}-4-(6-methylpyridin-2-yl)piperazine | 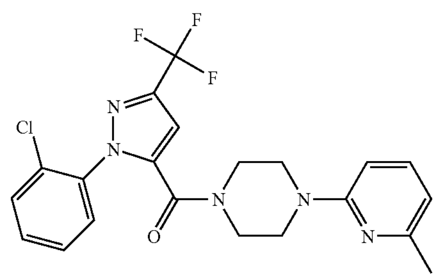 |
| 732 | 1-{[1-(2-chlorophenyl)-3-(trifluoromethyl)-1H-pyrazol-5-yl]carbonyl}-4-(pyridin-4-ylmethyl)piperazine | 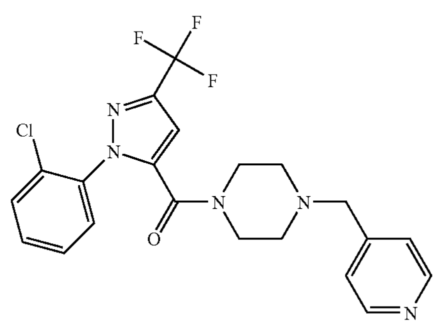 |
| 733 | methyl 1-{[1-(2-chlorophenyl)-3-(trifluoromethyl)-1H-pyrazol-5-yl]carbonyl}-L-prolinate | 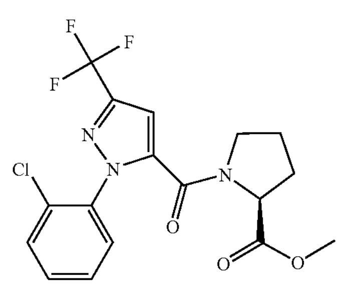 |

TABLE 8-continued

| # | IUPAC Name | Structure |
|---|---|---|
| 734 | 4-{[1-(2-chlorophenyl)-3-(trifluoromethyl)-1H-pyrazol-5-yl]carbonyl}-2,6-dimethylmorpholine | 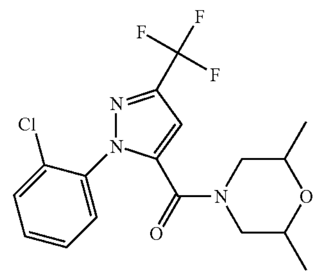 |
| 735 | 1-(2-chlorophenyl)-N-(furan-2-ylmethyl)-N-methyl-3-(trifluoromethyl)-1H-pyrazole-5-carboxamide | 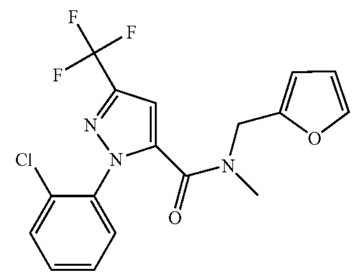 |
| 736 | 1-{[1-(2-chlorophenyl)-3-(trifluoromethyl)-1H-pyrazol-5-yl]carbonyl}-4-(2-fluorophenyl)piperazine | 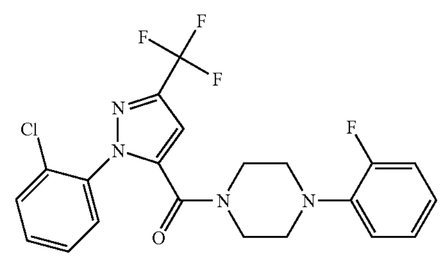 |
| 737 | ethyl N-{[1-(2-chlorophenyl)-3-(trifluoromethyl)-1H-pyrazol-5-yl]carbonyl}-N-(furan-2-ylmethyl)-beta-alaninate | 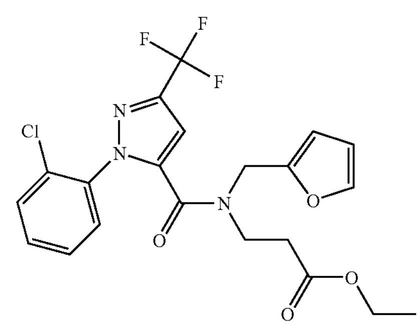 |
| 738 | 1-{[1-(2-chlorophenyl)-3-(trifluoromethyl)-1H-pyrazol-5-yl]carbonyl}-4-(tetrahydrofuran-2-ylcarbonyl)piperazine | 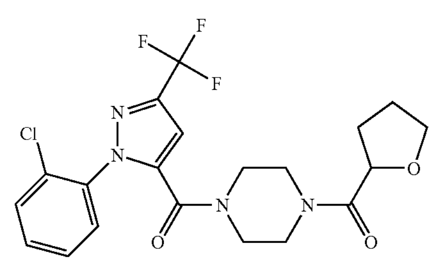 |

TABLE 8-continued

| # | IUPAC Name | Structure |
|---|---|---|
| 739 | ethyl 1-{[1-(2-chlorophenyl)-3-(trifluoromethyl)-1H-pyrazol-5-yl]carbonyl}piperidine-4-carboxylate | 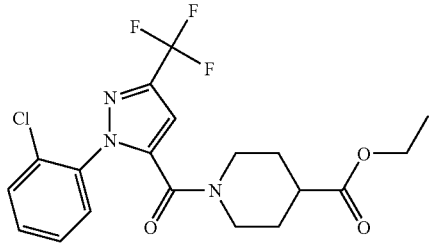 |
| 740 | 1-(2-chlorophenyl)-N-(3-furan-2-yl-1-methylpropyl)-N-methyl-3-(trifluoromethyl)-1H-pyrazole-5-carboxamide | 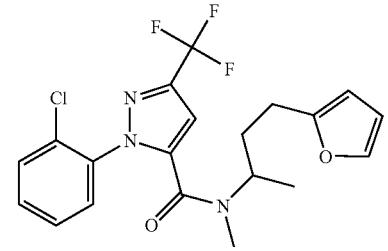 |
| 741 | 1-(2-chlorophenyl)-N-methyl-N-(2-pyridin-2-ylethyl)-3-(trifluoromethyl)-1H-pyrazole-5-carboxamide | 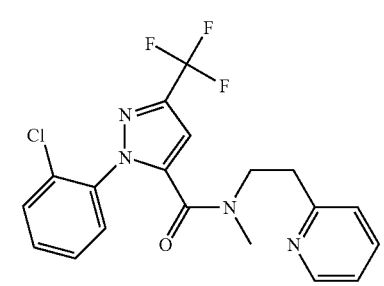 |
| 742 | 1-{[1-(2-chlorophenyl)-3-(trifluoromethyl)-1H-pyrazol-5-yl]carbonyl}-4-(pyridin-3-ylmethyl)piperazine | 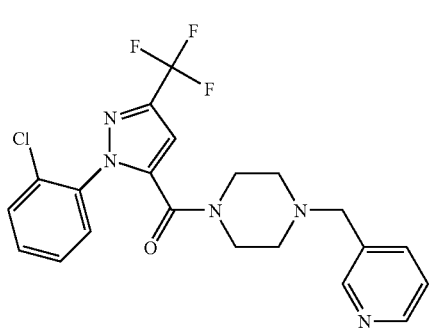 |
| 743 | 1-{[1-(2-chlorophenyl)-3-(trifluoromethyl)-1H-pyrazol-5-yl]carbonyl}-4-(furan-2-ylcarbonyl)piperazine | 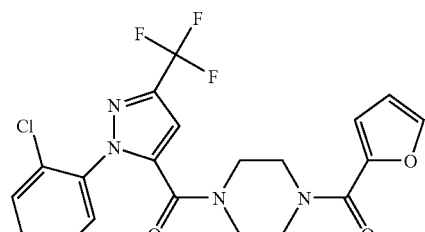 |

TABLE 8-continued

| # | IUPAC Name |
|---|---|
| 744 | 1-{[1-(2-chlorophenyl)-3-(trifluoromethyl)-1H-pyrazol-5-yl]carbonyl}piperidin-4-ol |
| 745 | methyl 1-{[1-(2-chlorophenyl)-3-trifluoromethyl)-1H-pyrazol-5-yl]carbonyl}piperidine-4-carboxylate |
| 746 | 1,1-dimethylethyl 4-{[1-(2-chlorophenyl)-3-(trifluoromethyl)-1H-pyrazol-5-yl]carbonyl}-1,4-diazepane-1-carboxylate |
| 747 | 1-(2-chlorophenyl)-N-(2-cyanoethyl)-N-(furan-2-ylmethyl)-3-(trifluoromethyl)-1H-pyrazole-5-carboxamide |
| 748 | 1-(2-chlorophenyl)-N-methyl-N-(1-pyridin-2-ylethyl)-3-(trifluoromethyl)-1H-pyrazole-5-carboxamide |
| 749 | 1-(2-chlorophenyl)-N-methyl-N-[(2-methyl-1,3-thiazol-4-yl)methyl]-3-(trifluoromethyl)-1H-pyrazole-5-carboxamide |

| # | IUPAC Name | Structure |
|---|---|---|
| 750 | 4-(1-{[1-(2-chlorophenyl)-3-(trifluoromethyl)-1H-pyrazol-5-yl]carbonyl}pyrrolidin-3-yl)pyridine | 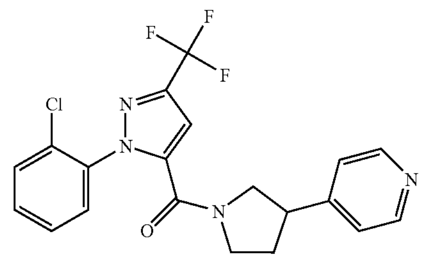 |
| 751 | 1-(2-chlorophenyl)-N-methyl-N-[(5-methyl-1H-pyrazol-3-yl)methyl]-3-(trifluoromethyl)-1H-pyrazole-5-carboxamide | 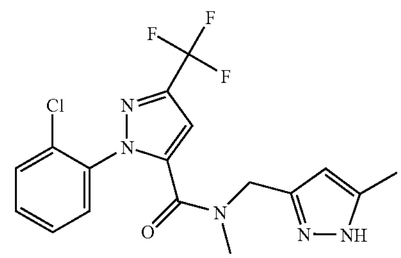 |
| 752 | 1-(2-chlorophenyl)-N-[1-(3,5-dimethyl-1H-pyrazol-4-yl)ethyl]-N-methyl-3-(trifluoromethyl)-1H-pyrazole-5-carboxamide | 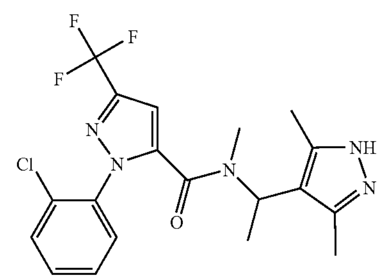 |
| 753 | 1-(2-chlorophenyl)-N-methyl-N-(1-pyridin-4-ylethyl)-3-(trifluoromethyl)-1H-pyrazole-5-carboxamide | 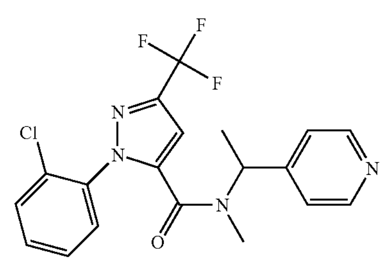 |
| 754 | 2-(1-{[1-(2-chlorophenyl)-3-(trifluoromethyl)-1H-pyrazol-5-yl[carbonyl}pyrrolidin-3-yl)pyridine | 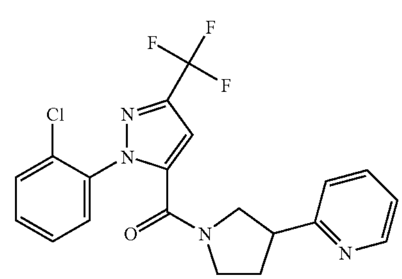 |

TABLE 8-continued

| # | IUPAC Name | Structure |
|---|---|---|
| 755 | 3-(1-}[1-(2-chlorophenyl)-3-(trifluoromethyl)-1H-pyrazol-5-yl]carbonyl}pyrrolidin-3-yl)pyridine | 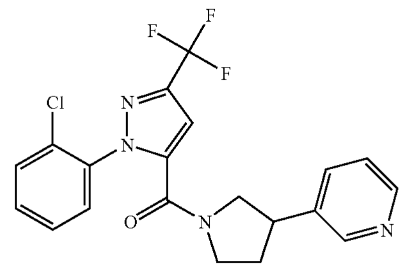 |
| 756 | ethyl N-{[1-(2-chlorophenyl)-3-(trifluoromethyl)-1H-pyrazol-5-yl]carbonyl}-N-(pyridin-2-ylmethyl)glycinate | 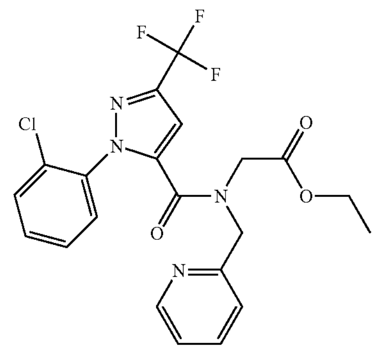 |
| 757 | 1-(2-chlorophenyl)-N-methyl-N-[(4-methyl-1H-imidazol-2-yl)methyl]-3-(trifluoromethyl)-1H-pyrazole-5-carboxamide | 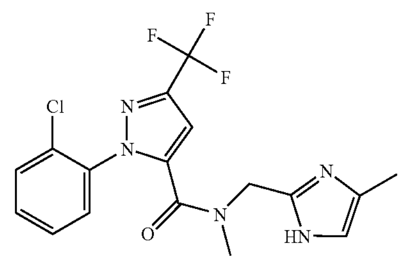 |
| 758 | 1-{[1-(2-chlorophenyl)-3-(trifluoromethyl)-1H-pyrazol-5-yl]carbonyl}-4-[(1-methyl-1H-imidazol-2-yl)methyl]piperazine | 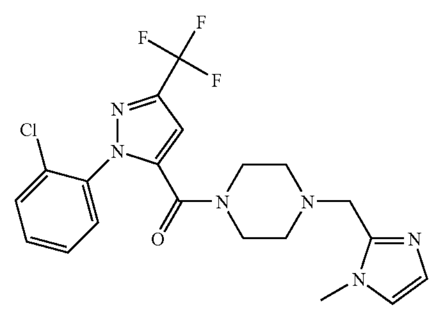 |
| 759 | 1-(2-chlorophenyl)-N-methyl-N-[(5-phenyl-1,3,4-oxadiazol-2-yl)methyl]-3-(trifluoromethyl)-1H-pyrazole-5-carboxamide | 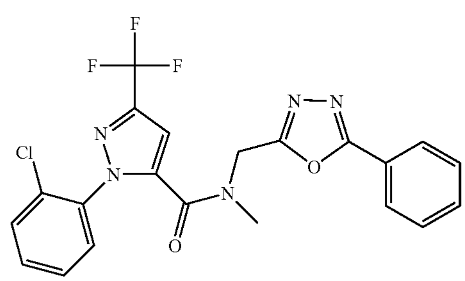 |

TABLE 8-continued

| # | IUPAC Name | Structure |
|---|---|---|
| 760 | 1-(2-chlorophenyl)-N-methyl-N-[2-(4-methyl-1,3-thiazol-5-yl)ethyl]-3-(trifluoromethyl)-1H-pyrazole-5-carboxamide | 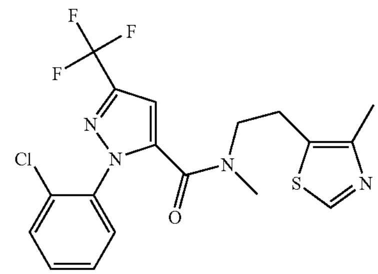 |
| 761 | 1-(2-chlorophenyl)-N-[2-(3,5-dimethyl-1H-pyrazol-1-yl)ethyl]-N-methyl-3-(trifluoromethyl)-1H-pyrazole-5-carboxamide | 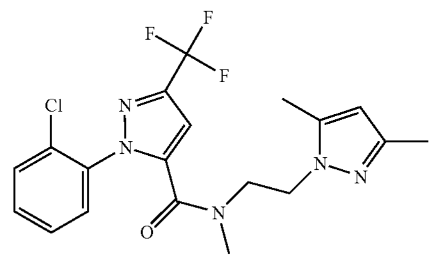 |
| 762 | (1-{[1-(2-chlorophenyl)-3-(trifluoromethyl)-1H-pyrazol-5-yl]carbonyl}piperidin-4-yl)(pyridin-3-yl)methanol | 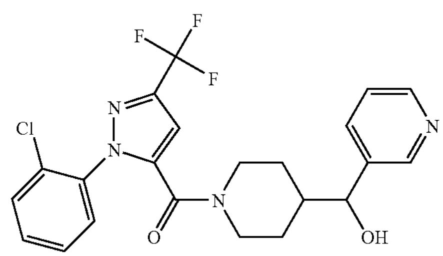 |
| 763 | 1-(2-chlorophenyl)-N-(furan-2-ylmethyl)-N-(pyridin-2-ylmethyl)-3-(trifluoromethyl)-1H-pyrazole-5-carboxamide | 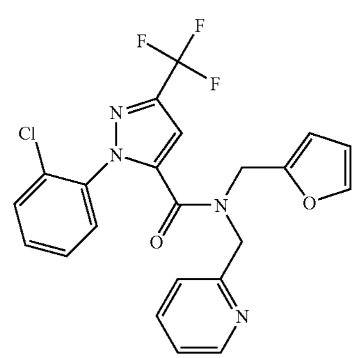 |
| 764 | 1-(2-chlorophenyl)-N-[(3,5-dimethyl-1H-pyrazol-4-yl)methyl]-N-methyl-3-(trifluoromethyl)-1H-pyrazole-5-carboxamide | 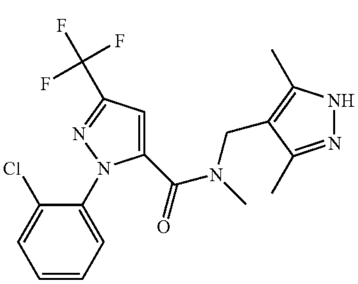 |

TABLE 8-continued

| # | IUPAC Name | Structure |
|---|---|---|
| 765 | [{[1-(2-chlorophenyl)-3-(trifluoromethyl)-1H-pyrazol-5-yl]carbonyl}(methyl)amino](pyridin-3-yl)acetic acid | 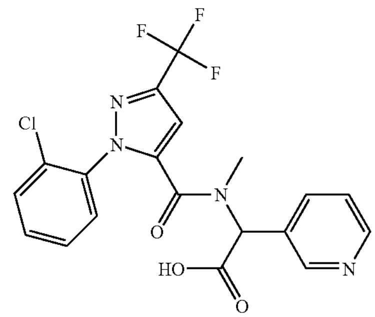 |
| 766 | 1-(2-chlorophenyl)-N-methyl-N-[(1-methyl-1H-imidazol-2-yl)methyl]-3-(trifluoromethyl)-1H-pyrazole-5-carboxamide | 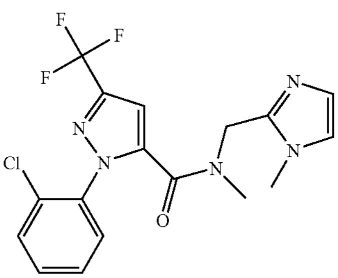 |
| 767 | 1-(2-chlorophenyl)-N-(3-hydroxypropyl)-N-(pyridin-2-ylmethyl)-3-(trifluoromethyl)-1H-pyrazole-5-carboxamide | 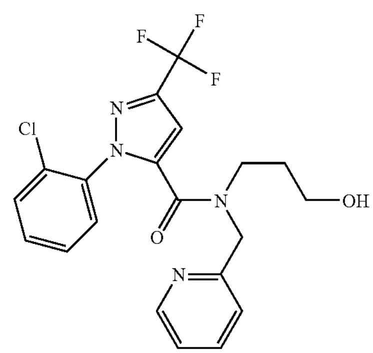 |
| 768 | (1-{[1-(2-chlorophenyl)-3-(trifluoromethyl)-1H-pyrazol-5-yl]carbonyl}piperidin-3-yl)(pyridin-3-yl)methanone | 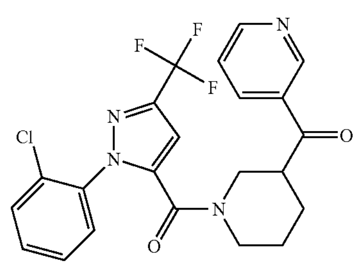 |
| 769 | (1-{[1-(2-chlorophenyl)-3-(trifluoromethyl)-1H-pyrazol-5-yl]carbonyl}piperidin-3-yl)(1-methyl-1H-imidazol-2-yl)methanone | 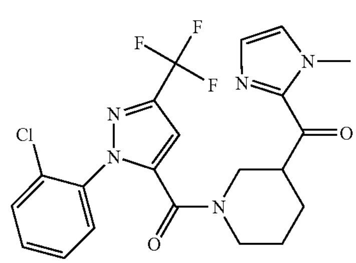 |

TABLE 8-continued

| # | IUPAC Name | Structure |
|---|---|---|
| 770 | 1-(2-chlorophenyl)-N-methyl-N-[(3-methylisoxazol-5-yl)methyl]-3-(trifluoromethyl)-1H-pyrazole-5-carboxamide | 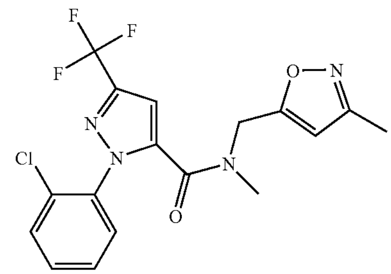 |
| 771 | 1-}[1-(2-chlorophenyl)-3-(trifluoromethyl)-1H-pyrazol-5-yl]carbonyl}-4-(5-nitropyridin-2-yl)-1,4-diazepane | 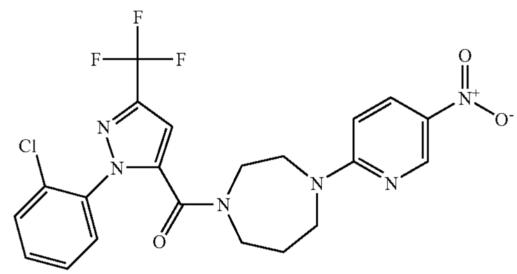 |
| 772 | 1-(2-chlorophenyl)-N-(2-cyanoethyl)-N-(2-pyridin-2-ylethyl)-3-(trifluoromethyl)-1H-pyrazole-5-carboxamide | 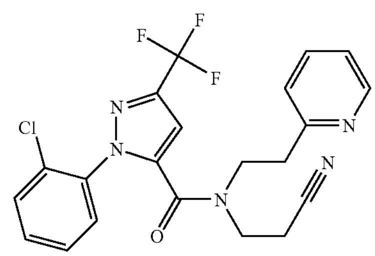 |
| 773 | N-{[1-(2-chlorophenyl)-3-(trifluoromethyl)-1H-pyrazol-5-yl]carbonyl}-N,2-dimethylalanine | 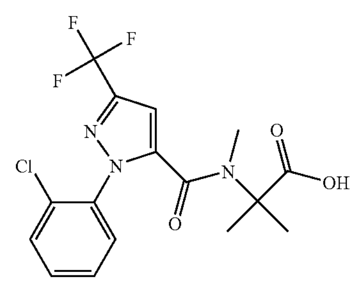 |
| 774 | N-butyl-1-(2-chlorophenyl)-N-(2-thienylmethyl)-3-(trifluoromethyl)-1H-pyrazole-5-carboxamide | 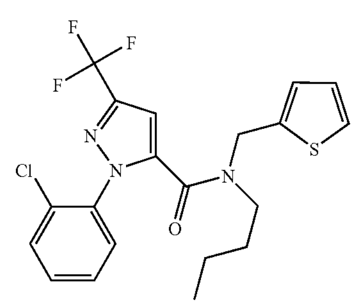 |

TABLE 8-continued

| # | IUPAC Name | Structure |
|---|---|---|
| 775 | 2-(4-{[1-(2-chlorophenyl)-3-(trifluoromethyl)-1H-pyrazol-5-yl]carbonyl}piperazin-1-yl)pyrimidine | 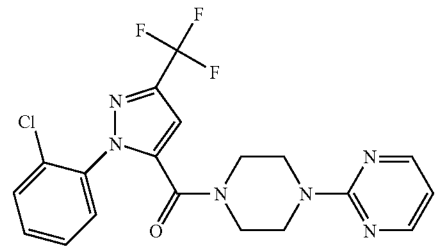 |
| 776 | 1-{[1-(2-chlorophenyl)-3-(trifluoromethyl)-1H-pyrazol-5-yl]carbonyl}-4-(3-furan-2-yl-1H-pyrazol-5-yl)piperidine | 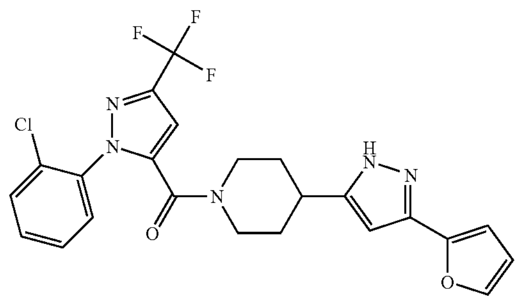 |
| 777 | 1-(2-chlorophenyl)-N-pyridin-2-yl-3-(trifluoromethyl)-1H-pyrazole-5-carboxamide | 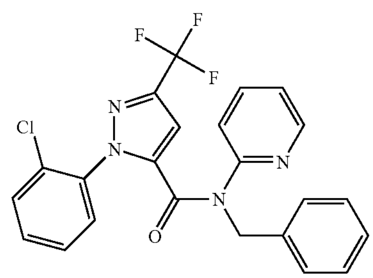 |
| 778 | 1-{[1-(2-chlorophenyl)-3-(trifluoromethyl)-1H-pyrazol-5-yl]carbonyl}-1,2,3,4-tetrahydroquinoline | 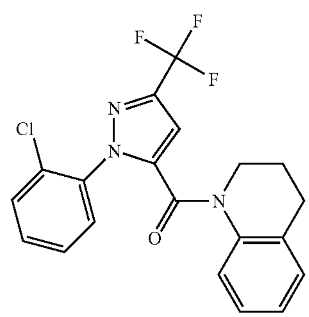 |
| 779 | 1-(2-chlorophenyl)-5-{[2-(3-chlorophenyl)pyrrolidin-1-yl]carbonyl}-3-(trifluoromethyl)-1H-pyrazole | 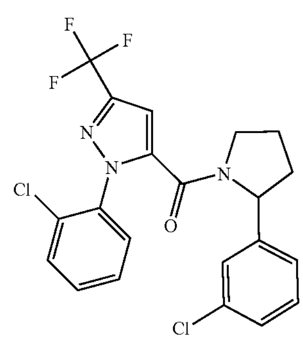 |

TABLE 8-continued

| # | IUPAC Name | Structure |
|---|---|---|
| 780 | 1-(2-chlorophenyl)-5-({2-[4-(ethyloxy)phenyl]pyrrolidin-1-yl}carbonyl)-3-(trifluoromethyl)-1H-pyrazole | 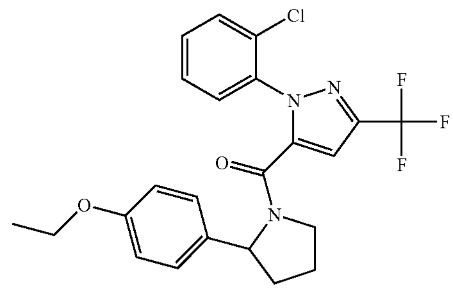 |
| 781 | 1-(2-chlorophenyl)-5-({2-[3-(methyloxy)phenyl]pyrrolidin-1-yl}carbonyl)-3-(trifluoromethyl)-1H-pyrazole | 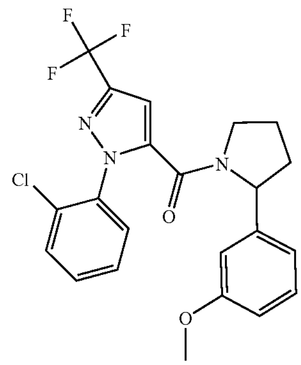 |
| 782 | 1-(2-chlorophenyl)-5-({2-[(3-chlorophenyl)methyl]pyrrolidin-1-yl}carbonyl)-3-(trifluoromethyl)-1H-pyrazole | 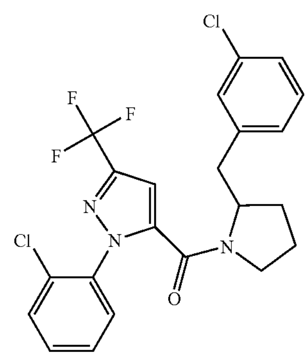 |
| 783 | N-[4-(acetylamino)-3,5-dichlorophenyl]-1-(2-chlorophenyl)-3-(trifluoromethyl)-1H-pyrazole-5-carboxamide | 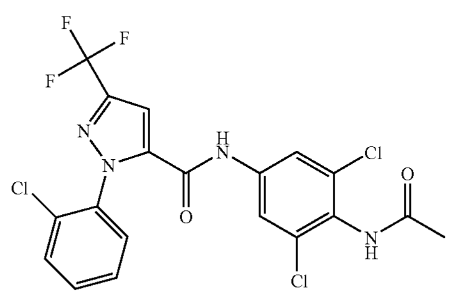 |
| 784 | 1-(2-chlorophenyl)-N-(1-methylethyl)-N-[4-(phenylamino)phenyl]-3-(trifluoromethyl)-1H-pyrazole-5-carboxamide | 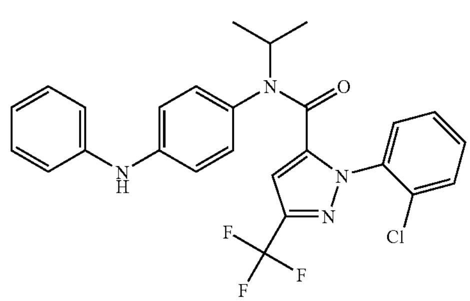 |

TABLE 8-continued

| # | IUPAC Name | Structure |
|---|---|---|
| 785 | 1-(2-chlorophenyl)-5-({2-[2-(methyloxy)phenyl] pyrrolidin-1-yl}carbonyl)-3-(trifluoromethyl)-1H-pyrazole | 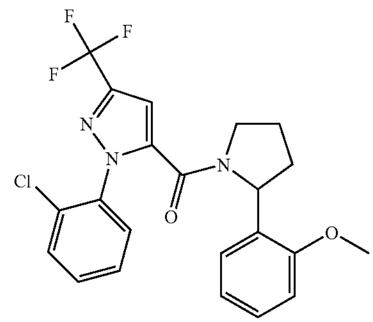 |
| 786 | 1-{[1-(2-chlorophenyl)-3-(trifluoromethyl)-1H-pyrazol-5-yl]carbonyl}-4-[2-(phenylsulfonyl)ethyl]piperazine | 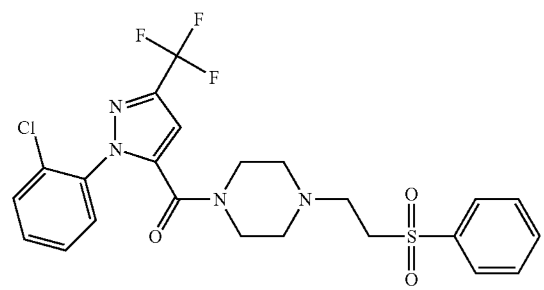 |
| 787 | 2-(4-{[1-(2-chlorophenyl)-3-(trifluoromethyl)-1H-pyrazol-5-yl]carbonyl}piperazin-1-yl)pyrazine | 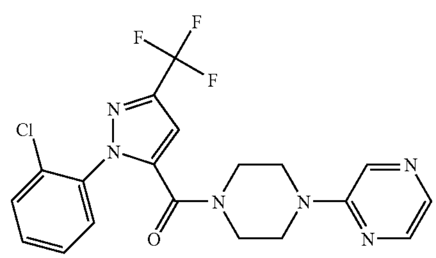 |
| 788 | 1-(2-chlorophenyl)-N-[2-fluoro-5-(methylsulfonyl)phenyl]-3-(trifluoromethyl)-1H-pyrazole-5-carboxamide | 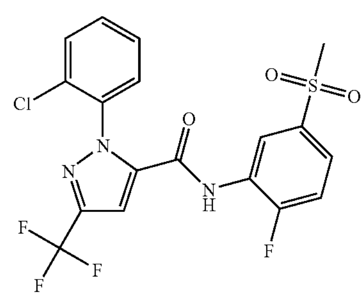 |

TABLE 9

| # | IUPAC Name | Structure |
|---|---|---|
| 789 | 4'-((1-(2,6-dichlorophenyl)-3-(trifluoromethyl)-1H-pyrazol-5-yl)methoxy)biphenyl-2-ol | 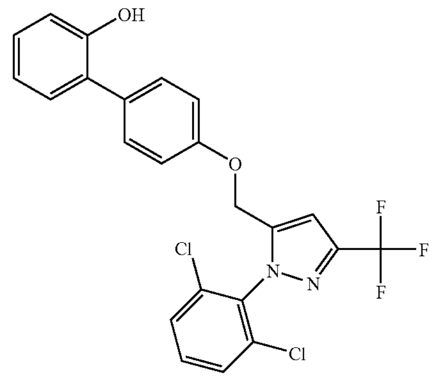 |
| 790 | (3-chloro-4'-((1-(2,6-dichlorophenyl)-3-(trifluoromethyl)-1H-pyrazol-5-yl)methoxy)biphenyl-4-yl)(morpholino)methanone | 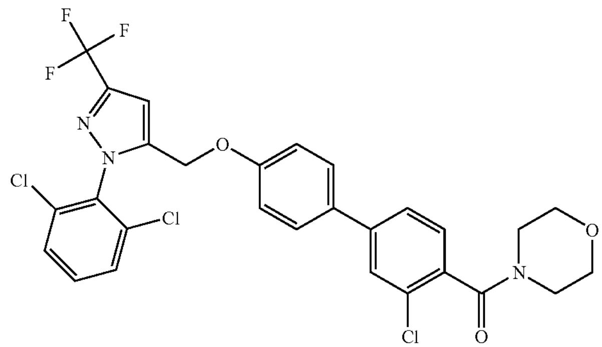 |
| 791 | 2-chloro-4'-((1-(2,6-dichlorophenyl)-3-(trifluoromethyl)-1H-pyrazol-5-yl)methoxy)biphenyl-4-carboxylic acid | 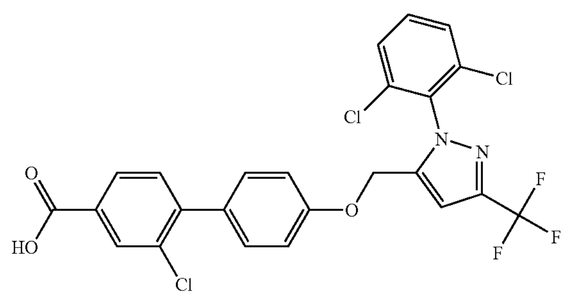 |
| 792 | 3-chloro-4'-((1-(2,6-dichlorophenyl)-3-(trifluoromethyl)-1H-pyrazol-5-yl)methoxy)-N-ethylbiphenyl-4-carboxamide | 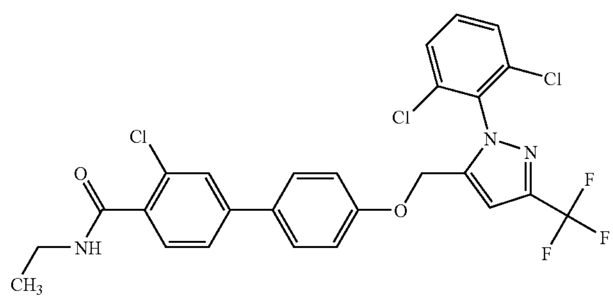 |
| 793 | (4'-((1-(2,6-dichlorophenyl)-3-(trifluoromethyl)-1H-pyrazol-5-yl)methoxy)biphenyl-4-yl)(morpholino)methanone | 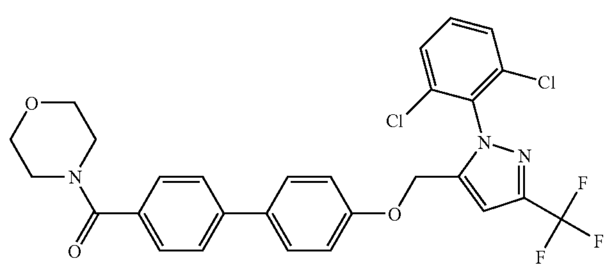 |

TABLE 9-continued

| # | IUPAC Name | Structure |
|---|---|---|
| 794 | 4'-((1-(2,6-dichlorophenyl)-3-(trifluoromethyl)-1H-pyrazol-5-yl)methoxy)-N,N-dimethylbiphenyl-4-carboxamide | 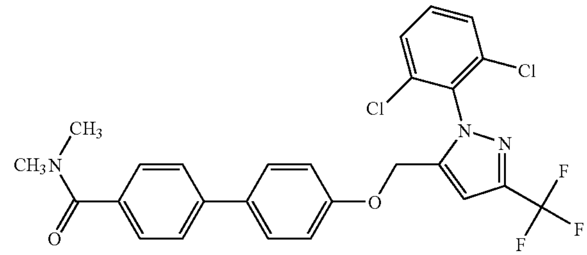 |
| 795 | 1-(2,6-dichlorophenyl)-5-((4'-methoxy-3'-methylbiphenyl-4-yloxy)methyl)-3-(trifluoromethyl)-1H-pyrazole | 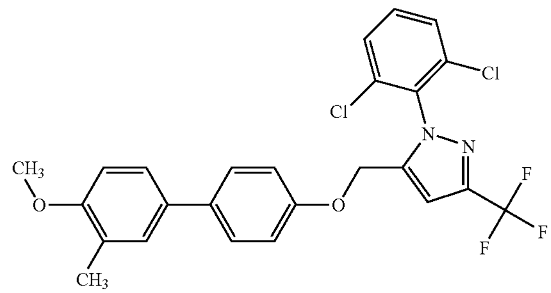 |
| 796 | N-(4'-((1-(2,6-dichlorophenyl)-3-(trifluoromethyl)-1H-pyrazol-5-yl)methoxy)biphenyl-4-yl)methanesulfonamide | 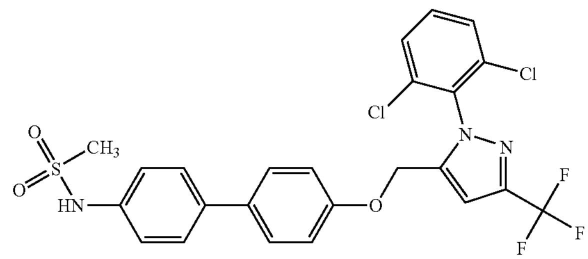 |
| 797 | N-cyclopropyl-4'-((1-(2,6-dichlorophenyl)-3-(trifluoromethyl)-1H-pyrazol-5-yl)methoxy)biphenyl-4-carboxamide | 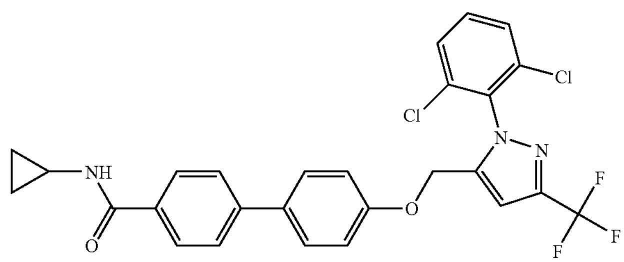 |
| 798 | 4'-((1-(2,6-dichlorophenyl)-3-(trifluoromethyl)-1H-pyrazol-5-yl)methoxy)-N-(furan-2-ylmethyl)biphenyl-4-carboxamide | 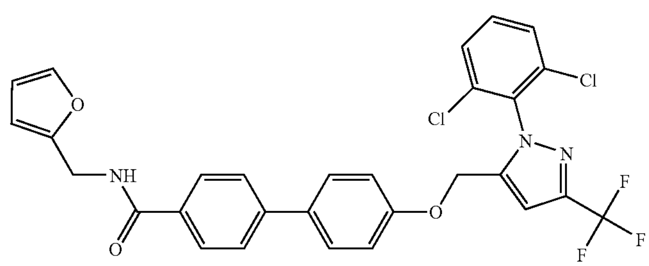 |
| 799 | 1-(2,6-dichlorophenyl)-5-((4'-(methylsulfonyl)biphenyl-4-yloxy)methyl)-3-(trifluoromethyl)-1H-pyrazole | 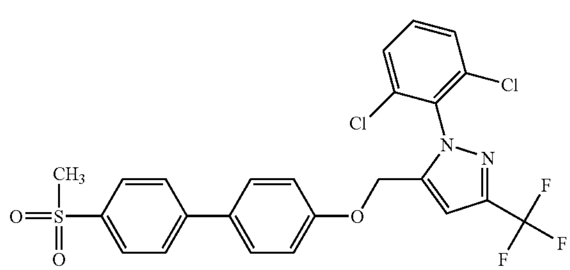 |

TABLE 9-continued

| # | IUPAC Name | Structure |
|---|---|---|
| 800 | 5-((4-(benzo[d][1,3]dioxol-5-yl)phenoxy)methyl)-1-(2,6-dichlorophenyl)-3-(trifluoromethyl)-1H-pyrazole | 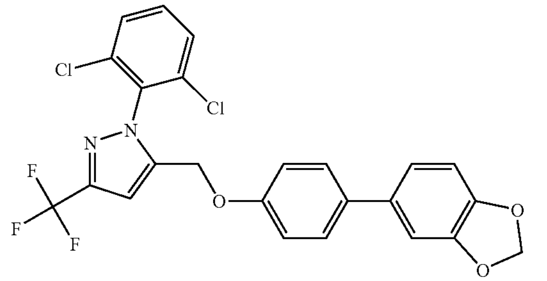 |
| 801 | 1-(2,6-dichlorophenyl)-5-((3'-(ethylthio)biphenyl-4-yloxy)methyl)-3-(trifluoromethyl)-1H-pyrazole | 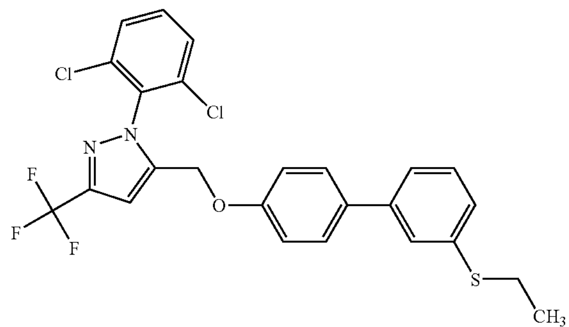 |
| 802 | (4'-((1-(2,6-dichlorophenyl)-3-(trifluoromethyl)-1H-pyrazol-5-yl)methoxy)biphenyl-4-yl)methanol | 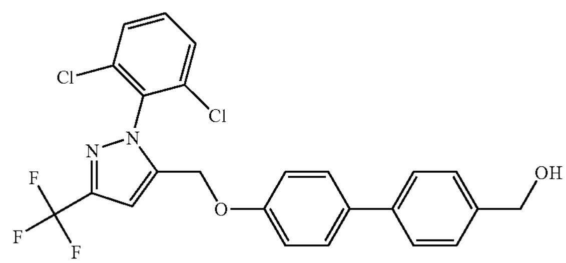 |
| 803 | 1-(4'-((1-(2,6-dichlorophenyl)-3-(trifluoromethyl)-1H-pyrazol-5-yl)methoxy)biphenylcarbonyl)piperidin-4-one | 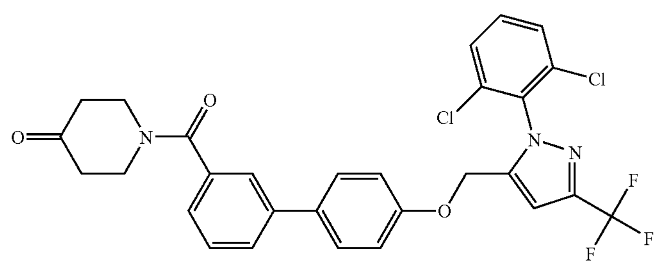 |
| 804 | 1-(2,6-dichlorophenyl)-5-((3',4'-difluorobiphenyl-4-yloxy)methyl)-3-(trifluoromethyl)-1H-pyrazole | 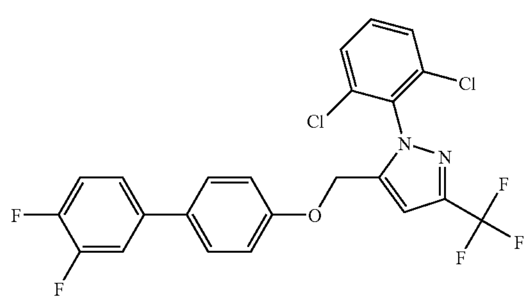 |

TABLE 9-continued

| # | IUPAC Name |
|---|---|
| 805 | 4'-((1-(2,6-dichlorophenyl)-3-(trifluoromethyl)-1H-pyrazol-5-yl)methoxy)-N-methylbiphenyl-4-carboxamide |
| 806 | 1-(4'-((1-(2,6-dichlorophenyl)-3-(trifluoromethyl)-1H-pyrazol-5-yl)methoxy)biphenyl-4-yl)ethanone |
| 807 | N-(4'-((1-(2,6-dichlorophenyl)-3-(trifluoromethyl)-1H-pyrazol-5-yl)methoxy)biphenyl-4-yl)acetamide |
| 808 | N-(4'-((1-(2,6-dichlorophenyl)-3-(trifluoromethyl)-1H-pyrazol-5-yl)methoxy)biphenyl-3-yl)acetamide |
| 809 | 1-(2,6-dichlorophenyl)-5-((2',3',4'-trifluorobiphenyl-4-yloxy)methyl)-3-(trifluoromethyl)-1H-pyrazole |

TABLE 9-continued

| # | IUPAC Name |
|---|---|
| 810 | 4-chloro-4'-((1-(2,6-dichlorophenyl)-3-(trifluoromethyl)-1H-pyrazol-5-yl)methoxy)-N-ethylbiphenyl-3-carboxamide |
| 811 | 4'-((1-(2,6-dichlorophenyl)-3-(trifluoromethyl)-1H-pyrazol-5-yl)methoxy)biphenyl-4-yl acetate |
| 812 | 4'-((1-(2,6-dichlorophenyl)-3-(trifluoromethyl)-1H-pyrazol-5-yl)methoxy)biphenyl-3-carboxylic acid |
| 813 | methyl 4'-((1-(2,6-dichlorophenyl)-3-(trifluoromethyl)-1H-pyrazol-5-yl)methoxy)biphenyl-4-ylcarbamate |
| 814 | 5-((3'-chloro-4'-(trifluoromethyl)biphenyl-4-yloxy)methyl)-1-(2,6-dichlorophenyl)-3-(trifluoromethyl)-1H-pyrazole |

TABLE 9-continued

| # | IUPAC Name | Structure |
|---|---|---|
| 815 | 4'-((1-(2,6-dichlorophenyl)-3-(trifluoromethyl)-1H-pyrazol-5-yl)methoxy)-N-isopropylbiphenyl-4-carboxamide | 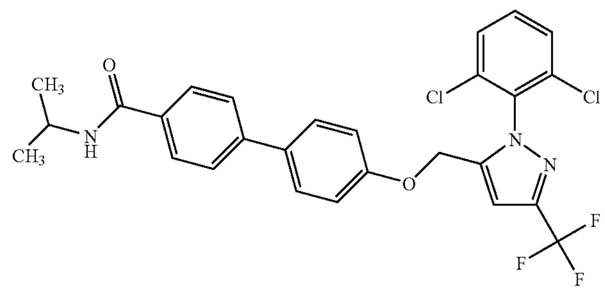 |
| 816 | tert-butyl 4'-((1-(2,6-dichlorophenyl)-3-(trifluoromethyl)-1H-pyrazol-5-yl)methoxy)biphenyl-2-ylcarbamate | 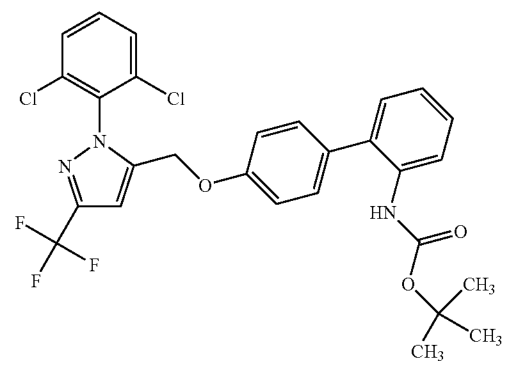 |
| 817 | 3-chloro-4'-((1-(2,6-dichlorophenyl)-3-(trifluoromethyl)-1H-pyrazol-5-yl)methoxy)-N-methylbiphenyl-4-carboxamide | 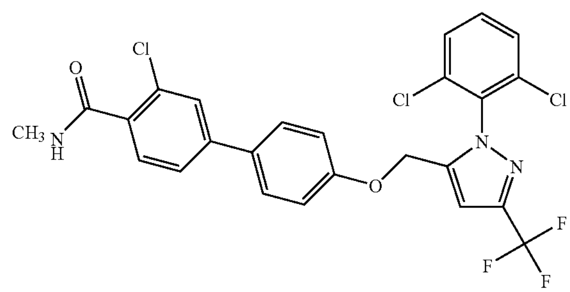 |
| 818 | 4-chloro-4'-((1-(2,6-dichlorophenyl)-3-(trifluoromethyl)-1H-pyrazol-5-yl)methoxy)biphenyl-3-carboxamide | 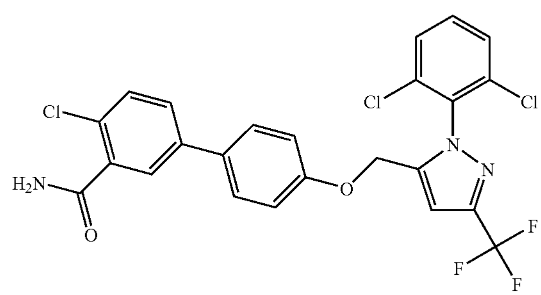 |
| 819 | 4'-((1-(2,6-dichlorophenyl)-3-(trifluoromethyl)-1H-pyrazol-5-yl)methoxy)biphenyl-4-amine | 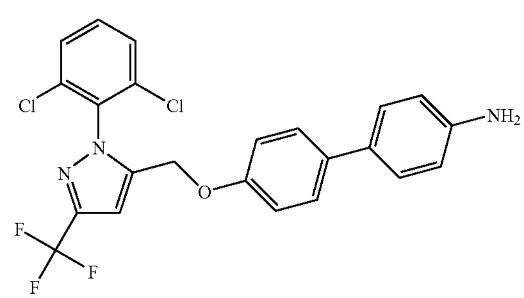 |

TABLE 9-continued

| # | IUPAC Name | Structure |
|---|---|---|
| 820 | 4'-((1-(2,6-dichlorophenyl)-3-(trifluoromethyl)-1H-pyrazol-5-yl)methoxy)-N,N-diethylbiphenyl-3-carboxamide | 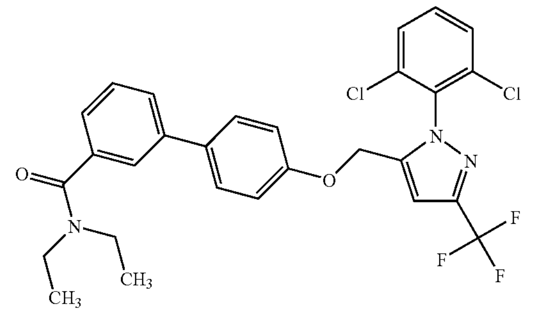 |
| 821 | (4'-((1-(2,6-dichlorophenyl)-3-(trifluoromethyl)-1H-pyrazol-5-yl)methoxy)biphenyl-2-yl)methanol | 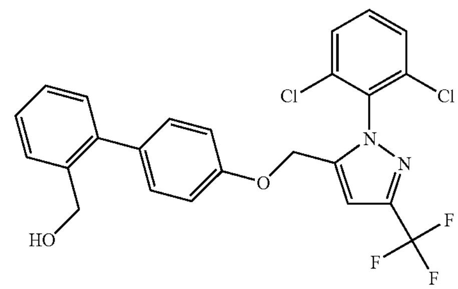 |
| 822 | 1-(2,6-dichlorophenyl)-5-((4'-(trifluoromethoxy)biphenyl-4-yloxy)methyl)-3-(trifluoromethyl)-1H-pyrazole | 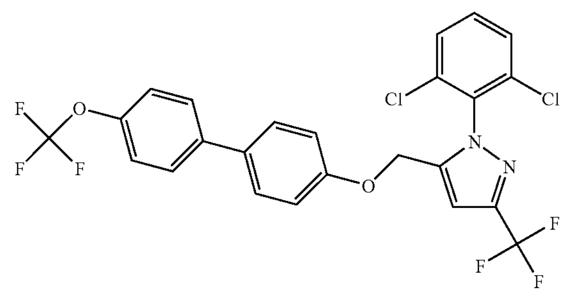 |
| 823 | 1-(2,6-dichlorophenyl)-5-((4'-ethoxybiphenyl-4-yloxy)methyl)-3-(trifluoromethyl)-1H-pyrazole | 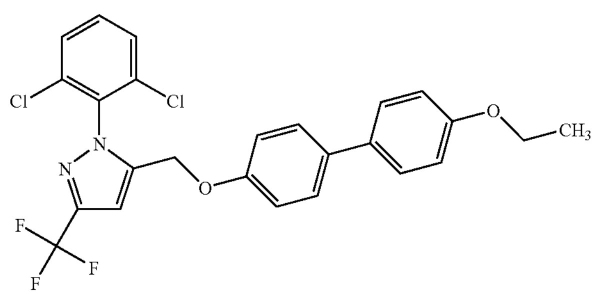 |
| 824 | 4'-((1-(2,6-dichlorophenyl)-3-(trifluoromethyl)-1H-pyrazol-5-yl)methoxy)-3-fluorobiphenyl-4-carboxylic acid | 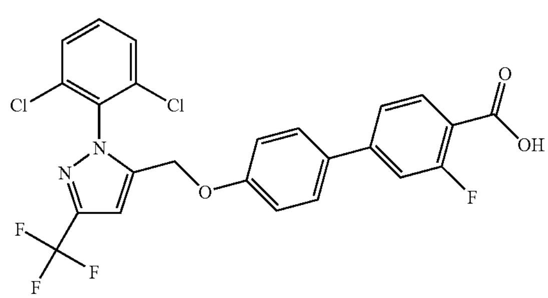 |

TABLE 9-continued

| # | IUPAC Name | Structure |
|---|---|---|
| 825 | ethyl 4'-((1-(2,6-dichlorophenyl)-3-(trifluoromethyl)-1H-pyrazol-5-yl)methoxy)biphenyl-2-carboxylate | 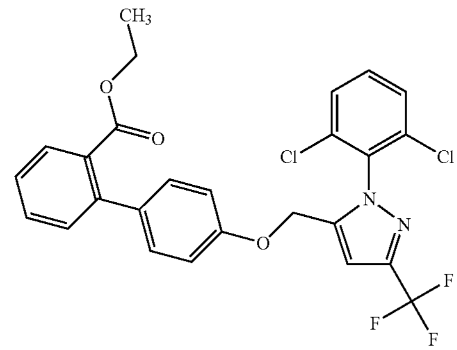 |
| 826 | 4'-((1-(2,6-dichlorophenyl)-3-(trifluoromethyl)-1H-pyrazol-5-yl)methoxy)-N-ethylbiphenyl-3-carboxamide | 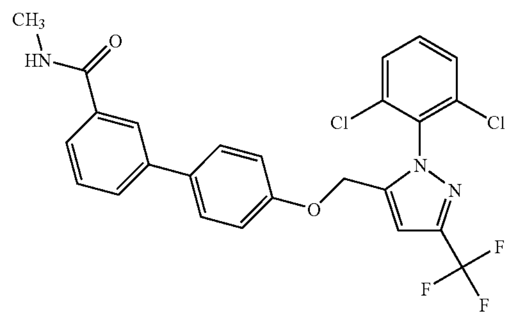 |
| 827 | 1-(2,6-dichlorophenyl)-5-((4'-methoxybiphenyl-4-yloxy)methyl)-3-(trifluoromethyl)-1H-pyrazole | 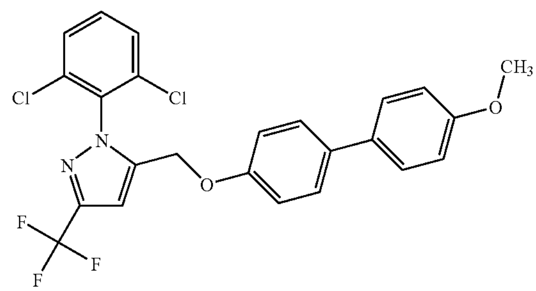 |
| 828 | 1-(2,6-dichlorophenyl)-5-((4-(2,3-dihydrobenzo[b][1,4]dioxin-6-yl)phenoxy)methyl)-3-(trifluoromethyl)-1H-pyrazole | 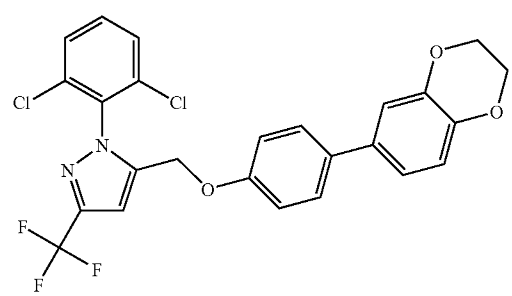 |
| 829 | 4'-((1-(2,6-dichlorophenyl)-3-(trifluoromethyl)-1H-pyrazol-5-yl)methoxy)-5-fluorobiphenyl-3-carboxylic acid | 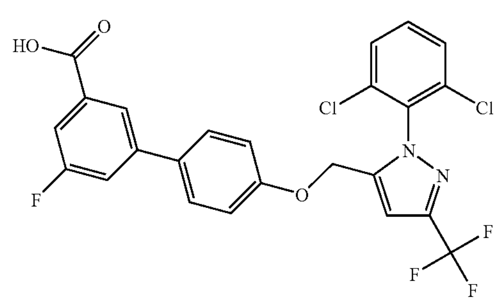 |

TABLE 9-continued

| # | IUPAC Name | Structure |
|---|---|---|
| 830 | 1-(4'-((1-(2,6-dichlorophenyl)-3-(trifluoromethyl)-1H-pyrazol-5-yl)methoxy)biphenyl-4-yl)-N,N,N-trimethylmethanaminium | 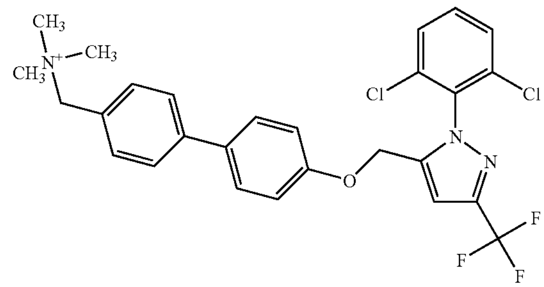 |
| 831 | 1-(4'-((1-(2,6-dichlorophenyl)-3-(trifluoromethyl)-1H-pyrazol-5-yl)methoxy)biphenylcarbonyl)piperidine-4-carboxylic acid | 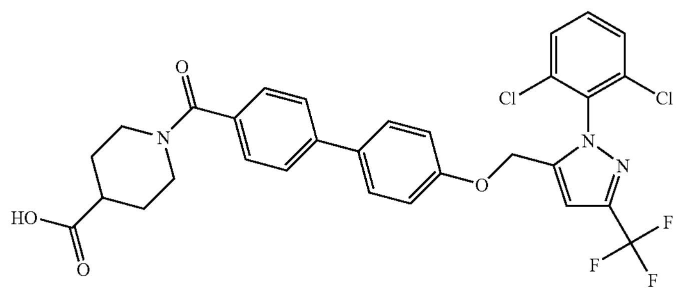 |
| 832 | 1-(2,6-dichlorophenyl)-5-((4'-methoxy-2'-methylbiphenyl-4-yloxy)methyl)-3-(trifluoromethyl)-1H-pyrazole | 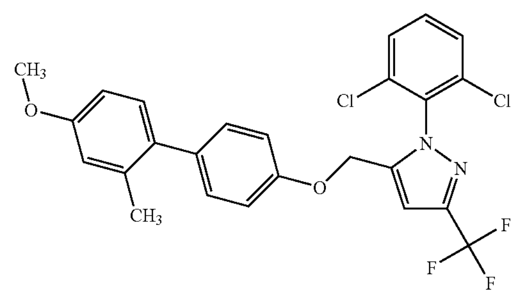 |
| 833 | 5-((2'-chlorobiphenyl-4-yloxy)methyl)-1-(2,6-dichlorophenyl)-3-(trifluoromethyl)-1H-pyrazole | 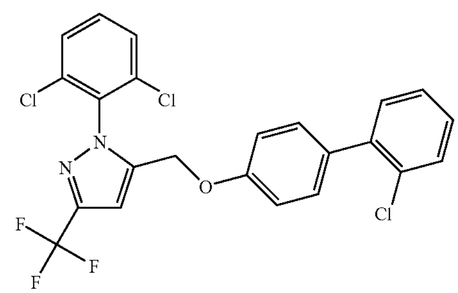 |
| 834 | tert-butyl 4'-((1-(2,6-dichlorophenyl)-3-(trifluoromethyl)-1H-pyrazol-5-yl)methoxy)biphenyl-4-ylcarbamate | 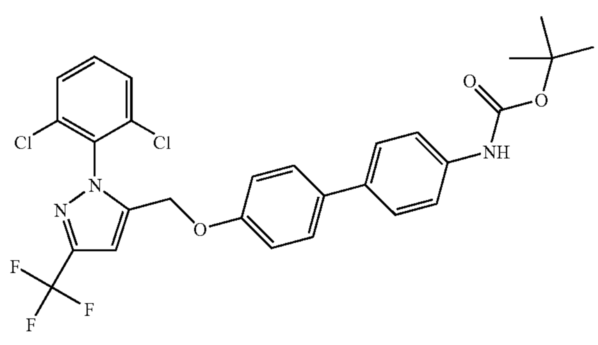 |

TABLE 9-continued

| # | IUPAC Name | Structure |
|---|---|---|
| 835 | 4'-((1-(26-dichloronhenx~D-3-(trifluoromethyl)-1H-pyrazol-5-yl)methoxy)biphenyl-4-ol | 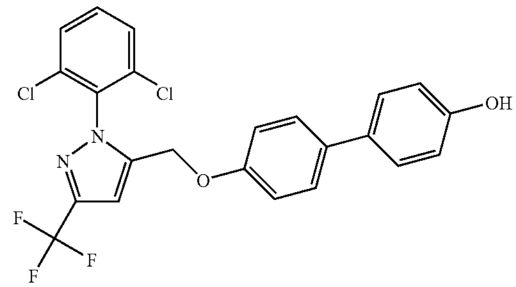 |
| 836 | 5-((4'-tert-butyl-3'-nitrobiphenyl-4-yloxy)methyl)-1-(2,6-dichlorophenyl)-3-(trifluoromethyl)-1H-pyrazole | 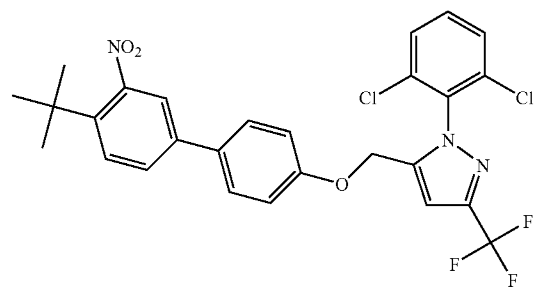 |
| 837 | N-(4'-((1-(2,6-dichlorophenyl)-3-(trifluoromethyl)-1H-pyrazol-5-yl)methoxy)biphenyl-2-yl)acetamide | 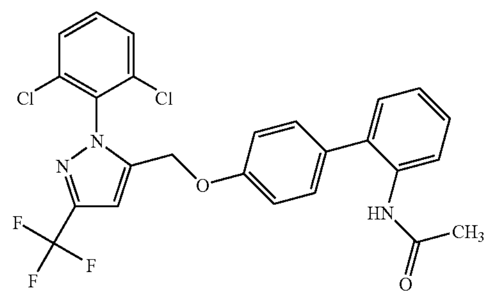 |
| 838 | 5-((2'-(benzyloxy)-4'-fluorobiphenyl-4-yloxy)methyl)-1-(2,6-dichlorophenyl)-3-(trifluoromethyl)-1H-pyrazole | 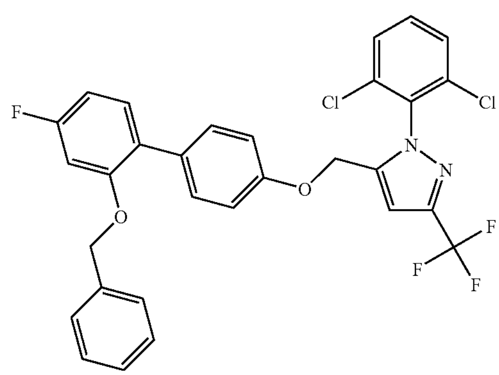 |
| 839 | 1-(2,6-dichlorophenyl)-5-((2'-(methylsulfonyl)biphenyl-4-yloxy)methyl)-3-(trifluoromethyl)-1H-pyrazole | 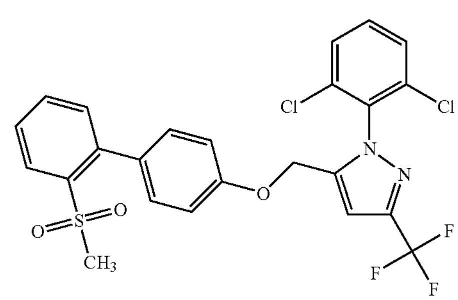 |

TABLE 9-continued

| # | IUPAC Name | Structure |
|---|---|---|
| 840 | methyl 4'-((1-(2,6-dichlorophenyl)-3-(trifluoromethyl)-1H-pyrazol-5-yl)methoxy)biphenyl-3-carboxylate | 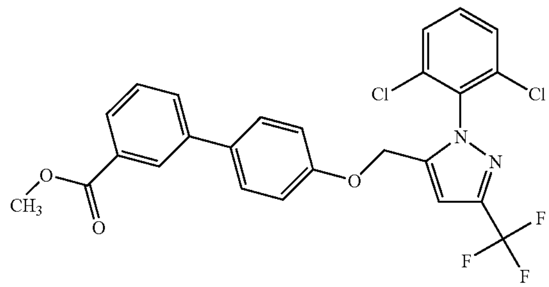 |
| 841 | (4-chloro-4'-((1-(2,6-dichlorophenyl)-3-(trifluoromethyl)-1H-pyrazol-5-yl)methoxy)biphenyl-3-yl)(pyrrolidin-1-yl)methanone | 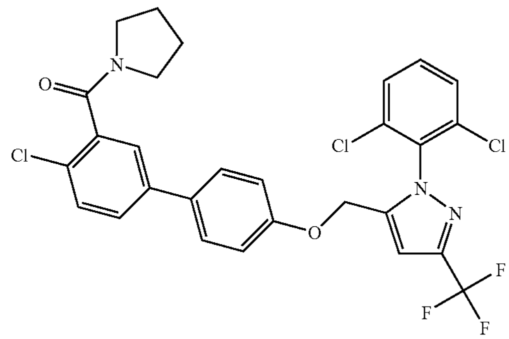 |
| 842 | 1-(2,6-dichlorophenyl)-5-((3',4'-dimethoxybiphenyl-4-yloxy)methyl)-3-(trifluoromethyl)-1H-pyrazole | 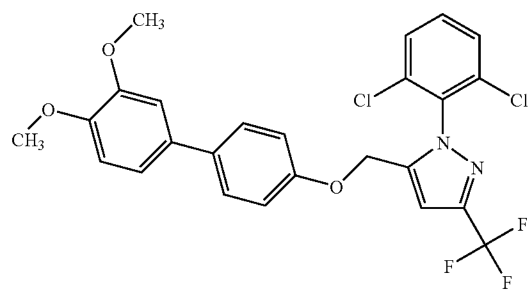 |
| 843 | 1-(2,6-dichlorophenyl)-5-((4'-fluoro-2'-methylbiphenyl-4-yloxy)methyl)-3-(trifluoromethyl)-1H-pyrazole | 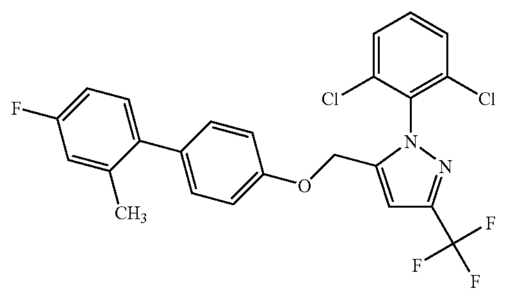 |
| 844 | 1-(2,6-dichlorophenyl)-3-(trifluoromethyl)-5-((2'-(trifluoromethyl)biphenyl-4-yloxy)methyl)-1H-pyrazole | 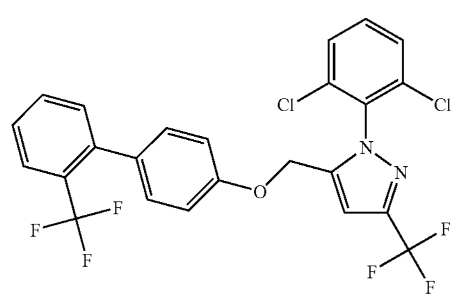 |

TABLE 9-continued

| # | IUPAC Name |
|---|---|
| 845 | 4'-((1-(2,6-dichlorophenyl)-3-(trifluoromethyl)-1H-pyrazol-5-yl)methoxy)-N-isopropylbiphenyl-3-carboxamide |
| 846 | 5-((3'-chloro-4'-methoxybiphenyl-4-yloxy)methyl)-1-(2,6-dichlorophenyl)-3-(trifluoromethyl)-1H-pyrazole |
| 847 | 5-((2'-chloro-6'-methoxybiphenyl-4-yloxy)methyl)-1-(2,6-dichlorophenyl)-3-(trifluoromethyl)-1H-pyrazole |
| 848 | 3-chloro-N-cyclopropyl-4'-((1-(2,6-dichlorophenyl)-3-(trifluoromethyl)-1H-pyrazol-5-yl)methoxy)biphenyl-4-carboxamide |
| 849 | 1-(2,6-dichlorophenyl)-5-((2'-phenoxybiphenyl-4-yloxy)methyl)-3-(trifluoromethyl)-1H-pyrazole |

TABLE 9-continued

| # | IUPAC Name | Structure |
|---|---|---|
| 850 | 1-(2,6-dichlorophenyl)-5-((3'-methylbiphenyl-4-yloxy)methyl)-3-(trifluoromethyl)-1H-pyrazole | 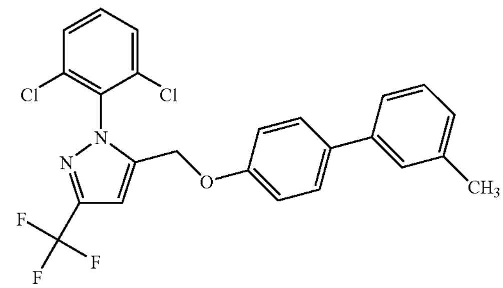 |
| 851 | 5-((4'-chlorobiphenyl-4-yloxy)methyl)-1-(2,6-dichlorophenyl)-3-(trifluoromethyl)-1H-pyrazole | 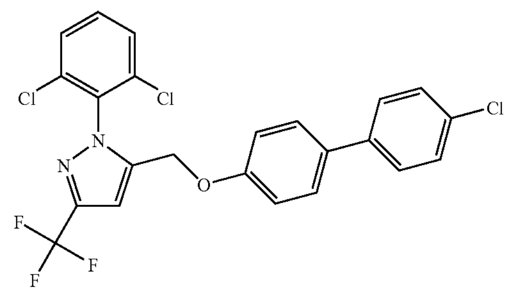 |
| 852 | 1-(4'-((1-(2,6-dichlorophenyl)-3-(trifluoromethyl)-1H-pyrazol-5-yl)methoxy)biphenyl-3-yl)ethanone | 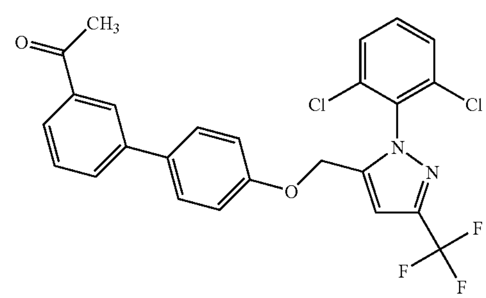 |
| 853 | 1-(2,6-dichlorophenyl)-5-((4'-fluoro-2'-methoxybiphenyl-4-yloxy)methyl)-3-(trifluoromethyl)-1H-pyrazole | 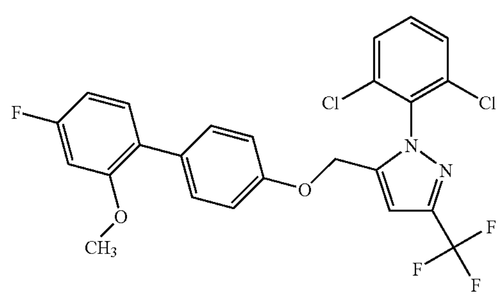 |
| 854 | ({[(4'-{[1-(2,6-dichlorophenyl)-3-(trifluoromethyl)-1H-pyrazol-5-yl]methoxy}biphenyl-4-yl)carbonyl]amino}methyl)boronic acid | 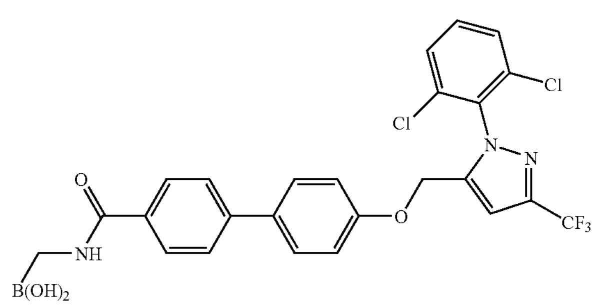 |

TABLE 9-continued

| # | IUPAC Name | Structure |
|---|---|---|
| 855 | 1-(2,6-dichlorophenyl)-5-((4'-propylbiphenyl-4-yloxy)methyl)-3-(trifluoromethyl)-1H-pyrazole | 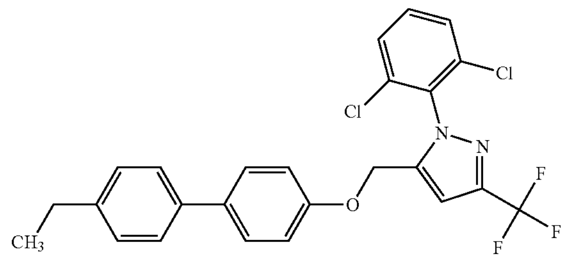 |
| 856 | 5-((2'-chloro-6'-fluorobiphenyl-4-yloxy)methyl)-1-(2,6-dichlorophenyl)-3-(trifluoromethyl)-1H-pyrazole | 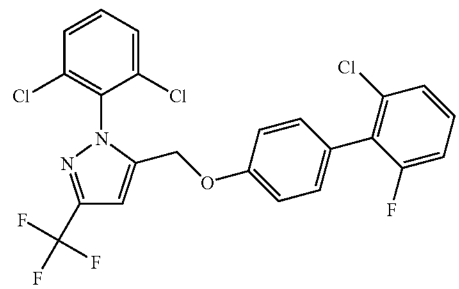 |
| 857 | 5-((2',4'-bis(trifluoromethyl)biphenyl-4-yloxy)methyl)-1-(2,6-dichlorophenyl)-3-(trifluoromethyl)-1H-pyrazole | 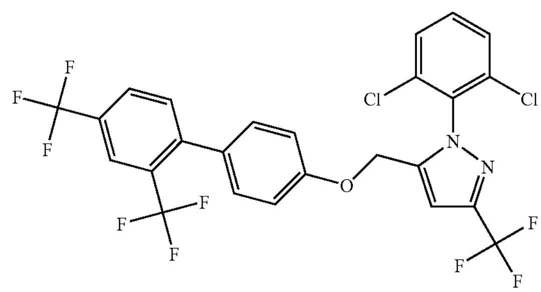 |
| 858 | 1-(2,6-dichlorophenyl)-5-((4'-fluorobiphenyl-4-yloxy)methyl)-3-(trifluoromethyl)-1H-pyrazole | 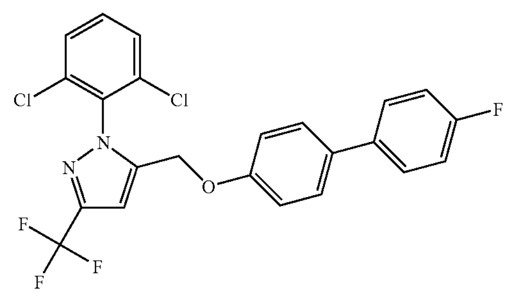 |
| 859 | 1-(2,6-dichlorophenyl)-5-((4'-phenoxybiphenyl-4-yloxy)methyl)-3-(trifluoromethyl)-1H-pyrazole | 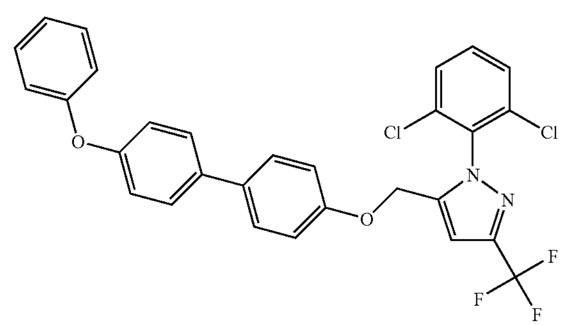 |

TABLE 9-continued

| # | IUPAC Name | Structure |
|---|---|---|
| 860 | 1-(2,6-dichlorophenyl)-5-((2',5'-difluorobiphenyl-4-yloxy)methyl)-3-(trifluoromethyl)-1H-pyrazole | 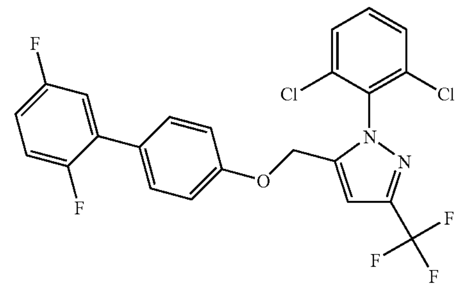 |
| 861 | 4'-((1-(2,6-dichlorophenyl)-3-(trifluoromethyl)-1H-pyrazol-5-yl)methoxy)biphenyl-4-carbonitrile | 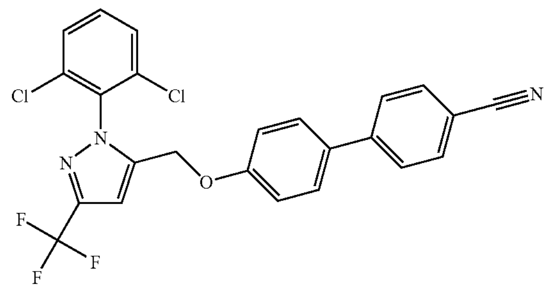 |
| 862 | 1-(2,6-dichlorophenyl)-5-((2',5'-dimethylbiphenyl-4-yloxy)methyl)-3-(trifluoromethyl)-1H-pyrazole | 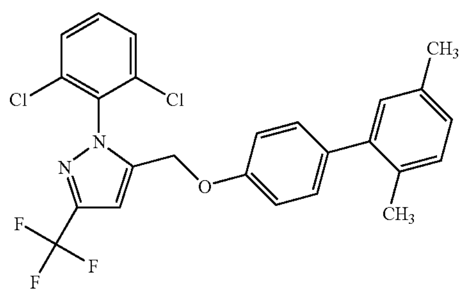 |
| 863 | 4'-((1-(2,6-dichlorophenyl)-3-(trifluoromethyl)-1H-pyrazol-5-yl)methoxy)-N-methylbiphenyl-3-sulfonamide | 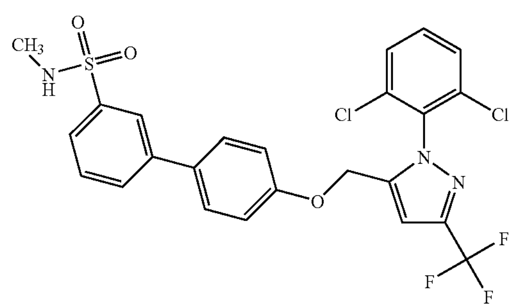 |
| 864 | 1-(2,6-dichlorophenyl)-5-((3'-methoxybiphenyl-4-yloxy)methyl)-3-(trifluoromethyl)-1H-pyrazole | 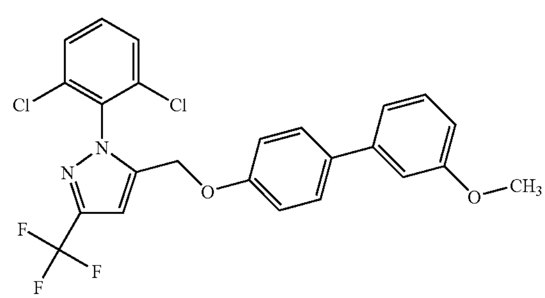 |

TABLE 9-continued

| # | IUPAC Name | Structure |
|---|---|---|
| 865 | 1-(2,6-dichlorophenyl)-5-((3'-fluorobiphenyl-4-yloxy)methyl)-3-(trifluoromethyl)-1H-pyrazole | 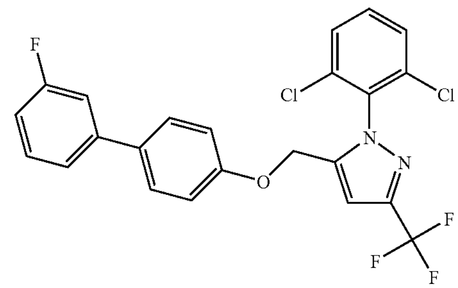 |
| 866 | 1-(2,6-dichlorophenyl)-5-((2'-(methylthio)biphenyl-4-yloxy)methyl)-3-(trifluoromethyl)-1H-pyrazole | 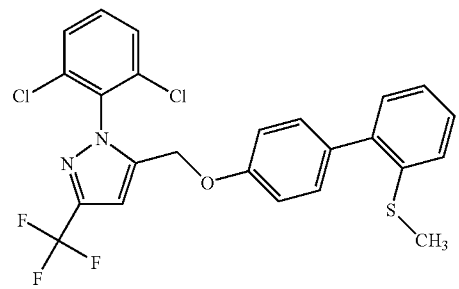 |
| 867 | 1-(2,6-dichlorophenyl)-5-((2'-ethylbiphenyl-4-yloxy)methyl)-3-(trifluoromethyl)-1H-pyrazole | 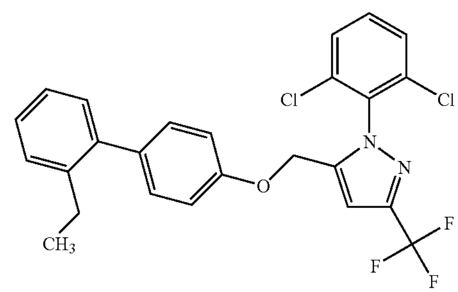 |
| 868 | 1-(2,6-dichlorophenyl)-5-((2'-isopropylbiphenyl-4-yloxy)methyl)-3-(trifluoromethyl)-1H-pyrazole | 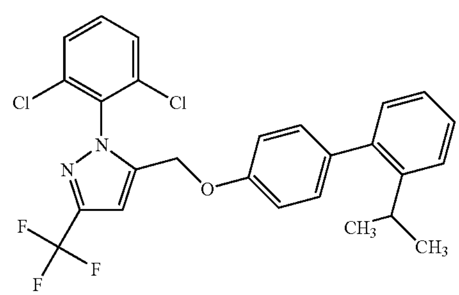 |
| 869 | 1-(2,6-dichlorophenyl)-5-((2',6'-dimethylbiphenyl-4-yloxy)methyl)-3-(trifluoromethyl)-1H-pyrazole | 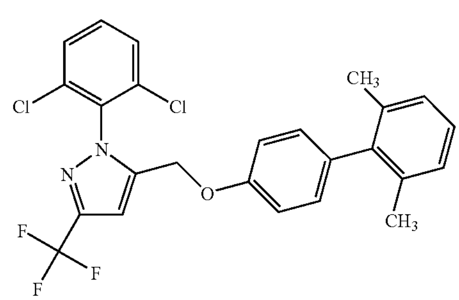 |

TABLE 9-continued

| # | IUPAC Name | Structure |
|---|---|---|
| 870 | 1-(2,6-dichlorophenyl)-5-((2',5'-dimethoxybiphenyl-4-yloxy)methyl)-3-(trifluoromethyl)-1H-pyrazole | 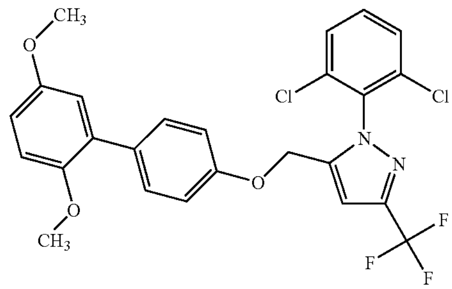 |
| 871 | 1-(2,6-dichlorophenyl)-5-((3'-fluoro-4'-methoxybiphenyl-4-yloxy)methyl)-3-(trifluoromethyl)-1H-pyrazole | 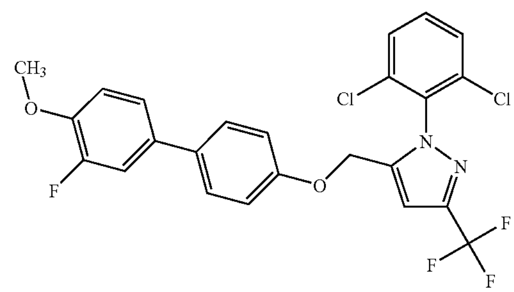 |
| 872 | 1-(2,6-dichlorophenyl)-5-((4'-fluoro-3'-methylbiphenyl-4-yloxy)methyl)-3-(trifluoromethyl)-1H-pyrazole | 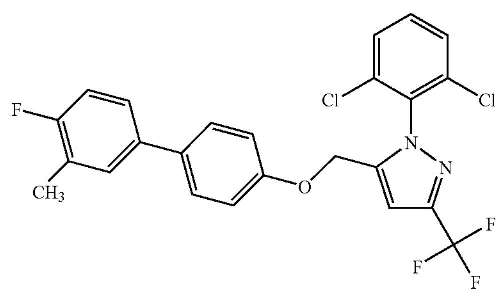 |
| 873 | 1-(2,6-dichlorophenyl)-5-((4'-methylbiphenyl-4-yloxy)methyl)-3-(trifluoromethyl)-1H-pyrazole | 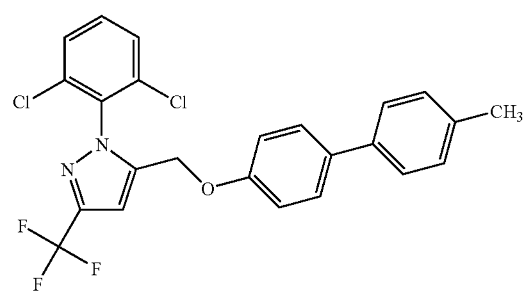 |
| 874 | 1-(2,6-dichlorophenyl)-5-((2'-ethoxybiphenyl-4-yloxy)methyl)-3-(trifluoromethyl)-1H-pyrazole | 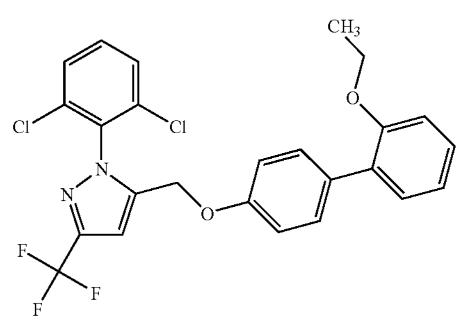 |

TABLE 9-continued

| # | IUPAC Name | Structure |
|---|---|---|
| 875 | 1-(2,6-dichlorophenyl)-5-((3',5'-difluorobiphenyl-4-yloxy)methyl)-3-(trifluoromethyl)-1H-pyrazole | 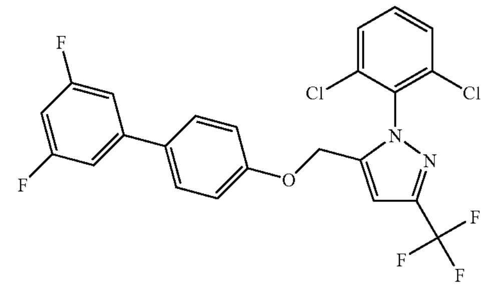 |
| 876 | 3-chloro-4'-((1-(2,6-dichlorophenyl)-3-(trifluoromethyl)-1H-pyrazol-5-yl)methoxy)-N-isopropylbiphenyl-4-carboxamide | 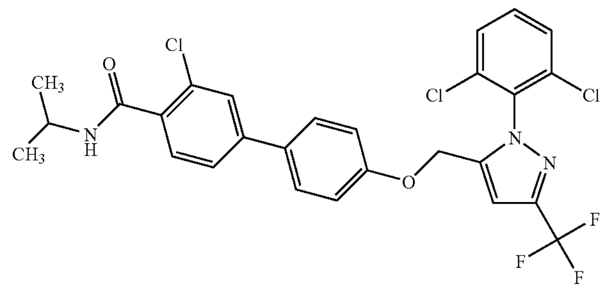 |
| 877 | 1-(2,6-dichlorophenyl)-5-((2',3'-dimethylbiphenyl-4-yloxy)methyl)-3-(trifluoromethyl)-1H-pyrazole | 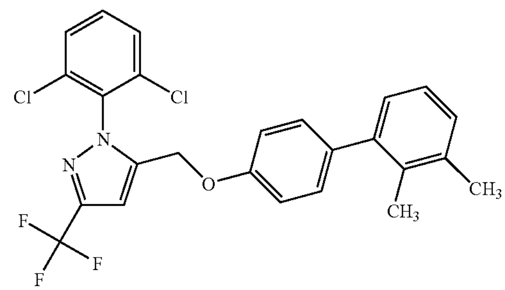 |
| 878 | 1-(2,6-dichlorophenyl)-5-((2',6'-dimethoxybiphenyl-4-yloxy)methyl)-3-(trifluoromethyl)-1H-pyrazole | 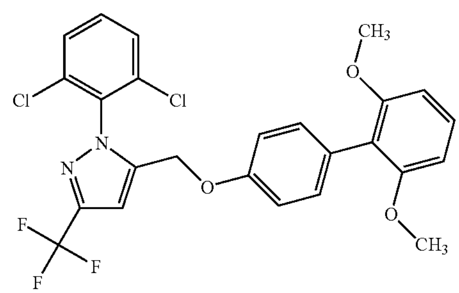 |
| 879 | 5-((3'-chlorobiphenyl-4-yloxy)methyl)-1-(2,6-dichlorophenyl)-3-(trifluoromethyl)-1H-pyrazole | 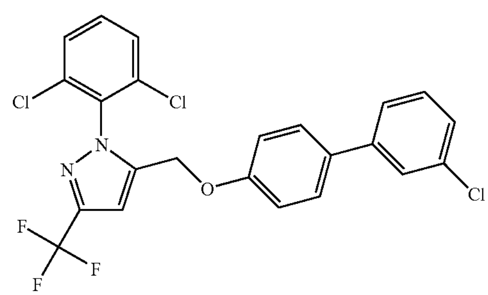 |

TABLE 9-continued

| # | IUPAC Name | Structure |
|---|---|---|
| 880 | methyl 2-(4'-((1-(2,6-dichlorophenyl)-3-(trifluoromethyl)-1H-pyrazol-5-yl)methoxy)biphenyl-3-yl)acetate | 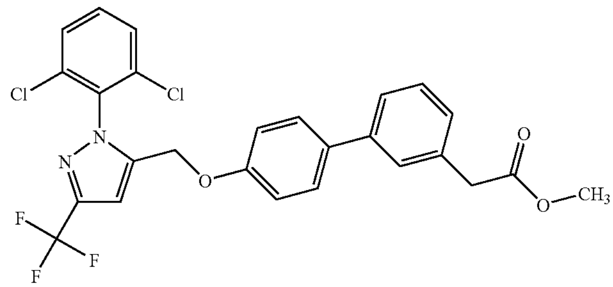 |
| 881 | 1-(2,6-dichlorophenyl)-5-((2',4'-difluorobiphenyl-4-yloxy)methyl)-3-(trifluoromethyl)-1H-pyrazole | 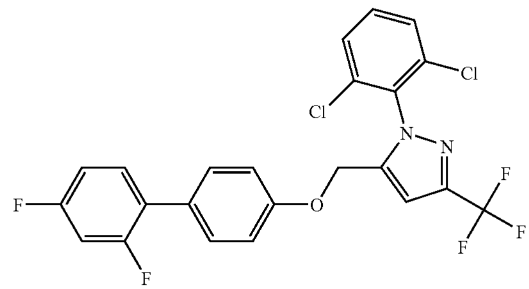 |
| 882 | 1-(2,6-dichlorophenyl)-5-((3',5'-difluoro-2'-methoxybiphenyl-4-yloxy)methyl)-3-(trifluoromethyl)-1H-pyrazole | 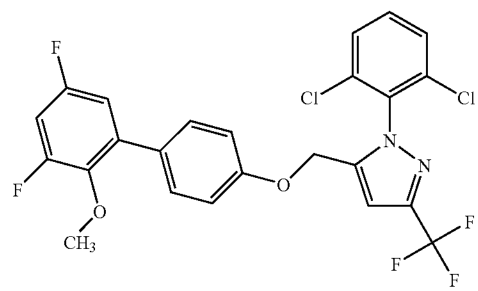 |
| 883 | 4'-((1-(2,6-dichlorophenyl)-3-(trifluoromethyl)-H-pyrazol-5-yl)methoxy)-N,N-dimethylbiphenyl-4-amine | 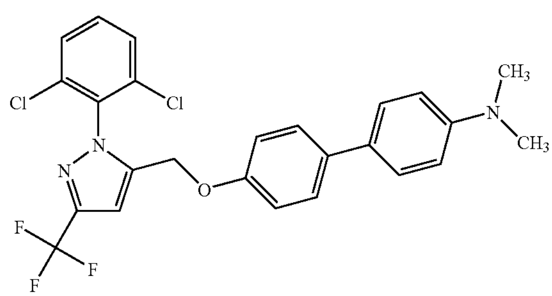 |
| 884 | 1-(2,6-dichlorophenyl)-5-((2'-ethoxy-5'-methylbiphenyl-4-yloxy)methyl)-3-(trifluoromethyl)-1H-pyrazole | 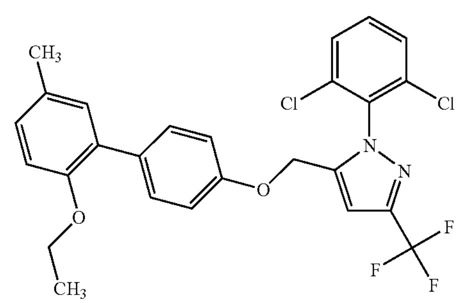 |

TABLE 9-continued

| # | IUPAC Name |
|---|---|
| 885 | 1-(2,6-dichlorophenyl)-5-((3'-fluoro-4'-methylbiphenyl-4-yloxy)methyl)-3-(trifluoromethyl)-1H-pyrazole |
| 886 | 1-(2,6-dichlorophenyl)-5-((3',4',5'-trifluorobiphenyl-4-yloxy)methyl)-3-(trifluoromethyl)-1H-pyrazole |
| 887 | 1-(2,6-dichlorophenyl)-3-(trifluoromethyl)-5-((3'-(trifluoromethyl)biphenyl-4-yloxy)methyl)-1H-pyrazole |
| 888 | N-benzyl-4'-((1-(2,6-dichlorophenyl)-3-(trifluoromethyl)-1H-pyrazol-5-yl)methoxy)biphenyl-4-carboxamide |
| 889 | 4'-((1-(2,6-dichlorophenyl)-3-(trifluoromethyl)-1H-pyrazol-5-yl)methoxy)-5-fluorobiphenyl-2-ol |

TABLE 9-continued

| # | IUPAC Name | Structure |
|---|---|---|
| 890 | 5-((4'-(benzyloxy)biphenyl-4-yloxy)methyl)-1-(2,6-dichlorophenyl)-3-(trifluoromethyl)-1H-pyrazole | 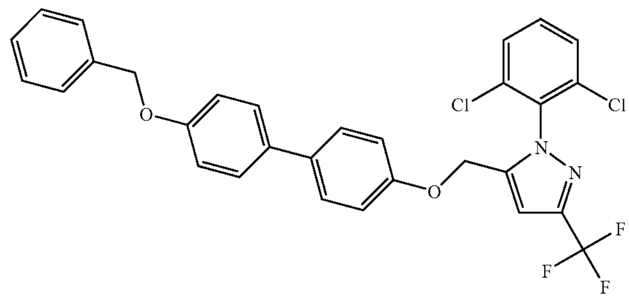 |
| 891 | 1-(2,6-dichlorophenyl)-5-((3'-(methylsulfonyl)biphenyl-4-yloxy)methyl)-3-(trifluoromethyl)-1H-pyrazole | 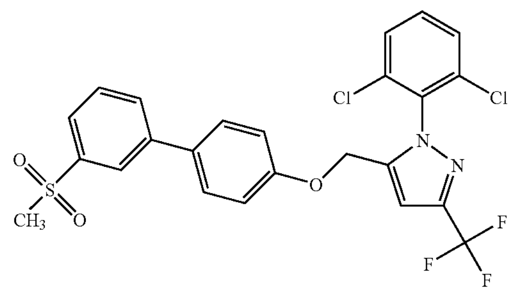 |
| 892 | 5-((3'-chloro-4'-fluorobiphenyl-4-yloxy)methyl)-1-(2,6-dichlorophenyl)-3-(trifluoromethyl)-1H-pyrazole | 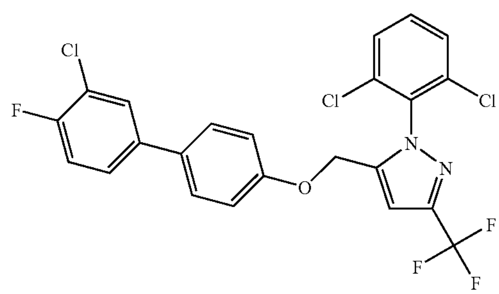 |
| 893 | ethyl 4'-((1-(2,6-dichlorophenyl)-3-(trifluoromethyl)-1H-pyrazol-5-yl)methoxy)biphenyl-4-carboxylate | 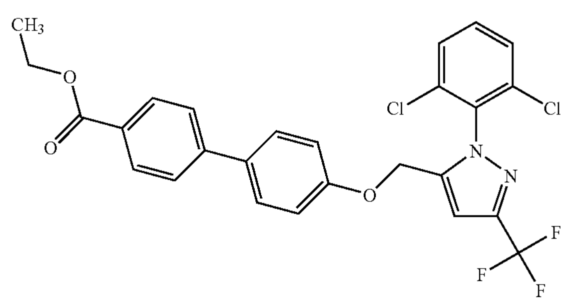 |
| 894 | 5-((3',5'-bis(trifluoromethyl)biphenyl-4-yloxy)methyl)-1-(2,6-dichlorophenyl)-3-(trifluoromethyl)-1H-pyrazole | 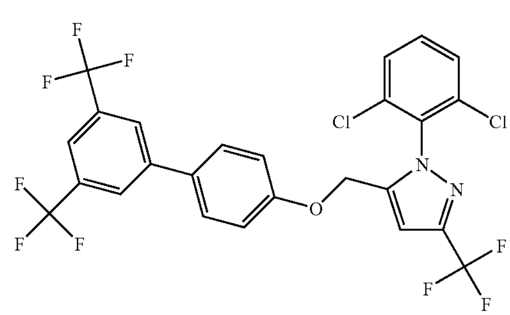 |

TABLE 9-continued

| # | IUPAC Name |
|---|---|
| 895 | 1-(2,6-dichlorophenyl)-5-((4'-methoxy-3',5'-dimethylbiphenyl-4-yloxy)methyl)-3-(trifluoromethyl)-1H-pyrazole |
| 896 | methyl 4'-((1-(2,6-dichlorophenyl)-3-(trifluoromethyl)-1H-pyrazol-5-yl)methoxy)biphenyl-2-carboxylate |
| 897 | 1-(2,6-dichlorophenyl)-5-((3'-isopropoxybiphenyl-4-yloxy)methyl)-3-(trifluoromethyl)-1H-pyrazole |
| 898 | 4'-((1-(2,6-dichlorophenyl)-3-(trifluoromethyl)-1H-pyrazol-5-yl)methoxy)biphenyl-3-sulfonamide |
| 899 | N-(4'-((1-(2,6-dichlorophenyl)-3-(trifluoromethyl)-1H-pyrazol-5-yl)methoxy)biphenyl-3-yl)methanesulfonamide |

TABLE 9-continued

| # | IUPAC Name | Structure |
|---|------------|-----------|
| 900 | 4-(4'-((1-(2,6-dichlorophenyl)-3-(trifluoromethyl)-1H-pyrazol-5-yl)methoxy)-6-methylbiphenyl-3-ylsulfonyl)morpholine | 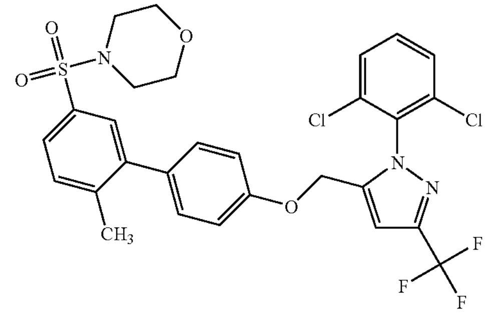 |
| 901 | 5-((4'-(benzyloxy)-2'-fluorobiphenyl-4-yloxy)methyl)-1-(2,6-dichlorophenyl)-3-(trifluoromethyl)-1H-pyrazole | 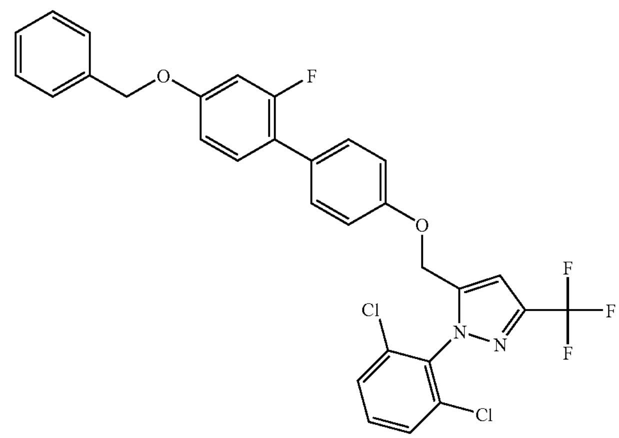 |

TABLE 10

| # | IUPAC Name | Structure |
|---|------------|-----------|
| 902 | 4'-((1-(2,6-dichlorophenyl)-3-(trifluoromethyl)-1H-pyrazol-5-yl)methoxy)-N-isopropyl-3'-methylbiphenyl-4-carboxamide | 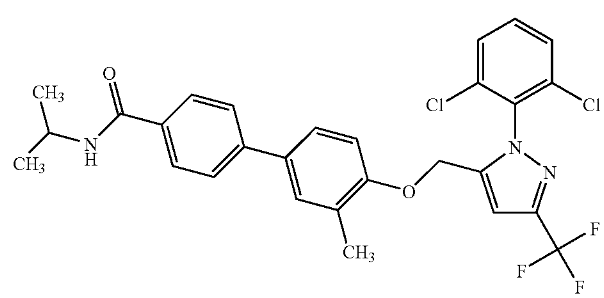 |
| 903 | 1-(4'-((1-(2,6-dichlorophenyl)-3-(trifluoromethyl)-1H-pyrazol-5-yl)methoxy)-3'-methylbiphenyl-2-yl)ethanone | 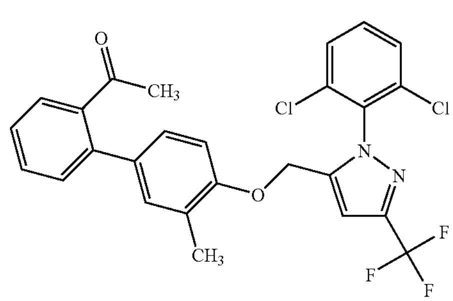 |

TABLE 10-continued

| # | IUPAC Name | Structure |
|---|---|---|
| 904 | (4'-((1-(2,6-dichlorophenyl)-3-(trifluoromethyl)-1H-pyrazol-5-yl)methoxy)-3'-methylbiphenyl-4-yl)(morpholino)methanone | 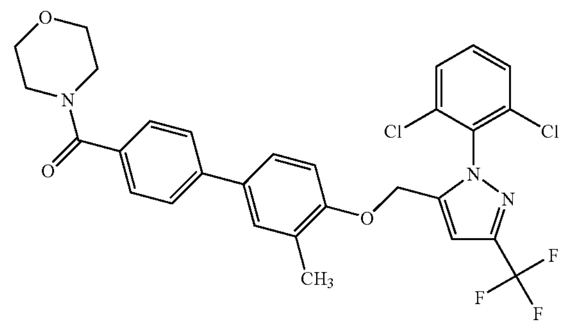 |
| 905 | N-(2-cyanoethyl)-4'-((1-(2,6-dichlorophenyl)-3-(trifluoromethyl)-1H-pyrazol-5-yl)methoxy)-3'-methylbiphenyl-4-carboxamide | 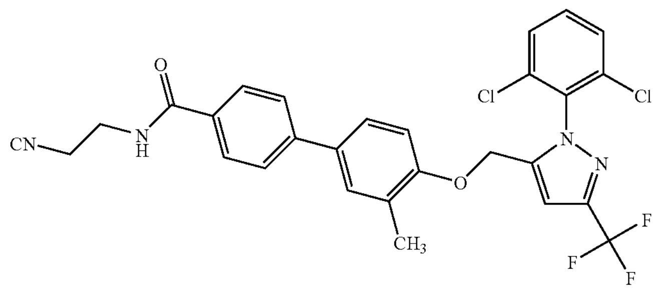 |

TABLE 11

| # | IUPAC Name | Structure |
|---|---|---|
| 906 | 2-chloro-4'-({[1-(2,6-dichlorophenyl)-3-(1-hydroxy-1-methylethyl)-1H-pyrazol-5-yl]methyl}oxy)biphenyl-4-carboxylic acid | 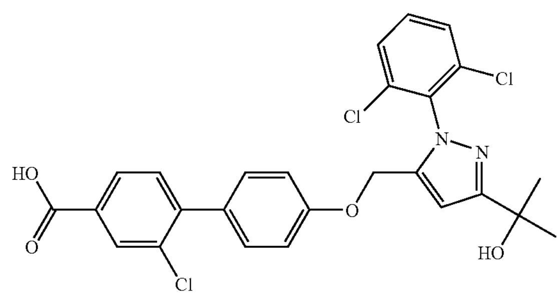 |
| 907 | 2-chloro-4'-({[1-(2,6-dichlorophenyl)-3-(1-methylethyl)-1H-pyrazol-5-yl]methyl}oxy)biphenyl-4-carboxylic acid | 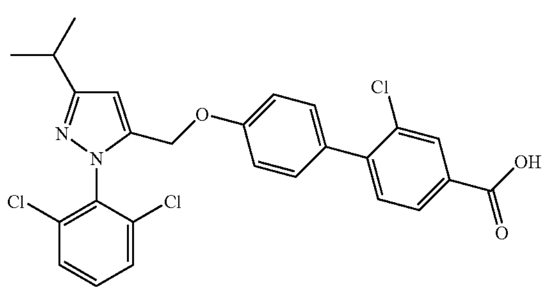 |

TABLE 11-continued

| # | IUPAC Name | Structure |
|---|---|---|
| 908 | 5-({[3-chloro-3'-(methylsulfonyl)biphenyl-4-yl]oxy}methyl)-1-(2-chlorophenyl)-3-(trifluoromethyl)-1H-pyrazole | 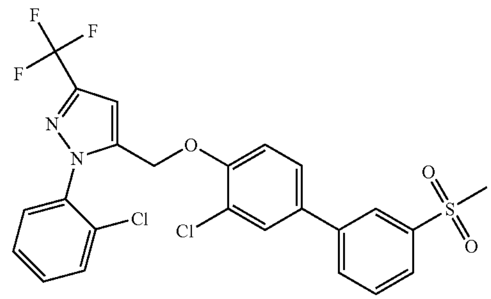 |
| 909 | 1-(2-chlorophenyl)-5-({[3-methyl-3'-(methylsulfonyl)biphenyl-4-yl]oxy}methyl)-3-(trifluoromethyl)-1H-pyrazole | 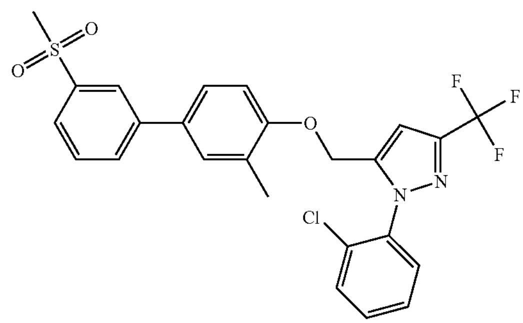 |
| 910 | 1-(2-chlorophenyl)-5-({[2-methyl-3'-(methylsulfonyl)biphenyl-4-]oxy}methyl)-3-(trifluoromethyl)-1H-pyrazole | 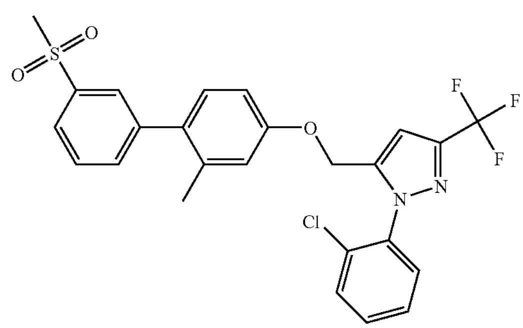 |
| 911 | 5-({[2-chloro-3'-(methylsulfonyl)biphenyl-4-yl]oxy}methyl)-1-(2-chlorophenyl)-3-(trifluoromethyl)-1H-pyrazole | 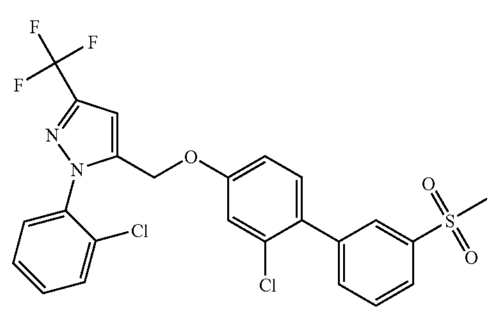 |

TABLE 12

| # | IUPAC Name | Structure |
|---|---|---|
| 912 | 4-(5-(4-((1-(2,6-dichlorophenyl)-3-(trifluoromethyl)-1H-pyrazol-5-yl)methoxy)phenyl)pyridin-2-yl)morpholine | 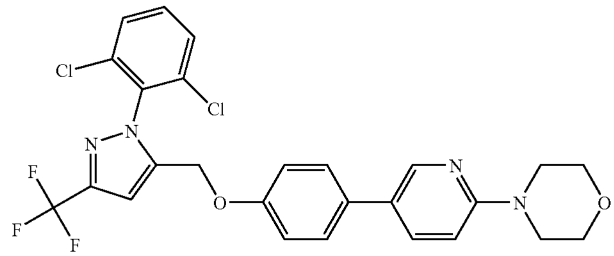 |
| 913 | 5-(4-((1-(2,6-dichlorophenyl)-3-(trifluoromethyl)-1H-pyrazol-5-yl)methoxy)phenyl)pyrimidine | 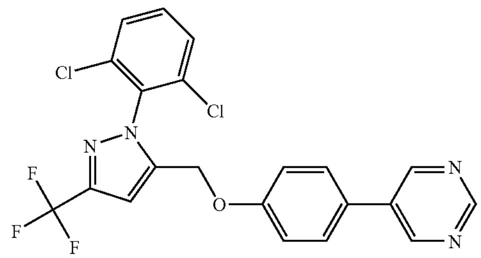 |
| 914 | 3-(4-((1-(2,6-dichlorophenyl)-3-(trifluoromethyl)-1H-pyrazol-5-yl)methoxy)phenyl)-2-methoxypyridine | 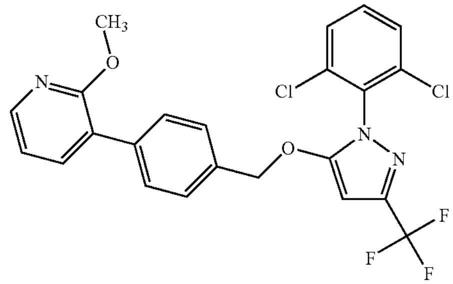 |
| 915 | 5-(4-((1-(2,6-dichlorophenyl)-3-(trifluoromethyl)-1H-pyrazol-5-yl)methoxy)phenyl)-1H-indole | 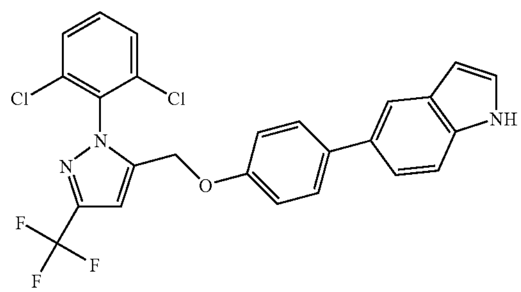 |
| 916 | 4-(4-((1-(2,6-dichlorophenyl)-3-(trifluoromethyl)-1H-pyrazol-5-yl)methoxy)phenyl)pyridine | 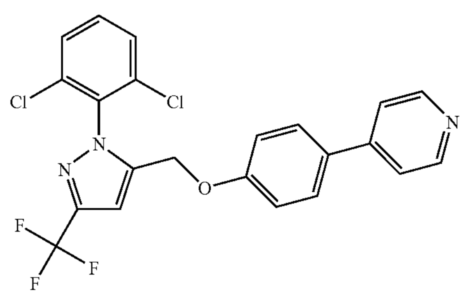 |

TABLE 12-continued

| # | IUPAC Name | Structure |
|---|---|---|
| 917 | 4-(4-((1-(2,6-dichlorophenyl)-3-(trifluoromethyl)-1H-pyrazol-5-yl)methoxy)phenyl)-1H-indole | 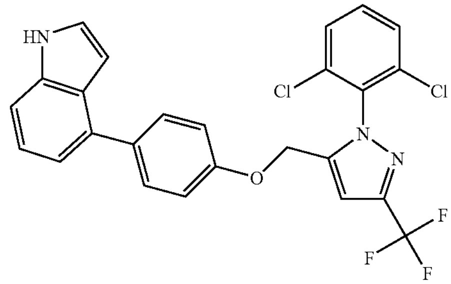 |
| 918 | 8-(4-((1-(2,6-dichlorophenyl)-3-(trifluoromethyl)-1H-pyrazol-5-yl)methoxy)phenyl)quinoline | 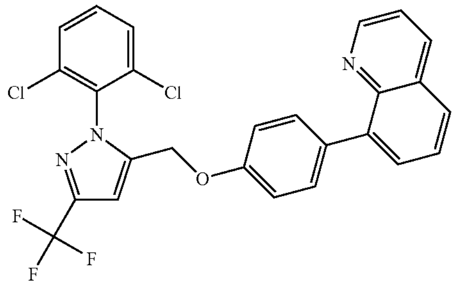 |
| 919 | 5-(4-((1-(2,6-dichlorophenyl)-3-(trifluoromethyl)-1H-pyrazol-5-yl)methoxy)phenyl)-1-methyl-1H-indole | 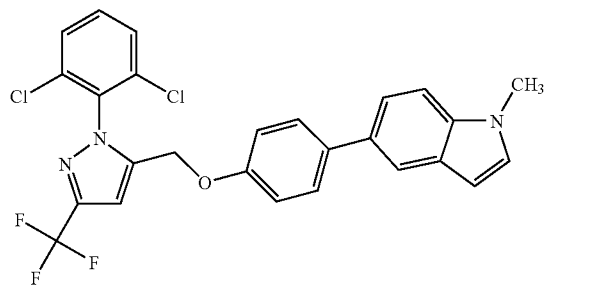 |
| 920 | tert-butyl 4-(5-(4-((1-(2,6-dichlorophenyl)-3-(trifluoromethyl)-1H-pyrazol-5-yl)methoxy)phenyl)pyridin-2-yl)piperazine-1-carboxylate | 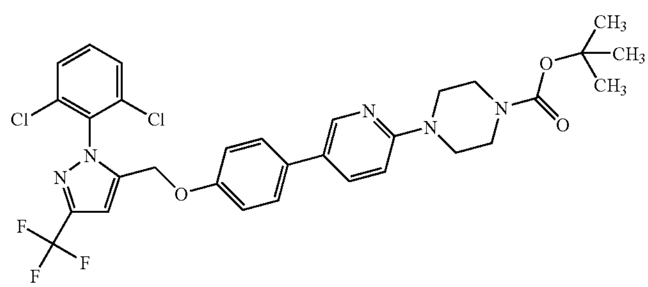 |

TABLE 13

| # | IUPAC Name | Structure |
|---|---|---|
| 921 | 4'-({[1-(2,6-dichlorophenyl)-3-(trifluoromethyl)-1H-pyrazol-5-yl]methyl}oxy)biphenyl-4-carboxylic acid | 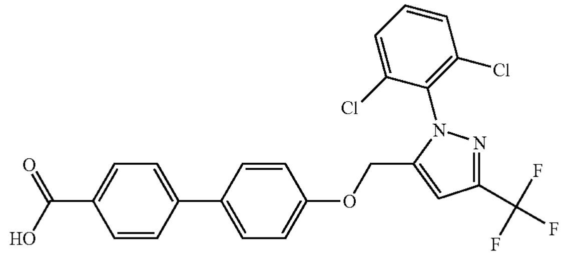 |

TABLE 13-continued

| # | IUPAC Name | Structure |
|---|---|---|
| 922 | 1-(2,6-dichlorophenyl)-5-({[4-(1H-pyrrol-1-yl)phenyl]oxy}methyl)-3-(trifluoromethyl)-1H-pyrazole | 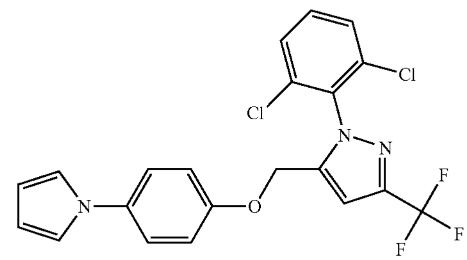 |
| 923 | 1-(2,6-dichlorophenyl)-5-({[4-(1H-imidazol-1-yl)phenyl]oxy}methyl)-3-(trifluoromethyl)-1H-pyrazole | 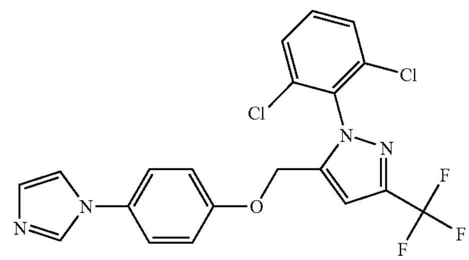 |
| 924 | 5-[(biphenyl-4-yloxy)methyl]-1-(2,6-dichlorophenyl)-3-(trifluoromethyl)-1H-pyrazole | 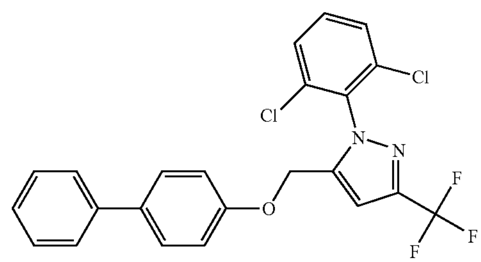 |
| 925 | 1-(2-chlorophenyl)-5-({[3-fluoro-3'-(methylsulfonyl)biphenyl-4-yl]oxy}methyl)-3-(trifluoromethyl)-1H-pyrazole | 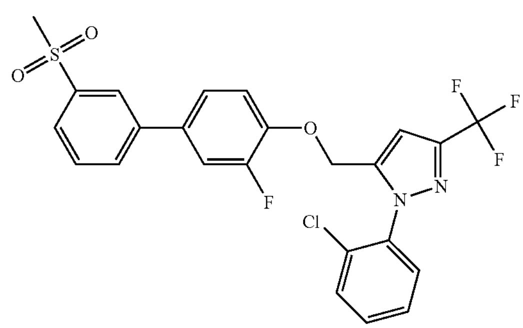 |
| 926 | 4-({[1-(2-chlorophenyl)-3-(trifluoromethyl)-1H-pyrazol-5-yl]methyl}oxy)-3'-(methylsulfonyl)biphenyl-3-carbonitrile | 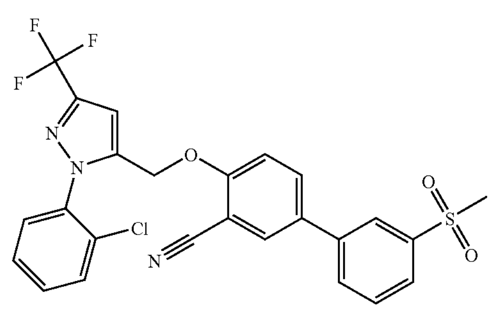 |

TABLE 13-continued

| # | IUPAC Name | Structure |
|---|---|---|
| 927 | 1-(2-chlorophenyl)-5-({[3,5-dimethyl-3'-(methylsulfonyl)biphenyl-4-yl]oxy}methyl)-3-(trifluoromethyl)-1H-pyrazole | 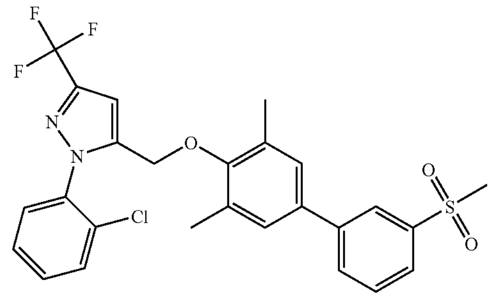 |

TABLE 14

| # | IUPAC Name | Structure |
|---|---|---|
| 928 | N-{[1-(2-chlorophenyl)-3-(trifluoromethyl)-1H-pyrazol-5-yl]methyl}-3'-(methylsulfonyl)biphenyl-4-amine | 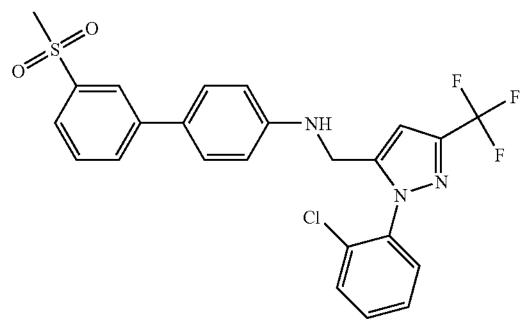 |
| 929 | N-{[1-(2-chlorophenyl)-3-(trifluoromethyl)-1H-pyrazol-5-yl]methyl}-N-methyl-3'-(methylsulfonyl)biphenyl-4-amine | 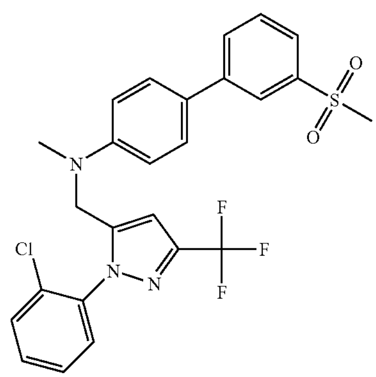 |

TABLE 15

| # | IUPAC Name | Structure |
|---|---|---|
| 930 | methyl {[1-(2-chlorophenyl)-5-{5-[3-(methylsulfonyl)phenyl]-2-thienyl}-1H-pyrazol-3-yl]oxy}acetate | 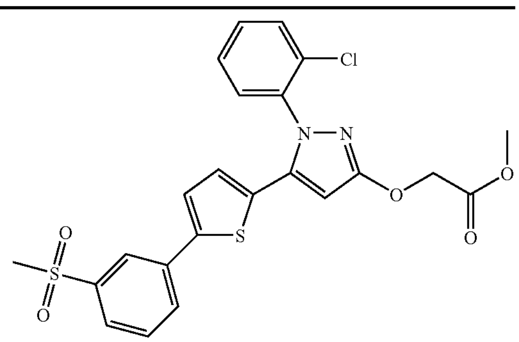 |

TABLE 15-continued

| # | IUPAC Name | Structure |
|---|---|---|
| 931 | {[1-(2-chlorophenyl)-5-{5-[3-(methylsulfonyl)phenyl]-2-thienyl}-1H-pyrazol-3-yl]oxy}acetic acid | 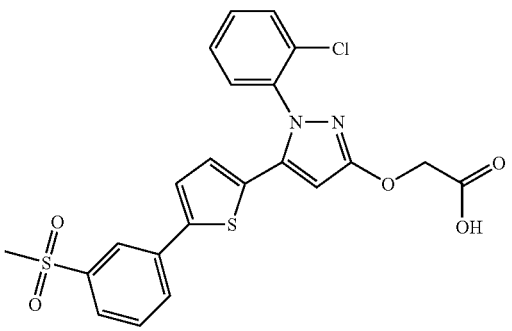 |
| 932 | 1-{[1-(2-chlorophenyl)-5-{5-[3-(methylsulfonyl)phenyl]-2-thienyl}-1H-pyrazol-3-yl]oxy}-2-methylpropan-2-ol | 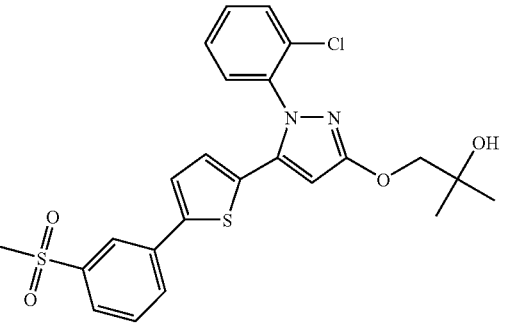 |
| 933 | 1-(2-chlorophenyl)-3-(methyloxy)-5-{5-[3-(methylsulfonyl)phenyl]-2-thienyl}-1H-pyrazole | 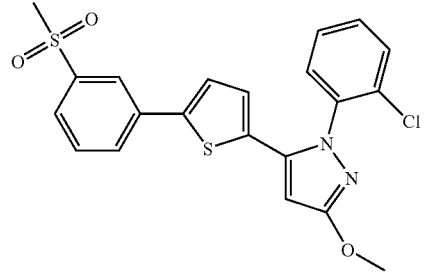 |

TABLE 16

| # | IUPAC Name | Structure |
|---|---|---|
| 934 | 2-{1-[3-chloro-3'-(methylsulfonyl)biphenyl-4-yl]-2-(2,6-dichlorophenyl)-1H-imidazol-4-yl}-4,4-dimethyl-4,5-dihydro-1,3-oxazole | 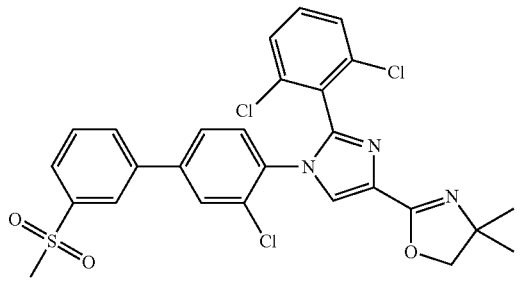 |

| # | IUPAC Name |
|---|---|
| 935 | 2-{1-[3-chloro-3'-(ethylsulfonyl)biphenyl-4-yl]-2-(2,6-dichlorophenyl)-1H-imidazol-4-yl}-4,4-dimethyl-4,5-dihydro-1,3-oxazole |
| 936 | 2-{1-[3-chloro-3'-(methylsulfonyl)biphenyl-4-yl]-2-(2,6-dichlorophenyl)-1H-imidazol-4-yl}-4,5-dihydro-1,3-oxazole |
| 937 | 2-{1-[3-chloro-3'-(methylsulfonyl)biphenyl-4-yl]-2-(2,6-dichlorophenyl)-1H-imidazol-4-yl}-5-methyl-4,5-dihydro-1,3-oxazole |
| 938 | 2-{1-[3-chloro-3'-(methylsulfonyl)biphenyl-4-yl]-2-(2,6-dichlorophenyl)-1H-imidazol-4-yl}-4-methyl-4,5-dihydro-1,3-oxazole |
| 939 | 2-{2-(2,6-dichlorophenyl)-1-[3'-(methylsulfonyl)biphenyl-4-yl]-1H-imidazol-4-yl}-4,4-dimethyl-4,5-dihydro-1,3-oxazole |

TABLE 16-continued

| # | IUPAC Name |
|---|---|
| 940 | 2-{1-[3-chloro-3'-(methylsulfonyl)biphenyl-4-yl]-2-(2,6-dichlorophenyl)-1H-imidazol-4-yl}-4,4-dimethyl-4,5-dihydro-1,3-thiazole |
| 941 | 1'-[3-chloro-3'-(methylsulfonyl)biphenyl-4-yl]-2'-(2,6-dichlorophenyl)-4,5-dihydro-1H,1'H-2,4'-biimidazole |
| 942 | 1'-[3-chloro-3'-(methylsulfonyl)biphenyl-4-yl]-2'-(2,6-dichlorophenyl)-5,5-dimethyl-4,5-dihydro-1H,1'H-2,4'-biimidazole |
| 943 | 2'-(2,6-dichlorophenyl)-5,5-dimethyl-1'-[3'-(methysulfonyl)biphenyl-4-yl]-4,5-dihydro-1H,1'H-2,4'-biimidazole |
| 944 | 5-{1-[3-chloro-3'-(methylsulfonyl)biphenyl-4-yl]-2-(2,6-dichlorophenyl)-1H-imidazol-4-yl}-3-methyl-1,2,4-oxadiazole |

TABLE 17

| # | IUPAC Name | Structure |
|---|---|---|
| 945 | 2-chloro-4'-({[1-(2,6-dichlorophenyl)-3-(1-hydroxy-1-methylethyl)-1H-pyrazol-5-yl]methyl}oxy)biphenyl-4-carboxylic acid | 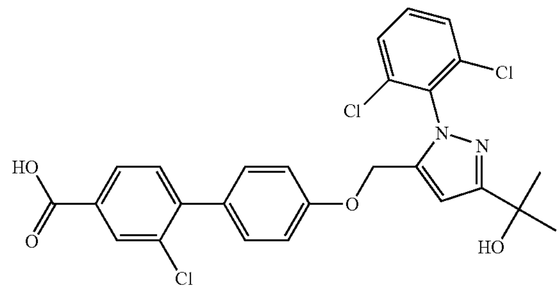 |
| 946 | 2-chloro-4'-({[1-(2,6-dichlorophenyl)-3-(trifluoromethyl)-1H-pyrazol-5-yl]methyl}oxy)biphenyl-4-carboxylic acid | 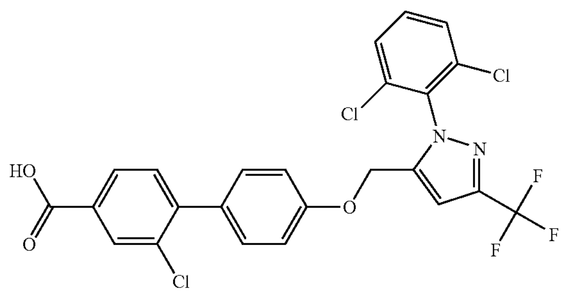 |
| 947 | 2-chloro-4'-({[1-(2,6-dichlorophenyl)-3-(1-methylethyl)-1H-pyrazol-5-yl]methyl}oxy)biphenyl-4-carboxylic acid | 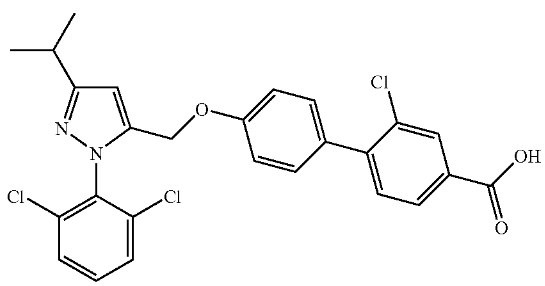 |

TABLE 18

| # | IUPAC Name | Structure |
|---|---|---|
| 948 | 2-[1-(2,6-difluorophenyl)-5-{5-[3-(methylsulfonyl)phenyl]-2-thienyl}-1H-pyrazol-3-yl]propan-2-ol | 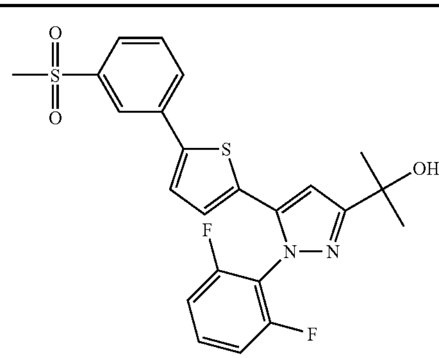 |

TABLE 18-continued
| # | IUPAC Name | Structure |
|---|---|---|
| 949 | 2-[1-(2,6-dichlorophenyl)-5-{5-[3-(methylsulfonyl)phenyl]-2-thienyl}-1H-pyrazol-3-yl]propan-2-ol | 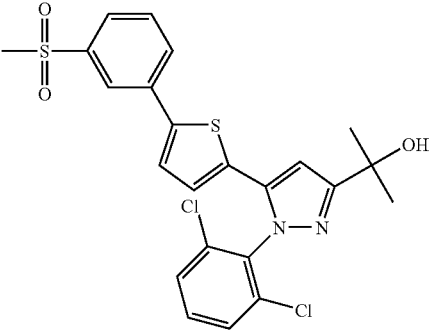 |
| 950 | 2-[1-(2-chloro-6-fluorophenyl)-5-{5-[3-(methylsulfonyl)phenyl]-2-thienyl}-1H-pyrazol-3-yl]propan-2-ol | 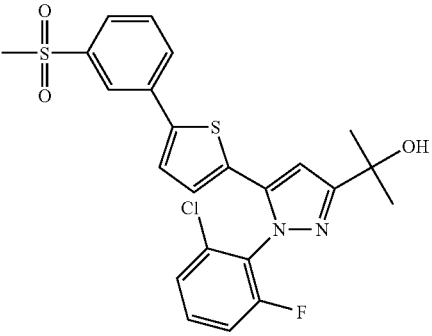 |
| 951 | 2-(1-[2-(fluoro-6-(trifluoromethyl)phenyl]-5-{5-[3-(methylsulfonyl)phenyl]-2-thienyl}-1H-pyrazol-3-yl)propan-2-ol | 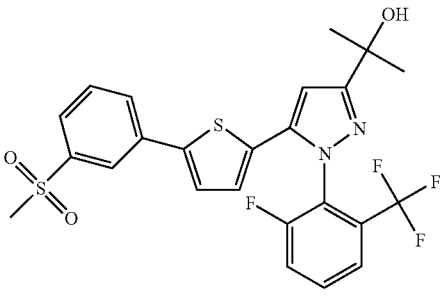 |
| 952 | 2-[1-(2-chloro-6-methylphenyl)-5-{5-[3-(methylsulfonyl)phenyl]-2-thienyl}-1H-pyrazol-3-yl]propan-2-ol | 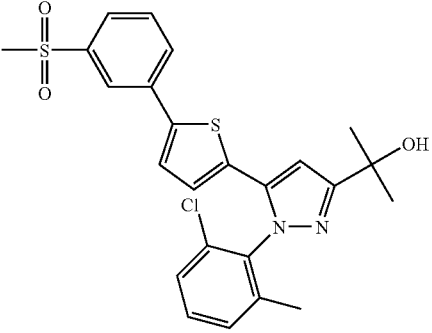 |

TABLE 18-continued

| # | IUPAC Name | Structure |
|---|---|---|
| 953 | 2-[4-chloro-1-(2,6-dichlorophenyl)-5-{5-[3-(methylsulfonyl)phenyl]-2-thienyl}-1H-pyrazol-3-yl]propan-2-ol | 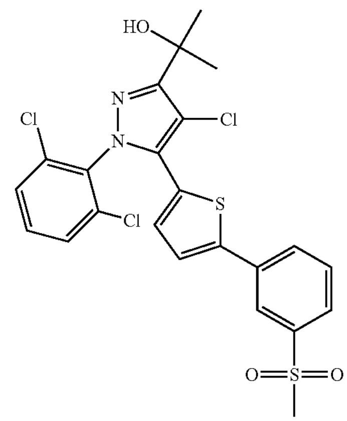 |
| 954 | 2-[4-chloro-1-(2-chloro-6-fluorophenyl)-5-{5-[3-(methylsulfonyl)phenyl]-2-thienyl}-1H-pyrazol-3-yl]propan-2-ol | 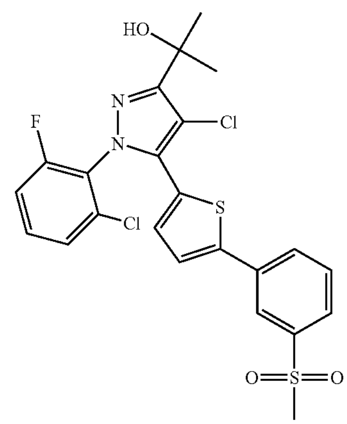 |
| 955 | 2-[1-(3,5-dichloropyridin-4-yl)-5-{5-[3-(methylsulfonyl)phenyl]-2-thienyl}-1H-pyrazol-3-yl]propan-2-ol | 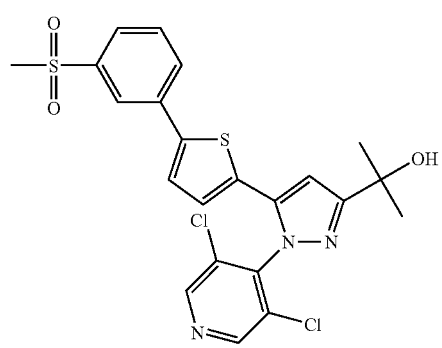 |
| 956 | 2-{1-(2,6-dichlorophenyl)-5-[3'-(methylsulfonyl)biphenyl-4-yl]-1H-pyrazol-3-yl}propan-2-ol | 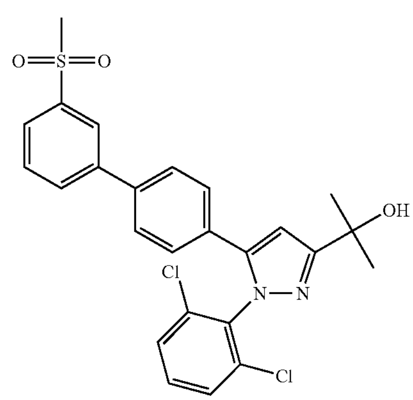 |

TABLE 18-continued

| # | IUPAC Name |
|---|---|
| 957 | 2-{4-chloro-1-(2,6-dichlorophenyl)-5-[3'-(methylsulfonyl)biphenyl-4-yl]-1H-pyrazol-3-yl}propan-2-ol |
| 958 | 2-{5-[3-chloro-3'-(methylsulfonyl)biphenyl-4-yl]-1-(2,6-dichlorophenyl)-1H-pyrazol-3-yl}propan-2-ol |
| 959 | 2-{4-chloro-5-[3-chloro-3'-(methysulfonyl)biphenyl-4-yl]-1-(2,6-dichlorophenyl)-1H-pyrazol-3-yl}propan-2-ol |
| 960 | 2-{1-(2,6-dichlorophenyl)-5-[3-methyl-3'-(methylsulfonyl)biphenyl-4-yl]-1H-pyrazol-3-yl}propan-2-ol |

TABLE 18-continued

| # | IUPAC Name |
|---|---|
| 961 | 2-{1-(2,6-dichlorophenyl)-5-[2-methyl-3'-(methylsulfonyl)biphenyl-4-yl]-1H-pyrazol-3-yl}propan-2-ol |
| 962 | 2-{5-(2-chloro-6-fluorophenyl)-1-[3'-(methylsulfonyl)biphenyl-4-yl]-1H-pyrazol-3-yl}propan-2-ol |
| 963 | 2-{5-(2,6-dichlorophenyl)-1-[3'-(methylsulfonyl)biphenyl-4-yl]-1H-pyrazol-3-yl}propan-2-ol |
| 964 | 2-{4-chloro-5-(2-chloro-6-fluorophenyl)-1-[3-fluoro-3'-(methysulfonyl)biphenyl-4-yl]-1H-pyrazol-3-yl}propan-2-ol |
| 965 | 2-{1-[3-chloro-3'-(methylsulfonyl)biphenyl-4-yl]-5-(2,6-dichlorophenyl)-1H-pyrazol-3-yl}propan-2-ol |

| # | IUPAC Name | Structure |
|---|---|---|
| 966 | 2-{5-(2,6-dichlorophenyl)-1-[3-methyl-3'-(methylsulfonyl)biphenyl-4-yl]-1H-pyrazol-3-yl}propan-2-ol | 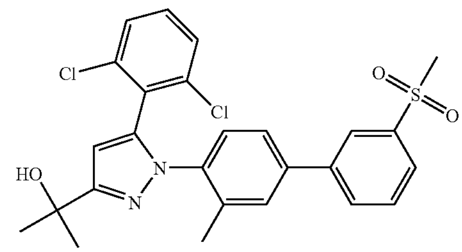 |
| 967 | 2-{4-chloro-5-(2,6-dichlorophenyl)-1-[3-methyl-3'-(methylsulfonyl)biphenyl-4-yl]-1H-pyrazol-3-yl}propan-2-ol | 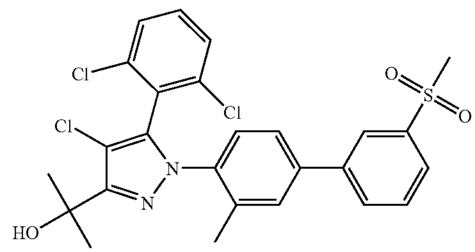 |
| 968 | 2-{4-chloro-5-(2-chloro-6-fluorophenyl)-1-[3-methyl-3'-(methylsulfonyl)biphenyl-4-yl]-1H-pyrazol-3-yl}propan-2-ol | 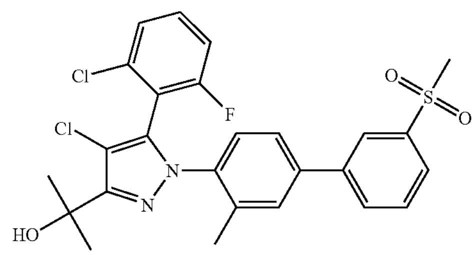 |
| 969 | 2-{5-(2-chloro-6-fluorophenyl)-1-[2-methyl-3'-(methylsulfonyl)biphenyl-4-yl]-1H-pyrazol-3-yl}propan-2-ol | 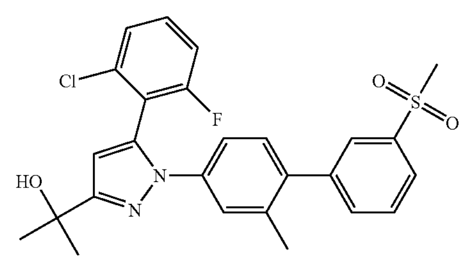 |
| 970 | 2-{5-(2,6-dichlorophenyl)-1-[2-methyl-3'-(methylsulfonyl)biphenyl-4-yl]-1H-pyrazol-3-yl}propan-2-ol | 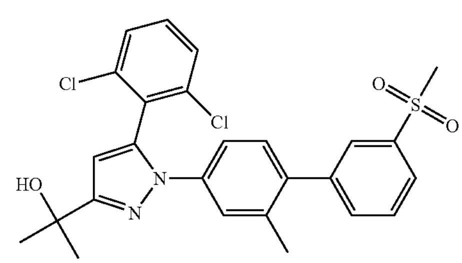 |

TABLE 18-continued

| # | IUPAC Name | Structure |
|---|---|---|
| 971 | 2-{4-chloro-4-(2-chloro-6-fluoropehnyl)-1-[2-methyl-3'-(methylsulfonyl)biphenyl-4-yl]-1H-pyrazol-3-yl}propan-2-ol | 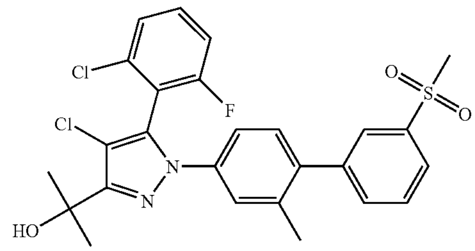 |
| 972 | 2-{4-chloro-5-(2,6-dichlorophenyl)-1-[2-methyl-3'-(methylsulfonyl)biphenyl-4-yl]-1H-pyrazol-3-yl}propan-2-ol | 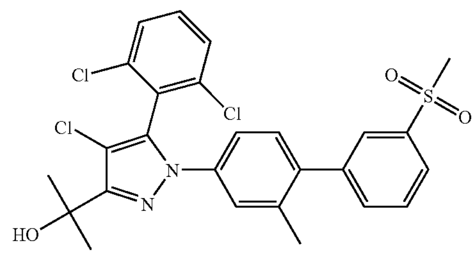 |

TABLE 19

| # | IUPAC Name | Structure |
|---|---|---|
| 973 | 2-(2-Chloro-phenyl)-5-trifluoromethyl-2H-pyrazole-3-carboxylic acid (4'-acetylamino-biphenyl-4-yl)-amide | 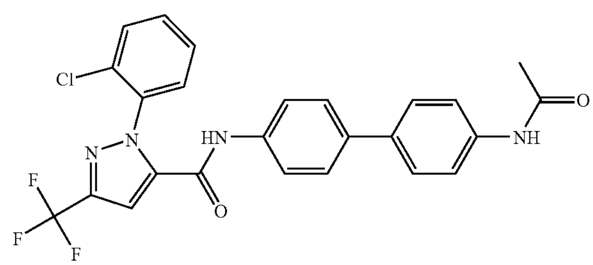 |
| 974 | 2-[2-(2-Chloro-phenyl)-5-trifluoromethyl-2H-pyrazol-3-yl]-N-quinolin-6-yl-acetamide | 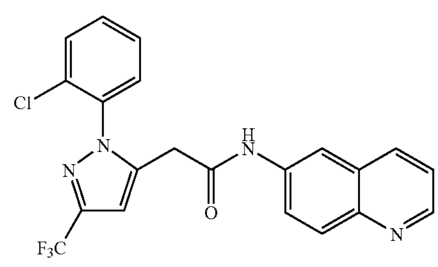 |

Scheme 23

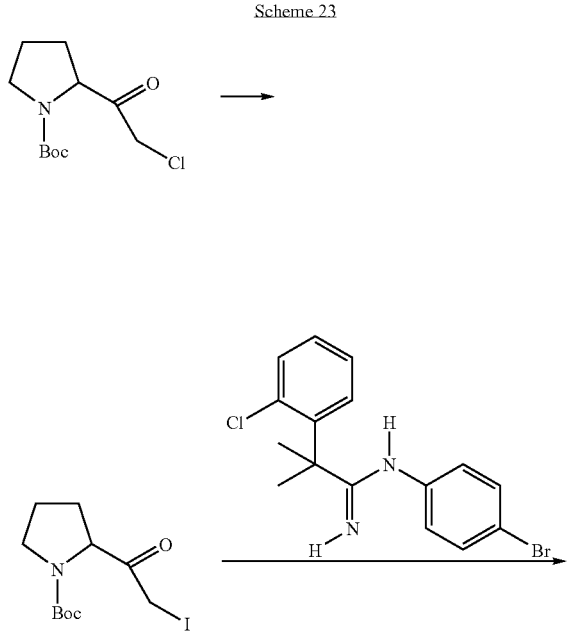

Example 23

Preparation of 1,1-dimethylethyl 2-{2-[1-(2-chlorophenyl)-1-methylethyl]-1-[3'-(methylsulfonyl)biphenyl-4-yl]-1H-imidazol-4-yl}pyrrolidine-1-carboxylate

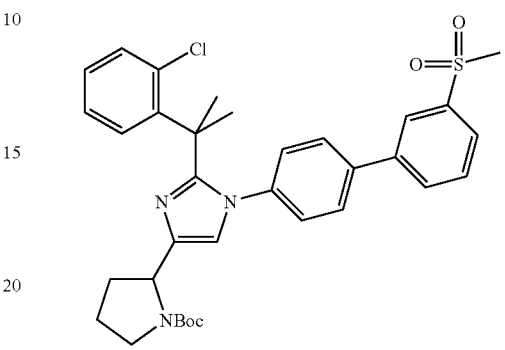

Step 1: To a solution of tert-butyl 2-(2-chloroacetyl)pyrrolidine-1-carboxylate (5 g, 20.24 mmol) in 200 mL of acetone was added 3 g (20.24 mmol) of NaI. The reaction was let to stir at room temperature for 18 h. The reaction was monitored by TLC (20% EtOAc/hexanes, the plate was developed by KMnO$_4$ stain). The reaction mixture was filtered over celite, concentrated and dried to afford tert-butyl 2-(2-iodoacetyl)pyrrolidine-1-carboxylate (8 g, 99% yield). $^1$H NMR (CDCl$_3$): δ 1.45 (d, 9H), 1.99 (s, 3H), 2.20 (m, 1H), 3.50 (m, 2H), 4.90 (m, 2H), 4.50 (m, 1H).

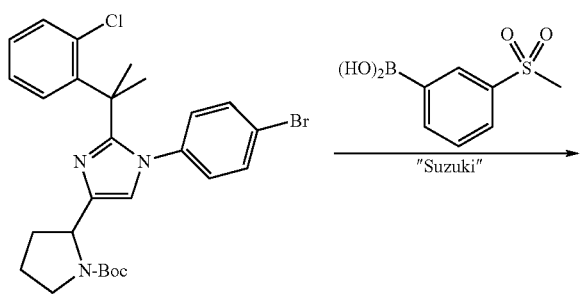

Step 2: To a solution of N-(4-bromophenyl)-2-(2-chlorophenyl)-2-methylpropanimidamide (3.51 g, 10 mmol) in 60 mL dioxane was added tert-butyl 2-(2-iodoacetyl)pyrrolidine-1-carboxylate (3.38 g, 10 mmol) and NaHCO$_3$ (2.5 g, 30 mmol). The mixture was heated to reflux with stirring for 2 days. The reaction was monitored by LC/MS. The reaction mixture was cooled and filtered over celite. The crude mixture was initially purified by silica gel column chromatography. The fraction containing the desired product was further purified by prep HPLC, affording 300 mg (5.5%) of tert-butyl 2-(1-(4-bromophenyl)-2-(2-(2-chlorophenyl)propan-2-yl)-1H-imidazol-4-yl)pyrrolidine-1-carboxylate. $^1$H NMR (CD$_3$OD): δ 1.4 (m, 10H), 1.6 (m, 3H,), 1.8 (m, 1H), 1.9-2.3 (m, 5H), 3.4 (m, 1H), 3.6 (m, 1H) 4.6 (m, 1H), 6.9 (m, 3H), 7.05 (m, 1H), 7.2 (m, 2H), 7.25 (m, 1H), 7.50 (m, 2H); LC/MS M+H 544 (observed).

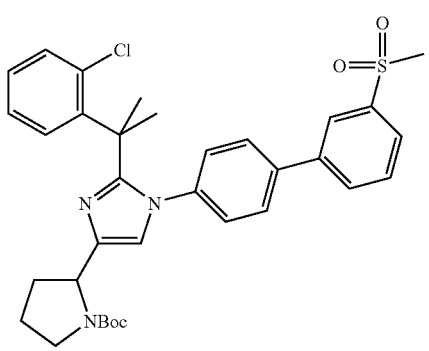

Step 3: To a solution of tert-butyl 2-(1-(4-bromophenyl)-2-(2-(2-chlorophenyl)propan-2-yl)-1H-imidazol-4-yl)pyrrolidine-1-carboxylate (20 mg, 0.036 mmol) in THF (3 mL) was added 3-(methylsulfonyl)phenylboronic acid (14.7 mg, 0.073 mmol). The resulting solution was stirred at 80-85° C. for 5 min and then tetrakistriphenylphosphine palladium (0) (5-10 mg) was added followed by the addition of 60 µL of 1.0 M sodium carbonate. The reaction was maintained at 80-85° C. for 30 min. LC/MS analysis indicated the reaction was complete. The reaction mixture was cooled and filtered over celite, concentrated. The crude product was purified by prep HPLC to give 1,1-dimethylethyl 2-{2-[1-(2-chlorophenyl)-1-methylethyl]-1-[3'-(methylsulfonyl)biphenyl-4-yl]-1H-imidazol-4-yl}pyrrolidine-1-carboxylate (10 mg, 50%). $^1$H NMR (CD$_3$OD): δ 1.4 (m, 9H), 1.6 (m, 3H,), 1.8 (m, 1H), 1.9-2.3 (m, 5H), 3.2 (s, 3H), 3.4 (m, 1H), 3.6 (m, 1H) 4.6 (m, 1H), 6.9 (m, 1H), 7.0 (m, 1H), 7.2 (m, 6H), 7.7 (m, 3H), 7.95 (m, 2H), 8.2 (m, 1H); LC/MS M+H 620 (observed).

Example 24

2-[1-(2-Chlorophenyl)-1-methylethyl]-1-[3'-(methylsulfonyl)biphenyl-4-yl]-4-pyrrolidin-2-yl-1H-imidazole

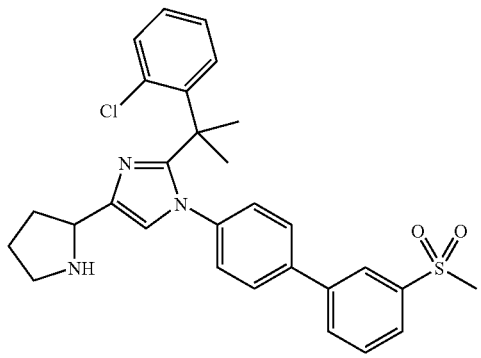

A mixture of 1,1-dimethylethyl 2-{2-[1-(2-chlorophenyl)-1-methylethyl]-1-[3'-(methylsulfonyl)biphenyl-4-yl]-1H-imidazol-4-yl}pyrrolidine-1-carboxylate (200 mg) and 5 mL of 50% TFA in DCM was stirred at room temperature for 20 min. After concentrated in vacuo, the reaction mixture was separated by prep HPLC to give 2-[1-(2-chlorophenyl)-1-methylethyl]-1-[3'-(methylsulfonyl)biphenyl-4-yl]-4-pyrrolidin-2-yl-1H-imidazole (150 mg): $^1$H NMR (CD$_3$OD): δ 1.6 (m, 3H,), 1.8 (m, 1H), 1.9 (s, 3H), 2.2-2.6 (m, 4H), 3.2 (s, 3H), 3.4 (m, 2H), 4.7 (m, 1H), 7.1 (m, 1H), 7.2 (m, 5H), 7.4 (s, 1H), 7.7 (m, 3H), 8.0 (m, 2H), 8.2 (m, 1H); LC/MS M+H 520 (observed).

Example 25

Methyl 2-{2-[1-(2-chlorophenyl)-1-methylethyl]-1-[3'-(methylsulfonyl)biphenyl-4-yl]-1H-imidazol-4-yl}pyrrolidine-1-carboxylate

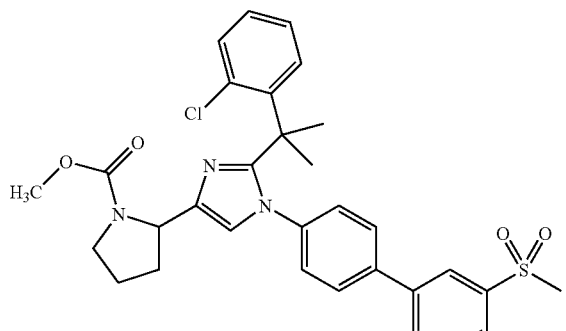

To a solution of 2-[1-(2-chlorophenyl)-1-methylethyl]-1-[3'-(methylsulfonyl)biphenyl-4-yl]-4-pyrrolidin-2-yl-1H-imidazole in THF was added triethylamine, followed by methylchlorocarbonate. The mixture was stirred at room temperature for 20 min. After a routing aqueous work up, the crude product was purified by prep HPLC to give methyl 2-{2-[1-(2-chlorophenyl)-1-methylethyl]-1-[3'-(methylsulfonyl)biphenyl-4-yl]-1H-imidazol-4-yl}pyrrolidine-1-carboxylate: $^1$H NMR (CD$_3$OD): δ 1.6 (m, 3H,), 1.8 (m, 1H), 1.9-2.3 (m, 5H), 3.2 (s, 3H), 3.4 (m, 1H), 3.7 (m, 4H), 4.6 (m, 1H), 5.1 (m, 1H), 6.9 (m, 1H), 7.2 (m, 6H), 7.7 (m, 3H), 7.95 (m, 2H), 8.2 (m, 1H); LC/MS M+H 578 (observed).

Example 26

4-(1-acetylpyrrolidin-2-yl)-2-[1-(2-chlorophenyl)-1-methylethyl]-1-[3'-(methylsulfonyl)biphenyl-4-yl]-1H-imidazole

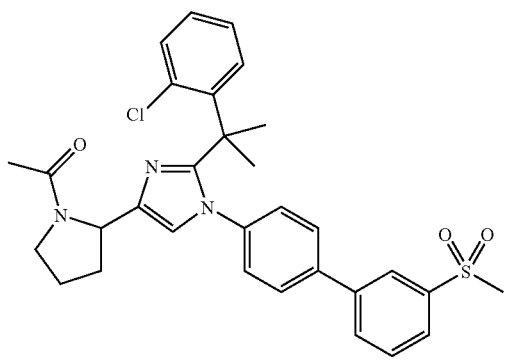

To a solution of 2-[1-(2-chlorophenyl)-1-methylethyl]-1-[3'-(methylsulfonyl)biphenyl-4-yl]-4-pyrrolidin-2-yl-1H-imidazole, acetonitrile and pyridine was added acetic anhydride. The solution was heated to reflux for 1 h. After a routine aqueous work up, the crude product was purified by prep HPLC to give 4-(1-acetylpyrrolidin-2-yl)-2-[1-(2-chlorophenyl)-1-methylethyl]-1-[3'-(methylsulfonyl)biphenyl-4-yl]-1H-imidazole: $^1$H NMR (CDCl$_3$): δ 1.6 (m, 3H,), 1.8 (m, 1H), 1.9 (br, 2H), 2.1 (m, 4H), 2.3 (m, 2H), 3.1 (s, 3H), 3.5 (m, 1H) 3.7 (m, 1H), 4.5 (m, 1H), 5.0 (m, 1H), 6.8 (m, 2H), 7.1 (m, 5H), 7.6 (m, 2H), 7.7 (m, 1H), 7.8 (m, 1H), 7.9 (m, 1H), 8.2 (m, 1H); LC/MS M+H 562 (observed).

Example 27

2-[1-(2-chlorophenyl)-1-methylethyl]-4-(1-methylpyrrolidin-2-yl)-1-[3'-(methylsulfonyl)biphenyl-4-yl]-1H-imidazole

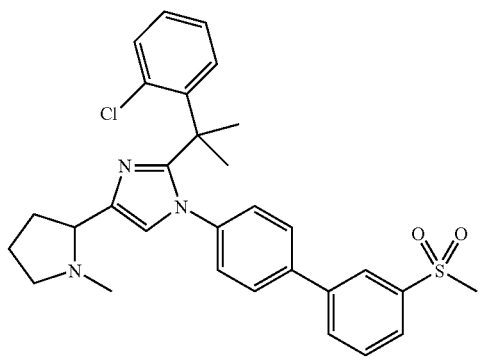

To a solution of 2-[1-(2-chlorophenyl)-1-methylethyl]-1-[3'-(methylsulfonyl)biphenyl-4-yl]-4-pyrrolidin-2-yl-1H-imidazole and MeOH was added formaldehyde, followed by AcOH. The reaction was stirred for 20 min, NaCNBH$_3$ was added to the reaction mixture and was continued to stir for another 30 min. After a routine aqueous work up, the crude product was purified by prep HPLC to give 2-[1-(2-chlorophenyl)-1-methylethyl]-4-(1-methylpyrrolidin-2-yl)-1-[3'-(methylsulfonyl)biphenyl-4-yl]-1H-imidazole: $^1$H NMR (CD$_3$OD): δ 1.6 (m, 3H,), 1.8 (s, 1H), 1.9 (s, 3H), 2.2-2.5 (m, 4H), 2.8 (s, 3H), 3.2 (s, 3H), 3.6 (br, 1H), 4.7 (m, 1H), 7.1 (m, 1H), 7.2 (m, 5H), 7.4 (s, 1H), 7.7 (m, 3H), 8.0 (m, 2H), 8.2 (m, 1H); LC/MS M+H 534 (observed).

Scheme 28

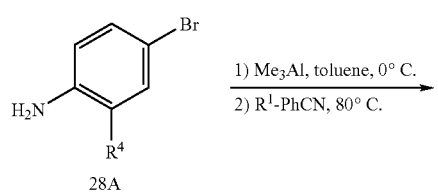

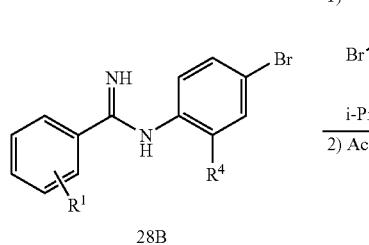

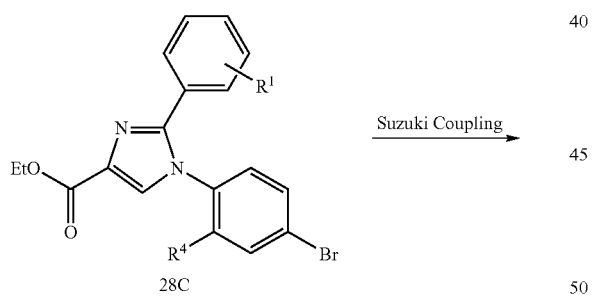

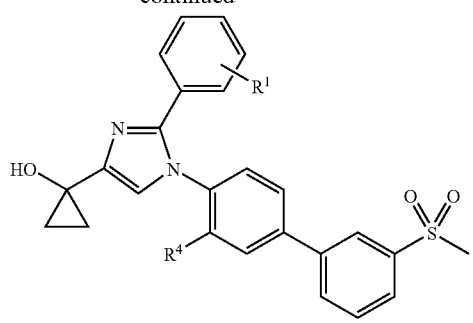

As depicted in Scheme 28, imidazole-ester intermediate was prepared according to Scheme 17 (compound 17C). The ester 28D was reacted with an Grignard reagent EtMgBr to afford cyclopropanol product 28E.

Example 28

1-(2-(2-chlorophenyl)-1-(3'-(methylsulfonyl)biphenyl-4-yl)-1H-imidazol-4-yl)cyclopropanol Example 28a Preparation of 1-(2-(2-chlorophenyl)-1-(3'-(methylsulfonyl)biphenyl-4-yl)-1H-imidazol-4-yl)cyclopropanol

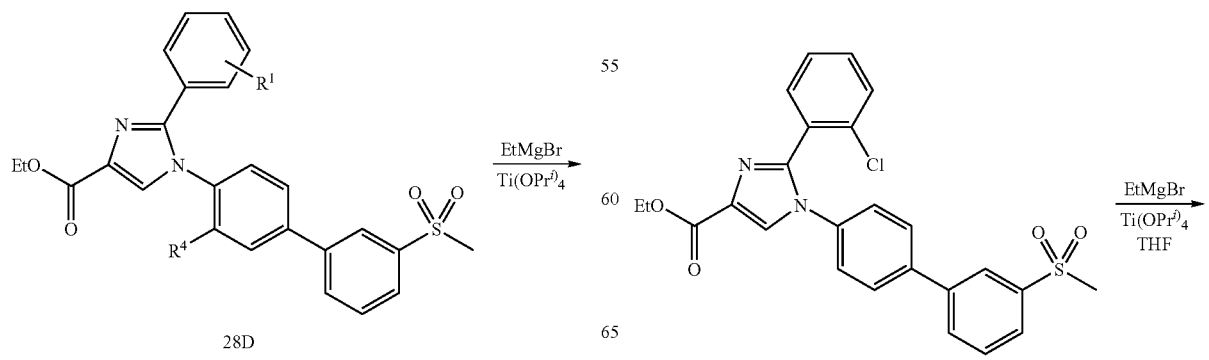

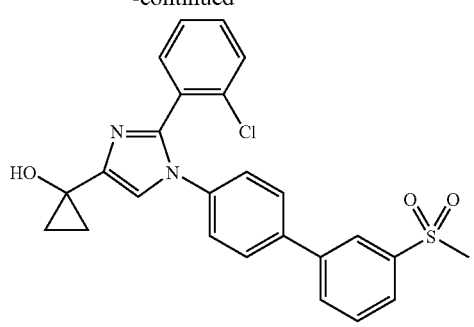

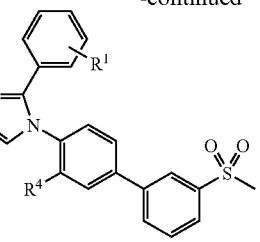

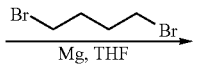

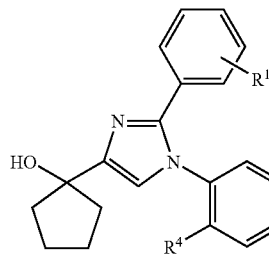

Under nitrogen atmosphere at room temperature to a solution of imidazole ester (ethyl 2-(2-chlorophenyl)-1-(3'-(methylsulfonyl)biphenyl-4-yl)-1H-imidazole-4-carboxylate, 1.3 g, 2.7 mmol) in 25 mL anhydrous THF was added Ti(O-Pr$^i$)$_4$ (0.95 mL, 3.24 mmol) dropwise, followed by ethylmagnesium bromide (15 ml, 15 mmol, 1.0 M in THF). After the addition, the reaction mixture was stirred at room temperature for 3 hrs. At 0° C. the reaction was quenched with sat. ammonium chloride. Filtered through celite, two layers were separated, and the aqueous layer was extracted three times with EtOAc. The combined organic layers were washed with brine, dried over Na$_2$SO$_4$, and concentrated in vacuo. The crude product was chromatographed through a silica gel column using a mobile phase gradient from 100% hexanes to 30% ethyl acetate to afford an white solid (126 mg, 10% yield). $^1$H-NMR (DMSO, 400 MHz) δ 7.97 (m, 4H), 7.79 (m, 2H), 7.57 (m, 1H), 7.45 (m, 4H), 7.30 (m, 2H), 5.98 (s, 1H), 3.26 (S, 3H), 1.03 (t, J=3.2 Hz, 2H); 1.00 (t, J=3.2 Hz, 2H), MS (ES): 465 [M+H]$^+$.

As depicted in Scheme 29, imidazole-ester intermediate was prepared according to Scheme 17 (compound 17C). The ester 29D was reacted with an Grignard reagent made in situ to afford cyclopentanol product 29E.

Example 29

Preparation of 1-(2-(2-chlorophenyl)-1-(3'-(methylsulfonyl)biphenyl-4-yl)-1H-imidazol-4-yl)cyclopentanol

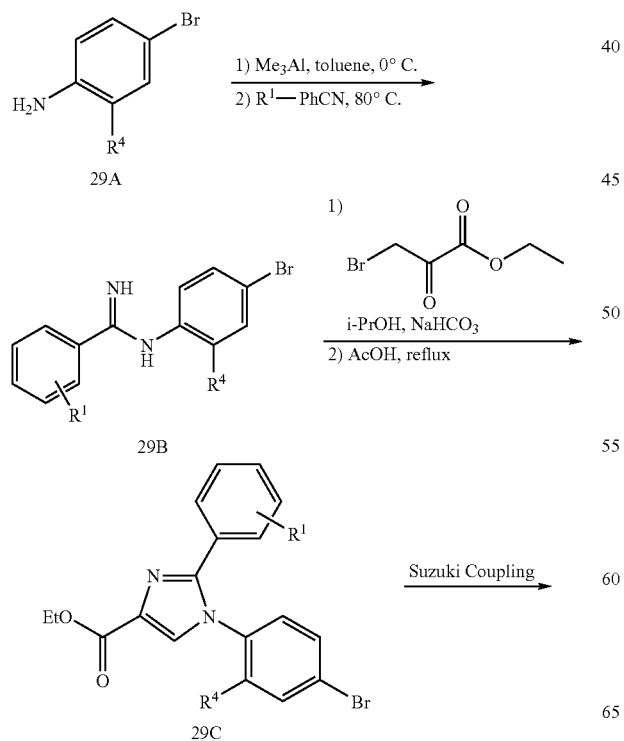

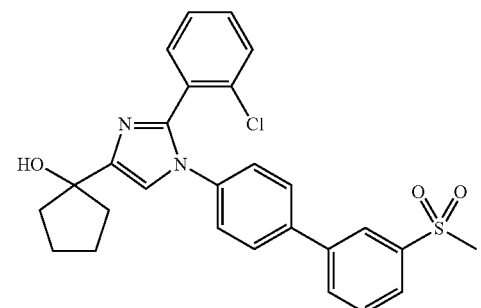

Example 29a

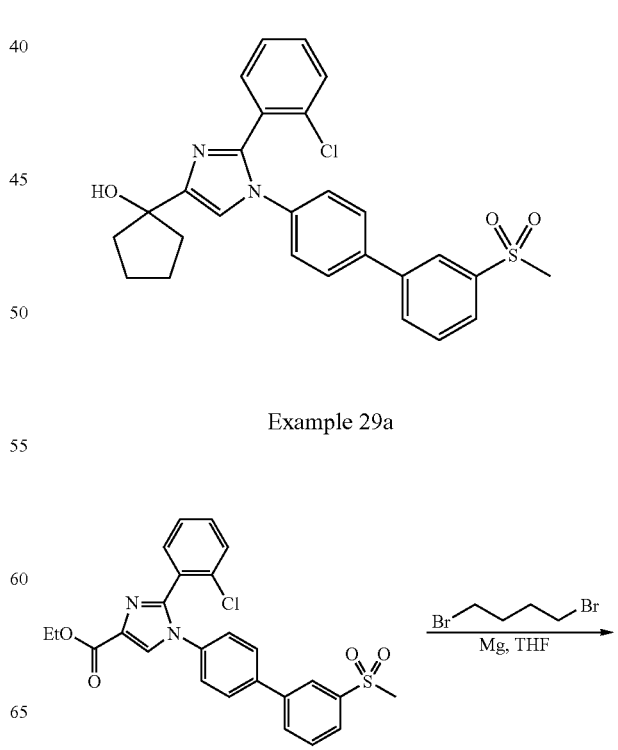

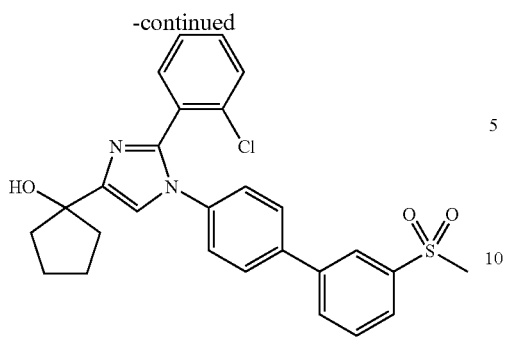

Under nitrogen atmosphere at room temperature magnesium (152 mg, 6.3 mmol) and 8 mL anhydrous THF were placed into a three-neck flask. To it was added a solution of dibromobutane (648 mg, 3 mmol) in 1.5 mL anhydrous THF dropwise. The mixture was stirred at room temperature for 1 h, then heated to 40° C. solution till all magnesium turnings went into solution. The mixture was allowed to cool to room temperature, then to it was added a solution of imidazole ester (ethyl 2-(2-chlorophenyl)-1-(3'-(methylsulfonyl)biphenyl-4-yl)-1H-imidazole-4-carboxylate, 1.2 g, 2.5 mmol) in 5 mL anhydrous THF. After the addition, the reaction mixture was stirred at room temperature for 2 hrs, the heated to 45° C. for 1 h. At room temperature the reaction was quenched with sat. ammonium chloride. Two layers were separated, and the aqueous layer was extracted three times with EtOAc. The combined organic layers were washed with brine, dried over $Na_2SO_4$, and concentrated in vacuo. The crude product was chromatographed through a Silica gel column using a mobile phase gradient from 90% hexanes to 90% ethyl acetate to afford a white solid (85 mg, 7% yield). $^1$H-NMR (CDCl$_3$, 400 MHz) δ 8.00 (m, 2H), 7.74 (m, 2H), 7.54 (m, 3H), 7.33 (m, 3H), 7.23 (m, 2H), 7.20 (s, 1H), 3.01 (s, 3H), 2.52 (br s, 1H), 2.18 (m, 2H); 2.04 (m, 4H), 1.85 (m, 2H); MS (ES): 493 [M+H]$^+$.

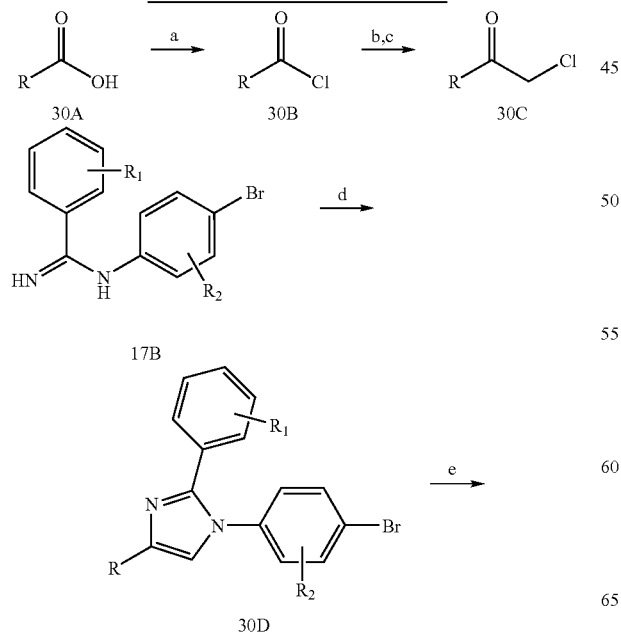

Scheme 30
Preparation of 4-aryl-imidazole anlogs:

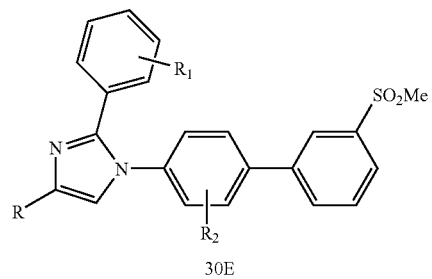

30E a) ClCOCOCl, CH$_2$Cl$_2$, 0-25° C.;
b) TMSCHN$_2$, 1:1-CH$_3$CN-THF, 0-25° C.;
c) HCl-dioxane; CH$_2$Cl$_2$, 0-25° C.;
d) i) NaHCO$_3$ As depicted in Scheme 30, carboxylic acids 30A were easily converted to more reactive acid halides 30B using a variety of reagents such as oxalyl chloride. Acid halides, and similarly reactive acyl derivatives, reacted with (trimethylsilyl)diazomethane (or diazomethane) to form a diazoketone. Such diazoketones were decomposed upon treatment with acid to form alpha-haloketones 30C. The amidine 17D was prepared according to Scheme 17. The reaction of alpha-haloketones 30C with aryl amidines 17B proceeded in a regioselective fashion to initially provide a hydroxyimidazoline which dehydrated to form imidazoles 30D under reaction conditions or with the aid of catalysts such as acetic acid. Imidazoles 30D were then coupled with aryl boronic acids to produce imidazoles 30E.

Example 30

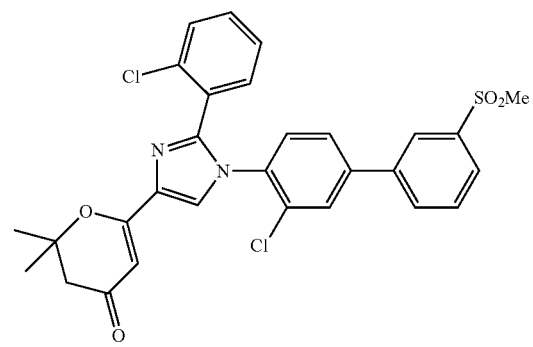

6-[1-(3-Chloro-3'-methanesulfonyl-biphenyl-4-yl)-2-(2-chlorophenyl)-1-H-imidazol-4-yl]-2,2-dimethyl-2,3-dihydro-pyran-4-one Example 30a Preparation of 6-(2-Chloroacetyl)-2,2-dimethyl-2,3-dihydropyran-4-one

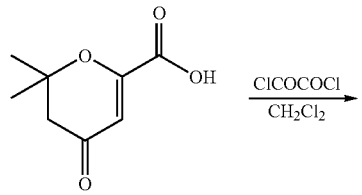

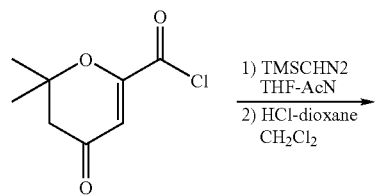

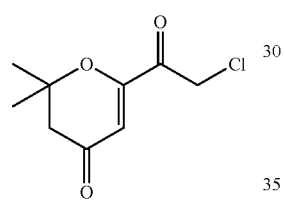

Into a 250 mL flask was weighed 4.97 g of 6,6-Dimethyl-4-oxo-5,6-dihydro-4H-pyran-2-carboxylic acid (29.2 mmol), 50 mL of dichloromethane, and 1 mL of DMF. The resulting solution was cooled to 0-3° C. in an ice bath and 2.55 mL (1.0 eq) of oxalyl chloride was added under nitrogen. The reaction was allowed to warm to room temperature over 1.5 hours then the reaction was washed into a separatory funnel with dichloromethane and saturated NaHCO₃. The dichloromethane was separated, dried (Na₂SO₄), and concentrated in vacuo. The resulting acid chloride was recovered as a colorless oil, yield: 5.00 g (91%).

A 250 mL flask was charged with 5.0 g of the acid chloride (26.5 mmol), 15.0 mL of each THF and acetonitrile, then 1.2 eq of TMS-diazomethane (1.0 M in diethyl ether, Aldrich) was added. The reaction was stirred at room temperature for 3 h then was washed into a separatory funnel with ethyl acetate and saturated NaHCO₃. The organic phase was separated, washed with brine, was dried, (Na₂SO₄), and concentrated in vacuo.

The residue was dissolved in 50 mL of dichloromethane and was treated with 1.0 eq of 4.0 M HCl-dioxane. The reaction was stirred at room temperature for 1 h then was washed into a separatory funnel with ethyl acetate and 1.0 M Na₂CO₃. The organic phase was separated, washed with brine, was dried (Na₂SO₄), and concentrated in vacuo. The residue was purified by silica gel flash chromatography (Biotage, 80 g SiO₂, gradient elution from 100% hexanes to 40% EtOAc over 1 h) affording the product as an orange solid, yield: 642 mg (11%); $^1$H NMR (400 MHz, CDCl₃): δ 6.15 (s, 1H), 4.52 (s, 2H), 2.58 (s, 2H), 1.51 (s, 6H); MS (EI): 202 [M]⁻.

Example 30b

Preparation of 6-[J-(4-Bromo-2-chlorophenyl)-2-(2-chlorophenyl)-1H-imidazol-4-yl]-2,2-dimethyl-2,3-dihydropyran-4-one

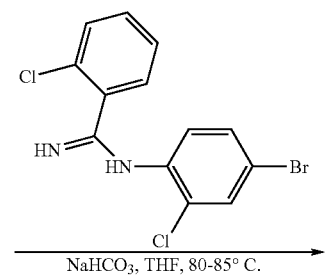

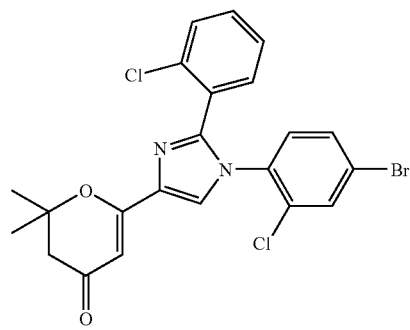

Into a 100 mL flask was weighed 642 mg of alpha-chloroketone (3.17 mmol), 1.05 g (3.05 mmol) of amidine, 258 mg of NaHCO₃, and 10 mL of THF. The resulting suspension was heated at 80-85° C. for 24 h then was washed into a separatory funnel with ethyl acetate and water. The ethyl acetate was separated, washed with brine, was dried (Na₂SO₄), and concentrated in vacuo. The residue was purified by silica gel flash chromatography (Biotage, 80 g SiO₂), gradient elution from 100% hexanes to 40% ethyl acetate over 1 h). Appropriate fractions were combined and concentrated in vacuo affording the product as an orange solid, yield: 650.7 mg (42%); $^1$H NMR (400 MHz, CDCl₃): δ 7.62 (d, J=2 Hz, 1H), 7.59 (s, 1H), 7.48 (d, J=8 Hz, 1H), 7.25-7.34 (m, 4H), 7.10 (d, J=8 Hz, 1H), 6.29 (s, 1H), 2.59 (s, 2H), 1.54 (s, 6H); MS (CI): 492 and 494, each [M+H]$^+$.

Example 30c

Preparation of 6-[1-(3-Chloro-3'-methanesulfonyl-biphenyl-4-yl)-2-(2-chlorophenyl)-1-H-imidazol-4-yl]-2,2-dimethyl-2,3-dihydro-pyran-4-one

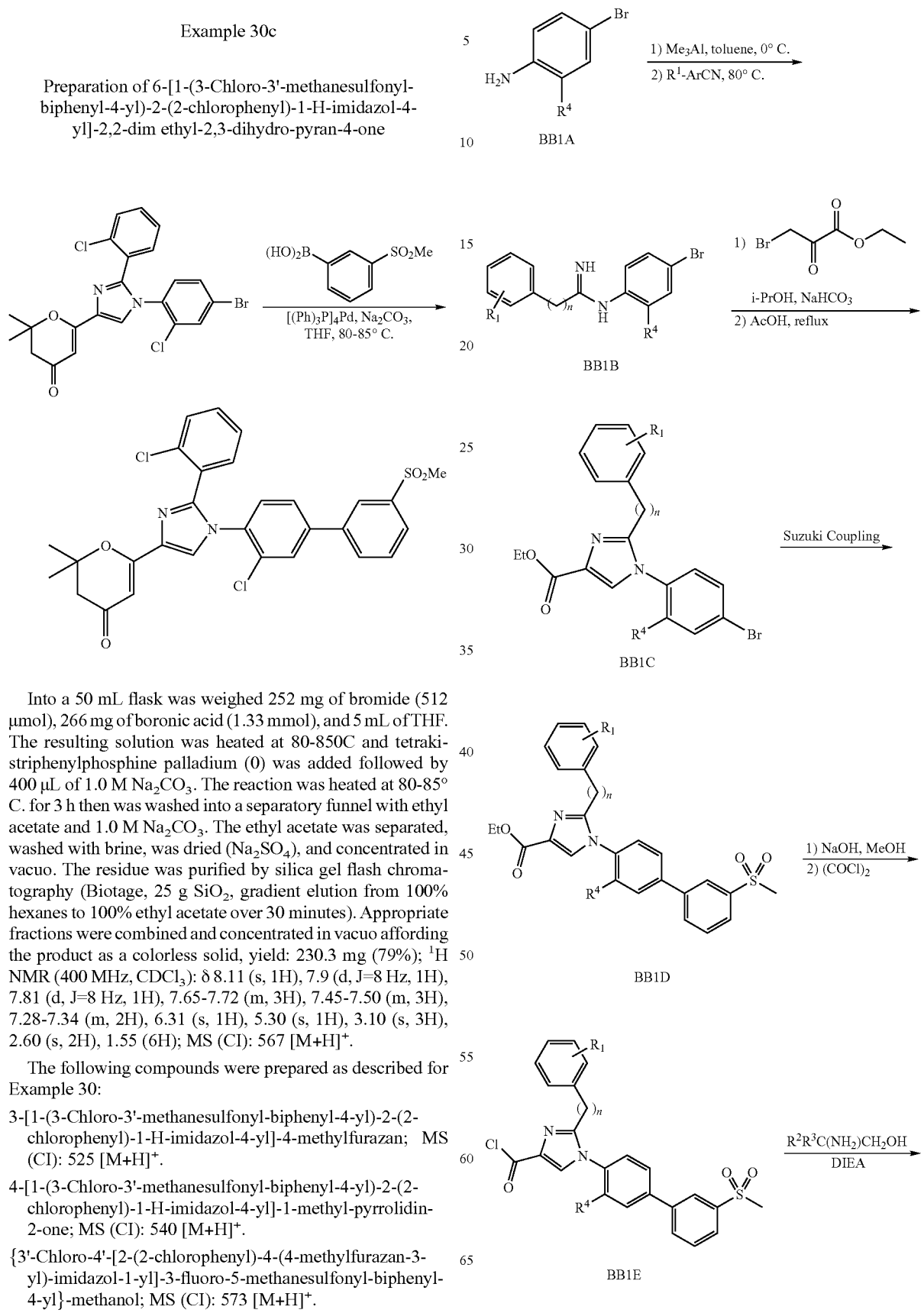

Scheme 31

Into a 50 mL flask was weighed 252 mg of bromide (512 µmol), 266 mg of boronic acid (1.33 mmol), and 5 mL of THF. The resulting solution was heated at 80-85°C and tetrakistriphenylphosphine palladium (0) was added followed by 400 µL of 1.0 M Na$_2$CO$_3$. The reaction was heated at 80-85° C. for 3 h then was washed into a separatory funnel with ethyl acetate and 1.0 M Na$_2$CO$_3$. The ethyl acetate was separated, washed with brine, was dried (Na$_2$SO$_4$), and concentrated in vacuo. The residue was purified by silica gel flash chromatography (Biotage, 25 g SiO$_2$, gradient elution from 100% hexanes to 100% ethyl acetate over 30 minutes). Appropriate fractions were combined and concentrated in vacuo affording the product as a colorless solid, yield: 230.3 mg (79%); $^1$H NMR (400 MHz, CDCl$_3$): δ 8.11 (s, 1H), 7.9 (d, J=8 Hz, 1H), 7.81 (d, J=8 Hz, 1H), 7.65-7.72 (m, 3H), 7.45-7.50 (m, 3H), 7.28-7.34 (m, 2H), 6.31 (s, 1H), 5.30 (s, 1H), 3.10 (s, 3H), 2.60 (s, 2H), 1.55 (6H); MS (CI): 567 [M+H]$^+$.

The following compounds were prepared as described for Example 30:

3-[1-(3-Chloro-3'-methanesulfonyl-biphenyl-4-yl)-2-(2-chlorophenyl)-1-H-imidazol-4-yl]-4-methylfurazan; MS (CI): 525 [M+H]$^+$.

4-[1-(3-Chloro-3'-methanesulfonyl-biphenyl-4-yl)-2-(2-chlorophenyl)-1-H-imidazol-4-yl]-1-methyl-pyrrolidin-2-one; MS (CI): 540 [M+H]$^+$.

{3'-Chloro-4'-[2-(2-chlorophenyl)-4-(4-methylfurazan-3-yl)-imidazol-1-yl]-3-fluoro-5-methanesulfonyl-biphenyl-4-yl}-methanol; MS (CI): 573 [M+H]$^+$.

599
-continued

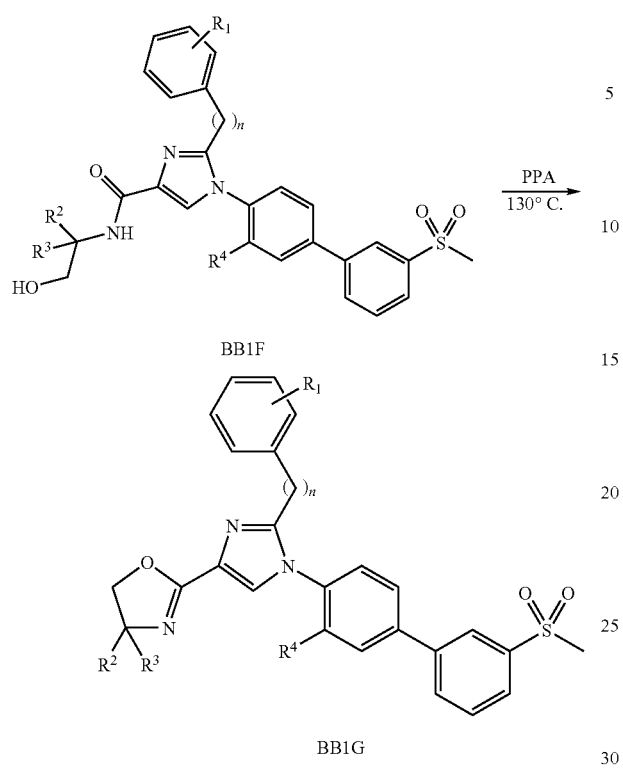

As depicted in Scheme 31, imidazole-oxazolines templates BB1G were prepared via cyclization of 2-hydroxyethylamide analogue BB1F using known methodology. The imidazole ester BB1D was prepared according to Scheme 17. The ester group on BB1D was hydrolyzed to afford the carboxylic acid derivative, which was treated with oxalyl chloride to yield acid chloride BB1E. Acid chloride BB1E was reacted with an ethanolamine derivative ($R^2R^3C(HN_2)CH_2OH$) to afford hydroxyethylamide BB1F, which was cyclized in the presence of PPA to afford oxazoline (4,5-dihydro-oxazoles) BB1G.

Example 31a 2-(1-(3-chloro-3'-(methylsulfonyl)biphenyl-4-yl)-2-(2-chlorophenyl)-1H-imidazol-4-yl)-4,4-dimethyl-4,5-dihydrooxazole

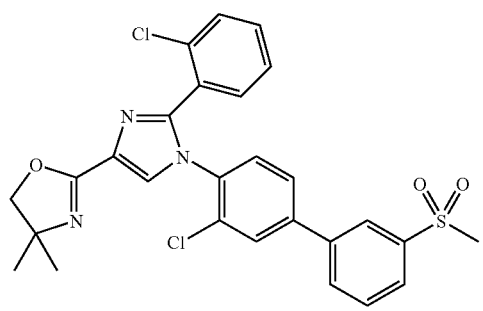

600

Example 31a1

Preparation of 1-(4-Bromo-2-chloro-phenyl)-2-(2-chlorophenyl)-1H-imidazole-4-carboxylic acid

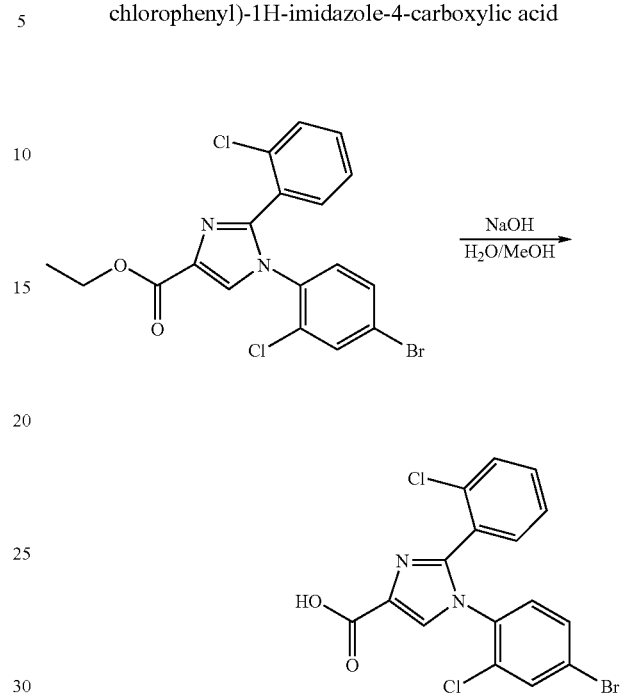

To a 250 mL round bottom flask was added 1-(4-Bromo-2-chloro-phenyl)-2-(2-chlorophenyl)-1H-imidazole-4-carboxylic acid ethyl ester (3.60 g, 8.18 mmol), MeOH (65 mL), and 1N aq NaOH (41 mL). The reaction solution was allowed to stir at 50° C. for 2 hr. The reaction solution was diluted with EtOAc (200 mL), neutralized by the addition of aq 1 N HCl, and poured into a separatory funnel. The organic phase was partitioned, and the aqueous phase was and extracted with EtOAc (150 mL×2). The combined organic phases were dried over $Na_2SO_4$, filtered into a round bottom flask and concentrated on the Rotavapor. The crude residue was reprecipitated in an EtOAc/hexane solution and the solid precipitate was filtered under vacuum to afford 2.98 g (88% yield) of title product. MS (ESI) 410.3, 412.3, 414.3 $[M+H]^+$.

Example 31a2

Preparation of 1-(4-bromo-2-chlorophenyl)-2-(2-chlorophenyl)-N-(1-hydroxy-2-methylpropan-2-yl)-1H-imidazole-4-carboxamide

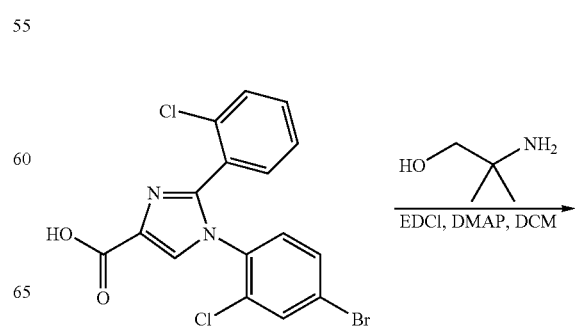

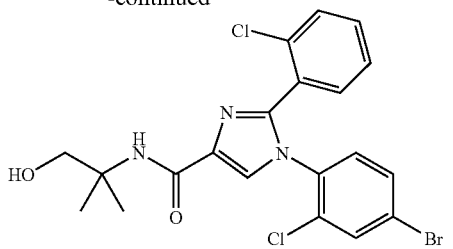

To a dry, N$_2$ purged 250 mL round bottom flask was added 1-(4-Bromo-2-chlorophenyl)-2-(2-chloro-phenyl)-1H-imidazole-4-carboxylic acid (2.97 g, 7.21 mmol) and anhydrous DCM (70 mL). To the reaction flask was added EDCI (2.76 g, 14.4 mmol), DMAP (180 mg, 1.44 mmol), and 2-amino-2-methyl-propanol (2.1 mL, 21.6 mmol). The reaction solution was allowed to stir at room temperature for 16 h. The reaction solution was concentrated in vacuo and the residue was dissolved in EtOAc (200 mL). The EtOAc solution was washed with aq HCl (100 mL×2) and aq NaCl (150 mL). The organic phase was dried over Na$_2$SO$_4$, filtered, concentrated on the Rotavapor and chromatographed through a 25 g SiO$_2$ column using a mobile phase gradient of 100% hexane to 100% EtOAc to afford 980 mg (28% yield) of amide product. MS (ESI) 481.2, 483.2, 485.2 [M+H]$^+$; $^1$H NMR (400 MHz, CDCl$_3$) δ 7.76 (s, 1H), 7.61 (d, J=2 Hz, 1H), 7.43 (d, J=7.6 Hz, 1H), 7.33-7.37 (m, 2H), 7.24-7.30 (m, 2H), 7.08 (d, J=9 Hz, 1H), 5.34 (br s, 1H), 3.72 (br s, 2H), 1.41 (s, 6H).

Example 31a3

Preparation of 1-(3-chloro-3'-(methylsulfonyl)biphenyl-4-yl)-2-(2-chlorophenyl)-N-(1-hydroxy-2-methylpropan-2-yl)-1H-imidazole-4-carboxamide

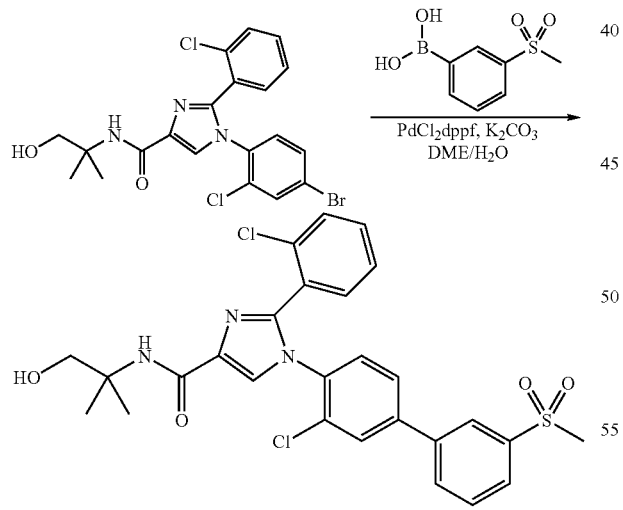

To a 100 mL round bottom flask attached with condenser column and magnetic stir bar was added 1-(4-bromo-2-chlorophenyl)-2-(2-chlorophenyl)-N-(1-hydroxy-2-methylpropan-2-yl)-1H-imidazole-4-carboxamide (956 mg, 1.98 mmol), 3-methylsulfonylphenyl boronic acid (435 mg, 2.18 mmol), PdCl$_2$dppf (150 mg, 10 mol %), K$_2$CO$_3$ (830 mg, 6.00 mmol), 1,2-dimethoxyethane (50 mL) and H$_2$O (13 mL). The reaction solution was allowed to stir at 80° C. for 2.5 hrs. The reaction solution was diluted with EtOAc (150 mL) and filtered through a Celite padded Buchner funnel to remove spent Pd. The filtrate was transferred to a separatory funnel and washed with aq NH$_4$Cl (100 mL) and aq NaCl (100 mL). The organic phase was dried over Na$_2$SO$_4$, filtered, concentrated on the Rotavapor and chromatographed through a 25 g SiO$_2$ column using a mobile phase gradient of 5% EtOAc to 100% EtOAc to afford 885 mg (80% yield) of the title compound. MS (ESI) 556.3, 558.3, 560.3 [M+H]$^+$; $^1$H NMR (400 MHz, DMSO-d$_6$) δ 8.22 (t, J=1.7 Hz, 1H), 8.06-8.13 (m, 2H), 8.03 (s, 1H), 7.96 (d, J=7.8 Hz, 1H), 7.82 (dd, J$_1$=7.3 Hz, J$_2$=1.5 Hz, 1H), 7.75 (t, J=7.8 Hz, 1H), 7.60 (d, J=8.2 Hz, 2H), 7.38-7.48 (m, 3H), 5.18 (br s, 1H), 3.45 (s, 2H), 3.36 (br s, 1H), 3.31 (s, 3H), 1.37 (s, 6H).

Example 31a4

Preparation of 2-(1-(3-chloro-3'-(methylsulfonyl) biphenyl-4-yl)-2-(2-chlorophenyl)-1H-imidazol-4-yl)-4,4-dimethyl-4,5-dihydrooxazole

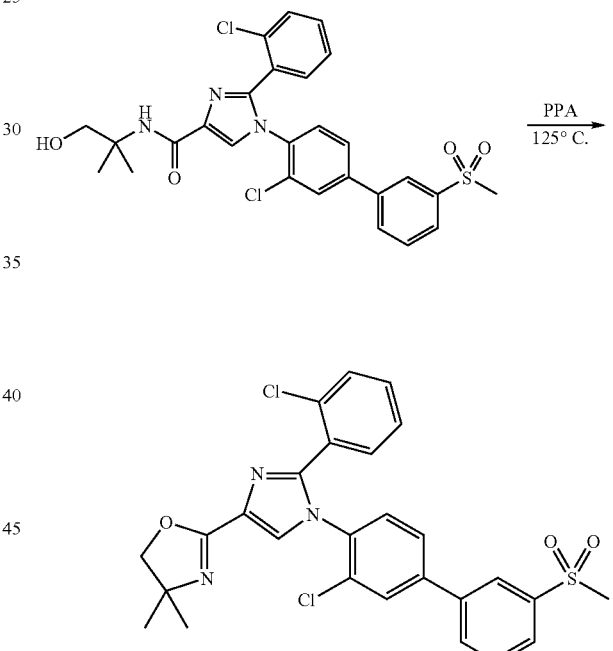

To a 40 mL glass vial containing 1-(3-chloro-3'-(methylsulfonyl)biphenyl-4-yl)-2-(2-chlorophenyl)-N-(1-hydroxy-2-methylpropan-2-yl)-1H-imidazole-4-carboxamide (315 mg, 564 μmol) was added polyphosphoric acid (19 g, 115% H$_3$PO$_4$). The mixture was allowed to heat and stir at 125° C. for 1.5 hr. The reaction mixture was cooled to room temperature prior to addition of ice/H$_2$O (400 mL). The aqueous reaction mixture was extracted with dichloromethane (50 mL×3). The organic phase was dried over Na$_2$SO$_4$, filtered and concentrated in vacuo. The crude product was chromatographed through a 12 g SiO$_2$ column using a gradient of 5% EtOAc to 100% EtOAc to afford 193 mg (63% yield) of title product. MS (ESI) 546.2, 548.2, 550.2 [M+H]$^+$; $^1$H NMR (400 MHz, CDCl$_3$) δ 8.10 (t, J=1.7 Hz, 1H), 7.97 (d, J=8.0 Hz, 1H), 7.83 (d, J=8.0 Hz, 1H), 7.81 (s, 1H), 7.65-7.70 (m, 2H), 7.57 (dd, J=7.3 Hz, J₂=1.5 Hz, 1H), 7.43 (dd, J=8.3 Hz, J₂=2.0 Hz, 1H), 7.25-7.32 (m, 4H), 4.15 (s, 2H), 3.10 (s, 3H), 1.42 (s, 6H).

Example 31b 2-(2-(2-(2-chlorophenyl)propan-2-yl)-1-(3'-(methylsulfonyl)biphenyl-4-yl)-1H-imidazol-4-yl)-4,4-dimethyl-4,5-dihydrooxazole

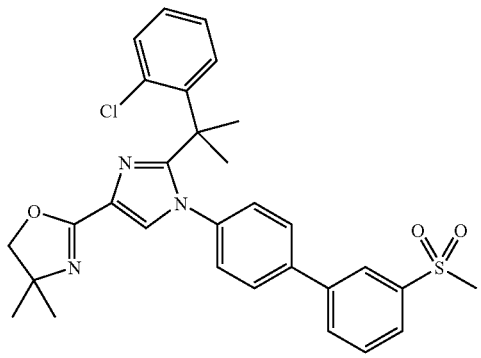

Example 31b1

Preparation of 2-(2-(2-chlorophenyl)propan-2-yl)-N-(1-hydroxy-2-methylpropan-2-yl)-1-(3'-(methylsulfonyl)biphenyl-4-yl)-H-imidazole-4-carboxamide

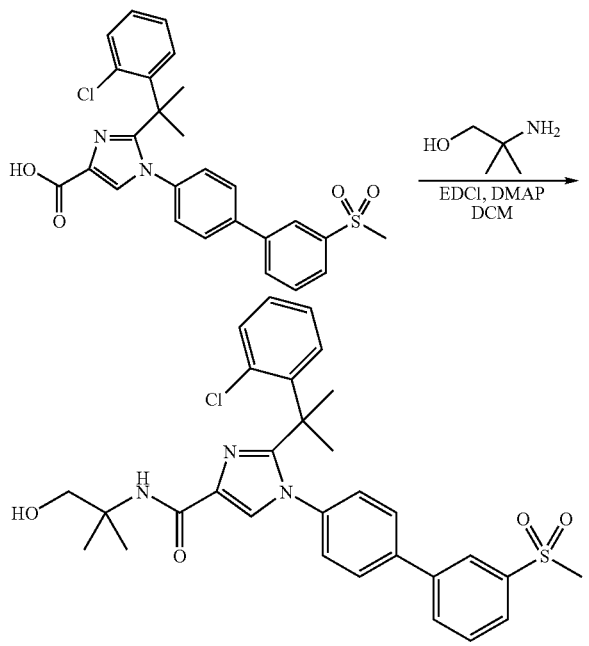

In a manner similar to that described in Example 31a 2-(2-(2-chlorophenyl)propan-2-yl)-N-(1-hydroxy-2-methylpropan-2-yl)-1-(3'-(methylsulfonyl)biphenyl-4-yl)-1H-imidazole-4-carboxamide can be synthesized from 2-(2-(2-chlorophenyl)propan-2-yl)-N-(1-hydroxy-2-methylpropan-2-yl)-1-(3'-(methylsulfonyl)biphenyl-4-yl)-1H-imidazole-4-carboxylic acid, obtained in a manner similar to that described in Example 28c. The title compound was isolated 210 mg (44% yield) as an off-white powder. MS (ESI) 566.3, 568.3 [M+H]⁺; ¹H NMR (400 MHz, CDCl₃) δ 8.01 (br s, 1H), 7.95 (d, J=7.6 Hz, 1H), 7.72 (d, J=8.3 Hz, 1H), 7.66 (t, J=8.3 Hz, 1H), 7.44 (s, 1H), 7.36 (br s, 1H), 7.25 (d, J=8.6 Hz, 2H), 7.20 (dd, J=8.0 Hz, J₂=1 Hz, 1H), 7.03 (t, J=7.6 Hz, 1H), 6.96 (d, J=8.6 Hz, 2H), 6.91 (d, J=8.0 Hz, 1H), 6.86 (t, J=8.0 Hz, 1H), 5.61 (t, J=6.0 Hz, 1H), 3.74 (d, J=6.0 Hz, 2H), 3.11 (s, 3H), 1.82 (s, 6H), 1.47 (s, 6H).

Example 31b2

Preparation of 2-(2-(2-(2-chlorophenyl)propan-2-yl)-1-(3'-(methylsulfonyl)biphenyl-4-yl)-1H-imidazol-4-yl)-4,4-dimethyl-4,5-dihydrooxazole

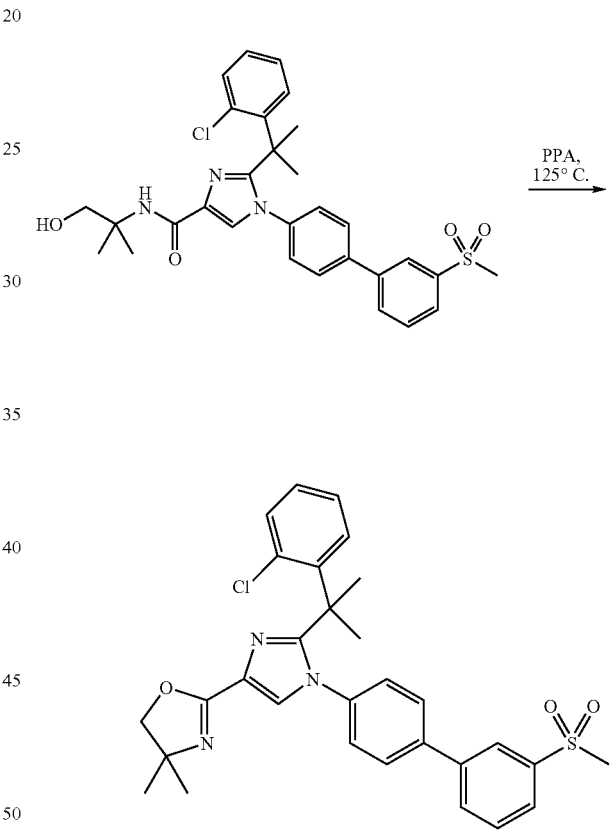

In a manner similar to that described in Example 31a2 2-(2-(2-(2-chlorophenyl)propan-2-yl)-1-(3'-(methylsulfonyl)biphenyl-4-yl)-1H-imidazol-4-yl)-4,4-dimethyl-4,5-dihydrooxazole can be synthesized from 2-(2-(2-chlorophenyl)propan-2-yl)-N-(1-hydroxy-2-methylpropan-2-yl)-1-(3'-(methylsulfonyl)biphenyl-4-yl)-1H-imidazole-4-carboxamide. The crude product was chromatographed through a 12 g SiO₂ column using a gradient of 5% EtOAc to 100% EtOAc to afford 79 mg (54% yield) of title product. MS (ESI) 548.2 [M+H]⁺; ¹H NMR (400 MHz, DMSO-d₆) δ 8.09 (br s, 1H) 8.00 (d, J=7.6 Hz, 1 Hz), 7.95 (d, J=7.6 Hz, 1H), 7.81 (t, J=8.0 Hz, 1H), 7.62 (s, 1H), 7.52 (d, J=8.6 Hz, 2H), 7.29 (dd, J=7.8 Hz, J₂=1 Hz, 1H), 7.05-7.18 (m, 4H), 6.99 (t, J=7.6 Hz, 1H), 4.07 (s, 2H), 3.37 (s, 3H), 1.81 (s, 6H), 1.34 (s, 6H).

Scheme 32

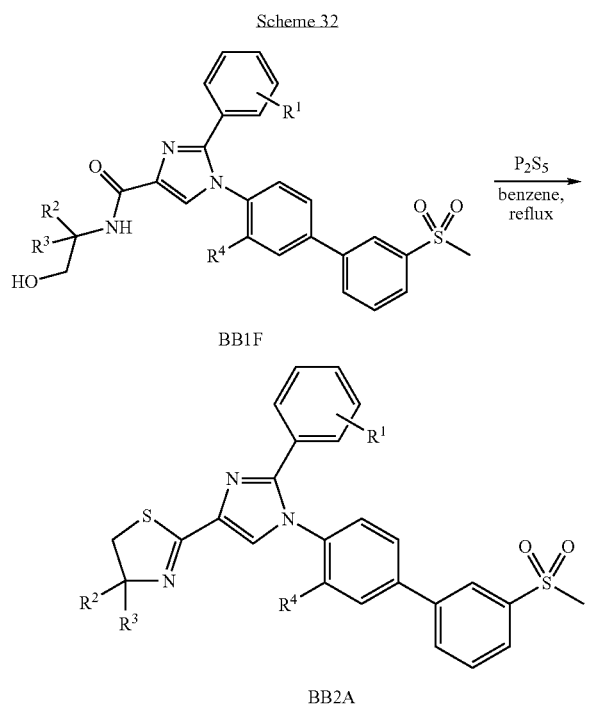

As depicted in Scheme 32, methods for the preparation of the thiazoline ring are known. By example, amide BB1F was treated with phosphorus pentasulfide in refluxing benzene to synthesize the thiazoline analogue BB2A.

Example 32

2-(1-(3-chloro-3'-(methylsulfonyl)biphenyl-4-yl)-2-(2-chlorophenyl)-1H-imidazol-4-yl)-4,4-dimethyl-4,5-dihydrothiazole

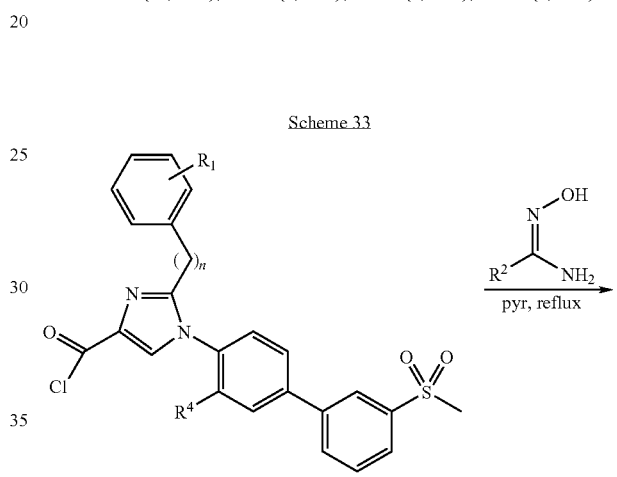

To a $N_2$ purged 50 mL round bottom flask attached with condenser was added 1-(3-chloro-3'-(methylsulfonyl)biphenyl-4-yl)-2-(2-chlorophenyl)-N-(1-hydroxy-2-methyl propan-2-yl)-1H-imidazole-4-carboxamide (361 mg, 646 μmol), anhydrous benzene (20 mL) and $P_2S_5$ (720 mg, 3.24 mmol). The reaction solution was stirred at reflux for 1.5 hr. The reaction solution was diluted with EtOAc (100 mL) and filtered through a Buchner funnel to remove excess $P_2S_5$. The filtrate was washed with aq. 0.1 N NaOH (60 mL) and $H_2O$ (100 mL). The partitioned organic phase was dried over $Na_2SO_4$, filtered, concentrated in vacuo, and chromatographed through a 12 g $SiO_2$ column using a gradient of 100% hexane to 95% EtOAc to afford 68 mg (19% yield) of title compound. MS (ESI) 556.3, 558.3 $[M+H]^+$; $^1H$ NMR (400 MHz, $CDCl_3$) δ 8.10 (t, J=2.0 Hz, 1H), 7.97 (d, J=8.0 Hz, 1H), 7.83 (d, J=8.0 Hz, 1H), 7.79 (br s, 1H), 7.66-7.70 (m, 2H), 7.55 (d, J=7.2 Hz, 1H), 7.43 (dd, $J_1$ 8.5=Hz, $J_2$=2.0 Hz, 1H), 7.27-7.33 (m, 4H), 3.22 (s, 2H), 3.10 (s, 3H), 1.51 (s, 6H).

Scheme 33

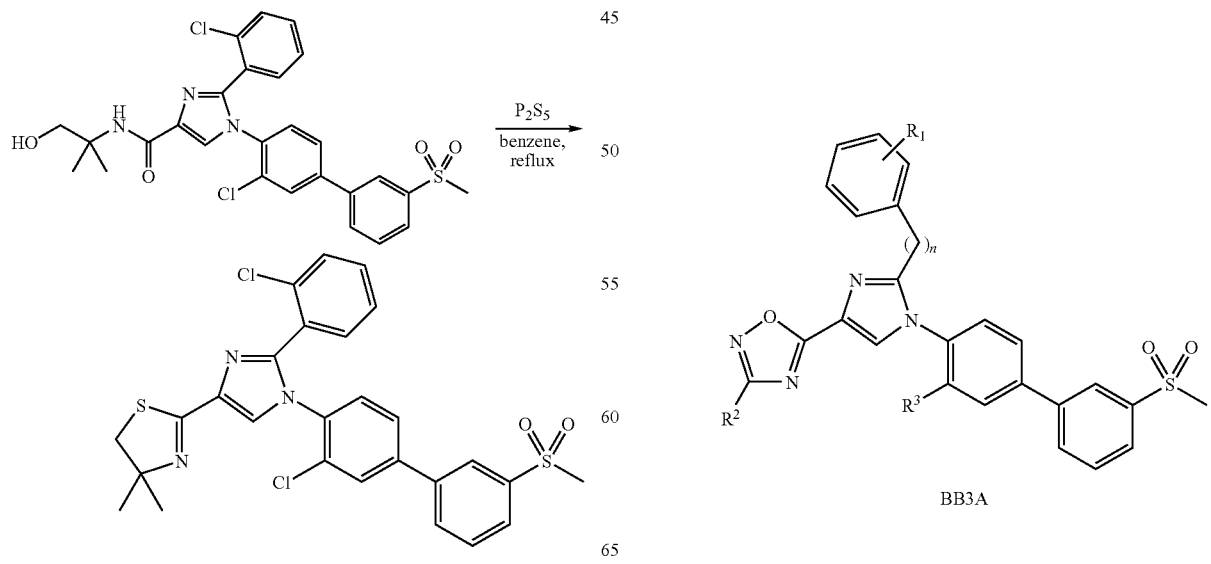

As depicted in Scheme 33, [1,2,4]-oxadiazole containing imidazole templates can be synthesized using known methods. By example, acid chloride BB1E was treated with acetamide oxime and base to afford [1,2,4]-oxadiazole BB3A.

Example 33

5-[1-(3'-methanesulfonyl-biphenyl-4-yl)-2-(2-chlorobenzyl)-1H-imidazol-4-yl]-3-methyl-[1,2,4]oxadiazole

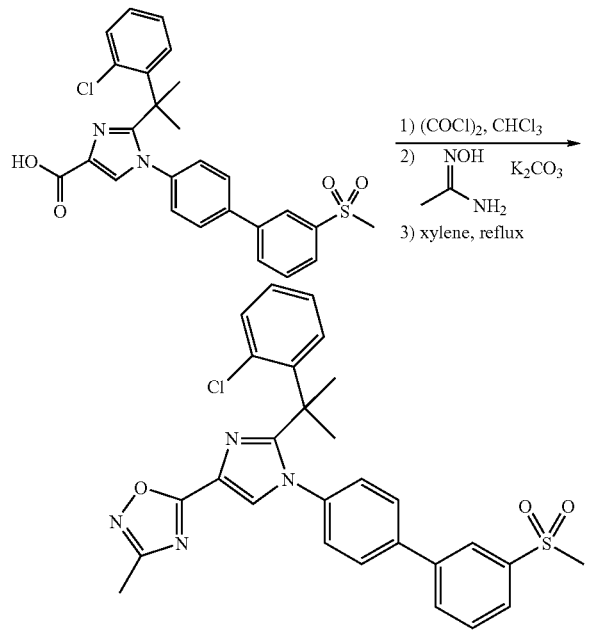

To a 100 mL round bottom flask was added 1-(3-Chloro-3'-methanesulfonylbiphenyl-4-yl)-2-(2-chlorobenzyl)-1H-imidazole-4-carboxylic acid, obtained in a manner similar to that described for 1-(4-Bromo-2-chloro-phenyl)-2-(2-chlorophenyl)-1H-imidazole-4-carboxylic acid in Example BB1 (350 mg, 707 µmol) and anhydrous CHCl$_3$ (15 mL). The reaction solution was cooled to 0° C. prior to addition of oxalyl chloride (310 µL, 3.54 mmol) and 1 drop of anhydrous DMF. The reaction solution was allowed to stir warming to room temperature over 1.5 h. The solution was concentrated in vacuo and the residue was dissolved in anhydrous 1,4-dioxane (20 mL). To the reaction flask was added acetamide oxime (104 mg, 1.41 mmol) and K$_2$CO$_3$ (293 mg, 2.12 mmol). The mixture was stirred at room temperature for 1 hr prior to addition of xylene (43 mL) and raising the reaction temperature to reflux for 16 hrs. The reaction solution was diluted with EtOAc (100 mL) and washed with sat aq. NH$_4$Cl (150 mL×2). The organic phase was dried over Na$_2$SO$_4$, filtered, concentrated in vacuo, and chromatographed through a 25 g SiO$_2$ column using a 100% hexane to 100% EtOAc gradient to yield 115 mg (31% yield) of title compound. MS (ESI) 533.3, 535.3 [M+H]$^+$; $^1$H NMR (400 MHz, DMSO-d$_6$) δ 8.16 (s, 1H), 8.06 (s, 1H), 7.97 (d, J=7.6 Hz, 1H), 7.91 (d, J=7.6 Hz, 1H), 7.76 (t, J=7.6 Hz, 1H), 7.50 (d, J=8.4 Hz, 2H), 7.26 (dd, J=7.8 Hz, J$_2$=1 Hz, 1H), 7.12 (d, J=8.4 Hz, 2H), 7.09 (m, 1H), 7.02 (dd, J=7.8 Hz, J$_2$=1 Hz, 1H), 6.95 (t, J=8 Hz, 1H), 3.32 (s, 3H), 2.39 (s, 3H), 1.79 (s, 3H).

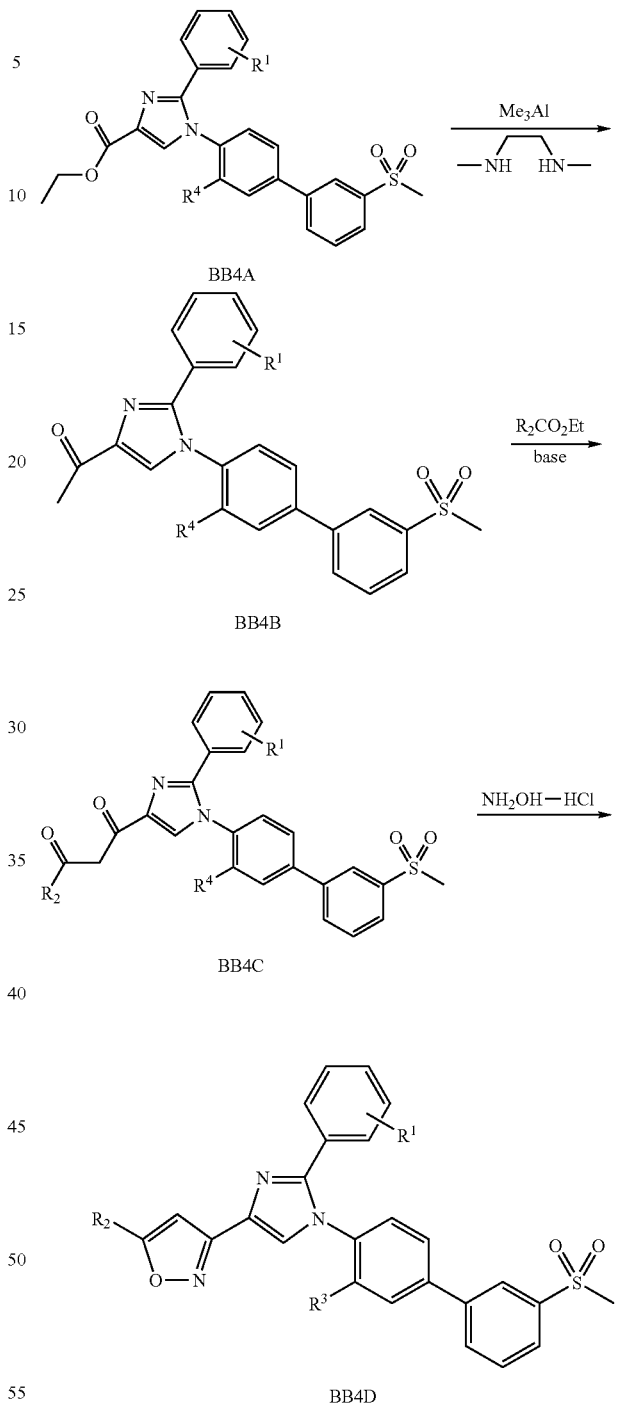

As depicted in Scheme 34, isoxazole containing imidazole template BB4D can be synthesized using known methods. Imidazole templates containing a ketone group at the C4 position, such as compound BB4B can be synthesized from imidazole ethylester BB4A by reaction with trimethylaluminum and N,N'-dimethylethylenediamine. 1,3-diketone compounds such as template BB4C can be synthesized from ketone compound BB4B using a variety of known Claisen type condensations. These 1,3-diketones can be used as starting materials to prepare isoxazoles. By example, 1,3-diketone BB4C was treated with hydroxyamine under typical condensation conditions to afford isoxazole BB4D.

Example 34

3-(1-(3-chloro-3'-(methylsulfonyl)biphenyl-4-yl)-2-(2-chlorophenyl)-1H-imidazol-4-yl)-5-(trifluoromethyl)isoxazole

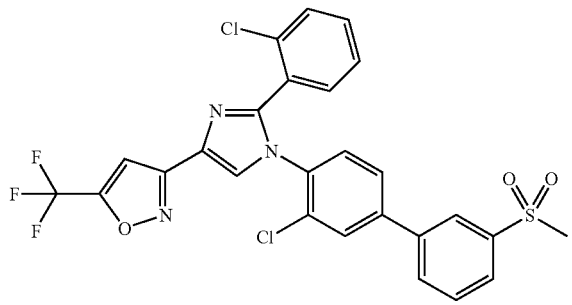

Example 34a

Preparation of 1-(1-(4-bromo-2-chlorophenyl)-2-(2-chlorophenyl)-1H-imidazol-4-yl)-4,4,4-trifluorobutane-1,3-dione

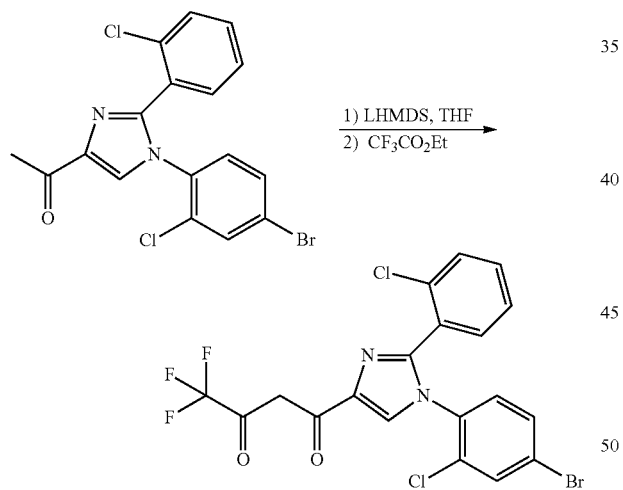

To a dry N₂ purged 50 mL round bottom flask attached with addition funnel was added 1-(1-(4-bromo-2-chlorophenyl)-2-(2-chlorophenyl)-1H-imidazol-4-yl)ethanone (640 mg, 1.56 mmol) and anhydrous THF (12 mL). The reaction solution was cooled to −78° C. prior to dropwise addition of a 1.0 M LHMDS solution in THF (1.72 mL). The enolate solution was allowed to stir, warming to −20°C over 1 h. The reaction solution was cooled to −60°C, and ethyl trifluoroacetate (370 µL, 3.12 mmol) was added. The reaction solution was stirred at room temperature for 16 h. The reaction solution was quenched with H₂O and diluted with EtOAc (100 mL). The EtOAc phase was partitioned, dried over Na₂SO₄, filtered, and concentrated in vacuo. The crude material was chromatographed through a 12 g SiO₂ column using a 100% hexane to 60% EtOAc gradient to yield 120 mg (86% yield) of title compound. MS (ESI) 507.0, 509.0 [M+H]⁺.

Example 34b

Preparation of 3-(1-(4-bromo-2-chlorophenyl)-2-(2-chlorophenyl)-1H-imidazol-4-yl)-5-(trifluoromethyl)isoxazole

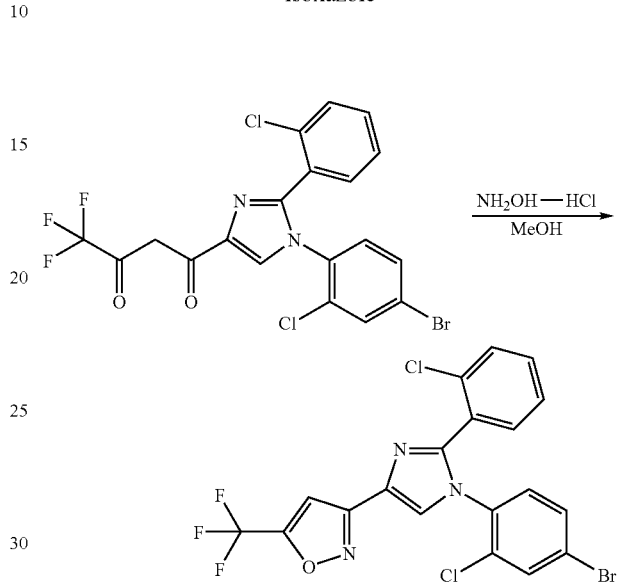

To a 50 mL flask attached with condenser was added 1-(1-(4-bromo-2-chlorophenyl)-2-(2-chlorophenyl)-1H-imidazol-4-yl)-4,4,4-trifluorobutane-1,3-dione (138 mg, 273 µmol) and MeOH (12 mL). To the solution was added hydroxylamine-HCl (190 mg, 2.73 mmol). The reaction solution was allowed to stir at reflux for 1.5 h. The solution was concentrated in vacuo and the residue was taken into EtOAc and washed with aq. NaHCO₃ (50 mL×2). The EtOAc phase was partitioned, dried over Na₂SO₄, filtered, and concentrated in vacuo. The crude material was chromatographed through a 12 g SiO₂ column using a 100% hexane to 60% EtOAc gradient to yield 120 mg (86% yield) of title compound. MS (ESI) 508.3, 510.3 [M+H]⁺.

Example 34c

Preparation of 3-(1-(3-chloro-3'-(methylsulfonyl)biphenyl-4-yl)-2-(2-chlorophenyl)-1H-imidazol-4-yl)-5-(trifluoromethyl)isoxazole

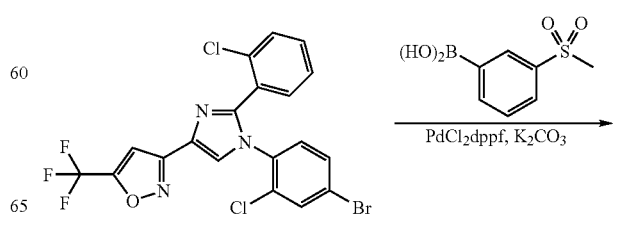

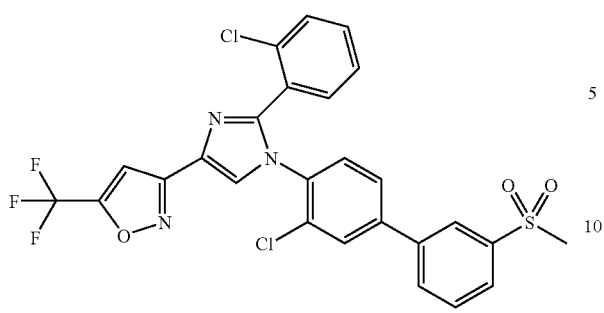

To an 8 mL glass vial was added 3-(1-(4-bromo-2-chlorophenyl)-2-(2-chlorophenyl)-1H-imidazol-4-yl)-5-(trifluoromethyl)isoxazole (120 mg, 236 μmol), 3-methylsulfonylphenyl boronic acid (52 mg, 260 μmol), PdCl$_2$dppf (20 mg, 10 mol %), K$_2$CO$_3$ (100 mg, 708 μmol), 1,2-dimethoxyethane (6 mL) and H$_2$O (1.5 mL). The reaction solution was allowed to stir at 80° C. for 2.5 hrs. The reaction solution was diluted with EtOAc (30 mL) and filtered through a celite padded Buchner funnel to remove spent Pd. The filtrate was transferred to a separatory funnel and washed with aq NH$_4$Cl (40 mL) and aq NaCl (40 mL). The organic phase was dried over Na$_2$SO$_4$, filtered, concentrated on the Rotavapor and chromatographed through a 12 g SiO$_2$ column using a mobile phase gradient of 5% EtOAc to 100% EtOAc to afford 72 mg (53% yield) of the title compound. MS (ESI) 578.0, 580.0 [M+H]$^+$; $^1$H NMR (400 MHz, DMSO-d$_6$) δ 8.93 (s, 1H), 8.38 (s, 1H), 8.21 (s, 1H), 8.13 (d, J=8 Hz, 1H), 8.08 (s, 1H), 7.96 (d, J=8 Hz, 1H), 7.71-7.79 (m, 2H), 7.69 (d, J=7 Hz, 1H), 7.62 (d, J=8 Hz, 1H), 7.48 (m, 1H), 7.36-7.42 (m, 2H), 3.34 (s, 3H) ppm; $^{19}$F NMR (400 MHz, DMSO-d$_6$) 6-81.9 ppm.

Scheme 35

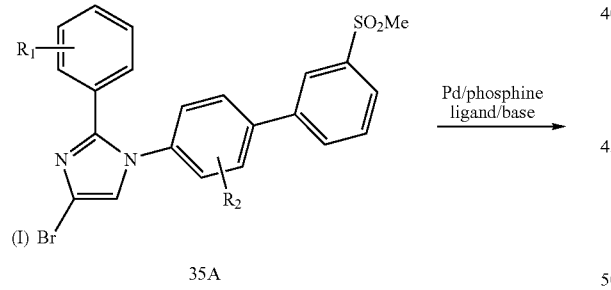

35A

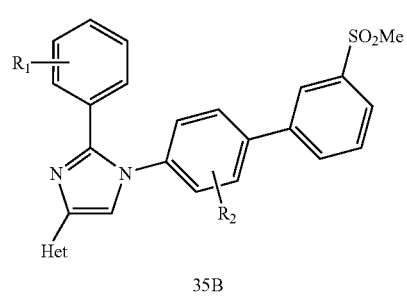

35B

As depicted in Scheme 35, the 4-bromo- or 4-iodo-imidazole template, prepared as described above, was coupling with different boronic acids or borates to afford a variety of heterocycles.

Example 35a

Preparation of 4-cyclopropyl-1-(3'-(methylsulfonyl)biphenyl-4-yl)-2-(2-(trifluoromethyl)phenyl)-1H-imidazole

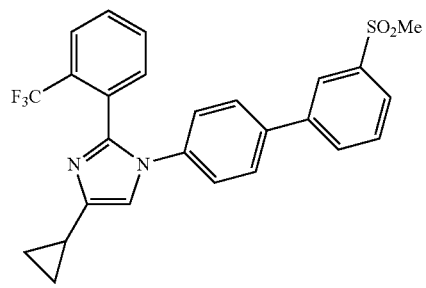

Example 35a1

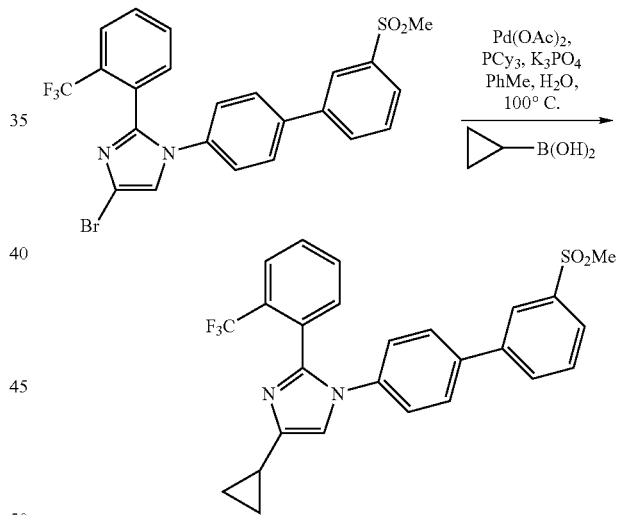

To a mixture of compound 4-bromo-1-(3'-(methylsulfonyl)biphenyl-4-yl)-2-(2-(trifluoromethyl)phenyl)-1H-imidazole (224 mg, 0.430 mmol), cyclopropyl boronic acid (55 mg, 0.640 mmol), P(Cy)$_3$ (23 mg, 0.082 mmol) and K$_3$PO$_4$.H$_2$O (345 mg, 1.50 mmol) in 2.5 mL toluene and 0.15 mL H$_2$O was added Pd(OAc)$_2$ (10 mg, 0.044 mmol) in a 5 mL microwave tube. The tube was sealed and purged with an argon balloon for five minutes. The reaction was stirred for 24 h at 100° C. and cooled to room temperature. The reaction was diluted with ethyl acetate, and washed with saturated NH$_4$Cl, brine, dried with MgSO$_4$ and the solvent removed in vacuo. The residue was purified by column chromatography using hexanes:ethyl acetate as eluents and further purified by preparatory HPLC using water:TFA:acetonitrile as eluents to afford 4-cyclopropyl-1-(3'-(methylsulfonyl)biphenyl-4-yl)-2-(2-(trifluoromethyl)phenyl)-1H-imidazole (56 mgs, 27%) as a white solid. ¹H-NMR (DMSO, 400 MHz) δ 8.13-8.12 (m, 1H), 8.03-8.00 (m, 1H), 7.91-7.88 (m, 1H), 7.83-7.80 (m, 1H), 7.77 (d, J=8.58 Hz, 2H), 7.74-7.69 (m, 1H), 7.64-7.62 (m, 2H), 7.46-7.44 (m, 1H), 7.41 (s, 1H), 7.25 (d, J=8.58 Hz, 2H), 3.28 (s, 3H), 1.93-1.87 (m, 1H), 0.86-0.82 (m, 2H), 0.76-0.72 (m, 2H); MS (ES): 483.0 [M+H]⁺.

Example 35b

Preparation of 2-(2,3-dichlorophenyl)-1-(3'-(methylsulfonyl)biphenyl-4-yl)-4-(thiophen-3-yl)-1H-imidazole

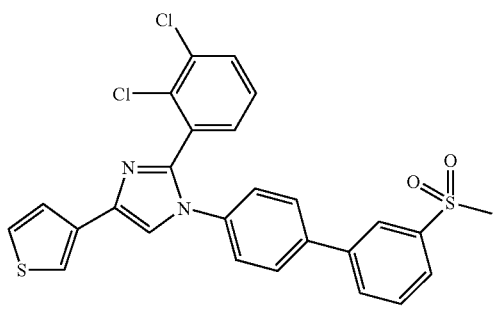

Example 35b1

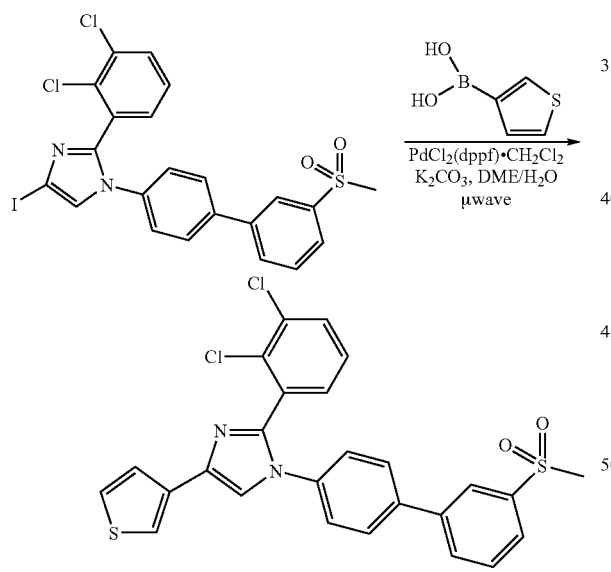

Into a 5 mL microwave vial was weighed 220 mg (0.39 mmol) of 2-(2,3-di-chlorophenyl)-4-iodo-1-(3'-(methylsulfonyl)biphenyl-4-yl)-1H-imidazole, 108 mg (0.84 mmol) of thiophen-3-ylboronic acid 25 mg (31 µmol) of PdCl₂(dppf)-CH₂Cl₂. The mixture was taken up in 1,2-dimethoxyethane (2 mL), and treated with 400 µL (0.1.4 mmol) of 3.5M aqueous potassium carbonate. The mixture was heated in the Biotage Initiator microwave reactor for 30 minutes at 120° C. LC/MS at this time showed a large peak for the product and some smaller impurity peaks. The reaction mixture was diluted with EtOAc, treated with some decolorizing carbon and Na₂SO₄. The mixture was filtered through a pad of Celite and the pad was washed with EtOAc. The filtrate was concentrated in vacuo to afford a dark brown oil. The crude product was adsorbed onto silica, loaded onto the top of a 12 g silica column and eluted with a gradient from 0% to 100% EtOAc in hexane. The main product peak was collected and concentrated in vacuo to afford a brown powder that was impure. This impure product was further purified by reverse phase prep HPLC (3 injections). (Phenomenex Axia Gemini C18 30×100 mm 5 µm, A=H₂O with 0.1% trifluoroacetic acid, B=acetonitrile with 0.1% trifluoroacetic acid, 17 minute gradient from 30% B to 100% B at 35 mL/minute). Product fractions were combined, made basic by the addition of sat. NaHCO₃, and concentrated in vacuo to remove the acetonitrile. The resulting basic aqueous was extracted with CH₂Cl₂ (3×), and the organics were dried over Na₂SO₄, filtered and concentrated in vacuo. The resulting 2-(2,3-dichlorophenyl)-1-(3'-(methylsulfonyl)biphenyl-4-yl)-4-(thiophen-3-yl)-1H-imidazole was isolated as a white powder, yield: 89.8 mg (44%) ¹H NMR (400 MHz, CDCl₃): δ 8.14-8.12 (m, 1H), 7.96-7.92 (m, 1H), 7.87-7.83 (m, 1H) 7.73-7.70 (m, 1H), 7.66 (t, J=7.8 Hz, 1H), 7.61-7.57 (m, 2H), 7.55-7.50 (m, 2H), 7.49-7.46 (m, 2H), 7.40-7.37 (m, 1H), 7.32-7.25 (m, 4H); 3.10 (s, 3H), MS (ES): 525.2 [M+H]⁺.

The following compounds were prepared as described above.

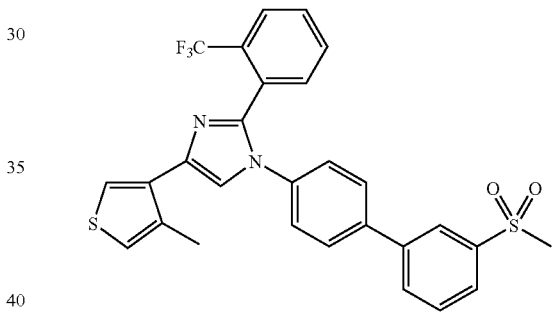

1-(3'-(methylsulfonyl)biphenyl-4-yl)-4-(4-methylthiophen-3-yl)-2-(2-(trifluoromethyl)phenyl)-1H-imidazole ¹H-NMR (CDCl₃, 400 MHz) δ 8.10 (m, 1H), 7.93 (m, 1H), 7.82 (m, 1H), 7.75 (m, 2H), 7.65 (t, J=7.8 Hz, 1H), 7.54 (m, 4H), 7.42 (m, 1H), 7.40 (s, 1H), 7.26 (m, 2H), 7.02 (m, 1H), 3.01 (s, 3H), 2.45 (s, 3H), MS (ES): 539 [M+H]⁺.

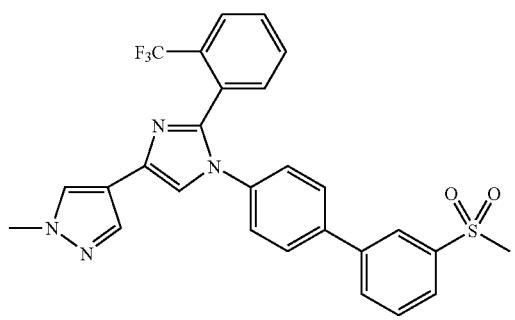

1-methyl-4-(1-(3'-(methylsulfonyl)biphenyl-4-yl)-2-(2-(trifluoromethyl)phenyl)-1H-imidazol-4-yl)-1H-pyrazole $^1$H-NMR (CDCl$_3$, 400 MHz) 8.10 (m, 1H), 7.93 (m, 1H), 7.82 (m, 3H), 7.73 (m, 1H), 7.65 (t, J=7.88, 1H), 7.54 (m, 4H), 744 (m, 1H), 7.35 (s, 1H), 7.24 (s, 1H), 7.22 (s, 1H), 3.95 (s, 3H), 3.09 (s, 3H); MS (ES): 523 [M+H]$^+$.

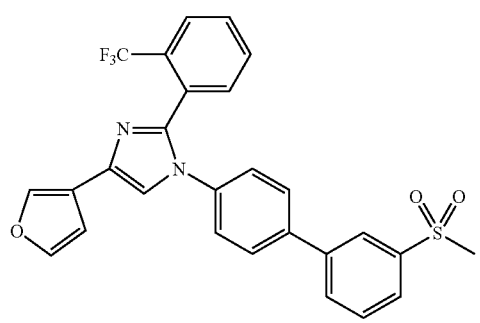

4-(furan-3-yl)-1-(3'-(methylsulfonyl)biphenyl-4-yl)-2-(2-(trifluoromethyl)phenyl)-1H-imidazole $^1$H-NMR (CDCl$_3$, 400 MHz) δ 8.10 (m, 1H), 7.93 (m, 2H), 7.82 (m, 1H), 7.74 (m, 1H), 7.65 (t, J=7.9 Hz, 1H), 7.55 (m, 4H), 7.48 (m, J=1.90, 1H), 7.45 (m, 1H), 7.37 (s, 1H), 7.25 (s, 1H), 7.22 (s, 1H), 6.74 (m, 1H), 3.09 (s, 3H), MS (ES): 509 [M+H]$^+$.

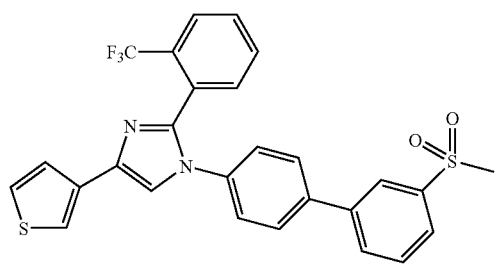

1-(3'-(methylsulfonyl)biphenyl-4-yl)-4-(thiophen-3-yl)-2-(2-(trifluoromethyl)phenyl)-1H-imidazole $^1$H NMR (400 MHz, CDCl$_3$): δ 8.11-8.09 (m, 1H), 7.95-7.91 (m, 1H), 7.84-7.80 (m, 1H), 7.75-7.69 (m, 2H), 7.65 (t, J=7.8 Hz, 1H), 7.57-7.51 (m, 4H), 7.49-7.43 (m, 3H), 7.39-7.36 (m, 1H), 7.27-7.22 (m, 2H), 3.10 (s, 3H); MS (ES): 525.3 [M+H]$^+$.

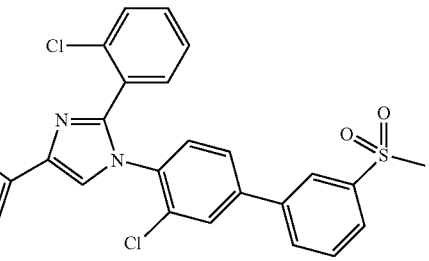

1-(3-chloro-3'-(methylsulfonyl)biphenyl-4-yl)-2-(2-chlorophenyl)-4-(thiophen-3-yl)-1H-imidazole $^1$H NMR (400 MHz, CDCl$_3$): δ 8.12-8.10 (m, 1H), 7.98-7.95 (m, 1H), 7.85-7.81 (m, 1H), 7.74-7.72 (m, 1H), 7.71-7.70 (m, 1H), 7.67 (t, J=7.8 Hz, 1H), 7.58-7.54 (m, 1H), 7.49-7.46 (m, 1H), 7.46-7.41 (m, 2H), 7.39-7.34 (m, 2H), 7.34-7.25 (m, 3H), 3.04 (s, 3H); MS (ES): 525.2 [M+H]$^+$.

Scheme 36

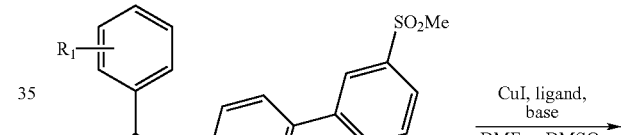
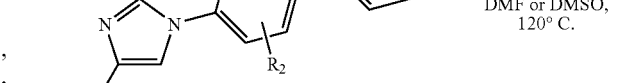

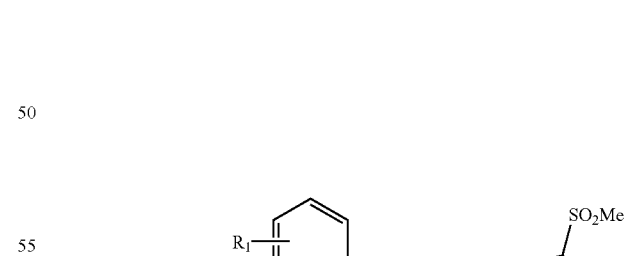

36A

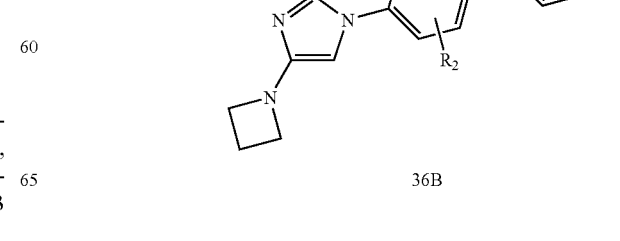

36B

As depicted in Scheme 36, the bromo- or iodo-imidazoles can be converted to a diversed set of heterocycles via Buchwald type reaction.

Example 36

Preparation of 4-(azetidin-1-yl)-1-(3'-(methylsulfonyl)biphenyl-4-yl)-2-(2-(trifluoromethyl)phenyl)-1H-imidazole

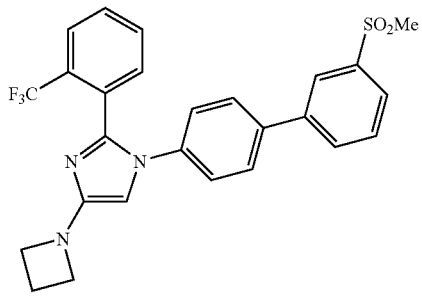

Example 36a

Preparation of 4-(azetidin-1-yl)-1-(3'-(methylsulfonyl)biphenyl-4-yl)-2-(2-(trifluoromethyl)phenyl)-1H-imidazole

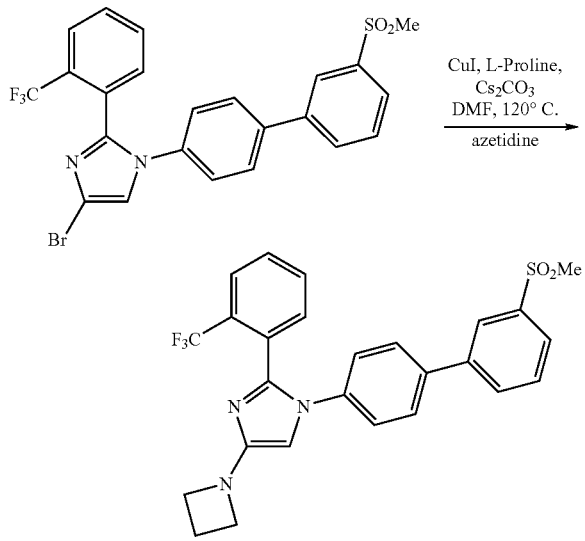

4-bromo-1-(3'-(methylsulfonyl)biphenyl-4-yl)-2-(2-(trifluoromethyl)phenyl)-1H-imidazole (188 mgs, 0.361 mmol), azetidine (0.4 mL 5.94 mmol), L-proline (50 mg, 0.434 mmol), Cs$_2$CO$_3$ (517 mg, 1.44 mmol), 2.5 mL anhydrous DMF, and CuI (69 mg, 362 mmol) were added to a 5 mL microwave tube and sealed. The tube was purged with an argon balloon for five minutes. The reaction was heated at 120° C. for 24 h and then cooled to room temperature. The crude reaction mixture was purified directly by HPLC using water: TFA: acetonitrile as eluents to afford 4-(azetidin-1-yl)-1-(3'-(methylsulfonyl)biphenyl-4-yl)-2-(2-(trifluoromethyl)phenyl)-1H-imidazole (47 mgs, 26%) as a light yellow solid.

$^1$H-NMR (DMSO, 400 MHz) δ 8.12-8.11 (m, 1H), 8.02-7.99 (m, 1H), 7.91-7.88 (m, 1H), 7.82-7.80 (m, 1H), 7.76 (d, J=8.60 Hz, 2H), 7.73-7.69 (m, 1H), 7.65-7.62 (m, 2H), 7.46-7.44 (m, 1H), 7.23 (d, J=8.60 Hz, 2H), 6.77 (s, 1H), 3.74 (t, J=7.34 Hz, 4H), 3.28 (s, 3H), 2.33-2.25 (m, 2H); MS (ES): 498.3 [M+H]$^+$.

The following compounds were prepared in similar way using Buchwald condition:

1-{2-(2,6-dichlorophenyl)-1-[3'-(methylsulfonyl)biphenyl-4-yl]-1H-imidazol-4-yl}-1H-pyrazole

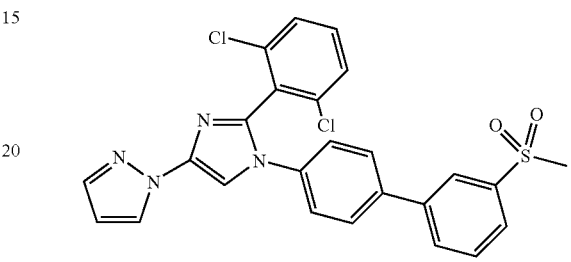

$^1$H NMR (400 MHz, CDCl$_3$): δ 8.30 (m, 1H), 8.11 (m, 1H), 7.94 (m, 1H), 7.84 (m, 1H), 7.71 (m, 1H), 7.66 (m, 1H), 7.60 (m, 1H), 7.58 (m, 2H), 7.42-7.31 (m, 5H), 6.44 (m, 1H), 3.09 (s, 3H). MS (ES): 509 [M+H]$^+$.

2'-(2,6-dichlorophenyl)-1'-[3'-(methylsulfonyl)biphenyl-4-yl]-1'H-1,4'-biimidazole

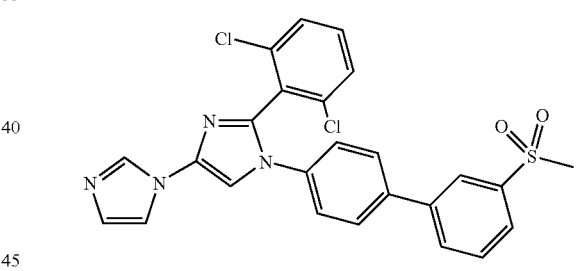

$^1$H NMR (400 MHz, CDCl$_3$): δ 8.12 (m, 2H), 7.95 (m, 1H), 7.64 (m, 1H), 7.67 (m, 1H), 7.62 (m, 1H), 7.60 (m, 1H), 7.49 (m, 1H), 7.41-7.31 (m, 6H), 7.22 (m, 1H). MS (ES): 509 [M+H]$^+$.

2'-(2,6-dichlorophenyl)-2-methyl-1'-[3'-(methylsulfonyl)biphenyl-4-yl]-1'H-1,4'-biimidazole

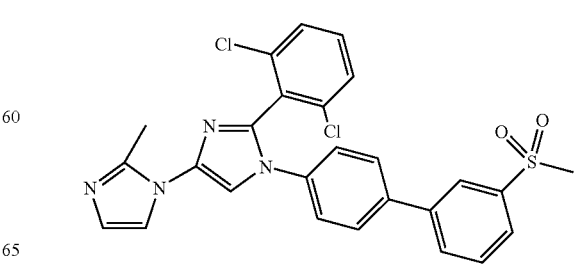

¹H NMR (400 MHz, CDCl₃): δ 8.12 (m, 1H), 7.96 (m, 1H), 7.85 (m, 1H), 7.70-7.63 (m, 3H), 7.56 (m, 1H), 7.44-7.37 (m, 7H), 3.10 (s, 3H), 3.03 (s, 3H). MS (ES): 523 [M+H]⁺.

2-(2,6-dichlorophenyl)-1-[3'-(methylsulfonyl)biphenyl-4-yl]-4-(pyrrolidin-1-yl)-1H-imidazole

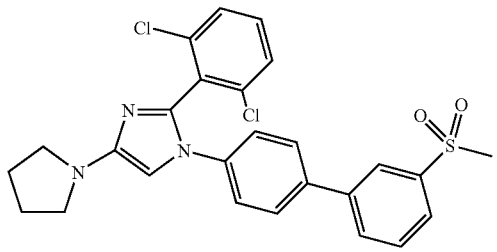

¹H NMR (400 MHz, CDCl₃): δ 8.10 (m, 1H), 7.91 (m, 1H), 7.82 (m, 1H), 7.63 (m, 1H), 7.54 (m, 1H), 7.52 (m, 1H), 7.32-7.22 (m, 5H), 6.41 (s, 1H), 3.35 (m, 4H), 3.08 (s, 3H), 2.01 (m, 4H). MS (ES): 512 [M+H]⁺.

1-(1-(3'-(methylsulfonyl)biphenyl-4-yl)-2-(2-(trifluoromethyl)phenyl)-1H-imidazol-4-yl)pyrrolidin-3-ol

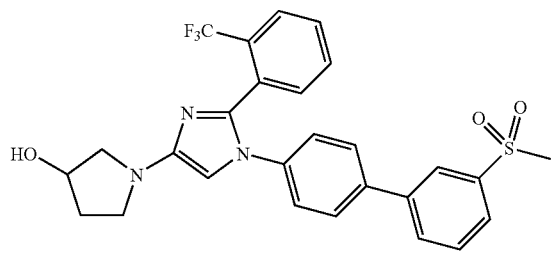

¹H NMR (400 MHz, CDCl₃): δ 8.09 (m, 1H), 7.92 (m, 1H), 7.81 (m, 1H), 7.72 (m, 1H), 7.64 (m, 1H), 7.55-7.48 (m, 3H), 7.38-7.30 (m, 2H), 7.22-7.17 (m, 2H). 6.44 (s, 1H), 4.58 (s, 1H), 3.53 (m, 2H), 3.36 (m, 2H), 3.10 (m, 1H), 3.08 (s, 3H), 2.24 (m, 1H), 2.05 (m, 1H).). MS (ES): 528 [M+H]⁺.

1-(1-(3'-(methylsulfonyl)biphenyl-4-yl)-2-(2-(trifluoromethyl)phenyl)-1H-imidazol-4-yl)piperidine

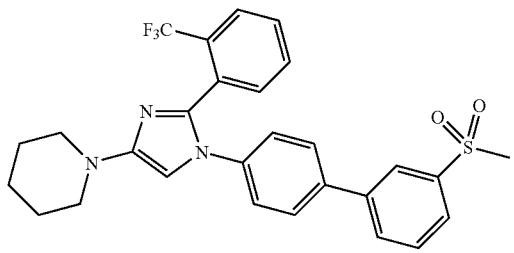

¹H NMR (400 MHz, CDCl₃): δ 8.09 (m, 1H), 7.91 (m, 1H), 7.80 (m, 1H), 7.70 (m, 1H), 7.63 (m, 1H), 7.51-7.47 (m, 4H), 7.36 (m, 1H), 7.19 (m, 1H), 7.16 (m, 1H), 6.51 (s, 1H), 3.19 (m, 4H), 3.08 (s, 3H), 1.75 (m, 4H), 1.60 (m, 2H). MS (ES): 526 [M+H]⁺.

1-{2-(2,6-dichlorophenyl)-1-[3'-(methylsulfonyl)biphenyl-4-yl]-1H-imidazol-4-yl}pyrrolidin-2-one

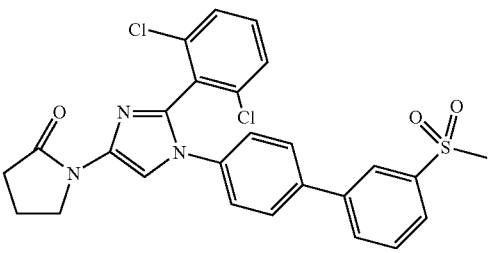

¹H NMR (400 MHz, CDCl₃): δ 8.10 (m, 1H), 7.93 (m, 1H), 7.92 (m, 1H), 7.83 (m, 1H), 7.64 (m, 1H), 7.57 (m, 1H), 7.55 (m, 1H), 7.36-7.28 (m, 5H), 4.14 (m, 2H), 3.09 (s, 3H), 2.63 (m, 2H), 2.24 (m, 2H). MS (ES): 526 [M+H]⁺.

2-(2,6-dichlorophenyl)-1-[(3'-(methylsulfonyl)biphenyl-4-y]-4-(1H-pyrrol-1-yl)-1H-imidazole

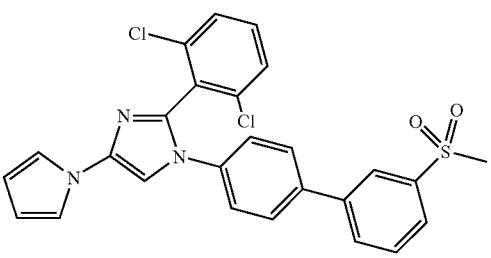

¹H NMR (400 MHz, CDCl₃): δ 8.12 (m, 1H), 7.94 (m, 1H), 7.84 (m, 1H), 7.66 (m, 1H), 7.60 (m, 1H), 7.58 (m, 1H), 7.39 (m, 1H), 7.37 (m, 1H), 7.35-7.29 (6H), 7.20 (m, 1H), 6.33 (m, 1H), 3.09 (s, 3H). MS (ES): 508 [M+H]⁺.

1-(3'-(methylsulfonyl)biphenyl-4-yl)-4-(1H-pyrrol-1-yl)-2-(2-(trifluoromethyl)phenyl)-1H-imidazole

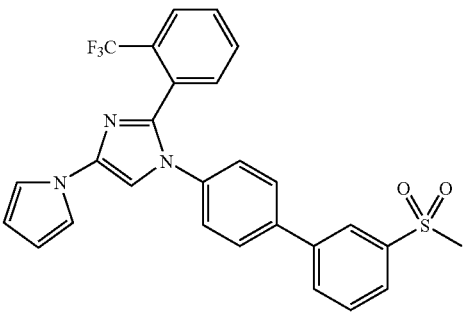

¹H-NMR (CDCl₃, 400 MHz) δ 8.10 (m, 1H), 7.94 (m, 1H), 7.82 (m, 1H), 7.75 (m, 1H), 7.65 (t, J=7.8 Hz, 1H), 7.55 (m,

4H), 7.42 (m, 1H), 7.40 (s, 1H), 7.28 (t, J=2.10, 2H), 7.25 (s, 1H), 7.18 (s, 1H), 6.33 (t, J=2.10, 2H), 3.01 (s, 3H), MS (ES): 508 [M+H]⁺.

1'-(3'-(methylsulfonyl)biphenyl-4-yl)-2'-(2-(trifluoromethyl)phenyl)-1'H-1,4'-biimidazole-4-carbonitrile

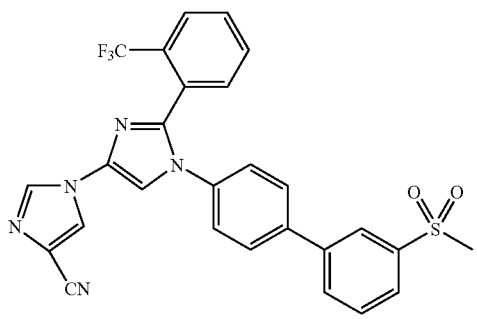

¹H-NMR (CDCl₃, 400 MHz) δ 8.11 (m, 1H), 8.10 (m, 1H), 8.00 (m, 1H), 7.95 (m, 1H), 7.82 (m, 1H), 7.79 (m, 1H), 7.69 (t, J=7.8 Hz, 1H), 7.59 (m, 4H), 7.40 (m, 1H), 7.39 (s, 1H), 7.28 (m, 2H), 3.10 (s, 3H), MS (ES): 534 [M+H]⁺.

(1'-(3'-(methylsulfonyl)biphenyl-4-yl)-2'-(2-(trifluoromethyl)phenyl)-1'H-1,4'-biimidazol-4-yl)methanol

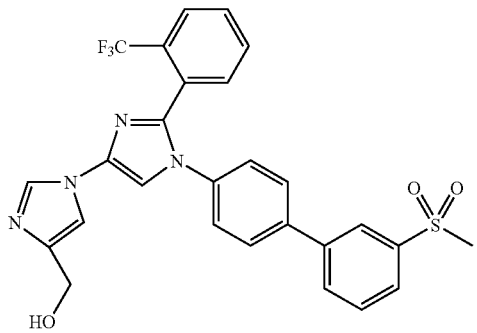

¹H-NMR (CDCl₃, 400 MHz) δ 8.10 (t, J=2.10, 1H), 8.07 (m, 1H), 7.95 (m, 1H), 7.82 (m, 1H), 7.77 (m, 1H), 7.66 (t, J=8.0 Hz, 1H), 7.57 (m, 4H), 7.42 (m, 1H), 7.40 (s, 1H), 7.28 (s, 1H), 7.26 (m, 2H), 4.69 (s, 2H), 3.10 (s, 3H), MS (ES): 539 [M+H]⁺.

1-(1-(3'-(methylsulfonyl)biphenyl-4-yl)-2-(2-(trifluoromethyl)phenyl)-1H-imidazol-4-yl)-1H-pyrrole-2-carbonitrile

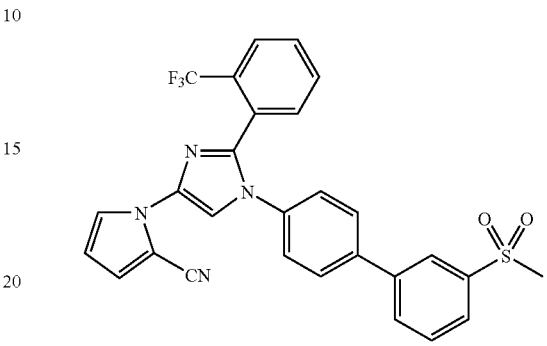

¹H-NMR (CDCl₃, 400 MHz) δ 8.10 (m, 1H), 7.95 (m, 1H), 7.83 (m, 1H), 7.78 (m, 1H), 7.66 (m, 3H), 7.57 (m, 4H), 7.40 (m, 1H), 7.40 (s, 1H), 7.28 (m, 2H), 7.25 (s, 1H), 7.01 (m, 1H), 3.01 (s, 3H), MS (ES): 533 [M+H]⁺.

Scheme 37

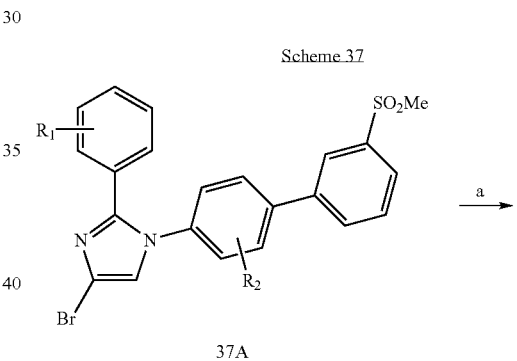

37A

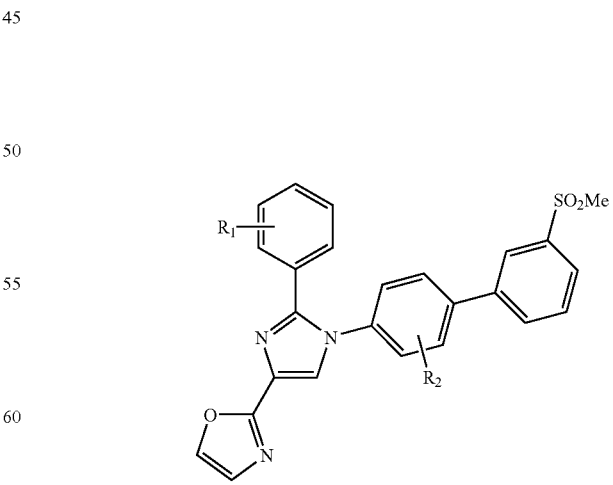

37B a. PdCl₂(dppf), PhMe, 2-(tributylstannyl)oxazole, 130° C.

As depicted in Scheme 37, the 4-oxazoleimidazole was synthesized from the 4-bromoimidazole template, shown in Scheme 28, via a Stille coupling utilizing PdCl$_2$(dppf).

Example 37

Preparation of 2-(1-(3'-(methylsulfonyl)biphenyl-4-yl)-2-(2-(trifluoromethyl)phenyl)-1H-imidazol-4-yl)oxazole

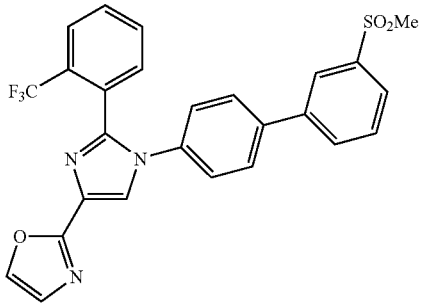

Example 37a

Preparation of 2-(1-(3'-(methylsulfonyl)biphenyl-4-yl)-2-(2-(trifluoromethyl)phenyl)-1H-imidazol-4-yl)oxazole

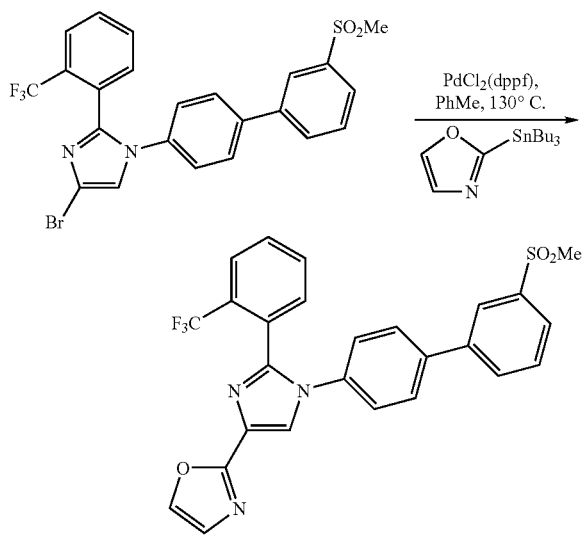

4-bromo-1-(3'-(methylsulfonyl)biphenyl-4-yl)-2-(2-(trifluoromethyl)phenyl)-1H-imidazole (163 mgs, 0.313 mmol), 2-(tributylstannyl)oxazole (236 mgs, 0.659 mmol), 1.5 mL toluene and PdCl$_2$(dppf) (23 mg, 0.031 mmol) were added to a microwave tube and sealed. The reaction was heated in the microwave for 1 h at 130° C. After cooling to room temperature the reaction was absorbed on to silica gel and purified by column chromatography using hexanes:ethyl acetate as eluents and further purified by preparatory HPLC using water:TFA:acetonitrile as eluents to afford 2-(1-(3'-(methylsulfonyl)biphenyl-4-yl)-2-(2-(trifluoromethyl)phenyl)-1H-imidazol-4-yl)oxazole (58 mgs, 36%) as a white solid.

$^1$H-NMR (DMSO, 400 MHz) δ 8.35 (s, 1H), 8.17-8.16 (m, 1H), 8.15-8.14 (m, 1H), 8.05-8.01 (m, 1H), 7.93-7.90 (m, 1H), 7.87-7.85 (m, 1H), 7.83 (d, J=8.58 Hz, 2H), 7.75-7.70 (m, 3H), 7.66-7.64 (m, 1H), 7.40 (d, J=8.58 Hz, 2H), 7.35-7.34 (m, 1H), 3.28 (s, 3H); MS (ES): 510.1 [M+H]$^+$ and 532.2 [M+Na]$^+$.

The following compound was synthesized as described above except a 4-iodoimidazole template was used.

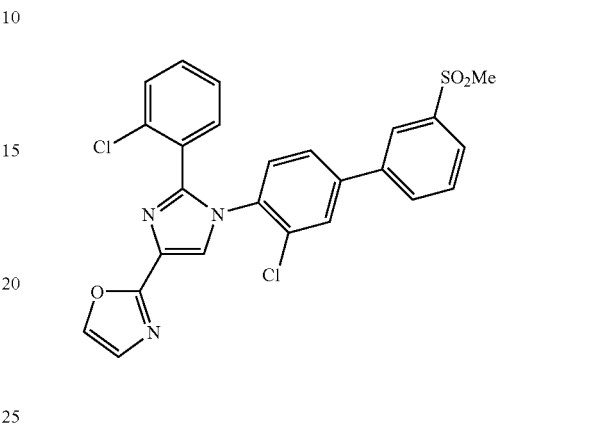

Preparation of 2-(1-(3-chloro-3'-(methylsulfonyl)biphenyl-4-yl)-2-(2-chlorophenyl)-1H-imidazol-4-yl)oxazole $^1$H-NMR (DMSO, 400 MHz) δ 8.28 (s, 1H), 8.23-8.21 (m, 1H), 8.18 (s, 1H), 8.12-8.09 (m, 2H), 7.96-7.94 (m, 1H), 7.85-7.83 (m, 1H), 7.75 (t, J=7.83 Hz, 1H), 7.66 (d, J=8.28 Hz, 1H), 7.59-7.56 (m, 1H), 7.50-7.43 (m, 2H), 7.41-7.36 (m, 1H), 7.35 (s, 1H), 3.30 (s, 3H); MS (ES): 511.0 [M+H]$^+$ and 533.0 [M+Na]$^+$.

Scheme 38

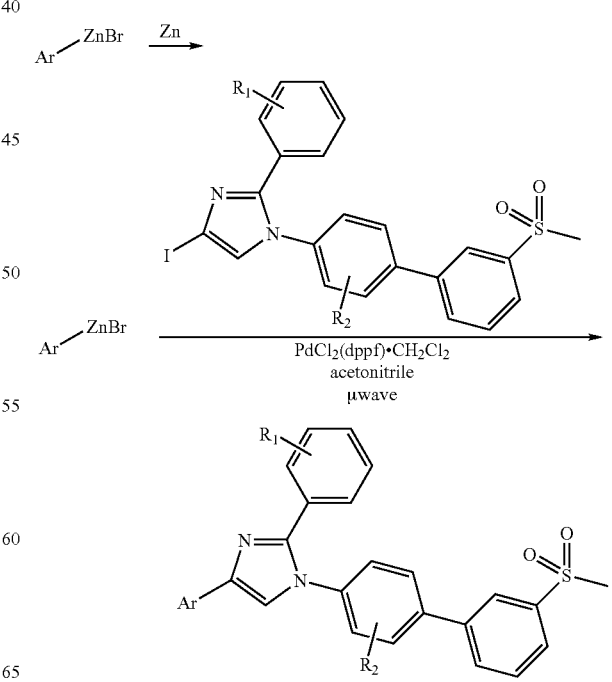

As depicted in Scheme 38, aryl or heteroarylzinc reagents can be coupled with iodo-imidazole intermediates via palladium mediated coupling procedures to afford heterocyclic analogs.

Example 38a

Preparation of 2-(2-(2,6-dichlorophenyl)-1-(3'-(methylsulfonyl)biphenyl-4-yl)-1H-imidazol-4-yl)-4-methylthiazole

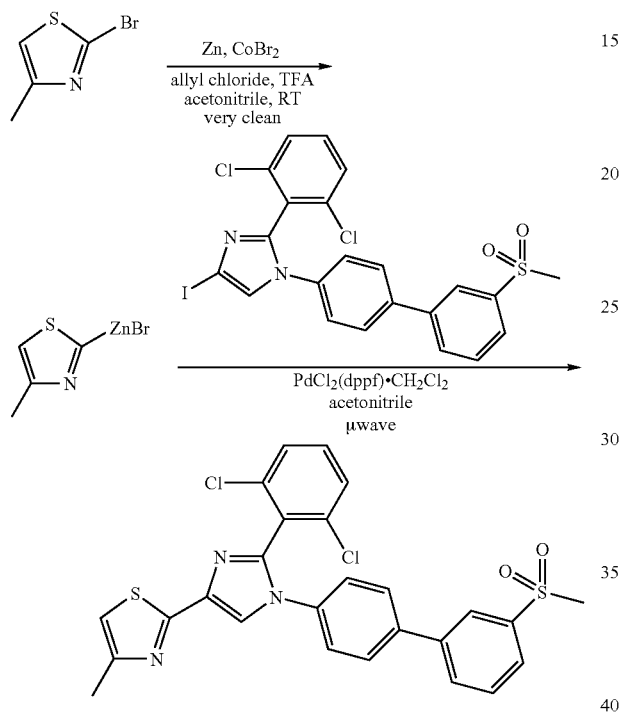

Into a 5 mL microwave vial was weighed 174 mg (2.7 mmol) of zinc powder and 45 mg (200 μmol) of anhydrous $CoBr_2$. The solids were suspended in 1.7 mL of acetonitrile, and the resulting suspension was treated with 45 μL (0.55 mmol) of allyl chloride, followed by 15 μL of trifluoroacetic acid (33% v/v on allyl chloride). After stirring for 10 minutes at ambient temperature, the suspension was treated with 302 mg (1.7 mmol) of 2-bromo-4-methylthiazole as a solution in 300 μL of acetonitrile. After 2 hours stirring at ambient temperature an aliquot of the reaction suspension was treated with iodine in $Et_2O$, quenched by addition of aqueous sodium thiosulfate to reduce the iodine, and dried over $Na_2SO_4$. GC/MS analysis of this sample showed a large quantity of iodo(methylthiazole) from iodination of the thiazole zinc reagent, and no trace of remaining 2-bromo-4-methylthiazole. Into the reaction vessel was added 156 mg (0.0.27 mmol) of 2-(2,6-dichlorophenyl)-4-iodo-1-(3'-(methylsulfonyl)biphenyl-4-yl)-1H-imidazole, 39 mg (48 μmol) of $PdCl_2(dppf)$ · $CH_2Cl_2$. The reaction mixture was heated to 120° C. for 1 hour in the Biotage Initiator microwave reactor. LC/MS at this time showed a large peak for the desired product. The reaction mixture was treated with decolorizing carbon and diluted with EtOAc and with 1N HCl. The black suspension was filtered through a pad of Celite. The layers were separated and the acidic aqueous was extracted with EtOAc (3×). Combined organics were washed with saturated aqueous $NaHCO_3$, brine, dried over $Na_2SO_4$, filtered and concentrated in vacuo to afford a brown film. The crude product was purified on the reverse phase preparative HPLC eluting with acetonitrile/water. (Phenomenex Axia Gemini C18 30×100 mm 5 μm, A=$H_2O$ with 0.1% trifluoroacetic acid, B=acetonitrile with 0.1% trifluoroacetic acid, 17 minute gradient from 30% B to 100% B at 35 mL/minute). Product fractions were combined, made basic by the addition of sat. $NaHCO_3$, and concentrated in vacuo to remove the acetonitrile. The resulting basic aqueous was extracted with $CH_2Cl_2$ (3×), and the organics were dried over $Na_2SO_4$, filtered and concentrated in vacuo. The resulting 2-(2-(2,6-dichlorophenyl)-1-(3'-(methylsulfonyl)biphenyl-4-yl)-1H-imidazol-4-yl)-4-methylthiazole was isolated as a pale brown powder, yield; 58.4 mg (39% yield); $^1$H NMR (400 MHz, $CDCl_3$): δ 8.12-8.10 (m, 1H), 7.95-7.92 (m, 2H), 7.86-7.82 (m, 1H), 7.68-7.63 (m, 1H) 7.61-7.56 (m, 2H), 7.41-7.36 (m, 2H), 7.35-7.29 (m, 3H), 6.87-6.86 (m, 1H), 3.09 (s, 3H), 2.51 (d, J=1.0 Hz, 3H); MS (ES): 540.0 $[M+H]^+$.

The following compounds were prepared as described above.

2-(2-(2,6-dichlorophenyl)-1-(3'-(methylsulfonyl) biphenyl-4-yl)-1H-imidazol-4-yl)thiazole

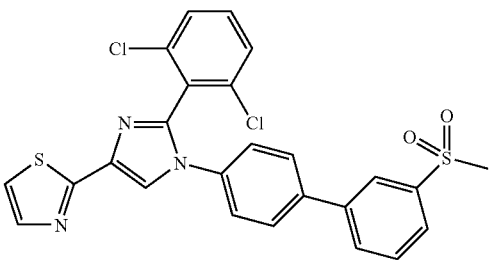

$^1$H NMR (400 MHz, $CDCl_3$): δ 8.12-8.11 (m, 1H), 7.96-7.94 (m, 1H), 7.94-7.92 (m, 1H), 7.86-7.83 (m, 2H), 7.66 (t, J=7.8 Hz, 1H), 7.62-7.58 (m, 2H), 7.42-7.38 (m, 2H), 7.36-7.28 (m, 4H), 3.10 (s, 1H); MS (ES): 526.3 $[M+H]^+$.

1-(3'-(methylsulfonyl)biphenyl-4-yl)-4-(thiophen-2-yl)-2-(2-(trifluoromethyl)phenyl)-1H-imidazole

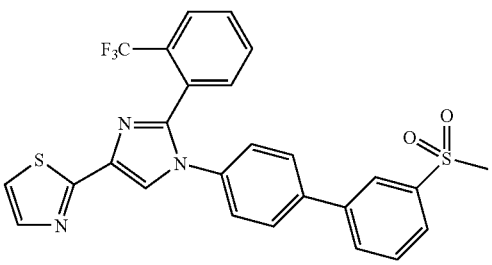

$^1$H NMR (400 MHz, $CDCl_3$): δ 8.11-8.09 (m, 1H), 7.95-7.91 (m, 1H), 7.84-7.80 (m, 1H), 7.75-7.70 (m, 1H), 7.65 (t, J=7.8 Hz, 1H), 7.57-7.51 (m, 4H), 7.49-7.48 (m, 1H), 7.47-

7.44 (m, 1H), 7.43-7.41 (m, 1H), 7.27-7.22 (m, 3H), 7.09-7.06 (m, 1H); MS (ES): 525.3 [M+H]⁺.

Example 38b

Preparation of 1-(3'-(methylsulfonyl)biphenyl-4-yl)-4-((R)-pyrrolidin-2-yl)-2-(2-(trifluoromethyl)phenyl)-1H-imidazole

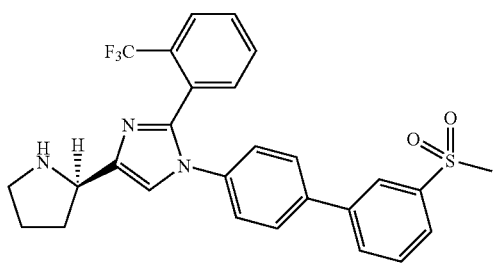

Example 38b1

Preparation of (R)-tert-butyl 2-(1-(3'-(methylsulfonyl)biphenyl-4-yl)-2-(2-(trifluoromethyl)phenyl)-1H-imidazol-4-yl)pyrrolidine-1-carboxylate

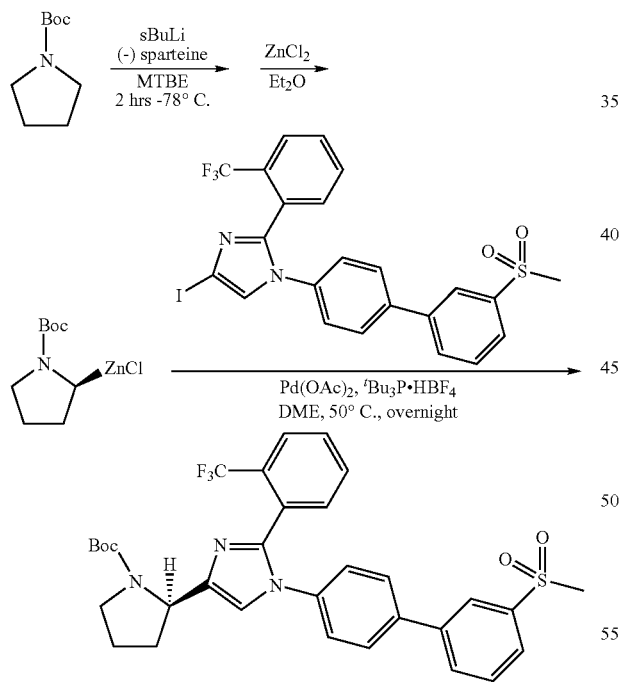

Into a 25 mL round bottom flask was added 480 μL (2.7 mmol) of tert-butyl pyrrolidine-1-carboxylate, 650 μL (2.8 mmol) of (−)-sparteine, and 8 mL of methyl-tert-butyl ether. The resulting solution was cooled in an acetone/dry ice bath. The cold solution was then treated dropwise with 2.4 ml (3.4 mmol) of a 1.4M solution of sec-butyllithium in cyclohexane. After stirring for 90 minutes at −78° C., a small sample of the reaction solution was treated with methyl iodide and analyzed by GC/MS. The GC/MS analysis showed about 60% conversion to the methylated derivative of the lithiated intermediate. After a total of 130 minutes at −78° C., the reaction was treated with 1.8 mL (1.8 mmol) of a 1M solution of ZnCl₂ in diethyl ether. The cooling bath was then removed and the reaction was allowed to warm to ambient temperature. After 1 hour at ambient temperature 438 mg (0.77 mmol) of 4-iodo-1-(3'-(methylsulfonyl)biphenyl-4-yl)-2-(2-(trifluoromethyl)phenyl)-1H-imidazole was added as a solution in 2 mL of methyl-tert-butyl ether. The mixture was then treated with 35 mg (160 μmol) of Pd(OAc)₂, and 50 mg (170 μmol) of ᵗBu₃P.HBF₄. The resulting pale brown suspension was heated to 50° C. After stirring for 16 hours at 50° C., most of the solvent had evaporated. The reaction was treated with 10 mL of methyl-tert-butyl ether and a sample analyzed by LC/MS. LC/MS showed no remaining 4-iodo-1-(3'-(methylsulfonyl)biphenyl-4-yl)-2-(2-(trifluoromethyl)phenyl)-1H-imidazole, a quantity of de-iodinated material and a smaller peak that appeared to be product. The reaction mixture was diluted with EtOAc and with 1N HCl. The layers were separated and the acidic aqueous was extracted with EtOAc (3×). Combined organics were washed with saturated aqueous NaHCO₃, brine, dried over Na₂SO₄, filtered and concentrated in vacuo to afford a brown semi-solid. The crude product was purified on the reverse phase preparative HPLC eluting with acetonitrile/water. (Phenomenex Axia Gemini C18 30×100 mm 5 μm, A=H₂O with 0.1% trifluoroacetic acid, B=acetonitrile with 0.1% trifluoroacetic acid, 8 minute gradient from 30% B to 65% B at 35 mL/minute). Product fractions were combined, made basic by the addition of sat. NaHCO₃, and concentrated in vacuo to remove the acetonitrile. The resulting basic aqueous was extracted with CH₂Cl₂ (3×), and the organics were dried over Na₂SO₄, filtered and concentrated in vacuo. The resulting (2R)-tert-butyl 2-(1-(3'-(methylsulfonyl)biphenyl-4-yl)-2-(2-(trifluoromethyl)phenyl)-1H-imidazol-4-yl)pyrrolidine-1-carboxylate was isolated as a clear film; 75 mg (15%). The NMR of the product was very complicated, possibly due to rotamers of the material. Treatment of the CDCl₃ NMR sample with 100 μL of trifluoroacetic acid for 65 hours showed complete conversion to a product by NMR. LC/MS analysis of the reaction solution showed a large peak with the correct mass for the desired deprotected amine product.

Example 38b2

Preparation of J-(3'-(methylsulfonyl)biphenyl-4-yl)-4-((R)-pyrrolidin-2-yl)-2-(2-(trifluoromethyl)phenyl)-1H-imidazole

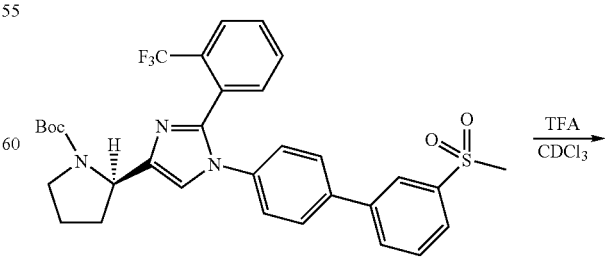

629

-continued

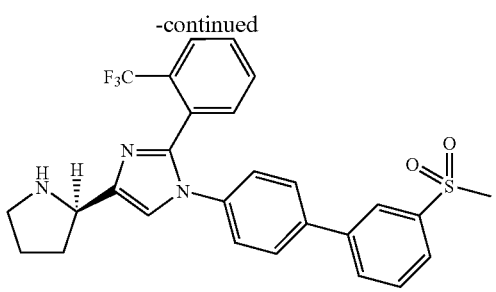

Into an 8 mL vial was weighed 70.2 mg (110 µmol) of (2R)-tert-butyl 2-(1-(3'-(methylsulfonyl)biphenyl-4-yl)-2-(2-(trifluoromethyl)phenyl)-1H-imidazol-4-yl)pyrrolidine-1-carboxylate. The material was dissolved in 1.0 mL of CDCl$_3$, and treated with 150 µL of trifluoroacetic acid. After 3 hours at ambient temperature, LC/MS showed complete conversion to product. The reaction mixture was concentrated in vacuo and the resulting brown oil was purified by reverse phase prep HPLC eluting with acetonitrile/water. (Phenomenex Axia Gemini C18 30×100 mm 5 µm, A=H$_2$O with 0.1% trifluoroacetic acid, B=acetonitrile with 0.1% trifluoroacetic acid, 17 minute gradient from 10% B to 100% B at 35 mL/minute). Product fractions were combined, made basic by the addition of sat. NaHCO$_3$, and concentrated in vacuo to remove the acetonitrile. The resulting basic aqueous was extracted with CH$_2$Cl$_2$ (3×), and the organics were dried over Na$_2$SO$_4$, filtered and concentrated in vacuo. The resulting 1-(3'-(methylsulfonyl)biphenyl-4-yl)-4-((R)-pyrrolidin-2-yl)-2-(2-(trifluoromethyl)phenyl)-1H-imidazole was recovered as a white foam, yield 57.7 mg (98%); $^1$H NMR (400 MHz, CDCl$_3$): δ 8.1-8.08 (m, 1H), 7.93-7.90 (m, 1H), 7.83-7.79 (m, 1H), 7.74-7.70 (m, 1H), 7.64 (t, J=7.8 Hz, 1H), 7.54-7.48 (m, 4H), 7.38-7.34 (m, 1H), 7.21-7.17 (m, 3H), 4.27-4.22 (m, 1H), 3.26-3.17 (m, 1H). 3.08 (s, 3H), 3.03-2.96 (m, 1H), 2.32-2.15 (m, 2H), 2.05-1.82 (m, 3H); MS (ES): 512.5 [M+H]$^+$.

Example 38b3

Preparation of 4-((R)-1-methylpyrrolidin-2-yl)-1-(3'-(methylsulfonyl)biphenyl-4-yl)-2-(2-(trifluoromethyl)phenyl)-1H-imidazole

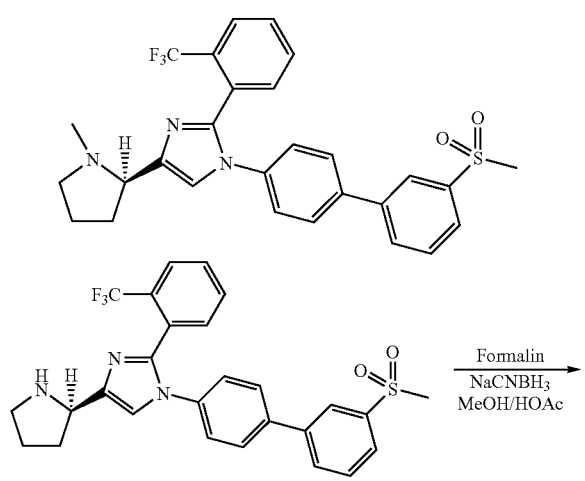

630

-continued

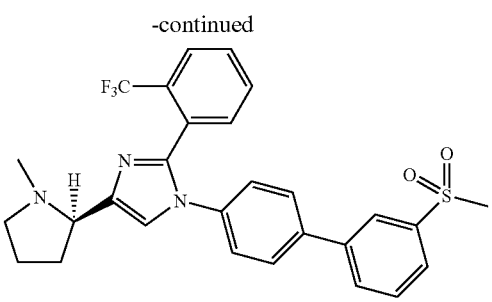

Into an 8 mL vial was weighed 20.7 mg (40 µmol) of 1-(3'-(methylsulfonyl)biphenyl-4-yl)-4-((R)-pyrrolidin-2-yl)-2-(2-(trifluoromethyl)phenyl)-1H-imidazole. The material was dissolved in MeOH (400 µL) and HOAc (100 µL). The solution was treated with 20 µL (240 µmol) of 37% aqueous formaldehyde solution, and then 8 mg (125 µmol) of sodium cyanoborohydride was added at ambient temperature. After stirring for 15 minutes at ambient temperature LC/MS analysis of the reaction showed complete conversion to product. The reaction solution was directly injected into the reverse phase preparative HPLC and eluted with acetonitrile/water. (Phenomenex Axia Gemini C18 30×100 mm 5 µm, A=H$_2$O with 0.1% trifluoroacetic acid, B=acetonitrile with 0.1% trifluoroacetic acid, 17 minute gradient from 10% B to 100% B at 35 mL/minute). Product fractions were combined, made basic by the addition of sat. NaHCO$_3$, and concentrated in vacuo to remove the acetonitrile. The resulting basic aqueous was extracted with CH$_2$Cl$_2$ (3×), and the organics were dried over Na$_2$SO$_4$, filtered and concentrated in vacuo. The resulting 4-((R)-1-methylpyrrolidin-2-yl)-1-(3'-(methylsulfonyl)biphenyl-4-yl)-2-(2-(trifluoromethyl)phenyl)-1H-imidazole was isolated as a white foam, yield: 16.9 mg (79%); $^1$H NMR (400 MHz, CDCl$_3$): δ 8.10-8.07 (m, 1H), 7.93-7.90 (m, 1H), 7.83-7.79 (m, 1H), 7.72-7.68 (m, 1H), 7.64 (t, J=7.8 Hz, 1H), 7.54-7.48 (m, 4H), 7.43-7.38 (m, 1H), 7.27-7.18 (m, 4H), 3.41-3.30 (m, 1H), 3.28-3.20 (m, 1H), 3.08 (s, 3H), 2.44 (s, 3H), 2.41-2.26 (m, 2H), 2.13-1.94 (m, 2H), 1.90-1.79 (m, 1H); MS (ES): 526.5 [M+H]$^+$.

Example 38b4

Preparation of 1-((2R)-2-(1-(3'-(methylsulfonyl)biphenyl-4-yl)-2-(2-(trifluoromethyl)phenyl)-1H-imidazol-4-yl)pyrrolidin-1-yl)ethanone

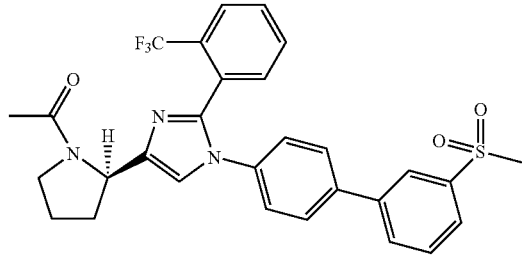

631
-continued

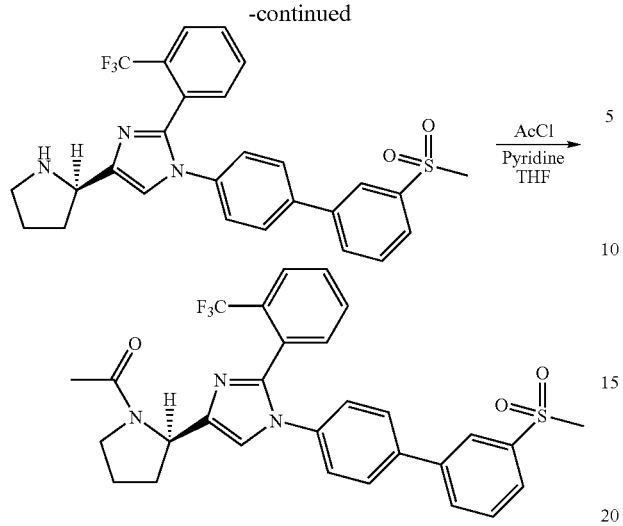

Into an 8 mL vial was weighed 26.8 mg (52 µmol) of 1-(3'-(methylsulfonyl)biphenyl-4-yl)-4-((R)-pyrrolidin-2-yl)-2-(2-(trifluoromethyl)phenyl)-1H-imidazole. The vial was charged with 0.5 mL of THF, followed by 15 µL (185 µmol) of pyridine, and 7 µL (98 µmol) of acetyl chloride. After stirring for 30 minutes at ambient temperature, LC/MS analysis of the reaction showed complete conversion to product. The reaction was quenched by addition of a small amount of water. The reaction solution was directly injected into the reverse phase preparative HPLC and eluted with acetonitrile/water. (Phenomenex Axia Gemini C18 30×100 mm 5 µm, A=H$_2$O with 0.1% trifluoroacetic acid, B=acetonitrile with 0.1% trifluoroacetic acid, 17 minute gradient from 10% B to 100% B at 35 mL/minute). Product fractions were combined, made basic by the addition of sat. NaHCO$_3$, and concentrated in vacuo to remove the acetonitrile. The resulting basic aqueous was extracted with CH$_2$Cl$_2$ (3×), and the organics were dried over Na$_2$SO$_4$, filtered and concentrated in vacuo. The resulting 1-((2R)-2-(1-(3'-(methylsulfonyl)biphenyl-4-yl)-2-(2-(trifluoromethyl)phenyl)-1H-imidazol-4-yl)pyrrolidin-1-yl)ethanone was isolated as a white powder, yield 20.2 mg (70%); $^1$H NMR (400 MHz, CDCl$_3$): δ 8.10-8.07 (m, 1H), 7.95-7.90 (m, 1H), 7.83-7.79 (m, 1H), 7.77-7.72 (m, 1H), 7.67-7.61 (m, 1H), 7.56-7.42 (m, 4H), 7.38-7.34 (m, 0.6H), 7.30-7.26 (m, 0.4H), 7.20-7.16 (m, 2.4H), 7.05-7.04 (m, 0.6H), 5.34-5.31 (m, 0.4H), 5.08-5.05 (m, 0.6H), 3.78-3.67 (m, 1H), 3.63-3.49 (m, 1H), 3.09 (s, 1.8H), 3.08 (s, 1.2H), 2.52-2.46 (m, 0.4H), 2.36-2.26 (m, 1.6H), 2.14 (s, 1.8H), 2.12 (s, 1.2H), 2.08-1.95 (m, 2H); MS (ES): 554.3 [M+H]$^+$.

632
-continued

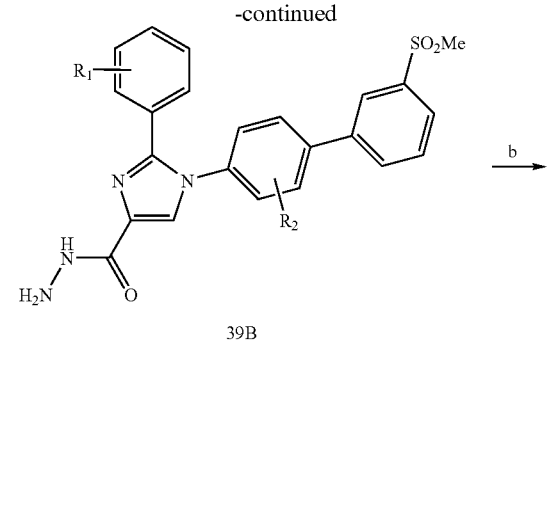

39B

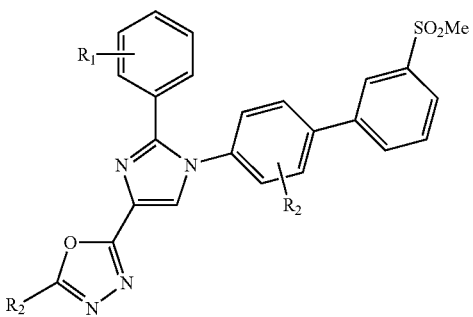

39C a. NH$_2$NH$_2$, PhMe, Dioxane, 90° C.; b) p-TsOH, triethyl orthoformate, xylenes, 130° C., 12 h.

As depicted in Scheme 39, oxadiazole-imidazole was synthesized from the hydrazide-imidazole intermediate via p-toluenesulfonic acid and triethyl orthoformate in xylenes. The hydrazide was synthesized from the ester-imidazole intermediate by heating with hydrazine in a mixture of toluene and dioxane. The ester-imidazole was prepared according to Scheme 17 (compound 17c).

Example 39

Preparation of 2-(1-(3'-(methylsulfonyl)biphenyl-4-yl)-2-(2-(trifluoromethyl)phenyl)-1H-imidazol-4-yl)-1,3,4-oxadiazole Scheme 39

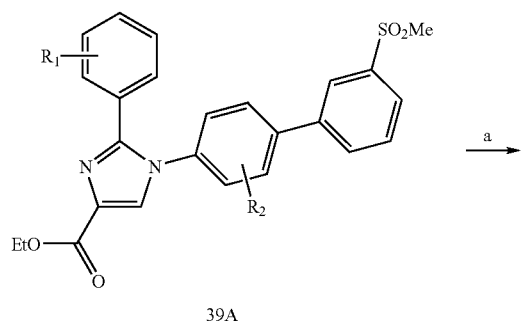

39A

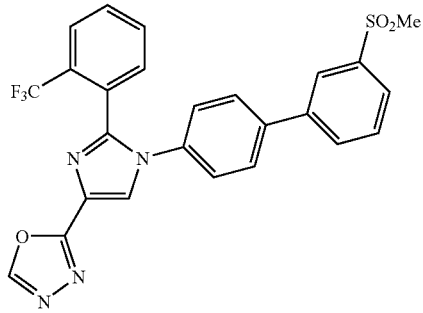

Example 39a

Preparation of 1-(3'-(methylsulfonyl)biphenyl-4-yl)-2-(2-(trifluoromethyl)phenyl)-1H-imidazole-4-carbohydrazide

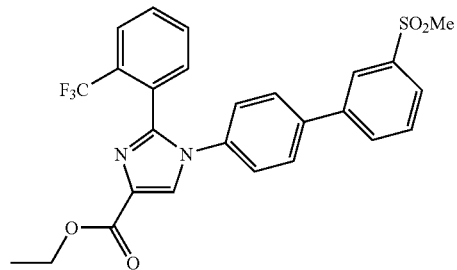

The following compound was prepared as described in Example 39a:

1-(3'-(methylsulfonyl)biphenyl-4-yl)-4-(thiophen-2-yl)-2-(2-(trifluoromethyl)phenyl)-1H-imidazole

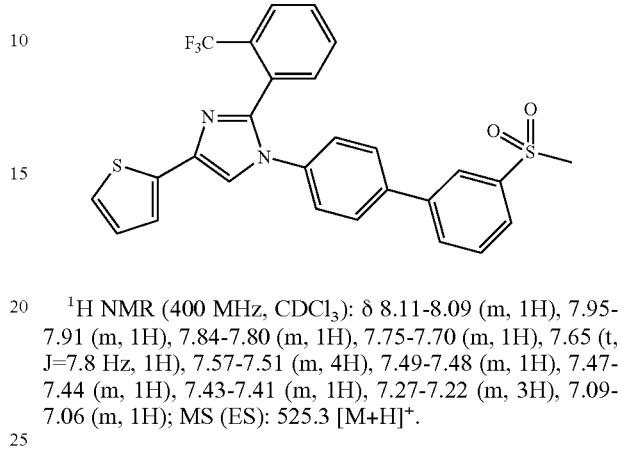

$^1$H NMR (400 MHz, CDCl$_3$): δ 8.11-8.09 (m, 1H), 7.95-7.91 (m, 1H), 7.84-7.80 (m, 1H), 7.75-7.70 (m, 1H), 7.65 (t, J=7.8 Hz, 1H), 7.57-7.51 (m, 4H), 7.49-7.48 (m, 1H), 7.47-7.44 (m, 1H), 7.43-7.41 (m, 1H), 7.27-7.22 (m, 3H), 7.09-7.06 (m, 1H); MS (ES): 525.3 [M+H]$^+$.

Example 39b

Preparation of 2-(1-(3'-(methylsulfonyl)biphenyl-4-yl)-2-(2-(trifluoromethyl)phenyl)-1H-imidazol-4-yl)-1,3,4-oxadiazole

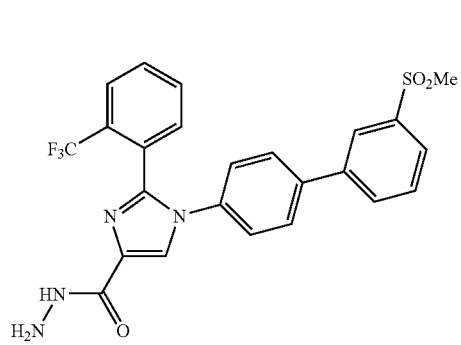

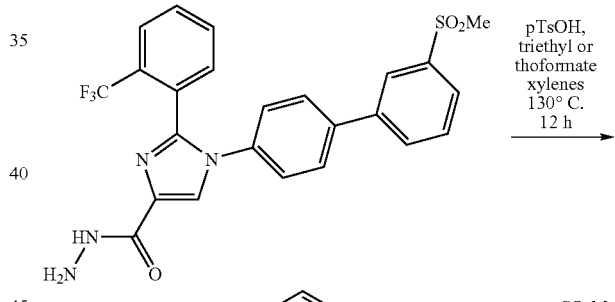

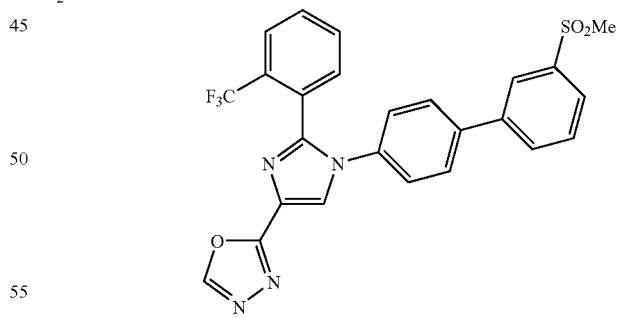

To a solution of ethyl 1-(3'-(methylsulfonyl)biphenyl-4-yl)-2-(2-(trifluoromethyl)-phenyl)-1H-imidazole-4-carboxylate (2.63 g, 5.110 mmol) in 8 mL of 1:1 PhMe:Dioxane was added hydrazine (1 mL, 31.86 mmol). The reaction was heated at 90° C. for 12 h and then cooled to room temperature. The reaction was filtered through a small amount of celite to remove a black precipitate and then concentrated and placed on the high vacuum pump. The residue was dissolved in a minimum amount of dichloromethane and slowly added to 200 mL ether with stirring. 100 mL of ether was added and the white precipitate was filtered and rinsed with ether to afford 1-(3'-(methylsulfonyl)biphenyl-4-yl)-2-(2-(trifluoromethyl)-phenyl)-1H-imidazole-4-carbohydrazide (1.77 g, 70%) as a white solid. $^1$H-NMR (DMSO, 400 MHz) δ 9.21 (s, 1H), 8.16 (s, 1H), 8.14-8.13 (m, 1H), 8.03-8.00 (m, 1H), 7.92-7.89 (m, 1H), 7.85-7.89 (m, 3H), 7.74-7.64 (m, 4H), 7.36 (d, J=8.58 Hz, 2H), 4.44 (brs, 2H), 3.28 (s, 3H); MS (ES): 501.3 [M+H]$^+$ and 523.2 [M+Na]$^+$.

To a suspension of 1-(3'-(methylsulfonyl)biphenyl-4-yl)-2-(2-(trifluoromethyl)-phenyl)-1H-imidazole-4-carbohydrazide (198 mg, 0.395 mmol) and triethyl orthoformate (1 mL, 6.01 mmol) in 1 mL xylenes was added a catalytic amount of p-toluenesulfonic acid. The reaction was heated at 130° C. for 12 h. The reaction was cooled and the mixture was absorbed onto silica and purified by column chromatography using hexanes:ethyl acetate as eluents to afford 2-(1-(3'-(methylsulfonyl)biphenyl-4-yl)-2-(2-(trifluoromethyl)phenyl)-1H-imidazol-4-yl)-1,3,4-oxadiazole (96 mgs, 48%) as a white solid. $^1$H-NMR (CDCl$_3$, 400 MHz) δ 8.48 (s, 1H), 8.12 (s, 1H), 8.11-8.10 (m, 1H), 7.97-7.94 (m, 1H), 7.85-7.82 (m, 1H), 7.77-7.75 (m, 1H), 7.67 (t, J=7.83 Hz, 1H), 7.61-7.58 (m, 4H), 7.48-7.45 (m, 1H), 7.29-7.27 (m, 2H), 3.09 (s, 3H); MS (ES): 511.4 [M+H]$^+$ and 533.0 [M+Na]$^+$.

As depicted in Scheme 40, the 4-methyl-1H-1,2,4-triazole-5(4H)-thione-imidazole was synthesized from the hydrazide with methyl isothiocyanate, potassium carbonate in water.

Example 40

Preparation of 4-methyl-3-(1-(3'-(methylsulfonyl)biphenyl-4-yl)-2-(2-(trifluoromethyl)phenyl)-1H-imidazol-4-yl)-1H-1,2,4-triazole-5(4H)-thione

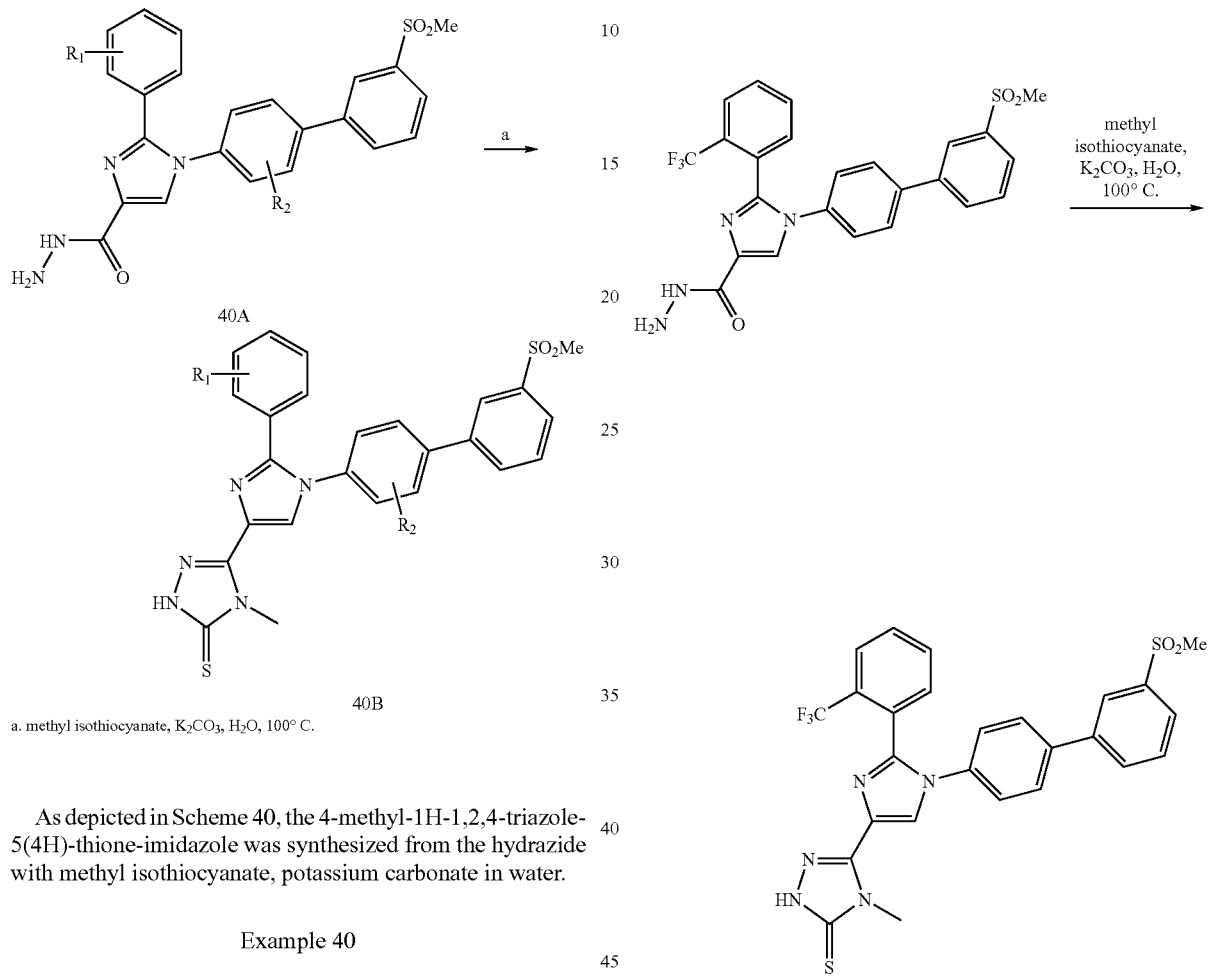

Example 40a

Preparation of 4-methyl-3-(1-(3'-(methylsulfonyl)biphenyl-4-yl)-2-(2-(trifluoromethyl)phenyl)-1H-imidazol-4-yl)-1H-1,2,4-triazole-5(4H)-thione

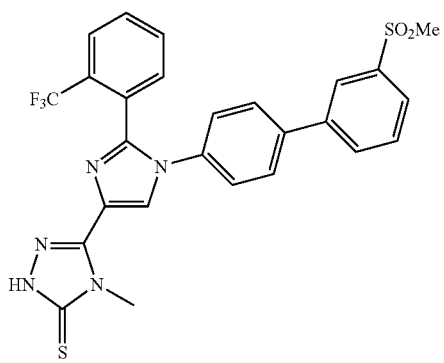

To a suspension of 1-(3'-(methylsulfonyl)biphenyl-4-yl)-2-(2-(trifluoromethyl)-phenyl)-1H-imidazole-4-carbohydrazide (215 mg, 0.430 mmol) in 8 mL 10% K$_2$CO$_3$ solution was added methyl isothiocyanate (0.06 mL, 0.877 mmol) via syringe. The reaction was refluxed 12 h and cooled to room temperature. The reaction was neutralized at 0° C. with 1M HCl and then extracted 3×10 mL with ethyl acetate. The combined organic layers were dried with MgSO$_4$ and the solvent removed in vacuo. The crude residue was absorbed onto silica and purified by column chromatography using hexanes:ethyl acetate as eluents to afford 4-methyl-3-(1-(3'-(methylsulfonyl)biphenyl-4-yl)-2-(2-(trifluoromethyl)phenyl)-1H-imidazol-4-yl)-1H-1,2,4-triazole-5(4H)-thione (27 mgs, 11 %) as a white solid. $^1$H-NMR (DMSO, 400 MHz) δ 13.89 (s, 1H), 8.37 (s, 1H), 8.15-8.14 (m, 1H), 8.05-8.02 (m, 1H), 7.93-7.89 (m, 2H), 7.85 (d, J=8.58 Hz, 2H), 7.75-7.73 (m, 1H), 7.72-7.68 (m, 2H), 7.62-7.59, (m, 1H), 7.41 (d, J=8.58 Hz, 2H), 3.78 (s, 3H), 3.28 (s, 3H); MS (ES): 556.0 [M+H]$^+$ and 578.3 [M+Na]$^+$.

Scheme 41

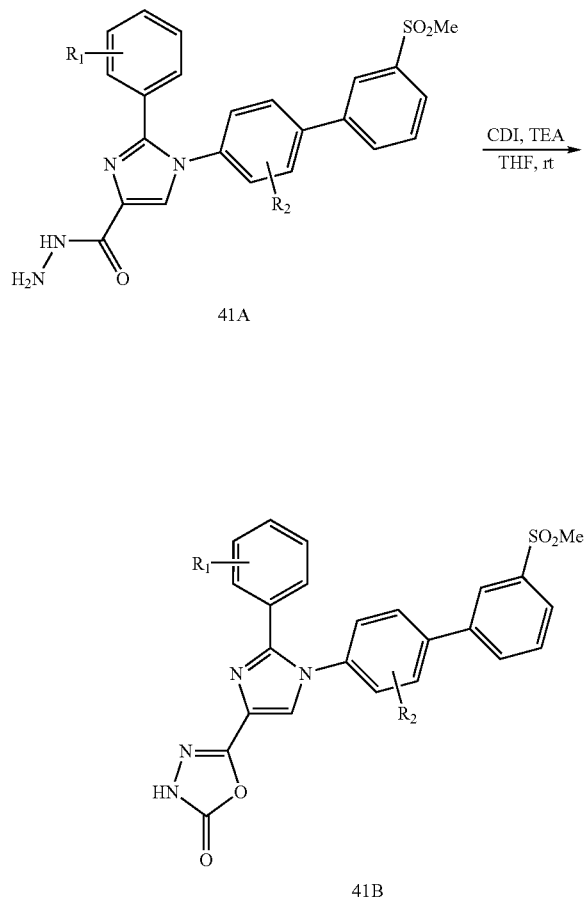

As depicted in Scheme 41, the 1,3,4-oxadiazol-2(3H)-one-imidazole was synthesized by treatment of the hydrazide with carbonyldiimidazole and triethyl amine in THF.

Example 41

Preparation of 5-(1-(3'-(methylsulfonyl)biphenyl-4-yl)-2-(2-(trifluoromethyl)phenyl)-1H-imidazol-4-yl)-1,3,4-oxadiazol-2(3H)-one

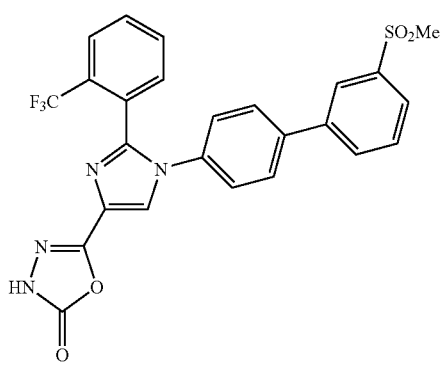

Example 41a

Preparation of 5-(1-(3'-(methylsulfonyl)biphenyl-4-yl)-2-(2-(trifluoromethyl)phenyl)-1H-imidazol-4-yl)-1,3,4-oxadiazol-2(3H)-one

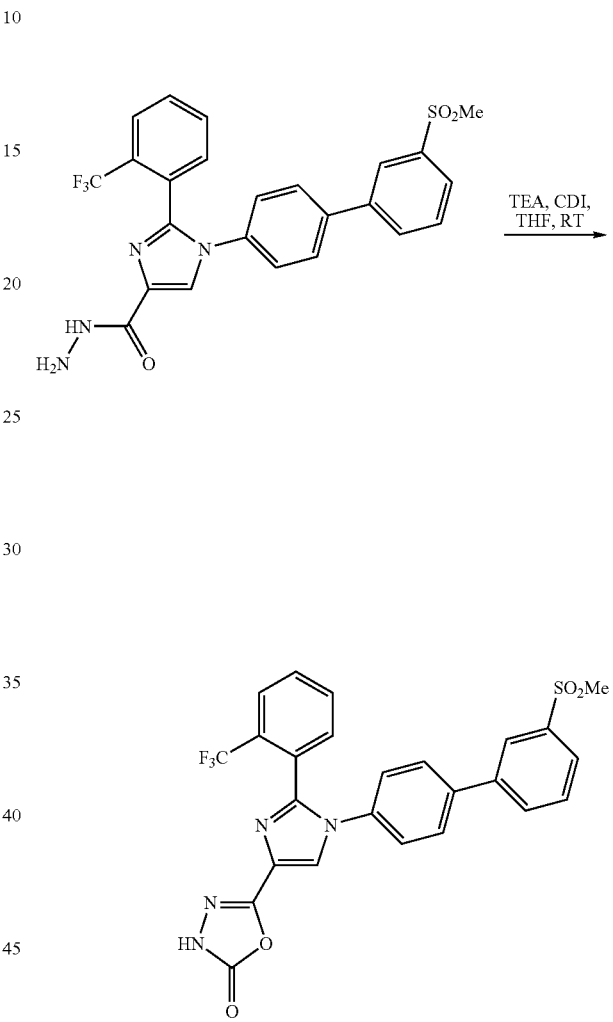

To a solution of 1-(3'-(methylsulfonyl)biphenyl-4-yl)-2-(2-(trifluoromethyl)phenyl)-1H-imidazole-4-carbohydrazide (216 mg, 0.432 mmol), triethylamine (0.132 mL, 0.949 mmol) in 1 mL anhydrous THF was added carbonyldiimidazole (140 mg, 0.864 mmol). The reaction was stirred for 24 h at room temperature. The reaction was diluted with ethyl acetate, washed with water, brine, and dried with MgSO$_4$. The residue was absorbed onto silica and purified by column chromatography using hexanes:ethyl acetate as eluents to afford 5-(1-(3'-(methylsulfonyl)biphenyl-4-yl)-2-(2-(trifluoromethyl)phenyl)-1H-imidazol-4-yl)-1,3,4-oxadiazol-2(3H)-one (120 mgs, 52%) as a white solid. $^1$H-NMR (DMSO, 400 MHz) δ 12.48 (s, 1H), 8.39 (s, 1H), 8.15-8.14 (m, 1H), 8.04-8.01 (m, 1H), 7.93-7.90 (m, 1H) 7.87-7.82 (m, 3H), 7.75-7.70 (m, 3H), 7.66-7.64 (m, 1H), 7.38 (d, J=8.61 Hz, 2H), 3.28 (s, 3H); MS (ES): 527.3 [M+H]$^+$ and 549.3 [M+Na]$^+$.

Scheme 42

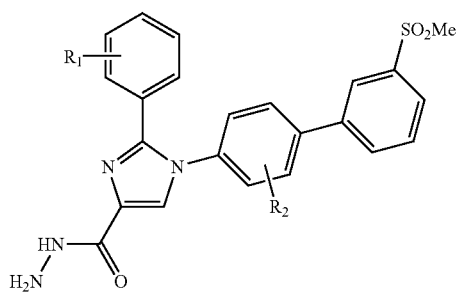

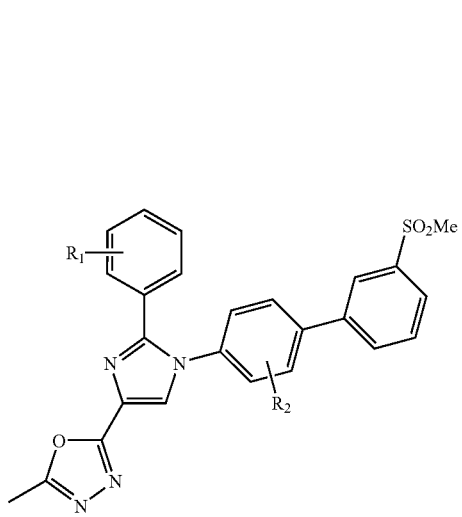

a) i. acetic anhydride, pyridine; ii. PPA, 120° C.

As depicted in Scheme 42, 2-methyl-1,3,4-oxadiazole-imidazole was synthesized from the hydrazine first by treatment with acetic anhydride, pyridine, then condensation with PPA at 120° C.

Example 42

Preparation of 2-methyl-5-(1-(3'-(methylsulfonyl)biphenyl-4-yl)-2-(2-(trifluoromethyl)phenyl)-1H-imidazol-4-yl)-1,3,4-oxadiazole

Example 42a

Preparation of 2-methyl-5-(1-(3'-(methylsulfonyl)biphenyl-4-yl)-2-(2-(trifluoromethyl)phenyl)-1H-imidazol-4-yl)-1,3,4-oxadiazole

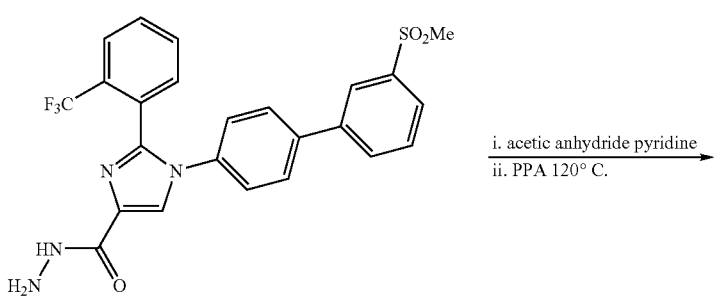

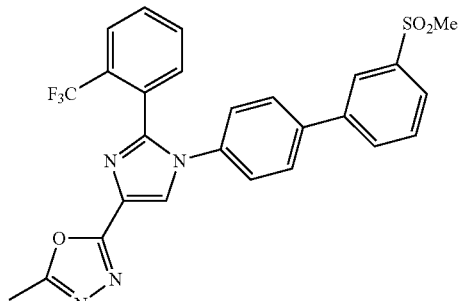

To a 0° C. solution of 1-(3'-(methylsulfonyl)biphenyl-4-yl)-2-(2-(trifluoromethyl)-phenyl)-1H-imidazole-4-carbohydrazide (192 mg, 0.383 mmol) in 1 mL pyridine was added acetic anhydride (0.085 mL, 0.767 mmol). The ice bath was removed and the reaction stirred for 1 h. The solvent was removed in vacuo and approximately 3 mL of PPA was added to the flask. The reaction was heated to 120° C. for 2 h. Upon completion of the reaction 10 mL ice water was added to the reaction. The mixture was transferred to a 150 mL Erlenmeyer flask and neutralized with 2M $Na_2CO_3$. Solid NaCl was added the solution was extracted with ethyl acetate 3×20 mL. The combined organic layers were dried with $MgSO_4$ and the solvent was removed in vacuo. The residue was absorbed onto silica and purified by column chromatography using hexanes: ethyl acetate as eluents to afford 2-methyl-5-(1-(3'-(methylsulfonyl)biphenyl-4-yl)-2-(2-(trifluoromethyl)phenyl)-1H-imidazol-4-yl)-1,3,4-oxadiazole (25 mgs, 13%) as a white solid. $^1$H-NMR (DMSO, 400 MHz) δ 8.53 (s, 1H), 8.15-8.14 (m, 1H), 8.05-8.02 (m, 1H), 7.93-7.90 (m, 1H), 7.88-7.83 (m, 3H), 7.75-7.71 (m, 3H), 7.69-7.66 (m, 1H), 7.41 (d, J=8.58 Hz, 2H), 3.28 (s, 3H), 2.58 (s, 3H); MS (ES): 525.0 $[M+H]^+$ and 547.3 $[M+Na]^+$.

The following compound was synthesized as described above except trifluoroethyl acetate was used in the acylation and the dehydration was accomplished using $POCl_3$ as a solvent and heating at 80° C.

2-(1-(3-chloro-3'-(methylsulfonyl)biphenyl-4-yl)-2-(2-chlorophenyl)-1H-imidazol-4-yl)-5-(trifluoromethyl)-1,3,4-oxadiazole

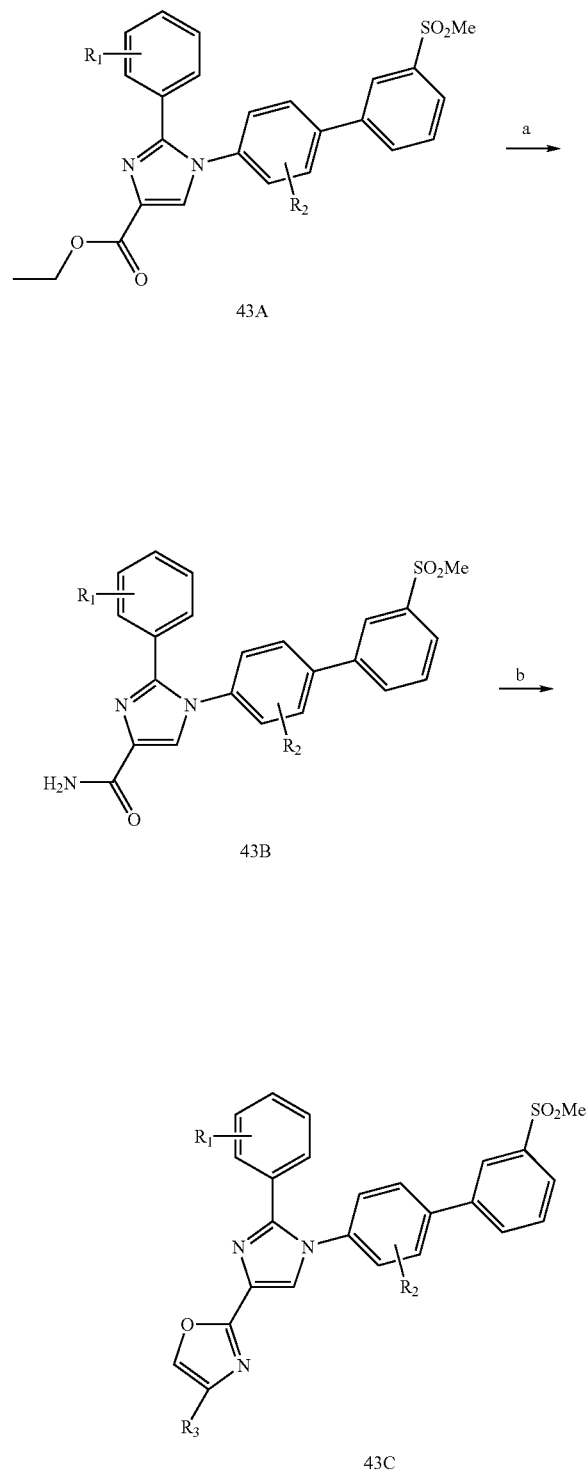

a) $NH_3$, NaCN, MeOH; b) $RCOCH_2X$, ethanol.

$^1$H-NMR (DMSO, 400 MHz) δ 8.80 (s, 1H), 8.24-8.22 (m, 1H), 8.13-8.10 (m, 2H), 7.97-7.96 (m, 1H) 7.87 (dd, J=8.36 Hz, 2.03 Hz, 1H), 7.76 (t, J=7.85 Hz, 1H), 7.73-7.71 (m, 1H), 7.62-7.60 (m, 1H), 7.53-7.46 (m, 2H), 7.43-7.39 (m, 1H), 3.30 (s, 3H); MS (ES): 579.0 $[M+H]^+$ and 601.3 $[M+Na]^+$.

As depicted in Scheme 44, the 4-substituted oxazole-imidazoles were generated by treatment of the amide with chloroacetone in ethanol and heated in the microwave at 140° C. The amide was synthesized by treatment of the ester-imidazole intermediate with ammonia in methanol using sodium cyanide as a catalyst. The imidazole-ester was prepared according to Scheme 17 (compound 17c).

Example 43

Preparation of 4-methyl-2-(1-(3'-(methylsulfonyl)biphenyl-4-yl)-2-(2-(trifluoromethyl)phenyl)-1H-imidazol-4-yl)oxazole

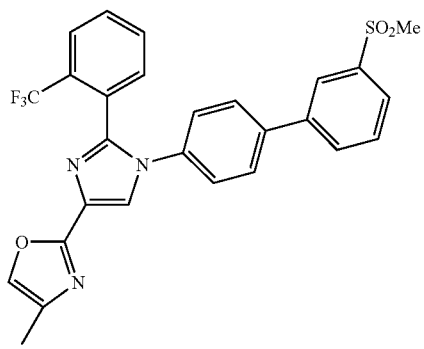

Example 43a

Preparation of 1-(3'-(methylsulfonyl)biphenyl-4-yl)-2-(2-(trifluoromethyl)phenyl)-1H-imidazole-4-carboxamide

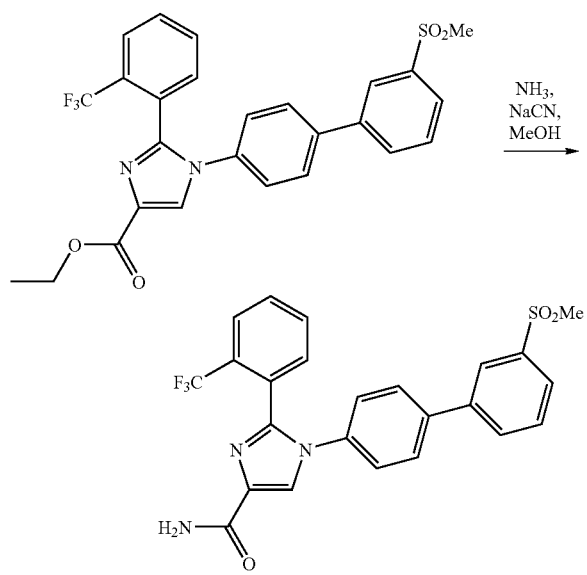

Ethyl-1-(3'-(methylsulfonyl)biphenyl-4-yl)-2-(2-(trifluoromethyl)phenyl)-1H imidazole-4-carboxylate (500 mg, 0.971 mmol), NaCN (10 mg, 0.194 mmol) and 6 mL 2M NH$_3$ in MeOH were added to a 15 mL sealed tube and heated at 60° C. for 72 h. The reaction was cooled and the compound was absorbed on to silica purified by column chromatography using hexanes:ethyl acetate as eluents to afford 1-(3'-(methylsulfonyl)biphenyl-4-yl)-2-(2-(trifluoromethyl)phenyl)-1H-imidazole-4-carboxamide (298 mgs, 63%) as a white solid. $^1$H-NMR (DMSO, 400 MHz) δ 8.14-8.13 (m, 2H), 8.04-8.01 (m, 1H), 7.92-7.89 (m 1H), 7.85-7.80 (m, 3H), 7.74-7.65 (m, 4H), 7.45 (s, 1H), 7.37-7.35 (m, 2H), 7.27 (s, 1H), 3.28 (s, 3H); MS (ES): 486.1 [M+H]$^+$ and 508.3 [M+Na]$^+$.

Example 43b

Preparation of 4-methyl-2-(1-(3'-(methylsulfonyl)biphenyl-4-yl)-2-(2-(trifluoromethyl)phenyl)-1H-imidazol-4-yl)oxazole

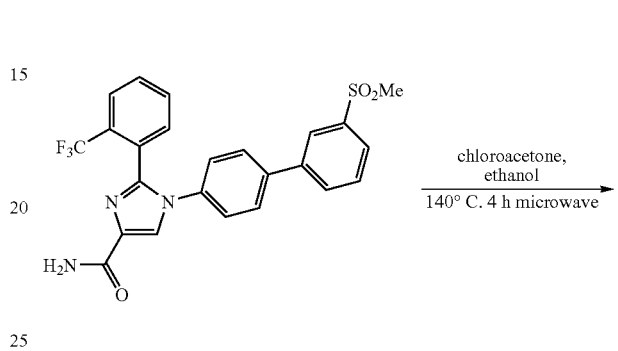

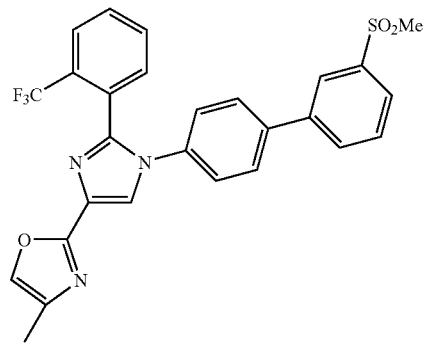

1-(3'-(methylsulfonyl)biphenyl-4-yl)-2-(2-(trifluoromethyl)phenyl)-1H-imidazole-4-carboxamide (266 mg, 0.547 mmol), chloroacetone (0.40 mL, 5.02 mmol) and 3 mL ethanol were added to a 5 mL microwave tube and sealed. The reaction tube was heated in the microwave for 4 h at 140° C. The solvent was removed in vacuo and sat. NaHCO$_3$ was added to the residue. The mixture was extracted with ethyl acetate 3×10 mL, dried with MgSO$_4$ and the solvent removed in vacuo. The crude residue was absorbed onto silica gel and by purified by column chromatography using hexanes:ethyl acetate as eluents and further purified by preparatory HPLC using water:TFA:acetonitrile as eluents to afford 4-methyl-2-(1-(3'-(methylsulfonyl)biphenyl-4-yl)-2-(2-(trifluoromethyl)phenyl)-1H-imidazol-4-yl)oxazole (30 mgs, 10%) as a white solid. $^1$H-NMR (DMSO, 400 MHz) δ 8.31 (s, 1H), 8.15-8.14 (m, 1H), 8.04-8.01 (m, 1H), 7.93-7.90 (m, 1H), 7.88-7.82 (m, 4H), 7.75-7.70 (m, 3H), 7.65-7.62 (m, 1H), 7.38 (d, J=8.58 Hz, 2H), 3.28 (s, 3H), 2.16 (s, 3H); MS (ES): 524.5 [M+H]$^+$ and 546.3 [M+Na]$^+$.

The following compound was prepared as described above except 3-bromo-1,1,1-trifluoroacetone and toluene-dioxane mixture were used in the place of chloroacetone and ethanol.

2-(1-(3-chloro-3'-(methylsulfonyl)biphenyl-4-yl)-2-(2-chlorophenyl)-1H-imidazol-4-yl)-4-(trifluoromethyl)oxazole

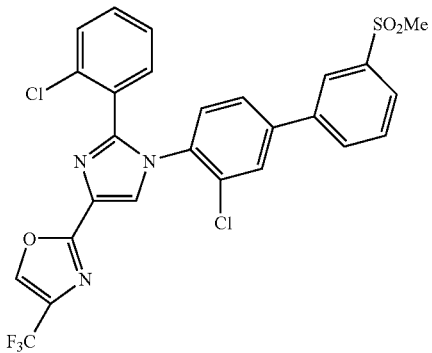

¹H-NMR (DMSO, 400 MHz) δ 8.87 (s, 1H), 8.25-8.24 (m, 1H), 8.20-8.18 (m, 1H), 8.14-8.11 (m, 1H), 7.99-7.97 (m, 3H), 7.84-7.80 (m, 1H), 7.79-7.75 (m, 1H), 7.74-7.73 (m, 1H), 7.70-7.66 (m, 1H), 7.56-7.52 (m, 1H), 7.25 (s, 1H), 3.30 (s, 3H); MS (ES): 579.0.

Scheme 44

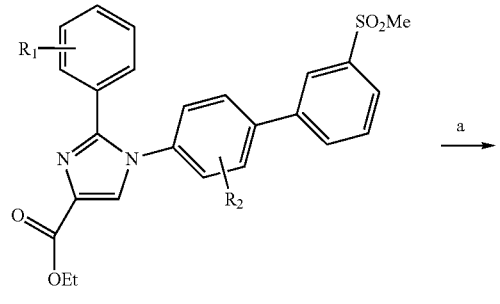
44A

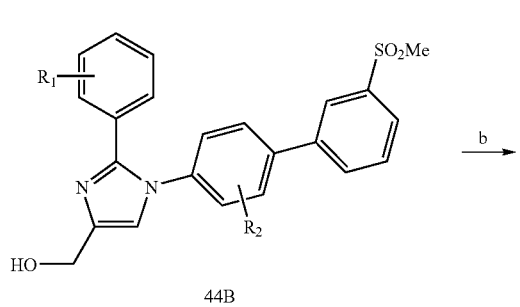
44B

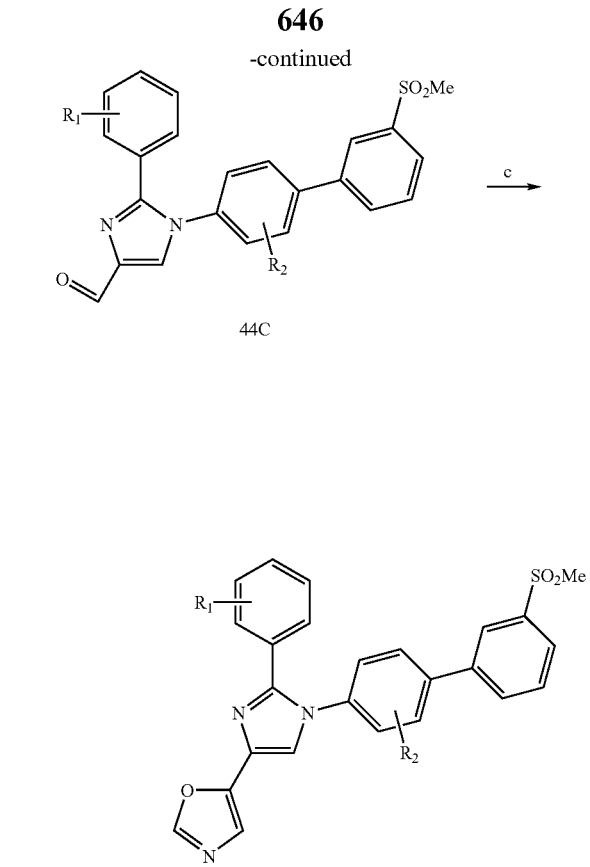
44C

44D a) DibalH, DCM; b) (COCl)₂, TEA, DMSO; c) TOSMIC, K₂CO₃, MeOH

As depicted in Scheme 44, the oxazole-imidazole compound was synthesized by treating the aldehyde with TOSMIC and K₂CO₃ in methanol. The aldehyde-oxazole intermediate was synthesized swern oxidation of the alcohol intermediate. The alcohol was made by Dibal hydrogen reduction of the imidazole-ester, which was prepared according to Scheme 44.

Example 44

Preparation of 5-(1-(3-chloro-3'-(methylsulfonyl)biphenyl-4-yl)-2-(2-chlorophenyl)-1H-imidazol-4-yl)oxazole

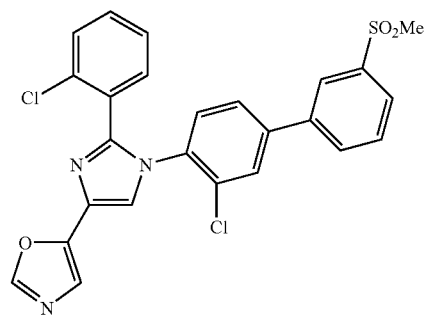

Example 44a

Preparation of (1-(3-chloro-3'-(methylsulfonyl)biphenyl-4-yl)-2-(2-chlorophenyl)-1H-imidazol-4-yl)methanol

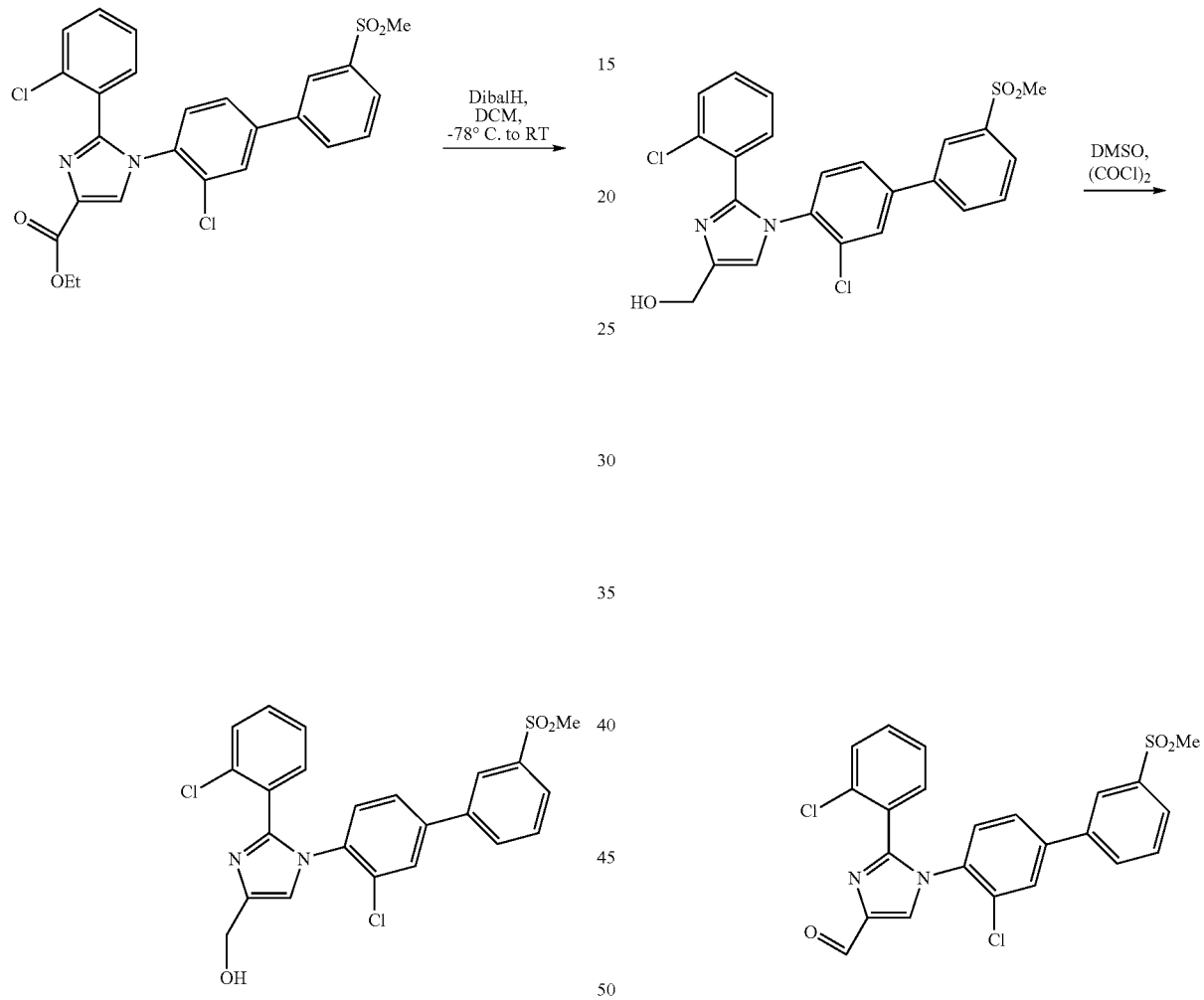

To a −78° C. solution of ethyl 1-(3-chloro-3'-(methylsulfonyl)biphenyl-4-yl)-2-(2-chlorophenyl)-1H-imidazole-4-carboxylate (1.00 g, 1.94 mmol) in 10 mL dichloromethane was added diisobutylaluminum hydride (9.7 mL, 9.70 mmol). The reaction was stirred from 78° C. to room temperature for 12 h. The reaction was quenched with 5 mL MeOH, followed by 10 mL Rochelle's salt. Dilute with ethyl acetate and stir for 1 h. The organic layer was separated and the water layer was extracted with ethyl acetate 1×10 mL. The combined organic layers were washed with brine and dried with MgSO$_4$ to afford (1-(3-chloro-3'-(methylsulfonyl)biphenyl-4-yl)-2-(2-chlorophenyl)-1H-imidazol-4-yl)methanol (770 mg, 84%) as a white solid. $^1$H-NMR (DMSO, 400 MHz) δ 8.21-8.20 (m, 1H), 8.10-8.07 (m, 1H), 8.05-8.04 (m, 1H), 7.95-7.92 (m, 1H), 7.80-7.77 (m, 1H), 7.74 (t, J=7.84 Hz, 1H), 7.49-7.46 (m, 2H), 7.45-7.31 (m, 4H), 5.11 (t, J=5.69 Hz, 1H), 4.50 (d, J=5.79 Hz, 2H), 3.29 (s, 3H); MS (ES) 473.3 [M+H]$^+$ and 495.0 [M+Na]$^+$.

Example 44b

Preparation of 1-(3-chloro-3'-(methylsulfonyl)biphenyl-4-yl)-2-(2-chlorophenyl)-1H-imidazole-4-carbaldehyde To a −78° C. solution of oxalyl chloride (0.20 mL, 2.33 mmol) in 5 mL dichloromethane was added DMSO dropwise followed by (1-(3-chloro-3'-(methylsulfonyl)biphenyl-4-yl)-2-(2-chlorophenyl)-1H-imidazol-4-yl)methanol (735 mg, 1.55 mmol) in 5 mL of dichloromethane. Triethylamine (1.3 mL, 9.30 mmol) was then added at −78° C. and the reaction was stirred 12 h and warmed to room temperature. The reaction was diluted with 50 mL ethyl acetate, washed with water 1×50 mL, brine, and dried with MgSO$_4$. The solvent was removed in vacuo and the residue was purified by column chromatography using hexanes:ethyl acetate as eluents to afford 1-(3-chloro-3'-(methylsulfonyl)biphenyl-4-yl)-2-(2-chlorophenyl)-1H-imidazole-4-carbaldehyde (338 mgs, 47%) as a white solid. $^1$H-NMR (DMSO, 400 MHz) δ 9.90 (s, 1H), 8.56 (s, 1H), 8.22-8.21 (m, 1H), 8.12-8.09 (m, 2H), 7.97-7.94 (m, 1H), 7.84 (dd, J=8.33 Hz, J=2.04 Hz, 1H), 7.75

(t, J=7.82 Hz, 1H), 7.67-7.65 (m, 1H), 7.58-7.56 (m, 1H), 7.50-7.43 (m, 2H), 7.40-7.36 (m, 1H), 3.30 (s, 3H); MS (ES) 471.0 [M+H]⁺.

Example 44c

Preparation of 5-(1-(3-chloro-3'-(methylsulfonyl)biphenyl-4-yl)-2-(2-chlorophenyl)-1H-imidazol-4-yl)oxazole

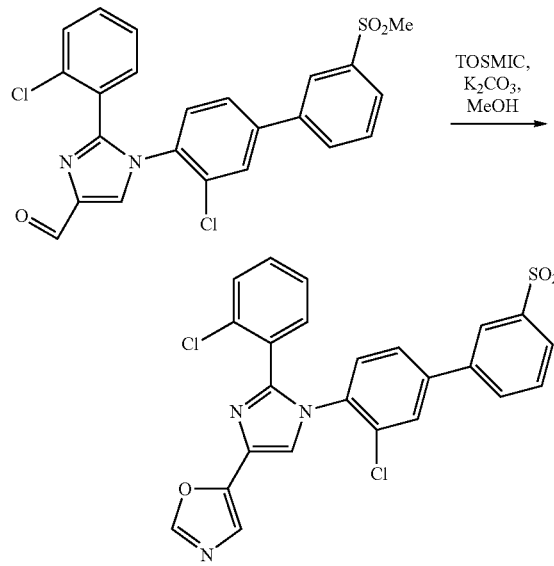

To a suspension of 1-(3-chloro-3'-(methylsulfonyl)biphenyl-4-yl)-2-(2-chlorophenyl)-1H-imidazole-4-carbaldehyde (197 mg, 0.418 mmol) in 2 mL methanol was added K₂CO₃. The reaction was heated in an oil bath at 65° C. for 5 h. Methanol was removed in vacuo and water was added to the vial. The mixture was then extracted with ethyl acetate 3×10 mL. The combined organic layers were washed with brine, dried with MgSO₄ and the solvent removed in vacuo. The residue was absorbed onto silica gel and purified by column chromatography using hexanes:ethyl acetate as eluents to afford 5-(1-(3-chloro-3'-(methylsulfonyl)biphenyl-4-yl)-2-(2-chlorophenyl)-1H-imidazol-4-yl)oxazole (127 mgs, 60%) as a white solid. ¹H-NMR (DMSO, 400 MHz) δ 8.42 (s, 1H), 8.22-8.21 (m, 1H), 8.12-8.09 (m, 2H), 8.03 (s, 1H), 7.96-7.94 (m, 1H), 7.83 (dd, J=8.34 Hz, 2.03 Hz, 1H), 7.75 (t, J=7.83 Hz, 1H), 7.65-7.62 (m, 1H), 7.59-7.57 (m, 1H), 7.49-7.42 (m, 3H), 7.40-7.36 (m, 1H), 3.30 (s, 3H); MS (ES) 510.0[M+H]⁺.

Scheme 45

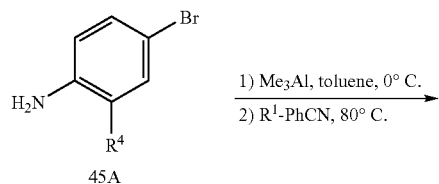

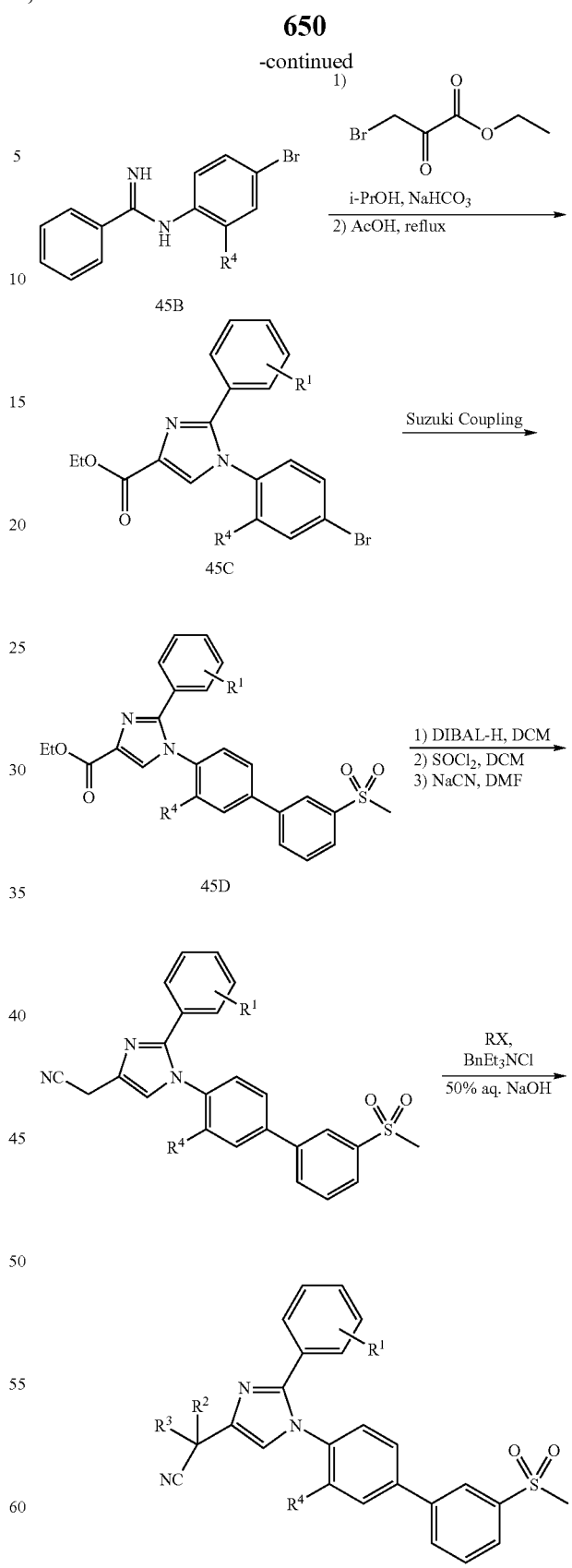

As depicted in Scheme 45, imidazole-ester intermediate was prepared according to Scheme 17 (compound 17D). The ester 17D was reacted with a reducing reagent to give alcohol that was converted to the substituted cyano-product in three steps using known methodology.

Example 45

Preparation of 1-(1-(3'-methylsulfonyl)biphenyl-4-yl)-2-(2-(trifluoromethyl)phenyl-1H-imidazol-4-yl)cyclopentanecarbonitrile

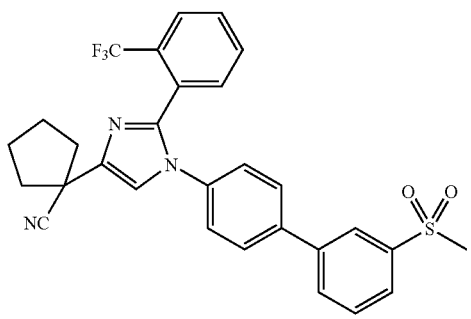

Example 45a

Preparation of 1-(3'-methylsulfonyl)biphenyl-4-yl)-2-(2-(trifluoromethyl)phenyl-1H-imidazol-4-yl)methanol

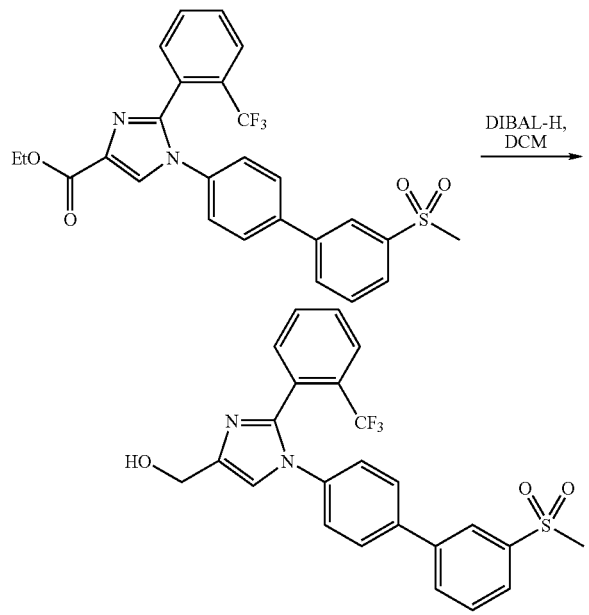

DIBAL-H (1.0M in THF, 10 mL) was added to a stirred solution of ethyl 1-(3'-methylsulfonyl)biphenyl-4-yl)-2-(2-(trifluoromethyl)phenyl-1H-imidazole-4-carboxylate (1.1 g, 2.138 mmol) in dry DCM (40 mL) at ambient temperature, the resulting mixture was stirred at room temperature under $N_2$ overnight. MeOH was added dropwise to quench the reaction, followed by 10% of Rochelle's salt. The mixture was extracted twice with EtOAc. The organic phase was washed with brine, dried over sodium sulfate, and evaporated in vacuo. The crude product was purified by flash chromatography (SiO$_2$, 100% EtOAc to 5% MeOH/EtOAc) to give 1-(3'-methylsulfonyl)biphenyl-4-yl)-2-(2-(trifluoromethyl)phenyl-1H-imidazol-4-yl)methanol as a white solid (976 mg, 96%). MS (ESI) 473 [M+H]$^+$.

Example 45b

Preparation of 1-(1-(3'-methylsulfonyl)biphenyl-4-yl)-2-(2-(trifluoromethyl)phenyl-1H-imidazole-4-carbonitrile

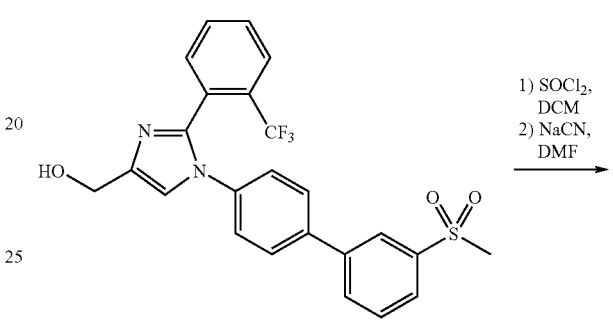

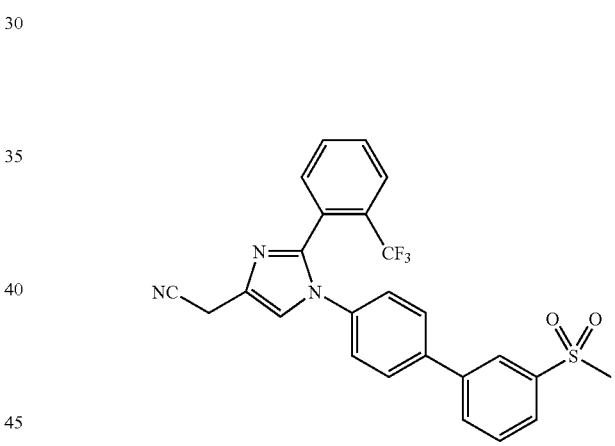

Thionyl chloride (2 mL, 27.5 mmol) was added to a stirred solution of 1-(3'-methylsulfonyl)biphenyl-4-yl)-2-(2-(trifluoromethyl)phenyl-1H-imidazol-4-yl)methanol (976 mg, 2.06 mmol) in dry DCM (30 mL), the resulting mixture was stirred at 30° C. under $N_2$ for 4 h. The volatiles were removed in vacuo to give 4-(chloromethyl)-1-(3'-methylsulfonyl)biphenyl-4-yl)-2-(2-(trifluoromethyl)phenyl-1H-imidazole (1.1 g) as a white solid, which was used in the next reaction without further purification.

A mixture of 4-(chloromethyl)-1-(3'-methylsulfonyl)biphenyl-4-yl)-2-(2-(trifluoromethyl)phenyl-1H-imidazole (1.1 g), NaCN (1.2 g, 24.5 mmol), and dry DMF was stirred at 100° C. for 12 h. The solvent was removed in vacuo, and the residue was partitioned between water and EtOAc, the phases were separated, and the aqueous phase was extracted with EtOAc. The combined extracts were washed with water, brine, dried over sodium sulfate, and evaporated in vacuo. The crude product was purified by flash chromatography (SiO$_2$, 80% EtOAc/hexanes) to give 1-(1-(3'-methylsulfonyl)

biphenyl-4-yl)-2-(2-(trifluoromethyl)phenyl-1H-imidazole-4-carbonitrile (730 mg, 74%) as a white solid. MS (ESI) 482 [M+H]⁺.

Example 45c

Preparation of 1-(1-(3'-methylsulfonyl)biphenyl-4-yl)-2-(2-(trifluoromethyl)phenyl-1H-imidazol-4-yl)cyclopentanecarbonitrile

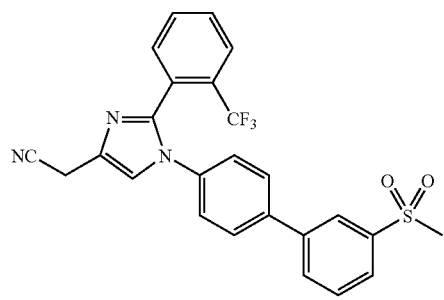

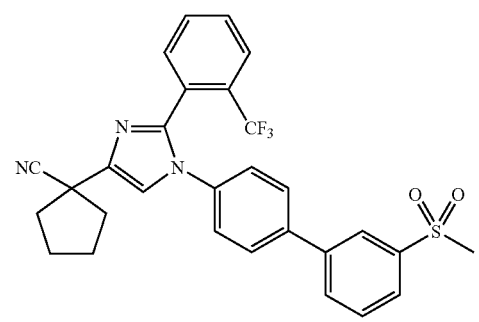

A mixture of give 1-(1-(3'-methylsulfonyl)biphenyl-4-yl)-2-(2-(trifluoromethyl)phenyl-1H-imidazole-4-carbonitrile (137 mg, 0.2845 mmol), 1,4-dibromobutane (0.2 mL, 1.69 mmol), triethylbenzylammonium chloride (40 mg), and 50% NaOH solution (3 mL) was stirred in a vial at ambient temperature overnight, diluted with ice —H₂O, extracted with EtOAc. The extracts were washed with H₂O, brine, dried over sodium sulfate, and evaporated in vacuo. The crude product was purified by flash chromatography (SiO₂, 70% EtOAc/hexanes) to give the title compound as a white solid (108 mg, 71%). MS (ESI) 536 [M+H]⁺; ¹H NMR (400 MHz, CDCl₃): δ 8.10-8.09 (m, 1H), 7.94-7.91 (m, 1H), 7.83-7.81 (m, 1H), 7.75-7.73 (m, 1H), 7.67-7.63 (m, 1H), 7.56-7.49 (m, 4H), 7.36-7.33 (m, 2H), 7.22-7.20 (m, 2H), 3.09 (s, 3H), 2.42-2.40 (m, 4H), 2.00-1.97 (m, 4H).

The following compounds were prepared as described above.

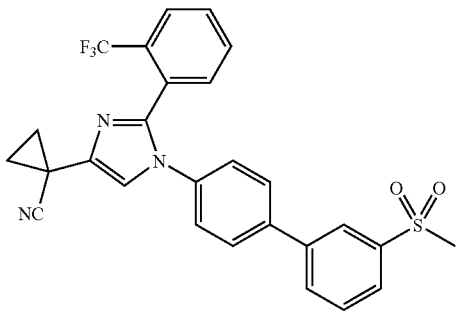

1-(1-(3'-ethylsulfonyl)biphenyl-4-yl)-2-(2-(trifluoromethyl)phenyl-1H-imidazol-4-yl)cyclopropanecarbonitrile MS (ESI) 508 [M+H]⁺; ¹H NMR (400 MHz, CDCl₃): δ 8.09-8.08 (m, 1H), 7.94-7.92 (m, 1H), 7.83-7.80 9 (m, 1H), 7.74-7.72 (m, 1H), 7.65 (t, J=7.93 Hz, 1H), 7.55-7.49 (m, 4H), 7.44 (s, 1H), 7.31-7.29 (m, 1H), 7.21-7.19 (m, 2H), 3.09 (s, 3H), 1.76-1.73 (m, 2H), 1.68-1.65 (m, 2H).

4-(1-(3'-ethylsulfonyl)biphenyl-4-yl)-2-(2-(trifluoromethyl)phenyl-1H-imidazol-4-yl)tetrahydro-2H-pyran-4-carbonitrile MS (ESI) 552 [M+H]⁺; ¹H NMR (400 MHz, CDCl₃): δ 8.10-8.09 (m, 1H), 7.95-7.92 (m, 1H), 7.83-7.81 (m, 1H), 7.76-7.74 (m, 1H), 7.65 (t, J=7.64 Hz, 1H), 7.57-7.48 (m, 4H), 7.36-7.33 (m, 2H), 7.23-7.21 (m, 2H), 4.09-4.05 (m, 2H), 3.92-3.85 (m, 2H), 3.09 (s, 3H), 2.44-2.37 (m, 2H), 2.18-2.15 (m, 2H).

Scheme 46

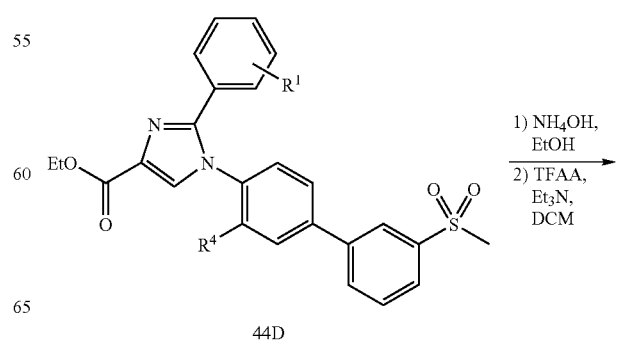

44D

655
-continued

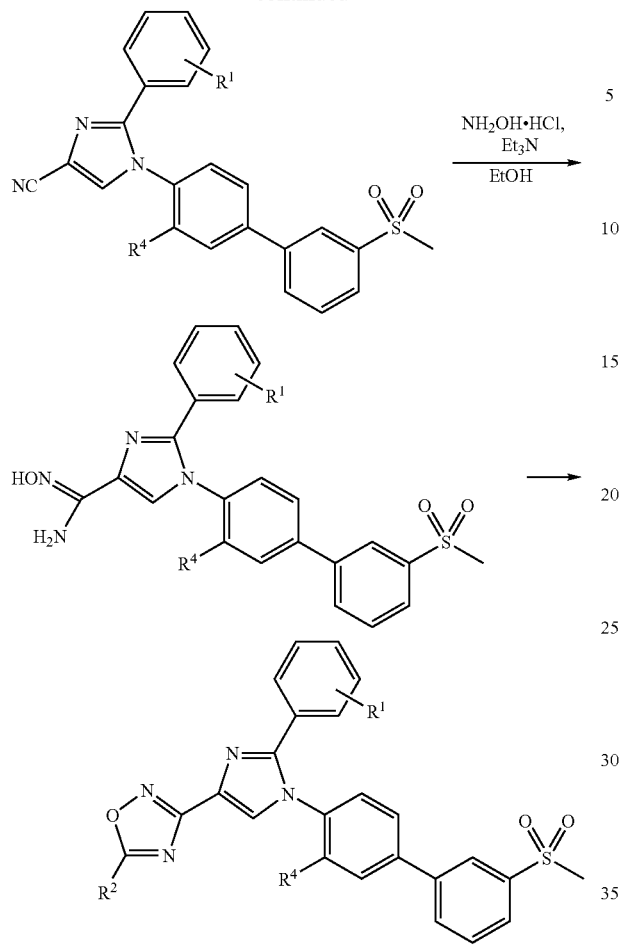

As depicted in Scheme 46, imidazole-ester intermediate was prepared according to Scheme 17 (compound 17D). After converting to cyano-intermediate via amide dehydration, the oxadiazoles analogs were prepared using known methodology.

Example 46a

Preparation of 5-methyl-3-(1-(3'-methylsulfonyl) biphenyl-4-yl)-2-(2-(trifluoromethyl)phenyl)-1H-imidazol-4-yl)-1,2,4-oxadiazole

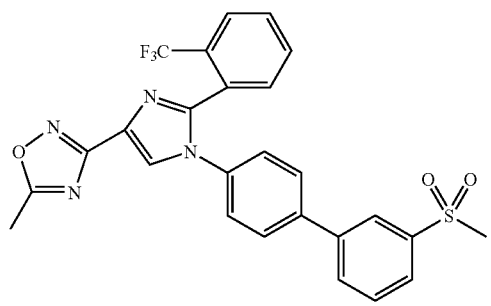

Example 46a1

Preparation of 1-(3'-methylsulfonyl)biphenyl-4-yl)-2-(2-(trifluoromethyl)phenyl-1H-imidazole-4-carbonitrile

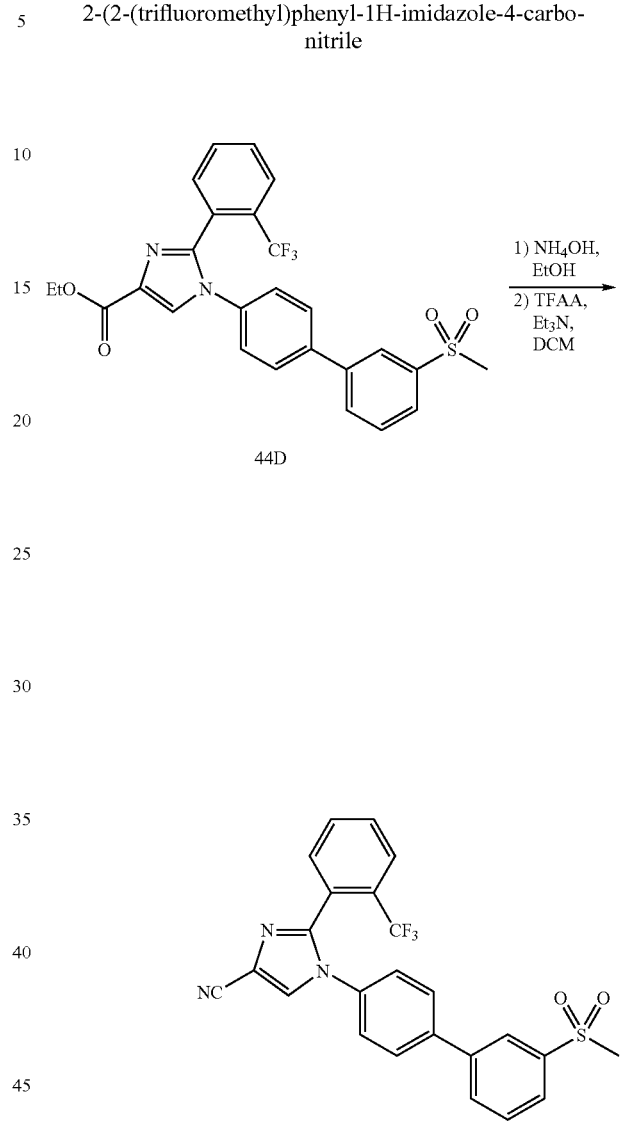

A mixture of ethyl 1-(3'-methylsulfonyl)biphenyl-4-yl)-2-(2-(trifluoromethyl)phenyl-1H-imidazole-4-carboxylate (2.03 g, 3.94 mmol), EtOH (20 mL), and concentrated ammonium hydroxide (20 mL) in a pressure flask was stirred at 90° C. overnight. After cooling to room temperature, N$_2$ was bubbled through the reaction mixture. 1-(3'-methylsulfonyl) biphenyl-4-yl)-2-(2-(trifluoromethyl)phenyl-1H-imidazole-4-carboxamide precipitated from the reaction mixture, was collected by filtration which used directly for the next step. MS (ESI) 486 [M+H]$^+$.

TFAA (2.5 mL, 17.7 mmol) was added at 0° C. to a stirred mixture of 1-(3'-methylsulfonyl)biphenyl-4-yl)-2-(2-(trifluoromethyl)phenyl-1H-imidazole-4-carboxamide (3.97 g, 8.177 mmol), Et$_3$N (5 mL, 35.87 mmol), and dry DCM (100mL), the resulting mixture was stirred at 0° C. for 2 h. The solvent was removed in vacuo, the residue was purified by flash chromatography (SiO$_2$, 80% EtOAc/hexanes) to give 1-(3'-methylsulfonyl)biphenyl-4-yl)-2-(2-(trifluoromethyl)

phenyl-1H-imidazole-4-carbonitrile as a pale-yellow to white solid (3.13 g, 82%). MS (ESI) 468 [M+H]+.

Example 46a2

Preparation of N'-hydroxy-1-(3'-ethylsulfonyl)biphenyl-4-yl)-2-(2-(trifluoromethyl)phenyl-1H-imidazole-4-carboximidamide

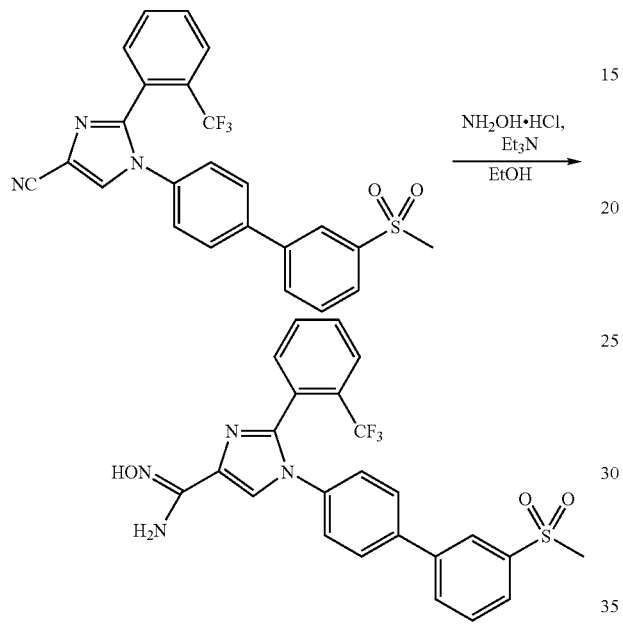

A mixture of give 1-(3'-methylsulfonyl)biphenyl-4-yl)-2-(2-(trifluoromethyl)phenyl-1H-imidazole-4-carbonitrile (694 mg, 1.485 mmol), NH$_2$OH.HCl (258 mg, 3.71 mmol), Et$_3$N (0.6 mL, 4.3 mmol), and dry EtOH (15 mL) was stirred at 55° C. for 5 h under N2. The solvent was removed in vacuo to give N'-hydroxy-1-(3'-methylsulfonyl)biphenyl-4-yl)-2-(2-(trifluoromethyl)phenyl-1H-imidazole-4-carboximidamide as a white solid, which was used in the next reaction without further purification. MS (ESI) 501 [M+H]+.

Example 46a3

Preparation of 5-methyl-3-(1-(3'-(methylsulfonyl) biphenyl-4-yl)-2-(2-(trifluoromethyl)phenyl)-1H-imidazol-4-yl)-1,2,4-oxadiazole

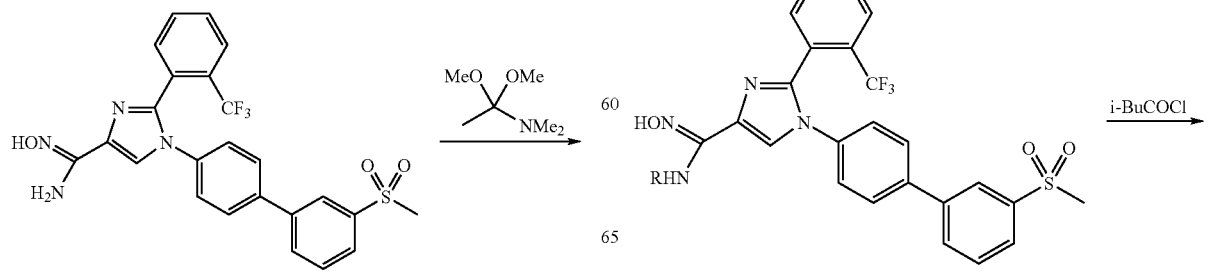

-continued

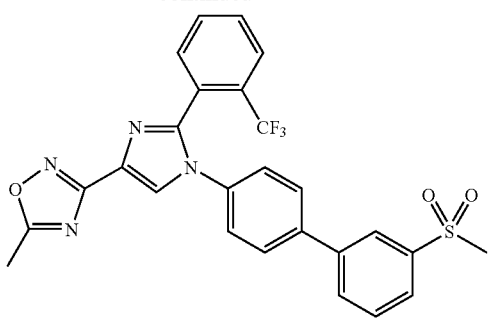

A mixture of the crude N'-hydroxy-1-(3'-methylsulfonyl) biphenyl-4-yl)-2-(2-(trifluoromethyl)phenyl-1H-imidazole-4-carboximidamide (184 mg, 0.36 mmol) and dimethylacetamide dimethyl acetal (3 mL) in a sealed vial was stirred at 120° C. for 2 h, the volatiles were removed in vacuo. The crude product was purified by flash chromatography (SiO$_2$, 90% EtOAc/hexanes) to give the title compounds as a white solid (113 mg, 60%). MS (ESI) 525 [M+H]+; $^1$H NMR (400 MHz, CDCl$_3$): δ 8.10-8.09 (m, 1H), 7.95-7.92 (m, 2H), 7.84-7.81 (m, 1H), 7.72-7.69 (m, 1H), 7.65 (t, J=7.74 Hz, 1H), 7.58-7.55 (m, 4H), 7.53-7.50 (m, 1H), 7.26-7.24 (m, 2H), 3.09 (s, 3H), 2.67 (s, 3H).

Example 46b

Preparation of 5-isopropyl-3-(1-(3'-ethylsulfonyl) biphenyl-4-yl)-2-(2-(trifluoromethyl)phenyl)-1H-imidazol-4-yl)-1,2,4-oxadiazole

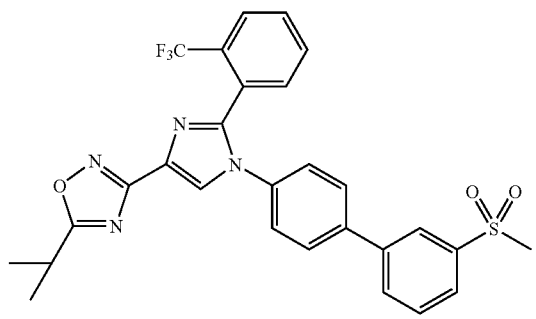

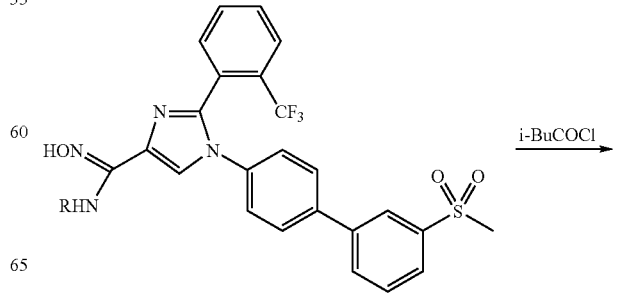

659
-continued

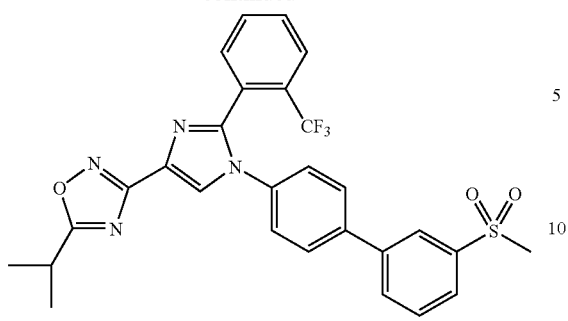

660
-continued

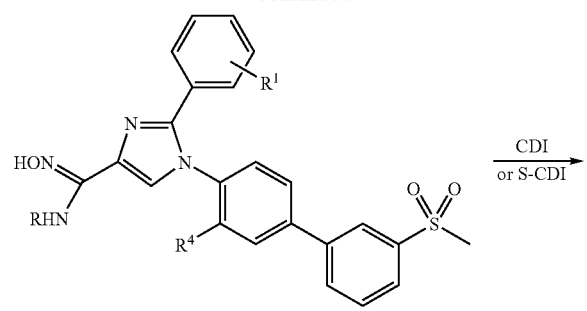

Isobutyryl chloride (00.1 mL, 0.94 mmol) was added dropwise to a stirred suspension of the crude N'-hydroxy-1-(3'-methylsulfonyl)biphenyl-4-yl)-2-(2-(trifluoromethyl)phenyl-1H-imidazole-4-carboximidamide (185 mg, 0.36 mmol) in dry pyridine (2 mL) at ambient temperature, the resulting mixture was stirred at 115° C. in a sealed vial for 5 h. After cooling to room temperature, the reaction mixture was partitioned between water and EtOAc. The aqueous layer was extracted with EtOAc. The combined extracts were washed with water, and then brine, dried over sodium sulfate, and evaporated in vacuo. The crude product was purified by flash chromatography (SiO$_2$, 80% EtOac/hexanes) to give the title compound as a white solid (88 mg, 43%). MS (ESI) 553[M+H]$^+$; $^1$H NMR (400 MHz, CDCl$_3$): δ 8.10-8.09 (m, 1H), 7.96 (s, 1H), 7.95-7.92 (m, 1H), 7.84-7.81 (m, 1H), 7.71-7.69 (m, 1H), 7.65 (t, J=7.74 Hz, 1H), 7.56-7.51 (m, 5H), 7.27-7.24 (m, 2H), 3.35-3.28 (m, 1H), 3.09 (s, 3H), 1.48 (s, 3H), 1.46 (s, 3H).

Scheme 47

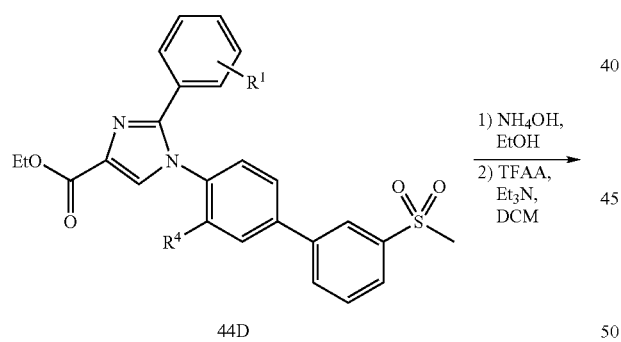

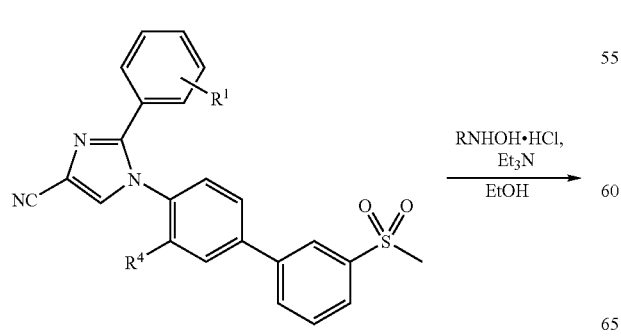

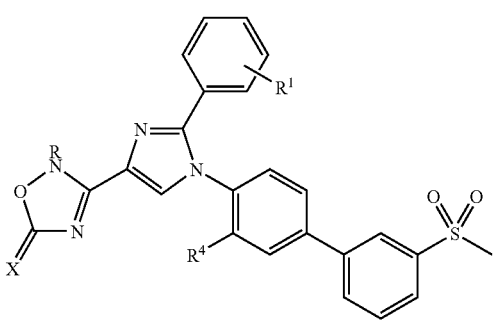

As depicted in Scheme 47, the carboximidamide was prepared according to general method described in Scheme 20. Oxadizol-one or oxadiazol-thione were prepared by reacting the carboximidamide with CDI or thio-CDI, respectively.

Example 47

Preparation of 2-methyl-3-(1-(3'-methylsulfonyl)biphenyl-4-yl)-2-(2-(trifluoromethyl)phenyl)-1H-imidazol-4-yl)-1,2,4-oxadiazol-5-(2H)-one

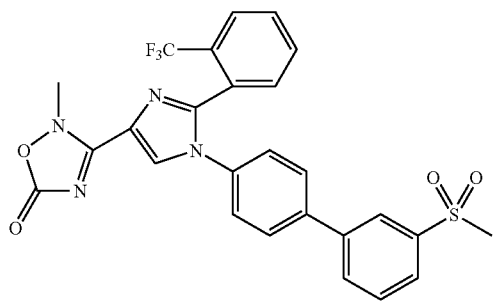

Example 47a

Preparation of N-hydroxy-N-methyl-1-(3'-methylsulfonyl)biphenyl-4-yl)-2-(2-(trifluoromethyl)phenyl-1H-imidazole-4-carboximidamide

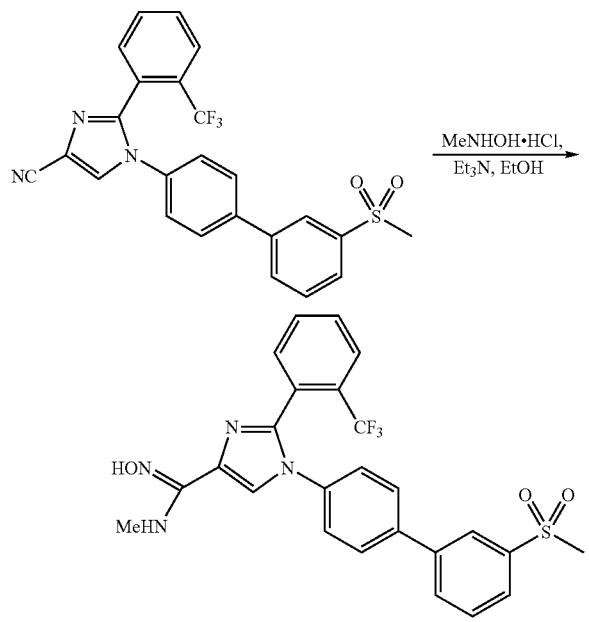

A mixture of 1-(3'-methylsulfonyl)biphenyl-4-yl)-2-(2-(trifluoromethyl)phenyl-1H-imidazole-4-carbonitrile (374 mg, 0.8 mmol), MeNHOH.HCl (167 mg, 2 mmol), Et₃N (0.5 mL), and dry EtOH in a sealed vial was stirred at 80° C. for 2 h, the volatiles were removed in vacuo to give N-hydroxy-N-methyl-1-(3'-methylsulfonyl)biphenyl-4-yl)-2-(2-(trifluoromethyl)phenyl-1H-imidazole-4-carboximidamide as a white solid, which was used in next reaction without further purification.

Example 47b

Preparation of 2-methyl-3-(1-(3'-methylsulfonyl) biphenyl-4-yl)-2-(2-(trifluoromethyl)phenyl)-1H-imidazol-4-yl)-1,2,4-oxadiazol-5-(2H)-one

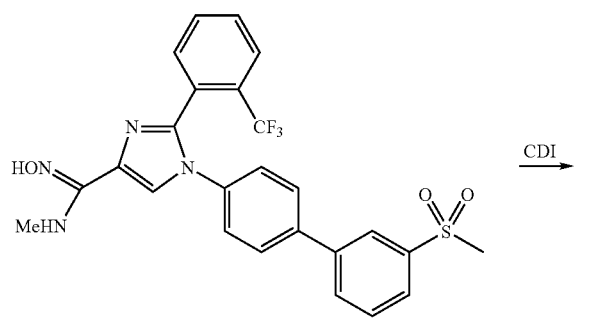

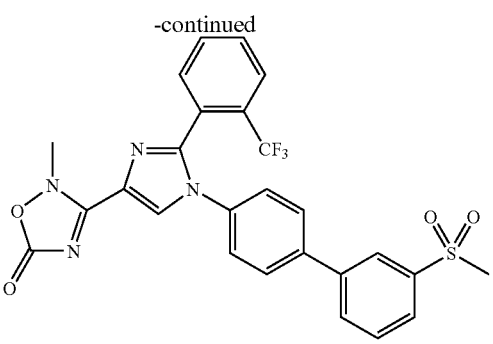

A mixture of the crude N-hydroxy-N-methyl-1-(3'-methylsulfonyl)biphenyl-4-yl)-2-(2-(trifluoromethyl)phenyl-1H-imidazole-4-carboximidamide (400 mg), CDI (425 mg, 2.62 mmol), and dry DCM (5 mL) in a sealed vial was stirred at 60° C. for 2 h, the volatiles were removed in vacuo. The crude product was purified by flash chromatography (SiO₂, 5% MeOH/EtOAc) to give the title compound as a white solid (150 mg). MS (ESI) 541 [M+H]⁺;]⁺; ¹H NMR (400 MHz, CDCl₃): δ 8.2 (s, 1H), 8.10-8.09 (m, 1H), 7.97-7.95 (m, 1H), 7.84-7.82 (m, 2H), 7.67 9t, J=7.75 Hz, 1H), 7.62-7.58 (m, 3H), 7.54-7.50 (m, 1H), 7.27-7.24 (m, 3H), 4.23 (s, 3H), 3.10 (s, 3H).

The following compound was prepared as described above, except hydroxylamine were used, instead of N-methyl hydroxylamine.

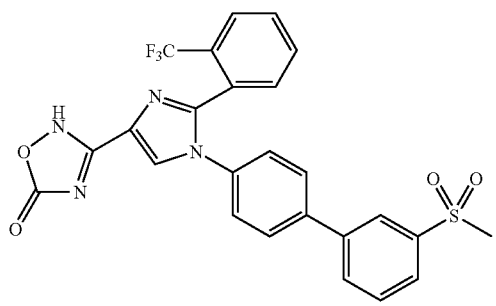

3-(1-(3'-methylsulfonyl)biphenyl-4-yl)-2-(2-(trifluoromethyl)phenyl)-1H-imidazol-4-yl)-1,2,4-oxadiazol-5-(2H)-one ¹H NMR (400 MHz, DMSO-d₆): δ 8.33 (s, 1H), 8.29 (s, 1H), 8.16-8.15 (m, 1H), 8.05-8.03 (m, 1H), 7.93-7.91 (m, 1H), 7.88-7.83 (m, 3H), 7.76-7.72 (m, 4H), 7.41-7.39 (m, 2H), 3.29 (s, 3H). MS (ESI) 527 [M+H]⁺.

The following compound was prepared in a manner similar as described in Scheme 20 using thio-CDI instead of CDI.

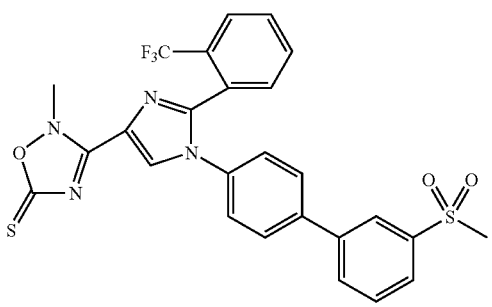

2-methyl-3-(1-(3'-methylsulfonyl)biphenyl-4-yl)-2-(2-(trifluoromethyl)phenyl)-1H-imidazol-4-yl)-1,2,4-oxadiazol-5-(2H)-thione ¹H NMR (400 MHz, CDCl₃): δ 8.28 (s, 1H), 8.11-8.10 (m, 1H), 7.97-7.95 (m, 1H), 7.85-7.83 (m, 1H), 7.68 (t, J=7.74 Hz, 1H), 7.63-7.59 (m, 3H), 7.56-7.52 (m, 1H), 7.27-7.23 (m, 3H), 4.38 (s, 3H), 3.10 (s, 3H). MS (ESI) 557 [M+H]⁺;]⁺.

Scheme 48

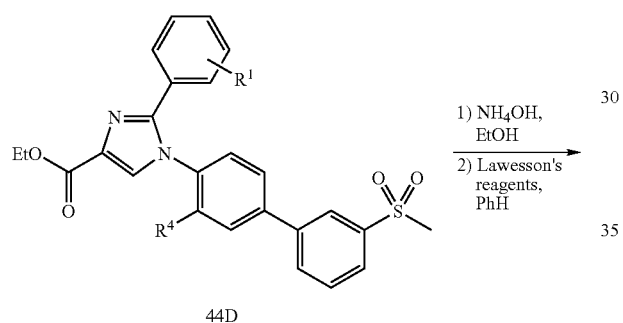

44D

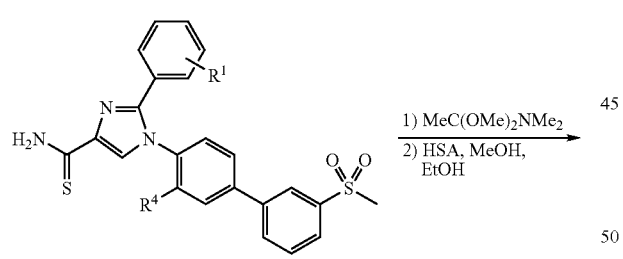

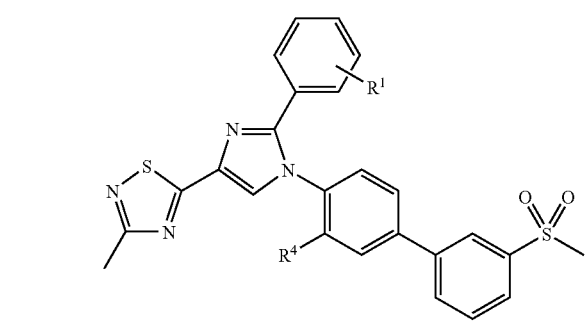

As depicted in Scheme 48, the carbothioamide was prepared from ester-imidazole, then converted to thiadiazole products using known procedure.

Example 48

Preparation of 3-methyl-5-(1-(3'-ethylsulfonyl)biphenyl-4-yl)-2-(2-(trifluoromethyl)phenyl)-1H-imidazol-4-yl)-1,2,4-thiadiazole

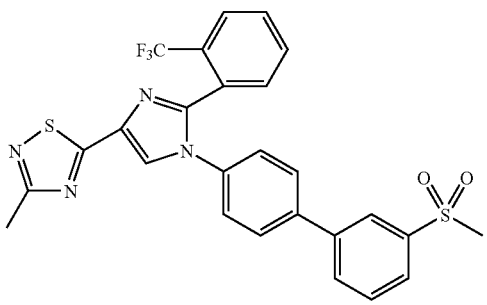

Example 48a

Preparation of 1-(3'-methylsulfonyl)biphenyl-4-yl)-2-(2-(trifluoromethyl)phenyl-1H-imidazole-4-carbothioamide

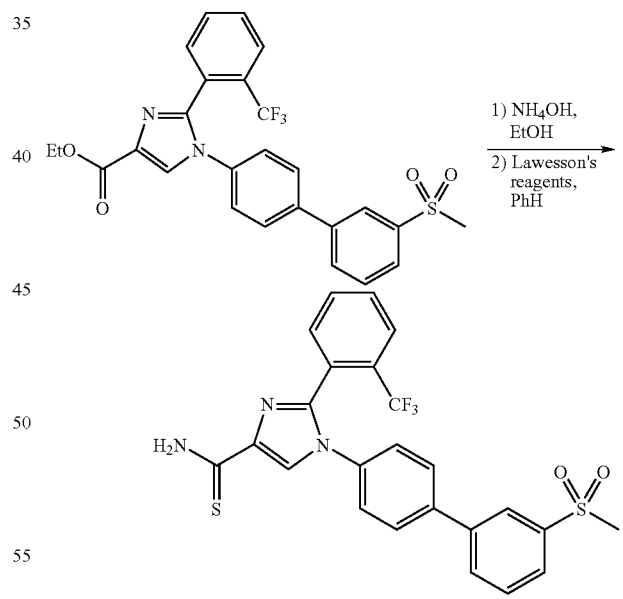

A mixture of 1-(3'-methylsulfonyl)biphenyl-4-yl)-2-(2-(trifluoromethyl)phenyl-1H-imidazole-4-carboxamide (243 mg, 0.5 mmol), Lawesson's reagent (243 mg, 0.6 mmol), and dry benzene (15 mL) was stirred at reflux for 2 h. The solvent was removed in vacuo, and the crude product was purified by flash chromatography (SiO₂, 90% EtOAc/hexanes) to give 1-(3'-methylsulfonyl)biphenyl-4-yl)-2-(2-(trifluoromethyl)phenyl-1H-imidazole-4-carbothioamide as a yellow solid (250 mg, 100%). MS (ESI) 502 [M+H]⁺.

Example 48b

Preparation of 3-methyl-5-(1-(3'-(methylsulfonyl)biphenyl-4-yl)-2-(2-(trifluoromethyl)phenyl)-1H-imidazol-4-yl)-1,2,4-thiadiazole

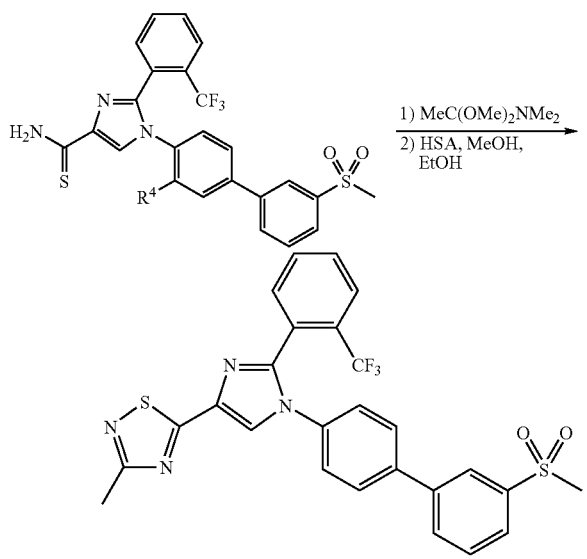

Dimethylacetamide dimethyl acetal (DMADA) (3 mL) was added to a solution of 1-(3'-methylsulfonyl)biphenyl-4-yl)-2-(2-(trifluoromethyl)phenyl-1H-imidazole-4-carbothioamide (251 mg, 0.5 mmol) in dry DCM (5 mL), the resulting mixture was stirred at room temperature under $N_2$ overnight, the volatiles were removed in vacuo. The residue was dissolved in dry EtOH (5 mL), and dry pyridine (0.5 mL) was added followed by a solution of hydroxyamino-O-sulfonic acid (HSA) (235 mg, 2.08 mmol) in dry MeOH (5 mL). The mixture was stirred at room temperature for 3 h. The volatiles were removed in vacuo, the residue was taken up in EtOAc, and washed with water, 0.1N NaOH solution, and brine, dried over sodium sulfate, and evaporated in vacuo. The crude product was purified by flash chromatography (SiO$_2$, 80% EtOAc/hexanes) to give the title compound as a reddish solid (116 mg, 43%). MS (ESI) 541 [M+H]$^+$; $^1$H NMR (400 MHz, CDCl$_3$): δ 8.11-8.10 (m, 1H), 8.00 (s, 1H), 7.96-7.93 (m, 1H), 7.84-7.82 (m, 1H), 7.77-7.75 (m, 1H), 7.66 (t, J=7.82 Hz, 1H), 7.60-7.56 (m, 4H), 7.45-7.43 (m, 1H), 7.27-7.25 (m, 2H), 3.09 (s, 3H0, 2.72 (s, 3H). The following compounds of the invention, in Table 20, were prepared according to one of the previous examples.

TABLE 20

| # | Ex. | IUPAC Name | Structure |
|---|---|---|---|
| 975 | 23 | 1,1-dimethylethyl 2-{2-[1-(2-chlorophenyl)-1-methylethyl]-1-[3'-(methylsulfonyl)biphenyl-4-yl]-1H-imidazol-4-yl}pyrrolidine-1-carboxylate | 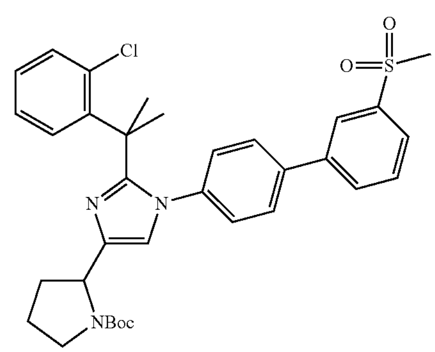 |
| 976 | 24 | 2-[1-(2-Chlorophenyl)-1-methylethyl]-1-[3'-(methylsulfonyl)biphenyl-4-yl]-4-pyrrolidin-2-yl-1H-imidazole | 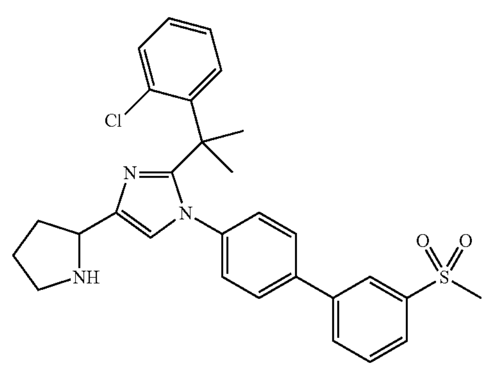 |

TABLE 20-continued

| # | Ex. | IUPAC Name | Structure |
|---|---|---|---|
| 977 | 25 | Methyl 2-{2-[1-(2-chlorophenyl)-1-methylethyl]-1-[3'-(methylsulfonyl)biphenyl-4-yl]-1H-imidazol-4-yl}pyrrolidine-1-carboxylate | 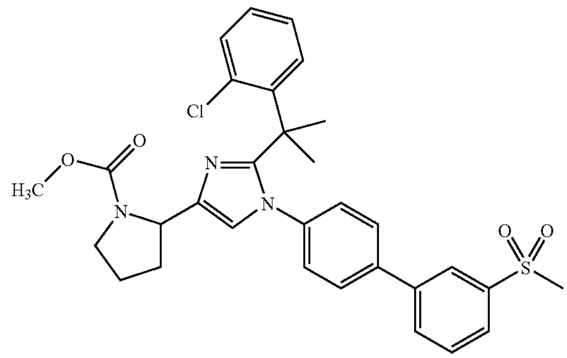 |
| 978 | 26 | 4-(1-acetylpyrrolidin-2-yl)-2-[1-(2-chlorophenyl)-1-methylethyl]-1-[3'-(methylsulfonyl)biphenyl-4-yl]-1H-imidazole | 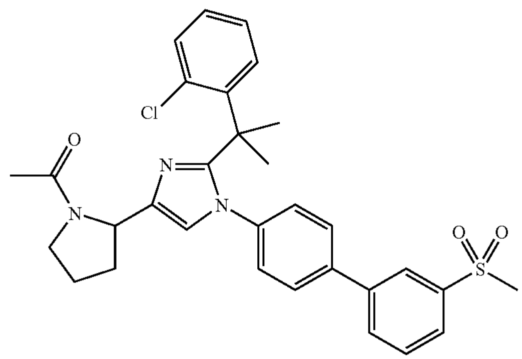 |
| 979 | 27 | 2-[1-(2-chlorophenyl)-1-methylethyl]-4-(1-methylpyrrolidin-2-yl)-1-[3'-(methylsulfonyl)biphenyl-4-1]-1H-imidazole | 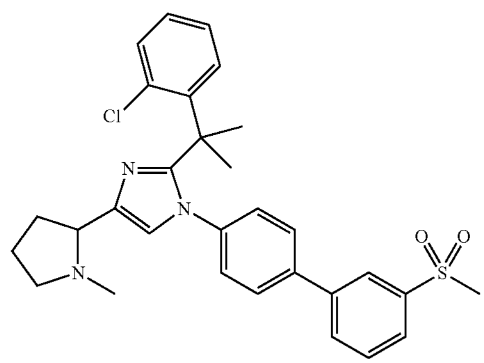 |
| 980 | 28 | 1-(2-(2-chlorophenyl)-1-(3'-(methylsulfonyl)biphenyl-4-yl)-1H-imidazol-4-yl)cyclopropanol | 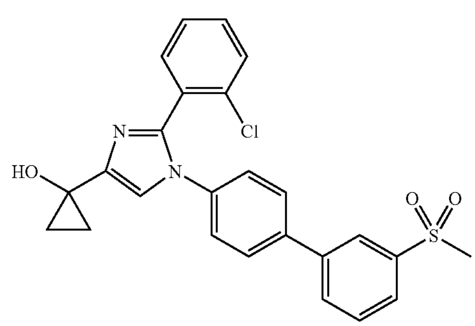 |

| # | Ex. | IUPAC Name | Structure |
|---|---|---|---|
| 981 | 29 | 1-(2-(2-chlorophenyl)-1-(3'-(methylsulfonyl)biphenyl-4-yl)-1H-imidazol-4-yl)cyclopentanol | 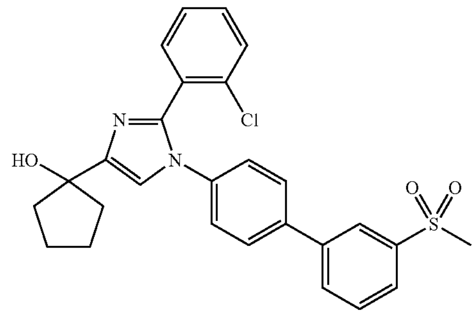 |
| 982 | 30 | 6-[1-(3-Chloro-3'-methanesulfonyl-biphenyl-4-yl)-2-(2-chlorophenyl)-1-H-imidazol-4-yl]-2,2-dimethyl-2,3-dihydro-pyran-4-one | 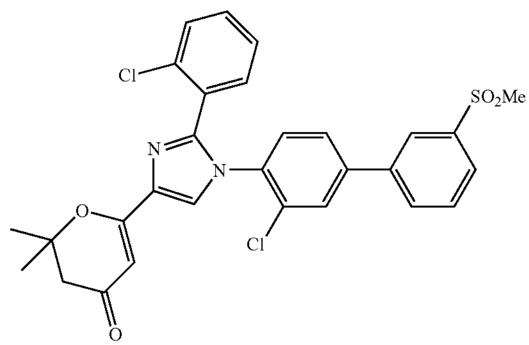 |
| 983 | 30-1 | 3-[1-(3-Chloro-3'-methanesulfonyl-biphenyl-4-yl)-2-(2-chlorophenyl)-1-H-imidazol-4-yl]-4-methylfurazan | 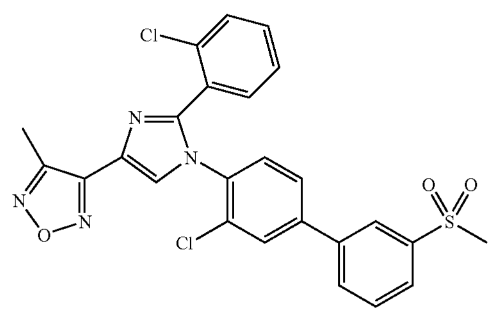 |
| 984 | 30-2 | 4-[1-(3-Chloro-3'-methanesulfonyl-biphenyl-4-yl)-2-(2-chlorophenyl)-1-H-imidazol-4-yl]-1-methyl-pyrrolidin-2-one | 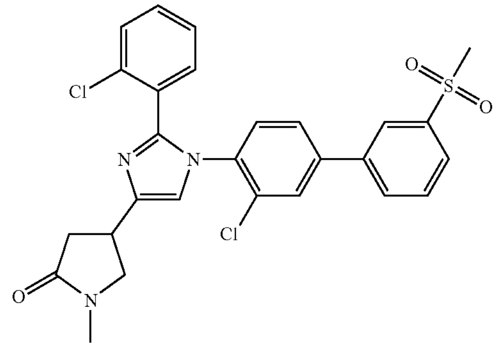 |

TABLE 20-continued

| # | Ex. | IUPAC Name | Structure |
|---|-----|------------|-----------|
| 985 | 30-3 | {3'-Chloro-4'-[2-(2-chlorophenyl)-4-(4-methylfurazan-3-yl)-imidazol-1-yl]-3-fluoro-5-methanesulfonyl-biphenyl-4-yl}-methanol | 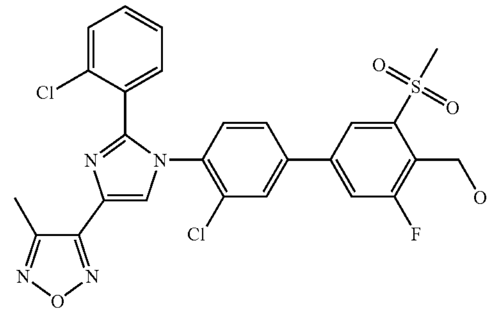 |
| 986 | 31a | 2-(1-(3-chloro-3'-(methylsulfonyl)biphenyl-4-yl)-2-(2-chlorophenyl)-1H-imidazol-4-yl)-4,4-dimethyl-4,5-dihydrooxazole | 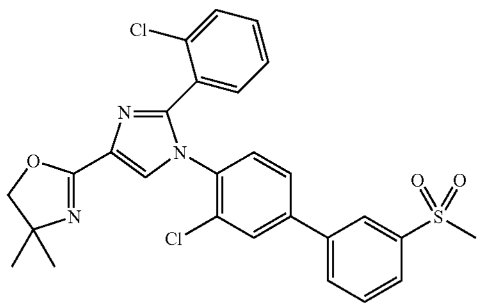 |
| 987 | 31b | 2-(2-(2-(2-chlorophenyl)propan-2-yl)-1-(3'-(methylsulfonyl)biphenyl-4-yl)-1H-imidazol-4-yl)-4,4-dimethyl-4,5-dihydrooxazole | 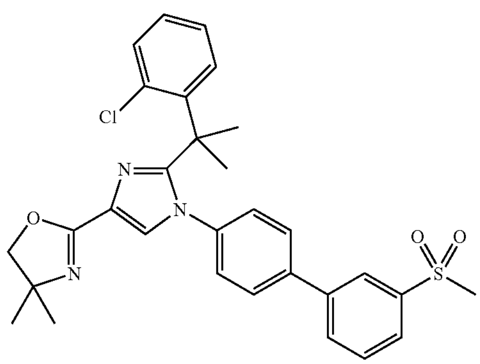 |
| 988 | 32 | 2-(1-(3-chloro-3'-(methylsulfonyl)biphenyl-4-yl)-2-(2-chlorophenyl)-1H-imidazol-4-yl)-4,4-dimethyl-4,5-dihdyrothiazole | 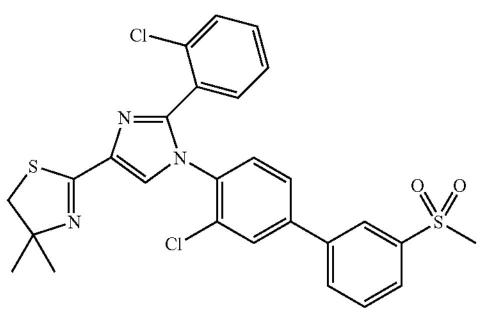 |

TABLE 20-continued

| # | Ex. | IUPAC Name | Structure |
|---|---|---|---|
| 989 | 33 | 5-[1-(3'-methanesulfonyl-biphenyl-4-yl)-2-(2-chlorobenzyl)-1H-imidazol-4-yl]-3-methyl-[1,2,4]oxadiazole | 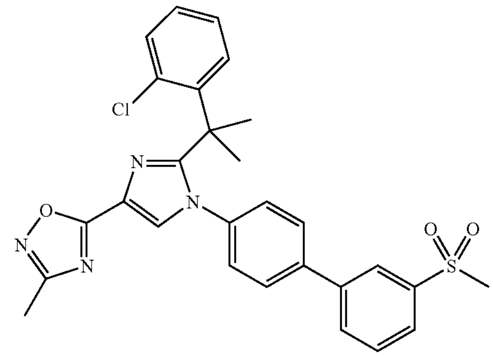 |
| 990 | 34 | 3-(1-(3-chloro-3'-(methylsulfonyl)biphenyl-4-yl)-2-(2-chlorophenyl)-1H-imidazol-4-yl)-5-(trifluoromethyl)isoxazole | 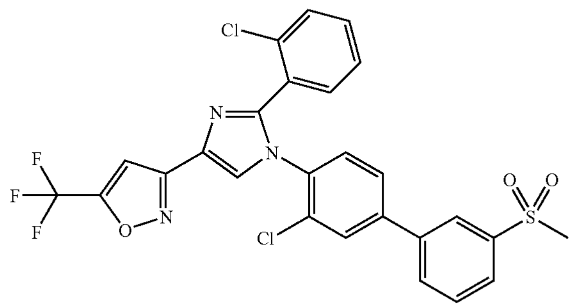 |
| 991 | 35a | 4-cyclopropyl-1-(3'-(methylsulfonyl)biphenyl-4-yl)-2-(2-(trifluoromethyl)phenyl)-1H-imdazole | 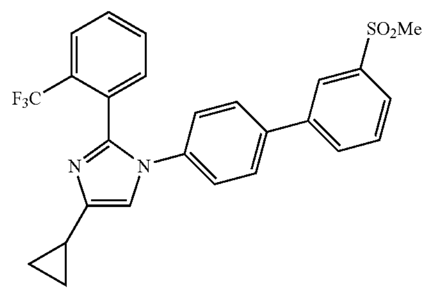 |
| 992 | 35b | 2-(2,3-dichlorophenyl)-1-(3'-(methylsulfonyl)biphenyl-4-yl)-4-(thiophen-3-yl)-1H-imidazole | 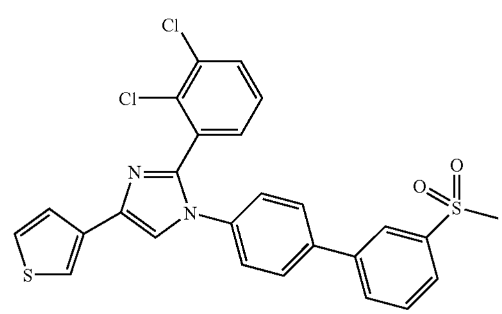 |
| 993 | 35-1 | 1-(3'-(methylsulfonyl)biphenyl-4-yl)-4-(4-methylthiophen-3-yl)-2-(2-(trifluoromethyl)phenyl)-1H-imidazole | 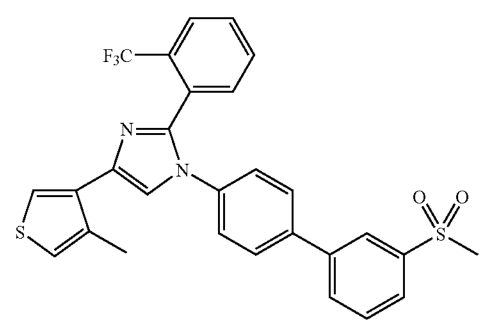 |

TABLE 20-continued

| # | Ex. | IUPAC Name | Structure |
|---|---|---|---|
| 994 | 35-2 | 1-methyl-4-(1-(3'-(methylsulfonyl)biphenyl-4-yl)-2-(2-(trifluoromethyl)phenyl)-1H-imidazol-4-yl)-1H-pyrazole | 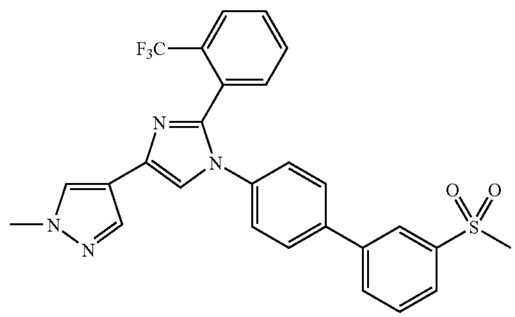 |
| 995 | 35-3 | 4-(furan-3-yl)-1-(3'-(methylsulfonyl)biphenyl-4-yl)-2-(2-(trifluoromethyl)phenyl)-1H-imidazole | 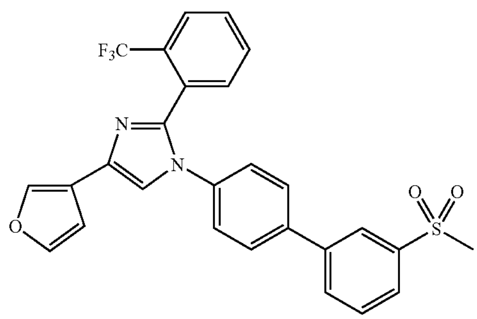 |
| 996 | 35-4 | 1-(3'-(methylsulfonyl)biphenyl-4-yl)-4-(thiophen-3-yl)-2-(2-(trifluoromethyl)phenyl)-1H-imidazole | 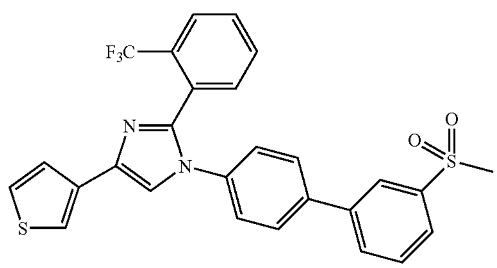 |
| 997 | 35-5 | 1-(3-chloro-3'-(methylsulfonyl)biphenyl-4-yl)-2-(2-chlorophenyl)-4-(thiophen-3-yl)-1H-imidazole | 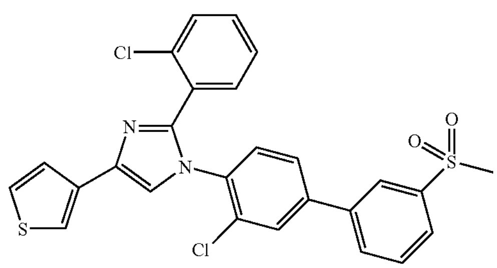 |
| 998 | 36 | 4-(azetidin-1-yl)-1-(3'-(methylsulfonyl)biphenyl-4-yl)-2-(2-(trifluoromethyl)phenyl)-1H-imidazole | 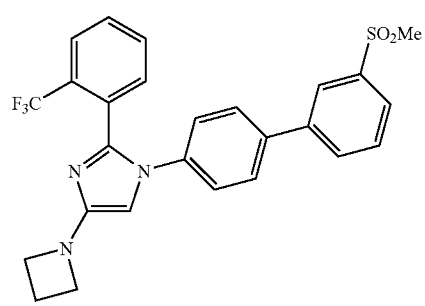 |

TABLE 20-continued

| # | Ex. | IUPAC Name | Structure |
|---|---|---|---|
| 999 | 36-1 | 1-{2-(2,6-dichlorophenyl)-1-[3'-(methylsulfonyl)biphenyl-4-yl]-1H-imidazol-4-yl}-1H-pyrazole | 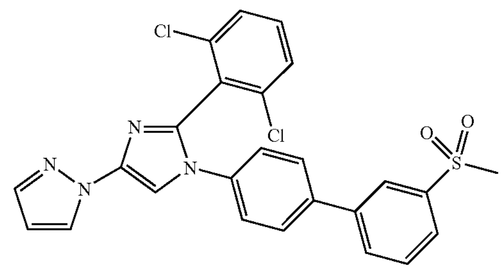 |
| 1000 | 36-2 | 2'-(2,6-dichlorophenyl)-1'-[3'-(methylsulfonyl)biphenyl-4-yl]-1'H-1,4'-biimidazole | 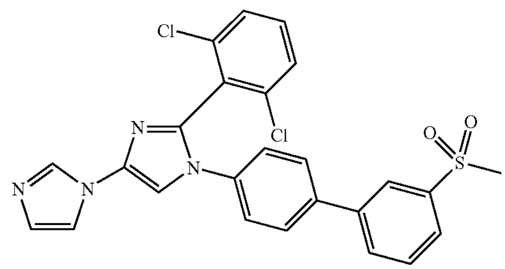 |
| 1001 | 36-3 | 2'-(2,6-dichlorophenyl)-2-methyl-1'-[3'-(methylsulfonyl)biphenyl-4-yl]-1'H-1,4'-biimidazole | 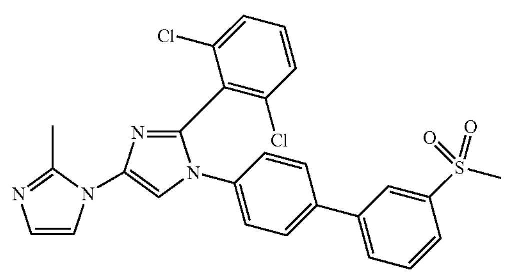 |
| 1002 | 36-4 | 2-(2,6-dichlorophenyl)-1-[3'-(methylsulfonyl)biphenyl-4-yl]-4-(pyrrolidin-1-yl)-1H-imidazole | 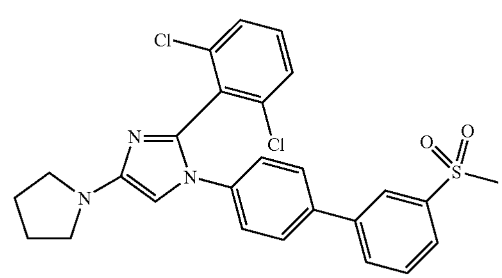 |
| 1003 | 36-5 | 1-(1-(3'-(methylsulfonyl)biphenyl-4-yl)-2-(2-(trifluoromethyl)phenyl)-1H-imidazol-4-yl)pyrrolidin-3-ol | 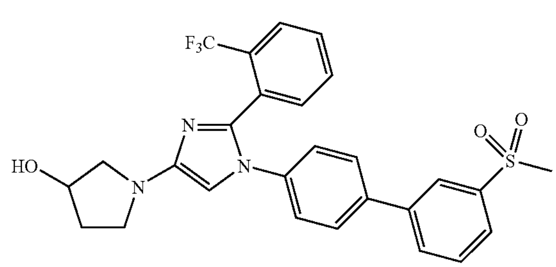 |
| 1004 | 36-6 | 1-(1-(3'-(methylsulfonyl)biphenyl-4-yl)-2-(2-(trifluoromethyl)phenyl)-1H-imidazol-4-yl)piperidine | 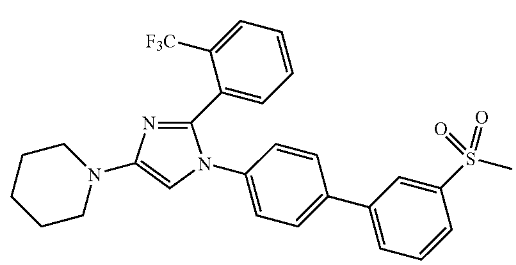 |

TABLE 20-continued

| # | Ex. | IUPAC Name | Structure |
|---|---|---|---|
| 1005 | 36-7 | 1-{2-(2,6-dichlorophenyl)-1-[3'-(methylsulfonyl)biphenyl-4-yl]-1H-imidazol-4-yl}pyrrolidin-2-one | 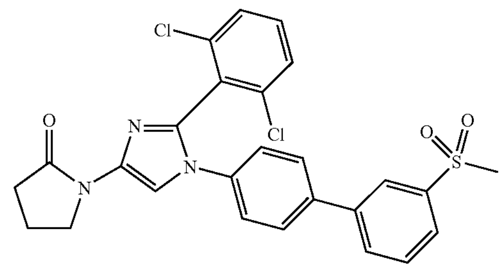 |
| 1006 | 36-8 | 2-(2,6-dichlorophenyl-1[(3'-(methylsulfonyl)biphenyl-4-y]-4-(1H-pyrrol-1-yl)-1H-imidazole | 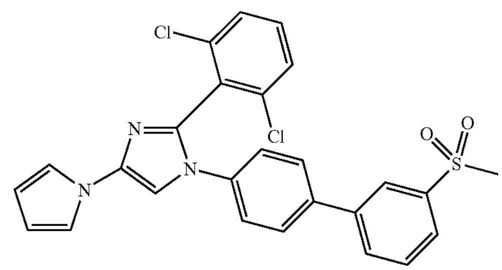 |
| 1007 | 36-9 | 1-(3'-(methylsulfonyl)biphenyl-4-yl)-4-(1H-pyrrol-1-yl)-2-(2-(trifluoromethyl)phenyl)-1H-imidazole | 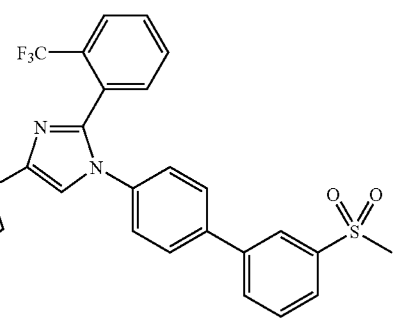 |
| 1008 | 36-10 | 1'-(3'-(methylsulfonyl)biphenyl-4-yl)-2'-(2-(trifluoromethyl)phenyl)-1'H-1,4'-biimidazole-4-carbonitrile | 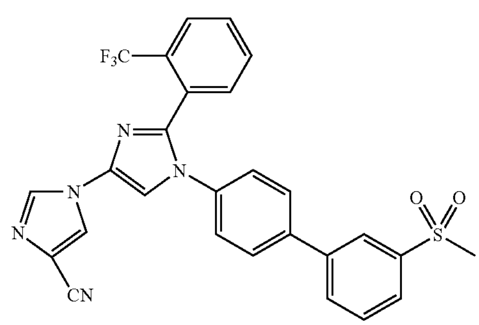 |
| 1009 | 36-11 | (1'-(3'-(methylsulfonyl)biphenyl-4-yl)-2'-(2-(trifluoromethyl)phenyl)-1'H-1,4'-biimidazol-4-yl)methanol | 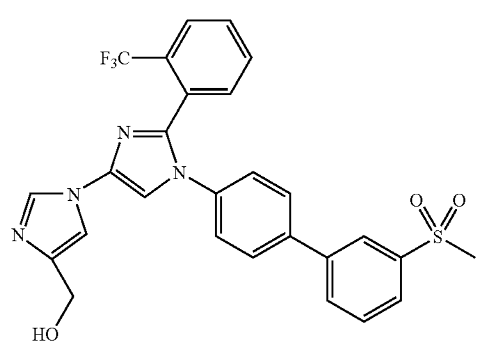 |

| # | Ex. | IUPAC Name | Structure |
|---|---|---|---|
| 1010 | 36-12 | 1-(1-(3'-(methylsulfonyl)biphenyl)-4-yl)-2-(2-(trifluoromethyl)phenyl)-1H-imidazol-4-yl)-1H-pyrrole-2-carbonitrile | 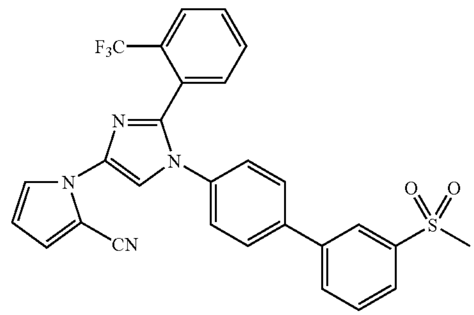 |
| 1011 | 37 | 2-(1-(3'-(methylsulfonyl)biphenyl-4-yl)-2-(2-(trifluoromethyl)phenyl)-1H-imidazol-4-yl)oxazole | 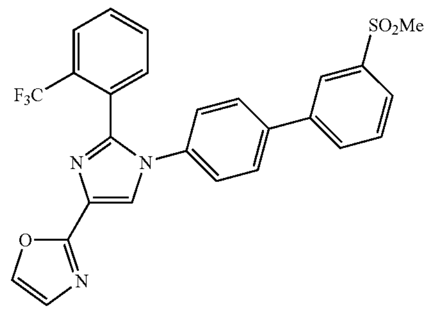 |
| 1012 | 37-1 | 2-(1-(3-chloro-3'-(methylsulfonyl)biphenyl-4-yl)-2-(2-chlorophenyl)-1H-imidazol-4-yl)oxazole | 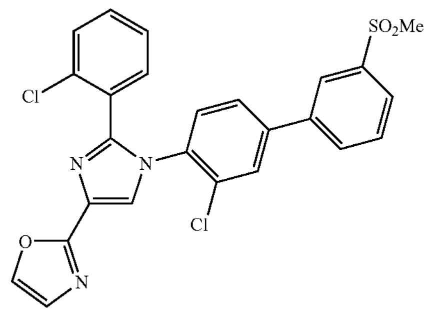 |
| 1013 | 38a | 2-(2-(2,6-dichlorophenyl)-1-(3'-(methylsulfonyl)biphenyl-4-yl)-1H-imidazol-4-yl)-4-methylthiazole | 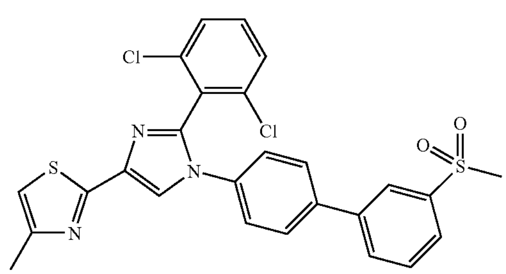 |
| 1014 | 38-1 | 2-(2-(2,6-dichlorophenyl)-1-(3'-(methylsulfonyl)biphenyl-4-yl)-1H-imidazol-4-yl)thiazole | 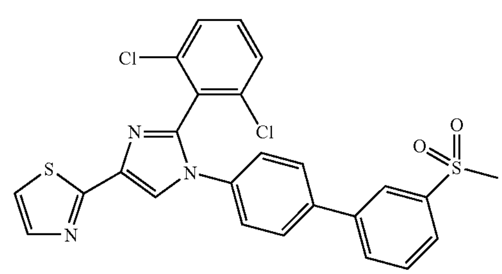 |

TABLE 20-continued

| # | Ex. | IUPAC Name | Structure |
|---|-----|------------|-----------|
| 1015 | 38-2 | 1-(3'-(methylsulfonyl)biphenyl-4-yl)-4-(thiophen-2-yl)-2-(2-(trifluoromethyl)phenyl)-1H-imidazole | 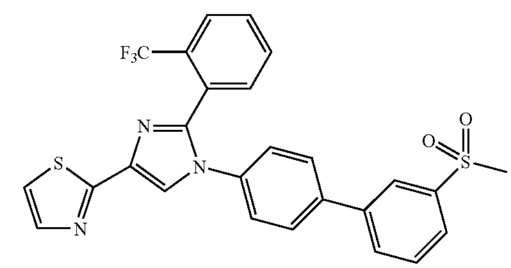 |
| 1016 | 38b | 1-(3'-(methylsulfonyl)biphenyl-4-yl)-4-((R)-pyrrolidin-2-yl)-2-(2-(trifluoromethyl)phenyl)-1H-imidazole | 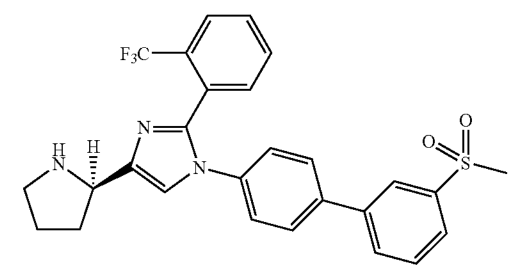 |
| 1017 | 38b1 | (R)-tert-butyl 2-(1-(3'-(methylsulfonyl)biphenyl-4-yl)-2-(2-(trifluoromethyl)phenyl)-1H-imidazol-4-yl)pyrrolidine-1-carboxylate | 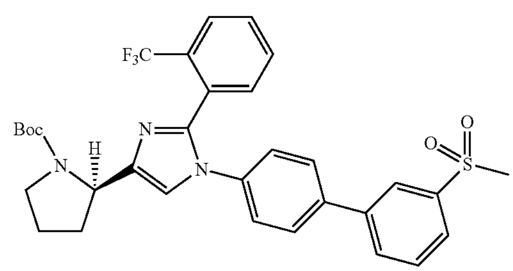 |
| 1018 | 38b3 | 4-((R)-1-methylpyrrolidin-2-yl)-1-(3'-(methylsulfonyl)biphenyl-4-yl)-2-(2-(trifluoromethyl)phenyl)-1H-imidazole | 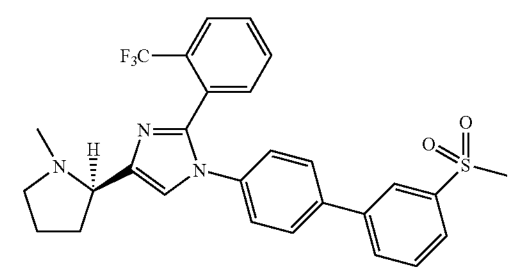 |
| 1019 | 38b4 | 1-((2R)-2-(1-(3'-(methylsulfonyl)biphenyl-4-yl)-2-(2-(trifluoromethyl)phenyl)-1H-imidazol-4-yl)pyrrolidin-1-yl)ethanone | 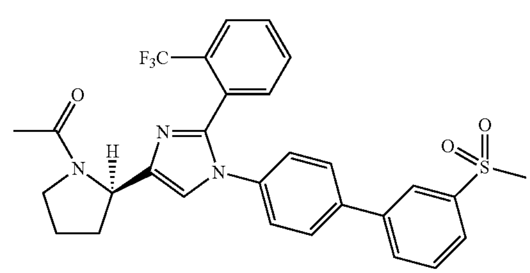 |

| # | Ex. | IUPAC Name | Structure |
|---|---|---|---|
| 1020 | 39 | 2-(1-(3'-(methylsulfonyl)biphenyl-4-yl)-2-(2-(trifluoromethyl)phenyl)-1H-imidazol-4-yl)-1,3,4-oxadiazole | 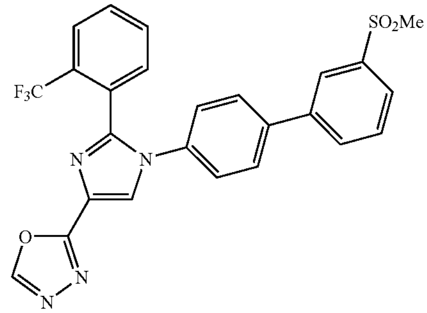 |
| 1021 | 39a-1 | 1-(3'-(methylsulfonyl)biphenyl-4-yl)-4-(thiophen-2-yl)-2-(2-(trifluoromethyl)phenyl)-1H-imidazole | 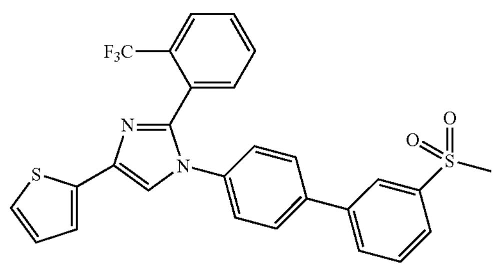 |
| 1022 | 40 | 4-methyl-3-(1-(3'-(methylsulfonyl)biphenyl-4-yl)-2-(2-(trifluoromethyl)phenyl)-1H-imidazol-4-yl)-1H-1,2,4-triazole-5(4H)-thione | 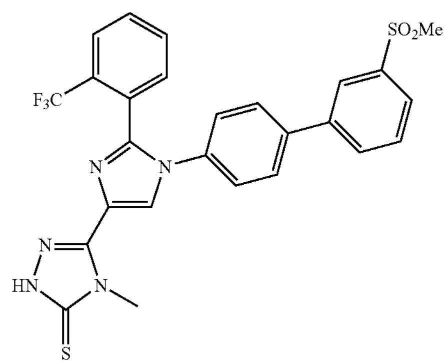 |
| 1023 | 41 | 5-(1-(3'-(methylsulfonyl)biphenyl-4-yl)-2-(2-(trifluoromethyl)phenyl)-1H-imidazol-4-yl)-1,3,4-oxadiazol-2(3H)-one | 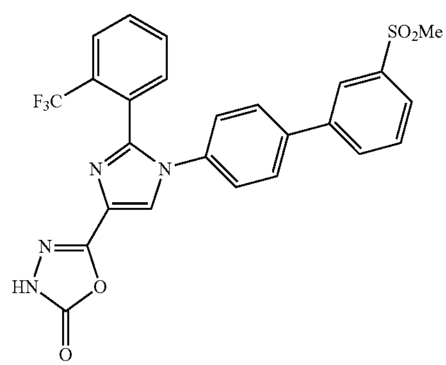 |

TABLE 20-continued

| # | Ex. | IUPAC Name | Structure |
|---|---|---|---|
| 1024 | 42 | 2-methyl-5-(1-(3'-(methylsulfonyl)biphenyl-4-yl)-2-(2-(trifluoromethyl)phenyl)-1H-imidazol-4-yl)-1,3,4-oxadiazole | 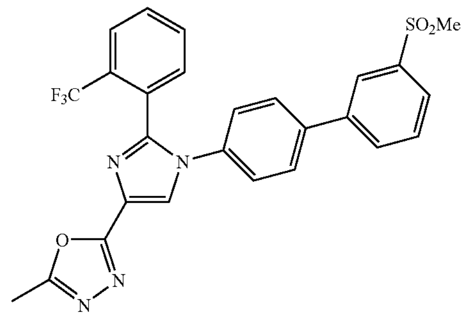 |
| 1025 | 42-1 | 2-(1-(3-chloro-3'-(methylsulfonyl)biphenyl-4-yl)-2-(2-chlorophenyl)-1H-imidazol-4-yl)-5-(trifluoromethyl)-1,3,4-oxadiazole | 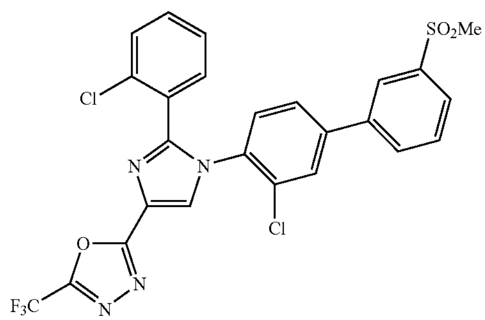 |
| 1026 | 43 | methyl-2-(1-(3'-(methylsulfonyl)biphenyl-4-yl)-2-(2-(trifluoromethyl)phenyl)-1H-imidazol-4-yl)oxazole | 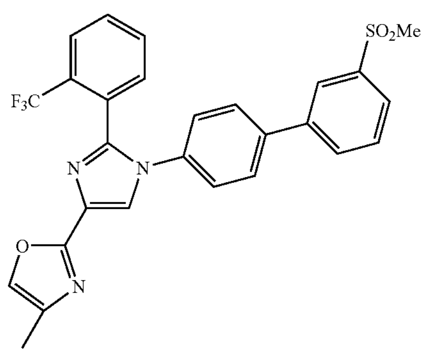 |
| 1027 | 43-1 | 2-(1-(3-chloro-3'-(methylsulfonyl)biphenyl-4-yl)-2-(2-chlorophenyl)-1H-imidazol-4-yl)-4-(trifluoromethyl)oxazole | 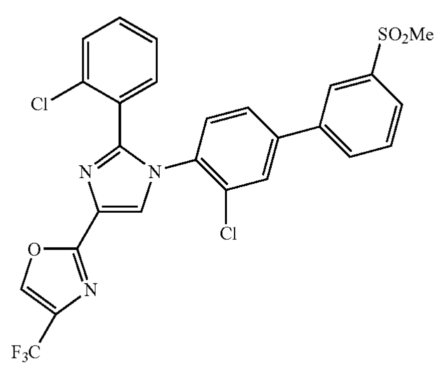 |

TABLE 20-continued

| # | Ex. | IUPAC Name | Structure |
|---|-----|------------|-----------|
| 1028 | 44 | 5-(1-(3-chloro-3'-(methylsulfonyl)biphenyl-4-yl)-2-(2-chlorophenyl)-1H-imidazol-4-yl)oxazole | 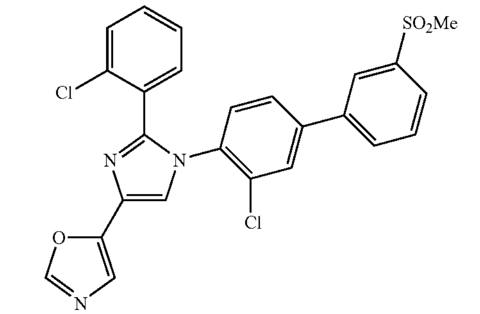 |
| 1029 | 45 | 1-(1-(3'-methylsulfonyl)biphenyl-4-yl)-2-(2-(trifluoromethyl)phenyl-1H-imidazol-4-yl)cyclopentanecarbonitrile | 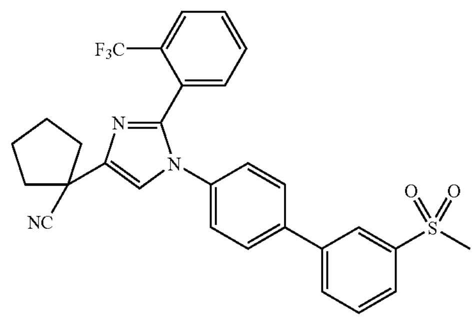 |
| 1030 | 45-1 | 1-(1-(3'-methylsulfonyl)biphenyl-4-yl)-2-(2-(trifluoromethyl)phenyl-1H-imidazol-4-yl)cyclopropanecarbonitrile | 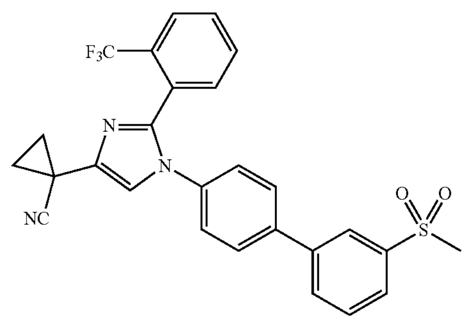 |
| 1031 | 45-2 | 4-(1-(3'-methylsulfonyl)biphenyl-4-yl)-2-(2-(trifluoromethyl)phenyl-1H-imidazol-4-yl)tetrahydro-2H-pyran-4-carbonitrile | 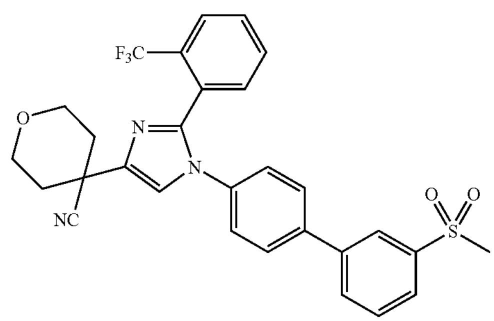 |
| 1032 | 46a | 5-methyl-3-(1-(3'-methylsulfonyl)biphenyl-4-yl)-2-(2-(trifluoromethyl)phenyl)-1H-imidazol-4-yl)-1,2,4-oxadiazole | 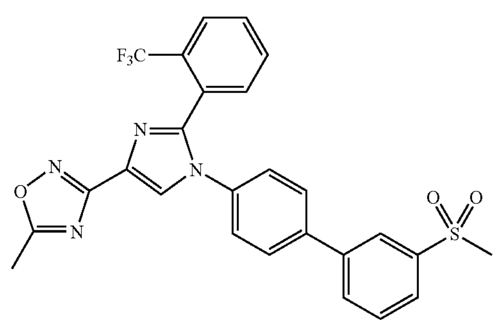 |

TABLE 20-continued

| # | Ex. | IUPAC Name | Structure |
|---|---|---|---|
| 1033 | 46b | 5-isopropyl-3-(1-(3'-methylsulfonyl)biphenyl-4-yl)-2-(2-(trifluoromethyl)phenyl)-1H-imidazol-4-yl)-1,2,4-oxadiazole | 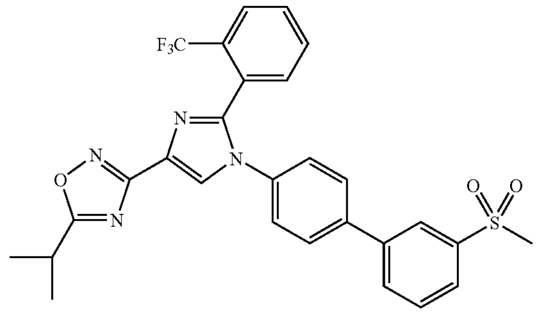 |
| 1034 | 47 | 2-methyl-3-(1-(3'-methylsulfonyl)biphenyl-4-yl)-2-(2-(trifluoromethyl)phenyl)-1H-imidazol-4-yl)-1,2,4-oxadiazol-5-(2H)-one | 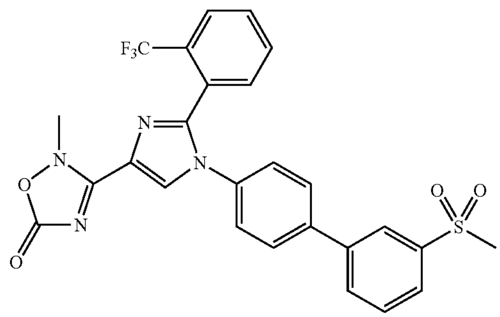 |
| 1035 | 47-1 | 3-(1-(3'-methylsulfonyl)biphenyl-4-yl)-2-(2-(trifluoromethyl)phenyl)-1H-imidazol-4-yl)-1,2,4-oxadiazol-5-(2H)-one | 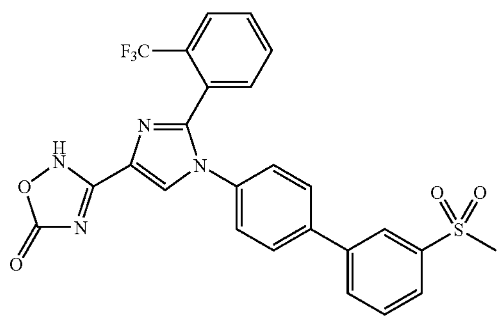 |
| 1036 | 47-2 | 2-methyl-3-(1-(3'-methylsulfonyl)biphenyl-4-yl)-2-(2-(trifluoromethyl)phenyl)-1H-imidazol-4-yl)-1,2,4-oxadiazol-5-(2H)-thione | 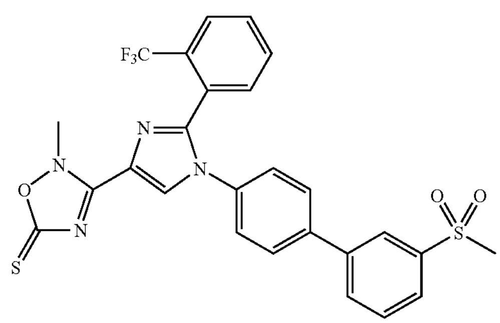 |
| 1037 | 48 | 3-methyl-5-(1-(3'-methylsulfonyl)biphenyl-4-yl)-2-(2-(trifluoromethyl)phenyl)-1H-imidazol-4-yl)-1,2,4-thiadiazole | 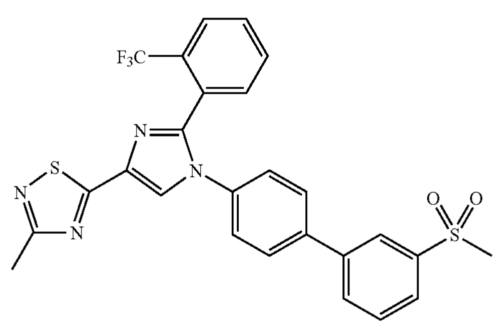 |

The biological assays disclosed in the following Examples are directed to the ability of the compounds of the invention to modulate $LXR_\alpha$ and $LXR_\beta$ activity, as well as FXR activity. It is understood, that one of ordinary skill in the art would recognize that the following assays could be used to test the ability of the compounds of the invention to modulate LXR and FXR activity.

Example A

FRET Coactivator Assay

The FRET coactivator assay measures the ability of LXR ligands to promote protein-protein interactions between the ligand binding domain (LBD) of LXR and transcriptional coactivator proteins. The assay involves the use a recombinant Glutathione-S-transferase (GST)-nuclear receptor ligand binding domain (LBD) fusion protein and a synthetic biotinylated peptide sequence derived from the receptor interacting domain of a co-activator peptide such as the steroid receptor coactivator 1 (SRC-1). Typically GST-LBD is labeled with a europium chelate (donor) via a europium-tagged anti-GST antibody, and the coactivator peptide is labeled with allophycocyanin via a streptavidin-biotin linkage.

In the presence of an agonist for the nuclear receptor, the peptide is recruited to the GST-LBD bringing europium and allophycocyanin into close proximity to enable energy transfer from the europium chelate to the allophycocyanin. Upon excitation of the complex with light at 340 nm excitation energy absorbed by the europium chelate is transmitted to the allophycocyanin moiety resulting in emission at 665 nm. If the europium chelate is not brought into close proximity to the allophycocyanin moiety there is little or no energy transfer and excitation of the europium chelate results in emission at 615 nm. Thus the intensity of light emitted at 665 nm gives an indication of the strength of the protein-protein interaction.

Required Materials:
a) Partially purified recombinant protein comprising glutathione-S-transferase fused in frame to the LXR-ligand binding domain (comprising amino acids 188-447 of human $LXR_\alpha$, or amino acids 198-461 of human $LXR_\beta$).
b) Biotinylated peptide containing a SRC-1 LXXLL receptor interaction motif (B-SRC-1).
c) Anti-GST antibody conjugated to a Europium chelate (UGST-K) (From Wallac/PE Life Sciences Cat# AD0064).
d) Streptavidin linked allophycocyanin (SA-APC) (From Wallac/PE Life Sciences CAT# AD0059A).
e) 1×FRET Buffer: (20 mM $KH_2PO_4/K_2HPO_4$ pH 7.3, 150 mM NaCl, 2.5 mM CHAPS, 2 mM EDTA, 1 mM DTT (add fresh)).
f) 96 well or 384 well black multiwell plates (from LJL)
Stock Solutions:
0.5 M $KH_2PO_4/K_2HPO_4$: pH 7.3
5 M NaCl
80 mM (5%) CHAPS
0.5 M EDTA pH 8.0
1 M DTT (keep at −20° C.)
Preparation of Screening Reagents:
Prepare reaction mixture for the appropriate number of wells by combining the following reagents 5 nM/well GST-hLXR$_\alpha$LBD, 5 nM/well GST-hLXR$_\beta$LBD, 5 nM/well Anti-GST antibody (Eu), 12 nM/well biotin-SRC-1 peptide, 12 nM/well APC-SA adjust the volume to 10 μL/well with 1x-FRET buffer.

Procedure:
Add 0.5 μL of a 1 mM stock compound (for approx. 10 μM final concentration) or solvent to each well in a 96 well or 384 well black plate (LJL). Add 10 μl reaction mixture (prepared above) to each well of the multiwell plate. Incubate covered or in the dark (the APC is light sensitive) at ambient temperature for 14 hours. After this time if reactions are not read they can be stored at 4° C. for several more hours without too much loss of signal.

Read the plate using an LJL Analyst, or similar instrument, using the following conditions:
Channel 1: Excitation is 330 nm and emission is 615. This is for Eu chelate
Channel 2: Excitation is 330 nm and emission is 665. This is for APC
For channel 1: Flashes per well=100; Integration time=1000 μs; interval between flashes=1×10 ms; Delay after flash=200 μs
For channel 2: Flashes per well=100; Integration time=100 μs; interval between flashes=1×10 ms; Delay after flashes=65 μs.

Example B

Scintillation Proximity Assay (SPA)

The SPA assay measures the radioactive signal generated by the binding of $^3$H-24,25-epoxycholesterol to $LXR_\alpha$ or $LXR_\beta$. The basis of the assay is the use of SPA beads containing a scintillant, such that when binding to the receptor brings the labeled ligand into proximity with the bead, the energy from the label stimulates the scintillant to emit light. The light is measured using a standard microplate scintillation reader. The ability of a ligand to bind to a receptor can be measured by assessing the degree to which the compound can compete off a radiolabelled ligand with known affinity for the receptor.

Required Materials:
1. Label: $^3$H-24,25-epoxy-cholesterol (Amersham)
2. $LXR_\alpha$ lysate: Baculoviris expressed $LXR_\beta$/RXR heterodimer with RXR having a 6-HIS tag produced as a crude lysate
3. $LXR_\beta$ lysate: Baculovirus expressed $LXR_\alpha$/RXR heterodimer with RXR having a 6-HIS tag produced as a crude lysate
4. SPA beads: Ysi copper His-tag SPA beads (Amersham)
5. Plates: Non-binding surface 96-well plate (Corning)
6. Protein lysate dilution buffer: (20 mM Tris-HCl pH 7.9, 500 mM NaCl, 5 mM Imidazole).
7. 2×SPA Buffer: (40 mM $K_2HPO_4/KH_2PO_4$ pH7.3, 100 mM NaCl, 0.05% Tween 20, 20% Glycerol, 4 mM EDTA)
8. 2×SPA Buffer w/o EDTA: (40 mM $K_2HPO_4/KH_2PO_4$ pH7.3, 100 mM NaCl, 0.05% Tween 20, 20% Glycerol)
Stock Solutions
0.5 M $K_2HPO_4/KH_2PO_4$ pH 7.3
0.5 M EDTA pH 8.0
5 M NaCl
10% Tween-20
Glycerol
Preparation of Protein Lysates
Baculovirus expression plasmids for human RXRα accession No NM_002957) $LXR_\alpha$ accession No U22662), $LXR_\beta$ accession No U07132) were made by cloning the appropriate full-length cDNAs into the pBacPakhisl vector (Clontech, CA) following standard procedures. Insertion of the cDNAs into the pBAcPakhisl vector polylinker created an in frame fusion to the cDNA to an N-terminal poly-His tag present in pBacPakhis1. Correct cloning was confirmed by restriction mapping, and/or sequencing.

Cell lysates were prepared by infecting healthy, Sf9 insect cells at a density of approximately $1.25 \times 10^6$/ml at 27° C., in a total volume of 500 mL per 1L sized spinner flasks, cultured under standard conditions. To prepare $LXR_\alpha$ lysate, insect cells were co-transfected with the LXR, expression cassette at an M.O.I. of 0.5 to 0.8 and with the RXR expression cassette at a M.O.I. of approximately 1.6. To prepare $LXR_\beta$ lysate, insect cells were co-transfected with the $LXR_\beta$ expression cassette at an M.O.I of approximately 1.6 and with the RXR expression cassette at a M.O.I. of approximately 1.6. In both cases cells were incubated for 48 hours at 27° C. with constant shaking prior to harvesting.

After incubation, cells were harvested by centrifugation and pelleted. Cell pellets were resuspended in two volumes of ice-cold freshly prepared extraction buffer (20 mM Tris pH 8.0, 110 mM Imidazole, 400 mM NaCl, containing one EDTA free protease inhibitor tablet (Roche Catalog No: 1836170) per 10 ml of extraction buffer).

Cells were homogenized slowly on ice using a Douncer to achieve 80-90% cell lysis. The homogenate was centrifuged in a pre-chilled rotor (Ti50 or Ti70, or equivalent) at 45,000 rpm for 30 minutes at 4° C. Aliquots of the supernatant were frozen on dry ice and stored frozen at −80° C. until quantification and quality control. Aliquots of the lysates were tested in the SPA assay to ensure lot to lot consistency, and via SDS-PAGE analysis after purification using Ni-NTA Resin (Qiagen) and adjusted for protein concentration and expression level prior to use in screening assays.

Preparation of Screening Reagents

[$^3$H] 24,25 Epoxycholesterol (EC) solution: For a single 384-well plate (or 400 wells), 21 µL of [$^3$H] EC (specific activity 76.5 Ci/mmol, concentration 3.2 mCi/mL) was added to 4.4 mL of 2×SPA buffer to provide for a final concentration of 200 nM. For each additional 384-well plate, an additional 19.1 µL of [$^3$H] EC was added to 4.0 mL of additional 2×SPA buffer. The final concentration of [$^3$H] EC in the well was 50 nM.

$LXR_\alpha$ lysate (prepared as above) was diluted with protein lysate dilution buffer. 1400 µL of diluted $LXR_\alpha$ lysate was prepared per 384-well plate, (or 200 wells) and 1120 µL of diluted LXR, lysate was prepared for each additional 384-well plate.

$LXR_\beta$ lysate (prepared as above) was diluted with protein lysate dilution buffer. 1400 µL of diluted $LXR_\beta$ lysate was prepared per 384-well plate, (or 200 wells) and 1120 µL of diluted LXRβ lysate was prepared for each additional 384-well plate.

SPA bead solution: For a 384-well plate (or 400 wells), 3.75 mL of 2×SPA buffer w/o EDTA, 2.25 mL of H$_2$O, and 1.5 mL of Ysi His-tag SPA beads (vortex well before taking) were mixed together. For each additional 384-well plate, an additional 3.5 mL of 2×SPA buffer w/o EDTA, 2.1 mL of H$_2$O, and 1.4 mL of Ysi His-tag SPA beads were mixed together.

Procedure:

Appropriate dilutions of each compound were prepared and pipetted into the appropriate wells of a multiwell plate.

9.1 µL of [$^3$H] EC was added to each well of column 2-23 of the multiwell plate.

5 µl of diluted LXR, lysate was added to each well of column 2-23 on odd rows of the multiwell plate.

5 µL of diluted LXR$_3$ lysate was added to each well of column 2-23 on even rows of the multiwell plate.

17.5 µL of SPA bead solution was added to each well of column 2-23 of the multiwell plate.

The plates were covered with clear sealer and placed in an incubator at ambient temperature for 1 hour.

After incubation plates were analyzed using a luminescent plate reader (MicroBeta, Wallac) using the program n ABASE 3H-384DPM. The setting for n ABASE 3H-384DPM was:

Counting Mode: DPM;
Sample Type: SPA;
ParaLux Mode: low background;
Count time: 30 sec.

Assays for $LXR_\alpha$ and $LXR_\beta$ were performed in the identical manner. The determined Ki represents the average of at least two independent dose response experiments. The binding affinity for each compound may be determined by non-linear regression analysis using the one site competition formula to determine the IC$_{50}$ where:

$$Y = \text{Bottom} + \frac{(\text{Top} - \text{Bottom})}{(1 + 10^{X - \log IC50})}$$

The Ki is than calculated using the Cheng and Prusoff equation where:

Ki=IC$_{50}$/(1+[Concentration of Ligand]/Kd of Ligand)

For this assay, typically the Concentration of Ligand=50 nM and the Kd of EC for the receptor is 200 nM as determined by saturation binding.

The compounds of the invention demonstrated the ability to bind to $LXR_\alpha$ and/or $LXR_\beta$, as well as FXR, when tested in this assay.

Example C

Co-Transfection Assay

To measure the ability of compounds to activate or inhibit the transcriptional activity of LXR in a cell based assay, the co-transfection assay was used. It has been shown that LXR functions as a heterodimer with RXR. For the co-transfection assay, expression plasmids for LXR and RXR are introduced via transient transfection into mammalian cells along with a luciferase reporter plasmid that contains one copy of a DNA sequence that is bound by LXR-RXR heterodimers (LXRE; Willy, P. et. al. 1995). Treatment of transfected cells with an LXR agonist increases the transcriptional activity of LXR, which is measured by an increase in luciferase activity. Similarly, LXR antagonist activity can be measured by determining the ability of a compound to competitively inhibit the activity of a LXR agonist.

Required Materials

1. CV-1 African Green Monkey Kidney Cells
2. Co-transfection expression plasmids, comprising full-length LXR, (pCMX-h $LXR_\alpha$, $LXR_\beta$ (pCMX-h$LXR_\beta$), or RXR, (pCMX-RXR), reporter plasmid (LXREx1-Tk-Luciferase), and control (pCMX-Galactosidase expression vector) (Willey et al. Genes & Development 9 1033-1045 (1995)).
3. Transfection reagent such as FuGLNE6 (Roche).
4. 1× Cell lysis buffer (1% Triton X 100 (JT Baker X200-07), 10% Glycerol (JT Baker M778-07), 5 mM Ditriotreitol (Quantum Bioprobe DTT03; add fresh before lysing), 1 mM EGTA (Ethylene Glycol-bis(B-Amino ethyl ether)-N,N, N',N'-Tetracetic Acid) (Sigma E-4378), 25 mM Tricine (ICN 807420) pH 7.8)

5. 1× Luciferase assay buffer (pH at 7.8) (0.73 mM ATP, 22.3 mM Tricine, 0.11 mM EDTA, 33.3 mM DTT)
6. 1× Luciferrin/CoA (11 mM Luciferin, 3.05 mM Coenzyme A, 10 mM HEPES)

Preparation of Screening Reagents

CV-1 cells were prepared 24 hours prior to the experiment by plating them into T-175 flasks or 500 cm² dishes in order to achieve 70-80% confluency on the day of the transfection. The number of cells to be transfected was determined by the number of plates to be screened. Each 384 well plate requires $1.92 \times 10^6$ cells or 5000 cells per well. DNA Transfection Reagent was prepared by mixing the required plasmid DNAs with a cationic lipid transfection reagent FuGENE6 (Roche) by following the instructions provided with the reagents. Optimal DNA amounts were determined empirically per cell line and size of vessel to be transfected. 10-12 mL of media was added to the DNA Transfection Reagent and this mixture was added to the cells after aspirating media from the T175 cm² flask. Cells were then incubated at least 5 hours at 37° C. to prepare screening cells.

Luciferase assay reagent was prepared by combining before use (per 10 mL):
 10 mL 1× Luciferase assay buffer;
 0.54 mL of 1× Luciferrin/CoA;
 0.54 mL of 0.2 M Magnesium sulfate Procedure Assay plates were prepared by dispensing 5 µL of compound per well of a 384 well plate to achieve final compound concentration of 10 µM and no more than 1% DMSO. Media was removed from the screening cells, the cells trypsinized, harvested cells by centrifugation, counted, and plated at a density of approximately 5000 cells per well in the 384 well assay plate prepared above in a volume of about 45 µL. Assay plates containing both compounds and screening cells (50 µL in total volume) were incubated for 20 hours at 37° C.

After incubation with compounds, media was removed from the cells and lysis buffer (30 µL/well) added. After 30 minutes at ambient temperature, luciferase assay buffer (30 µL/well) was added and the assay plates read on a luminometer (PE Biosystems Northstar reader with on-board injectors, or equivalent). Plates were read immediately after addition of luciferase assay buffer.

The LXR/LXRE co-transfection assay can be used to establish the $EC_{50}/IC_{50}$ values for potency and percent activity or inhibition for efficacy. Efficacy defines the activity of a compound relative to a high control ((N-(3-((4-fluorophenyl)-(naphthalene-2-sulfonyl)amino)propyl)-2,2-dimethylpropionamide)) or a low control (DMSO/vehicle). The dose response curves are generated from an 8 point curve with concentrations differing by /2 LOG units. Each point represents the average of 4 wells of data from a 384 well plate.

The data from this assay is fitted to the following equation, from the $EC_{50}$ value may be solved:

$$Y = Bottom + (Top - Bottom)/(1 + 10^{((logEC50-X)*HillSlope)})$$

The $EC_{50}/IC_{50}$ is therefore defined as the concentration at which an agonist or antagonist elicits a response that is halfway between the Top (maximum) and Bottom (baseline) values. The $EC_{50}/IC_{50}$ values represented are the averages of at least 3 independent experiments. The determination of the relative efficacy or % control for an agonist is by comparison to the maximum response achieved by ((N-(3-((4-fluorophenyl)-(naphthalene-2-sulfonyl)-amino)propyl)-2,2-dimethylpropionamide) that is measured individually in each dose response experiment.

For the antagonist assay, a LXR agonist can be added to each well of a 384 well plate to elicit a response. The % inhibition for each antagonist is therefore a measurement of the inhibition of the activity of the agonist. In this example, 100% inhibition would indicate that the activity of a specific concentration of LXR agonist has been reduced to baseline levels, defined as the activity of the assay in the presence of DMSO only.

Compounds of the invention, when tested in this assay, demonstrated the ability to modulate the activity of $LXR_\alpha$ and/or $LXR_\beta$, as well as FXR. Preferably, the active compounds modulate the activity of LXR with a $EC_{50}$ or $IC_{50}$ of about 10 µM or less. More preferably, the $EC_{50}$ or $IC_{50}$ of the preferred active compounds is about 1 µM or less. Moreover, the compounds exhibited agonist activity at or less than 1 µM $EC_{50}$ with greater than 100% efficacy as measured via the co-transfection assay.

Example D

Time Resolved Fluorescence Resonance Energy Transfer (TR-FRET) Assay

The TR-FRET assay was performed by incubating 8 nM of GST-farnesoid X receptor -LBD (comprising glutathione-S-transferase fused in frame to the farnesoid X receptor ligand binding domain, (amino acids 244-471 of the human farnesoid X receptor)), 8 nM of Europium-labeled anti-GST antibody (Wallac/PE Life Sciences Cat#AD0064), 16 nM biotin-SRC-1 peptide [5'-biotin-CPSSHSSLTERHKILHRLLQEGSPS-CONH2], 20 nM APC-SA [allophycocyanin conjugated streptavidin] (Wallac/PE Life Sciences, Cat# AD0059A) in FRET assay buffer (20 mM $KH_2PO_4/K_2HPO_4$ (pH 7.3), 150 mM NaCl, 2 mM CHAPS, 2 mM EDTA, 1 mM DTT) in the presence of the test compound(s) for 2-4 hours at room temperature in a 384 well assay plate. Data was collected using an LJL Analyst using the standard operating instructions and conditions with readings at emission wavelengths of 615 nm and 665 nm after a delay of 65 µs and an excitation wavelength of 330 nm.

Example E

FXR Co-Transfection Assay

The basic co-transfection protocol for measuring the farnesoid X receptor activity is as follows. CV-1 African Green Monkey Kidney cells were plated 24 hours before transfection to achieve approximately 70-80 percent confluency. Cells were transfected with the following expression vectors, CMX-farnesoid X receptor (full length human farnesoid X receptor), CMX-RXRα (full length human RXR), Luc12 ((ECREx7-Tk-Luciferase) luciferase reporter gene construct. (See WO 00/76523, Venkateswaran et al., (2000) J. Biol. Chem. 275 14700-14707). A CMX-β-Galactosidase expression vector was used as a transfection control. The transfection reagent used was DOTAP (Boehringer Mannheim). Cells were incubated with the DOTAP/DNA mixture for 5 hours after which the cells were harvested and plated onto either 96 well or 384 well plates containing the appropriate concentration of test compound. The assay was allowed to continue for an additional 18-20 hours, after which the cells were lysed, with lysis buffer (1% triton X 100, 10% glycerol, 5 mM Dithiothreitol, 1 mM EGTA, 25 mM Tricine, pH 7.8) and the luciferase activity measured in the presence of Luciferase assay buffer (0.73 mM ATP, 22.3 mM Tricine, 0.11 mM EGTA, 0.55 mM Luciferin, 0.15 mM Coenzyme A, 0.5 mM HEPES, 10 mM Magnesium sulphate) on a standard luminometer plate reader (PE Biosystems, NorthStar Reader), using recommended operating instructions and conditions.

Results of Examples D and E

Both the farnesoid X receptor /ECREx7 co-transfection assay (Example E) and the TR-FRET assay (Example D) can be used to establish the $EC_{50}/IC_{50}$ values for potency and percent activity or inhibition for efficacy. Efficacy defines the activity of a compound relative to a high control (chenodeoxycholic acid, CDCA) or a low control (DMSO/vehicle). The dose response curves are generated from an 8 point curve with concentrations differing by /2 LOG units. Each point represents the average of 4 wells of data from a 384 well plate. The curve for the data is generated by using the equation:

$$Y=\text{Bottom}+(\text{Top}-\text{Bottom})/(1+10^{((\log EC_{50}-X)*\text{HillSlope})})$$

The $EC_{50}/IC_{50}$ is therefore defined as the concentration at which an agonist or antagonist elicits a response that is half way between the Top (maximum) and Bottom (baseline) values. The $EC_{50}/IC_{50}$ values represented are the averages of at least 3 independent experiments. The determination of the relative efficacy or % control for an agonist is by comparison to the maximum response achieved by chenodeoxycholic acid that is measured individually in each dose response experiment.

For the antagonist assay, CDCA is added to each well of a 384 well plate to elicit a response. The % inhibition for each antagonist is therefore a measurement of the inhibition of the activity of CDCA. In this example, 100% inhibition would indicate that the activity of CDCA has been reduced to baseline levels, defined as the activity of the assay in the presence of DMSO only.

Most of the compounds disclosed herein and tested exhibited activity in at least one of the above assays ($EC_{50}$ or $IC_{50}$ less than 10 μM). Most compounds showed activity at or below 1 μM. Moreover, the compounds exhibited agonist activity at or less than 1 μM $EC_{50}$ with greater than 100% efficacy as measured via the co-transfection assay.

Example F

In Vivo Studies

In order to evaluate direct regulation of key target genes by the compounds of the invention, animals are administered a single oral dose of the test compound and tissues collected at various time points. Male C57BL/6 mice (n=8) are dosed by oral gavage with vehicle or compound. At various time points after the dose, animals are bled via the retro orbital sinus for plasma collection. Animals are then euthanized and tissues, such as liver and intestinal mucosa are collected and snap frozen for further analysis. Plasma is analyzed for a lipid parameters, such as total cholesterol, HDL cholesterol and triglyceride levels. RNA is extracted for frozen tissues and can be analyzed by quantitative real time PCR for regulation of key target genes. To identify specificity of target gene regulation by LXR subtypes, LXR deficient mice ($LXR_{\alpha-/-}$ or $LXR_{\beta-/-}$) and C57BL/6 wild-type controls are used in this same protocol.

Plasma Lipid Evaluation:

To compare the effects of compounds on plasma cholesterol and triglycerides, animals are dosed with compound for one week and plasma lipid levels are monitored throughout the study. Male C57BL/6 mice (n=8) are dosed daily by oral gavage with vehicle or compound. Plasma samples are taken on day -1 (in order to group animals), day 1, 3, and 7. Samples are collected three hours after the daily dose. On day 7 of the study, following plasma collection, animals are euthanized and tissues, such as liver and intestinal mucosa are collected and snap frozen for further analysis. Plasma is analyzed for lipid parameters, such as total cholesterol, HDL cholesterol and triglyceride levels. RNA is extracted for frozen tissues and can be analyzed by quantitative real time PCR for regulation of key target genes. To identify specificity of target gene regulation by LXR subtypes, LXR deficient mice ($LXR_{\alpha-/-}$ or $LXR_{\beta-/-}$) and C57BL/6 wild-type controls are used in this same protocol.

Cholesterol Absorption:

Evaluation of compounds to inhibit cholesterol absorption is done via measurement of labeled cholesterol in feces. Male A129 mice (n=7) are dosed daily by oral gavage with vehicle or compound for 7 days. On day 7 of the study, animals are administered [$^{14}$C]-cholesterol and [$^{3}$H]-sitostanol by oral gavage. Animals are individually housed on wire racks for the next 24 hours in order to collect feces. Feces are then dried and ground to a fine powder. Labeled cholesterol and sitostanol are extracted from the feces and ratios of the two are counted on a liquid scintillation counter in order to evaluate the amount of cholesterol absorbed by the individual animal.

Example G

Measured $EC_{50}$ or $IC_{50}$ for LXR, and FXR for Compounds of the Invention Compounds of the invention, when tested as described in Example 2552, demonstrated the ability to modulate the activity of $LXR_\alpha$ and/or $LXR_\beta$, as well as FXR. LXR and FXR activities for various compounds of the invention are presented in the following table; those compounds with $EC_{50}$ or $IC_{50}$ values <10 μM for at least one of $LXR_\alpha$, $LXR_\beta$ or FXR are considered to be active. In the following Table, $IC_{50}$ or $EC_{50}$ data is represented as follows: A<1 μM, B=1-10 μm, and C>10 μM.

| # | FXR | LXR |
|---|-----|-----|
| 1 | | C |
| 4 | | C |
| 5 | | C |
| 6 | | C |
| 7 | | C |
| 8 | | A |
| 9 | | C |
| 26 | | C |
| 27 | | B |
| 38 | | C |
| 44 | | C |
| 45 | | A |
| 92 | | B |
| 93 | | C |
| 95 | | C |
| 98 | | C |
| 99 | | C |
| 100 | | C |
| 101 | | C |
| 102 | | C |
| 103 | | C |
| 104 | | C |
| 105 | | C |
| 106 | | C |
| 107 | | B |
| 108 | | A |
| 109 | | A |
| 110 | | B |
| 111 | | B |
| 112 | | C |

701
-continued

| # | FXR | LXR |
|---|---|---|
| 113 | | C |
| 114 | | A |
| 115 | | C |
| 116 | | A |
| 117 | | A |
| 611 | | C |
| 891 | | A |
| 906 | B | B |
| 907 | A | B |
| 908 | | B |
| 909 | | A |
| 910 | | B |
| 911 | | A |
| 921 | B | C |
| 922 | | A |
| 923 | | A |
| 924 | | B |
| 925 | | A |
| 926 | | B |
| 928 | | A |
| 933 | | C |
| 934 | | A |
| 935 | | A |
| 936 | | A |
| 937 | | A |
| 938 | | A |
| 939 | | A |
| 940 | | A |
| 941 | | B |
| 942 | | C |
| 943 | | C |
| 944 | | A |
| 945 | B | B |
| 946 | B | A |
| 947 | A | A |
| 948 | B | A |
| 949 | B | A |
| 950 | B | A |
| 951 | B | A |
| 952 | B | A |
| 953 | B | A |
| 954 | B | A |
| 955 | B | A |
| 956 | B | A |
| 957 | A | A |
| 958 | A | A |
| 959 | A | A |
| 960 | A | A |
| 961 | A | B |
| 962 | B | A |
| 963 | B | A |
| 964 | B | A |
| 965 | B | A |
| 966 | B | A |
| 967 | B | A |
| 968 | C | A |
| 969 | B | B |
| 970 | B | B |
| 971 | B | A |
| 972 | B | B |
| 975 | | A |
| 976 | | B |
| 977 | | A |
| 978 | | A |
| 979 | | B |
| 980 | | A |
| 981 | | B |
| 982 | | A |
| 984 | | A |
| 989 | | A |
| 990 | | B |
| 991 | | A |
| 992 | | A |
| 993 | | B |
| 994 | | A |
| 995 | | A |
| 996 | | A |
| 997 | | A |

702
-continued

| # | FXR | LXR |
|---|---|---|
| 998 | | A |
| 999 | | A |
| 1001 | | A |
| 1002 | | A |
| 1003 | | A |
| 1004 | | A |
| 1005 | | A |
| 1008 | | A |
| 1009 | | A |
| 1010 | | A |
| 1011 | | C |
| 1012 | | B |
| 1013 | | A |
| 1014 | | A |
| 1016 | | A |
| 1017 | | A |
| 1019 | | C |
| 1023 | | A |
| 1024 | | A |
| 1025 | | A |
| 1026 | | A |
| 1028 | | A |
| 1031 | | A |
| 1032 | | A |
| 1034 | | A |
| 1035 | | A |
| 1036 | | A |
| 1037 | | C |
| 1038 | | A |
| 1039 | | A |

It is understood that the examples and embodiments described herein are for illustrative purposes only and that various modifications or changes in light thereof will be suggested to persons skilled in the art and are to be incorporated within the spirit and purview of this application and scope of the appended claims. All publications, patents, and patent applications cited herein are hereby incorporated herein by reference for all purposes.

All of the U.S. patents, U.S. patent application publications, U.S. patent applications, foreign patents, foreign patent applications and non-patent publications referred to in this specification and/or listed in the Application Data Sheet, are incorporated herein by reference, in their entirety.

From the foregoing it will be appreciated that, although specific embodiments of the invention have been described herein for purposes of illustration, various modifications may be made without deviating from the spirit and scope of the invention. Accordingly, the invention is not limited except as by the appended claims. This invention also encompasses all combinations of alternative aspects of the invention noted herein. It is understood that any and all embodiments of the present invention may be taken in conjunction with any other embodiment to describe additional embodiments of the present invention. Furthermore, any elements of an embodiment may be combined with any and all other elements from any of the embodiments to describe additional embodiments.

We claim:

1. A compound according to the formula,

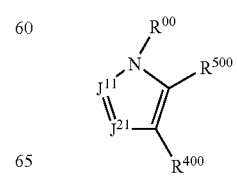

or a pharmaceutically acceptable salt thereof, wherein:

$J^{11}$ is —$CR^{200}$—;

$J^{21}$ is =N—;

$R^{00}$ is $G^{21}$;

$R^{200}$ is $G^1$;

$R^{400}$ is Q;

Q is $C_{3-6}$ cycloalkyl, heteroaryl or heterocyclyl, each optionally substituted with 1 to 4 $R^Q$, or Q is —X—Y—Z; wherein each $R^Q$ is independently aryloxy, aralkyloxy, aryloxyalkyl, aryl$C_0$-$C_6$alkylcarboxy, $C(R^{110})$=$C(R^{110})$—COOH, oxo, =S, —Z, —Y'—Z, or —X—Y—Z, wherein each $R^Q$ is optionally substituted with 1 to 4 $R^{80}$;

$R^{500}$ is $R^C$;

$G^{21}$ is -$J^0$-$K^0$, wherein $J^0$ and $K^0$ are independently aryl or heteroaryl, each optionally substituted with one to four $R^K$ groups;

each $R^K$ is independently hydrogen, halogen, $CR^{110}$=$CR^{110}COOR^{110}$, nitro, —Z, —Y—Z, or —X—Y—Z;

$G^1$ is -$L^{10}$-R, wherein $L^{10}$ is a bond, $L^{50}$, $L^{60}$, -$L^{50}$-$L^{60}$-$L^{50}$-, or -$L^{60}$-$L^{50}$-$L^{60}$-, wherein each $L^{50}$ is independently —$[C(R^{150})_2]_m$—;

each $L^{60}$ is independently —CS—, —CO—, —SO$_2$—, —O—, —CON($R^{110}$)—, —CONR$^{110}$N($R^{110}$)—, —C(=N$R^{110}$)—, —C(=NOR$^{110}$)—, —C(=N—N($R^{110}$)$_2$)—, —$C_3$-$C_8$cycloalkyl-, or -heterocyclyl-, wherein the cycloalkyl or heterocyclyl is optionally substituted with one to 4 $R^{140}$ groups;

or each $L^{60}$ is independently $C_2$-$C_6$ alidiyl, wherein the alidiyl chain is optionally interrupted by —$C(R^{110})_2$—, —$C(R^{110})_2C(R^{110})_2$—, —$C(R^{110})$=$C(R^{110})$—, —$C(R^{110})_2$O—, —$C(R^{110})_2NR^{110}$—, —C≡C—, —O—, —S—, —N($R^{100}$)CO—, —N($R^{100}$)CO$_2$—, —CON($R^{100}$)—, —CO—, —CO$_2$—, —OC(=O)—, —OC(=O)N($R^{100}$)—, —SO$_2$—, —N($R^{100}$)SO$_2$—, or —SO$_2$N($R^{100}$);

R is aryl, heterocyclyl, heteroaryl or —($C_3$-$C_6$)cycloalkyl, wherein R is optionally substituted with 1 to 4 $R^A$, wherein each $R^A$ is independently halogen, nitro, heterocyclyl, $C_1$-$C_6$ alkyl, $C_2$-$C_6$ alkenyl, $C_2$-$C_6$ alkynyl, $C_3$-$C_8$ cycloalkyl, ($C_3$-$C_8$ cycloalkyl)-$C_1$-$C_6$ alkyl-, ($C_3$-$C_8$ cycloalkenyl)-$C_1$-$C_6$ alkyl-, ($C_3$-$C_8$ cycloalkyl)-$C_2$-$C_6$ alkenyl-, arylalkyl, aryloxy, aryl$C_{1-6}$ alkoxy, $C_1$-$C_6$ haloalkyl, SO$_2R^{110}$, OR$^{110}$, SR$^{110}$, N$_3$, SOR$^{110}$, COR$^{110}$, SO$_2$N($R^{110}$)$_2$, SO$_2$NR$^{110}$COR$^{110}$, C≡N, C(O)OR$^{110}$, CON($R^{110}$)$_2$, CON($R^{110}$)OR$^{110}$, OCON($R^{110}$)$_2$, NR$^{110}$COR$^{110}$, NR$^{110}$CON($R^{110}$)$_2$, NR$^{110}$COOR$^{110}$, —C(=N—OH)R$^{110}$, —C(=S)N($R^{110}$)$_2$, —S(=O)N($R^{110}$)$_2$, —S(=O)OR$^{110}$, —N($R^{110}$)S(=O)$_2R^{110}$, —C(=O)N($R^{110}$)N($R^{110}$)$_2$, —OC(=O)—R$^{110}$, —OC(=O)—OR$^{110}$ or N($R^{110}$)$_2$, wherein each $R^A$ is optionally substituted with 1 to 4 groups which independently are -halogen, —$C_1$-$C_6$ alkyl, aryloxy, $C_{0-6}$ alkylSO$_2R^{110}$, $C_{0-6}$ alkylCOOR$^{110}$, $C_{1-6}$ alkoxyaryl, $C_1$-$C_6$ haloalkyl, —SO$_2R^{110}$, —OR$^{110}$, —SR$^{110}$, —N$_3$, —SO$_2R^{110}$, —COR$^{110}$, —SO$_2$N($R^{110}$)$_2$, —SO$_2$NR$^{110}$COR$^{110}$, —C≡N, —C(O)OR$^{110}$, —CON($R^{110}$)$_2$, —CON($R^{110}$)OR$^{110}$, —OCON($R^{110}$)$_2$—NR$^{110}$COR$^{110}$, —NR$^{110}$CON($R^{110}$)$_2$—NR$^{110}$COOR$^{110}$, or —N($R^{110}$)$_2$;

each $R^{80}$ is independently halogen, $C_1$-$C_6$ alkyl, $C_1$-$C_6$ alkoxy, $C_1$-$C_6$ haloalkyl, $C_1$-$C_6$ haloalkyl(OR$^{110}$), $C_0$-$C_6$ alkylOR$^{110}$, $C_0$-$C_6$ alkylCON($R^{110}$)$_2$, $C_0$-$C_6$ alkylCOR$^{110}$, $C_0$-$C_6$ alkylCOOR$^{110}$, or $C_0$-$C_6$ alkylSO$_2R^{110}$;

$R^C$ is hydrogen, halogen, nitro, cyano, $C_1$-$C_6$ alkyl, or $C_1$-$C_6$ haloalkyl;

each $R^{100}$ is independently —$R^{110}$, —C(=O)$R^{110}$, —CO$_2R^{110}$, or —SO$_2R^{110}$;

each $R^{110}$ is independently -hydrogen, —$C_1$-$C_6$ alkyl, $C_2$-$C_6$ alkenyl, $C_2$-$C_6$ alkynyl, —$C_1$-$C_6$ haloalkyl, or —N($R^{120}$)$_2$, wherein any of $R^{110}$ is optionally substituted with 1 to 4 radicals of $R^{120}$;

each $R^{120}$ is independently halogen, cyano, nitro, oxo, —B(OR$^{130}$)$_2$, $C_1$-$C_6$haloalkyl, $C_1$-$C_6$ alkyl, $C_1$-$C_6$ alkoxy, ($C_0$-$C_6$ alkyl)C=O(OR$^{130}$), $C_0$-$C_6$ alkylOR$^{130}$, $C_0$-$C_6$ alkylCOR$^{130}$, $C_0$-$C_6$alkylSO$_2R^{130}$, $C_0$-$C_6$alkylCON($R^{130}$)$_2$, $C_0$-$C_6$alkylCONR$^{130}$OR$^{130}$, $C_0$-$C_6$alkylSO$_2$N($R^{130}$)$_2$, $C_0$-$C_6$alkylSR$^{130}$, $C_0$-$C_6$ haloalkylOR$^{130}$, $C_0$-$C_6$alkylCN, —$C_0$-$C_6$alkylN($R^{130}$)$_2$, —NR$^{130}$SO$_2R^{130}$, or —OC$_{0-6}$ alkylCOOR$^{130}$;

each $R^{130}$ is independently hydrogen, $C_1$-$C_6$ alkyl, $C_2$-$C_6$ alkenyl, or $C_2$-$C_6$ alkynyl;

each $R^{140}$ is independently $C_1$-$C_6$ alkyl, $C_1$-$C_6$ alkoxy, halogen, $C_1$-$C_6$ haloalkyl, $C_0$-$C_6$ alkylCON($R^{110}$)$_2$, $C_0$-$C_6$ alkylCONR$^{110}$OR$^{110}$, $C_0$-$C_6$ alkylOR$^{110}$, or $C_0$-$C_6$ alkylCOOR$^{110}$; and each $R^{150}$ is independently hydrogen, halogen, OR$^{130}$, ($C_1$-$C_6$)alkyl, or ($C_1$-$C_6$)haloalkyl, wherein each alkyl is optionally substituted with at least one group which are each independently halogen, cyano, nitro, azido, OR$^{130}$, C(O)R$^{130}$, C(O)OR$^{130}$, C(O)N($R^{130}$)$_2$, N($R^{130}$)$_2$, N($R^{130}$)C(O)R$^{130}$, N($R^{130}$)S(O)$_2R^{130}$, OC(O)OR$^{130}$, OC(O)N($R^{130}$)$_2$, N($R^{130}$)C(O)OR$^{130}$, N($R^{130}$)C(O)N($R^{130}$), SR$^{130}$, S(O)R$^{130}$, S(O)$_2R^{130}$, or S(O)$_2$N($R^{130}$)$_2$;

or two $R^{150}$ (bonded to same or different atoms) can be taken together to form a $C_3$-$C_6$ cycloalkyl;

each X is independently —O—, —S—, or —N($R^{100}$)—;

each Y is independently —$[C(R^{150})_2]_p$—, or —$C_2$-$C_6$ alkenyl, wherein p is 1, 2, 3, 4, 5, or 6;

each Y' is independently —$[C(R^{150})_2]_p$—, —$C_2$-$C_6$ alkenyl, $C_3$-$C_8$ cycloalkyl, or heterocyclyl, wherein the cycloalkyl or heterocyclyl is optionally substituted with 1 to 3 Z groups;

each Z is independently —H, halogen, —OR$^{110}$, —SR$^{110}$, —C(=O)R$^{110}$, —C(=O)OR$^{110}$, —C(=O)N($R^{110}$)$_2$, —N($R^{100}$)$_2$, —N$_3$, —NO$_2$, —C(=N—OH)R$^{110}$, —C(=S)N($R^{110}$)$_2$, —CN, —S(=O)R$^{110}$, —S(=O)N($R^{110}$)$_2$, —S(=O)OR$^{110}$, —S(=O)$_2R^{110}$, S(=O)$_2$N($R^{110}$)$_2$, —NR$^{110}$COR$^{110}$, —N($R^{110}$)C(=O)N($R^{110}$)$_2$, —N($R^{110}$)COOR$^{110}$, —N($R^{110}$)S(=O)$_2R^{110}$, —C(=O)N($R^{110}$)N($R^{110}$)$_2$, —C(=O)N($R^{110}$)(OR$^{110}$), —OC(=O)—R$^{110}$, —OC(=O)—OR$^{110}$, or —OC(=O)—N($R^{110}$)$_2$; and each m is independently 0, 1, 2, 3, 4, 5, or 6.

2. The compound of claim 1 wherein Q is heteroaryl or heterocyclyl, each optionally substituted with 1 to 4 $R^Q$.

3. The compound according to claim 2, of one of the formulae:

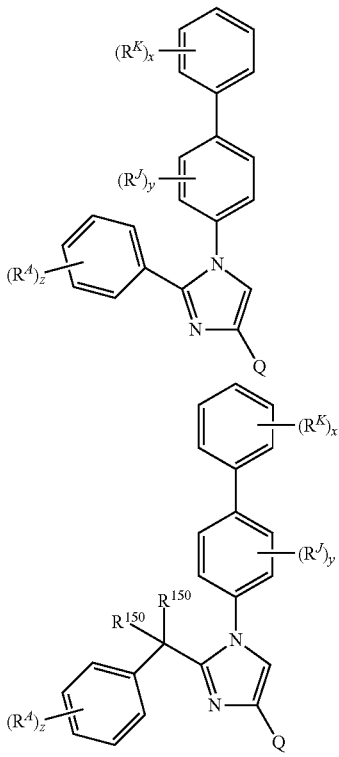

wherein
x and z are independently 0, 1, 2, 3, or 4; y is 0, 1, 2, or 3; and
each $R^J$ is independently halogen, $C_1$-$C_6$ alkyl, $C_1$-$C_6$ haloalkyl, —$OR^{110}$, —$SO_2R^{110}$, —$COR^{110}$, —$SO_2N(R^{110})_2$, —C≡N, —C(O)$OR^{110}$, —CON($R^{110}$)$_2$, —$NR^{110}COR^{110}$, or —N($R^{110}$)$_2$.

4. A compound according to the formula,

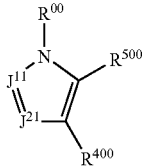

or a pharmaceutically acceptable salt thereof, wherein:
$J^{11}$ is —$CR^{200}$—;
$J^{21}$ is N;
$R^{00}$ is $G^{21}$;
$R^{200}$ is $G^1$;
$R^{400}$ is Q;
$R^{500}$ is $R^C$;
Q is $C_{3-6}$ cycloalkyl, heteroaryl or heterocyclyl, each optionally substituted with 1 to 4 $R^Q$;
$R^Q$ is independently))C($R^{110}$)=C($R^{110}$—COOH, oxo, =S, —Z, —Y—Z, or —X—Y—Z;
$G^{21}$ is -$J^O$-$K^O$, wherein
$J^O$ and $K^O$ are independently aryl or heteroaryl, each optionally substituted with one to four $R^K$ groups;
each $R^K$ is independently hydrogen, halogen, nitro, —Z, —Y—Z, or —X—Y—Z;

$G^1$ is -$L^{10}$-R, wherein
$L^{10}$ is a bond or —[C($R^{150}$)$_2$]$_m$—;
R is aryl or heteroaryl, wherein R is optionally substituted with 1 to 4 $R^A$, wherein
each $R^A$ is independently halogen, nitro, $C_1$-$C_6$ alkyl, $C_2$-$C_6$ alkenyl, $C_2$-$C_6$ alkynyl, $C_1$-$C_6$ haloalkyl, $SO_2R^{110}$, $OR^{110}$, $SR^{110}$, $SOR^{110}$, $COR^{110}$, $SO_2N(R^{110})_2$, $SO_2NR^{110}COR^{110}$, C≡N, C(O)$OR^{110}$, CON($R^{110}$)$_2$, CON($R^{110}$)$OR^{110}$, OCON($R^{110}$)$_2$, $NR^{110}COR^{110}$, $NR^{110}CON(R^{110})_2$, $NR^{110}COOR^{110}$, —C(=N—OH)$R^{110}$, —C(=S)N($R^{110}$)$_2$, —S(=O)N($R^{110}$)$_2$, —S(=O)$OR^{110}$, —N($R^{110}$)$_2R^{110}$, —C(=O)N($R^{110}$)N($R^{110}$)$^2$, —OC(=O)—$R^{110}$, —OC(=O)—$OR^{110}$ or N($R^{110}$)$_2$;
$R^C$ is hydrogen, halogen, nitro, cyano, $C_1$-$C_6$ alkyl, or $C_1$-$C_6$ haloalkyl;
each $R^{100}$ is independently —$R^{110}$, —C(=O)$R^{110}$, —$CO_2R^{110}$, or —$SO_2R^{110}$;
each $R^{110}$ is independently -hydrogen, —$C_1$-$C_6$ alkyl, $C_2$-$C_6$ alkenyl, $C_2$-$C_6$ alkynyl, —$C_1$-$C_6$ haloalkyl, or —N($R^{120}$)$_2$, wherein any of $R^{110}$ is optionally substituted with 1 to 4 radicals of $R^{120}$;
each $R^{120}$ is independently halogen, cyano, nitro, oxo, $C_1$-$C_6$haloalkyl, $C_1$-$C_6$ alkyl, $C_1$-$C_6$ alkoxy, ($C_0$-$C_6$ alkyl)C=O($OR^{130}$), $C_0$-$C_6$ alkyl$OR^{130}$, $C_0$-$C_6$ alkyl$COR^{130}$, $C_0$-$C_6$alkyl$SO_2R^{130}$, $C_0$-$C_6$alkyl$CON(R^{130})_2$, $C_0$-$C_6$alkyl$CONR^{130}OR^{130}$, $C_0$-$C_6$alkyl$SO_2N(R^{130})_2$, $C_0$-$C_6$ alkyl$SR^{130}$, $C_0$-$C_6$ haloalkyl$OR^{130}$, $C_0$-$C_6$ alkylCN, —$C_0$-$C_6$ alkylN($R^{130}$)$_2$, —NR or —$OC_{0-6}$ alkyl-$COOR^{130}$;
each $R^{130}$ is independently hydrogen, $C_1$-$C_6$ alkyl, $C_2$-$C_6$ alkenyl, or $C_2$-$C_6$ alkynyl;
each $R^{150}$ is independently hydrogen, halogen, $OR^{130}$, ($C_1$-$C_6$)alkyl, or ($C_1$-$C_6$)haloalkyl;
or two $R^{150}$ (bonded to the same or different atoms) taken together to form a $C_{3-6}$ cycloalkyl;
each X is independently —O—, —S—, or —N($R^{100}$)—;
each Y is independently —[C($R^{150}$)$_2$]$_p$—, or —$C_2$-$C_6$ alkenyl, wherein p is 1, 2, 3, 4, 5, or 6;
each Z is independently —H, halogen, —$OR^{110}$, —$SR^{110}$, —C(=O)$R^{110}$, —C(=O)$OR^{110}$, —C(=O)N($R^{110}$)$_2$, —N($R^{110}$)$_2$, —$N_3$, —$NO_2$, —C(=N—OH)$R^{110}$, —C(=S)N($R^{110}$)$_2$, —CN, —S(=O)$R^{110}$, —S(=O)N($R^{110}$)$_2$, —S(=O)$OR^{110}$, —S(=O)$_2R^{110}$, S(=O)$_2$N($R^{110}$)$_2$, —$NR^{110}COR^{110}$, —N($R^{110}$)C(=O)N($R^{110}$)$_2$, —N($R^{110}$)$COOR^{110}$, —N($R^{110}$)S(=O)$_2R^{110}$, —C(=O)N($R^{110}$)N($R^{110}$)$_2$, —C(=O)N($R^{110}$)($OR^{110}$), —OC(=O)—$R^{110}$, —OC(=O)—$OR^{110}$, or —OC(=O)—N($R^{110}$)$_2$; and
each m is independently 0, 1, 2, 3, 4, 5, or 6.

5. The compound according to claim 4, wherein G21 is -$J^O$-$K^O$, wherein $J^O$ and $K^O$ are independently thienyl, pyrrolyl, furyl, oxazolyl, thiazolyl, imidazolyl, pyrazolyl, isoxazolyl, isothiazolyl, phenyl, pyridyl, pyrazinyl, or pyrimidinyl, each optionally substituted with one to four $R^K$ groups.

6. The compound according to claim 5, wherein $J^O$ is phenyl optionally substituted with one or two $R^K$ groups; and $K^O$ is phenyl, pyridyl, pyrazinyl, or pyrimidinyl, each optionally substituted with one to four $R^K$ groups.

7. The compound according to claim 6, wherein $K^O$ is phenyl optionally substituted with 1 to 3 $R^K$ groups.

8. The compound according to claim 7, wherein $K^O$ is phenyl substituted with at least one S(=O)$_2$($C_{1-6}$ alkyl) group.

9. The compound according to claim 4, wherein $G^1$ is -$L^{10}$-R, wherein $L^{10}$ is a bond; and R is phenyl optionally substituted with 1 or 2 $R^A$.

10. The compound according to claim 9, wherein each $R^A$ is independently fluoro, chloro, methyl, trifluoromethyl, $-OR^{110}$, $-SR^{110}$, $-SO_2R^{110}$, or $-C(O)OR^{110}$.

11. The compound according to claim 9, wherein R is phenyl substituted with at least one chloro group.

12. The compound according to claim 9, wherein R is phenyl substituted with at least one trifluoromethyl group.

13. The compound according to claim 4, wherein $G^1$ is $-L^{10}$-R, wherein $L^{10}$ is $-[C(R^{150})_2]_m-$, wherein m is 1 or 2; and R is phenyl optionally substituted with 1 or 2 $R^A$.

14. The compound according to claim 13, wherein each $R^A$ is independently fluoro, chloro, methyl, trifluoromethyl, $N(R^{110})_2$, $N(R^{110})CON(R^{110})_2$, $CON(R^{110})_2$, $SO_2R^{110}$, $OR^{110}$, $SR^{110}$, or $C(O)OR^{110}$.

15. The compound according to claim 13, wherein R is phenyl substituted with at least one chloro group.

16. The compound according to claim 13, wherein R is phenyl substituted with at least one trifluoromethyl group.

17. The compound according to claim 4, wherein Q is a 5-membered heteroaryl optionally substituted with 1 to 4 $R^Q$.

18. The compound according to claim 17, wherein Q is pyrrolyl, pyrazolyl, furyl, thienyl, oxazolyl, isoxazolyl, thiazolyl, imidazolyl, oxadiazolyl, thiadiazolyl, triazolyl, or tetrazolyl, each optionally substituted with 1 to 4 $R^Q$.

19. The compound according to claim 18, wherein Q is 1,3-thiazolyl; 1,2,4-oxadiazolyl; 1,2,5-oxadiazolyl; 1,3,4-oxadiazolyl; 1,3,5-oxadiazolyl; pyrrolyl; thienyl; pyrazolyl; imidazolyl; furyl; isoxazolyl; or 1,3,5-thiadiazolyl, each optionally substituted with 1 or 2 $R^Q$.

20. The compound according to claim 4, Q is a 5-membered heterocyclyl optionally substituted with 1 to 4 $R^Q$.

21. The compound according to claim 4, Q is imidazolidinyl, oxazolidinyl, thiazolidinyl, pyrrolidinyl, dioxolanyl, oxathiolanyl, dithiolanyl, imidazolinyl, oxazolinyl, thiazolinyl, 1,3-dioxolyl, 1,3-oxathiolyl, or 1,3-dithiolyl, each optionally substituted with 1 to 4 $R^Q$.

22. The compound according to claim 4, Q is 4,5-dihydro-1,3-oxazolyl; 4,5-dihydro-1,3-thiazolyl; 4,5-dihydro-1H,1'H-2,4'-imidazolyl; pyrrolidinyl; piperidinyl; tetrahydropyranyl; 3,4-dihydro-2H-pyranyl; oxetanyl, or azetidinyl, each optionally substituted with 1 or 2 $R^Q$.

23. The compound according to claim 4, Q is $C_{3-6}$ cycloalkyl optionally substituted with 1 to 4 $R^Q$.

24. The compound according to claim 23, Q is cyclopropyl or cyclopentyl optionally substituted with 1 or 2 $R^Q$.

25. The compound according to claim 23, Q is cyclopropyl or cyclopentyl, substituted with CN, OH or $OC_{1-6}$ alkyl.

26. The compound according to claim 4, of one of the formulae:

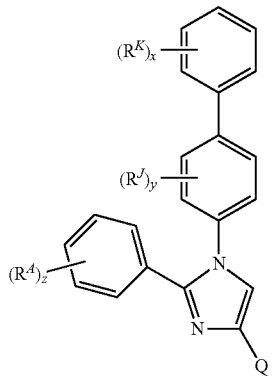

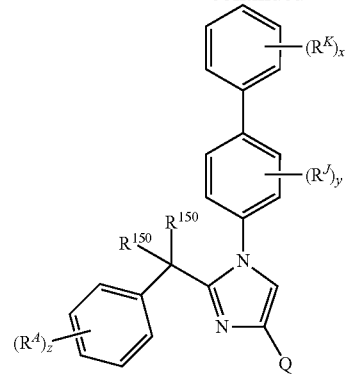

wherein x and z are independently 0, 1, 2, 3, or 4; y is 0, 1, 2, or 3; and each $R^J$ is independently halogen, $C_1$-$C_6$alkyl, $C_1$-$C_6$ haloalkyl, $-OR^{110}$, $-SO_2R^{110}$, $-COR^{110}$, $-SO_2N(R^{110})_2$, $-C\equiv N$, $-C(O)OR^{110}$, $-CON(R^{110})_2$, $-NR^{110}COR^{110}$, or $-N(R^{110})_2$.

27. The compound according to claim 26, wherein Q is a 5-membered heteroaryl optionally substituted with 1 to 4 $R^Q$.

28. The compound according to claim 26, wherein Q is pyrrolyl, pyrazolyl, furyl, thienyl, oxazolyl, isoxazolyl, thiazolyl, imidazolyl, oxadiazolyl, thiadiazolyl, triazolyl, or tetrazolyl, each optionally substituted with 1 to 4 $R^Q$.

29. The compound according to claim 28, wherein Q is 1,3-thiazolyl; 1,2,4-oxadiazolyl; 1,2,5-oxadiazolyl; 1,3,4-oxadiazolyl; 1,3,5-oxadiazolyl; pyrrolyl; thienyl; pyrazolyl; imidazolyl; furyl; isoxazolyl; or 1,3,5-thiadiazolyl, each optionally substituted with 1 or 2 $R^Q$.

30. The compound according to claim 26, Q is a 5-membered heterocyclyl optionally substituted with 1 to 4 $R^Q$.

31. The compound according to claim 26, Q is imidazolidinyl, oxazolidinyl, thiazolidinyl, pyrrolidinyl, dioxolanyl, oxathiolanyl, dithiolanyl, imidazolinyl, oxazolinyl, thiazolinyl, 1,3-dioxolyl, 1,3-oxathiolyl, or 1,3-dithiolyl, each optionally substituted with 1 to 4 $R^Q$.

32. The compound according to claim 26, Q is 4,5-dihydro-1,3-oxazolyl; 4,5-dihydro-1,3-thiazolyl; 4,5-dihydro-1H,1'H-2,4'-imidazolyl; pyrrolidinyl; piperidinyl; tetrahydropyranyl; 3,4-dihydro-2H-pyranyl; or azetidinyl, each optionally substituted with 1 or 2 $R^Q$.

33. The compound according to claim 26, Q is $C_{3-6}$ cycloalkyl optionally substituted with 1 to 4 $R^Q$.

34. The compound according to claim 33, Q is cyclopentyl or cyclopropyl optionally substituted with 1 or 2 $R^Q$.

35. The compound according to claim 33, Q is cyclopentyl or cyclopropyl, substituted with OH or $OC_{1-6}$ alkyl.

36. The compound according to claim 26, of one of the formulae:

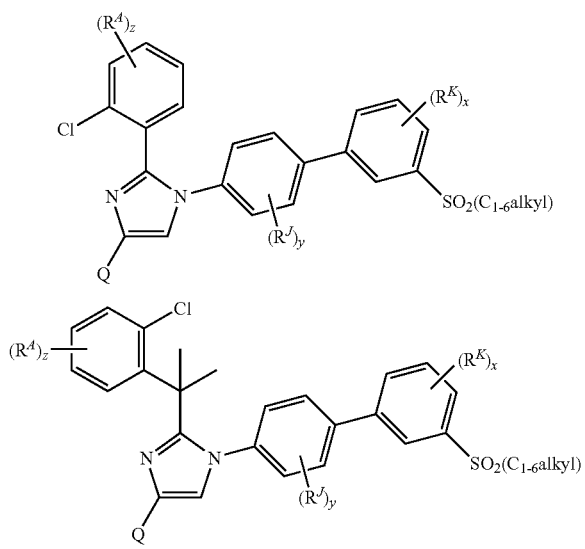

wherein
x and z are independently 0, 1, 2, or 3; y is 0, 1, or 2; and
each $R^K$ and $R^J$ is independently halogen, $C_1$-$C_6$ alkyl, $C_1$-$C_6$ haloalkyl, —$OR^{110}$, —$SO_2R^{110}$, —$COR^{110}$, —$SO_2N(R^{110})_2$, —C≡N, —$C(O)OR^{110}$, —$CON(R^{110})_2$, —$NR^{110}COR^{110}$ or —$N(R^{110})_2$.

37. The compound according to claim 36, of one of the formulae:

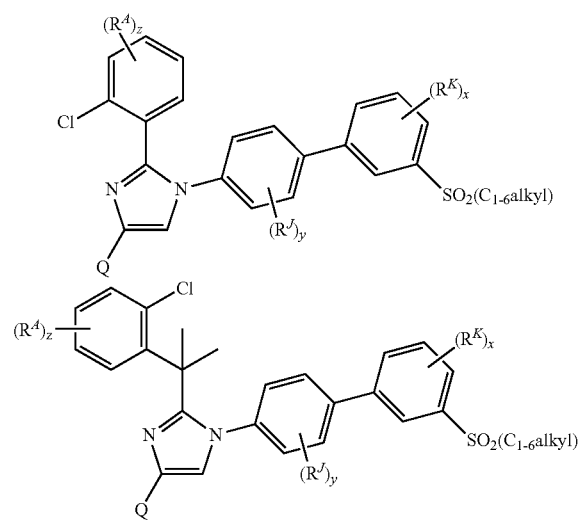

wherein
x and z are independently 0 or 1;
y is 0, 1, or 2;
each $R^K$ and $R^J$ is independently halogen, $C_1$-$C_6$ alkyl, $C_1$-$C_6$ haloalkyl, —$OR^{110}$, —$SO_2R^{110}$, —$COR^{110}$, —$SO_2N(R^{110})_2$, —C≡N, —$C(O)OR^{110}$, —$CON(R^{110})_2$, —$NR^{110}COR^{110}$ or —$N(R^{110})_2$.

38. The compound according to claim 37, of one of the formulae:

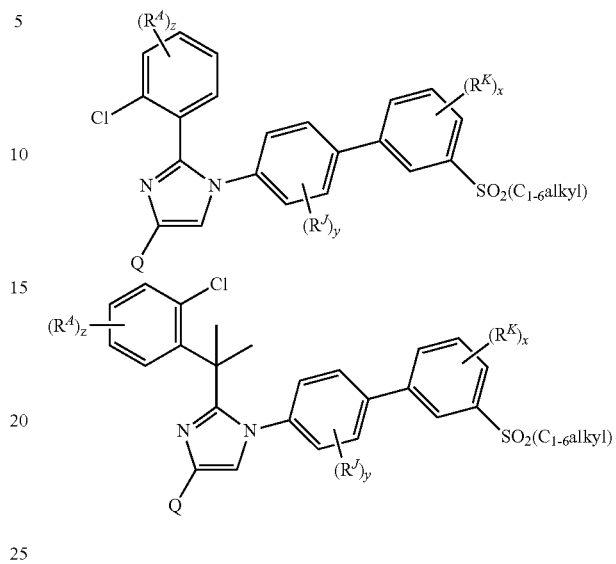

wherein
x and z are independently 0 or 1;
y is 0, 1, or 2;
each $R^A$ is independently halogen, $C_1$-$C_6$ alkyl, or $C_1$-$C_6$ haloalkyl; and
each $R^K$ and $R^J$ is independently halogen, $C_1$-$C_6$ alkyl, $C_1$-$C_6$ haloalkyl, —$OR^{110}$, —$SO_2R^{110}$, —$COR^{110}$, —$SO_2N(R^{110})_2$, —C≡N, —$C(O)OR^{110}$, —$CON(R^{110})_2$, —$NR^{110}COR^{110}$ or —$N(R^{110})_2$.

39. A compound according to the formula,

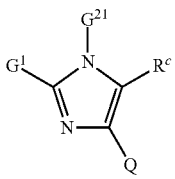

or a pharmaceutically acceptable salt thereof, wherein:
Q is $C_{3-6}$ cycloalkyl; 5 or 6 membered heteroaryl or 5 or 6 membered heterocyclyl, each optionally substituted with one or two $R^Q$;
$R^Q$ is independently oxo, =S, —Z, or —Y—Z;
$G^{21}$ is $J^0$-$K^0$, wherein
  $J^0$ and $K^0$ are phenyl, each optionally substituted with one or two $R^K$ groups;
  each $R^K$ is independently halogen, —Z, or —Y—Z;
$G^1$ is -$L^{10}$-R, wherein
  $L^{10}$ is a bond or —$[C(R^{150})_2]$—;
  R is phenyl, wherein R is optionally substituted with one or two $R^A$ groups, wherein
  each $R^A$ is independently halogen, $C_1$-$C_6$ alkyl, or $C_1$-$C_6$ haloalkyl;
$R^C$ is —Z;
each $R^{110}$ is independently hydrogen or —$C_1$-$C_6$ alkyl;
each $R^{110}$ is independently hydrogen, halogen, or ($C_1$-$C_6$) alkyl;
each Y is independently -$[C(R^{150})_2]_1$, wherein q is 1, 2, 3, 4, 5, or 6; and each Z is independently H, halogen, cyano, —OR$^{110}$, —C(=O)R$^{110}$, —C(=O)OR$^{110}$, or —S(=O)$_2$R$^{110}$.

40. The compound of claim 39 wherein:

each R$^Q$ is independently halogen, C$_{1-6}$ alkyl, CF$_3$, CN, oxo, =S, C$_{0-6}$ alkylOR$^{110}$, —C(O)R$^{110}$ or —C(=O)OR$^{110}$;

each R$^K$ is independently halogen or —S(=O)$_2$R$^{110}$;

each R$^A$ is halogen or C$_1$-C$_6$ haloalkyl; and

R$^C$ is H.

41. The compound according to claim 1 selected from the compounds listed in Tables 16 and 20.

42. A composition comprising a compound of claim 1, 4, 39, or 41 and one or more pharmaceutically acceptable carriers.

43. A method of treating or ameliorating a disease or disorder, comprising administering to a subject in need thereof a therapeutically effective amount of a compound according to claim 1, 4, 39 or 41, wherein the disease or disorder is hypercholesterolemia, hyperlipoproteinemia, hypertriglyceridemia, lipodystrophy, hyperglycemia, diabetes mellitus, dyslipidemia, or diabetes.

44. A method of treating or ameliorating a disease or disorder, comprising administering to a subject in need thereof a therapeutically effective amount of a compound according to claim 1, 4, 39 or 41, wherein the disease or disorder is atherosclerosis, gallstone disease, acne vulgaris, acneiform skin conditions, inflammation, obesity, or xanthomas.

45. A method of treating or ameliorating a disease or disorder, comprising administering to a subject in need thereof a therapeutically effective amount of a compound according to claim 1, 4, 39 or 41, wherein the disease or disorder is multiple sclerosis.

* * * * *

UNITED STATES PATENT AND TRADEMARK OFFICE
CERTIFICATE OF CORRECTION

PATENT NO. : 7,998,995 B2   Page 1 of 1
APPLICATION NO. : 12/517800
DATED : August 16, 2011
INVENTOR(S) : Brant Clayton Boren et al.

It is certified that error appears in the above-identified patent and that said Letters Patent is hereby corrected as shown below:

In the Claims:

Claim 1:

Column 703, lines 41 and 42, move "with 1 to 4 $R^A$, wherein" after "wherein R is optionally substituted".

The text should read:

-- wherein R is optionally substituted with 1 to 4 $R^A$, wherein --.

Claim 4:

Column 706, line 12, change "-N($R^{110}$)$_2 R^{110}$," to -- -N($R^{110}$)S(=O)$R^{110}$, --.

Column 706, line 29, change "-NR" to -- -$NR^{130}SO_2R^{130}$ --.

Claim 5:

Column 706, line 51, change "G21" to -- $G^{21}$ --.

Claim 39:

Column 710, line 64, change "$R^{110}$" to -- $R^{150}$ --.

Column 710, line 66, change "-[C($R^{150}$)$_2$]$_1$," to -- -[C($R^{150}$)$_2$]$_q$, --.

Signed and Sealed this
Eleventh Day of March, 2014

Michelle K. Lee
*Deputy Director of the United States Patent and Trademark Office*